(12) United States Patent
Kyle et al.

(10) Patent No.: US 9,221,831 B2
(45) Date of Patent: Dec. 29, 2015

(54) BUPRENORPHINE ANALOGS

(75) Inventors: Donald J. Kyle, Yardley, PA (US); Laykea Tafesse, Robbinsville, NJ (US)

(73) Assignee: Purdue Pharma, L.P., Stamford, CT (US)

( * ) Notice: Subject to any disclaimer, the term of this patent is extended or adjusted under 35 U.S.C. 154(b) by 0 days.

(21) Appl. No.: 13/825,241

(22) PCT Filed: Sep. 20, 2011

(86) PCT No.: PCT/IB2011/002208
§ 371 (c)(1),
(2), (4) Date: Mar. 20, 2013

(87) PCT Pub. No.: WO2012/038813
PCT Pub. Date: Mar. 29, 2012

(65) Prior Publication Data
US 2014/0057931 A1    Feb. 27, 2014

Related U.S. Application Data

(60) Provisional application No. 61/384,912, filed on Sep. 21, 2010, provisional application No. 61/503,674, filed on Jul. 1, 2011.

(51) Int. Cl.
*A61K 31/485* (2006.01)
*C07D 489/12* (2006.01)

(52) U.S. Cl.
CPC .................................. *C07D 489/12* (2013.01)

(58) Field of Classification Search
USPC ............................................ 514/279; 546/39
See application file for complete search history.

(56) References Cited

U.S. PATENT DOCUMENTS

| | | |
|---|---|---|
| 3,464,994 A | 9/1969 | Bentley et al. |
| 6,740,641 B2 | 5/2004 | Gao et al. |
| 6,825,205 B2 | 11/2004 | Kyle |
| 6,958,398 B1 | 10/2005 | Kupper et al. |
| 7,084,150 B2 | 8/2006 | Boer et al. |
| 7,125,884 B2 | 10/2006 | Reidenberg et al. |
| 7,202,259 B2 | 4/2007 | Chen |
| 7,687,518 B2 | 3/2010 | Chen |
| 8,026,254 B2 | 9/2011 | Chen |
| 8,426,594 B2 | 4/2013 | Kyle |
| 8,481,743 B2 | 7/2013 | Zhou |
| 8,530,494 B2 * | 9/2013 | Kyle et al. .................. 514/279 |
| 8,937,084 B2 | 1/2015 | Park et al. |
| 8,946,255 B2 | 2/2015 | Kassick et al. |
| 8,957,084 B2 | 2/2015 | Kyle |
| 8,969,358 B2 | 3/2015 | Goehring et al. |
| 8,980,906 B2 | 3/2015 | Tafesse |
| 8,987,287 B2 | 3/2015 | Goehring et al. |

(Continued)

FOREIGN PATENT DOCUMENTS

| | | |
|---|---|---|
| WO | 2010014229 A1 | 2/2010 |
| WO | WO-2013/084060 | 6/2013 |
| WO | WO-2013167963 | 11/2013 |
| WO | WO-2015097547 | 7/2015 |
| WO | WO-2015097548 | 7/2015 |
| WO | WO-2015099863 | 7/2015 |
| WO | WO-2015100092 | 7/2015 |
| WO | WO-2015102682 | 7/2015 |

OTHER PUBLICATIONS

Rennison, et al. "Cinnamoyl derivatives of 7-alpha-aminomethyl-6,14-endo-ethanotetrahydrothebaine and 7-alphaaminomethyl-6,14-endo-ethanotetrahydrooripavine and related opioid ligands." Journal of Medicinal Chemistry, vol. 50, no. 21, 2007, pp. 5176-5182.

(Continued)

*Primary Examiner* — Charanjit Aulakh
(74) *Attorney, Agent, or Firm* — Purdue Pharma, L.P.; Alan L. Koller; Weiying Yang

(57) ABSTRACT

The present invention is directed to Buprenorphine Analog compounds of the Formula (I), Formula (IA) or Formula (IB) shown below, wherein $R^1, R^2, R^8, R^{3a}, R^{3b}, G, X, Z$ and $Y$ are as defined herein. Compounds of the Invention are useful for treating pain, constipation, and other conditions modulated by activity of opioid and ORL-1 receptors.

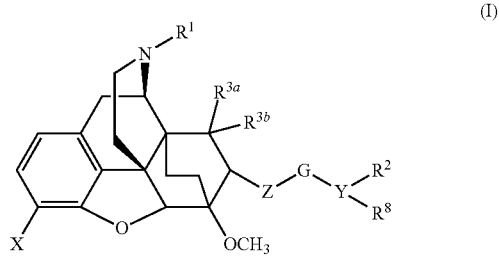

(I)

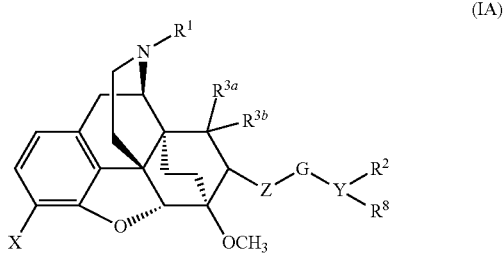

(IA)

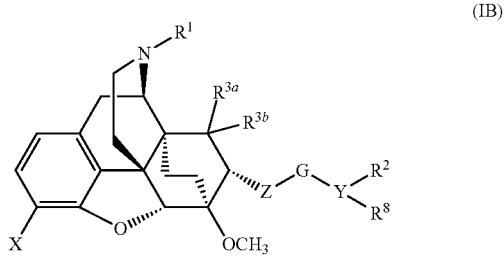

(IB)

47 Claims, 2 Drawing Sheets

(56) References Cited

U.S. PATENT DOCUMENTS

| | | |
|---|---|---|
| 2005/0192308 A1 | 9/2005 | Gale et al. |
| 2014/0057932 A1 | 2/2014 | Reisch |
| 2014/0135351 A1 | 5/2014 | Lockman et al. |
| 2014/0163058 A1 | 6/2014 | Youngman |
| 2014/0221419 A1 | 8/2014 | Lockman et al. |
| 2014/0275117 A1 | 9/2014 | Goehring et al. |
| 2014/0315783 A1 | 10/2014 | Bin Shao |
| 2015/0183787 A1 | 7/2015 | Lockman |

OTHER PUBLICATIONS

Derrick, et al. "Cinnamoyl derivatives of 7-alpha-amino- and 7-alpha-(aminomethyl)-N-(cyclopropylmethyl)-6,14-endoethanotetrahydronororipaavines are high-potency opioid antagonists." Helvetica Chimica Acta, vol. 83, 2000, pp. 3122-3130.

Bentley, et al. "Novel analgesics and molecular rearrangements in the morphine-thebaine group. Part VIII. 7-alkyl-6,14-endoethenotetrahydrothebaine and related compounds." J. Chem. Soc., 1969, pp. 826-830.

C. Altier et al., "ORL-1 receptor-mediated internalization of N-type calcium channelsm." Nature Neuroscience, 2005, 9:31.

D. Barlocco et al., "The opioid-receptor-like 1 (ORL-1) as a potential target for new analgesics." Eur. J. Med. Chem., 2000, 35:275.

Gutstein and Akil, "Opioid Analgesics," Goodman & Gilman's The Pharmacological Basis of Therapeutics, 547-590, Chapter 21, 11th Ed. 2004.

H. Ueda et al., "Enhanced Spinal Nociceptin Receptor Expression Develops Morphine Tolerance and Dependence," J. Neurosci., 2000, 20:7640.

Hawkinson et al., Opioid activity profiles indicate similarities between the nociceptin/orphanin FQ and opioid receptors. Eur. J. Pharmacol, 2000, 389:107-114.

J. Tian et al., "Functional studies using antibodies against orphanin FQ/nociceptin," Peptides, 2000, 21:1047.

J. Tian et al., "Involvement of endogenous Orphanin FQ in electroacupuncture-induced analgesia," NeuroReport, 1997, 8:497.

J.S. Mogil et al., "Orphanin FQ is a functional anti-opioid peptide." Neurosci., 1996, 75:333.

K. Lufty et al., "Buprenorphine-induced antinociception is mediated by μ- opioid receptors and compromised by concomitant activation of opioid receptor-like receptors." J. Neurosci., 2003, 23:10331-10337.

K. Lutfy et al., "Tolerance develops to the inhibitory effect of orphanin FQ on morphine-induced antinociception in the rat." NeuroReport, 1999, 10:103.

K.M. Foley, Pain, in Cecil Textbook of Medicine 100-107, J.C. Bennett and F. Plum eds. 20th ed. 1996.

Pergolizzi et al.,Opioids and the Management of Chronic Severe Pain in the Elderly: Consensus Statement of an International Expert Panel with Focus on the Six Clinically Most Often Used World Health Organization step IB Opioids (buprenorphine, Fentanyl, Hydromorphone, Methadone, Morphine, Oxycodone. Pain Practice, 2008, 8(4): 287-313).

Tzchentike, Behavioral pharmacology of buprenorphine, with a focus on preclinical models of reward and addiction. Psychopharmacology, 2002, 161: 1-16.

Wood & Galligan, "Function of opioids in the enteric nervous system," Neurogastroenterology & Motility 16 (Suppl.2): 17-28, 2004.

\* cited by examiner

BUPRENORPHINE ANALOGS

This is the National Stage of PCT application number PCT/IB2011/002208, filed 20 Sep. 2011, which claims the benefit of U.S. provisional application Ser. No. 61/384,912, filed 21 Sep. 2010, and U.S. provisional application Ser. No. 61/503,674, filed 1 Jul. 2011.

This application claims the benefit of U.S. provisional application Ser. No. 61/384,912, filed 21 Sep. 2010, and U.S. provisional application Ser. No. 61/503,674, filed 1 Jul. 2011, both of which are incorporated herein in their entireties.

The invention is in the field of medicinal chemistry. It relates to novel buprenorphine analogs having activity as opioid receptor agonists and/or antagonists. In certain embodiments compounds of the invention have dual activity as opioid agonists and ORL-1 receptor antagonists.

BACKGROUND OF THE INVENTION

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone or oxymorphone).

Although the term "narcotic" is often used to refer to opioids, the term is not specifically applicable to opioids. The term "narcotic", derived from the Greek word for "stupor", originally referred to any drug that induced sleep, only later being associated with opioids (Gutstein, Howard B., Akil, Huda, "Chapter 21. Opioid Analgesics" (Chapter 21), Brunton, L L, Lazo, J S, Parker, Kl: Goodman & Gilman's The Pharmacological Basis of Therapeutics, 11$^{th}$ Edition: http://www.accessmedicine.com/content.aspx?aID=940653). In the legal context, the term "narcotic" refers to a variety of mechanistically unrelated substances with abuse or addictive potential (Gutstein, Howard B., Akil, Huda, "Chapter 21. Opioid Analgesics" (Chapter 21), Brunton L L, Lazo J S, Parker Kl: Goodman & Gilman's The Pharmacological Basis of Therapeutics, 11$^{th}$ Edition: http://www.accessmedicine.com/content.aspx?aID=940653). Thus, the term "narcotic" not only refers to opioids, but also refers to such drugs as cocaine, methamphetamine, ecstasy, etc., which exert their pharmacological effects via different receptors than opioids. Furthermore, because the term "narcotic" refers to such a wide variety of unrelated drugs, many of which do not possess analgesic properties, it cannot be assumed that a drug that has "narcotic" properties is necessarily analgesic. For example, drugs such as ecstasy and methamphetamine are not analgesic, and are not used to treat pain.

Until recently, there was evidence of three major classes of opioid receptors in the central nervous system (CNS), with each class having subtype receptors. These receptor classes are known as $\mu$, $\delta$ and $\kappa$. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This newly discovered receptor was classified as an opioid receptor based only on structural grounds, as the receptor did not exhibit pharmacological homology. It was initially demonstrated that non-selective ligands having a high affinity for $\mu$, $\delta$ and $\kappa$ receptors had low affinity for the ORL-1 receptor. This characteristic, along with the fact that an endogenous ligand had not yet been discovered, led to the ORL-1 receptor being designated as an "orphan receptor".

Subsequent research led to the isolation and structure of the endogenous ligand of the ORL-1 receptor. This ligand, nociceptin (also known as orphanin FQ (OFQ)), is a seventeen amino acid peptide structurally similar to members of the opioid peptide family. (C. Altier et al., "ORL-1 receptor-mediated internalization of N-type calcium channels." *Nature Neuroscience*, 2005, 9:31).

The discovery of the ORL-1 receptor and its endogenous ligand, presents an opportunity for the discovery of novel compounds that can be administered for pain management or other syndromes influenced by this receptor.

Many publications in the ORL-1/nociceptin field provide evidence that activation of ORL-1 receptors in the brain can inhibit opioid-mediated analgesia (e.g., D. Barlocco et al., "The opioid-receptor-like 1 (ORL-1) as a potential target for new analgesics." *Eur. J. Med. Chem.*, 2000, 35:275; J. S. Mogil et al., "Orphanin FQ is a functional anti-opioid peptide." *Neurosci.*, 1996, 75:333; K. Lutfy et al., "Tolerance develops to the inhibitory effect of orphanin FQ on morphine-induced antinociception in the rat." *NeuroReport*, 1999, 10:103; M. M. Morgan et al., "Antinociception mediated by the periaqueductal gray is attenuated by orphanin FQ." *NeuroReport*, 1997, 8:3431; and J. Tian et al., "Involvement of endogenous Orphanin FQ in electroacupuncture-induced analgesia." *NeuroReport*, 1997, 8:497).

A growing body of evidence supports a more generalized regulatory role for ORL-1 against the actions of the $\mu$ receptor, possibly contributing to the development of $\mu$-agonist tolerance in patients being treated with classical opiates (e.g., J. Tian et al., "Functional studies using antibodies against orphanin FQ/nociceptin." *Peptides*, 2000, 21:1047; and H. Ueda et al., "Enhanced Spinal Nociceptin Receptor Expression Develops Morphine Tolerance and Dependence." *J. Neurosci.*, 2000, 20:7640). Moreover, ORL-1 activation appears to have an inhibitory effect on the rewarding properties of several drugs of abuse, including $\mu$ agonists.

Certain compounds have been described as at least partial agonists for ORL-1 (e.g., buprenorphine ($IC_{50}$ of 8.4 nM), fentanyl ($IC_{50}$ of about 10,000 nM), 7-benzylidenenaltrexone ($IC_{50}$ about 10,000 nM) (S. Wnendt et al., "Agonistic effect of buprenorphine in a nociceptin/OFQ receptor-triggered reporter gene assay." *Molec. Pharmacol.*, 1999, 56:334-338), and etorphine ($IC_{50}$ of about 2000 nM) (Hawkinson et al., "Opioid activity profiles indicate similarities between the nociceptin/orphanin FQ and opioid receptors." *Eur. J. Pharmacol*, 2000, 389:107-114)). However, buprenorphine's $\mu$ potency is disclosed to be much greater than its ORL-1 potency.

Recent data have shown that the analgesic efficacy of buprenorphine is enhanced by pre-treatment with an ORL-1 receptor antagonist. Using the tail-flick test in mice, Lutfy et al. demonstrated that buprenorphine's typical bell-shaped dose-response curve (wherein low and high doses induce little analgesia, and mid-range doses produce maximal analgesia) is eliminated by pre-treatment with the ORL-1 antagonist J-113397, and analgesic efficacy is improved at the higher range of doses (K. Lutfy et al., "Buprenorphine-induced antinociception is mediated by $\mu$-opioid receptors and compromised by concomitant activation of opioid receptor-like receptors." *J. Neurosci.*, 2003, 23:10331-10337).

Recently, a multidisciplinary group of experts in the fields of pharmacology, toxicology, pain management, and anesthesia have recommended buprenorphine as the best opioid for treating chronic severe pain in elderly patients (Pergolizzi, et al. (2008). Opioids and the Management of Chronic Severe Pain in the Elderly: Consensus Statement of an International Expert Panel with Focus on the Six Clinically Most Often Used World Health Organization step IB Opioids (buprenorphine, Fentanyl, Hydromorphone, Methadone, Morphine, Oxycodone. *Pain Practice* 8(4): 287-313). It was found that of the opioids studied, buprenorphine provided the best analgesic-to-side effect profile. Buprenorphine was the most effective opioid for treating neuropathic pain. Buprenorphine was the only opioid for which metabolism was not affected by impaired renal function. Buprenorphine was the only opioid demonstrating a ceiling effect for respiratory depression, indicating that higher doses may be used. Also, buprenorphine was the least likely to induce immunosuppression. The panel of experts attributed the improved therapeutic efficacy of buprenorphine to its unique pharmacological profile.

Buprenorphine has also been shown to have an improved side effect profile in animal models. A review of recent data in animal models of reward and addiction has shown that buprenorphine has a low addictive and dependence-inducing profile compared to other opioids (Tzschentike (2002). Behavioral pharmacology of buprenorphine, with a focus on preclinical models of reward and addiction. *Psychopharmacology* 161: 1-16).

Use of opioid analgesics often leads to constipation as a side effect. Constipation associated with the use of opioid analgesics is presumed to occur primarily and mechanistically as a result of the action of μ opioid agonists directly upon μ opioid receptors located in the bowel (Wood & Galligan (2004), Function of opioids in the enteric nervous system. *Neurogastroenterology & Motility* 16(Suppl. 2): 17-28.). Stimulation of the μ opioid receptors in the bowel causes inhibition of normal gastrointestinal (GI) motility, leading to constipation. The effect of μ opioid agonism on μ opioid receptors in the bowel can be observed via the action of loperamide (Imodium™) in treating diarrhea. Loperamide is a potent μ opioid agonist that is administered orally, but which has little to no absorption into the blood stream. As a result, loperamide exerts its action locally upon the μ opioid receptors in the bowel, and this results in inhibition of GI motility, which treats diarrhea.

There has been recent interest in developing combinations of μ receptor agonists and antagonists having defined biodistribution properties that might serve to limit opioid-induced constipation. For example, the co-administration of an orally bio-available μ opioid receptor agonist (such as morphine, codeine, oxycodone or hydrormorphone) together with a potent μ opioid receptor antagonist (such as N-methylnaloxone or N-methylnaltrexone) that is not orally bio-available may serve to prevent or reduce the constipation otherwise associated with μ opioid receptor agonist therapy. The rationale is that the agonist component will be absorbed and distributed throughout the periphery and the central nervous system (CNS), resulting in the desired analgesia, while the antagonist component will remain in the bowel where it will prevent or reduce any agonist-induced constipation that might otherwise occur.

BRIEF SUMMARY OF THE INVENTION

The present invention provides novel buprenorphine analog compounds useful for treating a variety of conditions, including pain, in particular chronic pain, and constipation. More specifically, the present invention provides compounds of Formula I, Formula IA, Formula IB, Formula II, or Formula III, below, and the pharmaceutically acceptable salts, prodrugs and solvates thereof, that exhibit affinity for one or more of the ORL-1, μ, δ, and/or κ opioid receptors. Such compounds, salts, prodrugs and solvates are collectively referred to hereinafter as "Compounds of the Invention" (each is individually referred to hereinafter as a "Compound of the Invention").

The present invention provides compounds of Formula I:

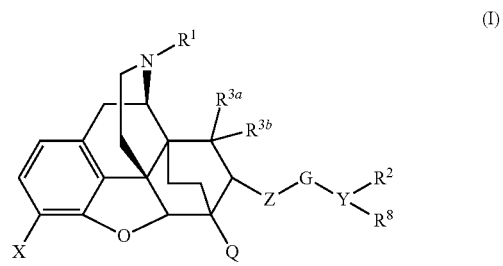

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —CONR$^9$R$^{10}$, —NR$^9$COR$^{10}$, —SR$^{11}$, -(5- to 12-membered)carbocyclic ring, -(5- to 12-membered)heterocycle, phenyl, and benzyl;

$R^2$ and $R^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of —OH, (═O), halo, —C(halo)$_3$, —CH(halo)$_2$, —CH$_2$(halo), —($C_1$-

$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —$NH_2$, —NH($C_1$-$C_6$)alkyl, —($C_1$-$C_6$)alkyl-NH ($C_1$-$C_6$)alkyl-$R^{14}$, —CN, —SH, —$OR^4$, —$CONR^5R^6$, —($C_1$-$C_6$alkyl)-CO—$NR^5R^6$, —$COOR^7$, —($C_1$-$C_6$)alkyl-CO—$OR^7$, —($C_1$-$C_6$)alkoxy-$COOR^7$, —($OCH_2CH_2$)$_s$—O($C_1$-$C_6$)alkyl, —($CH_2CH_2O$)$_s$—($C_1$-$C_6$)alkyl, (($C_1$-$C_6$)alkyl)sulfonyl($C_1$-$C_6$)alkyl-, —NH—$SO_2$($C_1$-$C_6$)alkyl, —N($SO_2$($C_1$-$C_6$)alkyl)$_2$, —C(=NH)$NH_2$, —NH—CO—($C_1$-$C_6$)alkyl, —NH—CO—$NH_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$—$C_6$)alkyl-CO—$OR^7$, —NH—C(=O)—($C_1$-$C_6$)alkyl-CO—$OR^7$, —NH—C(=O)—CH($NH_2$)—($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)$NR^5R^6$, —NH—($C_1$-$C_6$)alkylC(O)—$NR^5R^6$, —C(O)NH—($C_1$-$C_6$)alkyl-$COOR^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —$CH_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-$COOR^7$, —($C_1$-$C_6$)alkoxy-$COOR^7$, —($C_3$-$C_{12}$)cycloalkyl, (($C_3$-$C_2$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, (5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$)alkoxy-($C_1$-$C_6$)alkyl-, or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —$CH_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —$COOR^7$, —($C_1$-$C_6$)alkyl-CO—$OR^7$, —$CONH_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($OCH_2CH_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —$CH_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, $NH_2$, —NH($C_1$-$C_6$)alkyl, CN, SH, $OR^4$, —$CONR^5R^6$, —$COOR^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —$COOR^7$, —($C_1$-$C_6$)alkyl-CO—$OR^7$, —C(=O)—($C_1$-$C_6$)alkyl-$COOR^7$, —($C_1$-$C_6$)alkyl-C(=O)—($C_1$-$C_6$)alkyl-$COOR^7$, —$CONH_2$, ($C_1$-$C_6$)alkyl-CONH—;

G is selected from O, —OCO—, —C(=O), $NR^9$, NR', S, SO, and $SO_2$;

R' is —C(=O)($C_1$-$C_6$)alkyl or —$SO_2$($C_1$-$C_6$)alkyl;

X is selected from OH, hydroxy($C_1$-$C_6$)alkyl-, dihydroxy($C_1$-$C_6$)alkyl-, halogen, —$NH_2$, —$NR^2$(C=O)$R^{12}$, —$CONR^{12}R^{13}$, —($C_1$-$C_6$)alkyl-$CONH_2$, —($C_1$-$C_6$)alkyl-COOH, —COOH, —O—($C_1$-$C_6$)alkyl-COOH, —O—($C_1$-$C_6$)alkyl-$CONH_2$, —($C_1$-$C_{10}$)alkyl, —($C_2$-$C_{10}$)alkenyl, —($C_2$-$C_{10}$)alkynyl, —($C_1$-$C_{10}$)alkoxy, —($OCH_2CH_2$)$_s$—O($C_1$-$C_6$)alkyl, —($OCH_2CH_2$)$_s$—OH, —($CH_2$)$_p$CHOH$CH_2$OH, CN, —NH—$SO_2R^9$, —($C_3$-$C_{12}$)cycloalkyl, (($C_3$-$C_{12}$)cycloalkyl)-($C_1$-$C_6$)alkyl-, (($C_3$-$C_2$)cycloalkyl)-($C_1$-$C_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-;

Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$)$_s$—OH, —O(C=O)R$^9$, —O—(C$_1$-C$_6$)alkyl-COOR$^7$, —NH—(C$_1$-C$_6$)alkyl-COOR$^7$, —O—C(O)—(C$_1$-C$_6$)alkyl-C(O)OR$^7$, —NH—C(O)—(C$_1$-C$_6$)alkyl-C(O)OR$^7$, —O—(C$_1$-C$_6$)alkyl-C(O)NR$^9$R$^{10}$, —NH—(C$_1$-C$_6$)alkyl-C(O)NR$^9$R$^{10}$, —O—C(O)—(C$_1$-C$_6$)alkyl-C(O)NR$^9$R$^{10}$, —NH—C(O)—(C$_1$-C$_6$)alkyl-C(O)NR$^9$R$^{10}$ and R$^{14}$;

Z is —(CH$_2$)$_m$—, optionally substituted with 1 or 2 —(C$_1$-C$_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

In one embodiment, the present invention provides novel compounds of Formula I:

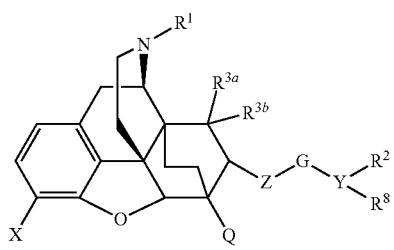

(I)

wherein

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —CONR$^9$R$^{10}$, —NR$^9$COR$^{10}$, —SR$^{11}$, -(5- to 12-membered)carbocyclic ring, -(5- to 12-membered)heterocycle, phenyl, and benzyl;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, —NH$_2$, —NH(C$_1$-C$_6$)alkyl, CN, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_4$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, —NH$_2$, —NH(C$_1$-C$_6$)alkyl, —(C$_1$-C$_6$)alkyl-NH (C$_1$-C$_6$)alkyl-R$^{14}$, —CN, —SH, —OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O (C$_1$-C$_6$)alkyl, —(CH$_2$CH$_2$O)$_s$—(C$_1$-C$_6$)alkyl, ((C$_1$-C$_6$)alkyl) sulfonyl(C$_1$-C$_6$)alkyl-, —NH—SO$_2$(C$_1$-C$_6$)alkyl, —N(SO$_2$ (C$_1$-C$_6$)alkyl)$_2$, —C(=NH)NH$_2$, —NH—CO—(C$_1$-C$_6$) alkyl, —NH—CO—NH$_2$, —NH—C(=O)—NH—(C$_1$-C$_6$) alkyl, —NH—C(=O)-(5- to 12-membered)aryl, —NH—C (=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered) aryloxy, —(C$_1$-C$_6$)alkoxyC(O)NR$^5$R$^6$, —NH—(C$_1$-C$_6$) alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$) alkyl-, -(3- to 12-membered)heterocycle, ((3- to 12-membered)heterocycle)-(C$_1$-C$_6$)alkyl-, -(7- to 12-membered) bicycloheterocycle, and ((7- to 12-membered) bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C (=O)—(C$_1$-C$_6$)alkoxy, —(C$_1$-C$_6$)alkoxy-C(=O)—(C$_1$-C$_6$) alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$) alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$) alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered) aryl)-(C$_1$-C$_6$)alkoxy-(C$_1$-C$_6$)alkyl-, -(5- to 12-membered) heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-

($C_1$-$C_6$)alkoxy-, ((3- to 12 membered)heterocycle)-($C_1$-$C_6$)alkoxy-($C_1$-$C_6$)alkyl-, or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_9$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_2$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_7$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12 membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy($C_1$-$C_6$)alkyl-, halogen, —NH$_2$, —NR$^2$(C=O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN, —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$;

Z is —(CH$_2$)$_m$—, optionally substituted with 1 or 2 —($C_1$-$C_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

provided that when X is OH or —($C_1$-$C_6$)alkoxy, Q is OMe, Z is unsubstituted, and G is O, then either:

a) $R^1$ is selected from;
  i. hydrogen, or ($C_1$-$C_{10}$)alkoxy or tetrazolyl-($C_1$-$C_6$)alkyl any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or
  ii. —($C_1$-$C_{10}$)alkyl, —($C_2$-$C_{12}$)alkenyl, —($C_2$-$C_{12}$)alkynyl, —($C_3$-$C_{12}$)cycloalkyl, —($C_4$-$C_{12}$)cycloalkenyl, (($C_3$-$C_{12}$)cycloalkyl)-($C_3$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((3- to 12 membered)heterocycle)-, (5- to 12-membered)heteroaryl-($C_1$-$C_6$)alkyl-, (3- to 12-membered)heterocycle —(C$_1$-C$_6$)alkyl-, phenyl, or benzyl; each of which is substituted with 1, 2, or 3 substituents independently selected from the group consisting of —(C$_1$-C$_6$)alkyl-COOR$^7$, —COOR$^7$, NR$^9$R$^{10}$, —CONR$^9$R$^{10}$, —NR$^9$COR$^{10}$, and SR$^{11}$, provided that NR$^9$R$^{10}$ is other than NH$_2$ or —NH(C$_1$-C$_6$)alkyl, and SR$^{11}$ is other than SH;

or b) at least one of R$^2$ and R$^8$ is selected from:

i. —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, and —(C$_1$-C$_6$)alkoxy-COOR$^7$; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, NH$_2$, —NH(C$_1$-C$_6$)alkyl, —(C$_1$-C$_6$)alkyl-NH(C$_1$-C$_6$)alkyl-R$^{14}$, CN, SH, OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)—(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; or ii. —(C$_1$-C$_6$)alkyl-COOR$^7$, —(C$_3$-C$_{12}$)cycloalkyl, —((C$_3$-C$_{12}$)cycloalkyl)-(C$_1$-C$_6$)alkyl, —(C$_4$-C$_{12}$)cycloalkenyl, —(C$_6$-C$_{14}$)bicycloalkyl, —(C$_8$-C$_{20}$)tricycloalkyl, —(C$_7$-C$_{14}$)bicycloalkenyl, —(C$_8$-C$_{20}$)tricycloalkenyl, -(5- to 12-membered)aryl, ((5- to 12-membered)aryl)-(C$_1$-C$_6$)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl, benzyl, ((C$_4$-C$_{12}$)cycloalkenyl)-(C$_1$-C$_6$)alkyl-, ((C$_6$-C$_{14}$)bicycloalkyl)-(C$_1$-C$_6$)alkyl-, ((C$_8$-C$_{20}$)tricycloalkyl)-(C$_1$-C$_6$)alkyl-, ((C$_7$-C$_{14}$)bicycloalkenyl)-(C$_1$-C$_6$)alkyl-, ((C$_8$-C$_{20}$)tricycloalkenyl)-(C$_1$-C$_6$)alkyl-, ((7- to 12-membered)bicyclic ring system)-(C$_1$-C$_6$)alkyl-, ((7- to 12-membered)bicyclic aryl)-(C$_1$-C$_6$)alkyl-, ((5- to 12-membered)heteroaryl)-(C$_1$-C$_6$)alkyl-, ((3- to 12 membered)heterocycle)-(C$_1$-C$_6$)alkyl-, ((7- to 12-membered)bicycloheterocycle)-(C$_1$-C$_6$)alkyl-, and naphthyl; each of which is substituted with one or two substituents independently selected from the group consisting of —CONHR$^6$, dihydroxy(C$_1$-C$_6$)alkyl-, —(C$_1$-C$_6$)alkyl-NH(C$_1$-C$_6$)alkyl-R$^{14}$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$—(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; or iii. —(C$_1$-C$_{10}$)alkyl, —(C$_2$-C$_{12}$)alkenyl, and —(C$_2$-C$_{12}$)alkynyl, each of which is substituted with one or two substituents independently selected from the group consisting of —CONHR$^6$, —(C$_1$-C$_6$)alkyl-NH(C$_1$-C$_6$)alkyl-R$^{14}$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_1$-C$_6$)alkoxyC(O)NR$^5$R$^6$, —NH—(C$_1$-C$_6$)alkylC(O)—NR$^5$R$^6$, or —C(O)NH—(C$_1$-C$_6$)alkyl-COOR$^7$; or iv. 2,3-dihydroxypropyl; or v. 4-isoxazolyl, 4-isoxazolyl(C$_1$-C$_6$)alkyl, 5-isoxazolyl, or 5-isoxazolyl(C$_1$-C$_6$)alkyl substituted with one or two alkyl groups, or vi. —C(=O)NH$_2$ or —(C$_1$-C$_6$)alkyl-C(=O)NH$_2$;

or c) at least one of R$^{3a}$ or R$^{3b}$ is independently selected from —(C$_7$-C$_{10}$)alkyl, —(C$_7$-C$_{10}$)alkenyl, —(C$_7$-C$_{10}$)alkynyl, —(C$_1$-C$_{10}$)alkoxy, —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, and ((3- to 12 membered)heterocycle)-(C$_1$-C$_6$)alkoxy-(C$_1$-C$_6$)alkyl-; or provided that when X is OH or —(C$_1$-C$_6$)alkoxy, Q is OMe, R$^{3a}$ and R$^{3b}$ are both hydrogen, Z is substituted, G is O, and Y is a bond, then R$^2$ is other than hydrogen.

or a pharmaceutically acceptable salt, prodrug or solvate thereof.

In another embodiment, the present invention provides novel compounds of Formula I:

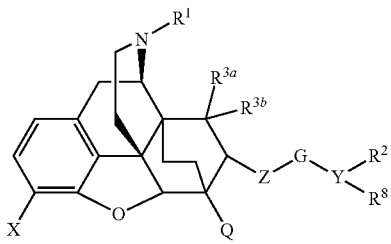

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

$R^2$ and $R^8$ are each independently hydrogen, —($C_1$-$C_{10}$)alkyl, —($C_2$-$C_{12}$)alkenyl, —($C_2$-$C_{12}$)alkynyl, —($C_7$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$alkyl)-CO—NR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; any of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$—$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$)alkoxy-($C_1$-$C_6$)alkyl-, or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or R$^5$ and R$^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-

$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-CO—OR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from hydroxy($C_1$-$C_6$)alkyl-, dihydroxy($C_1$-$C_6$)alkyl-, halogen, —NH$_2$, —NR$^2$(C=O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_7$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN, —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$;

Z is —(CH$_2$)$_m$—, optionally substituted with 1 or 2-($C_1$-$C_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

In another embodiment, the present invention provides novel compounds of Formula I:

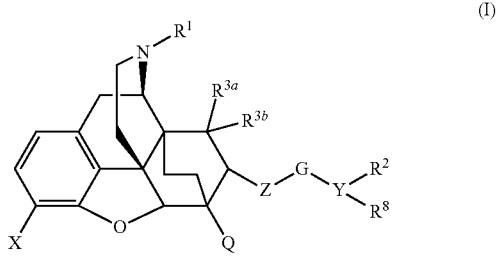

(I)

wherein

R$^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

R$^2$ and R$^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$—$C_6$)alkyl, —($C_1$-$C_6$)alkyl-NH ($C_1$-$C_6$)alkyl-$R^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl) sulfonyl($C_1$-$C_6$)alkyl-, —N(SO$_2$($C_1$-$C_6$)alkyl)$_2$, —C(=NH) NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C (=O)—CH(NH$_2$)—($C_1$-$C_6$)alkyl-CO—OR$^7$, —($C_3$-$C_{12}$) cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$) alkyl-, -(5- to 12-membered)heteroaryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C (=O)—($C_1$-$C_6$)alkoxy, —($C_1$-$C_6$)alkoxy-C(=O)—($C_1$-$C_6$) alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$) cycloalkyl)-($C_1$-$C_6$)alkyl-, (($C_3$-$C_{12}$)cycloalkyl)-($C_1$-$C_6$) alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$) alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered) aryl)-($C_1$-$C_6$)alkoxy-($C_1$-$C_6$)alkyl-, -(5- to 12-membered) heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$) alkoxy-($C_1$-$C_6$)alkyl-, or together form (=O);

$R^4$ is selected from —($C_1$-$C_6$)alkyl, —($C_2$-$C_6$)alkenyl, —($C_2$-$C_6$)alkynyl, —C(halo)$_3$, hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$) alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$) bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-;

$R^5$ and $R^6$ are each independently hydrogen, —($C_1$-$C_6$) alkyl, —($C_3$-$C_8$)cycloalkyl, (($C_3$-$C_8$)cycloalkyl)-($C_1$-$C_6$) alkyl-, —COOR$^7$, —($C_1$-$C_6$)alkyl-CO—OR$^7$, —CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$) alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$) cycloalkenyl)-($C_1$-$C_6$)alkyl-;

each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$) alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$) bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered) bicyclic ring system)-($C_1$-$C_6$)alkyl-, -(7- to 12-membered) bicyclic aryl, ((7- to 12-membered)bicyclic aryl)-($C_1$-$C_6$) alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH (halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$) cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$) alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C (=O)—($C_1$-$C_6$)alkyl-COOR$^7$, CONH$_2$, ($C_1$-$C_6$)alkyl-CONH—;

G is selected from —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy ($C_1$-$C_6$)alkyl-, halogen, —NH$_2$, —NR$^2$(C=O)R$^{12}$, CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-

$C_6$)alkyl-$CONH_2$, —($C_1$-$C_{10}$)alkyl, —($C_2$-$C_{10}$)alkenyl, —($C_2$-$C_{10}$)alkynyl, —($C_1$-$C_{10}$)alkoxy, —($OCH_2CH_2$)$_s$—O($C_1$-$C_6$)alkyl, —($OCH_2CH_2$)$_s$—OH, —($CH_2$)$_p$CHOHCH$_2$OH, CN and —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —($OCH_2CH_2$)$_s$—O($C_1$-$C_6$)alkyl, —($CH_2CH_2O$)$_s$—($C_1$-$C_6$)alkyl, —($OCH_2CH_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$;

Z is —($CH_2$)$_m$—, optionally substituted with 1 or 2-($C_1$-$C_6$)alkyl;

Y is —($CH_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

provided that when X is OH or —($C_1$-$C_6$)alkoxy, Q is OMe, Z is unsubstituted, G is OCO, and Y is a direct bond, then either:

a) R$^1$ is selected from;
  i. hydrogen, or ($C_1$-$C_{10}$)alkoxy or tetrazolyl-($C_1$-$C_6$)alkyl, any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or
  ii. —($C_1$-$C_{10}$)alkyl, —($C_2$-$C_{12}$)alkenyl, —($C_2$-$C_{12}$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((3- to 12 membered)heterocycle)-, (5- to 12-membered)heteroaryl-($C_1$-$C_6$)alkyl-, (3- to 12-membered)heterocycle —($C_1$-$C_6$)alkyl-, phenyl, or benzyl; each of which is substituted with 1, 2, or 3 substituents independently selected from the group consisting of —($C_1$-$C_6$)alkyl-COOR$^7$, —COOR$^7$, NR$^9$R$^{10}$, —CONR$^9$R$^{10}$, —NR$^9$COR$^{10}$, and SR$^{11}$, provided that NR$^9$R$^{10}$ is other than NH$_2$ or —NH($C_1$-$C_6$)alkyl, and SR$^{11}$ is other than SH;

or b) R$^2$ is selected from:
  i. —($C_1$-$C_{10}$)alkoxy, —($OCH_2CH_2$)$_s$—O($C_1$-$C_6$)alkyl, —($CH_2CH_2O$)$_s$—($C_1$-$C_6$)alkyl, CONHR$^6$, —($C_1$-$C_6$)alkyl-CO—NHR$^6$, —($C_1$-$C_6$)alkoxy-COOR$^7$, —($C_3$-$C_{12}$)cycloalkyl, —($C_4$-$C_{12}$)cycloalkenyl, —($C_6$-$C_{14}$)bicycloalkyl, —($C_8$-$C_{20}$)tricycloalkyl, —($C_7$-$C_{14}$)bicycloalkenyl, —($C_8$-$C_{20}$)tricycloalkenyl, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, (($C_4$-$C_{12}$)cycloalkenyl)-($C_1$-$C_6$)alkyl-, (($C_6$-$C_{14}$)bicycloalkyl)-($C_1$-$C_6$)alkyl-, (($C_8$-$C_{20}$)tricycloalkyl)-($C_1$-$C_6$)alkyl-, (($C_7$-$C_{14}$)bicycloalkenyl)-($C_1$-$C_6$)alkyl-, (($C_8$-$C_{20}$)tricycloalkenyl)-($C_1$-$C_6$)alkyl-, ((7- to 12-membered)bicyclic ring system)-($C_1$-$C_6$)alkyl-, ((7- to 12-membered)bicyclic aryl)-($C_1$-$C_6$)alkyl-, ((5- to 12-membered)heteroaryl)-($C_1$-$C_6$)alkyl-, ((3- to 12 membered)heterocycle)-($C_1$-$C_6$)alkyl-, ((7- to 12-membered)bicycloheterocycle)-($C_1$-$C_6$)alkyl-, and naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —($OCH_2CH_2$)$_s$—O($C_1$-$C_6$)alkyl, —($CH_2CH_2O$)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; or
  ii. —($C_1$-$C_{10}$)alkyl, —($C_2$-$C_{12}$)alkenyl, —($C_2$-$C_{12}$)alkenyl, —($C_1$-$C_6$)alkyl-CO—OR$^7$, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, phenyl, and benzyl; each of which is substituted with one or two substituents independently selected from the group consisting of —CONHR$^6$, dihydroxy($C_1$-$C_6$)alkyl-, —($C_1$-$C_6$)alkyl-NH($C_1$-$C_6$)alkyl-R$^{14}$, —($C_1$-$C_6$)alkyl-CO—OR$^7$, —($C_1$-$C_6$)alkoxy-COOR$^7$, —($OCH_2CH_2$)$_s$—O($C_1$-$C_6$)alkyl, —($CH_2CH_2O$)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_2$)cycloalkyl, (($C_3$-$C_{12}$)cycloalkyl)-($C_1$-$C_6$)alkyl-, —($C_1$-$C_6$)alkoxyC(O)NR$^5$R$^6$, —NH—($C_1$-

$C_6$)alkylC(O)—$NR^5R^6$, —C(O)NH—($C_1$-$C_6$)alkyl-$COOR^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; or c) at least one of $R^{3a}$ or $R^{3b}$ is independently selected from —($C_7$-$C_{10}$)alkyl, —($C_7$-$C_{10}$)alkenyl, —($C_7$-$C_{10}$)alkynyl, —($C_1$-$C_{10}$)alkoxy, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-$COOR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-;

provided that when X is OH or —($C_1$-$C_6$)alkoxy, Q is OMe, $R^{3a}$ and $R^{3b}$ are both hydrogen, Z is substituted, G is O, and Y is a bond, then $R^2$ is other than hydrogen.

or a pharmaceutically acceptable salt, prodrug or solvate thereof.

In another embodiment, the present invention provides novel compounds of Formula I:

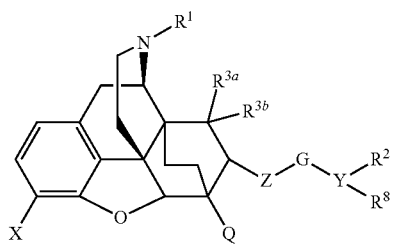

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-$COOR^7$, —$COOR^7$, $NH_2$, —NH($C_1$-$C_6$)alkyl, —$NR^9R^{10}$, CN, —$CONR^9R^{10}$, —$NR^9COR^{10}$, $SR^{11}$, -(5- to 12-membered)carbocyclic ring, -(5- to 12-membered)heterocycle, phenyl, and benzyl;

$R^2$ and $R^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, $NH_2$, —NH($C_1$-$C_6$)alkyl, CN, —$CONR^5R^6$, —($C_1$-$C_6$alkyl)-CO—$NR^5R^6$, —$COOR^7$, —($C_1$-$C_6$)alkyl-CO—$OR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_8$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, $NH_2$, —NH($C_1$—$C_6$)alkyl, —($C_1$-$C_6$)alkyl-NH ($C_1$-$C_6$)alkyl-$R^{14}$, CN, SH, $OR^4$, —$CONR^5R^6$, —($C_1$-$C_6$alkyl)-CO—$NR^5R^6$, —$COOR^7$, —($C_1$-$C_6$)alkyl-CO—$OR^7$, —($C_1$-$C_6$)alkoxy-$COOR^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH) $NH_2$, —NH—CO—($C_1$-$C_6$)alkyl, —NH—CO—$NH_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—$OR^7$, —NH—C(=O)—($C_1$-$C_6$)alkyl-CO—$OR^7$, —NH—C(=O)—CH(NH$_2$)—($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)$NR^5R^6$, —NH—($C_1$-$C_6$)alkylC(O)—$NR^5R^6$, —C(O)NH—($C_1$-$C_6$)alkyl-$COOR^7$, ((5- to 12-membered) aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-$COOR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_2$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$)alkoxy-($C_1$-$C_6$)alkyl-, or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_4$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy($C_1$-$C_6$)alkyl-, halogen, —NH$_2$, —NR$^2$(C=O)R$^{12}$, CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN and —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_2$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$;

Z is —(CH$_2$)$_m$—, optionally substituted with 1 or 2-($C_1$-$C_6$)alkyl;

Y is —(CH$_2$)$_n$—CH or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

In another embodiment, the present invention provides novel compounds of Formula I:

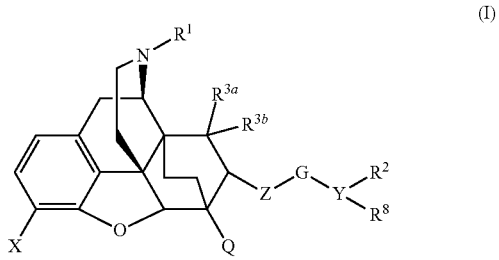

(I)

wherein $R^1$ is selected from a) hydrogen, or ($C_1$-$C_{10}$)alkoxy or tetrazolyl-($C_1$-$C_6$)alkyl-; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or b) —($C_1$-$C_{10}$)alkyl, —($C_2$-$C_{12}$)alkenyl, —($C_2$-$C_{12}$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((3- to 12 membered)heterocycle)-, (5- to 12-membered)heteroaryl-($C_1$-$C_6$)alkyl-, (3- to 12-membered)heterocycle-($C_1$-$C_6$)alkyl, phenyl, or benzyl; each of which is substituted with 1, 2, or 3 substituents independently selected from the group consisting of —($C_1$-$C_6$)alkyl-COOR$^7$, —COOR$^7$, NR$^9$R$^{10}$, —CONR$^9$R$^{10}$, —NR$^9$COR$^{10}$, and SR$^{11}$, provided that NR$^9$R$^{10}$ is other than NH$_2$ or —NH($C_1$-$C_6$)alkyl, and SR$^{11}$ is other than SH;

R$^2$ and R$^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$—$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{3a}$ and R$^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$)alkoxy-($C_1$-$C_6$)alkyl-, or together form (=O);

R$^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_2$)cycloalkyl)-($C_1$-$C_6$)alkyl-, —($C_6$-$C_{14}$)bicycloalkyl, (($C_6$-$C_4$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^5$ and R$^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, or ($C_1$-$C_6$)alkyl-CONH—, or R$^5$ and R$^6$ together with the nitrogen atom to which they are attached form a (4- to 8-membered)heterocycle;

R$^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

R$^9$ and R$^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

each R$^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

R$^{12}$ and R$^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-

($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((5- to 12-membered) bicyclic ring system)-($C_1$-$C_6$)alkyl-, -(7- to 12-membered) bicyclic aryl, ((7- to 12-membered)bicyclic aryl)-($C_1$-$C_6$) alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

—R$^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, —CONH($C_1$-$C_6$)alkyl;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy($C_1$-$C_6$)alkyl-, halogen, —NH$_2$, —NR$^2$(C=O)R$^8$, CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN, NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$;

Z is —(CH$_2$)$_m$—, optionally substituted with 1 or 2-($C_1$-$C_6$)alkyl;

Y is —(CH$_2$)$_n$—CH or a direct bond, provided that when Y is a direct bond then R$^8$ is absent;

m is an integer 1, 2, 3, 4, 5, or 6;
n is an integer 0, 1, 2, 3, 4, 5 or 6;
p is an integer 0, 1 or 2;
s is an integer 1, 2, 3, 4, 5, 6, 7, 8, 9, 10, 11, 12, or 13;

or a pharmaceutically acceptable salt, prodrug or solvate thereof.

In another embodiment, the present invention provides novel compounds of Formula I:

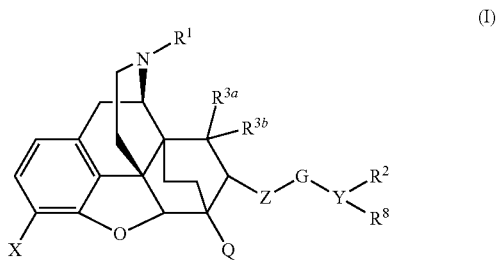

(I)

wherein

R$^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; each of which is optionally substituted with 1, 2, or 3 substituents independently selected from the group consisting of —($C_1$-$C_6$)alkyl, —OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, NR$^9$R$^{10}$, —CN, —CONR$^9$R$^{10}$, —NR$^9$COR$^{10}$, —SR$^{11}$, -(5- to 12-membered)carbocyclic ring, -(5- to 12-membered)heterocycle, phenyl, and benzyl;

R$^2$ is:
a) —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, and —($C_1$-$C_6$)alkoxy-COOR$^7$; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)

aryl)-($C_1$-$C_6$)alkyl-, -(5- to 12-membered)heteroaryl, -(5- to 12-membered)aryloxy, —($C_1$-$C_6$)alkoxyC(O) $NR^5R^6$, —NH—($C_1$-$C_6$)alkylC(O), $NR^5R^6$, —C(O) NH—($C_1$-$C_6$)alkyl-$COOR^7$, ((5- to 12-membered)heteroaryl)-($C_1$-$C_6$)alkyl-, -(3- to 12-membered) heterocycle, ((3- to 12-membered)heterocycle)-($C_1$-$C_6$) alkyl-, -(7- to 12-membered)bicycloheterocycle, and ((7- to 12-membered)bicycloheterocycle)-($C_1$-$C_6$) alkyl-; or b) —($C_1$-$C_6$)alkyl-CO—$OR^7$, —($C_3$-$C_{12}$)cycloalkyl, —(($C_3$-$C_{12}$)cycloalkyl)-($C_1$-$C_6$)alkyl-, —($C_4$-$C_{12}$)cycloalkenyl, —($C_6$-$C_{14}$)bicycloalkyl, —($C_8$-$C_{20}$)tricycloalkyl, —($C_7$-$C_{14}$)bicycloalkenyl, —($C_8$-$C_{20}$)tricycloalkenyl, -(5- to 12-membered)aryl, ((5- to 12-membered)aryl)-($C_1$-$C_6$)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl, benzyl, (($C_4$-$C_{12}$)cycloalkenyl)-($C_1$-$C_6$)alkyl-, (($C_6$-$C_4$)bicycloalkyl)-($C_1$-$C_6$)alkyl-, (($C_8$-$C_{20}$)tricycloalkyl)-($C_1$-$C_6$)alkyl-, (($C_7$-$C_{14}$)bicycloalkenyl)-($C_1$-$C_6$)alkyl-, (($C_8$-$C_{20}$)tricycloalkenyl)-($C_1$-$C_6$)alkyl, ((7- to 12-membered)bicyclic ring system)-($C_1$-$C_6$)alkyl-, ((7- to 12-membered)bicyclic aryl)-($C_1$-$C_6$)alkyl-, ((5- to 12-membered)heteroaryl)-($C_1$-$C_6$)alkyl-, ((3- to 12 membered)heterocycle)-($C_1$-$C_6$) alkyl-, ((7- to 12-membered)bicycloheterocycle)-($C_1$-$C_6$)alkyl-, and naphthyl; each of which is substituted with one or two substituents independently selected from the group consisting of —$CONHR^6$, dihydroxy ($C_1$-$C_6$)alkyl-, —($C_1$-$C_6$)alkoxy, (($C_1$-$C_6$)alkoxy)CO ($C_1$-$C_6$)alkoxy-, —($C_1$-$C_6$)alkyl-NH($C_1$-$C_6$)alkyl-$R^4$, —($C_1$-$C_6$)alkyl-CO—$OR^7$, —($C_1$-$C_6$)alkoxy-$COOR^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—$OR^7$, —NH—C(=O)—($C_1$-$C_6$)alkyl-CO—$OR^7$, —NH—C(=O)—CH(NH$_2$)—($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, —($C_1$-$C_6$)alkoxyC(O)$NR^5R^6$, —NH—($C_1$-$C_6$)alkylC(O)—$NR^5R^6$, —C(O)NH—($C_1$— $C_6$)alkyl-$COOR^7$, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; or c) —($C_1$-$C_{10}$)alkyl, —($C_2$-$C_{12}$)alkenyl, and —($C_2$-$C_{12}$)alkynyl, each of which is substituted with one or two substituents independently selected from the group consisting of —$CONHR^6$, —($C_1$-$C_6$)alkyl-NH($C_1$-$C_6$)alkyl-$R^{14}$, —($C_1$-$C_6$)alkoxy-$COOR^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—$OR^7$, —NH—C(=O)—($C_1$-$C_6$)alkyl-CO—$OR^7$, —NH—C(=O)—CH(NH$_2$)—($C_1$-$C_6$)alkyl-CO—$OR^7$, —($C_1$-$C_6$)alkoxyC(O)$NR^5R^6$, —NH—($C_1$-$C_6$)alkylC(O)—$NR^5R^6$, and —C(O)NH—($C_1$-$C_6$)alkyl-$COOR^7$; or d) 2,3-dihydroxypropyl; or e) 4-isoxazolyl, 4-isoxazolyl($C_1C_6$)alkyl, 5-isoxazolyl, or 5-isoxazolyl($C_1$-$C_6$)alkyl substituted with one or two alkyl groups, or f) —C(=O)NH$_2$ or —($C_1$-$C_6$)alkyl-C(=O)NH$_2$;

$R^8$ is hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —$CONR^5R^6$, —($C_1$-$C_6$)alkyl-CO—$NR^5R^6$, —$COOR^7$, —($C_1$-$C_6$)alkyl-CO—$OR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, -($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH ($C_1$-$C_6$)alkyl-$R^{14}$, CN, SH, $OR^4$, —$CONR^5R^6$, —($C_1$-$C_6$alkyl)-CO—$NR^5R^6$, —$COOR^7$, —($C_1$-$C_6$)alkyl-CO—$OR^7$, —($C_1$-$C_6$)alkoxy-$COOR^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—$OR^7$, —NH—C(=O)—($C_1$-$C_6$)alkyl-CO—$OR^7$, —NH—C(=O)—CH(NH$_2$)—($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O) $NR^5R^6$, —NH—($C_1$-$C_6$)alkylC(O)—$NR^5R^6$, —C(O)NH—($C_1$-$C_6$)alkyl-$COOR^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C (=O)—(C₁-C₆)alkoxy, —(C₁-C₆)alkoxy-C(=O)—(C₁-C₆) alkyl, —(C₁-C₆)alkyl-CN, —(C₁-C₆)alkyl-COOR⁷, —(C₁-C₆)alkoxy-COOR⁷, —(C₃-C₁₂)cycloalkyl, ((C₃-C₁₂)cycloalkyl)-(C₁-C₆)alkyl-, ((C₃-C₁₂)cycloalkyl)-(C₁-C₆)alkoxy-, ((C₃-C₁₂)cycloalkyl)-(C₁-C₆)alkoxy-(C₁-C₆)alkyl-, —(C₄-C₁₂)cycloalkenyl, ((C₄-C₁₂)cycloalkenyl)-(C₁-C₆)alkyl-, ((C₄-C₁₂)cycloalkenyl)-(C₁-C₆)alkoxy-, ((C₄-C₁₂)cycloalkenyl)-(C₁-C₆)alkoxy-(C₁-C₆)alkyl-, -(5- to 12-membered)aryl, ((5- to 12-membered)aryl)-(C₁-C₆)alkyl-, ((5- to 12-membered)aryl)-(C₁-C₆)alkoxy-, ((5- to 12-membered)aryl)-(C₁-C₆)alkoxy-(C₁-C₆)alkyl-, -(5- to 12-membered)heteroaryl, ((5- to 12-membered)heteroaryl)-(C₁-C₆)alkyl-, ((5- to 12-membered)heteroaryl)-(C₁-C₆)alkoxy-, ((5- to 12-membered)heteroaryl)-(C₁-C₆)alkoxy-(C₁-C₆)alkyl-, -(3- to 12-membered)heterocycle, ((3- to 12 membered)heterocycle)-(C₁-C₆)alkyl-, ((3- to 12 membered)heterocycle)-(C₁-C₆)alkoxy-, ((3- to 12 membered)heterocycle)-(C₁-C₆)alkoxy-(C₁-C₆)alkyl-, or together form (=O);

$R^4$ is selected from —(C₁-C₆)alkyl, —(C₂-C₆)alkenyl, —(C₂-C₆)alkynyl, —C(halo)₃, —CH(halo)₂, —CH₂(halo), hydroxy(C₁-C₆)alkyl-, —(C₃-C₁₂)cycloalkyl, ((C₃-C₁₂)cycloalkyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₄-C₁₂)cycloalkenyl, ((C₄-C₁₂)cycloalkenyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

$R^5$ and $R^6$ are each independently hydrogen, —(C₁-C₆)alkyl, —(C₃-C₈)cycloalkyl, or ((C₃-C₈)cycloalkyl)-(C₁-C₆)alkyl-, —COOR⁷, —(C₁-C₆)alkyl-CO—OR⁷, —CONH₂, or (C₁-C₆)alkyl-CONH—, or $R^5$ and $R^6$ together with the nitrogen atom to which they are attached form a (4- to 8-membered)heterocycle;

$R^7$ is selected from hydrogen, —(C₁-C₆)alkyl, —(C₂-C₆)alkenyl, —(C₂-C₆)alkynyl, —(C₃-C₁₂)cycloalkyl, —(C₄-C₁₂)cycloalkenyl, ((C₃-C₁₂)cycloalkyl)-(C₁-C₆)alkyl-, and ((C₄-C₁₂)cycloalkenyl)-(C₁-C₆)alkyl-;

$R^9$ and $R^{10}$ are each independently selected from hydrogen, —(C₁-C₆)alkyl, —(C₂-C₆)alkenyl, —(C₂-C₆)alkynyl, —(C₁-C₁₀)alkoxy, —(C₃-C₁₂)cycloalkyl, —(C₃-C₁₂)cycloalkenyl, ((C₃-C₁₂)cycloalkyl)-(C₁-C₆)alkyl-, or ((C₃-C₁₂)cycloalkenyl)-(C₁-C₆)alkyl-;

each $R^{11}$ is independently selected from hydrogen, —(C₁-C₁₀)alkyl, —(C₂-C₁₀)alkenyl, —(C₂-C₁₀)alkynyl, —(C₁-C₁₀)alkoxy, ((C₁-C₆)alkyl)sulfonyl(C₁-C₆)alkyl-, —(C₃-C₁₂)cycloalkyl, ((C₃-C₁₂)cycloalkyl)-(C₁-C₆)alkyl-, —(C₄-C₁₂)cycloalkenyl, or ((C₄-C₁₂)cycloalkenyl)-(C₁-C₆)alkyl-;

$R^{12}$ and $R^{13}$ are each independently selected from hydrogen, —(C₁-C₁₀)alkyl, —(C₂-C₁₂)alkenyl, —(C₂-C₁₂)alkynyl, —(C₁-C₁₀)alkoxy, —(OCH₂CH₂)ₛ—O(C₁-C₆)alkyl, —(C₃-C₁₂)cycloalkyl, ((C₃-C₁₂)cycloalkyl)-(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, ((7- to 12-membered)bicycloheterocycle)-(C₁-C₆)alkyl-, phenyl, benzyl or naphthyl; each of which is optionally substituted with one or two substituents independently selected from the group consisting of OH, (=O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, phenyl, benzyl, NH₂, —NH(C₁-C₆)alkyl, CN, SH, OR⁴, —CONR⁵R⁶, —COOR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

$R^{14}$ is selected from —COOR⁷, —(C₁-C₆)alkyl-CO—OR⁷, —C(=O)—(C₁-C₆)alkyl-COOR⁷, —(C₁-C₆)alkyl-C(=O)—(C₁-C₆)alkyl-COOR⁷, —CONH₂, (C₁-C₆)alkyl-CONH—;

G is selected from O, —OCO—, —C(=O), NR⁹, NR', S, SO, and SO₂;

R' is —C(=O)(C₁-C₆)alkyl or —SO₂(C₁-C₆)alkyl;

X is selected from OH, hydroxy(C₁-C₆)alkyl-, dihydroxy(C₁-C₆)alkyl-, halogen, —NH₂, —NR²(C=O)R¹², CONR¹²R¹³, —(C₁-C₆)alkyl-CONH₂, —(C₁-C₆)alkyl-COOH, —COOH, —O—(C₁-C₆)alkyl-COOH, —O—(C₁-C₆)alkyl-CONH₂, —(C₁-C₁₀)alkyl, —(C₂-C₁₀)alkenyl, —(C₂-C₁₀)alkynyl, —(C₁-C₁₀)alkoxy, —(OCH₂CH₂)ₛ—O(C₁-C₆)alkyl, —(OCH₂CH₂)ₛ—OH, —(CH₂)ₚCHOHCH₂OH, CN, —NH—SO₂R⁹, —(C₃-C₁₂)cycloalkyl, ((C₃-C₁₂)cycloalkyl)-(C₁-C₆)alkyl-, ((C₃-C₁₂)cycloalkyl)-(C₁-C₆)alkoxy-, -(5- to 12-membered)aryl, ((5- to 12-membered)aryl)-(C₁-C₆)alkyl-, ((5- to 12-membered)aryl)-(C₁-C₆)alkoxy-, -(5- to 12-membered)heteroaryl, ((5- to 12-membered)heteroaryl)-(C₁-C₆)alkyl-, ((5- to 12-membered)heteroaryl)-(C₁-C₆)alkoxy-, -(3- to 12-membered)heterocycle, ((3- to 12-membered)heterocycle)-(C₁-C₆)alkyl-, ((3- to 12-membered)heterocycle)-(C₁-C₆)alkoxy-, -(7- to 12-membered)bicycloheterocycle, ((7- to 12-membered)bicycloheterocycle)-(C₁-C₆)alkyl-, and ((7- to 12-membered)bicycloheterocycle)-(C₁-C₆)alkoxy-;

Q is selected from OH, —(C₁-C₁₀)alkoxy, —(C₁-C₁₀)alkyl, —(C₃-C₁₂)cycloalkyl, -(5- to 12-membered)aryl, ((C₃-C₁₂)cycloalkyl)-(C₁-C₆)alkyl-, (5- to 12-membered)aryl)-(C₁-C₆)alkyl-, —(OCH₂CH₂)ₛ—O(C₁-C₆)alkyl, —(CH₂CH₂O)ₛ—(C₁-C₆)alkyl, —(OCH₂CH₂)—OH, —O(C=O)R⁹, —O—(C₁-C₆)alkyl-COOR⁷, —NH—(C₁-C₆)alkyl-COOR⁷, —O—C(O)—(C₁-C₆)alkyl-C(O)OR⁷, —NH—C(O)—(C₁-C₆)alkyl-C(O)OR⁷, —O—(C₁-C₆)alkyl-C(O)NR⁹R¹⁰, —NH—(C₁-C₆)alkyl-C(O)NR⁹R¹⁰, —O—C(O)—(C₁-C₆)alkyl-C(O)NR⁹R¹⁰, —NH—C(O)—(C₁-C₆)alkyl-C(O)NR⁹R¹⁰ and R¹⁴;

Z is —(CH₂)ₘ—, optionally substituted with 1 or 2-(C₁-C₆)alkyl;

Y is —(CH₂)ₙ—CH or a direct bond, provided that when Y is a direct bond then R⁸ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

In another embodiment, the present invention provides novel compounds of Formula I:

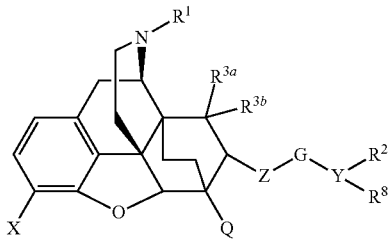

(I)

wherein

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; each of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, NR$^9$R$^{10}$, CN, —CONR$^9$R$^{10}$, —NR$^9$COR$^{10}$, SR$^{11}$, -(5- to 12-membered) carbocyclic ring, -(5- to 12-membered)heterocycle, phenyl, and benzyl;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, NH$_2$, —NH(C$_1$-C$_6$)alkyl, CN, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, -(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (═O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, NH$_2$, —NH(C$_1$-C$_6$)alkyl, —(C$_1$-C$_6$)alkyl-NH(C$_1$-C$_6$)alkyl-R$^{14}$, CN, SH, OR$^4$, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —N(SO$_2$(C$_1$-C$_6$)alkyl)$_2$, —C(═NH)NH$_2$, —NH—CO—(C$_1$-C$_6$)alkyl, —NH—CO—NH$_2$, —NH—C(═O)—NH—(C$_1$-C$_6$)alkyl, —NH—C(═O)-(5- to 12-membered)aryl, —NH—C(═O)—(C$_1$-C$_6$)alkyl-(5- to 12-membered)aryl, —NH—(C$_1$-C$_6$)alkyl-CO—OR$^7$, —NH—C(═O)—(C$_1$-C$_6$)alkyl-CO—OR$^7$, —NH—C(═O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(═O)—(C$_1$-C$_6$)alkoxy, —(C$_1$-C$_6$)alkoxy-C(═O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_2$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12-membered)heterocycle)-(C$_1$-C$_6$)alkoxy-, and ((3- to 12 membered)heterocycle)-(C$_1$-C$_6$)alkoxy-(C$_1$-C$_6$)alkyl-, provided that at least one of R$^{3a}$ or R$^{3b}$ is selected from —(C$_7$-C$_{10}$)alkyl, —(C$_7$-C$_{10}$)alkenyl, —(C$_7$-C$_{10}$)alkynyl, —(C$_1$-C$_{10}$)alkoxy, —(C$_1$-C$_6$)alkyl-C(═O)—(C$_1$-C$_6$)alkoxy, —(C$_1$-C$_6$)alkoxy-C(═O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12-membered)heterocycle)-(C$_1$-C$_6$)alkoxy-, and ((3- to 12 membered)heterocycle)-(C$_1$-C$_6$)alkoxy-(C$_1$-C$_6$)alkyl-;

R$^4$ is selected from —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-

($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, —($C_1$-$C_6$)alkyl-CONH;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, halogen, —NH$_2$, —NR$^2$(C=O)R$^{12}$, CONR$^{12}$R$^{13}$, COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN and NH—SO$_2$R$^9$, —($C_3$-$C_2$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-CC(O)NR$^9$R$^{10}$ and R$^{14}$;

Z is —(CH$_2$)$_m$—, optionally substituted with 1 or 2-($C_1$-$C_6$)alkyl;

Y is —(CH$_2$)$_n$—CH or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

The present invention further provides novel compounds of Formula III:

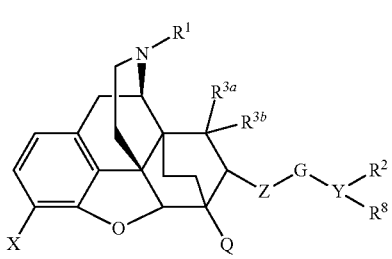

(III)

wherein

X is OH or —($C_1$-$C_6$)alkoxy;

Q is OMe;

Z is —(CH$_2$)$_m$—;

G is —OCO—;

Y is —CH;

$R^8$ is NH$_2$;

$R^2$ is —($C_1$-$C_6$)alkyl, —($C_2$-$C_6$)alkenyl, —($C_2$-$C_6$)alkynyl, phenyl, benzyl, hydroxy($C_1$-$C_6$)alkyl-, dihydroxy($C_{1-6}$)alkyl, —($C_1$-$C_6$)alkyl-NH$_2$, —($C_1$-$C_6$)alkyl-CO—NH$_2$, —($C_1$-$C_6$)alkyl-CO—NH—($C_1$-$C_4$)alkyl, —($C_1$-$C_6$)alkyl-CO—OH, or —($C_1$-$C_6$)alkyl-CO—O($C_1$-$C_4$)alkyl;

$R^1$ is selected from hydrogen, —($C_1$-$C_6$)alkyl, —($C_3$-$C_6$)cycloalkyl, and (($C_3$-$C_6$)cycloalkyl)-($C_1$-$C_6$)alkyl;

$R^{3a}$ and $R^{3b}$ are both hydrogen;

m is an integer 1 or 2;

or a pharmaceutically acceptable salt, prodrug or solvate thereof.

The present invention further provides novel compounds of Formula I:

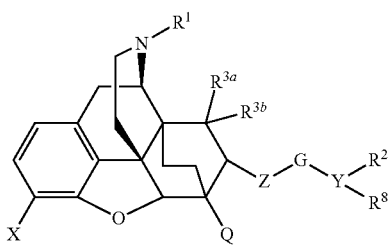

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered) carbocyclic ring, -(5- to 12-membered)heterocycle, phenyl, and benzyl;

$R^2$ and $R^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, or —CH$_2$(halo), or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_6$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered) bicyclic ring system)-($C_1$-$C_6$)alkyl-, -(7- to 12-membered) bicyclic aryl, ((7- to 12-membered)bicyclic aryl)-($C_1$-$C_6$) alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy($C_1$-$C_6$)alkyl-, halogen, —NH$_2$, —NR$^2$(C=O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN and —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$R$^{10}$, and R$^{14}$;

Z is —(CH$_2$)$_m$—, optionally substituted with 1 or 2-($C_1$-$C_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

provided that when X is OH or —($C_1$-$C_6$)alkoxy, Q is OMe, Z is unsubstituted, and G is O, then either:

a) R$^1$ is selected from;
  i. hydrogen, ($C_1$-$C_{10}$)alkoxy, ((5- to 12-membered)heteroaryl)-($C_1$-$C_6$)alkyl-, and (3- to 12-membered)heterocycle)-($C_1$-$C_6$)alkyl-; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or
  ii. —($C_1$-$C_{10}$)alkyl, —($C_2$-$C_{12}$)alkenyl, —($C_2$-$C_{12}$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((3- to 12 membered)heterocycle)-($C_1$-$C_6$)alkyl-, phenyl, or benzyl; each of which is substituted with 1, 2, or 3 substituents independently selected from the group consisting of —($C_1$-$C_6$)alkyl-COOR$^7$, NR$^9$R$^{10}$, —CONR$^9$R$^{10}$, —NR$^9$COR$^{10}$, and SR$^{11}$;

or
b) at least one of R$^2$ and R$^8$ is selected from:
  i. —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, (($C_4$-$C_{12}$)cycloalkenyl)-($C_1$-$C_6$)alkyl-, (($C_6$-$C_{14}$)bicycloalkyl)-($C_1$-$C_6$)alkyl-, (($C_8$-$C_{20}$)tricycloalkyl)-($C_1$-$C_6$)alkyl-, (($C_7$-$C_{14}$)bicycloalkenyl)-($C_1$-$C_6$)alkyl-, (($C_8$-$C_{20}$)tricycloalkenyl)-($C_1$-$C_6$)alkyl-, -(7- to 12-membered)bicyclic ring system)-($C_1$-$C_6$)alkyl-, ((7- to 12-membered)bicyclic aryl)-($C_1$-$C_6$)alkyl-, ((5- to 12-membered)heteroaryl)-($C_1$-$C_6$)alkyl-, ((3- to 12 membered)heterocycle)-($C_1$-$C_6$)alkyl-, ((7- to 12-membered)bicycloheterocycle)-($C_1$-$C_6$)alkyl-, or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —COOR$^7$, —($C_1$-$C_6$)alkyl-CO—OR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, N-methyl-N-(methylsulfonyl)methanesulfonamide, or acetimidamide;
  ii. hydrogen, —($C_1$-$C_{10}$)alkyl, —($C_2$-$C_{12}$)alkenyl, —($C_2$-$C_{12}$)alkynyl, —($C_3$-$C_{12}$)cycloalkyl, —(($C_3$-$C_{12}$)cycloalkyl)-($C_1$-$C_6$)alkyl, —($C_4$-$C_{12}$)cycloalkenyl, —($C_6$-$C_{14}$)bicycloalkyl, —($C_8$-$C_{20}$)tricycloalkyl, —($C_7$-$C_{14}$)bicycloalkenyl, —($C_9$-$C_{20}$)tricycloalkenyl, -(5- to 12-membered)aryl, ((5- to 12-membered)aryl)-($C_1$-$C_6$)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl and benzyl; each of which is substituted with one or two substituents independently selected from the group consisting of dihydroxy($C_1$-$C_6$)alkyl-, —($C_1$-$C_6$)alkyl-NH($C_1$-$C_6$)alkyl-R$^{14}$, —($C_1$-$C_6$)alkyl-CO—OR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-(C$_1$-C$_6$)alkyl-;

or c) at least one of R$^{3a}$ or R$^{3b}$ is independently selected from —(C$_7$-C$_{10}$)alkyl, —(C$_7$-C$_{10}$)alkenyl, —(C$_7$-C$_{10}$)alkynyl, or —(C$_1$-C$_{10}$)alkoxy;

or a pharmaceutically acceptable salt, prodrug or solvate thereof.

In one embodiment, the present invention provides novel compounds of Formula I:

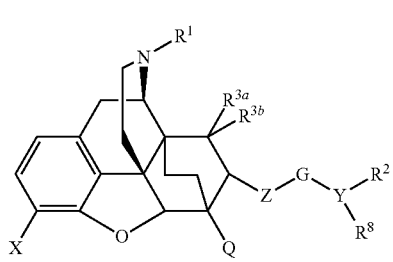

(I)

wherein

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, NH$_2$, —NH(C$_1$-C$_6$)alkyl, NR$^9$R$^{10}$, CN, —CONR$^9$R$^{10}$, —NR$^9$COR$^{10}$, SR$^{11}$, -(5- to 12-membered) carbocyclic ring, -(5- to 12-membered)heterocycle, phenyl, and benzyl;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, NH$_2$, —NH(C$_1$-C$_6$)alkyl, CN, —CONR$^5$R$^6$, —(C$_1$-C$_6$alkyl)-CO—NR$^5$R$^6$, —(C$_1$-C$_6$)alkyl-CO—NR$^5$R$^6$, —COOR$^7$, —(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl and naphthyl; any of which is optionally substituted with one or two substituents independently selected from the group consisting of OH, (═O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, NH$_2$, —NH(C$_1$-C$_6$)alkyl, —(C$_1$-C$_6$)alkyl-NH (C$_1$-C$_6$)alkyl-R$^{14}$, CN, SH, OR$^4$, —CONR$^5$R$^6$, —COOR$^7$, —(C$_1$-C$_6$)alkyl-CO—OR$^7$, —(OCH$_2$CH$_2$)$_s$—O(C$_1$-C$_6$) alkyl, —(CH$_2$CH$_2$O)$_s$—(C$_1$-C$_6$)alkyl, ((C$_1$-C$_6$)alkyl)sulfonyl(C$_1$-C$_6$)alkyl-, —N(SO$_2$(C$_1$-C$_6$)alkyl)$_2$, —C(═NH)NH$_2$, —NH—CO—(C$_1$-C$_6$)alkyl, —NH—CO—NH$_2$, —NH— (C$_1$-C$_6$)alkyl-CO—OR$^7$, —(C$_3$-C$_{12}$)cycloalkyl, ((C$_3$-C$_{12}$) cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$) alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, or —CH$_2$(halo), or together form (═O);

R$^4$ is selected from —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$) alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^5$ and R$^6$ are each independently hydrogen, —(C$_1$-C$_6$)alkyl, —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-CO—OR$^7$, —CONH$_2$, or (C$_1$-C$_6$)alkyl-CONH—, or R$^5$ and R$^6$ together with the nitrogen atom to which they are attached form a (4- to 8-membered)heterocycle;

R$^7$ is selected from hydrogen, —(C$_1$-C$_6$)alkyl, —(C$_2$-C$_6$) alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

R$^9$ and R$^{10}$ are each independently selected from hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, or ((C$_3$-C$_{12}$) cycloalkenyl)-(C$_1$-C$_6$)alkyl-;

Each R$^{11}$ is independently selected from hydrogen, —(C$_1$-C$_{10}$)alkyl, —(C$_2$-C$_{10}$)alkenyl, —(C$_2$-C$_{10}$)alkynyl, —(C$_7$-C$_{10}$)alkoxy, ((C$_1$-C$_6$)alkyl)sulfonyl(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, or ((C$_4$-C$_{12}$)cycloalkenyl)-(C$_1$-C$_6$)alkyl-;

R$^{12}$ and R$^{13}$ are each independently selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$) alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$) bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered) bicyclic ring system)-($C_1$-$C_6$)alkyl-, -(7- to 12-membered) bicyclic aryl, ((7- to 12-membered)bicyclic aryl)-($C_1$-$C_6$) alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{14}$ is selected from —COOR$^7$, —($C_1$-$C_6$)alkyl-COOR$^7$, —C(=O)—($C_1$-$C_6$)alkyl-CO—OR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, NR$^9$, NR', S, SO, and SO$_2$;

R' is —C(=O)($C_1$-$C_6$)alkyl or —SO$_2$($C_1$-$C_6$)alkyl;

X is selected from hydroxy($C_1$-$C_6$)alkyl-, dihydroxy($C_1$-$C_6$)alkyl-, halogen, —NH$_2$, —NR$^2$(C=O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_7$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN and —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$R$^{10}$, and R$^{14}$;

Z is —(CH$_2$)$_m$—, optionally substituted with 1 or 2-($C_1$-$C_6$)alkyl;

Y is —(CH$_2$)$_n$—CH— or a direct bond, provided that when Y is a direct bond then R$^8$ is absent;

m is an integer 1, 2, 3, 4, 5, or 6;
n is an integer 0, 1, 2, 3, 4, 5 or 6;
p is an integer 0, 1 or 2;
s is an integer 1 to 13;
or a pharmaceutically acceptable salt, prodrug or solvate thereof.

In another embodiment, the present invention provides novel compounds of Formula I:

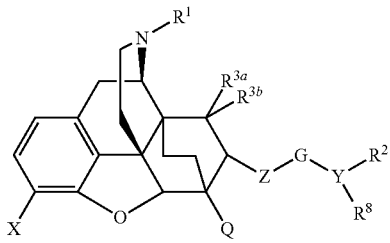

(I)

wherein

R$^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, NH$_2$, —NH($C_1$-$C_6$)alkyl, —NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

R$^2$ and R$^8$ are each independently hydrogen, —($C_1$-$C_{10}$)alkyl, —($C_2$-$C_{12}$)alkenyl, —($C_2$-$C_2$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, or —CH$_2$(halo), or together form (=O);

$R^4$ is selected from —($C_1$-$C_6$)alkyl, —($C_2$-$C_6$)alkenyl, —($C_2$-$C_6$)alkynyl, —C(halo)$_3$, hydroxy($C_1$-$C_6$)alkyl-, —($C_3$-$C_2$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5-to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, ($C_1$-$C_6$)alkyl-CONH—;

G is selected from O, —OCO—, NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy($C_1$-$C_6$)alkyl-, halogen, —NH$_2$, —NR$^2$(C=O)R$^{12}$, CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN and —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$R$^{10}$ and R$^{14}$ Z is —(CH$_2$)$_m$—, optionally substituted with 1 or 2-($C_1$-$C_6$)alkyl;

Y is —(CH$_2$)$_n$—CH— or a direct bond, provided that when Y is a direct bond then R$^8$ is absent;

m is an integer 1, 2, 3, 4, 5, or 6;
n is an integer 0, 1, 2, 3, 4, 5 or 6;
p is an integer 0, 1 or 2;
s is an integer 1 to 13;
or a pharmaceutically acceptable salt, prodrug or solvate thereof.

In another embodiment, the present invention provides novel compounds of Formula I:

(I)

wherein
R$^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, NH$_2$, —NH($C_1$-$C_6$)alkyl, —NR$^9$R$^{10}$, CN, —CONR$^9$R$^{10}$, —NR$^9$COR$^{10}$, SR$^{11}$, -(5- to 12-membered) carbocyclic ring, -(5- to 12-membered)heterocycle, phenyl, and benzyl;

R$^2$ and R$^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$alkyl)-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_2$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_4$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{3a}$ and R$^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, or —CH$_2$(halo), or together form (=O);

R$^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^5$ and R$^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, or ($C_1$-$C_6$)alkyl-CONH—, or R$^5$ and R$^6$ together with the nitrogen atom to which they are attached form a (4- to 8-membered)heterocycle;

R$^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

R$^9$ and R$^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each R$^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

R$^{12}$ and R$^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, NR$^9$, NR', S, SO, and SO$_2$;

R' is —C(=O)(C$_1$-C$_6$)alkyl or —SO$_2$(C$_1$-C$_6$)alkyl;

X is selected from OH, hydroxy(C$_1$-C$_6$)alkyl-, dihydroxy (C$_1$-C$_6$)alkyl-, halogen, —NH$_2$, —NR$^2$(C=O)R$^{12}$, CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O(C$_1$-C$_6$)alkyl, —(OCH$_2$CH$_2$)$_s$—OH, —(CH$_2$)$_p$ CHOHCH$_2$OH, CN and —NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-;

Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$)$_s$—OH, —O(C=O)R$^9$R$^{10}$ and R$^{14}$; provided that Q is not OMe;

Z is —(CH$_2$)$_m$—, optionally substituted with 1 or 2-(C$_1$-C$_6$)alkyl;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

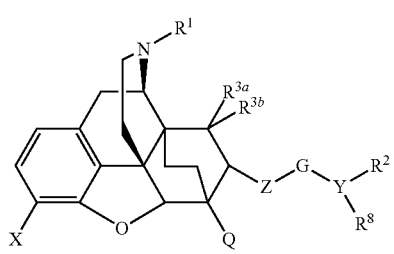

(I)

wherein

R$^1$ is selected from a) hydrogen, (C$_1$-C$_{10}$)alkoxy, ((5- to 12-membered)heteroaryl)-(C$_1$-C$_6$)alkyl-, and ((3- to 12-membered)heterocycle)-(C$_1$-C$_6$)alkyl-; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, NH$_2$, —NH(C$_1$-C$_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or b) —(C$_1$-C$_{10}$)alkyl, —(C$_2$-C$_{12}$)alkenyl, —(C$_2$-C$_{12}$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((3- to 12 membered)heterocycle)-(C$_1$-C$_6$)alkyl-, phenyl, or benzyl; each of which is substituted with 1, 2, or 3 substituents independently selected from the group consisting of —(C$_1$-C$_6$)alkyl-COOR$^7$, NR$^9$R$^{10}$, —CONR$^9$R$^{10}$, —NR$^9$COR$^{10}$, and SR$^{11}$;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, NH$_2$, —NH(C$_1$-C$_6$)alkyl, CN, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, NH$_2$, —NH(C$_1$-C$_6$)alkyl, —(C$_1$-C$_6$)alkyl-NH(C$_1$-C$_6$)alkyl-R$^{14}$, CN, SH, OR$^4$, —CONR$^5$R$^6$, —(C$_1$-C$_6$)alkyl-CO—NR$^5$R$^6$, —COOR$^7$, —(C$_1$-C$_6$)alkyl-CO—OR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, or —CH$_2$(halo), or together form (=O);

R$^4$ is selected from —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —$COOR^7$, —($C_1$-$C_6$)alkyl-CO—$OR^7$, $CONH_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($OCH_2CH_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered) bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, $NH_2$, —NH($C_1$-$C_6$)alkyl, CN, SH, $OR^4$, —$CONR^5R^6$, —$COOR^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —$COOR^7$, —($C_1$-$C_6$)alkyl-CO—$OR^7$, —C(=O)—($C_1$-$C_6$)alkyl-$COOR^7$, —($C_1$-$C_6$)alkyl-C(=O)—($C_1$-$C_6$)alkyl-$COOR^7$, $CONH_2$, —CONH($C_1$-$C_6$)alkyl;

G is selected from O, —OCO—, $NR^9$, NR', S, SO, and $SO_2$;

R' is —C(=O)($C_1$-$C_6$)alkyl or —$SO_2$($C_1$-$C_6$)alkyl;

X is selected from OH, hydroxy($C_1$-$C_6$)alkyl-, dihydroxy($C_1$-$C_6$)alkyl-, halogen, —$NH_2$, —$NR^2$(C=O)$R^8$, $CONR^{12}R^{13}$, —($C_1$-$C_6$)alkyl-$CONH_2$, —($C_1$-$C_6$)alkyl-COOH, —COOH, —O—($C_1$-$C_6$)alkyl-COOH, —O—($C_1$-$C_6$)alkyl-$CONH_2$, —($C_1$-$C_{10}$)alkyl, —($C_2$-$C_{10}$)alkenyl, —($C_2$-$C_{10}$)alkynyl, —($C_1$-$C_{10}$)alkoxy, —($OCH_2CH_2$)$_s$—O($C_1$-$C_6$)alkyl, —($OCH_2CH_2$)$_s$—OH, —($CH_2$)$_p$CHOHCH$_2$OH—, CN and NH—$SO_2R^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered) bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —($OCH_2CH_2$)$_s$—O($C_1$-$C_6$)alkyl, —($CH_2CH_2O$)$_s$—($C_1$-$C_6$)alkyl, —($OCH_2CH_2$)$_s$—OH, —O(C=O)$R^9R^{10}$ and $R^{14}$;

Z is —($CH_2$)$_m$—, optionally substituted with 1 or 2-($C_1$-$C_6$)alkyl;

Y is —($CH_2$)$_n$—CH— or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

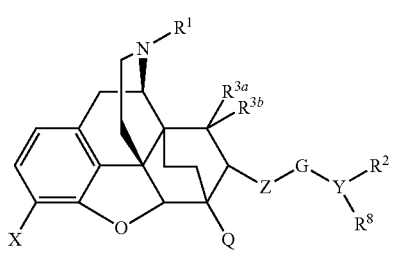

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; each of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-$COOR^7$, $NH_2$, —NH($C_1$-$C_6$)alkyl, $NR^9R^{10}$, CN, —$CONR^9R^{10}$, —$NR^9COR^{10}$, $SR^{11}$, -(5- to 12-membered)carbocyclic ring, -(5- to 12-membered)heterocycle, phenyl, and benzyl;

At least one of $R^2$ or $R^8$ is independently selected from:
a) —$(C_1-C_{10})$alkoxy, —$(OCH_2CH_2)_s$—$O(C_1-C_6)$alkyl, —$(CH_2CH_2O)_s$—$(C_1-C_6)$alkyl, $NH_2$, —$NH(C_1-C_6)$alkyl, CN, —$CONR^5R^6$, —$(C_1-C_6)$alkyl-CO—$NR^5R^6$, —$COOR^7$, —$N(SO_2(C_1-C_6)$alkyl$)_2$, —$C(=NH)NH_2$, —NH—CO—$(C_1-C_6)$alkyl, —NH—CO—$NH_2$, —NH—$(C_1-C_6)$alkyl-CO—$OR^7$, —$(C_1-C_6)$alkyl-CO—$OR^7$, $((C_4-C_{12})$cycloalkenyl)-$(C_1-C_6)$alkyl-, $((C_6-C_{14})$bicycloalkyl)-$(C_1-C_6)$alkyl-, $((C_8-C_{20})$tricycloalkyl)-$(C_1-C_6)$alkyl-, $((C_7-C_{14})$bicycloalkenyl)-$(C_1-C_6)$alkyl-, $((C_8-C_{20})$tricycloalkenyl)-$(C_1-C_6)$alkyl, ((7- to 12-membered)bicyclic ring system)-$(C_1-C_6)$alkyl-, ((7- to 12-membered)bicyclic aryl)-$(C_1-C_6)$alkyl-, ((5- to 12-membered)heteroaryl)-$(C_1-C_6)$alkyl-, ((3- to 12 membered)heterocycle)-$(C_1-C_6)$alkyl-, ((7- to 12-membered)bicycloheterocycle)-$(C_1-C_6)$alkyl-, or naphthyl; each of which is optionally substituted with one or two substituents independently selected from the group consisting of OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, dihydroxy$(C_1-C_6)$alkyl-, —$(C_1-C_6)$alkoxy, $((C_1-C_6)$alkoxy)CO$(C_1-C_6)$alkoxy-, phenyl, benzyl, $NH_2$, —$NH(C_1-C_6)$alkyl, —$(C_1-C_6)$alkyl-$NH(C_1-C_6)$alkyl-$R^{14}$, CN, SH, $OR^4$, —$CONR^5R^6$, —$COOR^7$, —$(C_1-C_6)$alkyl-CO—$OR^7$—$N(SO_2(C_1-C_6)$alkyl$)_2$, —$C(=NH)NH_2$, —NH—CO—$(C_1-C_6)$alkyl, —NH—CO—$NH_2$, —NH—$(C_1-C_6)$alkyl-CO—$OR^7$; or
b) hydrogen, —$(C_1-C_{10})$alkyl, —$(C_2-C_{12})$alkenyl, —$(C_2-C_{12})$alkynyl, —$(C_3-C_{12})$cycloalkyl, —$((C_3-C_{12})$cycloalkyl)-$(C_1-C_6)$alkyl, —$(C_4-C_{12})$cycloalkenyl, —$(C_6-C_{14})$bicycloalkyl, —$(C_8-C_{20})$tricycloalkyl, —$(C_7-C_{14})$bicycloalkenyl, —$(C_8-C_{20})$tricycloalkenyl, -(5- to 12-membered)aryl, ((5- to 12-membered)aryl)-$(C_1-C_6)$alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl and benzyl; each of which is substituted with one or two substituents independently selected from the group consisting of dihydroxy$(C_1-C_6)$alkyl-, —$(C_1-C_6)$alkoxy, $((C_1-C_6)$alkoxy)CO$(C_1-C_6)$alkoxy-, —$(C_1-C_6)$alkyl-$NH(C_1-C_6)$alkyl-$R^{14}$, and —$(C_1-C_6)$alkyl-CO—$OR^7$, —$(C_1-C_6)$alkyl-CO—$OR^7$, —$(OCH_2CH_2)_s$—$O(C_1-C_6)$alkyl, —$(CH_2CH_2O)_s$—$(C_1-C_6)$alkyl, $((C_1-C_6)$alkyl)sulfonyl$(C_1-C_6)$alkyl-, —$N(SO_2(C_1-C_6)$alkyl$)_2$, —$C(=NH)NH_2$, —NH—CO—$(C_1-C_6)$alkyl, —NH—CO—$NH_2$, —NH—$(C_1-C_6)$alkyl-CO—$OR^7$, —$(C_3-C_{12})$cycloalkyl, $((C_3-C_{12})$cycloalkyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

$R^{3a}$ and $R^{3b}$ are each independently selected from hydrogen, —$(C_1-C_{10})$alkyl, —$(C_2-C_{10})$alkenyl, —$(C_2-C_{10})$alkynyl, —$(C_1-C_{10})$alkoxy, OH, hydroxy$(C_1-C_6)$alkyl-, —C(halo)$_3$, —CH(halo)$_2$, or —CH$_2$(halo), or together form (=O);

$R^4$ is selected from —$(C_1-C_6)$alkyl, —$(C_2-C_6)$alkenyl, —$(C_2-C_6)$alkynyl, —C(halo)$_3$, —CH(halo)$_2$, —CH$_2$(halo), hydroxy$(C_1-C_6)$alkyl-, —$(C_3-C_{12})$cycloalkyl, $((C_3-C_{12})$cycloalkyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_4-C_{12})$cycloalkenyl, $((C_4-C_{12})$cycloalkenyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

$R^5$ and $R^6$ are each independently hydrogen, —$(C_1-C_6)$alkyl, —$(C_3-C_8)$cycloalkyl, or $((C_3-C_8)$cycloalkyl)-$(C_1-C_6)$alkyl-, —$COOR^7$, —$(C_1-C_6)$alkyl-CO—$OR^7$, —$CONH_2$, or $(C_1-C_6)$alkyl-CONH—, or $R^5$ and $R^6$ together with the nitrogen atom to which they are attached form a (4- to 8-membered)heterocycle;

$R^7$ is selected from hydrogen, —$(C_1-C_6)$alkyl, —$(C_2-C_6)$alkenyl, —$(C_2-C_6)$alkynyl, —$(C_3-C_2)$cycloalkyl, —$(C_4-C_{12})$cycloalkenyl, $((C_3-C_{12})$cycloalkyl)-$(C_1-C_6)$alkyl-, and $((C_4-C_{12})$cycloalkenyl)-$(C_1-C_6)$alkyl-;

$R^9$ and $R^{10}$ are each independently selected from hydrogen, —$(C_1-C_6)$alkyl, —$(C_2-C_6)$alkenyl, —$(C_2-C_6)$alkynyl, —$(C_1-C_{10})$alkoxy, —$(C_3-C_{12})$cycloalkyl, —$(C_3-C_{12})$cycloalkenyl, $((C_3-C_{12})$cycloalkyl)-$(C_1-C_6)$alkyl-, or $((C_3-C_{12})$cycloalkenyl)-$(C_1-C_6)$alkyl-;

Each $R^{11}$ is independently selected from hydrogen, —$(C_1-C_{10})$alkyl, —$(C_2-C_{10})$alkenyl, —$(C_2-C_{10})$alkynyl, —$(C_1-C_{10})$alkoxy, $((C_1-C_6)$alkyl)sulfonyl$(C_1-C_6)$alkyl-, —$(C_3-C_{12})$cycloalkyl, $((C_3-C_{12})$cycloalkyl)-$(C_1-C_6)$alkyl-, —$(C_4-C_{12})$cycloalkenyl, or $((C_4-C_{12})$cycloalkenyl)-$(C_1-C_6)$alkyl-;

$R^{12}$ and $R^{13}$ are each independently selected from hydrogen, —$(C_1-C_{10})$alkyl, —$(C_2-C_{12})$alkenyl, —$(C_2-C_{12})$alkynyl, —$(C_1-C_{10})$alkoxy, —$(OCH_2CH_2)_s$—$O(C_1-C_6)$alkyl, —$(C_3-C_{12})$cycloalkyl, $((C_3-C_{12})$cycloalkyl)-$(C_1-C_6)$alkyl-, —$(C_4-C_{12})$cycloalkenyl, $((C_4-C_{12})$cycloalkenyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(5- to 12-membered)aryl, ((5- to 12-membered)aryl)-$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, phenyl, benzyl, $NH_2$, —$NH(C_1-C_6)$alkyl, CN, SH, $OR^4$, —$CONR^5R^6$, —$COOR^7$, —$(C_3-C_{12})$cycloalkyl, $((C_3-C_{12})$cycloalkyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

$R^{14}$ is selected from —$COOR^7$, —$(C_1-C_6)$alkyl-CO—$OR^7$, —$C(=O)$—$(C_1-C_6)$alkyl-$COOR^7$, —$(C_1-C_6)$alkyl-C(=O)—$(C_1-C_6)$alkyl-$COOR^7$, —$CONH_2$, $(C_1-C_6)$alkyl-CONH—;

G is selected from O, —OCO—, NR$^9$, NR', S, SO, and SO$_2$;

R' is —C(=O)(C$_1$-C$_6$)alkyl or —SO$_2$(C$_1$-C$_6$)alkyl;

X is selected from OH, hydroxy(C$_1$-C$_6$)alkyl-, dihydroxy (C$_1$-C$_6$)alkyl-, halogen, —NH$_2$, —NR$^2$(C=O)R$^{12}$, CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O (C$_1$-C$_6$)alkyl, —(OCH$_2$CH$_2$)$_s$—OH, —(CH$_2$)$_p$CHOHCH$_2$OH, CN and —NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-;

Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$)$_s$—OH, —O(C=O)R$^9$R$^{10}$ and R$^{14}$;

Z is —(CH$_2$)$_m$—, optionally substituted with 1 or 2-(C$_1$-C$_6$)alkyl;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

a pharmaceutically acceptable salt, prodrug or solvate thereof.

In another embodiment, the present invention provides novel compounds of Formula I:

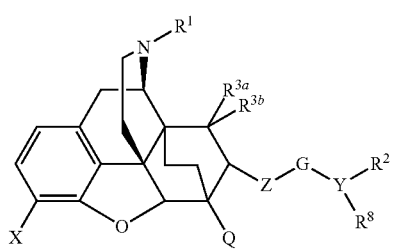

(I)

wherein

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; each of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, NH$_2$, —NH(C$_1$-C$_6$)alkyl, NR$^9$R$^{10}$, CN, —CONR$^9$R$^{10}$, —NR$^9$COR$^{10}$, SR$^{11}$, -(5- to 12-membered) carbocyclic ring, -(5- to 12-membered)heterocycle, phenyl, and benzyl;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, NH$_2$, —NH(C$_1$-C$_6$)alkyl, CN, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_3$-C$_{12}$)cycloalkyl, ((C$_3$-C$_2$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy) CO(C$_1$-C$_6$)alkoxy-, phenyl, benzyl, NH$_2$, —NH(C$_1$-C$_6$) alkyl, —(C$_1$-C$_6$)alkyl-NH(C$_1$-C$_6$)alkyl-R$^{14}$, CN, SH, OR$^4$, —CONR$^5$R$^6$, —(C$_1$-C$_6$)alkyl-CO—NR$^5$R$^6$, —COOR$^7$, —(C$_1$-C$_6$)alkyl-CO—OR$^7$, —(OCH$_2$CH$_2$)$_s$—O(C$_1$-C$_6$) alkyl, —(CH$_2$CH$_2$O)$_s$—(C$_1$-C$_6$)alkyl, ((C$_1$-C$_6$)alkyl)sulfonyl(C$_1$-C$_6$)alkyl-, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$) alkyl-;

R$^{3a}$ and R$^{3b}$ are each independently selected from —(C$_1$-C$_{10}$)alkyl, —(C$_2$-C$_{10}$)alkenyl, —(C$_2$-C$_{10}$)alkynyl, and —(C$_1$-C$_{10}$)alkoxy; provided that at least one of R$^{3a}$ or R$^{3b}$ is selected from —(C$_7$-C$_{10}$)alkyl, —(C$_7$-C$_1$)alkenyl, —(C$_7$-C$_{10}$)alkynyl, or —(C$_1$-C$_{10}$)alkoxy;

R$^4$ is selected from —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$) alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

$R^5$ and $R^6$ are each independently hydrogen, —$(C_1\text{-}C_6)$alkyl, —$(C_3\text{-}C_8)$cycloalkyl, or $((C_3\text{-}C_8)$cycloalkyl)-$(C_1\text{-}C_6)$alkyl-, —$COOR^7$, —$(C_1\text{-}C_6)$alkyl-CO—$OR^7$, $CONH_2$, or $(C_1\text{-}C_6)$alkyl-CONH—, or $R^5$ and $R^6$ together with the nitrogen atom to which they are attached form a (4- to 8-membered)heterocycle;

$R^7$ is selected from hydrogen, —$(C_1\text{-}C_6)$alkyl, —$(C_2\text{-}C_6)$alkenyl, —$(C_2\text{-}C_6)$alkynyl, —$(C_3\text{-}C_{12})$cycloalkyl, —$(C_4\text{-}C_{12})$cycloalkenyl, $((C_3\text{-}C_{12})$cycloalkyl)-$(C_1\text{-}C_6)$alkyl-, and $((C_4\text{-}C_{12})$cycloalkenyl)-$(C_1\text{-}C_6)$alkyl-;

$R^9$ and $R^{10}$ are each independently selected from hydrogen, —$(C_1\text{-}C_6)$alkyl, —$(C_2\text{-}C_6)$alkenyl, —$(C_2\text{-}C_6)$alkynyl, —$(C_1\text{-}C_{10})$alkoxy, —$(C_3\text{-}C_{12})$cycloalkyl, —$(C_3\text{-}C_{12})$cycloalkenyl, $((C_3\text{-}C_{12})$cycloalkyl)-$(C_1\text{-}C_6)$alkyl-, or $((C_3\text{-}C_{12})$cycloalkenyl)-$(C_1\text{-}C_6)$alkyl-;

Each $R^{11}$ is independently selected from hydrogen, —$(C_1\text{-}C_{10})$alkyl, —$(C_2\text{-}C_{10})$alkenyl, —$(C_2\text{-}C_{10})$alkynyl, —$(C_1\text{-}C_{10})$alkoxy, $((C_1\text{-}C_6)$alkyl)sulfonyl$(C_1\text{-}C_6)$alkyl-, —$(C_3\text{-}C_{12})$cycloalkyl, $((C_3\text{-}C_{12})$cycloalkyl)-$(C_1\text{-}C_6)$alkyl-, —$(C_4\text{-}C_{12})$cycloalkenyl, or $((C_4\text{-}C_{12})$cycloalkenyl)-$(C_1\text{-}C_6)$alkyl-;

$R^{12}$ and $R^{13}$ are each independently selected from hydrogen, —$(C_1\text{-}C_{10})$alkyl, —$(C_2\text{-}C_{10})$alkenyl, —$(C_2\text{-}C_{10})$alkynyl, —$(C_1\text{-}C_{10})$alkoxy, —$(OCH_2CH_2)_s$—$O(C_1\text{-}C_6)$alkyl, —$(C_3\text{-}C_{12})$cycloalkyl, $((C_3\text{-}C_{12})$cycloalkyl)-$(C_1\text{-}C_6)$alkyl-, —$(C_4\text{-}C_{12})$cycloalkenyl, $((C_4\text{-}C_{12})$cycloalkenyl)-$(C_1\text{-}C_6)$alkyl-, —$(C_6\text{-}C_{14})$bicycloalkyl, $((C_6\text{-}C_{14})$bicycloalkyl)-$(C_1\text{-}C_6)$alkyl-, —$(C_8\text{-}C_{20})$tricycloalkyl, $((C_8\text{-}C_{20})$tricycloalkyl)-$(C_1\text{-}C_6)$alkyl-, —$(C_7\text{-}C_{14})$bicycloalkenyl, $((C_7\text{-}C_{14})$bicycloalkenyl)-$(C_1\text{-}C_6)$alkyl-, —$(C_8\text{-}C_{20})$tricycloalkenyl, $((C_8\text{-}C_{20})$tricycloalkenyl)-$(C_1\text{-}C_6)$alkyl-, -(5- to 12-membered)aryl, ((5- to 12-membered)aryl)-$(C_1\text{-}C_6)$alkyl-, -(7- to 12-membered)bicyclic ring system, ((7- to 12-membered)bicyclic ring system)-$(C_1\text{-}C_6)$alkyl-, -(7- to 12-membered)bicyclic aryl, ((7- to 12-membered)bicyclic aryl)-$(C_1\text{-}C_6)$alkyl-, -(5- to 12-membered)heteroaryl, ((5- to 12-membered)heteroaryl)-$(C_1\text{-}C_6)$alkyl-, -(3- to 12-membered)heterocycle, ((3- to 12 membered)heterocycle)-$(C_1\text{-}C_6)$alkyl-, -(7- to 12-membered)bicycloheterocycle, ((7- to 12-membered)bicycloheterocycle)-$(C_1\text{-}C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —$(C_1\text{-}C_6)$alkyl, halo$(C_1\text{-}C_6)$alkyl-, —$(C_2\text{-}C_6)$alkenyl, —$(C_2\text{-}C_6)$alkynyl, hydroxy$(C_1\text{-}C_6)$alkyl-, phenyl, benzyl, $NH_2$, —$NH(C_1\text{-}C_6)$alkyl, CN, SH, $OR^4$, —$CONR^5R^6$, —$COOR^7$, —$(C_3\text{-}C_{12})$cycloalkyl, $((C_3\text{-}C_{12})$cycloalkyl)-$(C_1\text{-}C_6)$alkyl-, -(5- to 12-membered)aryl, ((5- to 12-membered)aryl)-$(C_1\text{-}C_6)$alkyl-, -(5- to 12-membered)heteroaryl, ((5- to 12-membered)heteroaryl)-$(C_1\text{-}C_6)$alkyl-, -(3- to 12-membered)heterocycle, ((3- to 12-membered)heterocycle)-$(C_1\text{-}C_6)$alkyl-, -(7- to 12-membered)bicycloheterocycle, and ((7- to 12-membered)bicycloheterocycle)-$(C_1\text{-}C_6)$alkyl-;

$R^{14}$ is selected from —$COOR^7$, —$(C_1\text{-}C_6)$alkyl-CO—$OR^7$, —$C(=O)$—$(C_1\text{-}C_6)$alkyl-$COOR^7$, —$(C_1\text{-}C_6)$alkyl-C(=O)—$(C_1\text{-}C_6)$alkyl-$COOR^7$, $CONH_2$, —$(C_1\text{-}C_6)$alkyl-CONH;

G is selected from O, —OCO—, $NR^9$, NR', S, SO, and $SO_2$;

R' is —$C(=O)(C_1\text{-}C_6)$alkyl or —$SO_2(C_1\text{-}C_6)$alkyl;

X is selected from OH, hydroxy$(C_1\text{-}C_6)$alkyl-, halogen, —$NH_2$, —$NR^2(C=O)R^{12}$, $CONR^{12}R^{13}$, COOH, —COOH, —O—$(C_1\text{-}C_6)$alkyl-COOH, —O—$(C_1\text{-}C_6)$alkyl-$CONH_2$, —$(C_1\text{-}C_{10})$alkyl, —$(C_2\text{-}C_{10})$alkenyl, —$(C_2\text{-}C_{10})$alkynyl, —$(C_1\text{-}C_{10})$alkoxy, —$(OCH_2CH_2)_s$—$O(C_1\text{-}C_6)$alkyl, —$(OCH_2CH_2)_s$—OH, —$(CH_2)_p$CHOHCH$_2$OH—, CN and NH—$SO_2R^9$, —$(C_3\text{-}C_{12})$cycloalkyl, $((C_3\text{-}C_{12})$cycloalkyl)-$(C_1\text{-}C_6)$alkyl-, $((C_3\text{-}C_{12})$cycloalkyl)-$(C_1\text{-}C_6)$alkoxy-, -(5- to 12-membered)aryl, ((5- to 12-membered)aryl)-$(C_1\text{-}C_6)$alkyl-, ((5- to 12-membered)aryl)-$(C_1\text{-}C_6)$alkoxy-, -(5- to 12-membered)heteroaryl, ((5- to 12-membered)heteroaryl)-$(C_1\text{-}C_6)$alkyl-, ((5- to 12-membered)heteroaryl)-$(C_1\text{-}C_6)$alkoxy-, -(3- to 12-membered)heterocycle, ((3- to 12-membered)heterocycle)-$(C_1\text{-}C_6)$alkyl-, ((3- to 12-membered)heterocycle)-$(C_1\text{-}C_6)$alkoxy-, -(7- to 12-membered)bicycloheterocycle, ((7- to 12-membered)bicycloheterocycle)-$(C_1\text{-}C_6)$alkyl-, and ((7- to 12-membered)bicycloheterocycle)-$(C_1\text{-}C_6)$alkoxy-;

Q is selected from OH, —$(C_1\text{-}C_{10})$alkoxy, —$(C_1\text{-}C_{10})$alkyl, —$(C_3\text{-}C_{12})$cycloalkyl, -(5- to 12-membered)aryl, $((C_3\text{-}C_{12})$cycloalkyl)-$(C_1\text{-}C_6)$alkyl-, ((5- to 12-membered)aryl)-$(C_1\text{-}C_6)$alkyl-, —$(OCH_2CH_2)_s$—$O(C_1\text{-}C_6)$alkyl, —$(CH_2CH_2O)_s$—$(C_1\text{-}C_6)$alkyl, —$(OCH_2CH_2)_s$—OH, —$O(C=O)R^9R^{10}$ and $R^{14}$;

Z is —$(CH_2)_m$—, optionally substituted with 1 or 2-$(C_1\text{-}C_6)$alkyl;

Y is —$(CH_2)_n$—CH— or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

The present invention further provides novel compounds of Formula I:

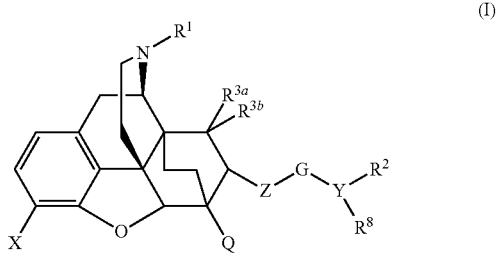

(I)

wherein $R^1$ is selected from hydrogen, —$(C_1\text{-}C_{10})$alkyl, —$(C_2\text{-}C_{12})$alkenyl, —$(C_2\text{-}C_{12})$alkynyl, —$(C_1\text{-}C_{10})$alkoxy, —$(C_3\text{-}C_{12})$cycloalkyl, —$(C_4\text{-}C_{12})$cycloalkenyl, $((C_3\text{-}C_{12})$cycloalkyl)-$(C_1\text{-}C_6)$alkyl-, $((C_4\text{-}C_{12})$cycloalkenyl)-$(C_1\text{-}C_6)$alkyl-, -(5- to 12-membered)aryl, ((5- to 12-membered)aryl)-$(C_1\text{-}C_6)$alkyl-, -(5- to 12-membered)heteroaryl, ((5- to 12-membered)heteroaryl)-$(C_1\text{-}C_6)$alkyl-, -(3- to 12-membered)heterocycle, ((3- to 12 membered)heterocycle)-$(C_1\text{-}C_6)$alkyl-, phenyl, and benzyl; any of which is optionally substituted with 1, 2, or 3 substituents independently selected from the group consisting of —$(C_1\text{-}C_6)$alkyl, OH, halo, —C(halo)$_3$, —CH(halo)$_2$, —CH$_2$(halo), $NH_2$, $NH(C_1\text{-}C_6)$alkyl-, $NR^9R^{10}$, CN, —$CONR^9R^{10}$, —$NR^9COR^{10}$, $SR^{11}$, -(5- to 12-membered)carbocyclic ring, -(5- to 12-membered)heterocycle, phenyl, and benzyl;

$R^2$ and $R^8$ are each independently hydrogen, —$(C_1\text{-}C_{10})$alkyl, —$(C_2\text{-}C_{12})$alkenyl, —$(C_2\text{-}C_{12})$alkynyl, —$(C_1\text{-}C_{10})$alkoxy, —$(OCH_2CH_2)_s$—$O(C_1\text{-}C_6)$alkyl, $NH_2$, $NH(C_1\text{-}C_6)$alkyl-, CN, —$CONR^5R^6$, —$(C_1\text{-}C_6$alkyl)-CO—$NR^5R^6$, —$COOR^7$, —$(C_1\text{-}C_6)$alkyl-CO—$OR^7$, —$(C_3\text{-}C_{12})$cycloalkyl, $((C_3\text{-}C_{12})$cycloalkyl)-$(C_1\text{-}C_6)$alkyl-, —$(C_4\text{-}C_{12})$cycloalkenyl, $((C_4\text{-}C_{12})$cycloalkenyl)-$(C_1\text{-}C_6)$alkyl-, —$(C_6\text{-}C_{14})$bicycloalkyl, $((C_6\text{-}C_{14})$bicycloalkyl)-$(C_1\text{-}C_6)$alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, phenyl, benzyl, NH$_2$, NH($C_1$-$C_6$)alkyl-, —($C_1$-$C_6$)alkyl-NH($C_1$-$C_6$)alkyl-$R^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, or —CH$_2$(halo), or together form (=O);

$R^4$ is selected from —($C_1$-$C_6$)alkyl, —($C_2$-$C_6$)alkenyl, —($C_2$-$C_6$)alkynyl, —C(halo)$_3$, hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_2$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or —($C_1$-$C_6$)alkyl-CONH, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, and (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, and (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_2$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$, $^-$COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, and —($C_1$-$C_6$)alkyl-CONH;

G is selected from O, —OCO—, NR$^9$, S, SO, and SO$_2$;

X is selected from OH, hydroxy($C_1$-$C_6$)alkyl-, halogen, —NH$_2$, —NR$^2$(C=O)R$^{12}$, —CONR$^{12}$R$^{13}$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN and —NH—SO$_2$R$^9$;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(OCH$_2$CH$_2$)$_s$—OH, —O(C=O)R$^9$R$^{10}$, and R$^{14}$;

Z is —(CH$_2$)$_m$—;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

provided that when X is OH or —($C_1$-$C_6$)alkoxy, and Q is OMe, and G is O, then either:

a) R$^1$ is selected from;
  i. hydrogen, ($C_1$-$C_{10}$)alkoxy, ((5- to 12-membered)heteroaryl)-($C_1$-$C_6$)alkyl-, and ((3- to 12-membered)heterocycle)-($C_1$-$C_6$)alkyl-; each of which is optionally substituted with 1, 2, or 3 substituents independently selected from the group consisting of —($C_1$-$C_6$)alkyl, OH, halo, —C(halo)₃, —CH(halo)₂, —CH₂(halo), NH₂, NH(C₁-C₆)alkyl-, NR⁹R¹⁰, CN, —CONR⁹R¹⁰, —NR⁹COR¹⁰, SR¹¹, -(5- to 12-membered)carbocyclic ring, -(5- to 12-membered)heterocycle, phenyl, and benzyl; or ii. —(C₁-C₁₀)alkyl, —(C₂-C₁₂)alkenyl, —(C₂-C₁₂)alkynyl, —(C₃-C₁₂)cycloalkyl, —(C₄-C₁₂)cycloalkenyl, ((C₃-C₁₂)cycloalkyl)-(C₁-C₆)alkyl-, ((C₄-C₁₂)cycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((3- to 12 membered)heterocycle)-(C₁-C₆)alkyl-, phenyl, and benzyl; each of which is substituted with 1, 2, or 3 substituents independently selected from the group consisting of NR⁹R¹⁰, —CONR⁹R¹⁰, —NR⁹COR¹⁰, and SR¹¹;

or b) at least one of R² and R⁸ is selected from:

i. —(C₁-C₁₀)alkoxy, —(OCH₂CH₂)ₛ—O(C₁-C₆)alkyl, NH₂, NH(C₁-C₆)alkyl-, CN, —CONR⁵R⁶, —(C₁-C₆)alkyl-CO—NR⁵R⁶, —COOR⁷, —(C₁-C₆)alkyl-CO—OR⁷, ((C₄-C₁₂)cycloalkenyl)-(C₁-C₆)alkyl-, ((C₆-C₁₄)bicycloalkyl)-(C₁-C₆)alkyl-, ((C₈-C₂₀)tricycloalkyl)-(C₁-C₆)alkyl-, ((C₇-C₁₄)bicycloalkenyl)-(C₁-C₆)alkyl-, ((C₈-C₂₀)tricycloalkenyl)-(C₁-C₆)alkyl-, ((7- to 12-membered)bicyclic ring system)-(C₁-C₆)alkyl-, ((7- to 12-membered)bicyclic aryl)-(C₁-C₆)alkyl-, ((5- to 12-membered)heteroaryl)-(C₁-C₆)alkyl-, ((3- to 12 membered)heterocycle)-(C₁-C₆)alkyl-, ((7- to 12-membered)bicycloheterocycle)-(C₁-C₆)alkyl-, or naphthyl; each of which is optionally substituted with one or two substituents independently selected from the group consisting of OH, (═O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, phenyl, benzyl, NH₂, NH(C₁-C₆)alkyl-, —(C₁-C₆)alkyl-NH(C₁-C₆)alkyl-R¹⁴, CN, SH, OR⁴, —CONR⁵R⁶, —COOR⁷, and —(C₁-C₆)alkyl-CO—OR⁷;

ii. hydrogen, —(C₁-C₁₀)alkyl, —(C₂-C₁₂)alkenyl, —(C₂-C₁₂)alkynyl, —(C₃-C₁₂)cycloalkyl, —((C₃-C₁₂)cycloalkyl)-(C₁-C₆)alkyl, —(C₄-C₁₂)cycloalkenyl, —(C₆-C₁₄)bicycloalkyl, —(C₈-C₂₀)tricycloalkyl, —(C₇-C₁₄)bicycloalkenyl, —(C₈-C₂₀)tricycloalkenyl, -(5- to 12-membered)aryl, ((5- to 12-membered)aryl)-(C₁-C₆)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl and benzyl; each of which is substituted with one or two substituents independently selected from the group consisting of dihydroxy(C₁-C₆)alkyl-, —(C₁-C₆)alkyl-NH(C₁-C₆)alkyl-R¹⁴, CN, SH, OR⁴, —CONR⁵R⁶, —COOR⁷, and —(C₁-C₆)alkyl-CO—OR⁷;

or c) at least one of R³ᵃ or R³ᵇ is independently selected from —(C₇-C₁₀)alkyl, —(C₇-C₁₀)alkenyl, —(C₇-C₁₀)alkynyl, or —(C₇-C₁₀)alkoxy;

a pharmaceutically acceptable salt, prodrug or solvate thereof.

In one embodiment, the present invention provides novel compounds of Formula I:

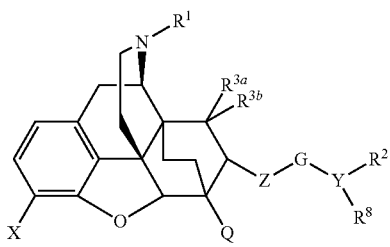

(I)

wherein

R¹ is selected from hydrogen, —(C₁-C₁₀)alkyl, —(C₂-C₁₂)alkenyl, —(C₂-C₁₂)alkynyl, —(C₇-C₁₀)alkoxy, —(C₃-C₁₂)cycloalkyl, —(C₄-C₁₂)cycloalkenyl, ((C₃-C₁₂)cycloalkyl)-(C₁-C₆)alkyl-, ((C₄-C₁₂)cycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, phenyl, and benzyl; any of which is optionally substituted with 1, 2, or 3 substituents independently selected from the group consisting of —(C₁-C₆)alkyl, OH, halo, —C(halo)₃, —CH(halo)₂, —CH₂(halo), NH₂, NH(C₁-C₆)alkyl-, NR⁹R¹⁰, CN, —CONR⁹R¹⁰, —NR⁹COR¹⁰, SR¹¹, -(5- to 12-membered)carbocyclic ring, -(5- to 12-membered)heterocycle, phenyl, and benzyl;

R² and R⁸ are each independently hydrogen, —(C₁-C₁₀)alkyl, —(C₂-C₁₂)alkenyl, —(C₂-C₁₂)alkynyl, —(C₁-C₁₀)alkoxy, —(OCH₂CH₂)ₛ—O(C₁-C₆)alkyl, NH₂, NH(C₁-C₆)alkyl-, CN, —CONR⁵R⁶, —(C₁-C₆alkyl)-CO—NR⁵R⁶, —(C₁-C₆)alkyl-CO—NR⁵R⁶, —COOR⁷, —(C₁-C₆)alkyl-CO—OR⁷, —(C₃-C₁₂)cycloalkyl, ((C₃-C₁₂)cycloalkyl)-(C₁-C₆)alkyl-, —(C₄-C₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, ((7- to 12-membered)bicycloheterocycle)-(C₁-C₆)alkyl-, phenyl, benzyl and naphthyl; any of which is optionally substituted with one or two substituents independently selected from the group consisting of OH, (═O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, phenyl, benzyl, NH₂, NH(C₁-C₆)alkyl-, —(C₁-C₆)alkyl-NH(C₁-C₆)alkyl-R¹⁴, CN, SH, OR⁴, —CONR⁵R⁶, —COOR⁷, —(C₁-C₆)alkyl-CO—OR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

$R^{3a}$ and $R^{3b}$ are each independently selected from hydrogen, —$(C_1-C_{10})$alkyl, —$(C_2-C_{10})$alkenyl, —$(C_2-C_{10})$alkynyl, —$(C_1-C_{10})$alkoxy, OH, hydroxy$(C_1-C_6)$alkyl-, —C(halo)$_3$, —CH(halo)$_2$, or —CH$_2$(halo), or together form (=O);

$R^4$ is selected from —$(C_1-C_6)$alkyl, —$(C_2-C_6)$alkenyl, —$(C_2-C_6)$alkynyl, —C(halo)$_3$, —CH(halo)$_2$, —CH$_2$(halo), hydroxy$(C_1-C_6)$alkyl-, —$(C_3-C_{12})$cycloalkyl, ($(C_3-C_{12})$cycloalkyl)-$(C_1-C_6)$alkyl-, —$(C_6-C_{14})$bicycloalkyl, ($(C_6-C_{14})$bicycloalkyl)-$(C_1-C_6)$alkyl-, —$(C_8-C_{20})$tricycloalkyl, ($(C_8-C_{20})$tricycloalkyl)-$(C_1-C_6)$alkyl-, —$(C_4-C_2)$cycloalkenyl, ($(C_4-C_{12})$cycloalkenyl)-$(C_1-C_6)$alkyl-, —$(C_7-C_{14})$bicycloalkenyl, ($(C_7-C_{14})$bicycloalkenyl)-$(C_1-C_6)$alkyl-, —$(C_8-C_{20})$tricycloalkenyl, ($(C_8-C_{20})$tricycloalkenyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

$R^5$ and $R^6$ are each independently hydrogen, —$(C_1-C_6)$alkyl, —$(C_3-C_8)$cycloalkyl, ($(C_3-C_8)$cycloalkyl)-$(C_1-C_6)$alkyl-, —COOR$^7$, —$(C_1-C_6)$alkyl-CO—OR$^7$, —CONH$_2$, or —$(C_1-C_6)$alkyl-CONH, or $R^5$ and $R^6$ together with the nitrogen atom to which they are attached form a (4- to 8-membered)heterocycle;

$R^7$ is selected from hydrogen, —$(C_1-C_6)$alkyl, —$(C_2-C_6)$alkenyl, —$(C_2-C_6)$alkynyl, —$(C_3-C_{12})$cycloalkyl, —$(C_4-C_{12})$cycloalkenyl, ($(C_3-C_{12})$cycloalkyl)-$(C_1-C_6)$alkyl-, and ($(C_4-C_{12})$cycloalkenyl)-$(C_1-C_6)$alkyl-;

$R^9$ and $R^{10}$ are each independently selected from hydrogen, —$(C_1-C_6)$alkyl, —$(C_2-C_6)$alkenyl, —$(C_2-C_6)$alkynyl, —$(C_1-C_{10})$alkoxy, —$(C_3-C_{12})$cycloalkyl, —$(C_3-C_{12})$cycloalkenyl, ($(C_3-C_{12})$cycloalkyl)-$(C_1-C_6)$alkyl-, or ($(C_3-C_{12})$cycloalkenyl)-$(C_1-C_6)$alkyl-;

Each $R^{11}$ is independently selected from hydrogen, —$(C_1-C_{10})$alkyl, —$(C_2-C_{10})$alkenyl, —$(C_2-C_{10})$alkynyl, —$(C_1-C_{10})$alkoxy, —$(C_3-C_{12})$cycloalkyl, ($(C_3-C_{1-12})$cycloalkyl)-$(C_1-C_6)$alkyl-, —$(C_4-C_{12})$cycloalkenyl, or ($(C_4-C_{12})$cycloalkenyl)-$(C_1-C_6)$alkyl-;

$R^{12}$ and $R^{13}$ are each independently selected from hydrogen, —$(C_1-C_{10})$alkyl, —$(C_2-C_{12})$alkenyl, —$(C_2-C_{12})$alkynyl, —$(C_1-C_{10})$alkoxy, —(OCH$_2$CH$_2$)$_s$—O$(C_1-C_6)$alkyl, —$(C_3-C_{12})$cycloalkyl, ($(C_3-C_{12})$cycloalkyl)-$(C_1-C_6)$alkyl-, —$(C_4-C_{12})$cycloalkenyl, ($(C_4-C_{12})$cycloalkenyl)-$(C_1-C_6)$alkyl-, —$(C_6-C_{14})$bicycloalkyl, ($(C_6-C_{14})$bicycloalkyl)-$(C_1-C_6)$alkyl-, —$(C_8-C_{20})$tricycloalkyl, ($(C_8-C_{20})$tricycloalkyl)-$(C_1-C_6)$alkyl-, —$(C_7-C_{14})$bicycloalkenyl, ($(C_7-C_{14})$bicycloalkenyl)-$(C_1-C_6)$alkyl-, —$(C_8-C_{20})$tricycloalkenyl, ($(C_8-C_{20})$tricycloalkenyl)-$(C_1-C_6)$alkyl-, -(5- to 12-membered)aryl, ((5- to 12-membered)aryl)-$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, phenyl, benzyl, NH$_2$, NH(C$_1$—C$_6$)alkyl-, CN, SH, OR$^4$, —CONR$^5$R$^6$, —COOR$^7$, —$(C_3-C_{12})$cycloalkyl, ($(C_3-C_{12})$cycloalkyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, ((7- to 12-membered)bicycloheterocycle)-$(C_1-C_6)$alkyl-;

$R^{14}$ is selected from —COOR$^7$, —$(C_1-C_6)$alkyl-CO—OR$^7$, —C(=O)—$(C_1-C_6)$alkyl-CO—OR$^7$, —$(C_1-C_6)$alkyl-C(=O)—$(C_1-C_6)$alkyl-COOR$^7$, —CONH$_2$, $(C_1-C_6)$alkyl-CONH;

G is selected from O, —OCO—, NR$^9$, S, SO, and SO$_2$;

X is selected from hydroxy$(C_1-C_6)$alkyl-, halogen, —NH$_2$, —NR$^2$(C=O)R$^{12}$, CONR$^{12}$R$^{13}$, —$(C_1-C_{10})$alkyl, —$(C_2-C_{10})$alkenyl, —$(C_2-C_{10})$alkynyl, —$(C_7-C_{10})$alkoxy, —(OCH$_2$CH$_2$)$_s$—O$(C_1-C_6)$alkyl, —(OCH$_2$CH$_2$)$_s$—OH, —(CH$_2$)$_p$CHOHCH$_2$OH—, CN and NH—SO$_2$R$^9$;

Q is selected from OH, —$(C_1-C_{10})$alkoxy, —$(C_1-C_{10})$alkyl, —$(C_3-C_{12})$cycloalkyl, -(5- to 12-membered)aryl, ($(C_3-C_{12})$cycloalkyl)-$(C_1-C_6)$alkyl-, ((5- to 12-membered)aryl)-$(C_1-C_6)$alkyl-, —(OCH$_2$CH$_2$)$_s$—O$(C_1-C_6)$alkyl, —(OCH$_2$CH$_2$)$_s$—OH, —O(C=O)R$^9$R$^{10}$, and R$^{14}$;

Z is —(CH$_2$)$_m$—;

Y is —(CH$_2$)$_n$—CH— or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

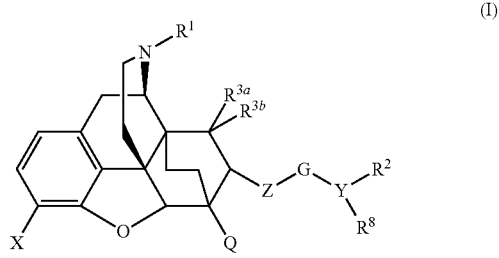

(I)

wherein $R^1$ is selected from hydrogen, —$(C_1-C_{10})$alkyl, —$(C_2-C_{12})$alkenyl, —$(C_2-C_{12})$alkynyl, —$(C_1-C_{10})$alkoxy, —$(C_3-C_{12})$cycloalkyl, —$(C_4-C_{12})$cycloalkenyl, ($(C_3-C_{12})$cycloalkyl)-$(C_1-C_6)$alkyl-, ($(C_4-C_{12})$cycloalkenyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, phenyl, and benzyl; any of which is optionally substituted with 1, 2, or 3 substituents independently selected from the group consisting of —$(C_1-C_6)$alkyl, OH, halo, —C(halo)$_3$, —CH(halo)$_2$, —CH$_2$(halo), NH$_2$, NH$(C_1-C_6)$alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered) heterocycle, phenyl, and benzyl;

$R^2$ and $R^8$ are each independently —$(C_1-C_{10})$alkyl, —$(C_2-C_{12})$alkenyl, —$(C_2-C_{12})$alkynyl, —$(C_1-C_{10})$alkoxy, —(OCH$_2$CH$_2$)$_s$—O$(C_1-C_6)$alkyl, NH$_2$, NH$(C_1-C_6)$alkyl-, CN, —CONR$^5$R$^6$, —$(C_1-C_6)$alkyl-CO—NR$^5$R$^6$, —COOR$^7$, —$(C_1-C_6)$alkyl-CO—OR$^7$, —$(C_3-C_{12})$cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicloalkenyl)-(C$_1$-C$_6$)alkyl-, —(C$_8$-C$_{20}$)tricycloalkenyl, ((C$_8$-C$_{20}$)tricloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, phenyl, benzyl, NH$_2$, NH(C$_1$-C$_6$)alkyl-, —(C$_1$-C$_6$)alkyl-NH(C$_1$-C$_6$)alkyl-R$^{14}$, CN, SH, OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, or —CH$_2$(halo), or together form (=O);

R$^4$ is selected from —(C$_1$-C$_6$)alkyl, —(C$_2$-C$_6$)alkenyl, —(C$_2$-C$_6$)alkynyl, —C(halo)$_3$, hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^5$ and R$^6$ are each independently hydrogen, —(C$_1$-C$_6$)alkyl, —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-CO—OR$^7$, —CONH$_2$, or —(C$_1$-C$_6$)alkyl-CONH, or R$^5$ and R$^6$ together with the nitrogen atom to which they are attached form a (4- to 8-membered)heterocycle;

R$^7$ is selected from hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

R$^9$ and R$^{10}$ are each independently from hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, or ((C$_3$-C$_{12}$)cycloalkenyl)-(C$_1$-C$_6$)alkyl-;

Each R$^{11}$ is independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, or ((C$_4$-C$_{12}$)cycloalkenyl)-(C$_1$-C$_6$)alkyl-;

R$^{12}$ and R$^{13}$ are each independently selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, phenyl, benzyl, NH$_2$, NH(C$_1$-C$_6$)alkyl-, CN, SH, OR$^4$, —CONR$^5$R$^6$, —COOR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{14}$ is selected from —COOR$^7$, —(C$_1$-C$_6$)alkyl-CO—OR$^7$, —C(=O)—(C$_1$-C$_6$)alkyl-COOR$^7$, —(C$_1$-C$_6$)alkyl-C(=O)—(C$_1$-C$_6$)alkyl-COOR$^7$, CONH$_2$, —(C$_1$-C$_6$)alkyl-CONH;

G is selected from —OCO—, NR$^9$, S, SO, and SO$_2$;

X is selected from OH, hydroxy(C$_1$-C$_6$)alkyl-, halogen, —NH$_2$, —NR$^2$(C=O)R$^2$, CONR$^{12}$R$^{13}$, —(C$_1$-C$_{10}$)alkyl, —(C$_2$-C$_{10}$)alkenyl, —(C$_2$-C$_{10}$)alkynyl, —(C$_7$-C$_{10}$)alkoxy, —(OCH$_2$CH$_2$)$_s$—O(C$_1$-C$_6$)alkyl, —(OCH$_2$CH$_2$)$_s$—OH, —(CH$_2$)$_p$CHOHCH$_2$OH—, CN and NH—SO$_2$R$^9$;

Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(OCH$_2$CH$_2$)$_s$—OH, —O(C=O)R$^9$R$^{10}$ and R$^{14}$;

Z is —(CH$_2$)$_m$—;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

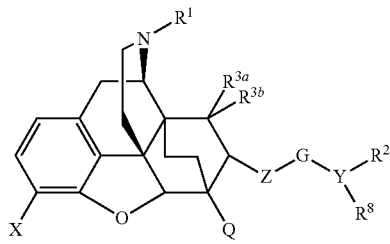

wherein $R^1$ is selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, $((C_4$-$C_{12})$cycloalkenyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, phenyl, and benzyl; any of which is optionally substituted with 1, 2, or 3 substituents independently selected from the group consisting of —$(C_1$-$C_6)$alkyl, OH, halo, —C(halo)$_3$, —CH(halo)$_2$, —CH$_2$(halo), NH$_2$, NH($C_1$-$C_6$)alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered) heterocycle, phenyl, and benzyl;

$R^2$ and $R^8$ are each independently hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —(OCH$_2$CH$_2$)$_s$—O($C_1$-$C_6$)alkyl, NH$_2$, NH($C_1$-$C_6$)alkyl-, CN, —CONR$^5$R$^6$, —($C_1$-$C_6$alkyl)-CO—NR$^5$R$^6$, —COOR$^7$, —($C_1$-$C_6$)alkyl-CO—OR$^7$, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —$(C_2$-$C_6)$alkenyl, —$(C_2$-$C_6)$alkynyl, hydroxy($C_1$-$C_6$)alkyl-, dihydroxy($C_1$-$C_6$)alkyl-, phenyl, benzyl, NH$_2$, NH($C_1$-$C_6$)alkyl-, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —$(C_3$-$C_{12})$cycloalkyl, $((C_3$-$C_{12})$cycloalkyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^{3a}$ and $R^{3b}$ are each independently selected from hydrogen, —$(C_1$-$C_{10})$alkyl, —$(C_2$-$C_{10})$alkenyl, —$(C_2$-$C_{10})$alkynyl, —$(C_1$-$C_{10})$alkoxy, OH, hydroxy($C_1$-$C_6$)alkyl-, —C(halo)$_3$, —CH(halo)$_2$, or —CH$_2$(halo), or together form (=O);

$R^4$ is selected from —$(C_1$-$C_6)$alkyl, —$(C_2$-$C_6)$alkenyl, —$(C_2$-$C_6)$alkynyl, —C(halo)$_3$, —CH(halo)$_2$, —CH$_2$(halo), hydroxy($C_1$-$C_6$)alkyl-, —$(C_3$-$C_{12})$cycloalkyl, $((C_3$-$C_{12})$cycloalkyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^5$ and $R^6$ are each independently hydrogen, —$(C_1$-$C_6)$alkyl, —$(C_3$-$C_8)$cycloalkyl, or $((C_3$-$C_8)$cycloalkyl)-$(C_1$-$C_6)$alkyl-, —COOR$^7$, —($C_1$-$C_6$)alkyl-CO—OR$^7$, CONH$_2$, or —($C_1$-$C_6$)alkyl-CONH, or $R^5$ and $R^6$ together with the nitrogen atom to which they are attached form a (4- to 8-membered)heterocycle;

$R^7$ is selected from hydrogen, —$(C_1$-$C_6)$alkyl, —$(C_2$-$C_6)$alkenyl, —$(C_2$-$C_6)$alkynyl, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, and $((C_4$-$C_{12})$cycloalkenyl)-$(C_1$-$C_6)$alkyl-;

$R^9$ and $R^{10}$ are each independently selected from hydrogen, —$(C_1$-$C_6)$alkyl, —$(C_2$-$C_6)$alkenyl, —$(C_2$-$C_6)$alkynyl, —$(C_1$-$C_{10})$alkoxy, —$(C_3$-$C_{12})$cycloalkyl, —$(C_3$-$C_{12})$cycloalkenyl, $((C_3$-$C_{12})$cycloalkyl)-$(C_1$-$C_6)$alkyl-, or $((C_3$-$C_{12})$cycloalkenyl)-$(C_1$-$C_6)$alkyl-;

Each $R^{11}$ is independently selected from hydrogen, —$(C_1$-$C_{10})$alkyl, —$(C_2$-$C_{10})$alkenyl, —$(C_2$-$C_{10})$alkynyl, —$(C_1$-$C_{10})$alkoxy, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, or $((C_4$-$C_{12})$cycloalkenyl)-$(C_1$-$C_6)$alkyl-;

$R^{12}$ and $R^{13}$ are each independently selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —(OCH$_2$CH$_2$)$_s$—O($C_1$-$C_6$)alkyl, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_4)$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —$(C_2$-$C_6)$alkenyl, —$(C_2$-$C_6)$alkynyl, hydroxy($C_1$-$C_6$)alkyl-, phenyl, benzyl, NH$_2$, NH($C_1$-$C_6$)alkyl-, CN, SH, OR$^4$, —CONR⁵R⁶, —COOR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R¹⁴ is selected from —COOR⁷, —(C₁-C₆)alkyl-CO—OR⁷, —C(=O)—(C₁-C₆)alkyl-COOR⁷, —(C₁-C₆)alkyl-C(=O)—(C₁-C₆)alkyl-COOR⁷, —CONH₂, —(C₁-C₆)alkyl-CONH;

G is selected from O, —OCO—, NR⁹, S, SO, and SO₂;

X is selected from OH, hydroxy(C₁-C₆)alkyl-, halogen, —NH₂, —NR²(C=O)R¹², CONR¹²R¹³, —(C₁-C₁₀)alkyl, —(C₂-C₁₀)alkenyl, —(C₂-C₁₀)alkynyl, —(C₁-C₁₀)alkoxy, —(OCH₂CH₂)ₛ—O(C₁-C₆)alkyl, —(OCH₂CH₂)ₛ—OH, —(NH₂)ₚCHOHCH₂OH—, CN and NH—SO₂R⁹;

Q is selected from OH, —(C₁-C₁₀)alkoxy, —(C₁-C₁₀)alkyl, —(C₃-C₁₂)cycloalkyl, -(5- to 12-membered)aryl, ((C₃-C₁₂)cycloalkyl)-(C₁-C₆)alkyl-, ((5- to 12-membered)aryl)-(C₁-C₆)alkyl-, —(OCH₂CH₂)ₛ—O(C₁-C₆)alkyl, —(OCH₂CH₂)ₛ—OH, —O(C=O)R⁹R¹⁰ and R¹⁴; provided that Q is not OMe;

Z is —(CH₂)ₘ—;

Y is —(CH₂)ₙ—CH— or a direct bond, provided that when Y is a direct bond then R⁸ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

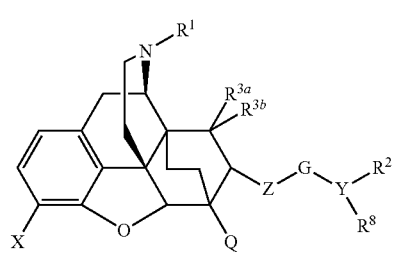

(I)

wherein

R¹ is selected from a) hydrogen, (C₁-C₁₀)alkoxy, ((5- to 12-membered)heteroaryl)-(C₁-C₆)alkyl-, and ((3- to 12-membered)heterocycle)-(C₁-C₆)alkyl-; any of which is optionally substituted with 1, 2, or 3 substituents independently selected from the group consisting of —(C₁-C₆)alkyl, OH, halo, —C(halo)₃, —CH(halo)₂, —CH₂(halo), NH₂, NH(C₁-C₆)alkyl-, NR⁹R¹⁰CN, —CONR⁹R¹⁰, —NR⁹COR¹⁰, SR¹¹, -(5- to 12-membered)carbocyclic ring, -(5- to 12-membered)heterocycle, phenyl, and benzyl; or b) —(C₁-C₁₀)alkyl, —(C₂-C₁₂)alkenyl, —(C₂-C₁₂)alkynyl, —(C₃-C₁₂)cycloalkyl, —(C₄-C₁₂)cycloalkenyl, ((C₃-C₁₂)cycloalkyl)-(C₁-C₆)alkyl-, ((C₄-C₁₂)cycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((3- to 12 membered)heterocycle)-(C₁-C₆)alkyl-, phenyl, or benzyl; each of which is substituted with 1, 2, or 3 substituents independently selected from the group consisting of NR⁹R¹⁰, —CONR⁹R¹⁰, —NR⁹COR¹⁰, and SR¹¹;

R² and R⁸ are each independently hydrogen, —(C₁-C₁₀)alkyl, —(C₂-C₁₂)alkenyl, —(C₂-C₁₂)alkynyl, —(C₁-C₁₀)alkoxy, —(OCH₂CH₂)ₛ—O(C₁-C₆)alkyl, NH₂, NH(C₁-C₆)alkyl-, CN, —CONR⁵R⁶, —(C₁-C₆)alkyl-CO—NR⁵R⁶, —COOR⁷, —(C₁-C₆)alkyl-CO—OR⁷, —(C₃-C₁₂)cycloalkyl, ((C₃-C₁₂)cycloalkyl)-(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, ((7- to 12-membered)bicycloheterocycle)-(C₁-C₆)alkyl-, phenyl, benzyl or naphthyl; each of which is optionally substituted with one or two substituents independently selected from the group consisting of OH, (=O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, phenyl, benzyl, NH₂, NH(C₁-C₆)alkyl-, —(C₁-C₆)alkyl-NH(C₁-C₆)alkyl-R¹⁴, CN, SH, OR⁴, —CONR⁵R⁶, —(C₁-C₆)alkyl-CO—NR⁵R⁶, —COOR⁷, —(C₁-C₆)alkyl-CO—OR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R³ᵃ and R³ᵇ are each independently selected from hydrogen, —(C₁-C₁₀)alkyl, —(C₂-C₁₀)alkenyl, —(C₂-C₁₀)alkynyl, —(C₁-C₁₀)alkoxy, OH, hydroxy(C₁-C₆)alkyl-, —C(halo)₃, —CH(halo)₂, or —CH₂(halo), or together form (=O);

R⁴ is selected from —(C₁-C₆)alkyl, —(C₂-C₆)alkenyl, —(C₂-C₆)alkynyl, —C(halo)₃, —CH(halo)₂, —CH₂(halo), hydroxy(C₁-C₆)alkyl-, —(C₃-C₁₂)cycloalkyl, ((C₃-C₁₂)cycloalkyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₄-C₁₂)cycloalkenyl, ((C₄-C₁₂)cycloalkenyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R⁵ and R⁶ are each independently hydrogen, —(C₁-C₆)alkyl, —(C₃-C₈)cycloalkyl, or ((C₃-C₈)cycloalkyl)-(C₁-C₆)alkyl-, —COOR⁷, —(C₁-C₆)alkyl-CO—OR⁷, CONH₂, or —(C₁-C₆)alkyl-CONH, or R⁵ and R⁶ together with the nitrogen atom to which they are attached form a (4- to 8-membered)heterocycle;

$R^7$ is selected from hydrogen, —$(C_1$-$C_6)$alkyl, —$(C_2$-$C_6)$alkenyl, —$(C_2$-$C_6)$alkynyl, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, and $((C_4$-$C_{12})$cycloalkenyl)-$(C_1$-$C_6)$alkyl-;

$R^9$ and $R^{10}$ are each independently selected from hydrogen, —$(C_1$-$C_6)$alkyl, —$(C_2$-$C_6)$alkenyl, —$(C_2$-$C_6)$alkynyl, —$(C_1$-$C_{10})$alkoxy, —$(C_3$-$C_{12})$cycloalkyl, —$(C_3$-$C_{12})$cycloalkenyl, $((C_3$-$C_{12})$cycloalkyl)-$(C_1$-$C_6)$alkyl-, or $((C_3$-$C_{12})$cycloalkenyl)-$(C_1$-$C_6)$alkyl-;

Each $R^{11}$ is independently selected from hydrogen, —$(C_1$-$C_{10})$alkyl, —$(C_2$-$C_{10})$alkenyl, —$(C_2$-$C_{10})$alkynyl, —$(C_1$-$C_{10})$alkoxy, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, or $((C_4$-$C_{12})$cycloalkenyl)-$(C_1$-$C_6)$alkyl-;

$R^{12}$ and $R^{13}$ are each independently selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(OCH_2CH_2)_s$—$O(C_1$-$C_6)$alkyl, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, phenyl, benzyl, NH$_2$, NH$(C_1$—$C_6)$alkyl-, CN, SH, OR$^4$, —CONR$^5$R$^6$, —COOR$^7$, —$(C_3$-$C_{12})$cycloalkyl, $((C_3$-$C_{12})$cycloalkyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^{14}$ is selected from —COOR$^7$, —$(C_1$-$C_6)$alkyl-CO—OR$^7$, —C(=O)—$(C_1$-$C_6)$alkyl-COOR$^7$, —$(C_1$-$C_6)$alkyl-C(=O)—$(C_1$-$C_6)$alkyl-COOR$^7$, CONH$_2$, CONH$(C_1$-$C_6)$alkyl-;

G is selected from O, —OCO—, NR$^9$, S, SO, and SO$_2$;

X is selected from OH, hydroxy$(C_1$-$C_6)$alkyl-, halogen, —NH$_2$, —NR$^2$(C=O)R$^8$, CONR$^{12}$R$^{13}$, —$(C_1$-$C_{10})$alkyl, —$(C_2$-$C_{10})$alkenyl, —$(C_2$-$C_{10})$alkynyl, —$(C_1$-$C_{10})$alkoxy, —$(OCH_2CH_2)_s$—$O(C_1$-$C_6)$alkyl, —$(OCH_2CH_2)_s$—OH, —$(CH_2)_p$CHOHCH$_2$OH—, CN and NH—SO$_2$R$^9$;

Q is selected from OH, —$(C_1$-$C_{10})$alkoxy, —$(C_1$-$C_{10})$alkyl, —$(C_3$-$C_{12})$cycloalkyl, -(5- to 12-membered)aryl, $((C_3$-$C_{12})$cycloalkyl)-$(C_1$-$C_6)$alkyl-, ((5- to 12-membered)aryl)-$(C_1$-$C_6)$alkyl-, —$(OCH_2CH_2)_s$—$O(C_1$-$C_6)$alkyl, —$(OCH_2CH_2)_s$—OH, —O(C=O)R$^9$R$^{10}$ and R$^{14}$;

Z is —$(CH_2)_m$—;

Y is —$(CH_2)_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

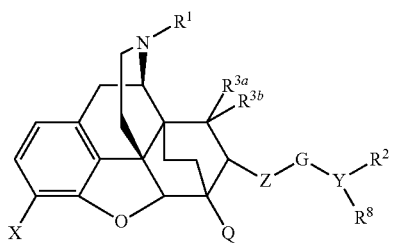

(I)

wherein $R^1$ is selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, $((C_4$-$C_{12})$cycloalkenyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, phenyl, and benzyl; each of which is optionally substituted with 1, 2, or 3 substituents independently selected from the group consisting of —$(C_1$-$C_6)$alkyl, OH, halo, —C(halo)$_3$, —CH(halo)$_2$, —CH$_2$(halo), NH$_2$, NH$(C_1$-$C_6)$alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

At least one of $R^2$ or $R^8$ is independently selected from:

a) —$(C_1$-$C_{10})$alkoxy, —$(OCH_2CH_2)_s$—$O(C_1$-$C_6)$alkyl, NH$_2$, NH$(C_1$-$C_6)$alkyl-, CN, —CONR$^5$R$^6$, —$(C_1$-$C_6)$alkyl-CO—NR$^5$R$^6$, —COOR$^7$, —$(C_1$-$C_6)$alkyl-CO—OR$^7$, $((C_4$-$C_{12})$cycloalkenyl)-$(C_1$-$C_6)$alkyl-, $((C_6$-$C_{14})$bicycloalkyl)-$(C_1$-$C_6)$alkyl-, $((C_8$-$C_{20})$tricycloalkyl)-$(C_1$-$C_6)$alkyl-, $((C_7$-$C_{14})$bicycloalkenyl)-$(C_1$-$C_6)$alkyl-, $((C_8$-$C_{20})$tricycloalkenyl)-$(C_1$-$C_6)$alkyl-, ((7- to 12-membered)bicyclic ring system)-$(C_1$-$C_6)$alkyl-, ((7- to 12-membered)bicyclic aryl)-$(C_1$-$C_6)$alkyl-, ((5- to 12-membered)heteroaryl)-$(C_1$-$C_6)$alkyl-, ((3- to 12 membered)heterocycle)-$(C_1$-$C_6)$alkyl-, ((7- to 12-membered)bicycloheterocycle)-$(C_1$-$C_6)$alkyl-, or naphthyl; each of which is optionally substituted with one or two substituents independently selected from the group consisting of OH, (=O), halo, —C(halo)$_3$, —CH(halo)$_2$, —CH$_2$(halo), —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, dihydroxy$(C_1$-$C_6)$alkyl-, phenyl, benzyl, NH$_2$, NH$(C_1$-$C_6)$alkyl-, —$(C_1$-$C_6)$alkyl-NH$(C_1$-$C_6)$alkyl-R$^{14}$, CN, SH, OR$^4$, —CONR$^5$R$^6$, —COOR$^7$, —$(C_1$-$C_6)$alkyl-CO—OR$^7$;

b) hydrogen, —$(C_1$-$C_{10})$alkyl, —$(C_2$-$C_{12})$alkenyl, —$(C_2$-$C_{12})$alkynyl, —$(C_3$-$C_{12})$cycloalkyl, —$((C_3$-$C_{12})$cycloalkyl)-$(C_1$-$C_6)$alkyl, —$(C_4$-$C_{12})$cycloalkenyl, —$(C_6$-$C_4)$bicycloalkyl, —$(C_8$-$C_{20})$tricycloalkyl, —$(C_7$-$C_{14})$bicycloalkenyl, —$(C_8$-$C_{20})$tricycloalkenyl, -(5- to 12-membered)aryl, ((5- to 12-membered)aryl)-$(C_1$-$C_6)$alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl and benzyl; each of which is substituted with one or two substituents independently selected from the group consisting of dihydroxy($C_1$-$C_6$)alkyl-, —($C_1$-$C_6$)alkyl-NH($C_1$-$C_6$)alkyl-$R^{14}$, and —($C_1$-$C_6$)alkyl-CO—$OR^7$, —($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, or —CH$_2$(halo), or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —$COOR^7$, —($C_1$-$C_6$)alkyl-CO—$OR^7$, —$CONH_2$, or —($C_1$-$C_6$)alkyl-CONH, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_9$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, $OR^4$, —$CONR^5R^6$, —$COOR^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —$COOR^7$, —($C_1$-$C_6$)alkyl-CO—$OR^7$, —C(=O)—($C_1$-$C_6$)alkyl-$COOR^7$, —($C_1$-$C_6$)alkyl-C(=O)—($C_1$-$C_6$)alkyl-$COOR^7$, —$CONH_2$, —($C_1$-$C_6$)alkyl-CONH;

G is selected from O, —OCO—, $NR^9$, S, SO, and $SO_2$;

X is selected from OH, hydroxy($C_1$-$C_6$)alkyl-, halogen, —NH$_2$, —$NR^2$(C=O)$R^{12}$, $CONR^{12}R^{13}$, —($C_1$-$C_{10}$)alkyl, —($C_2$-$C_{10}$)alkenyl, —($C_2$-$C_{10}$)alkynyl, —($C_7$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN and NH—$SO_2R^9$;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(OCH$_2$CH$_2$)$_s$—OH, —O(C=O)$R^9R^{10}$ and $R^{14}$;

Z is —(CH$_2$)$_m$—;

Y is —(CH$_2$)$_n$—CH— or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

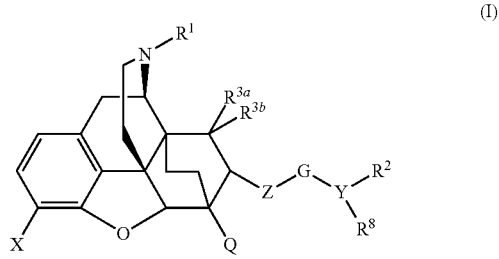

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; each of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$) alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered) heterocycle, phenyl, and benzyl;

R$^2$ and R$^8$ are each independently hydrogen, —($C_1$-$C_{10}$) alkyl, —($C_2$-$C_{12}$)alkenyl, —($C_2$-$C_{12}$)alkynyl, —($C_1$-$C_{10}$) alkoxy, —(OCH$_2$CH$_2$)$_s$—O($C_1$-$C_6$)alkyl, NH$_2$, NH($C_1$-$C_6$) alkyl-, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_4$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, phenyl, benzyl, NH$_2$, NH($C_1$-$C_6$)alkyl-, —($C_1$-$C_6$)alkyl-NH ($C_1$-$C_6$)alkyl-R$^{14}$, CN, SH, OR$^4$, —CONR$^5$R$^6$, —($C_1$-$C_6$)alkyl-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{3a}$ and R$^{3b}$ are each independently selected from —($C_1$-$C_{10}$)alkyl, —($C_2$-$C_{10}$)alkenyl, —($C_2$-$C_{10}$)alkynyl, and —($C_1$-$C_{10}$)alkoxy; provided that at least one of R$^{3a}$ or R$^{3b}$ is selected from —($C_7$-$C_{10}$)alkyl, —($C_7$-$C_{10}$)alkenyl, —($C_7$-$C_{10}$)alkynyl, or —($C_1$-$C_{10}$)alkoxy;

R$^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^5$ and R$^6$ are each independently hydrogen, —($C_1$-$C_6$) alkyl, —($C_3$-$C_8$)cycloalkyl, or (($C_3$-$C_8$)cycloalkyl)-($C_1$-$C_6$) alkyl-, —COOR$^7$, —($C_1$-$C_6$)alkyl-CO—OR$^7$, CONH$_2$, or —($C_1$-$C_6$)alkyl-CONH, or R$^5$ and R$^6$ together with the nitrogen atom to which they are attached form a (4- to 8-membered)heterocycle;

R$^7$ is selected from hydrogen, —($C_1$-$C_6$)alkyl, —($C_2$-$C_6$) alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

R$^9$ and R$^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each R$^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

R$^{12}$ and R$^{13}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$) alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$) bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered) bicyclic ring system)-($C_1$-$C_6$)alkyl-, -(7- to 12-membered) bicyclic aryl, ((7- to 12-membered)bicyclic aryl)-($C_1$-$C_6$) alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$, —COOR$^7$, —($C_3$-$C_{12}$)cycloalkyl, (($C_3$-$C_{12}$) cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$) alkyl-;

R$^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C (=O)—($C_1$-$C_6$)alkyl-COOR$^7$, CONH$_2$, —($C_1$-$C_6$)alkyl-CONH;

G is selected from O, —OCO—, NR$^9$, S, SO, and SO$_2$;

X is selected from OH, hydroxy($C_1$-$C_6$)alkyl-, halogen, —NH$_2$, —NR$^2$(C=O)R$^{12}$, CONR$^{12}$R$^{13}$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN and NH—SO$_2$R$^9$;

Q is selected from OH, —($C_1$-$C_{10}$)alkoxy, —($C_1$-$C_{10}$) alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(OCH$_2$CH$_2$)$_s$—OH, —O(C=O)R$^9$R$^{10}$ and R$^{14}$;

Z is —(CH$_2$)$_m$—;
Y is —(CH$_2$)$_n$—CH— or a direct bond, provided that when Y is a direct bond then R$^8$ is absent;
m is an integer 1, 2, 3, 4, 5, or 6;
n is an integer 0, 1, 2, 3, 4, 5 or 6;
p is an integer 0, 1 or 2;
s is an integer 1 to 13;
or a pharmaceutically acceptable salt, prodrug or solvate thereof.

In one embodiment, YR$^2$R$^8$ taken together form R$^{15}$.

In certain embodiments, the present invention provides novel compounds of Formula I as defined above, but having the general Formula II:

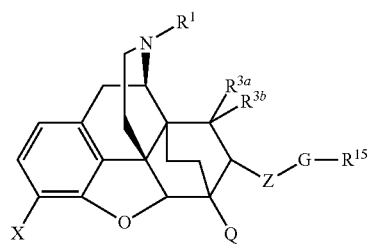

Wherein R$^1$, R$^{3a}$, R$^{3b}$, X, Q, and Z are as previously defined;
G is O or NH$_2$;
R$^{15}$ is selected from:

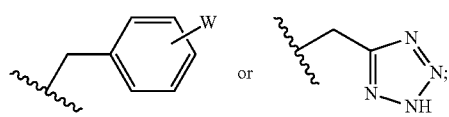

and
W is selected from:

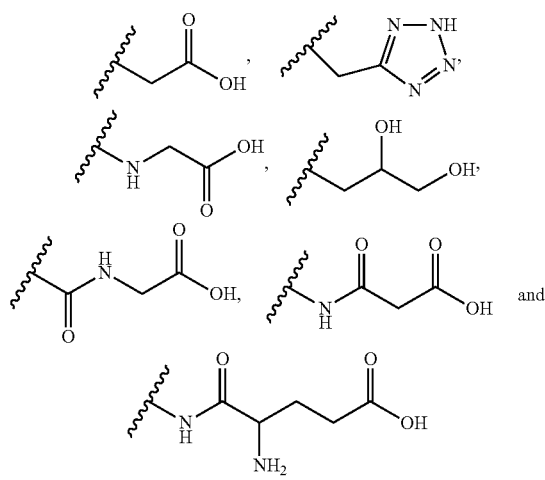

or a pharmaceutically acceptable salt, prodrug or solvate thereof.

In certain embodiments, the present invention provides novel compounds of Formula I having the general Formula II:

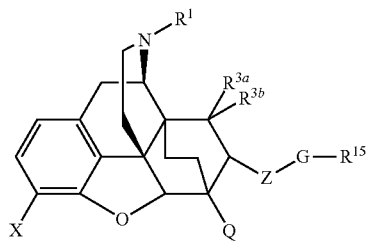

wherein R$^1$, R$^{3a}$, R$^{3b}$, X, Q, and Z are as previously defined;
G is O;
R$^{15}$ is selected from —(OCH$_2$CH$_2$)$_s$—O(C$_1$-C$_6$)alkyl,

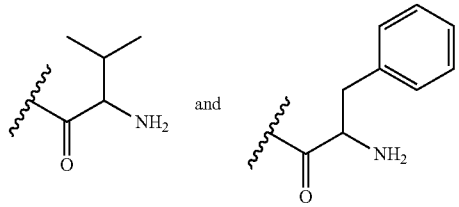

or a pharmaceutically acceptable salt, prodrug or solvate thereof.

In certain embodiments, the present invention provides novel compounds of Formula I having the general Formula II:

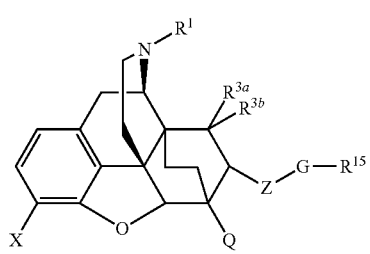

wherein R$^1$, R$^{3a}$, R$^{3b}$, X, Q, and Z are as previously defined;
G is NH;
R$^{15}$ is selected from —(OCH$_2$CH$_2$)$_s$—O(C$_1$-C$_6$)alkyl,

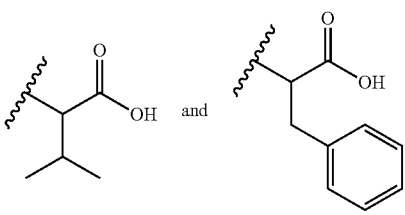

or a pharmaceutically acceptable salt, prodrug or solvate thereof.

The present invention further provides compounds of Formula I(A):

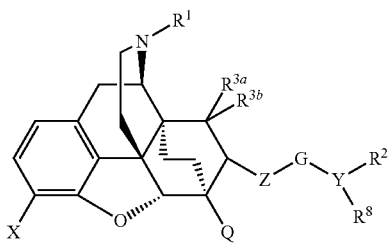

(IA)

wherein $R^1$ $R^2$, $R^{3a}$, $R^{3b}$, $R^8$, G, X, Q, Y, and Z are as defined above for Formula I.

In certain embodiments, the invention provides compounds of Formula I(B):

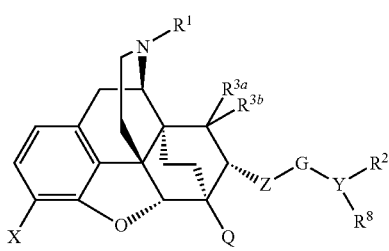

(IB)

wherein $R^1$ $R^2$, $R^{3a}$, $R^{3b}$, $R^8$, G, X, Q, Y, and Z are as defined above for Formula I.

In certain embodiments, the present invention provides novel compounds of Formula I wherein:

$R^1$ is $CH_3$ or cyclopropyl;

X is selected from F, $NH_2$, $NHCOCH_3$, $NHSO_2CH_3$, CN, $CO_2H$, $CONH_2$, —$(OCH_2CH_2)_s$—$O(C_1-C_6)$alkyl, and —$(OCH_2CH_2)_s$—OH;

or a pharmaceutically acceptable salt, prodrug or solvate thereof.

It is an object of certain embodiments of the present invention to provide new Compounds of the Invention that have antagonist activity at the ORL-1 receptor which is greater than compounds currently available, e.g., JTC-801 (described in WO 99/48492; and Shinkai et al., "4-aminoquinolines: Novel nociceptin antagonists with analgesic activity", J. Med. Chem., 2000, 43:4667-4677) and J-113397 (described in WO 98/54168; and Kawamoto et al., "Discovery of the first potent and selective small molecule opioid receptor-like (ORL-1) antagonist: 1-[(3R,4R)-1-cyclooctylmethyl-3-hydroxymethyl-4-piperidyl]-3-ethyl-1,3-dihydro-2H-benzimidazol-2-one (J-113397)", J. Med. Chem., 1999, 42:5061-6063).

Certain Compounds of the Invention have agonist activity at the μ, δ and/or κ receptors which is greater than currently available compounds, e.g., morphine.

Certain Compounds of the Invention have both: (i) antagonist activity at the ORL-1 receptor; and (ii) agonist activity at one or more of the μ, δ and/or κ receptors. Certain Compounds of the Invention have both: (i) antagonist activity at the ORL-1 receptor; and (ii) agonist activity at the μ receptor. Certain compounds of the invention will have both: (i) antagonist activity at the μ receptor; and (ii) agonist activity at the κ receptor. Certain compounds of the invention will have: (i) antagonist activity at the ORL-1 receptor; (ii) antagonist activity at the μ receptor; and (iii) agonist activity at the κ receptor. Certain compounds of the invention will have: (i) antagonist activity at the μ receptor; (ii) agonist activity at the κ receptor; and (iii) antagonist activity at the δ receptor.

Compounds of the Invention may be useful as analgesics; anti-inflammatories; diuretics; anesthetics; neuroprotective agents; anti-hypertensives; anxiolytics; agents for appetite control; hearing regulators; anti-tussives; anti-asthmatics; anti-epileptics; anti-convulsants; modulators of locomotor activity; modulators of learning and memory; regulators of neurotransmitter release; modulators of hormone release; kidney function modulators; anti-depressants; agents to treat memory loss due to Alzheimer's disease or other dementias; agents to treat withdrawal from alcohol and/or drugs of addiction; or agents to control water balance or sodium excretion; agents to treat arterial blood pressure disorders, UI, ulcers, IBD, IBS, diarrhea, constipation, addictive disorders, Parkinson's disease, parkinsonism, anxiety, epilepsy, stroke, a seizure, pruritic conditions, psychosis, cognitive disorders, memory deficits, restricted brain function, Huntington's chorea, ALS, dementia, retinopathy, muscle spasms, migraines, vomiting, dyskinesia, and/or depression (each being a "Condition").

The present invention further provides methods for treating a Condition, comprising administering to a subject in need thereof a therapeutically effective amount of a Compound of the Invention. In certain embodiments, the Condition is pain (chronic or acute pain). The Compounds of the Invention are particularly useful for treating chronic pain. In certain embodiments, the Compound of the Invention is an ORL-1 receptor antagonist. In other embodiments, the Compound of the Invention is an agonist at one or more of the μ, δ and/or κ receptor. In other embodiments, the Compound of the Invention is both an ORL-1 receptor antagonist and an agonist at one or more of the μ, δ and/or κ receptor. In other embodiments, the Compound of the Invention is both an ORL-1 receptor antagonist and an agonist at the μ receptor. In certain non-limiting embodiments, the Compound of the Invention produces fewer side effects and/or less severe side effects than currently available analgesic opioid compounds when administered at doses producing equivalent levels of analgesia and/or anti-hyperalgesia.

In certain non-limiting embodiments, the Compound of the Invention exhibits a substantially linear dose response curve, such that the bell-shaped dose response curve observed for most opioid analgesics (i.e. low and high doses do not produce significant analgesia, whereas mid-range doses produce analgesia) is not observed for the Compound of the Invention. It is expected, therefore, that it will be easier to titrate to an effective dose of the Compound of the Invention in a patient than it is for conventional opioid analgesics. It is further expected that the Compound of the Invention will produce effective analgesia and/or anti-hyperalgesia in a patient who has become tolerant to conventional opioids, and for whom a conventional opioid is no longer an effective treatment. It is further expected that a Compound of the Invention will produce effective analgesia and/or anti-hyperalgesia at doses that do not induce side effects such as respiratory depression in patients for whom a dose of a conventional opioid that is high enough to be an effective treatment also induces significant side effects such as respiratory depression.

The present invention further provides methods for preventing a Condition, comprising administering to an animal in need thereof a Condition-preventing effective amount of a Compound of the Invention.

Another object of the invention is to provide buprenorphine analog compounds useful for treating or preventing constipation, preferably μ opioid receptor-induced constipation. More specifically, the present invention provides compounds of Formula I below, and the pharmaceutically acceptable salts, prodrugs and solvates thereof having activity as µ receptor antagonists (collectively referred to hereafter as "Compounds of the Invention"; individually referred to hereafter as "Compound of the Invention"). In certain embodiments, Compounds of the Invention are expected to have dual activity as both µ receptor antagonists and κ receptor agonists. In other embodiments, Compounds of the Invention are expected to have an activity wherein they are µ receptor antagonists, κ receptor agonists, and Y receptor antagonists, and inactive at ORL-1 receptors. In yet other embodiments, certain Compounds of the Invention are expected to have an activity wherein they are µ receptor antagonists, κ receptor agonists, and δ receptor antagonists, and ORL-1 receptor antagonists. In other embodiments, certain Compounds of the Invention are expected to have an activity wherein they are µ receptor antagonists, κ receptor agonists, and δ receptor antagonists, and ORL-1 receptor partial agonists. Certain Compounds of the Invention are expected to be substantially restricted to the GI tract.

Compounds of the Invention that have µ antagonist activity and are substantially restricted to the GI tract will significantly reduce or prevent constipation that would otherwise occur in a patient as a result of treatment with a µ agonist. In one embodiment, the reduction or prevention of constipation is obtained without reducing the desired analgesic effect of the µ agonist. Compounds of the Invention that also exhibit κ agonist activity should additionally stimulate GI motility via a non-µ receptor mediated mechanism.

The present invention provides a method for treating a Condition in an animal. In certain embodiments, the Condition treated will be pain (acute or chronic pain). The present invention further provides a method for treating or preventing constipation, preferably constipation associated with µ-opioid agonist therapy, by administering an effective amount of a Compound of the Invention to a patient in need of such treatment or prevention. In one embodiment, the Compound of the Invention is a µ antagonist that is substantially restricted to the GI tract. In another embodiment, the Compound of the Invention is both a µ antagonist and a κ agonist, and is substantially restricted to the GI tract. In another embodiment, the method comprises co-administering to a patient both an effective amount of a Compound of the Invention that is a µ antagonist and is substantially restricted to the GI tract, and an analgesically effective amount of a µ agonist. In another embodiment, the method comprises co-administration to a patient of both an effective amount of a Compound of the Invention that is both a µ antagonist and a κ agonist, and which is substantially restricted to the GI tract, and an analgesically effective amount of a µ agonist.

The present invention further provides pharmaceutical compositions comprising a therapeutically effective amount of a Compound of the Invention admixed with a pharmaceutically acceptable carrier or excipient. Such compositions are useful for treating or preventing a Condition in an animal. The pharmaceutical compositions of the present invention may be formulated as immediate release formulations, or as controlled release formulations. Pharmaceutical compositions of the present invention may be formulated for administration by any of a number of different routes known in the art, including but not limited to, oral, intradermal, intramuscular, intraperitoneal, parenteral, intravenous, subcutaneous, intranasal, epidural, sublingual, intracerebral, intravaginal, transdermal, transmucosal, rectal, by inhalation, or topical (particularly to the ears, nose, eyes, or skin).

The present invention further provides methods for preparing a composition, comprising the step of admixing a Compound of the Invention and a pharmaceutically acceptable carrier or excipient to form a pharmaceutical composition.

The invention still further relates to a kit comprising a container containing an effective amount of a Compound of the Invention.

DETAILED DESCRIPTION OF THE INVENTION

Figure 1:
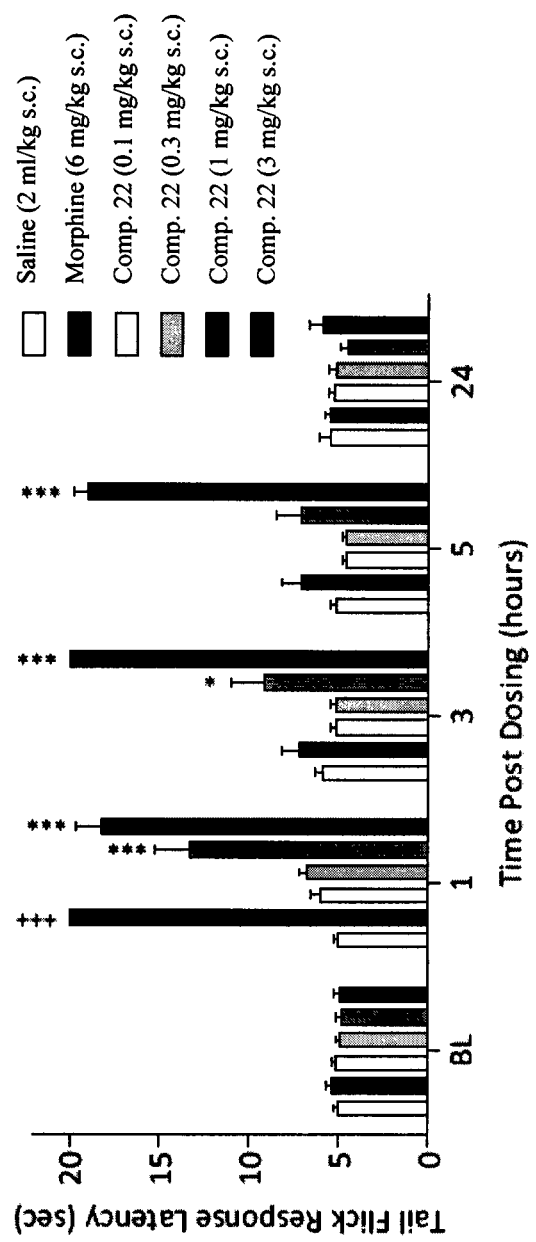
FIG. 1 shows tail flick latency in rats prior to drug administration (BL), and 1, 3, 5, and 24 hours after subcutaneous (s.c.) administration of either saline, 6 mg/kg morphine, or 0.1, 0.3, 1.0, or 3.0 mg/kg of Compound 22.

The Compounds of the Invention are novel buprenorphine analogs. They are useful for treating one or more Conditions, such as pain or constipation. Compounds of the Invention may provide a reduced liability for developing analgesic tolerance and physical dependence.

The Compounds of the Invention are useful for modulating a pharmacodynamic response from ORL-1 receptors either centrally or peripherally, or both. The Compounds of the Invention may also be useful for modulating a pharmacodynamic response from one or more opioid receptors (µ, δ, κ) either centrally or peripherally, or both. The pharmacodynamic response may be attributed to the compound stimulating (agonizing) or inhibiting (antagonizing) the one or more receptors. Certain Compounds of the Invention may inhibit (or antagonize) the ORL-1 receptor, while also stimulating (or agonizing) one or more other receptors (e.g. as a µ, δ and/or κ agonist). Compounds of the Invention having agonist activity may be either full or partial agonists.

In certain embodiments, Compounds of the Invention can be used in combination with at least one other therapeutic agent. The other therapeutic agent can be, but is not limited to, a µ-opioid agonist, a non-opioid analgesic, a non-steroidal anti-inflammatory agent, a Cox-II inhibitor, an anti-emetic, a β-adrenergic blocker, an anticonvulsant, an antidepressant, a $Ca^{2+}$-channel blocker, an anticancer agent, or a mixture thereof.

Various objects and advantages of the present invention will become apparent from the following detailed description.

The present invention provides novel compounds of Formula I:

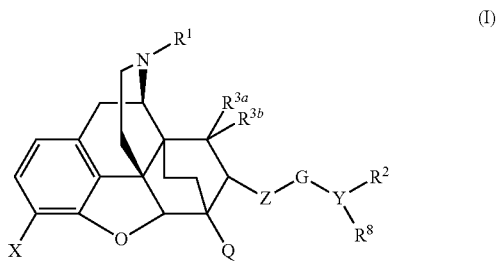

wherein
$R^1$ is selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(C_3$-

$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —CONR$^9$R$^{10}$, —NR$^9$COR$^{10}$, —SR$^{11}$, -(5- to 12-membered)carbocyclic ring, -(5- to 12-membered)heterocycle, phenyl, and benzyl;

R$^2$ and R$^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —CN, —SH, —OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{3a}$ and R$^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12-membered)heterocycle)-($C_1$-$C_6$)alkoxy-, ((3- to 12-membered)heterocycle)-($C_1$-$C_6$)alkoxy-($C_1$-$C_6$)alkyl-, or together form (=O);

R$^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^5$ and R$^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or R$^5$ and R$^6$ together with the nitrogen atom to which they are attached form a (4- to 8-membered)heterocycle;

R$^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

R$^9$ and R$^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

each R$^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

R$^{12}$ and R$^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)($C_1$-$C_6$)alkyl-, -(7- to 12-membered)bicyclic ring system, ((7- to 12-membered)bicyclic ring system)-($C_1$-$C_6$)alkyl-, -(7- to 12-membered)

bicyclic aryl, ((7- to 12-membered)bicyclic aryl)-($C_1$-$C_6$) alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy($C_1$-$C_6$)alkyl-, halogen, —NH$_2$, —NR$^2$(C=O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN, —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and $R^{14}$;

Z is —(CH$_2$)$_m$—, optionally substituted with 1 or 2-($C_1$-$C_6$)alkyl;

Y is —(CH$_2$)$_n$—CH or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

In one embodiment, the present invention provides novel compounds of Formula I:

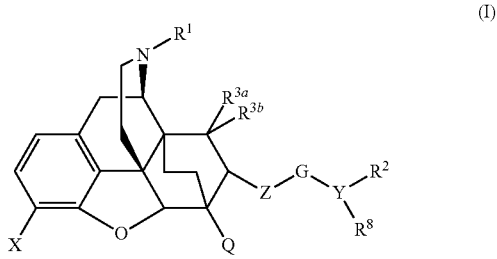

(I)

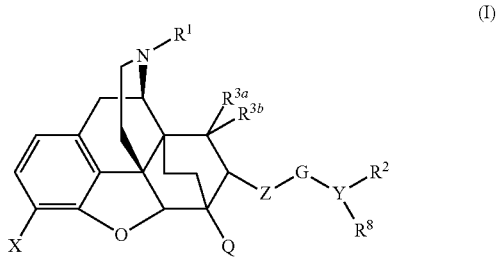

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, —NR$^9$R$^{10}$, —CN, —CONR$^9$R$^{10}$, —NR$^9$COR$^{10}$, —SR$^{11}$, -(5- to 12-membered)carbocyclic ring, -(5- to 12-membered)heterocycle, phenyl, and benzyl;

$R^2$ and $R^8$ are each independently hydrogen, —($C_1$-$C_{10}$)alkyl, —($C_2$-$C_{12}$)alkenyl, —($C_2$-$C_{12}$)alkynyl, —($C_7$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_4$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_4$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, —NH$_2$, —NH(C$_1$-C$_6$)alkyl, —(C$_1$-C$_6$)alkyl-NH(C$_1$-C$_6$)alkyl-R$^{14}$, —CN, —SH, —OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$—C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered) bicycloheterocycle, and ((7- to 12-membered) bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_2$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, ((3- to 12 membered)heterocycle)-(C$_1$-C$_6$)alkoxy-(C$_1$-C$_6$)alkyl-, or together form (=O);

R$^4$ is selected from —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^5$ and R$^6$ are each independently hydrogen, —(C$_1$-C$_6$)alkyl, —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-CO—OR$^7$, —CONH$_2$, or (C$_1$-C$_6$)alkyl-CONH—, or R$^5$ and R$^6$ together with the nitrogen atom to which they are attached form a (4- to 8-membered)heterocycle;

R$^7$ is selected from hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

R$^9$ and R$^{10}$ are each independently selected from hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, or ((C$_3$-C$_{12}$)cycloalkenyl)-(C$_1$-C$_6$)alkyl-;

each R$^{11}$ is independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, ((C$_1$-C$_6$)alkyl)sulfonyl(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, or ((C$_4$-C$_{12}$)cycloalkenyl)-(C$_1$-C$_6$)alkyl-;

R$^{12}$ and R$^{13}$ are each independently selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(C$_3$-C$_2$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)(C$_1$-C$_6$)alkyl-, -(7- to 12-membered)bicyclic ring system, ((7- to 12-membered) bicyclic ring system)-(C$_1$-C$_6$)alkyl-, -(7- to 12-membered) bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, phenyl, benzyl, NH$_2$, —NH(C$_1$-C$_6$)alkyl, CN, SH, OR$^4$, —CONR$^5$R$^6$, —COOR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{14}$ is selected from —COOR$^7$, —(C$_1$-C$_6$)alkyl-CO—OR$^7$, —C(=O)—(C$_1$-C$_6$)alkyl-COOR$^7$, —(C$_1$-C$_6$)alkyl-C(=O)—(C$_1$-C$_6$)alkyl-COOR$^7$, —CONH$_2$, (C$_1$-C$_6$)alkyl-CONH—;

G is selected from O, —OCO—, —C(=O), NR$^9$, NR', S, SO, and SO$_2$;

R' is —C(=O)(C$_1$-C$_6$)alkyl or —SO$_2$(C$_1$-C$_6$)alkyl;

X is selected from OH, hydroxy(C$_1$-C$_6$)alkyl-, dihydroxy(C$_1$-C$_6$)alkyl-, halogen, —NH$_2$, —NR$^2$(C=O)R$^{12}$, —CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O(C$_1$-C$_6$)alkyl, —(OCH$_2$CH$_2$)$_s$—OH, —(CH$_2$)$_p$CHOHCH$_2$OH, CN, —NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$;

Z is —(CH$_2$)$_m$—, optionally substituted with 1 or 2 —($C_1$-$C_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

provided that when X is OH or —($C_1$-$C_6$)alkoxy, Q is OMe, Z is unsubstituted, and G is O, then either:

a) R$^1$ is selected from;

iii. hydrogen, or ($C_1$-$C_{10}$)alkoxy or tetrazolyl-($C_1$-$C_6$)alkyl any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or iv. —($C_1$-$C_{10}$)alkyl, —($C_2$-$C_{12}$)alkenyl, —($C_2$-$C_{12}$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((3- to 12 membered)heterocycle)-, (5- to 12-membered)heteroaryl-($C_1$-$C_6$)alkyl-, (3- to 12-membered)heterocycle —($C_1$-$C_6$)alkyl-, phenyl, or benzyl; each of which is substituted with 1, 2, or 3 substituents independently selected from the group consisting of —($C_1$-$C_6$)alkyl-COOR$^7$, —COOR$^7$, NR$^9$R$^{10}$, —CONR$^9$R$^{10}$, —NR$^9$COR$^{10}$, and SR$^{11}$, provided that NR$^9$R$^{10}$ is other than NH$_2$ or —NH($C_1$-$C_6$)alkyl, and SR$^{11}$ is other than SH;

or b) at least one of R$^2$ and R$^8$ is selected from:

vii. —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, and —($C_1$-$C_6$)alkoxy-COOR$^7$; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; or viii. —($C_1$-$C_6$)alkyl-COOR$^7$, —($C_3$-$C_{12}$)cycloalkyl, —(($C_3$-$C_{12}$)cycloalkyl)-($C_1$-$C_6$)alkyl, —($C_4$-$C_{12}$)cycloalkenyl, —($C_6$-$C_{14}$)bicycloalkyl, —($C_8$-$C_{20}$)tricycloalkyl, —($C_7$-$C_{14}$)bicycloalkenyl, —($C_8$-$C_{20}$)tricycloalkenyl, -(5- to 12-membered)aryl, ((5- to 12-membered)aryl)-($C_1$-$C_6$)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl, benzyl, (($C_4$-$C_{12}$)cycloalkenyl)-($C_1$-$C_6$)alkyl-, (($C_6$-$C_{14}$)bicycloalkyl)-($C_1$-$C_6$)alkyl-, (($C_8$-$C_{20}$)tricycloalkyl)-($C_1$-$C_6$)alkyl-, (($C_7$-$C_{14}$)bicycloalkenyl)-($C_1$-$C_6$)alkyl-, (($C_8$-$C_{20}$)tricycloalkenyl)-($C_1$-$C_6$)alkyl-, ((7- to 12-membered)bicyclic ring system)-($C_1$-$C_6$)alkyl-, ((7- to 12-membered)bicyclic aryl)-($C_1$-$C_6$)alkyl-, ((5- to 12-membered)heteroaryl)-($C_1$-$C_6$)alkyl-, ((3- to 12 membered)heterocycle)-($C_1$-$C_6$)alkyl-, ((7- to 12-membered)bicycloheterocycle)-($C_1$-$C_6$)alkyl-, and naphthyl; each of which is substituted with one or two substituents independently selected from the group consisting of —CONHR$^6$, dihydroxy($C_1$-$C_6$)alkyl-, —($C_1$-$C_6$)alkyl-NH($C_1$-$C_6$)alkyl-R$^{14}$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$—(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; or ix. —($C_1$-$C_{10}$)alkyl, —($C_2$-$C_{12}$)alkenyl, and —($C_2$-$C_{12}$)alkynyl, each of which is substituted with one or two substituents independently selected from the group consisting of —CONHR$^6$, —($C_1$-$C_6$)alkyl-NH($C_1$-$C_6$)

alkyl-$R^{14}$, —($C_1$-$C_6$)alkoxy-COO$R^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—O$R^7$, —NH—C(=O)—($C_1$-$C_6$)alkyl-CO—O$R^7$, —NH—C(=O)—CH(NH$_2$)—($C_1$-$C_6$)alkyl-CO—O$R^7$, —($C_1$-$C_6$)alkoxyC(O)N$R^5R^6$, —NH—($C_1$-$C_6$)alkylC(O)—N$R^5R^6$, or —C(O)NH—($C_1$-$C_6$)alkyl-COO$R^7$; or x. 2,3-dihydroxypropyl; or xi. 4-isoxazolyl, 4-isoxazolyl($C_1$-$C_6$)alkyl, 5-isoxazolyl, or 5-isoxazolyl($C_1$-$C_6$)alkyl substituted with one or two alkyl groups, or xii. —C(=O)NH$_2$ or —($C_1$-$C_6$)alkyl-C(=O)NH$_2$;
or c) at least one of $R^{3a}$ or $R^{3b}$ is independently selected from —($C_7$-$C_{10}$)alkyl, —($C_7$-$C_{10}$)alkenyl, —($C_7$-$C_{10}$)alkynyl, —($C_1$-$C_{10}$)alkoxy, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COO$R^7$, —($C_1$-$C_6$)alkoxy-COO$R^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-; or provided that when X is OH or —($C_1$-$C_6$)alkoxy, Q is OMe, $R^{3a}$ and $R^{3b}$ are both hydrogen, Z is substituted, G is O, and Y is a bond, then $R^2$ is other than hydrogen.

or a pharmaceutically acceptable salt, prodrug or solvate thereof.

In another embodiment, the present invention provides novel compounds of Formula I:

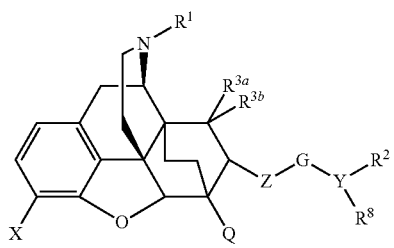

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COO$R^7$, —COO$R^7$, NH$_2$, —NH($C_1$-$C_6$)alkyl, N$R^9R^{10}$, CN, —CON$R^9R^{10}$, —N$R^9$CO$R^{10}$, S$R^{11}$, -(5- to 12-membered) carbocyclic ring, -(5- to 12-membered)heterocycle, phenyl, and benzyl;

$R^2$ and $R^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CON$R^5R^6$, —($C_1$-$C_6$alkyl)-CO—N$R^5R^6$, —($C_1$-$C_6$)alkyl-CO—N$R^5R^6$, —COO$R^7$, —($C_1$-$C_6$)alkyl-CO—O$R^7$, —($C_1$-$C_6$)alkoxy-COO$R^7$, —($C_3$-$C_{12}$)cycloalkyl, (($C_3$-$C_2$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_4$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl and naphthyl; any of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy) CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-$R^{14}$, CN, SH, O$R^4$, —CON$R^5R^6$, —COO$R^7$, —($C_1$-$C_6$)alkyl-CO—O$R^7$, —($C_1$-$C_6$)alkoxy-COO$R^7$, —(OCH$_2$CH$_2$)$_s$—O($C_1$-$C_6$)alkyl, —(CH$_2$CH$_2$O)—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—O$R^7$, —NH—C(=O)—($C_1$-$C_6$)alkyl-CO—O$R^7$, —NH—C(=O)—CH(NH$_2$)—($C_1$-$C_6$)alkyl-CO—O$R^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)N$R^5R^6$, —NH—($C_1$-$C_6$)alkylC(O)—N$R^5R^6$, —C(O)NH—($C_1$-$C_6$)alkyl-COO$R^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COO$R^7$, —($C_1$-$C_6$)alkoxy-COO$R^7$, —($C_3$-$C_{12}$)cycloalkyl, (($C_3$-$C_{12}$)

cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$)alkoxy-($C_1$-$C_6$)alkyl-, or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_4$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-CO—OR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from hydroxy($C_1$-$C_6$)alkyl-, dihydroxy($C_1$-$C_6$)alkyl-, halogen, —NH$_2$, —NR$^2$(C=O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_7$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN, —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$;

Z is —(CH$_2$)$_m$—, optionally substituted with 1 or 2-($C_1$-$C_6$)alkyl;

Y is —(CH$_2$)$_n$—CH or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

In another embodiment, the present invention provides novel compounds of Formula I:

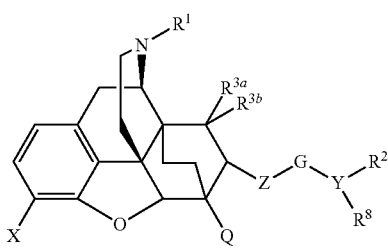

(I)

wherein

R¹ is selected from hydrogen, —(C₁-C₁₀)alkyl, —(C₂-C₁₂)alkenyl, —(C₂-C₁₂)alkynyl, —(C₁-C₁₀)alkoxy, —(C₃-C₁₂)cycloalkyl, —(C₄-C₁₂)cycloalkenyl, ((C₃-C₁₂)cycloalkyl)-(C₁-C₆)alkyl-, ((C₄-C₁₂)cycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, phenyl, and benzyl; any of which is optionally substituted with 1, 2, or 3 substituents independently selected from the group consisting of —(C₁-C₆)alkyl, OH, halo, —C(halo)₃, —CH(halo)₂, —CH₂(halo), —(C₁-C₆)alkyl-COOR⁷, —COOR⁷, NH₂, —NH(C₁-C₆)alkyl, —NR⁹R¹⁰, CN, —CONR⁹R¹⁰, —NR⁹COR¹⁰, SR¹¹, -(5- to 12-membered)carbocyclic ring, -(5- to 12-membered)heterocycle, phenyl, and benzyl;

R² and R⁸ are each independently hydrogen, —(C₁-C₁₀)alkyl, —(C₂-C₁₂)alkenyl, —(C₂-C₁₂)alkynyl, —(C₁-C₁₀)alkoxy, —(OCH₂CH₂)ₛ—O(C₁-C₆)alkyl, —(CH₂CH₂O)ₛ—(C₁-C₆)alkyl, NH₂, —NH(C₁-C₆)alkyl, CN, —CONR⁵R⁶, —(C₁-C₆)alkyl-CO—NR⁵R⁶, —COOR⁷, —(C₁-C₆)alkyl-CO—OR⁷, —(C₁-C₆)alkoxy-COOR⁷, —(C₃-C₁₂)cycloalkyl, ((C₃-C₁₂)cycloalkyl)-(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, ((7- to 12-membered)bicycloheterocycle)-(C₁-C₆)alkyl-, phenyl, benzyl or naphthyl; each of which is optionally substituted with one or two substituents independently selected from the group consisting of OH, (=O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, —(C₁-C₆)alkoxy, ((C₁-C₆)alkoxy)CO(C₁-C₆)alkoxy-, phenyl, benzyl, NH₂, —NH(C₁—C₆)alkyl, —(C₁-C₆)alkyl-NH(C₁-C₆)alkyl-R¹⁴, CN, SH, OR⁴, —CONR⁵R⁶, —(C₁-C₆alkyl)-CO—NR⁵R⁶, —COOR⁷, —(C₁-C₆)alkyl-CO—OR⁷, —(C₁-C₆)alkoxy-COOR⁷, —(OCH₂CH₂)ₛ—O(C₁-C₆)alkyl, —(CH₂CH₂O)ₛ—(C₁-C₆)alkyl, ((C₁-C₆)alkyl)sulfonyl(C₁—C₆)alkyl-, —N(SO₂(C₁-C₆)alkyl)₂, —C(=NH)NH₂, —NH—CO—(C₁-C₆)alkyl, —NH—CO—NH₂, —NH—C(=O)—NH—(C₁-C₆)alkyl, —NH—C(=O)-(5- to 12-membered)aryl, —NH—C(=O)—(C₁-C₆)alkyl-(5- to 12-membered)aryl, —NH—(C₁-C₆)alkyl-CO—OR⁷, —NH—C(=O)—(C₁-C₆)alkyl-CO—OR⁷, —NH—C(=O)—CH(NH₂)—(C₁-C₆)alkyl-CO—OR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, -(5- to 12-membered)aryloxy, —(C₁-C₆)alkoxyC(O)NR⁵R⁶, —NH—(C₁-C₆)alkylC(O)—NR⁵R⁶, —C(O)NH—(C₁-C₆)alkyl-COOR⁷, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R³ᵃ and R³ᵇ are each independently selected from hydrogen, —(C₁-C₁₀)alkyl, —(C₂-C₁₀)alkenyl, —(C₂-C₁₀)alkynyl, —(C₁-C₁₀)alkoxy, OH, hydroxy(C₁-C₆)alkyl-, —C(halo)₃, —CH(halo)₂, —CH₂(halo), —(C₁-C₆)alkyl-C(=O)—(C₁-C₆)alkoxy, —(C₁-C₆)alkoxy-C(=O)—(C₁-C₆)alkyl, —(C₁-C₆)alkyl-CN, —(C₁-C₆)alkyl-COOR⁷, —(C₁-C₆)alkoxy-COOR⁷, —(C₃-C₁₂)cycloalkyl, ((C₃-C₁₂)cycloalkyl)-(C₁-C₆)alkyl-, ((C₃-C₁₂)cycloalkyl)-(C₁-C₆)alkoxy-, ((C₃-C₁₂)cycloalkyl)-(C₁-C₆)alkoxy-(C₁-C₆)alkyl-, —(C₄-C₁₂)cycloalkenyl, ((C₄-C₁₂)cycloalkenyl)-(C₁-C₆)alkyl-, ((C₄-C₁₂)cycloalkenyl)-(C₁-C₆)alkoxy-, ((C₄-C₁₂)cycloalkenyl)-(C₁-C₆)alkoxy-(C₁-C₆)alkyl-, -(5- to 12-membered)aryl, ((5- to 12-membered)aryl)-(C₁-C₆)alkyl-, ((5- to 12-membered)aryl)-(C₁-C₆)alkoxy-, ((5- to 12-membered)aryl)-(C₁-C₆)alkoxy-(C₁-C₆)alkyl-, -(5- to 12-membered)heteroaryl, ((5- to 12-membered)heteroaryl)-(C₁-C₆)alkyl-, ((5- to 12-membered)heteroaryl)-(C₁-C₆)alkoxy-, ((5- to 12-membered)heteroaryl)-(C₁-C₆)alkoxy-(C₁-C₆)alkyl-, -(3- to 12-membered)heterocycle, ((3- to 12 membered)heterocycle)-(C₁-C₆)alkyl-, ((3- to 12 membered)heterocycle)-(C₁-C₆)alkoxy-, ((3- to 12 membered)heterocycle)-(C₁-C₆)alkoxy-(C₁-C₆)alkyl-, or together form (=O);

R⁴ is selected from —(C₁-C₆)alkyl, —(C₂-C₆)alkenyl, —(C₂-C₆)alkynyl, —C(halo)₃, hydroxy(C₁-C₆)alkyl-, —(C₃-C₁₂)cycloalkyl, ((C₃-C₁₂)cycloalkyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₄-C₁₂)cycloalkenyl, ((C₄-C₁₂)cycloalkenyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R⁵ and R⁶ are each independently hydrogen, —(C₁-C₆)alkyl, —(C₃-C₈)cycloalkyl, ((C₃-C₈)cycloalkyl)-(C₁-C₆)alkyl-, —COOR⁷, —(C₁-C₆)alkyl-CO—OR⁷, —CONH₂, or (C₁-C₆)alkyl-CONH—, or R⁵ and R⁶ together with the nitrogen atom to which they are attached form a (4- to 8-membered)heterocycle;

R⁷ is selected from hydrogen, —(C₁-C₆)alkyl, —(C₂-C₆)alkenyl, —(C₂-C₆)alkynyl, —(C₃-C₁₂)cycloalkyl, —(C₄-C₁₂)cycloalkenyl, ((C₃-C₁₂)cycloalkyl)-(C₁-C₆)alkyl-, and ((C₄-C₁₂)cycloalkenyl)-(C₁-C₆)alkyl-;

R⁹ and R¹⁰ are each independently selected from hydrogen, —(C₁-C₆)alkyl, —(C₂-C₆)alkenyl, —(C₂-C₆)alkynyl, —(C₁-C₁₀)alkoxy, —(C₃-C₁₂)cycloalkyl, —(C₃-C₁₂)cycloalkenyl, ((C₃-C₁₂)cycloalkyl)-(C₁-C₆)alkyl-, or ((C₃-C₁₂)cycloalkenyl)-(C₁-C₆)alkyl-;

each R¹¹ is independently selected from hydrogen, —(C₁-C₁₀)alkyl, —(C₂-C₁₀)alkenyl, —(C₂-C₁₀)alkynyl, —(C₁-

$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_2$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered) bicyclic ring system)-($C_1$-$C_6$)alkyl-, -(7- to 12-membered) bicyclic aryl, ((7- to 12-membered)bicyclic aryl)-($C_1$-$C_6$) alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$) alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, ($C_1$-$C_6$)alkyl-CONH—;

G is selected from —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy ($C_1$-$C_6$)alkyl-, halogen, —NH$_2$, —NR$^2$(C=O)R$^{12}$, CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O ($C_1$-$C_6$)alkyl, —(OCH$_2$CH$_2$)$_s$—OH, —(CH$_2$)$_p$ CHOHCH$_2$OH, CN and —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered) aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$) alkyl, —($C_3$-$C_{12}$)cycloalkyl, -(5- to 12-membered)aryl, (($C_3$-$C_{12}$)cycloalkyl)-($C_1$-$C_6$)alkyl-, (5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$) alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$;

Z is —(CH$_2$)$_m$—, optionally substituted with 1 or 2-($C_1$-$C_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

provided that when X is OH or —($C_1$-$C_6$)alkoxy, Q is OMe, Z is unsubstituted, G is OCO, and Y is a direct bond, then either:

a) R$^1$ is selected from;
  iii. hydrogen, or ($C_1$-$C_{10}$)alkoxy or tetrazolyl-($C_1$-$C_6$) alkyl, any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or
  iv. —($C_1$-$C_{10}$)alkyl, —($C_2$-$C_{12}$)alkenyl, —($C_2$-$C_{12}$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((3- to 12 membered)heterocycle)-, (5- to 12-membered)heteroaryl-($C_1$-$C_6$)alkyl-, (3- to 12-membered)heterocycle —($C_1$-$C_6$)alkyl-, phenyl, or benzyl; each of which is substituted with 1, 2, or 3 substituents independently selected from the group consisting of —($C_1$-$C_6$)alkyl-COOR$^7$, —COOR$^7$, NR$^9$R$^{10}$, —CONR$^9$R$^{10}$, —NR$^9$COR$^{11}$, and SR$^{11}$, provided that NR$^9$R$^{10}$ is other than NH$_2$ or —NH($C_1$-$C_6$)alkyl, and SR$^{11}$ is other than SH;

or b) R$^2$ is selected from:
  iii. —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, CONHR$^6$, —($C_1$-$C_6$) alkyl-CO—NHR$^6$, —($C_1$-$C_6$)alkoxy-COOR$^7$, —($C_3$-$C_{12}$)cycloalkyl, —($C_4$-$C_{12}$)cycloalkenyl, —($C_6$-$C_{14}$)bicycloalkyl, —($C_8$-$C_{20}$)tricycloalkyl, —($C_7$-$C_{14}$) bicycloalkenyl, —($C_8$-$C_{20}$)tricycloalkenyl, -(7- to 12-membered)bicyclic ring system, -(7- to 12-membered)bicyclic aryl, -(5- to 12-membered)heteroaryl, -(3- to 12-membered)heterocycle, -(7- to 12-membered) bicycloheterocycle, (($C_4$-$C_{12}$)cycloalkenyl)-($C_1$-$C_6$) alkyl-, (($C_6$-$C_{14}$)bicycloalkyl)-($C_1$-$C_6$)alkyl-, (($C_8$-$C_{20}$) tricycloalkyl)-($C_1$-$C_6$)alkyl-, (($C_7$-$C_{14}$)bicycloalkenyl)-($C_1$-$C_6$)alkyl-, (($C_9$-$C_{20}$)tricycloalkenyl)-($C_1$-$C_6$)alkyl-, ((7- to 12-membered)bicyclic ring system)-($C_1$-$C_6$) alkyl-, ((7- to 12-membered)bicyclic aryl)-($C_1$-$C_6$) alkyl-, ((5- to 12-membered)heteroaryl)-($C_1$-$C_6$)alkyl-, ((3- to 12 membered)heterocycle)-($C_1$-$C_6$)alkyl-, ((7- to 12-membered)bicycloheterocycle)-($C_1$-$C_6$)alkyl-, and naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)

alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, NH$_2$, —NH(C$_1$-C$_6$)alkyl, —(C$_1$-C$_6$)alkyl-NH(C$_1$-C$_6$)alkyl-R$^{14}$, CN, SH, OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; or iv. —(C$_1$-C$_{10}$)alkyl, —(C$_2$-C$_{12}$)alkenyl, —(C$_2$-C$_{12}$)alkenyl, —(C$_1$-C$_6$)alkyl-CO—OR$^7$, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, phenyl, and benzyl; each of which is substituted with one or two substituents independently selected from the group consisting of —CONHR$^6$, dihydroxy(C$_1$-C$_6$)alkyl-, —(C$_1$-C$_6$)alkyl-NH(C$_1$-C$_6$)alkyl-R$^{14}$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; or c) at least one of R$^{3a}$ or R$^{3b}$ is independently selected from —(C$_7$-C$_{10}$)alkyl, —(C$_7$-C$_{10}$)alkenyl, —(C$_7$-C$_{10}$)alkynyl, —(C$_1$-C$_{10}$)alkoxy, —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, and ((3- to 12 membered)heterocycle)-(C$_1$-C$_6$)alkoxy-(C$_1$-C$_6$)alkyl-.

provided that when X is OH or —(C$_1$-C$_6$)alkoxy, Q is OMe, R$^{3a}$ and R$^{3b}$ are both hydrogen, Z is substituted, G is O, and Y is a bond, then R$^2$ is other than hydrogen.

or a pharmaceutically acceptable salt, prodrug or solvate thereof.

In another embodiment, the present invention provides novel compounds of Formula I:

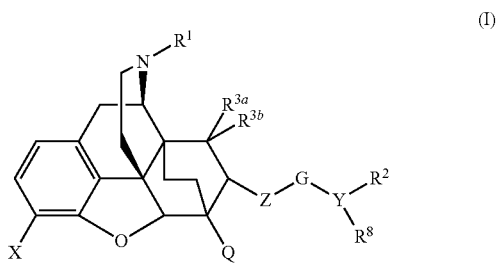

(I)

wherein

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, NH$_2$, —NH(C$_1$-C$_6$)alkyl, CN, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-$R^{14}$, CN, SH, $OR^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$)alkoxy-($C_1$-$C_6$)alkyl-, or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy($C_1$-$C_6$)alkyl-, halogen, —NH$_2$, —NR$^2$(C=O)R$^{12}$, CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN and —NH—SO$_2$R$^9$, —($C_3$-$C_{12}$)cycloalkyl, (($C_3$-$C_2$)cycloalkyl)-($C_1$-$C_6$)alkyl-, (($C_3$-$C_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-;

Q is selected from OH, —(C$_2$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$)$_s$—OH, —O(C=O)R$^9$, —O—(C$_1$-C$_6$)alkyl-COOR$^7$, —NH—(C$_1$-C$_6$)alkyl-COOR$^7$, —O—C(O)—(C$_1$-C$_6$)alkyl-C(O)OR$^7$, —NH—C(O)—(C$_1$-C$_6$)alkyl-C(O)OR$^7$, —O—(C$_1$-C$_6$)alkyl-C(O)NR$^9$R$^{10}$, —NH—(C$_1$-C$_6$)alkyl-C(O)NR$^9$R$^{10}$, —O—C(O)—(C$_1$-C$_6$)alkyl-C(O)NR$^9$R$^{10}$, —NH—C(O)—(C$_1$-C$_6$)alkyl-C(O)NR$^9$R$^{10}$ and R$^{14}$;

Z is —(CH$_2$)$_m$—, optionally substituted with 1 or 2-(C$_1$-C$_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

In another embodiment, the present invention provides novel compounds of Formula I:

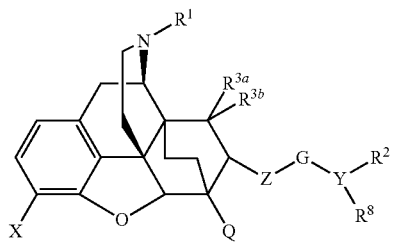

(I)

wherein

R$^1$ is selected from c) hydrogen, or (C$_1$-C$_{10}$)alkoxy or tetrazolyl-(C$_1$-C$_6$)alkyl-; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or d) —(C$_1$-C$_{10}$)alkyl, —(C$_2$-C$_{12}$)alkenyl, —(C$_2$-C$_{12}$)alkynyl, —(C$_3$-C$_2$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((3- to 12 membered)heterocycle)-, (5- to 12-membered)heteroaryl-(C$_1$-C$_6$)alkyl-, (3- to 12-membered)heterocycle-(C$_1$-C$_6$)alkyl, phenyl, or benzyl; each of which is substituted with 1, 2, or 3 substituents independently selected from the group consisting of —(C$_1$-C$_6$)alkyl-COOR$^7$, —COOR$^7$, NR$^9$R$^{10}$, —CONR$^9$R$^{10}$, —NR$^9$COR$^{10}$, and SR$^{11}$, provided that NR$^9$R$^{10}$ is other than NH$_2$ or —NH(C$_1$-C$_6$)alkyl, and SR$^{11}$ is other than SH;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, NH$_2$, —NH(C$_1$-C$_6$)alkyl, CN, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, NH$_2$, —NH(C$_1$-C$_6$)alkyl, —(C$_1$-C$_6$)alkyl-NH(C$_1$-C$_6$)alkyl-R$^{14}$, CN, SH, OR$^4$, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-($C_1$-$C_6$)alkoxy-, ((5- to 12-membered) aryl)-($C_1$-$C_6$)alkoxy-($C_1$-$C_6$)alkyl-, -(5- to 12-membered) heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$) alkoxy-($C_1$-$C_6$)alkyl-, or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$) alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$) alkyl, —($C_3$-$C_8$)cycloalkyl, or (($C_3$-$C_8$)cycloalkyl)-($C_1$-$C_6$) alkyl-, —COOR$^7$, —($C_1$-$C_6$)alkyl-CO—OR$^7$, CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$) alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$) cycloalkenyl)-($C_1$-$C_6$)alkyl-;

each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_2$)cycloalkenyl, (($C_4$-$C_{12}$)cycloalkenyl)-($C_1$-$C_6$) alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered) bicyclic ring system)-($C_1$-$C_6$)alkyl-, -(7- to 12-membered) bicyclic aryl, ((7- to 12-membered)bicyclic aryl)-($C_1$-$C_6$) alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$) cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$) alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, —CONH($C_1$-$C_6$) alkyl;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy ($C_1$-$C_6$)alkyl-, halogen, —NH$_2$, —NR$^2$(C=O)R$^8$, CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN, NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered) bicycloheterocycle)-($C_1$-$C_6$)alkoxy-;

Q is selected from OH, —($C_1$-$C_{10}$)alkoxy, —($C_1$-$C_{10}$) alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$) alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$ and R$^{14}$;

Z is —(CH$_2$)$_m$—, optionally substituted with 1 or 2-($C_1$-$C_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

In another embodiment, the present invention provides novel compounds of Formula I:

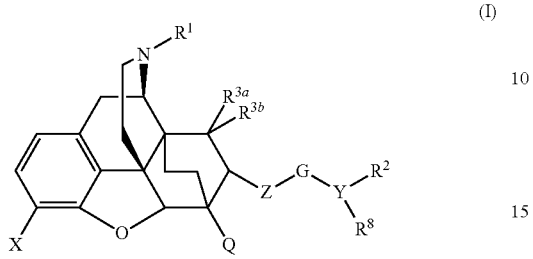

(I)

wherein

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; each of which is optionally substituted with 1, 2, or 3 substituents independently selected from the group consisting of —(C$_1$-C$_6$)alkyl, —OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, NR$^9$R$^{10}$, —CN, —CONR$^9$R$^{10}$, —NR$^9$COR$^{10}$, —SR$^{11}$, -(5- to 12-membered)carbocyclic ring, -(5- to 12-membered)heterocycle, phenyl, and benzyl;

R$^2$ is:

g) —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, and —(C$_1$-C$_6$)alkoxy-COOR$^7$; each of which is optionally substituted with one or two substituents independently selected from the group consisting of OH, (═O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, NH$_2$, —NH(C$_1$-C$_6$)alkyl, —(C$_1$-C$_6$)alkyl-NH(C$_1$-C$_6$)alkyl-R$^{14}$, CN, SH, OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NHSO$_2$(C$_1$-C$_6$)alkyl, —N(SO$_2$(C$_1$—C$_6$)alkyl)$_2$, —C(═NH)NH$_2$, —NH—CO—(C$_1$-C$_6$)alkyl, —NH—CO—NH$_2$, —NH—C(═O)—NH—(C$_1$-C$_6$)alkyl, —NH—C(═O)-(5- to 12-membered)aryl, —NH—C(═O)—(C$_1$-C$_6$)alkyl-(5- to 12-membered)aryl, —NH—(C$_1$-C$_6$)alkyl-CO—OR$^7$, —NH—C(═O)—(C$_1$-C$_6$)alkyl-CO—OR$^7$, —NH—C(═O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, -(5- to 12-membered)aryloxy, —(C$_1$-C$_6$)alkoxyC(O)NR$^5$R$^6$, —NH—(C$_1$-C$_6$)alkylC(O), NR$^5$R$^6$, —C(O)NH—(C$_1$-C$_6$)alkyl-COOR$^7$, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; or h) —(C$_1$-C$_6$)alkyl-CO—OR$^7$, —(C$_3$-C$_{12}$)cycloalkyl, —((C$_3$-C$_{12}$)cycloalkyl)-(C$_1$-C$_6$)alkyl, —(C$_4$-C$_{12}$)cycloalkenyl, —(C$_6$-C$_{14}$)bicycloalkyl, —(C$_8$-C$_{20}$)tricycloalkyl, —(C$_7$-C$_{14}$)bicycloalkenyl, —(C$_8$-C$_{20}$)tricycloalkenyl, -(5- to 12-membered)aryl, ((5- to 12-membered)aryl)-(C$_1$-C$_6$)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl, benzyl, ((C$_4$-C$_{12}$)cycloalkenyl)-(C$_1$-C$_6$)alkyl-, ((C$_6$-C$_{14}$)bicycloalkyl)-(C$_1$-C$_6$)alkyl-, ((C$_8$-C$_{20}$)tricycloalkyl)-(C$_1$-C$_6$)alkyl-, ((C$_7$-C$_{14}$)bicycloalkenyl)-(C$_1$-C$_6$)alkyl-, ((C$_8$-C$_{20}$)tricycloalkenyl)-(C$_1$-C$_6$)alkyl, ((7- to 12-membered)bicyclic ring system)-(C$_1$-C$_6$)alkyl-, ((7- to 12-membered)bicyclic aryl)-(C$_1$-C$_6$)alkyl-, ((5- to 12-membered)heteroaryl)-(C$_1$-C$_6$)alkyl-, ((3- to 12 membered)heterocycle)-(C$_1$-C$_6$)alkyl-, ((7- to 12-membered)bicycloheterocycle)-(C$_1$-C$_6$)alkyl-, and naphthyl; each of which is substituted with one or two substituents independently selected from the group consisting of —CONHR$^6$, dihydroxy(C$_1$-C$_6$)alkyl-, —(C$_1$-C$_6$)alkoxy, ((C$_1$-C$_6$)alkoxy)CO(C$_1$-C$_6$)alkoxy-, —(C$_1$-C$_6$)alkyl-NH(C$_1$-C$_6$)alkyl-R$^{14}$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —N(SO$_2$(C$_1$-C$_6$)alkyl)$_2$, —C(═NH)NH$_2$, —NH—CO—(C$_1$-C$_6$)alkyl, —NH—CO—NH$_2$, —NH—C(═O)—NH—(C$_1$-C$_6$)alkyl, —NH—C(═O)-(5- to 12-membered)aryl, —NH—C(═O)—(C$_1$-C$_6$)alkyl-(5- to 12-membered)aryl, —NH—(C$_1$-C$_6$)alkyl-CO—OR$^7$, —NH—C(═O)—(C$_1$-C$_6$)alkyl-CO—OR$^7$, —NH—C(═O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; or i) —(C$_1$-C$_{10}$)alkyl, —(C$_2$-C$_{12}$)alkenyl, and —(C$_2$-C$_{12}$)alkynyl, each of which is substituted with one or two substituents independently selected from the group consisting of —CONHR$^6$, —(C$_1$-C$_6$)alkyl-NH(C$_1$-C$_6$)alkyl-R$^{14}$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NHSO$_2$(C$_1$-C$_6$)alkyl, —N(SO$_2$(C$_1$-C$_6$)alkyl)$_2$, —C(═NH)NH$_2$, —NH—CO—(C$_1$-C$_6$)alkyl, —NH—CO—NH$_2$, —NH—C(═O)—NH—(C$_1$-C$_6$)alkyl, —NH—C(═O)-(5- to 12-membered)aryl, —NH—C(═O)—(C$_1$-C$_6$)alkyl-(5- to 12-membered)aryl, —NH—(C$_1$-C$_6$)alkyl-CO—OR$^7$, —NH—C(═O)—(C$_1$-C$_6$)alkyl-CO—OR$^7$, —NH—C(═O)—CH(NH$_2$)—(C$_1$-C$_6$)alkyl-CO—OR$^7$, —(C$_1$-C$_6$)alkoxyC(O)NR$^5$R$^6$, —NH—(C$_1$-C$_6$)alkylC(O)—NR$^5$R$^6$, and —C(O)NH—(C$_1$-C$_6$)alkyl-COOR$^7$; or j) 2,3-dihydroxypropyl; or
k) 4-isoxazolyl, 4-isoxazolyl($C_1C_6$)alkyl, 5-isoxazolyl, or 5-isoxazolyl($C_1$-$C_6$)alkyl substituted with one or two alkyl groups, or
l) —C(=O)NH$_2$ or —($C_1$-$C_6$)alkyl-C(=O)NH$_2$;

$R^8$ is hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_4$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$—$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, ((3- to 12 membered)heterocycle)-($C_1$-$C_6$)alkoxy-($C_1$-$C_6$)alkyl-, or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, —CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, phenyl, benzyl, NH₂, —NH(C₁-C₆)alkyl, CN, SH, OR⁴, —CONR⁵R⁶, —COOR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R¹⁴ is selected from —COOR⁷, —(C₁-C₆)alkyl-CO—OR⁷, —C(=O)—(C₁-C₆)alkyl-COOR⁷, —(C₁-C₆)alkyl-C(=O)—(C₁-C₆)alkyl-COOR⁷, —CONH₂, (C₁-C₆)alkyl-CONH—;

G is selected from O, —OCO—, —C(=O), NR⁹, NR', S, SO, and SO₂;

R' is —C(=O)(C₁-C₆)alkyl or —SO₂(C₁-C₆)alkyl;

X is selected from OH, hydroxy(C₁-C₆)alkyl-, dihydroxy(C₁-C₆)alkyl-, halogen, —NH₂, —NR²(C=O)R¹², CONR¹²R¹³, —(C₁-C₆)alkyl-CONH₂, —(C₁-C₆)alkyl-COOH, —COOH, —O—(C₁-C₆)alkyl-COOH, —O—(C₁-C₆)alkyl-CONH₂, —(C₁-C₁₀)alkyl, —(C₂-C₁₀)alkenyl, —(C₂-C₁₀)alkynyl, —(C₁-C₁₀)alkoxy, —(OCH₂CH₂)ₛ—O(C₁-C₆)alkyl, —(OCH₂CH₂)ₛ—OH, —(CH₂)ₚCHOHCH₂OH, CN, —NH—SO₂R⁹, —(C₃-C₁₂)cycloalkyl, ((C₃-C₁₂)cycloalkyl)-(C₁-C₆)alkyl-, ((C₃-C₁₂)cycloalkyl)-(C₁-C₆)alkoxy-, -(5- to 12-membered)aryl, ((5- to 12-membered)aryl)-(C₁-C₆)alkyl-, ((5- to 12-membered)aryl)-(C₁-C₆)alkoxy-, -(5- to 12-membered)heteroaryl, ((5- to 12-membered)heteroaryl)-(C₁-C₆)alkyl-, ((5- to 12-membered)heteroaryl)-(C₁-C₆)alkoxy-, -(3- to 12-membered)heterocycle, ((3- to 12-membered)heterocycle)-(C₁-C₆)alkyl-, ((3- to 12-membered)heterocycle)-(C₁-C₆)alkoxy-, -(7- to 12-membered)bicycloheterocycle, ((7- to 12-membered)bicycloheterocycle)-(C₁-C₆)alkyl-, and ((7- to 12-membered)bicycloheterocycle)-(C₁-C₆)alkoxy-;

Q is selected from OH, —(C₁-C₁₀)alkoxy, —(C₁-C₁₀)alkyl, —(C₃-C₁₂)cycloalkyl, -(5- to 12-membered)aryl, ((C₃-C₁₂)cycloalkyl)-(C₁-C₆)alkyl-, ((5- to 12-membered)aryl)-(C₁-C₆)alkyl-, —(OCH₂CH₂)ₛ—O(C₁-C₆)alkyl, —(CH₂CH₂O)ₛ—(C₁-C₆)alkyl, —(OCH₂CH₂)ₛ—OH, —O(C=O)R⁹, —O—(C₁-C₆)alkyl-COOR⁷, —NH—(C₁-C₆)alkyl-COOR⁷, —O—C(O)—(C₁-C₆)alkyl-C(O)OR⁷, —NH—C(O)—(C₁-C₆)alkyl-C(O)OR⁷, —O—(C₁-C₆)alkyl-C(O)NR⁹R¹⁰, —NH—(C₁-C₆)alkyl-C(O)NR⁹R¹⁰, —O—C(O)—(C₁-C₆)alkyl-C(O)NR⁹R¹⁰, —NH—C(O)—(C₁-C₆)alkyl-C(O)NR⁹R¹⁰ and R¹⁴;

Z is —(CH₂)ₘ—, optionally substituted with 1 or 2 —(C₁-C₆)alkyl;

Y is —(CH₂)ₙ—CH or a direct bond, provided that when Y is a direct bond then R⁸ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

In another embodiment, the present invention provides novel compounds of Formula I:

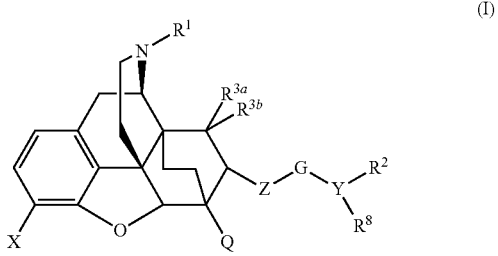

(I)

wherein

R¹ is selected from hydrogen, —(C₁-C₁₀)alkyl, —(C₂-C₁₂)alkenyl, —(C₂-C₁₂)alkynyl, —(C₁-C₁₀)alkoxy, —(C₃-C₁₂)cycloalkyl, —(C₄-C₁₂)cycloalkenyl, ((C₃-C₁₂)cycloalkyl)-(C₁-C₆)alkyl-, ((C₄-C₁₂)cycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, phenyl, and benzyl; each of which is optionally substituted with 1, 2, or 3 substituents independently selected from the group consisting of —(C₁-C₆)alkyl, OH, halo, —C(halo)₃, —CH(halo)₂, —CH₂(halo), —(C₁-C₆)alkyl-COOR⁷, —COOR⁷, NH₂, —NH(C₁-C₆)alkyl, NR⁹R¹⁰, CN, —CONR⁹R¹⁰, —NR⁹COR¹⁰, SR¹¹, -(5- to 12-membered)carbocyclic ring, -(5- to 12-membered)heterocycle, phenyl, and benzyl;

R² and R⁸ are each independently hydrogen, —(C₁-C₁₀)alkyl, —(C₂-C₁₂)alkenyl, —(C₂-C₁₂)alkynyl, —(C₁-C₁₀)alkoxy, —(OCH₂CH₂)ₛ—O(C₁-C₆)alkyl, —(CH₂CH₂O)ₛ—(C₁-C₆)alkyl, NH₂, —NH(C₁-C₆)alkyl, CN, —CONR⁵R⁶, —(C₁-C₆)alkyl-CO—NR⁵R⁶, —COOR⁷, —(C₁-C₆)alkyl-CO—OR⁷, —(C₁-C₆)alkoxy-COOR⁷, —(C₃-C₁₂)cycloalkyl, ((C₃-C₁₂)cycloalkyl)-(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, ((7- to 12-membered)bicycloheterocycle)-(C₁-C₆)alkyl-, phenyl, benzyl or naphthyl; each of which is optionally substituted with one or two substituents independently selected from the group consisting of OH, (=O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, —(C₁-C₆)alkoxy, ((C₁-C₆)alkoxy)CO(C₁-C₆)alkoxy-, phenyl, benzyl, NH₂, —NH(C₁—C₆)alkyl, —(C₁-C₆)alkyl-NH(C₁-C₆)alkyl-R¹⁴, CN, SH, OR⁴, —CONR⁵R⁶, —(C₁-C₆)alkyl-CO—NR⁵R⁶, —COOR⁷, —(C₁-C₆)alkyl-CO—OR⁷, —(C₁-C₆)alkoxy-COOR⁷, —(OCH₂CH₂)ₛ—O(C₁-C₆)alkyl, —(CH₂CH₂O)ₛ—(C₁-C₆)alkyl, ((C₁-C₆)alkyl)sulfonyl(C₁-C₆)alkyl-, —N(SO₂(C₁-C₆)alkyl)₂, —C(=NH)NH₂, —NH—CO—(C₁-C₆)alkyl, —NH—CO—NH₂, —NH—C(=O)—NH—(C₁-C₆)alkyl, —NH—C(=O)-(5- to 12-membered)aryl, —NH—C(=O)—(C₁-C₆)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{3a}$ and R$^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, —CH$_2$(halo), —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-; provided that at least one of R$^{3a}$ or R$^{3b}$ is selected from —($C_7$-$C_{10}$)alkyl, —($C_7$-$C_{10}$)alkenyl, —($C_7$-$C_{10}$)alkynyl, —($C_1$-$C_{10}$)alkoxy, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-;

R$^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_2$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^5$ and R$^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, or ($C_1$-$C_6$)alkyl-CONH—, or R$^5$ and R$^6$ together with the nitrogen atom to which they are attached form a (4- to 8-membered)heterocycle;

R$^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

R$^9$ and R$^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

each R$^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

R$^{12}$ and R$^{13}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, —($C_1$-$C_6$)alkyl-CONH;

G is selected from O, —OCO—, —C(=O), NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, halogen, —NH$_2$, —NR$^2$(C=O)R$^{12}$, CONR$^{12}$R$^{13}$, COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN and NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-;

Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$)$_s$—OH, —O(C=O)R$^9$, —O—(C$_1$-C$_6$)alkyl-COOR$^7$, —NH—(C$_1$-C$_6$)alkyl-COOR$^7$, —O—C(O)—(C$_1$-C$_6$)alkyl-C(O)OR$^7$, —NH—C(O)—(C$_1$-C$_6$)alkyl-C(O)OR$^7$, —O—(C$_1$-C$_6$)alkyl-C(O)NR$^9$R$^{10}$, —NH—(C$_1$-C$_6$)alkyl-C(O)NR$^9$R$^{10}$, —O—C(O)—(C$_1$-C$_6$)alkyl-C(O)NR$^9$R$^{10}$, —NH—C(O)—(C$_1$-C$_6$)alkyl-C(O)NR$^9$R$^{10}$ and R$^{14}$;

Z is —(CH$_2$)$_m$—, optionally substituted with 1 or 2-(C$_1$-C$_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1, 2, 3, 4, 5, 6, 7, 8, 9, 10, 11, 12, or 13;

or a pharmaceutically acceptable salt, prodrug or solvate thereof.

The present invention further provides novel compounds of Formula III:

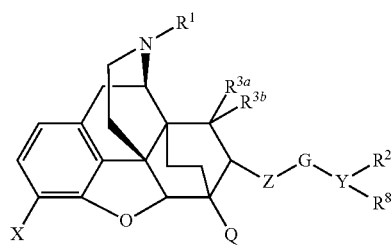

wherein

X is OH or —(C$_1$-C$_6$)alkoxy;

Q is OMe;

Z is —(CH$_2$)$_m$—;

G is —OCO—;

Y is —CH;

R$^8$ is NH$_2$;

R$^2$ is —(C$_1$-C$_6$)alkyl, —(C$_2$-C$_6$)alkenyl, —(C$_2$-C$_6$)alkynyl, phenyl, benzyl, hydroxy(C$_1$-C$_6$)alkyl-, dihydroxy(C$_{1-6}$)alkyl, —(C$_1$-C$_6$)alkyl-NH$_2$, —(C$_1$-C$_6$)alkyl-CO—NH$_2$, —(C$_1$-C$_6$)alkyl-CO—NH—(C$_1$-C$_4$)alkyl, —(C$_1$-C$_6$)alkyl-CO—OH, or —(C$_1$-C$_6$)alkyl-CO—O(C$_1$-C$_4$)alkyl;

R$^1$ is selected from hydrogen, —(C$_1$-C$_6$)alkyl, —(C$_3$-C$_6$)cycloalkyl, and ((C$_3$-C$_6$)cycloalkyl)-(C$_1$-C$_6$)alkyl;

R$^{3a}$ and R$^{3b}$ are both hydrogen;

m is an integer 1 or 2;

or a pharmaceutically acceptable salt, prodrug or solvate thereof.

The present invention further provides novel compounds of Formula I:

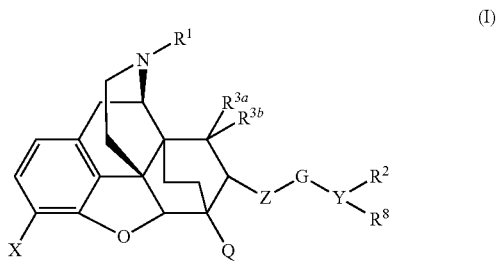

wherein

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, NH$_2$, —NH(C$_1$-C$_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, NH$_2$, —NH(C$_1$-C$_6$)alkyl, CN, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_3$-C$_{12}$)cycloalkyl, ((C$_3$-C$_2$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, NH$_2$, —NH(C$_1$-C$_6$)alkyl, —(C$_1$-C$_6$)alkyl-NH(C$_1$-C$_6$)alkyl-R$^{14}$, CN, SH, OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, or —CH$_2$(halo), or together form (=O);

R$^4$ is selected from —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^5$ and R$^6$ are each independently hydrogen, —(C$_1$-C$_6$)alkyl, —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-CO—OR$^7$, —CONH$_2$, or (C$_1$-C$_6$)alkyl-CONH—, or R$^5$ and R$^6$ together with the nitrogen atom to which they are attached form a (4- to 8-membered)heterocycle;

R$^7$ is selected from hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_2$)cycloalkyl)-(C$_1$-C$_6$)alkyl-, and ((C$_4$-C$_{12}$)cycloalkenyl)-(C$_1$-C$_6$)alkyl-;

R$^9$ and R$^{10}$ are each independently selected from hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, or ((C$_3$-C$_{12}$)cycloalkenyl)-(C$_1$-C$_6$)alkyl-;

Each R$^{11}$ is independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, ((C$_1$-C$_6$)alkyl)sulfonyl(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, or ((C$_4$-C$_{12}$)cycloalkenyl)-(C$_1$-C$_6$)alkyl-;

R$^{12}$ and R$^{13}$ are each independently selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, phenyl, benzyl, NH$_2$, —NH(C$_1$-C$_6$)alkyl, CN, SH, OR$^4$, —CONR$^5$R$^6$, —COOR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{14}$ is selected from —COOR$^7$, —(C$_1$-C$_6$)alkyl-CO—OR$^7$, —C(=O)—(C$_1$-C$_6$)alkyl-COOR$^7$, —(C$_1$-C$_6$)alkyl-C(=O)—(C$_1$-C$_6$)alkyl-COOR$^7$, —CONH$_2$, (C$_1$-C$_6$)alkyl-CONH—;

G is selected from O, —OCO—, NR$^9$, NR', S, SO, and SO$_2$;

R' is —C(=O)(C$_1$-C$_6$)alkyl or —SO$_2$(C$_1$-C$_6$)alkyl;

X is selected from OH, hydroxy(C$_1$-C$_6$)alkyl-, dihydroxy(C$_1$-C$_6$)alkyl-, halogen, —NH$_2$, —NR$^2$(C=O)R$^{12}$, —CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O(C$_1$-C$_6$)alkyl, —(OCH$_2$CH$_2$)$_s$—OH, —(CH$_2$)$_p$CHOHCH$_2$OH, CN and —NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-;

Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$), —OH, —O(C=O)R$^9$R$^{10}$, and R$^{14}$;

Z is —(CH$_2$)$_m$—, optionally substituted with 1 or 2-(C$_1$-C$_6$)alkyl;

Y is —(CH$_2$)$_n$—CH or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

provided that when X is OH or —(C$_1$-C$_6$)alkoxy, Q is OMe, Z is unsubstituted, and G is O, then either:

a) R$^1$ is selected from;
   iii. hydrogen, (C$_1$-C$_{10}$)alkoxy, ((5- to 12-membered)heteroaryl)-(C$_1$-C$_6$)alkyl-, and ((3- to 12-membered)heterocycle)-(C$_1$-C$_6$)alkyl-; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), —(C$_1$-C$_6$)alkyl-COOR$^7$, NH$_2$, —NH(C$_1$-C$_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or iv. —(C₁-C₁₀)alkyl, —(C₂-C₁₂)alkenyl, —(C₂-C₁₂)alkynyl, —(C₃-C₁₂)cycloalkyl, —(C₄-C₁₂)cycloalkenyl, ((C₃-C₁₂)cycloalkyl)-(C₁-C₆)alkyl-, ((C₄-C₁₂)cycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((3- to 12 membered)heterocycle)-(C₁-C₆)alkyl-, phenyl, or benzyl; each of which is substituted with 1, 2, or 3 substituents independently selected from the group consisting of —(C₁-C₆)alkyl-COOR⁷, NR⁹R¹⁰, —CONR⁹R¹⁰, —NR⁹COR¹⁰, and SR¹¹;

or b) at least one of R² and R⁸ is selected from:
iii. —(C₁-C₁₀)alkoxy, —(OCH₂CH₂)ₛ—O(C₁-C₆)alkyl, —(CH₂CH₂O)ₛ—(C₁-C₆)alkyl, NH₂, —NH(C₁-C₆)alkyl, CN, —CONR⁵R⁶, —(C₁-C₆)alkyl-CO—NR⁵R⁶, —COOR⁷, —(C₁-C₆)alkyl-CO—OR⁷, ((C₄-C₁₂)cycloalkenyl)-(C₁-C₆)alkyl-, ((C₆-C₁₄)bicycloalkyl)-(C₁-C₆)alkyl-, ((C₈-C₂₀)tricycloalkyl)-(C₁-C₆)alkyl-, ((C₇-C₁₄)bicycloalkenyl)-(C₁-C₆)alkyl-, ((C₈-C₂₀)tricycloalkenyl)-(C₁-C₆)alkyl-, ((7- to 12-membered)bicyclic ring system)-(C₁-C₆)alkyl-, ((7- to 12-membered)bicyclic aryl)-(C₁-C₆)alkyl-, ((5- to 12-membered)heteroaryl)-(C₁-C₆)alkyl-, ((3- to 12 membered)heterocycle)-(C₁-C₆)alkyl-, ((7- to 12-membered)bicycloheterocycle)-(C₁-C₆)alkyl-, or naphthyl; each of which is optionally substituted with one or two substituents independently selected from the group consisting of OH, (=O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, —(C₁-C₆)alkoxy, ((C₁-C₆)alkoxy)CO(C₁—C₆)alkoxy-, phenyl, benzyl, NH₂, —NH(C₁-C₆)alkyl, —(C₁-C₆)alkyl-NH(C₁-C₆)alkyl-R¹⁴, CN, SH, OR⁴, —CONR⁵R⁶, —COOR⁷, —(C₁-C₆)alkyl-CO—OR⁷, —(OCH₂CH₂)ₛ—O(C₁-C₆)alkyl, —(CH₂CH₂O)ₛ—(C₁-C₆)alkyl, ((C₁-C₆)alkyl)sulfonyl(C₁-C₆)alkyl-, N-methyl-N-(methylsulfonyl)methanesulfonamide, or acetimidamide;

iv. hydrogen, —(C₁-C₁₀)alkyl, —(C₂-C₁₂)alkenyl, —(C₂-C₁₂)alkynyl, —(C₃-C₁₂)cycloalkyl, —((C₃-C₁₂)cycloalkyl)-(C₁-C₆)alkyl, —(C₄-C₁₂)cycloalkenyl, —(C₆-C₁₄)bicycloalkyl, —(C₈-C₂₀)tricycloalkyl, —(C₇-C₁₄)bicycloalkenyl, —(C₈-C₂₀)tricycloalkenyl, -(5- to 12-membered)aryl, ((5- to 12-membered)aryl)-(C₁-C₆)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl and benzyl; each of which is substituted with one or two substituents independently selected from the group consisting of dihydroxy(C₁-C₆)alkyl-, —(C₁-C₆)alkyl-NH(C₁-C₆)alkyl-R¹⁴, —(C₁-C₆)alkyl-CO—OR⁷, —(OCH₂CH₂)ₛ—O(C₁-C₆)alkyl, —(CH₂CH₂O)ₛ—(C₁-C₆)alkyl, ((C₁-C₆)alkyl)sulfonyl(C₁-C₆)alkyl-, —N(SO₂(C₁-C₆)alkyl)₂, —C(=NH)NH₂, —NH—CO—(C₁-C₆)alkyl, —NH—CO—NH₂, —NH—(C₁-C₆)alkyl-CO—OR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

or c) at least one of R³ᵃ or R³ᵇ is independently selected from —(C₇-C₁₀)alkyl, —(C₇-C₁₀)alkenyl, —(C₇-C₁₀)alkynyl, or —(C₁-C₁₀)alkoxy;

or a pharmaceutically acceptable salt, prodrug or solvate thereof.

In one embodiment, the present invention provides novel compounds of Formula I:

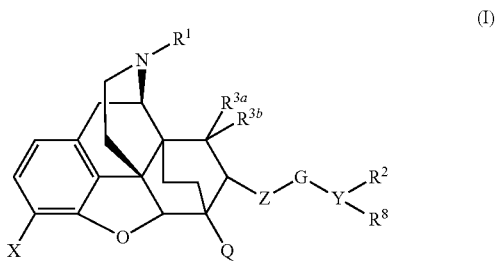

(I)

wherein

R¹ is selected from hydrogen, —(C₁-C₁₀)alkyl, —(C₂-C₁₂)alkenyl, —(C₂-C₁₂)alkynyl, —(C₁-C₁₀)alkoxy, —(C₃-C₁₂)cycloalkyl, —(C₄-C₁₂)cycloalkenyl, ((C₃-C₁₂)cycloalkyl)-(C₁-C₆)alkyl-, ((C₄-C₁₂)cycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, phenyl, and benzyl; any of which is optionally substituted with 1, 2, or 3 substituents independently selected from the group consisting of —(C₁-C₆)alkyl, OH, halo, —C(halo)₃, —CH(halo)₂, —CH₂(halo), —(C₁-C₆)alkyl-COOR⁷, NH₂, —NH(C₁-C₆)alkyl, NR⁹R¹⁰, CN, —CONR⁹R¹⁰, —NR⁹COR¹⁰, SR¹¹, -(5- to 12-membered)carbocyclic ring, -(5- to 12-membered)heterocycle, phenyl, and benzyl;

R² and R⁸ are each independently hydrogen, —(C₁-C₁₀)alkyl, —(C₂-C₁₂)alkenyl, —(C₂-C₁₂)alkynyl, —(C₁-C₁₀)alkoxy, —(OCH₂CH₂)ₛ—O(C₁-C₆)alkyl, —(CH₂CH₂O)ₛ—(C₁-C₆)alkyl, NH₂, —NH(C₁-C₆)alkyl, CN, —CONR⁵R⁶, —(C₁-C₆alkyl)-CO—NR⁵R⁶, —(C₁-C₆)alkyl-CO—NR⁵R⁶, —COOR⁷, —(C₁-C₆)alkyl-CO—OR⁷, —(C₃-C₁₂)cycloalkyl, ((C₃-C₁₂)cycloalkyl)-(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₇-C₁₄)bicycloalkenyl, ((C₇-C₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, ((7- to 12-membered)bicycloheterocycle)-(C₁-C₆)alkyl-, phenyl, benzyl and naphthyl; any of which is optionally substituted with one or two substituents independently selected from the group consisting of OH, (=O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, —(C₁-C₆)alkoxy, ((C₁-C₆)alkoxy)CO(C₁-C₆)alkoxy-, phenyl, benzyl, NH₂, —NH(C₁—C₆)alkyl, —(C₁-C₆)alkyl-NH(C₁-C₆)alkyl-R¹⁴, CN, SH, OR⁴, —CONR⁵R⁶, —COOR⁷, —(C₁-C₆)alkyl-CO—OR⁷, —(OCH₂CH₂)ₛ—O(C₁-C₆)alkyl, —(CH₂CH₂O)ₛ—(C₁-C₆)alkyl, ((C₁-C₆)alkyl)sulfonyl(C₁-C₆)alkyl-, —N(SO₂(C₁-C₆)alkyl)₂, —C(=NH)NH₂, —NH—CO—(C$_1$-C$_6$)alkyl, —NH—CO—NH$_2$, —NH—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, or —CH$_2$(halo), or together form (=O);

R$^4$ is selected from —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^5$ and R$^6$ are each independently hydrogen, —(C$_1$-C$_6$)alkyl, —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-CO—OR$^7$, —CONH$_2$, or (C$_1$-C$_6$)alkyl-CONH—, or R$^5$ and R$^6$ together with the nitrogen atom to which they are attached form a (4- to 8-membered)heterocycle;

R$^7$ is selected from hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

R$^9$ and R$^{10}$ are each independently selected from hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, or ((C$_3$-C$_{12}$)cycloalkenyl)-(C$_1$-C$_6$)alkyl-;

Each R$^{11}$ is independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, ((C$_1$-C$_6$)alkyl)sulfonyl(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, or ((C$_4$-C$_{12}$)cycloalkenyl)-(C$_1$-C$_6$)alkyl-;

R$^{12}$ and R$^{13}$ are each independently selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, phenyl, benzyl, NH$_2$, —NH(C$_1$-C$_6$)alkyl, CN, SH, OR$^4$, —CONR$^5$R$^6$, —COOR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{14}$ is selected from —COOR$^7$, —(C$_1$-C$_6$)alkyl-CO—OR$^7$, —C(=O)—(C$_1$-C$_6$)alkyl-CO—OR$^7$, —(C$_1$-C$_6$)alkyl-C(=O)—(C$_1$-C$_6$)alkyl-COOR$^7$, —CONH$_2$, (C$_1$-C$_6$)alkyl-CONH—;

G is selected from O, —OCO—, NR$^9$, NR', S, SO, and SO$_2$;

R' is —C(=O)(C$_1$-C$_6$)alkyl or —SO$_2$(C$_1$-C$_6$)alkyl;

X is selected from hydroxy(C$_1$-C$_6$)alkyl-, dihydroxy(C$_1$-C$_6$)alkyl-, halogen, —NH$_2$, —NR$^2$(C=O)R$^{12}$, —CONR$^{12}$R$^{13}$, —(C$_1$-C$_6$)alkyl-CONH$_2$, —(C$_1$-C$_6$)alkyl-COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_7$-C$_{10}$)alkoxy, —(OCH$_2$CH$_2$)$_s$—O(C$_1$-C$_6$)alkyl, —(OCH$_2$CH$_2$)$_s$—OH, —(CH$_2$)$_p$CHOHCH$_2$OH, CN and —NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-;

Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$)$_s$—OH, —O(C=O)R$^9$R$^{10}$, and R$^{14}$;

Z is —(CH$_2$)$_m$—, optionally substituted with 1 or 2-(C$_1$-C$_6$)alkyl;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

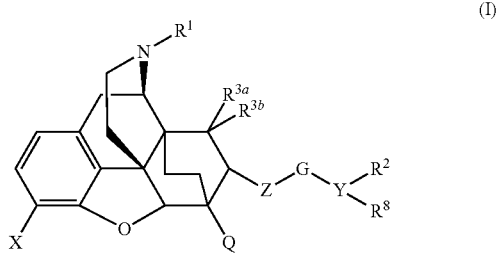

(I)

wherein $R^1$ is selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, $((C_4$-$C_{12})$cycloalkenyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, phenyl, and benzyl; any of which is optionally substituted with 1, 2, or 3 substituents independently selected from the group consisting of —$(C_1$-$C_6)$alkyl, OH, halo, —C(halo)$_3$, —CH(halo)$_2$, —CH$_2$(halo), —$(C_1$-$C_6)$alkyl-COOR$^7$, NH$_2$, —NH$(C_1$-$C_6)$alkyl, —NR$^9$R$^{10}$, CN, —CONR$^9$R$^{10}$, —NR$^9$COR$^{10}$, SR$^{11}$, -(5- to 12-membered) carbocyclic ring, -(5- to 12-membered)heterocycle, phenyl, and benzyl;

$R^2$ and $R^8$ are each independently hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(OCH_2CH_2)_s$—O$(C_1$-$C_6)$alkyl, —$(CH_2CH_2O)_s$—$(C_1$-$C_6)$alkyl, NH$_2$, —NH$(C_1$-$C_6)$alkyl, CN, —CONR$^5$R$^6$, —$(C_1$-$C_6)$alkyl-CO—NR$^5$R$^6$, —COOR$^7$, —$(C_1$-$C_6)$alkyl-CO—OR$^7$, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(7- to 12-membered)bicyclic ring system, ((7- to 12-membered)bicyclic ring system)-$(C_1$-$C_6)$alkyl-, -(7- to 12-membered)bicyclic aryl, ((7- to 12-membered)bicyclic aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12 membered)heterocycle)-$(C_1$-$C_6)$alkyl-, -(7- to 12-membered)bicycloheterocycle, ((7- to 12-membered)bicycloheterocycle)-$(C_1$-$C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —$(C_1$-$C_6)$alkyl, halo$(C_1$-$C_6)$alkyl-, —$(C_2$-$C_6)$alkenyl, —$(C_2$-$C_6)$alkynyl, hydroxy$(C_1$-$C_6)$alkyl-, dihydroxy$(C_1$-$C_6)$alkyl-, —$(C_1$-$C_6)$alkoxy, $((C_1$-$C_6)$alkoxy)CO$(C_1$-$C_6)$alkoxy-, phenyl, benzyl, NH$_2$, —NH$(C_1$-$C_6)$alkyl, —$(C_1$-$C_6)$alkyl-NH$(C_1$-$C_6)$alkyl-R$^{14}$, CN, SH, OR$^4$, —CONR$^5$R$^6$, —$(C_1$-$C_6)$alkyl)-CO—NR$^5$R$^6$, —COOR$^7$, —$(C_1$-$C_6)$alkyl-CO—OR$^7$, —$(OCH_2CH_2)_s$—O$(C_1$-$C_6)$alkyl, —$(CH_2CH_2O)_s$—$(C_1$-$C_6)$alkyl, $((C_1$-$C_6)$alkyl)sulfonyl$(C_1$-$C_6)$alkyl-, —N(SO$_2$$(C_1$-$C_6)$alkyl)$_2$, —C(=NH)NH$_2$, —NH—CO—$(C_1$—$C_6)$alkyl, —NH—CO—NH$_2$, —NH—$(C_1$-$C_6)$alkyl-CO—OR$^7$, —$(C_3$-$C_{12})$cycloalkyl, $((C_3$-$C_{12})$cycloalkyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^{3a}$ and $R^{3b}$ are each independently selected from hydrogen, —$(C_1$-$C_{10})$alkyl, —$(C_2$-$C_{10})$alkenyl, —$(C_2$-$C_{10})$alkynyl, —$(C_1$-$C_{10})$alkoxy, OH, hydroxy$(C_1$-$C_6)$alkyl-, —C(halo)$_3$, —CH(halo)$_2$, or —CH$_2$(halo), or together form (=O);

$R^4$ is selected from —$(C_1$-$C_6)$alkyl, —$(C_2$-$C_6)$alkenyl, —$(C_2$-$C_6)$alkynyl, —C(halo)$_3$, hydroxy$(C_1$-$C_6)$alkyl-, —$(C_3$-$C_{12})$cycloalkyl, $((C_3$-$C_{12})$cycloalkyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(5- to 12-membered)heteroaryl, ((5- to 12-membered)heteroaryl)-$(C_1$-$C_6)$alkyl-, -(3- to 12-membered)heterocycle, ((3- to 12-membered)heterocycle)-$(C_1$-$C_6)$alkyl-, -(7- to 12-membered)bicycloheterocycle, and ((7- to 12-membered)bicycloheterocycle)-$(C_1$-$C_6)$alkyl-;

$R^5$ and $R^6$ are each independently hydrogen, —$(C_1$-$C_6)$alkyl, —$(C_3$-$C_8)$cycloalkyl, $((C_3$-$C_8)$cycloalkyl)-$(C_1$-$C_6)$alkyl-, —COOR$^7$, —$(C_1$-$C_6)$alkyl-CO—OR$^7$, —CONH$_2$, or $(C_1$-$C_6)$alkyl-CONH—, or $R^5$ and $R^6$ together with the nitrogen atom to which they are attached form a (4- to 8-membered)heterocycle;

$R^7$ is selected from hydrogen, —$(C_1$-$C_6)$alkyl, —$(C_2$-$C_6)$alkenyl, —$(C_2$-$C_6)$alkynyl, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, and $((C_4$-$C_{12})$cycloalkenyl)-$(C_1$-$C_6)$alkyl-;

$R^9$ and $R^{10}$ are each independently selected from hydrogen, —$(C_1$-$C_6)$alkyl, —$(C_2$-$C_6)$alkenyl, —$(C_2$-$C_6)$alkynyl, —$(C_1$-$C_{10})$alkoxy, —$(C_3$-$C_{12})$cycloalkyl, —$(C_3$-$C_{12})$cycloalkenyl, $((C_3$-$C_{12})$cycloalkyl)-$(C_1$-$C_6)$alkyl-, or $((C_3$-$C_{12})$cycloalkenyl)-$(C_1$-$C_6)$alkyl-;

Each $R^{11}$ is independently selected from hydrogen, —$(C_1$-$C_{10})$alkyl, —$(C_2$-$C_{10})$alkenyl, —$(C_2$-$C_{10})$alkynyl, —$(C_1$-$C_{10})$alkoxy, $((C_1$-$C_6)$alkyl)sulfonyl$(C_1$-$C_6)$alkyl-, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, or $((C_4$-$C_{12})$cycloalkenyl)-$(C_1$-$C_6)$alkyl-;

$R^{12}$ and $R^{13}$ are each independently selected from hydrogen, —$(C_1$-$C_{10})$alkyl, —$(C_2$-$C_{12})$alkenyl, —$(C_2$-$C_{12})$alkynyl, —$(C_1$-$C_{10})$alkoxy, —$(OCH_2CH_2)_s$—O$(C_1$-$C_6)$alkyl, —$(C_3$-$C_{12})$cycloalkyl, $((C_3$-$C_{12})$cycloalkyl)-$(C_1$-$C_6)$alkyl-, —$(C_4$-$C_{12})$cycloalkenyl, $((C_4$-$C_{12})$cycloalkenyl)-$(C_1$-$C_6)$alkyl-, —$(C_6$-$C_{14})$bicycloalkyl, $((C_6$-$C_{14})$bicycloalkyl)-$(C_1$-$C_6)$alkyl-, —$(C_8$-$C_{20})$tricycloalkyl, $((C_8$-$C_{20})$tricycloalkyl)-$(C_1$-$C_6)$alkyl-, —$(C_7$-$C_{14})$bicycloalkenyl, $((C_7$-$C_{14})$bicycloalkenyl)-$(C_1$-$C_6)$alkyl-, —$(C_8$-$C_{20})$tricycloalkenyl, $((C_8$-$C_{20})$tricycloalkenyl)-$(C_1$-$C_6)$alkyl-, -(5- to 12-membered)aryl, ((5- to 12-membered)aryl)-$(C_1$-$C_6)$alkyl-, -(7- to 12-membered)bicyclic ring system, ((7- to 12-membered) bicyclic ring system)-$(C_1$-$C_6)$alkyl-, -(7- to 12-membered) bicyclic aryl, ((7- to 12-membered)bicyclic aryl)-$(C_1$-$C_6)$alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$—$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, ($C_1$-$C_6$)alkyl-CONH—;

G is selected from O, —OCO—, NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy($C_1$-$C_6$)alkyl-, halogen, —NH$_2$, —NR$^2$(C=O)R$^{12}$, CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN and —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_2$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$R$^{10}$ and R$^{14}$;

Z is —(CH$_2$)$_m$—, optionally substituted with 1 or 2-($C_1$-$C_6$)alkyl;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

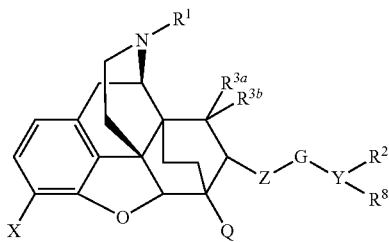

wherein

R$^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, NH$_2$, —NH($C_1$-$C_6$)alkyl, —NR$^9$R$^{10}$, CN, —CONR$^9$R$^{10}$, —NR$^9$COR$^{10}$, SR$^{11}$, -(5- to 12-membered) carbocyclic ring, -(5- to 12-membered)heterocycle, phenyl, and benzyl;

R$^2$ and R$^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$alkyl)-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, or —CH$_2$(halo), or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, or ($C_1$-$C_6$)alkyl-CONH—, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, ($C_1$-$C_6$)alkyl-CONH—;

G is selected from O, —OCO—, NR$^9$, NR', S, SO, and SO$_2$;

R' is —C(=O)($C_1$-$C_6$)alkyl or —SO$_2$($C_1$-$C_6$)alkyl;

X is selected from OH, hydroxy($C_1$-$C_6$)alkyl-, dihydroxy ($C_1$-$C_6$)alkyl-, halogen, —NH$_2$, —NR$^2$(C=O)R$^{12}$, CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN and —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$R$^{10}$ and R$^{14}$; provided that Q is not OMe;

Z is —(CH$_2$)$_m$—, optionally substituted with 1 or 2-($C_1$-$C_6$)alkyl;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

(I)

wherein $R^1$ is selected from c) hydrogen, ($C_1$-$C_{10}$)alkoxy, ((5- to 12-membered)heteroaryl)-($C_1$-$C_6$)alkyl-, and ((3- to 12-membered)heterocycle)-$(C_1-C_6)$alkyl-; any of which is optionally substituted with 1, 2, or 3 substituents independently selected from the group consisting of —$(C_1-C_6)$alkyl, OH, halo, —C(halo)$_3$, —CH(halo)$_2$, —CH$_2$(halo), —$(C_1-C_6)$alkyl-COOR$^7$, NH$_2$, —NH$(C_1-C_6)$alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or d) —$(C_1-C_{10})$alkyl, —$(C_2-C_{12})$alkenyl, —$(C_2-C_{12})$alkynyl, —$(C_3-C_{12})$cycloalkyl, —$(C_4-C_{12})$cycloalkenyl, $((C_3-C_{12})$cycloalkyl)-$(C_1-C_6)$alkyl-, $((C_4-C_{12})$cycloalkenyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(5- to 12-membered)heterocycle, ((3- to 12 membered)heterocycle)-$(C_1-C_6)$alkyl-, phenyl, or benzyl; each of which is substituted with 1, 2, or 3 substituents independently selected from the group consisting of —$(C_1-C_6)$alkyl-COOR$^7$, NR$^9$R$^{10}$, —CONR$^9$R$^{10}$, —NR$^9$COR$^{10}$, and SR$^{11}$;

R$^2$ and R$^8$ are each independently hydrogen, —$(C_1-C_{10})$alkyl, —$(C_2-C_{12})$alkenyl, —$(C_2-C_{12})$alkynyl, —$(C_1-C_{10})$alkoxy, —$(OCH_2CH_2)_s$—$O(C_1-C_6)$alkyl, —$(CH_2CH_2O)_s$—$(C_1-C_6)$alkyl, NH$_2$, —NH$(C_1-C_6)$alkyl, CN, —CONR$^5$R$^6$, —$(C_1-C_6)$alkyl-CO—NR$^5$R$^6$, —COOR$^7$, —$(C_1-C_6)$alkyl-CO—OR$^7$, —$(C_3-C_{12})$cycloalkyl, $((C_3-C_{12})$cycloalkyl)-$(C_1-C_6)$alkyl-, —$(C_4-C_{12})$cycloalkenyl, $((C_4-C_{12})$cycloalkenyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(5- to 12-membered)aryl, ((5- to 12-membered)aryl)-$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, dihydroxy$(C_1-C_6)$alkyl-, —$(C_1-C_6)$alkoxy, $((C_1-C_6)$alkoxy)CO$(C_1-C_6)$alkoxy-, phenyl, benzyl, NH$_2$, —NH$(C_1-C_6)$alkyl, —$(C_1-C_6)$alkyl-NH$(C_1-C_6)$alkyl-R$^{14}$, CN, SH, OR$^4$, —CONR$^5$R$^6$, —$(C_1-C_6)$alkyl-CO—NR$^5$R$^6$, —COOR$^7$, —$(C_1-C_6)$alkyl-CO—OR$^7$, —$(OCH_2CH_2)_s$—$O(C_1-C_6)$alkyl, —$(CH_2CH_2O)_s$—$(C_1-C_6)$alkyl, $((C_1-C_6)$alkyl)sulfonyl$(C_1-C_6)$alkyl-, —$N(SO_2(C_1-C_6)$alkyl)$_2$, —C(=NH)NH$_2$, —NH—CO—$(C_1-C_6)$alkyl, —NH—CO—NH$_2$, —NH—$(C_1-C_6)$alkyl-CO—OR$^7$, —$(C_3-C_{12})$cycloalkyl, $((C_3-C_{12})$cycloalkyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

R$^{3a}$ and R$^{3b}$ are each independently selected from hydrogen, —$(C_1-C_{10})$alkyl, —$(C_2-C_{10})$alkenyl, —$(C_2-C_{10})$alkynyl, —$(C_1-C_{10})$alkoxy, OH, hydroxy$(C_1-C_6)$alkyl-, —C(halo)$_3$, —CH(halo)$_2$, or —CH$_2$(halo), or together form (=O);

R$^4$ is selected from —$(C_1-C_6)$alkyl, —$(C_2-C_6)$alkenyl, —$(C_2-C_6)$alkynyl, —C(halo)$_3$, —CH(halo)$_2$, —CH$_2$(halo), hydroxy$(C_1-C_6)$alkyl-, —$(C_3-C_{12})$cycloalkyl, $((C_3-C_{12})$cycloalkyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_4-C_{12})$cycloalkenyl, $((C_4-C_{12})$cycloalkenyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

R$^5$ and R$^6$ are each independently hydrogen, —$(C_1-C_6)$alkyl, —$(C_3-C_8)$cycloalkyl, or $((C_3-C_8)$cycloalkyl)-$(C_1-C_6)$alkyl-, —COOR$^7$, —$(C_1-C_6)$alkyl-CO—OR$^7$, CONH$_2$, or $(C_1-C_6)$alkyl-CONH—, or R$^5$ and R$^6$ together with the nitrogen atom to which they are attached form a (4- to 8-membered)heterocycle;

R$^7$ is selected from hydrogen, —$(C_1-C_6)$alkyl, —$(C_2-C_6)$alkenyl, —$(C_2-C_6)$alkynyl, —$(C_3-C_{12})$cycloalkyl, —$(C_4-C_{12})$cycloalkenyl, $((C_3-C_{12})$cycloalkyl)-$(C_1-C_6)$alkyl-, and $((C_4-C_{12})$cycloalkenyl)-$(C_1-C_6)$alkyl-;

R$^9$ and R$^{10}$ are each independently selected from hydrogen, —$(C_1-C_6)$alkyl, —$(C_2-C_6)$alkenyl, —$(C_2-C_6)$alkynyl, —$(C_1-C_{10})$alkoxy, —$(C_3-C_{12})$cycloalkyl, —$(C_3-C_{12})$cycloalkenyl, $((C_3-C_{12})$cycloalkyl)-$(C_1-C_6)$alkyl-, or $((C_3-C_{12})$cycloalkenyl)-$(C_1-C_6)$alkyl-;

Each R$^{11}$ is independently selected from hydrogen, —$(C_1-C_{10})$alkyl, —$(C_2-C_{10})$alkenyl, —$(C_2-C_{10})$alkynyl, —$(C_1-C_{10})$alkoxy, $((C_1-C_6)$alkyl)sulfonyl$(C_1-C_6)$alkyl-, —$(C_3-C_{12})$cycloalkyl, $((C_3-C_{12})$cycloalkyl)-$(C_1-C_6)$alkyl-, —$(C_4-C_{12})$cycloalkenyl, or $((C_4-C_{12})$cycloalkenyl)-$(C_1-C_6)$alkyl-;

R$^{12}$ and R$^{13}$ are each independently selected from hydrogen, —$(C_1-C_{10})$alkyl, —$(C_2-C_{12})$alkenyl, —$(C_2-C_{12})$alkynyl, —$(C_1-C_{10})$alkoxy, —$(OCH_2CH_2)_s$—$O(C_1-C_6)$alkyl, —$(C_3-C_{12})$cycloalkyl, $((C_3-C_{12})$cycloalkyl)-$(C_1-C_6)$alkyl-, —$(C_4-C_{12})$cycloalkenyl, $((C_4-C_{12})$cycloalkenyl)-$(C_1-C_6)$alkyl-, —$(C_6-C_{14})$bicycloalkyl, $((C_6-C_{14})$bicycloalkyl)-$(C_1-C_6)$alkyl-, —$(C_8-C_{20})$tricycloalkyl, $((C_8-C_{20})$tricycloalkyl)-$(C_1-C_6)$alkyl-, —$(C_7-C_{14})$bicycloalkenyl, $((C_7-C_{14})$bicycloalkenyl)-$(C_1-C_6)$alkyl-, —$(C_8-C_{20})$tricycloalkenyl, $((C_8-C_{20})$tricycloalkenyl)-$(C_1-C_6)$alkyl-, -(5- to 12-membered)aryl, ((5- to 12-membered)aryl)-$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, phenyl, benzyl, NH$_2$, —NH$(C_1-C_6)$alkyl, CN, SH, OR$^4$, —CONR$^5$R$^6$, —COOR$^7$, —$(C_3-C_{12})$cycloalkyl, $((C_3-C_{12})$cycloalkyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COO$R^7$, —($C_1$-$C_6$)alkyl-CO—O$R^7$, —C(=O)—($C_1$-$C_6$)alkyl-COO$R^7$, —($C_1$-$C_6$)alkyl-C(=O)—($C_1$-$C_6$)alkyl-COO$R^7$, CON$H_2$, —CONH($C_1$-$C_6$)alkyl;

G is selected from O, —OCO—, N$R^9$, NR', S, SO, and S$O_2$;

R' is —C(=O)($C_1$-$C_6$)alkyl or —S$O_2$($C_1$-$C_6$)alkyl;

X is selected from OH, hydroxy($C_1$-$C_6$)alkyl-, dihydroxy($C_1$-$C_6$)alkyl-, halogen, —N$H_2$, —N$R^2$(C=O)$R^8$, CON$R^{12}R^{13}$, —($C_1$-$C_6$)alkyl-CON$H_2$, —($C_1$-$C_6$)alkyl-COOH, —COOH, —O—($C_1$-$C_6$)alkyl-COOH, —O—($C_1$-$C_6$)alkyl-CON$H_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OC$H_2$C$H_2$)$_s$—O($C_1$-$C_6$)alkyl, —(OC$H_2$C$H_2$)$_s$—OH, —(C$H_2$)$_p$CHOHC$H_2$OH—, CN and NH—S$O_2$$R^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, (5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, and ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OC$H_2$C$H_2$)$_s$—O($C_1$-$C_6$)alkyl, —(C$H_2$C$H_2$O)$_s$—($C_1$-$C_6$)alkyl, —(OC$H_2$C$H_2$)$_s$—OH, —O(C=O)$R^9R^{10}$ and $R^{14}$;

Z is —(C$H_2$)$_m$—, optionally substituted with 1 or 2-($C_1$-$C_6$)alkyl;

Y is —(C$H_2$)$_n$—CH— or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

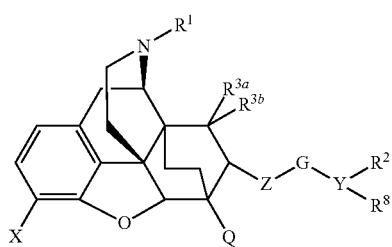

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; each of which is optionally substituted with 1, 2, or 3 substituents independently selected from the group consisting of —($C_1$-$C_6$)alkyl, OH, halo, —C(halo)$_3$, —CH(halo)$_2$, —C$H_2$(halo), —($C_1$-$C_6$)alkyl-COO$R^7$, N$H_2$, —NH($C_1$-$C_6$)alkyl, N$R^9R^{10}$, CN, —CON$R^9R^{10}$, —N$R^9$CO$R^{10}$, S$R^{11}$, -(5- to 12-membered)carbocyclic ring, -(5- to 12-membered)heterocycle, phenyl, and benzyl;

At least one of $R^2$ or $R^8$ is independently selected from:

c) —($C_1$-$C_{10}$)alkoxy, —(OC$H_2$C$H_2$)$_s$—O($C_1$-$C_6$)alkyl, —(C$H_2$C$H_2$O)$_s$—($C_1$-$C_6$)alkyl, N$H_2$, —NH($C_1$-$C_6$)alkyl, CN, —CON$R^5R^6$, —($C_1$-$C_6$)alkyl-CO—N$R^5R^6$, —COO$R^7$, —N(S$O_2$($C_1$-$C_6$)alkyl)$_2$, —C(=NH)N$H_2$, —NH—CO—($C_1$-$C_6$)alkyl, —NH—CO—N$H_2$, —NH—($C_1$-$C_6$)alkyl-CO—O$R^7$, —($C_1$-$C_6$)alkyl-CO—O$R^7$, (($C_4$-$C_{12}$)cycloalkenyl)-($C_1$-$C_6$)alkyl-, (($C_6$-$C_{14}$)bicycloalkyl)-($C_1$-$C_6$)alkyl-, (($C_8$-$C_{20}$)tricycloalkyl)-($C_1$-$C_6$)alkyl-, (($C_7$-$C_{14}$)bicycloalkenyl)-($C_1$-$C_6$)alkyl-, (($C_8$-$C_{20}$)tricycloalkenyl)-($C_1$-$C_6$)alkyl, ((7- to 12-membered)bicyclic ring system)-($C_1$-$C_6$)alkyl-, ((7- to 12-membered)bicyclic aryl)-($C_1$-$C_6$)alkyl-, ((5- to 12-membered)heteroaryl)-($C_1$-$C_6$)alkyl-, -(3- to 12 membered)heterocycle)-($C_1$-$C_6$)alkyl-, ((7- to 12-membered)bicycloheterocycle)-($C_1$-$C_6$)alkyl-, or naphthyl; each of which is optionally substituted with one or two substituents independently selected from the group consisting of OH, (=O), halo, —C(halo)$_3$, —CH(halo)$_2$, —C$H_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, N$H_2$, —NH($C_1$-$C_6$)alkyl, —($C_1$-$C_6$)alkyl-NH($C_1$-$C_6$)alkyl-$R^{14}$, CN, SH, O$R^4$, —CON$R^5R^6$, —COO$R^7$, —($C_1$-$C_6$)alkyl-CO—O$R^7$—N(S$O_2$($C_1$-$C_6$)alkyl)$_2$, —C(=NH)N$H_2$, —NH—CO—($C_1$-$C_6$)alkyl, —NH—CO—N$H_2$, —NH—($C_1$-$C_6$)alkyl-CO—O$R^7$; or d) hydrogen, —($C_1$-$C_{10}$)alkyl, —($C_2$-$C_{12}$)alkenyl, —($C_2$-$C_{12}$)alkynyl, —($C_3$-$C_{12}$)cycloalkyl, —(($C_3$-$C_{12}$)cycloalkyl)-($C_1$-$C_6$)alkyl, —($C_4$-$C_{12}$)cycloalkenyl, —($C_6$-$C_{14}$)bicycloalkyl, —($C_8$-$C_{20}$)tricycloalkyl, —($C_7$-$C_{14}$)bicycloalkenyl, —($C_8$-$C_{20}$)tricycloalkenyl, -(5- to 12-membered)aryl, ((5- to 12-membered)aryl)-($C_1$-$C_6$)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl and benzyl; each of which is substituted with one or two substituents independently selected from the group consisting of dihydroxy($C_1$-$C_6$)alkyl-, —($C_1$-$C_6$)alkoxy, (($C_1$-$C_6$)alkoxy)CO($C_1$-$C_6$)alkoxy-, —($C_1$-$C_6$)alkyl-NH($C_1$-$C_6$)alkyl-$R^{14}$, and —($C_1$-$C_6$)alkyl-CO—O$R^7$, —($C_1$-$C_6$)alkyl-CO—O$R^7$, —(OC$H_2$C$H_2$)$_s$—O($C_1$-$C_6$)alkyl, —(C$H_2$C$H_2$O)$_s$—($C_1$-$C_6$)alkyl, (($C_1$-$C_6$)alkyl)sulfonyl($C_1$-$C_6$)alkyl-, —N(S$O_2$($C_1$-$C_6$)alkyl)$_2$, —C(=NH)N$H_2$, —NH—CO—($C_1$-$C_6$)alkyl, —NH—CO—N$H_2$, —NH—($C_1$-$C_6$)alkyl-CO—O$R^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —$(C_1-C_{10})$alkyl, —$(C_2-C_{10})$alkenyl, —$(C_2-C_{10})$alkynyl, —$(C_1-C_{10})$alkoxy, OH, hydroxy$(C_1-C_6)$alkyl-, —C(halo)$_3$, —CH(halo)$_2$, or —CH$_2$(halo), or together form (=O);

$R^4$ is selected from —$(C_1-C_6)$alkyl, —$(C_2-C_6)$alkenyl, —$(C_2-C_6)$alkynyl, —C(halo)$_3$, —CH(halo)$_2$, —CH$_2$(halo), hydroxy$(C_1-C_6)$alkyl-, —$(C_3-C_{12})$cycloalkyl, ($(C_3-C_{12})$cycloalkyl)-$(C_1-C_6)$alkyl-, —$(C_6-C_{14})$bicycloalkyl, ($(C_6-C_{14})$bicycloalkyl)-$(C_1-C_6)$alkyl-, —$(C_8-C_{20})$tricycloalkyl, ($(C_8-C_{20})$tricycloalkyl)-$(C_1-C_6)$alkyl-, —$(C_4-C_{12})$cycloalkenyl, ($(C_4-C_{12})$cycloalkenyl)-$(C_1-C_6)$alkyl-, —$(C_7-C_{14})$bicycloalkenyl, ($(C_7-C_{14})$bicycloalkenyl)-$(C_1-C_6)$alkyl-, —$(C_8-C_{20})$tricycloalkenyl, ($(C_8-C_{20})$tricycloalkenyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

$R^5$ and $R^6$ are each independently hydrogen, —$(C_1-C_6)$alkyl, —$(C_3-C_8)$cycloalkyl, or ($(C_3-C_8)$cycloalkyl)-$(C_1-C_6)$alkyl-, —COOR$^7$, —$(C_1-C_6)$alkyl-CO—OR$^7$, —CONH$_2$, or $(C_1-C_6)$alkyl-CONH—, or $R^5$ and $R^6$ together with the nitrogen atom to which they are attached form a (4- to 8-membered)heterocycle;

$R^7$ is selected from hydrogen, —$(C_1-C_6)$alkyl, —$(C_2-C_6)$alkenyl, —$(C_2-C_6)$alkynyl, —$(C_3-C_{12})$cycloalkyl, —$(C_4-C_{12})$cycloalkenyl, ($(C_3-C_{12})$cycloalkyl)-$(C_1-C_6)$alkyl-, and ($(C_4-C_{12})$cycloalkenyl)-$(C_1-C_6)$alkyl-;

$R^9$ and $R^{10}$ are each independently selected from hydrogen, —$(C_1-C_6)$alkyl, —$(C_2-C_6)$alkenyl, —$(C_2-C_6)$alkynyl, —$(C_1-C_{10})$alkoxy, —$(C_3-C_{12})$cycloalkyl, —$(C_3-C_{12})$cycloalkenyl, ($(C_3-C_{12})$cycloalkyl)-$(C_1-C_6)$alkyl-, or ($(C_3-C_{12})$cycloalkenyl)-$(C_1-C_6)$alkyl-;

Each $R^{11}$ is independently selected from hydrogen, —$(C_1-C_{10})$alkyl, —$(C_2-C_{10})$alkenyl, —$(C_2-C_{10})$alkynyl, —$(C_1-C_{10})$alkoxy, ($(C_1-C_6)$alkyl)sulfonyl$(C_1-C_6)$alkyl-, —$(C_3-C_{12})$cycloalkyl, ($(C_3-C_{12})$cycloalkyl)-$(C_1-C_6)$alkyl-, —$(C_4-C_{12})$cycloalkenyl, or ($(C_4-C_{12})$cycloalkenyl)-$(C_1-C_6)$alkyl-;

$R^{12}$ and $R^{13}$ are each independently selected from hydrogen, —$(C_1-C_{10})$alkyl, —$(C_2-C_{12})$alkenyl, —$(C_2-C_{12})$alkynyl, —$(C_1-C_{10})$alkoxy, —$(OCH_2CH_2)_s$—O$(C_1-C_6)$alkyl, —$(C_3-C_{12})$cycloalkyl, ($(C_3-C_{12})$cycloalkyl)-$(C_1-C_6)$alkyl-, —$(C_4-C_{12})$cycloalkenyl, ($(C_4-C_{12})$cycloalkenyl)-$(C_1-C_6)$alkyl-, —$(C_6-C_{14})$bicycloalkyl, ($(C_6-C_{14})$bicycloalkyl)-$(C_1-C_6)$alkyl-, —$(C_8-C_{20})$tricycloalkyl, ($(C_8-C_{20})$tricycloalkyl)-$(C_1-C_6)$alkyl-, —$(C_7-C_{14})$bicycloalkenyl, ($(C_7-C_{14})$bicycloalkenyl)-$(C_1-C_6)$alkyl-, —$(C_8-C_{20})$tricycloalkenyl, ($(C_8-C_{20})$tricycloalkenyl)-$(C_1-C_6)$alkyl-, -(5- to 12-membered)aryl, ((5- to 12-membered)aryl)-$(C_1-C_6)$alkyl-, -(7- to 12-membered)bicyclic ring system, ((7- to 12-membered)bicyclic ring system)-$(C_1-C_6)$alkyl-, -(7- to 12-membered)bicyclic aryl, ((7- to 12-membered)bicyclic aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12 membered)heterocycle)-$(C_1-C_6)$alkyl-, -(7- to 12-membered)bicycloheterocycle, ((7- to 12-membered)bicycloheterocycle)-$(C_1-C_6)$alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —$(C_1-C_6)$alkyl, halo$(C_1-C_6)$alkyl-, —$(C_2-C_6)$alkenyl, —$(C_2-C_6)$alkynyl, hydroxy$(C_1-C_6)$alkyl-, phenyl, benzyl, NH$_2$, —NH$(C_1-C_6)$alkyl, CN, SH, OR$^4$, —CONR$^5$R$^6$, —COOR$^7$, —$(C_3-C_{12})$cycloalkyl, ($(C_3-C_{12})$cycloalkyl)-$(C_1-C_6)$alkyl-, -(5- to 12-membered)aryl, ((5- to 12-membered)aryl)-$(C_1-C_6)$alkyl-, -(5- to 12-membered)heteroaryl, ((5- to 12-membered)heteroaryl)-$(C_1-C_6)$alkyl-, -(3- to 12-membered)heterocycle, ((3- to 12-membered)heterocycle)-$(C_1-C_6)$alkyl-, -(7- to 12-membered)bicycloheterocycle, and ((7- to 12-membered)bicycloheterocycle)-$(C_1-C_6)$alkyl-;

$R^{14}$ is selected from —COOR$^7$, —$(C_1-C_6)$alkyl-CO—OR$^7$, —C(=O)—$(C_1-C_6)$alkyl-COOR$^7$, —$(C_1-C_6)$alkyl-C(=O)—$(C_1-C_6)$alkyl-COOR$^7$, —CONH$_2$, $(C_1-C_6)$alkyl-CONH—;

G is selected from O, —OCO—, NR$^9$, NR', S, SO, and SO$_2$;

R' is —C(=O)$(C_1-C_6)$alkyl or —SO$_2$$(C_1-C_6)$alkyl;

X is selected from OH, hydroxy$(C_1-C_6)$alkyl-, dihydroxy$(C_1-C_6)$alkyl-, halogen, —NH$_2$, —NR$^2$(C=O)R$^{12}$, CONR$^{12}$R$^{13}$, —$(C_1-C_6)$alkyl-CONH$_2$, —$(C_1-C_6)$alkyl-COOH, —COOH, —O—$(C_1-C_6)$alkyl-COOH, —O—$(C_1-C_6)$alkyl-CONH$_2$, —$(C_1-C_{10})$alkyl, —$(C_2-C_{10})$alkenyl, —$(C_2-C_{10})$alkynyl, —$(C_1-C_{10})$alkoxy, —$(OCH_2CH_2)_s$—O$(C_1-C_6)$alkyl, —$(OCH_2CH_2)_s$—OH, —$(CH_2)_p$CHOHCH$_2$OH, CN and —NH—SO$_2$R$^9$, —$(C_3-C_{12})$cycloalkyl, ($(C_3-C_{12})$cycloalkyl)-$(C_1-C_6)$alkyl-, ($(C_3-C_{12})$cycloalkyl)-$(C_1-C_6)$alkoxy-, -(5- to 12-membered)aryl, ((5- to 12-membered)aryl)-$(C_1-C_6)$alkyl-, ((5- to 12-membered)aryl)-$(C_1-C_6)$alkoxy-, -(5- to 12-membered)heteroaryl, ((5- to 12-membered)heteroaryl)-$(C_1-C_6)$alkyl-, ((5- to 12-membered)heteroaryl)-$(C_1-C_6)$alkoxy-, -(3- to 12-membered)heterocycle, ((3- to 12-membered)heterocycle)-$(C_1-C_6)$alkyl-, ((3- to 12-membered)heterocycle)-$(C_1-C_6)$alkoxy-, -(7- to 12-membered)bicycloheterocycle, ((7- to 12-membered)bicycloheterocycle)-$(C_1-C_6)$alkyl-, and ((7- to 12-membered)bicycloheterocycle)-$(C_1-C_6)$alkoxy-;

Q is selected from OH, —$(C_1-C_{10})$alkoxy, —$(C_1-C_{10})$alkyl, —$(C_3-C_{12})$cycloalkyl, -(5- to 12-membered)aryl, ($(C_3-C_{12})$cycloalkyl)-$(C_1-C_6)$alkyl-, ((5- to 12-membered)aryl)-$(C_1-C_6)$alkyl-, —$(OCH_2CH_2)_s$—O$(C_1-C_6)$alkyl, —$(CH_2CH_2O)_s$—$(C_1-C_6)$alkyl, —$(OCH_2CH_2)_s$—OH, —O(C=O)R$^9$R$^{10}$ and R$^{14}$;

Z is —$(CH_2)_m$—, optionally substituted with 1 or 2-$(C_1-C_6)$alkyl;

Y is —$(CH_2)_n$—CH— or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

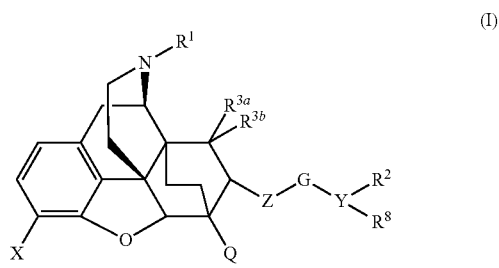

(I)

wherein $R^1$ is selected from hydrogen, —$(C_1-C_{10})$alkyl, —$(C_2-C_{12})$alkenyl, —$(C_2-C_{12})$alkynyl, —$(C_1-C_{10})$alkoxy, —$(C_3-$ $C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; each of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered) carbocyclic ring, -(5- to 12-membered)heterocycle, phenyl, and benzyl;

R$^2$ and R$^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, NH$_2$, —NH($C_1$-$C_6$)alkyl, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$)alkyl-CO—NR$^5$R$^6$, —COOR$^7$, —($C_1$-$C_6$)alkyl-CO—OR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —N(SO$_2$($C_1$-$C_6$)alkyl)$_2$, —C(=NH)NH$_2$, —NH—CO—($C_1$-$C_6$)alkyl, —NH—CO—NH$_2$, —NH—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{3a}$ and R$^{3b}$ are each independently selected from —($C_1$-$C_{10}$)alkyl, —($C_2$-$C_{10}$)alkenyl, —($C_2$-$C_{10}$)alkynyl, and —($C_1$-$C_{10}$)alkoxy; provided that at least one of R$^{3a}$ or R$^{3b}$ is selected from —($C_7$-$C_{10}$)alkyl, —($C_7$-$C_{10}$)alkenyl, —($C_7$-$C_{10}$)alkynyl, or —($C_1$-$C_{10}$)alkoxy;

R$^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^5$ and R$^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, or ($C_1$-$C_6$)alkyl-CONH—, or R$^5$ and R$^6$ together with the nitrogen atom to which they are attached form a (4- to 8-membered)heterocycle;

R$^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

R$^9$ and R$^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each R$^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, (($C_1$-$C_6$)alkyl)sulfonyl($C_1$-$C_6$)alkyl-, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

R$^{12}$ and R$^{13}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, —($C_1$-$C_6$)alkyl-CONH;

G is selected from O, —OCO—, NR$^9$, NR', S, SO, and SO$_2$;

R' is —C(=O)(C$_1$-C$_6$)alkyl or —SO$_2$(C$_1$-C$_6$)alkyl;

X is selected from OH, hydroxy(C$_1$-C$_6$)alkyl-, halogen, —NH$_2$, —NR$^2$(C=O)R$^{12}$CONR$^{12}$R$^{13}$, COOH, —COOH, —O—(C$_1$-C$_6$)alkyl-COOH, —O—(C$_1$-C$_6$)alkyl-CONH$_2$, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(OCH$_2$CH$_2$)$_s$—O(C$_1$-C$_6$)alkyl, —(OCH$_2$CH$_2$)$_s$—OH, —(CH$_2$)$_p$CHOHCH$_2$OH—, CN and NH—SO$_2$R$^9$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, -(5- to 12-membered)aryl, ((5- to 12-membered)aryl)-(C$_1$-C$_6$)alkyl-, ((5- to 12-membered)aryl)-(C$_1$-C$_6$)alkoxy-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, -(3- to 12-membered)heterocycle, ((3- to 12-membered)heterocycle)-(C$_1$-C$_6$)alkyl-, ((3- to 12-membered)heterocycle)-(C$_1$-C$_6$)alkoxy-, -(7- to 12-membered)bicycloheterocycle, ((7- to 12-membered)bicycloheterocycle)-(C$_1$-C$_6$)alkyl-, and ((7- to 12-membered)bicycloheterocycle)-(C$_1$-C$_6$)alkoxy-;

Q is selected from OH, —(C$_1$-C$_{10}$)alkoxy, —(C$_1$-C$_{10}$)alkyl, —(C$_3$-C$_{12}$)cycloalkyl, -(5- to 12-membered)aryl, ((C$_3$-C$_{12}$)cycloalkyl)-(C$_1$-C$_6$)alkyl-, ((5- to 12-membered)aryl)-(C$_1$-C$_6$)alkyl-, —(OCH$_2$CH$_2$)$_s$—O(C$_1$-C$_6$)alkyl, —(CH$_2$CH$_2$O)$_s$—(C$_1$-C$_6$)alkyl, —(OCH$_2$CH$_2$)$_s$—OH, —O(C=O)R$^9$R$^{10}$ and R$^{14}$;

Z is —(CH$_2$)$_m$—, optionally substituted with 1 or 2-(C$_1$-C$_6$)alkyl;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

The present invention further provides novel compounds of Formula I:

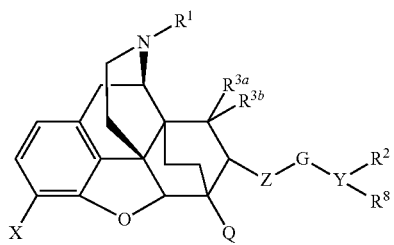

(I)

wherein

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), NH$_2$, NH(C$_1$-C$_6$)alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, NH$_2$, NH(C$_1$-C$_6$)alkyl-, CN, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, phenyl, benzyl, NH$_2$, NH(C$_1$-C$_6$)alkyl-, —(C$_1$-C$_6$)alkyl-NH (C$_1$-C$_6$)alkyl-R$^{14}$, CN, SH, OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, or —CH$_2$(halo), or together form (=O);

R$^4$ is selected from —(C$_1$-C$_6$)alkyl, —(C$_2$-C$_6$)alkenyl, —(C$_2$-C$_6$)alkynyl, —C(halo)$_3$, hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^5$ and R$^6$ are each independently hydrogen, —(C$_1$-C$_6$)alkyl, —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-CO—OR$^7$, —CONH$_2$, or —(C$_1$-C$_6$)alkyl-CONH, or R$^5$ and R$^6$ together with the nitrogen atom to which they are attached form a (4- to 8-membered)heterocycle;

R$^7$ is selected from hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-

$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_7$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, and (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, and (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($OCH_2CH_2$)$_s$—$O(C_1$-$C_6)$alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$, COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-COOR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, and —($C_1$-$C_6$)alkyl-CONH;

G is selected from O, —OCO—, NR$^9$, S, SO, and SO$_2$;

X is selected from OH, hydroxy($C_1$-$C_6$)alkyl-, halogen, —NH$_2$, —NR$^2$(C=O)R$^{12}$, —CONR$^{12}$R$^{13}$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN and —NH—SO$_2$R$^9$;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(OCH$_2$CH$_2$)$_s$—OH, —O(C=O)R$^9$R$^{10}$, and R$^{14}$;

Z is —(CH$_2$)$_m$—;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

provided that when X is OH or —($C_1$-$C_6$)alkoxy, and Q is OMe, and G is O, then either:

d) R$^1$ is selected from;
  iii. hydrogen, ($C_1$-$C_{10}$)alkoxy, ((5- to 12-membered)heteroaryl)-($C_1$-$C_6$)alkyl-, and ((3- to 12-membered)heterocycle)-($C_1$-$C_6$)alkyl-; each of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or
  iv. —($C_1$-$C_{10}$)alkyl, —($C_2$-$C_{12}$)alkenyl, —($C_2$-$C_{12}$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((3- to 12 membered)heterocycle)-($C_1$-$C_6$)alkyl-, phenyl, and benzyl; each of which is substituted with 1, 2, or 3 substituents independently selected from the group consisting of NR$^9$R$^{10}$, —CONR$^9$R$^{10}$, —NR$^9$COR$^{10}$, and SR$^{11}$;

or e) at least one of R$^2$ and R$^8$ is selected from:
  iii. —($C_1$-$C_{10}$)alkoxy, —(OCH$_2$CH$_2$)$_s$—O($C_1$-$C_6$)alkyl, NH$_2$, NH($C_1$-$C_6$)alkyl-, CN, —CONR$^5$R$^6$, —($C_1$-$C_6$)alkyl-CO—NR$^5$R$^6$, —COOR$^7$, —($C_1$-$C_6$)alkyl-CO—OR$^7$, (($C_4$-$C_{12}$)cycloalkenyl)-($C_1$-$C_6$)alkyl-, (($C_6$-$C_{14}$)bicycloalkyl)-($C_1$-$C_6$)alkyl-, (($C_8$-$C_{20}$)tricycloalkyl)-($C_1$-$C_6$)alkyl-, (($C_7$-$C_4$)bicycloalkenyl)-($C_1$-$C_6$)alkyl-, (($C_8$-$C_{20}$)tricycloalkenyl)-($C_1$-$C_6$)alkyl-, ((7- to 12-membered)bicyclic ring system)-($C_1$-$C_6$)alkyl-, ((7- to 12-membered)bicyclic aryl)-($C_1$-$C_6$)alkyl-, ((5- to 12-membered)heteroaryl)-($C_1$-$C_6$)alkyl-, ((3- to 12 membered)heterocycle)-($C_1$-$C_6$)alkyl-, ((7- to 12-membered)bicycloheterocycle)-($C_1$-$C_6$)alkyl-, or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, phenyl, benzyl, NH$_2$, NH($C_1$-$C_6$)alkyl-, —($C_1$-$C_6$)alkyl-NH($C_1$-$C_6$)alkyl-R$^{14}$, CN, SH, OR$^4$, —CONR$^5$R$^6$, —COOR$^7$, and —($C_1$-$C_6$)alkyl-CO—OR$^7$;
  iv. hydrogen, —($C_1$-$C_{10}$)alkyl, —($C_2$-$C_{12}$)alkenyl, —($C_2$-$C_{12}$)alkynyl, —($C_3$-$C_{12}$)cycloalkyl, —(($C_3$-$C_{12}$)cycloalkyl)-($C_1$-$C_6$)alkyl-, —($C_4$-$C_{12}$)cycloalkenyl, —($C_6$-$C_{14}$)bicycloalkyl, —($C_8$-$C_{20}$)tricycloalkyl, —($C_7$-$C_{14}$)bicycloalkenyl, —($C_8$-$C_{20}$)tricycloalkenyl, -(5- to 12-membered)aryl, ((5- to 12-membered)aryl)-($C_1$-$C_6$)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl and benzyl; each of which is substituted with one or two substituents independently selected from the group consisting of dihydroxy($C_1$-$C_6$)alkyl-, —($C_1$-$C_6$)alkyl-NH($C_1$-$C_6$)alkyl-R$^{14}$, CN, SH, OR$^4$, —CONR$^5$R$^6$, —COOR$^7$, and —($C_1$-$C_6$)alkyl-CO—OR$^7$;

or f) at least one of R$^{3a}$ or R$^{3b}$ is independently selected from —($C_7$-$C_{10}$)alkyl, —($C_7$-$C_{10}$)alkenyl, —($C_7$-$C_{10}$)alkynyl, or —($C_1$-$C_{10}$)alkoxy;

or a pharmaceutically acceptable salt, prodrug or solvate thereof.

In one embodiment, the present invention provides novel compounds of Formula I:

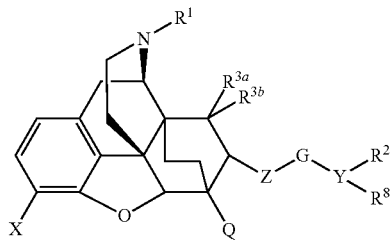

wherein

R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; any of which is optionally substituted with 1, 2, or 3 substituents independently selected from the group consisting of —(C$_1$-C$_6$)alkyl, OH, halo, —C(halo)$_3$, —CH(halo)$_2$, —CH$_2$(halo), NH$_2$, NH(C$_1$-C$_6$)alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

R$^2$ and R$^8$ are each independently hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, NH$_2$, NH(C$_1$-C$_6$)alkyl-, CN, —CONR$^5$R$^6$, —(C$_1$-C$_6$alkyl)-CO—NR$^5$R$^6$, —(C$_1$-C$_6$)alkyl-CO—NR$^5$R$^6$, —COOR$^7$, —(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl and naphthyl; any of which is optionally substituted with one or two substituents independently selected from the group consisting of OH, (═O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, phenyl, benzyl, NH$_2$, NH(C$_1$-C$_6$)alkyl-, —(C$_1$-C$_6$)alkyl-NH(C$_1$-C$_6$)alkyl-R$^{14}$, CN, SH, OR$^4$, —CONR$^5$R$^6$, —COOR$^7$, —(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, or —CH$_2$(halo), or together form (═O);

R$^4$ is selected from —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^5$ and R$^6$ are each independently hydrogen, —(C$_1$-C$_6$)alkyl, —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-CO—OR$^7$, —CONH$_2$, or —(C$_1$-C$_6$)alkyl-CONH, or R$^5$ and R$^6$ together with the nitrogen atom to which they are attached form a (4- to 8-membered)heterocycle;

R$^7$ is selected from hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

R$^9$ and R$^{10}$ are each independently selected from hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, or ((C$_3$-C$_{12}$)cycloalkenyl)-(C$_1$-C$_6$)alkyl-;

Each R$^{11}$ is independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, or ((C$_4$-C$_{12}$)cycloalkenyl)-(C$_1$-C$_6$)alkyl-;

R$^{12}$ and R$^{13}$ are each independently selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of OH, (═O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, phenyl, benzyl, NH$_2$, NH(C$_1$-C$_6$)alkyl-, CN, SH, OR$^4$, —CONR⁵R⁶, —COOR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R¹⁴ is selected from —COOR⁷, —(C₁-C₆)alkyl-CO—OR⁷, —C(=O)—(C₁-C₆)alkyl-CO—OR⁷, —(C₁-C₆)alkyl-C(=O)—(C₁-C₆)alkyl-COOR⁷, —CONH₂, (C₁-C₆)alkyl-CONH;

G is selected from O, —OCO—, NR⁹, S, SO, and SO₂;

X is selected from hydroxy(C₁-C₆)alkyl-, halogen, —NH₂, —NR²(C=O)R¹²CONR¹²R¹³, —(C₁-C₁₀)alkyl, —(C₂-C₁₀)alkenyl, —(C₂-C₁₀)alkynyl, —(C₇-C₁₀)alkoxy, —(OCH₂CH₂)ₛ—O(C₁-C₆)alkyl, —(OCH₂CH₂)ₛ—OH, —(CH₂)ₚCHOHCH₂OH—, CN and NH—SO₂R⁹;

Q is selected from OH, —(C₁-C₁₀)alkoxy, —(C₁-C₁₀)alkyl, —(C₃-C₁₂)cycloalkyl, -(5- to 12-membered)aryl, ((C₃-C₁₂)cycloalkyl)-(C₁-C₆)alkyl-, ((5- to 12-membered)aryl)-(C₁-C₆)alkyl-, —(OCH₂CH₂)ₛ—O(C₁-C₆)alkyl, —(OCH₂CH₂)ₛ—OH, —O(C=O)R⁹R¹⁰, and R¹⁴;

Z is —(CH₂)ₘ—;

Y is —(CH₂)ₙ—CH— or a direct bond, provided that when Y is a direct bond then R⁸ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

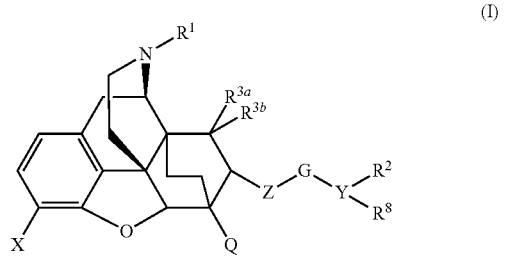

(I)

wherein

R¹ is selected from hydrogen, —(C₁-C₁₀)alkyl, —(C₂-C₁₂)alkenyl, —(C₂-C₁₂)alkynyl, —(C₁-C₁₀)alkoxy, —(C₃-C₁₂)cycloalkyl, —(C₄-C₁₂)cycloalkenyl, ((C₃-C₁₂)cycloalkyl)-(C₁-C₆)alkyl-, ((C₄-C₁₂)cycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, phenyl, and benzyl; any of which is optionally substituted with 1, 2, or 3 substituents independently selected from the group consisting of —(C₁-C₆)alkyl, OH, halo, —C(halo)₃, —CH(halo)₂, —CH₂(halo), NH₂, NH(C₁-C₆)alkyl-, NR⁹R¹⁰, CN, —CONR⁹R¹⁰, —NR⁹COR¹⁰, SR¹¹, -(5- to 12-membered)carbocyclic ring, -(5- to 12-membered)heterocycle, phenyl, and benzyl;

R² and R⁸ are each independently hydrogen, —(C₁-C₁₀)alkyl, —(C₂-C₁₂)alkenyl, —(C₂-C₁₂)alkynyl, —(C₁-C₁₀)alkoxy, —(OCH₂CH₂)ₛ—O(C₁-C₆)alkyl, NH₂, NH(C₁-C₆)alkyl-, CN, —CONR⁵R⁶, —(C₁-C₆)alkyl-CO—NR⁵R⁶, —COOR⁷, —(C₁-C₆)alkyl-CO—OR⁷, —(C₃-C₁₂)cycloalkyl, ((C₃-C₁₂)cycloalkyl)-(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, -(C₈-C₂₀)tricycloalkyl, ((C₈-C₂₀)tricycloalkyl)-(C₁-C₆)alkyl-, —(C₇-C₁₄)bicycloalkenyl, ((C₇-C₁₄)bicloalkenyl)-(C₁-C₆)alkyl-, —(C₈-C₂₀)tricycloalkenyl, ((C₈-C₂₀)tricloalkenyl)-(C₁-C₆)alkyl-, -(5- to 12-membered)aryl, ((5- to 12-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, ((7- to 12-membered)bicycloheterocycle)-(C₁-C₆)alkyl-, phenyl, benzyl or naphthyl; each of which is optionally substituted with one or two substituents independently selected from the group consisting of OH, (=O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, phenyl, benzyl, NH₂, NH(C₁-C₆)alkyl-, —(C₁-C₆)alkyl-NH(C₁-C₆)alkyl-R¹⁴, CN, SH, OR⁴, —CONR⁵R⁶, —(C₁-C₆alkyl)-CO—NR⁵R⁶, —COOR⁷, —(C₁-C₆)alkyl-CO—OR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R³ᵃ and R³ᵇ are each independently selected from hydrogen, —(C₁-C₁₀)alkyl, —(C₂-C₁₀)alkenyl, —(C₂-C₁₀)alkynyl, —(C₁-C₁₀)alkoxy, OH, hydroxy(C₁-C₆)alkyl-, —C(halo)₃, —CH(halo)₂, or —CH₂(halo), or together form (=O);

R⁴ is selected from —(C₁-C₆)alkyl, —(C₂-C₆)alkenyl, —(C₂-C₆)alkynyl, —C(halo)₃, hydroxy(C₁-C₆)alkyl-, —(C₃-C₁₂)cycloalkyl, ((C₃-C₁₂)cycloalkyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₄-C₁₂)cycloalkenyl, ((C₄-C₁₂)cycloalkenyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R⁵ and R⁶ are each independently hydrogen, —(C₁-C₆)alkyl, —(C₃-C₈)cycloalkyl, ((C₃-C₈)cycloalkyl)-(C₁-C₆)alkyl-, —COOR⁷, —(C₁-C₆)alkyl-CO—OR⁷, —CONH₂, or —(C₁-C₆)alkyl-CONH, or R⁵ and R⁶ together with the nitrogen atom to which they are attached form a (4- to 8-membered)heterocycle;

R⁷ is selected from hydrogen, —(C₁-C₆)alkyl, —(C₂-C₆)alkenyl, —(C₂-C₆)alkynyl, —(C₃-C₁₂)cycloalkyl, —(C₄-C₁₂)cycloalkenyl, ((C₃-C₁₂)cycloalkyl)-(C₁-C₆)alkyl-, and ((C₄-C₁₂)cycloalkenyl)-(C₁-C₆)alkyl-;

R⁹ and R¹⁰ are each independently selected from hydrogen, —(C₁-C₆)alkyl, —(C₂-C₆)alkenyl, —(C₂-C₆)alkynyl, —(C₁-C₁₀)alkoxy, —(C₃-C₁₂)cycloalkyl, —(C₃-C₁₂)cycloalkenyl, ((C₃-C₁₂)cycloalkyl)-(C₁-C₆)alkyl-, or ((C₃-C₁₂)cycloalkenyl)-(C₁-C₆)alkyl-;

Each R¹¹ is independently selected from hydrogen, —(C₁-C₁₀)alkyl, —(C₂-C₁₀)alkenyl, —(C₂-C₁₀)alkynyl, —(C₁-C₁₀)alkoxy, —(C₃-C₁₂)cycloalkyl, ((C₃-C₁₂)cycloalkyl)-(C₁-C₆)alkyl-, —(C₄-C₁₂)cycloalkenyl, or ((C₄-C₁₂)cycloalkenyl)-(C₁-C₆)alkyl-;

R¹² and R¹³ are each independently selected from hydrogen, —(C₁-C₁₀)alkyl, —(C₂-C₁₂)alkenyl, —(C₂-C₁₂)alkynyl, —(C₁-C₁₀)alkoxy, —(OCH₂CH₂)ₛ—O(C₁-C₆)alkyl, —(C₃-C₁₂)cycloalkyl, ((C₃-C₂)cycloalkyl)-(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, ((7- to 12-membered)bicycloheterocycle)-(C₁-C₆)alkyl-, phenyl, benzyl or naphthyl; each of which is optionally substituted with one or two substituents independently selected from the group consisting of OH, (═O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, phenyl, benzyl, NH₂, NH(C₁—C₆)alkyl-, CN, SH, OR⁴, —CONR⁵R⁶, —COOR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R¹⁴ is selected from —COOR⁷, —(C₁-C₆)alkyl-COOR⁷, —C(═O)—(C₁-C₆)alkyl-COOR⁷, —(C₁-C₆)alkyl-C(═O)—(C₁-C₆)alkyl-COOR⁷, CONH₂, —(C₁-C₆)alkyl-CONH;

G is selected from —OCO—, NR⁹, S, SO, and SO₂;

X is selected from OH, hydroxy(C₁-C₆)alkyl-, halogen, —NH₂, —NR²(C═O)R², CONR¹²R¹³, —(C₁-C₁₀)alkyl, —(C₂-C₁₀)alkenyl, —(C₂-C₁₀)alkynyl, —(C₁-C₁₀)alkoxy, —(OCH₂CH₂)ₛ—O(C₁-C₆)alkyl, —(OCH₂CH₂)ₛ—OH, —(CH₂)ₚCHOHCH₂OH—, CN and NH—SO₂R⁹;

Q is selected from OH, —(C₁-C₁₀)alkoxy, —(C₁-C₁₀)alkyl, —(C₃-C₁₂)cycloalkyl, -(5- to 12-membered)aryl, ((C₃-C₁₂)cycloalkyl)-(C₁-C₆)alkyl-, ((5- to 12-membered)aryl)-(C₁-C₆)alkyl-, —(OCH₂CH₂)ₛ—O(C₁-C₆)alkyl, —(OCH₂CH₂)ₛ—OH, —O(C═O)R⁹R¹⁰ and R¹⁴;

Z is —(CH₂)ₘ—;

Y is —(CH₂)ₙ—CH— or a direct bond, provided that when Y is a direct bond then R⁸ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

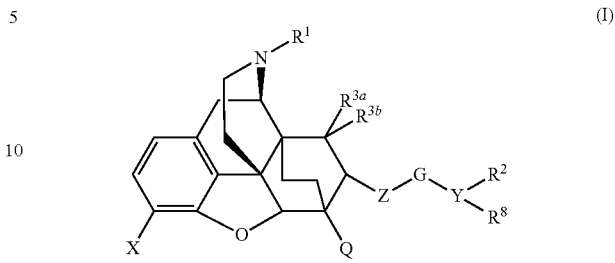

(I)

wherein

R¹ is selected from hydrogen, —(C₁-C₁₀)alkyl, —(C₂-C₁₂)alkenyl, —(C₂-C₁₂)alkynyl, —(C₇-C₁₀)alkoxy, —(C₃-C₁₂)cycloalkyl, —(C₄-C₁₂)cycloalkenyl, ((C₃-C₁₂)cycloalkyl)-(C₁-C₆)alkyl-, ((C₄-C₁₂)cycloalkenyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, phenyl, and benzyl; any of which is optionally substituted with 1, 2, or 3 substituents independently selected from the group consisting of —(C₁-C₆)alkyl, OH, halo, —C(halo)₃, —CH(halo)₂, —CH₂(halo), NH₂, NH(C₁-C₆)alkyl-, NR⁹R¹⁰, CN, —CONR⁹R¹⁰, —NR⁹COR¹⁰, SR¹¹, -(5- to 12-membered)carbocyclic ring, -(5- to 12-membered)heterocycle, phenyl, and benzyl;

R² and R⁸ are each independently hydrogen, —(C₁-C₁₀)alkyl, —(C₂-C₁₂)alkenyl, —(C₂-C₁₂)alkynyl, —(C₁-C₁₀)alkoxy, —(OCH₂CH₂)ₛ—O(C₁-C₆)alkyl, NH₂, NH(C₁-C₆)alkyl-, CN, —CONR⁵R⁶, —(C₁-C₆alkyl)-CO—NR⁵R⁶, —COOR⁷, —(C₁-C₆)alkyl-CO—OR⁷, —(C₃-C₁₂)cycloalkyl, ((C₃-C₁₂)cycloalkyl)-(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(5- to 12-membered)aryl, ((5- to 12-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, ((7- to 12-membered)bicycloheterocycle)-(C₁-C₆)alkyl-, phenyl, benzyl or naphthyl; each of which is optionally substituted with one or two substituents independently selected from the group consisting of OH, (═O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, phenyl, benzyl, NH₂, NH(C₁-C₆)alkyl-, —(C₁-C₆)alkyl-NH(C₁-C₆)alkyl-R¹⁴, CN, SH, OR⁴, —CONR⁵R⁶, —(C₁-C₆alkyl)-CO—NR⁵R⁶, —COOR⁷, —(C₁-C₆)alkyl-CO—OR⁷, —(C₃-C₁₂)cycloalkyl, ((C₃-C₁₂)cycloalkyl)-(C₁-C₆)alkyl-, -(5- to 12-membered)aryl, ((5- to 12-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-

$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, or —CH$_2$(halo), or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, —($C_1$-$C_6$)alkyl-CONH, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_4$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, —($C_1$-$C_6$)alkyl-CONH;

G is selected from O, —OCO—, NR$^9$, S, SO, and SO$_2$;

X is selected from OH, hydroxy($C_1$-$C_6$)alkyl-, halogen, —NH$_2$, —NR$^2$(C=O)R$^{12}$CONR$^{12}$R$^{13}$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN and NH—SO$_2$R$^9$;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(OCH$_2$CH$_2$)$_s$—OH, —O(C=O)R$^9$R$^{10}$ and R$^{14}$; provided that Q is not OMe;

Z is —(CH$_2$)$_m$—;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

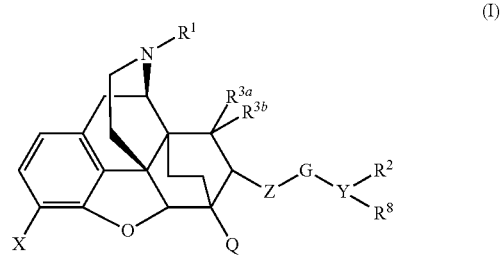

(I)

wherein $R^1$ is selected from c) hydrogen, ($C_1$-$C_{10}$)alkoxy, ((5- to 12-membered)heteroaryl)-($C_1$-$C_6$)alkyl-, and ((3- to 12-membered)heterocycle)-($C_1$-$C_6$)alkyl-; any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or d) —($C_1$-$C_{10}$)alkyl, —($C_2$-$C_{12}$)alkenyl, —($C_2$-$C_{12}$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((3- to 12 membered)heterocycle)-

($C_1$-$C_6$)alkyl-, phenyl, or benzyl; each of which is substituted with 1, 2, or 3 substituents independently selected from the group consisting of $NR^9R^{10}$, —$CONR^9R^{10}$, —$NR^9COR^{10}$, and $SR^{11}$;

$R^2$ and $R^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($OCH_2CH_2$)$_s$—$O$($C_1$-$C_6$)alkyl, $NH_2$, $NH$($C_1$-$C_6$)alkyl-, CN, —$CONR^5R^6$, —($C_1$-$C_6$)alkyl-CO—$NR^5R^6$, —$COOR^7$, —($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, phenyl, benzyl, NH$_2$, NH($C_1$-$C_6$)alkyl-, —($C_1$-$C_6$)alkyl-NH ($C_1$-$C_6$)alkyl-$R^{14}$, CN, SH, $OR^4$, —$CONR^5R^6$, —($C_1$-$C_6$)alkyl-CO—$NR^5R^6$, —$COOR^7$, —($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, or —CH$_2$(halo), or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_2$)cycloalkyl, (($C_3$-$C_{12}$)cycloalkyl)-($C_1$-$C_6$)alkyl-, —($C_6$-$C_{14}$)bicycloalkyl, (($C_6$-$C_4$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —$COOR^7$, —($C_1$-$C_6$)alkyl-CO—$OR^7$, $CONH_2$, or —($C_1$-$C_6$)alkyl-CONH, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($OCH_2CH_2$)$_s$—$O$($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_4$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, $OR^4$, —$CONR^5R^6$, —$COOR^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5-to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —$COOR^7$, —($C_1$-$C_6$)alkyl-CO—$OR^7$, —C(=O)—($C_1$-$C_6$)alkyl-$COOR^7$, —($C_1$-$C_6$)alkyl-C(=O)—($C_1$-$C_6$)alkyl-$COOR^7$, $CONH_2$, $CONH$($C_1$-$C_6$)alkyl-;

G is selected from O, —OCO—, $NR^9$, S, SO, and $SO_2$;

X is selected from OH, hydroxy($C_1$-$C_6$)alkyl-, halogen, —$NH_2$, —$NR^2$(C=O)$R^8$, $CONR^{12}R^{13}$, —($C_1$-$C_{10}$)alkyl, —($C_2$-$C_{10}$)alkenyl, —($C_2$-$C_{10}$)alkynyl, —($C_1$-$C_{10}$)alkoxy, —($OCH_2CH_2$)$_s$—$O$($C_1$-$C_6$)alkyl, —($OCH_2CH_2$)$_s$—OH, —(CH$_2$)$_p$CHOHCH$_2$OH—, CN and NH—$SO_2R^9$;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —($OCH_2CH_2$)$_s$—$O$($C_1$-$C_6$)alkyl, —($OCH_2CH_2$)$_s$—OH, —O(C=O)$R^9R^{10}$ and $R^{14}$;

Z is —(CH$_2$)$_m$—;

Y is —(CH$_2$)$_n$—CH— or a direct bond, provided that when Y is a direct bond then $R^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

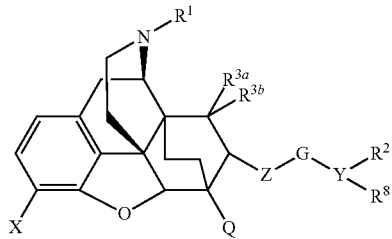

(I)

wherein $R^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; each of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

At least one of $R^2$ or $R^8$ is independently selected from:

c) —($C_1$-$C_{10}$)alkoxy, —(OCH$_2$CH$_2$)$_s$—O($C_1$-$C_6$)alkyl, NH$_2$, NH($C_1$-$C_6$)alkyl-, CN, —CONR$^5$R$^6$, —($C_1$-$C_6$)alkyl-CO—NR$^5$R$^6$, —COOR$^7$, —($C_1$-$C_6$)alkyl-CO—OR$^7$, (($C_4$-$C_{12}$)cycloalkenyl)-($C_1$-$C_6$)alkyl-, (($C_6$-$C_{14}$)bicycloalkyl)-($C_1$-$C_6$)alkyl-, (($C_8$-$C_{20}$)tricycloalkyl)-($C_1$-$C_6$)alkyl-, (($C_7$-$C_{14}$)bicycloalkenyl)-($C_1$-$C_6$)alkyl-, (($C_8$-$C_{20}$)tricycloalkenyl)-($C_1$-$C_6$)alkyl-, ((7- to 12-membered)bicyclic ring system)-($C_1$-$C_6$)alkyl-, ((7- to 12-membered)bicyclic aryl)-($C_1$-$C_6$)alkyl-, ((5- to 12-membered)heteroaryl)-($C_1$-$C_6$)alkyl-, ((3- to 12 membered)heterocycle)-($C_1$-$C_6$)alkyl-, ((7- to 12-membered)bicycloheterocycle)-($C_1$-$C_6$)alkyl-, or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, phenyl, benzyl, NH$_2$, NH($C_1$-$C_6$)alkyl-, —($C_1$-$C_6$)alkyl-NH($C_1$-$C_6$)alkyl-R$^{14}$, CN, SH, OR$^4$, —CONR$^5$R$^6$, —COOR$^7$, —($C_1$-$C_6$)alkyl-CO—OR$^7$;

d) hydrogen, —($C_1$-$C_{10}$)alkyl, —($C_2$-$C_{12}$)alkenyl, —($C_2$-$C_{12}$)alkynyl, —($C_3$-$C_{12}$)cycloalkyl, —(($C_3$-$C_{12}$)cycloalkyl)-($C_1$-$C_6$)alkyl, —($C_4$-$C_{12}$)cycloalkenyl, —($C_6$-$C_{14}$)bicycloalkyl, —($C_8$-$C_{20}$)tricycloalkyl, —($C_7$-$C_{14}$)bicycloalkenyl, —($C_8$-$C_{20}$)tricycloalkenyl, -(5- to 12-membered)aryl, ((5- to 12-membered)aryl)-($C_1$-$C_6$)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl and benzyl; each of which is substituted with one or two substituents independently selected from the group consisting of dihydroxy($C_1$-$C_6$)alkyl-, —($C_1$-$C_6$)alkyl-NH($C_1$-$C_6$)alkyl-R$^{14}$, and —($C_1$-$C_6$)alkyl-CO—OR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{3a}$ and $R^{3b}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, OH, hydroxy($C_1$-$C_6$)alkyl-, —C(halo)$_3$, —CH(halo)$_2$, or —CH$_2$(halo), or together form (=O);

$R^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^5$ and $R^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, —CONH$_2$, or —($C_1$-$C_6$)alkyl-CONH, or $R^5$ and $R^6$ together with the nitrogen atom to which they are attached form a (4- to 8-membered)heterocycle;

$R^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, —($C_1$-$C_6$)alkyl-CONH;

G is selected from O, —OCO—, NR$^9$, S, SO, and SO$_2$;

X is selected from OH, hydroxy($C_1$-$C_6$)alkyl-, halogen, —NH$_2$, —NR$^2$(C=O)R$^{12}$, CONR$^{12}$R$^{13}$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN and NH—SO$_2$R$^9$;

Q is selected from OH, —($C_7$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(OCH$_2$CH$_2$)$_s$—OH, —O(C=O)R$^9$R$^{10}$ and R$^{14}$;

Z is —(CH$_2$)$_m$—;

Y is —(CH$_2$)$_n$—CH— or a direct bond, provided that when Y is a direct bond then R$^8$ is absent;

m is an integer 1, 2, 3, 4, 5, or 6;

n is an integer 0, 1, 2, 3, 4, 5 or 6;

p is an integer 0, 1 or 2;

s is an integer 1 to 13;

or a pharmaceutically acceptable salt, prodrug or solvate thereof.

In another embodiment, the present invention provides novel compounds of Formula I:

wherein

R$^1$ is selected from hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, phenyl, and benzyl; each of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), NH$_2$, NH($C_1$-$C_6$)alkyl-, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl;

R$^2$ and R$^8$ are each independently hydrogen, —($C_1$-$C_{10}$)alkyl, —($C_2$-$C_{12}$)alkenyl, —($C_2$-$C_{12}$)alkynyl, —($C_1$-$C_{10}$)alkoxy, —(OCH$_2$CH$_2$)$_s$—O($C_1$-$C_6$)alkyl, NH$_2$, NH($C_1$-$C_6$)alkyl-, CN, —CONR$^5$R$^6$, —($C_1$-$C_6$)alkyl-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, phenyl, benzyl, NH$_2$, NH($C_1$-$C_6$)alkyl-, —($C_1$-$C_6$)alkyl-NH($C_1$-$C_6$)alkyl-R$^{14}$, CN, SH, OR$^4$, —CONR$^5$R$^6$, —($C_1$-$C_6$)alkyl-CO—NR$^5$R$^6$, —COOR$^7$, —($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^{3a}$ and R$^{3b}$ are each independently selected from —($C_1$-$C_{10}$)alkyl, —($C_2$-$C_{10}$)alkenyl, —($C_2$-$C_{10}$)alkynyl, and —($C_1$-$C_{10}$)alkoxy; provided that at least one of R$^{3a}$ or R$^{3b}$ is selected from —($C_7$-$C_{10}$)alkyl, —($C_7$-$C_{10}$)alkenyl, —($C_7$-$C_{10}$)alkynyl, or —($C_1$-$C_{10}$)alkoxy;

R$^4$ is selected from —($C_1$-$C_6$)alkyl, —($C_2$-$C_6$)alkenyl, —($C_2$-$C_6$)alkynyl, —C(halo)$_3$, —CH(halo)$_2$, —CH$_2$(halo), hydroxy($C_1$-$C_6$)alkyl-, —($C_3$-$C_{12}$)cycloalkyl, (($C_3$-$C_{12}$)cycloalkyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_9$-$C_{20}$)tricycloalkyl, (($C_8$-$C_{20}$)tricycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

R$^5$ and R$^6$ are each independently hydrogen, —($C_1$-$C_6$)alkyl, —($C_3$-$C_8$)cycloalkyl, or (($C_3$-$C_8$)cycloalkyl)-($C_1$-$C_6$)alkyl-, —COOR$^7$, —($C_1$-$C_6$)alkyl-CO—OR$^7$, CONH$_2$, or —($C_1$-$C_6$)alkyl-CONH, or R$^5$ and R$^6$ together with the nitrogen atom to which they are attached form a (4- to 8-membered)heterocycle;

R$^7$ is selected from hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

$R^9$ and $R^{10}$ are each independently selected from hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, or (($C_3$-$C_{12}$)cycloalkenyl)-($C_1$-$C_6$)alkyl-;

Each $R^{11}$ is independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, or (($C_4$-$C_{12}$)cycloalkenyl)-($C_1$-$C_6$)alkyl-;

$R^{12}$ and $R^{13}$ are each independently selected from hydrogen, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$) alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, —($C_1$-$C_6$)alkyl-CONH;

G is selected from O, —OCO—, NR$^9$, S, SO, and SO$_2$;

X is selected from OH, hydroxy($C_1$-$C_6$)alkyl-, halogen, —NH$_2$, —NR$^2$(C=O)R$^{12}$, CONR$^{12}$R$^{13}$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH—, CN and NH—SO$_2$R$^9$;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(OCH$_2$CH$_2$)$_s$—OH, —O(C=O)R$^9$R$^{10}$ and R$^{14}$;

Z is —(CH$_2$)$_m$—;

Y is —(CH$_2$)$_n$—CH— or a direct bond, provided that when Y is a direct bond then R$^8$ is absent;

m is an integer 1, 2, 3, 4, 5, or 6;
n is an integer 0, 1, 2, 3, 4, 5 or 6;
p is an integer 0, 1 or 2;
s is an integer 1 to 13;
or a pharmaceutically acceptable salt, prodrug or solvate thereof.

In certain embodiments, the present invention provides novel compounds of Formula I as defined above, but having the general Formula II:

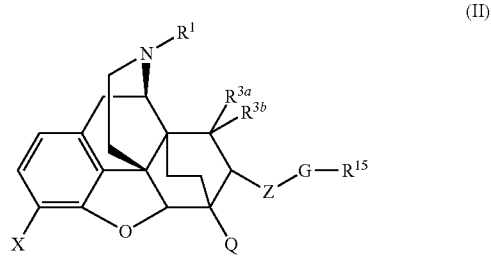

(II)

Wherein $R^1$, $R^{3a}$, $R^{3b}$, X, Q, and Z are as previously defined;

G is O or NH$_2$;

$R^{15}$ is selected from:

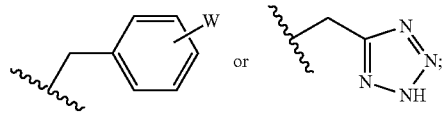

and

W is selected from:

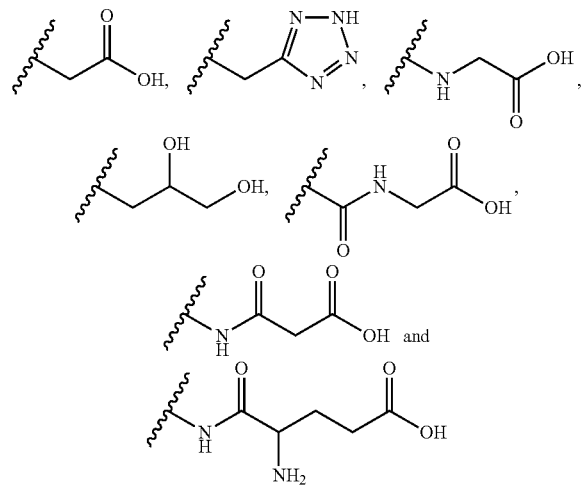

or a pharmaceutically acceptable salt, prodrug or solvate thereof.

In certain embodiments, the present invention provides novel compounds of Formula I having the general Formula II:

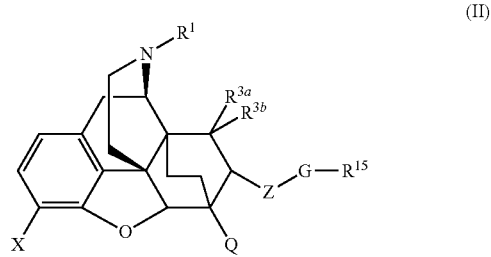

(II)

wherein $R^1$, $R^{3a}$, $R^{3b}$, X, Q, and Z are as previously defined;

G is O;

$R^{15}$ is selected from —$(OCH_2CH_2)_s$—$O(C_1$-$C_6)$alkyl,

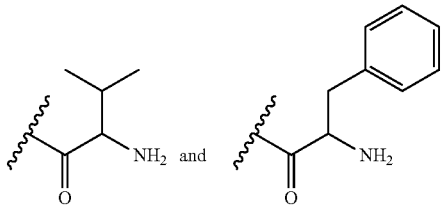 and or a pharmaceutically acceptable salt, prodrug or solvate thereof.

In certain embodiments, the present invention provides novel compounds of Formula I having the general Formula II:

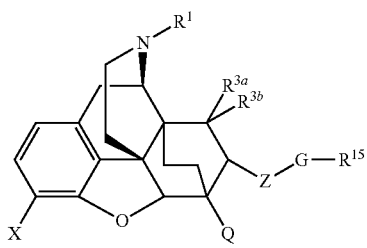

(II)

wherein $R^1$, $R^{3a}$, $R^{3b}$, X, Q, and Z are as previously defined;

G is NH;

$R^{15}$ is selected from —$(OCH_2CH_2)_s$—$O(C_1$-$C_6)$alkyl,

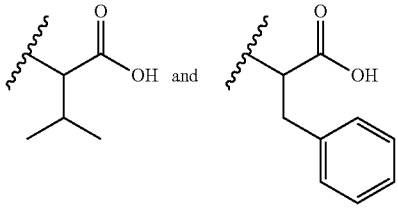 and or a pharmaceutically acceptable salt, prodrug or solvate thereof.

In certain embodiments, the present invention provides novel compounds of Formula I wherein:

$R^1$ is $CH_3$ or cyclopropylmethyl;

X is selected from F, $NH_2$, $NHCOCH_3$, $NHSO_2CH_3$, CN, $CO_2H$, $CONH_2$, —$(OCH_2CH_2)_s$—$O(C_1$-$C_6)$alkyl, and —$(OCH_2CH_2)_s$—OH;

or a pharmaceutically acceptable salt, prodrug or solvate thereof.

The present invention further provides compounds of Formula IA:

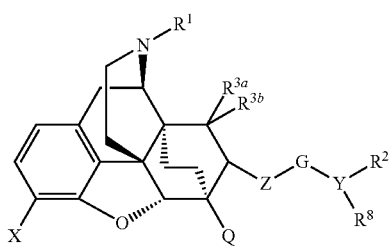

(IA)

wherein $R^1$ $R^2$, $R^{3a}$, $R^{3b}$, $R^8$, G, X, Q, Y, and Z are as defined above for Formula I.

In certain embodiments, the invention provides compounds of Formula IB:

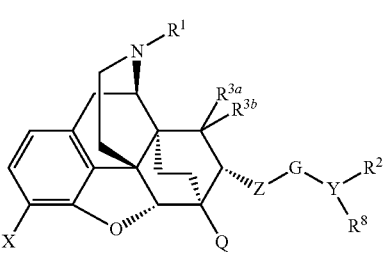

(IB)

wherein $R^1$ $R^2$, $R^{3a}$, $R^{3b}$, $R^8$, G, X, Q, Y, and Z are as defined above for Formula I.

In one embodiment, $R^1$ is —$(C_1$-$C_{10})$alkyl optionally substituted with 1, 2, or 3 substituents independently selected from the group consisting of —$(C_1$-$C_6)$alkyl, OH, halo, —C(halo)$_3$, —CH(halo)$_2$, —CH$_2$(halo), $NH_2$, NH$(C_1$-$C_6)$alkyl-, CN, SH, -(5- to 12-membered)carbocyclic ring, -(5- to 12-membered)heterocycle, phenyl, and benzyl.

In one embodiment, $R^1$ is selected from the group consisting of methyl, ethyl, or isopropyl, and preferably methyl, each of which is optionally substituted with 1, 2, or 3 substituents independently selected from the group consisting of —$(C_1$-$C_6)$alkyl, OH, halo, —C(halo)$_3$, —CH(halo)$_2$, —CH$_2$(halo), $NH_2$, NH$(C_1$-$C_6)$alkyl-, CN, SH, -(5- to 12-membered)carbocyclic ring, -(5- to 12-membered)heterocycle, phenyl, and benzyl.

In another embodiment, $R^1$ is —$(C_2$-$C_{12})$alkenyl optionally substituted with 1, 2, or 3 substituents independently selected from the group consisting of —$(C_1$-$C_6)$alkyl, OH, halo, —C(halo)$_3$, —CH(halo)$_2$, —CH$_2$(halo), $NH_2$, NH$(C_1$-$C_6)$alkyl-, CN, SH, -(5- to 12-membered)carbocyclic ring, -(5- to 12-membered)heterocycle, phenyl, and benzyl.

In another embodiment, $R^1$ is selected from the group consisting of ethenyl and propenyl, each of which is optionally substituted with 1, 2, or 3 substituents independently selected from the group consisting of —$(C_1$-$C_6)$alkyl, OH, halo, —C(halo)$_3$, —CH(halo)$_2$, —CH$_2$(halo), $NH_2$, NH$(C_1$-$C_6)$alkyl-, CN, SH, -(5- to 12-membered)carbocyclic ring, -(5- to 12-membered)heterocycle, phenyl, and benzyl.

In another embodiment, $R^1$ is —$(C_3$-$C_{12})$cycloalkyl optionally substituted with 1, 2, or 3 substituents independently selected from the group consisting of —$(C_1$-$C_6)$alkyl, OH, halo, —C(halo)$_3$, —CH(halo)$_2$, —CH$_2$(halo), $NH_2$, NH$(C_1$-$C_6)$alkyl-, CN, SH, -(5- to 12-membered)carbocyclic ring, -(5- to 12-membered)heterocycle, phenyl, and benzyl.

In another embodiment, $R^1$ is —$(C_4$-$C_{12})$cycloalkenyl optionally substituted with 1, 2, or 3 substituents independently selected from the group consisting of —$(C_1$-$C_6)$alkyl, OH, halo, —C(halo)$_3$, —CH(halo)$_2$, —CH$_2$(halo), $NH_2$, NH$(C_1$-$C_6)$alkyl-, CN, SH, -(5- to 12-membered)carbocyclic ring, -(5- to 12-membered)heterocycle, phenyl, and benzyl.

In another embodiment, $R^1$ is $((C_3$-$C_{12})$cycloalkyl)-$(C_1$-$C_6)$alkyl-, each of which is optionally substituted.

In another embodiment, $R^1$ is selected from the group consisting of cyclopropylmethyl, cyclobutylmethyl, cyclopentylmethyl, and cyclohexylmethyl, and preferably cyclopropylmethyl, each of which is optionally substituted.

In another embodiment, $R^1$ is -(5- to 12-membered)aryl, -(5- to 12-membered)heteroaryl, or -(3- to 12-membered) heterocycle, each of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —NH$_2$, NH($C_1$-$C_6$)alkyl-, CN, SH, -(5- to 12-membered)carbocyclic ring, -(5- to 12-membered)heterocycle, phenyl, and benzyl.

In one embodiment, at least one of $R^2$ or $R^8$ is —($C_1$-$C_{10}$)alkyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In another embodiment, at least one of $R^2$ or $R^8$ is selected from the group consisting of methyl, ethyl, propyl, isopropyl, butyl, iso-butyl, tert-butyl, pentyl and hexyl, each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In one embodiment, both $R^2$ and $R^8$ are —($C_1$-$C_{10}$)alkyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$—$C_6$)alkyl-, CN, SH, OR$^4$, —CONR$^5$R$^6$ and —COOR$^7$.

In another embodiment, both $R^2$ are $R^8$ are selected from the group consisting of methyl, ethyl, propyl, isopropyl, butyl, iso-butyl, tert-butyl, pentyl and hexyl, each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In one embodiment, at least one of $R^2$ or $R^8$ is —($C_2$-$C_{12}$)alkenyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In another embodiment, at least one of $R^2$ or $R^8$ is selected from the group consisting of 2-methyl-but-2-enyl and propenyl, each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In one embodiment, at least one of $R^2$ or $R^8$ is —($C_2$-$C_{12}$)alkynyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In another embodiment, at least one of $R^2$ or $R^8$ is propynyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In one embodiment, at least one of $R^2$ or $R^8$ is —($C_3$-$C_{12}$)cycloalkyl, and preferably cyclobutyl or cyclohexyl, optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In another embodiment, both $R^2$ and $R^8$ are —($C_3$-$C_{12}$)cycloalkyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In another embodiment, at least one of $R^2$ or $R^8$ is —($C_4$-$C_{12}$)cycloalkenyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In another embodiment, at least one of $R^2$ or $R^8$ is —($C_6$-$C_{14}$)bicycloalkyl, —($C_8$-$C_{20}$)tricycloalkyl, —($C_7$-$C_{14}$) bicycloalkenyl, or —($C_8$-$C_{20}$)tricycloalkenyl, each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In another embodiment, at least one of $R^2$ or $R^8$ is -(5- to 12-membered)aryl, and preferably phenyl or naphthalenyl, optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In another embodiment, at least one of $R^2$ or $R^8$ is phenyl optionally substituted with one or two substituents independently selected from —($C_1$-$C_6$)alkyl, OH, halo, NH$_2$, NH($C_1$-$C_6$)alkyl-, CN, (=O), SH, phenyl, —C(halo)$_3$, —OC(halo)$_3$, and —O($C_1$-$C_6$)alkyl.

In another embodiment, at least one of $R^2$ or $R^8$ is benzyl optionally substituted with one or two substituents independently selected from —($C_1$-$C_6$)alkyl, OH, halo, NH$_2$, NH($C_1$-$C_6$)alkyl-, CN, (=O), SH, phenyl, —C(halo)$_3$, —OC(halo)$_3$, and —O($C_1$-$C_6$)alkyl.

In one embodiment, both $R^2$ and $R^8$ are -(5- to 12-membered)aryl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, NH($C_1$-$C_6$)alkyl-, CN, SH, OR$^4$, —CONR$^5$R$^6$ and —COOR$^7$.

In another embodiment, both $R^2$ and $R^8$ are phenyl optionally substituted with one or two substituents independently selected from —($C_1$-$C_6$)alkyl, OH, halo, phenyl, NH$_2$, NH($C_1$-$C_6$)alkyl-, CN, (=O), and SH.

In another embodiment, both $R^2$ and $R^8$ are benzyl optionally substituted with one or two substituents independently selected from —($C_1$-$C_6$)alkyl, OH, halo, $NH_2$, NH($C_1$-$C_6$)alkyl-, CN, (=O), and SH.

In one embodiment, at least one of $R^2$ or $R^8$ is ((5- to 12-membered)aryl)-($C_1$-$C_6$)alkyl- optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, $NH_2$, NH($C_1$-$C_6$)alkyl-, CN, SH, $OR^4$, —CONR$^5$R$^6$ and —COOR$^7$.

In another embodiment, at least one of $R^2$ or $R^8$ is phenyl-($C_1$-$C_6$)alkyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, $NH_2$, NH($C_1$-$C_6$)alkyl-, CN, SH, $OR^4$, —CONR$^5$R$^6$ and —COOR$^7$.

In another embodiment, at least one of $R^2$ or $R^8$ is benzyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, $NH_2$, NH($C_1$-$C_6$)alkyl-, CN, SH, $OR^4$, —CONR$^5$R$^6$ and —COOR$^7$.

In one embodiment, both $R^2$ and $R^8$ are ((5- to 12-membered)aryl)-($C_1$-$C_6$)alkyl- optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, $NH_2$, NH($C_1$-$C_6$)alkyl-, CN, SH, $OR^4$, —CONR$^5$R$^6$ and —COOR$^7$.

In one embodiment, Y, $R^2$ and $R^8$ taken together are diphenylpropyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, $NH_2$, NH($C_1$-$C_6$)alkyl-, CN, SH, $OR^4$, —CONR$^5$R$^6$ and —COOR$^7$.

In another embodiment, both $R^2$ and $R^8$ are benzyl optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, $NH_2$, NH($C_1$-$C_6$)alkyl-, CN, SH, $OR^4$, —CONR$^5$R$^6$ and —COOR$^7$.

In another embodiment, at least one of $R^2$ or $R^8$ is -(5- to 12-membered)heteroaryl, -(3- to 12-membered)heterocycle, or -(7- to 12-membered)bicycloheterocycle, and preferably pyridinyl, each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, $NH_2$, NH($C_1$-$C_6$)alkyl-, CN, SH, $OR^4$, —CONR$^5$R$^6$ and —COOR$^7$.

In one embodiment, at least one of $R^{3a}$ or $R^{3b}$ is hydrogen.
In another embodiment, both $R^{3a}$ and $R^{3b}$ are hydrogen.
In another embodiment, at least one of $R^{3a}$ or $R^{3b}$ is OH.
In another embodiment, at least one of $R^{3a}$ or $R^{3b}$ is —($C_1$-$C_6$)alkyl.

In another embodiment, at least one of $R^{3a}$ or $R^{3b}$ is selected from the group consisting of methyl, ethyl and isopropyl.

In another embodiment, at least one of $R^{3a}$ and $R^{3b}$ is selected from —($C_1$-$C_6$)alkyl-C(=O)—($C_1$-$C_6$)alkoxy, —($C_1$-$C_6$)alkyl-CN, —($C_1$-$C_6$)alkyl-COOR$^7$, or ((5- to 12-membered)aryl)-($C_1$-$C_6$)alkoxy-($C_1$-$C_6$)alkyl-.

In another embodiment, at least one of $R^{3a}$ and $R^{3b}$ is selected from $CH_2CH_2C(O)OCH_2CH_3$, $CH_2CN$, $CH_2CH_2C(O)OH$, or $CH_2OCH_2C_6H_5$ In another embodiment, both $R^{3a}$ and $R^{3b}$ are —($C_1$-$C_6$)alkyl.

In another embodiment, at least one of $R^{3a}$ or $R^{3b}$ is —CH$_2$(halo).

In another embodiment, at least one of $R^{3a}$ or $R^{3b}$ is selected from the group consisting of $CH_2F$ and $CH_2Cl$.

In another embodiment, Z is —CH$_2$—.
In another embodiment, Y is —CH.
In another embodiment, Z is —CH$_2$— and Y is —CH.
In another embodiment, Y is a direct bond.
In another embodiment, Z is —CH$_2$— and Y is a direct bond.
In another embodiment, Y is —CH$_2$—CH.
In another embodiment, Z is —CH$_2$—CH$_2$—.
In another embodiment, Z is —C(CH$_3$)$_2$—
In another embodiment, Y is —CH$_2$—CH and Z is —CH$_2$—CH$_2$—.
In another embodiment, Z is —CH$_2$—CH$_2$— and Y is a direct bond.
In another embodiment, Z is —CH$_2$— and Y is —CH$_2$—CH.
In another embodiment, Z is —CH$_2$—CH$_2$— and Y is —CH.
In another embodiment, Y is —CH$_2$—CH$_2$—CH.
In another embodiment, Z is —CH$_2$—CH$_2$—CH$_2$—.
In another embodiment, Y is a direct bond and Z is —CH$_2$—CH$_2$—CH$_2$—.
In another embodiment, Y is —CH$_2$—CH$_2$—CH and Z is —CH$_2$—.
In another embodiment, Y is —CH and Z is —CH$_2$—CH$_2$—CH$_2$—.
In another embodiment, Y is —CH$_2$—CH$_2$—CH and Z is —CH$_2$—CH$_2$—.
In another embodiment, Y is —CH$_2$—CH and Z is —CH$_2$—CH$_2$—CH$_2$—.
In another embodiment, Y is —CH and least one of $R^2$ or $R^8$ is phenyl.
In another embodiment, Y is a direct bond and $R^2$ is benzyl.
In another embodiment, Y is —CH and both $R^2$ and $R^8$ are phenyl.
In another embodiment, Z is —CH$_2$, Y is —CH$_2$—CH$_2$—, $R^1$ is —($C_1$-$C_6$)alkyl, $R^2$ is —($C_2$-$C_6$)alkynyl, and at least one of $R^{3a}$ and $R^{3b}$ is H.
In another embodiment, Z is —CH$_2$, Y is —CH$_2$—CH$_2$—, $R^1$ is —($C_1$-$C_6$)alkyl, $R^2$ is —($C_2$-$C_6$)alkynyl, and both $R^{3a}$ and $R^{3b}$ are H.
In another embodiment, Z is —CH$_2$, Y is —CH$_2$—CH$_2$—, $R^1$ is —($C_1$-$C_6$)alkyl, $R^2$ is -(5- to 12-membered)aryl, and at least one of $R^{3a}$ and $R^{3b}$ is H.
In another embodiment, Z is —CH$_2$, Y is —CH$_2$—CH$_2$—, $R^1$ is —($C_1$-$C_6$)alkyl, $R^2$ is -(5- to 12-membered)aryl, and both $R^{3a}$ and $R^{3b}$ are H.
In another embodiment, Z is —CH$_2$, Y is —CH$_2$—CH$_2$—, $R^1$ is (($C_3$-$C_{12}$)cycloalkyl)-($C_1$-$C_6$)alkyl-, $R^2$ is —($C_2$-$C_6$)alkenyl, and at least one of $R^{3a}$ and $R^{3b}$ is H.

In another embodiment, Z is —CH$_2$, Y is —CH$_2$—CH$_2$—, R$^1$ is ((C$_3$-C$_{12}$)cycloalkyl)-(C$_1$-C$_6$)alkyl-, R$^2$ is —(C$_2$-C$_6$)alkenyl, and both R$^{3a}$ and R$^{3b}$ are H.

In another embodiment, Z is —CH$_2$, Y is —CH$_2$—CH$_2$—, R$^1$ is ((C$_3$-C$_{12}$)cycloalkyl)-(C$_1$-C$_6$)alkyl-, R$^2$ is —(C$_2$-C$_6$)alkynyl, and least one of R$^{3a}$ and R$^{3b}$ is H.

In another embodiment, Z is —CH$_2$, Y is —CH$_2$—CH$_2$—, R$^1$ is ((C$_3$-C$_{12}$)cycloalkyl)-(C$_1$-C$_6$)alkyl-, R$^2$ is —(C$_2$-C$_6$)alkynyl, and both R$^{3a}$ and R$^{3b}$ are H.

In another embodiment, Z is —CH$_2$, Y is —CH$_2$—CH$_2$—, R$^1$ is ((C$_3$-C$_{12}$)cycloalkyl)-(C$_1$-C$_6$)alkyl-, R$^2$ is -(5- to 12-membered)aryl, and at least one of R$^{3a}$ and R$^{3b}$ is H.

In another embodiment, Z is —CH$_2$, Y is —CH$_2$—CH$_2$—, R$^1$ is ((C$_3$-C$_{12}$)cycloalkyl)-(C$_1$-C$_6$)alkyl-, R$^2$ is -(5- to 12-membered)aryl, and both R$^{3a}$ and R$^{3b}$ are H.

In another embodiment, Z is —CH$_2$, Y is —CH$_2$—CH$_2$—, R$^1$ is —(C$_1$-C$_6$)alkyl, R$^2$ is —(C$_2$-C$_6$)alkenyl, and at least one of R$^{3a}$ and R$^{3b}$ is OH.

In another embodiment, Z is —CH$_2$, Y is —CH$_2$—CH$_2$—, R$^1$ is —(C$_1$-C$_6$)alkyl, R$^2$ is —(C$_2$-C$_6$)alkynyl, and at least one of R$^{3a}$ and R$^{3b}$ is OH.

In another embodiment, Z is —CH$_2$, Y is —CH$_2$—CH$_2$—, R$^1$ is —(C$_1$-C$_6$)alkyl, R$^2$ is -(5- to 12-membered)aryl, and at least one of R$^{3a}$ and R$^{3b}$ is OH.

In another embodiment, Z is —CH$_2$, Y is —CH$_2$—CH$_2$—, R$^1$ is ((C$_3$-C$_{12}$)cycloalkyl)-(C$_1$-C$_6$)alkyl-, R$^2$ is —(C$_2$-C$_6$)alkenyl, and at least one of R$^{3a}$ and R$^{3b}$ is OH.

In another embodiment, Z is —CH$_2$, Y is —CH$_2$—CH$_2$—, R$^1$ is ((C$_3$-C$_{12}$)cycloalkyl)-(C$_1$-C$_6$)alkyl-, R$^2$ is —(C$_2$-C$_6$)alkynyl, and at least one of R$^{3a}$ and R$^{3b}$ is OH.

In another embodiment, Z is —CH$_2$, Y is —CH$_2$—CH$_2$—, R$^1$ is ((C$_3$-C$_{12}$)cycloalkyl)-(C$_1$-C$_6$)alkyl-, R$^2$ is -(5- to 12-membered)aryl, and at least one of R$^{3a}$ and R$^{3b}$ is OH.

In another embodiment, Z is —CH$_2$, Y is absent, R$^1$ is ((C$_3$-C$_{12}$)cycloalkyl)-(C$_1$-C$_6$)alkyl-, R$^2$ is -(5- to 12-membered)-aryl, and at least one of R$^{3a}$ and R$^{3b}$ is H.

In another embodiment, Z is —CH$_2$, Y is absent, R$^1$ is ((C$_3$-C$_{12}$)cycloalkyl)-(C$_1$-C$_6$)alkyl-, R$^2$ is -(5- to 12-membered)-aryl, and both R$^{3a}$ and R$^{3b}$ are H.

In another embodiment, Z is —CH$_2$, Y absent, R$^1$ is —(C$_1$-C$_6$)alkyl, R$^2$ is —(C$_2$-C$_6$)alkenyl, and at least one of R$^{3a}$ and R$^{3b}$ is OH.

In another embodiment, Z is —CH$_2$, Y is absent, R$^1$ is —(C$_1$-C$_6$)alkyl, R$^2$ is —(C$_2$-C$_6$)alkynyl, and at least one of R$^{3a}$ and R$^{3b}$ is OH.

In another embodiment, Z is —CH$_2$, Y is absent, R$^1$ is —(C$_1$-C$_6$)alkyl, R$^2$ is -(5- to 12-membered)aryl, and at least one of R$^{3a}$ and R$^{3b}$ is OH.

In another embodiment, Z is —CH$_2$, Y is absent, R$^1$ is ((C$_3$-C$_{12}$)cycloalkyl)-(C$_1$-C$_6$)alkyl-, R$^2$ is —(C$_2$-C$_6$)alkenyl, and at least one of R$^{3a}$ and R$^{3b}$ is OH.

In another embodiment, Z is —CH$_2$, Y absent, R$^1$ is ((C$_3$-C$_{12}$)cycloalkyl)-(C$_1$-C$_6$)alkyl-, R$^2$ is —(C$_2$-C$_6$)alkynyl, and at least one of R$^{3a}$ and R$^{3b}$ is OH.

In another embodiment, Z is —CH$_2$, Y is absent, R$^1$ is ((C$_3$-C$_{12}$)cycloalkyl)-(C$_1$-C$_6$)alkyl-, R$^2$ is -(5- to 12-membered)aryl, and at least one of R$^{3a}$ and R$^{3b}$ is OH.

In another embodiment, X is halogen.
In another embodiment, X is fluorine.
In another embodiment, X is —NH$_2$.
In another embodiment, X is —NR$^2$(C=O)R$^8$.
In another embodiment, at least one of R$^2$ or R$^8$ is phenyl.
In another embodiment, both of R$^2$ and R$^8$ are phenyl.
In another embodiment, X is —CONR$^2$R$^8$.
In another embodiment, at least one of R$^2$ or R$^8$ is phenyl.
In another embodiment, both R$^2$ and R$^8$ are phenyl.
In one embodiment G is O.

In another embodiment G is NR$^9$.

In one embodiment, when R$^1$ is methyl or cyclopropylmethyl, then X is selected from F, —NH$_2$, NHCOCH$_3$, —NHSO$_2$CH$_3$, CN, —CO$_2$H, —CONH$_2$, —(OCH$_2$CH$_2$)$_3$—O(C$_1$-C$_6$)alkyl and —(OCH$_2$CH$_2$)$_s$—OH.

In another embodiment, when X is OH or NH$_2$, then R$^2$ is selected from ((C$_3$-C$_{12}$)cycloalkyl)-(C$_1$-C$_6$)alkyl-, ((C$_3$-C$_{12}$)aryl(C$_1$-C$_6$)alkyl-, ((3- to 12-membered)heterocycle)-(C$_1$-C$_6$)alkyl-, ((5- to 12-membered)aryl)-(C$_1$-C$_6$)alkyl-, ((5-12-membered)heteroaryl-(C$_1$-C$_6$)alkyl-; each of which is optionally substituted.

Specific compounds of the invention include:

2-(((4R,4aS,6R,7R,7aR,12bS)-7-methoxy-3-methyl-6-(((2-methylbenzyl)oxy)methyl)-1,2,3,4,5,6,7,7a-octahydro-4a,7-ethano-4,12-methanobenzofuro[3,2-e]isoquinolin-9-yl)oxy)ethanol (Compound 1);

(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquiuinolin-9-amine (Compound 2);

(4R,4aS,6R,7R,7aR,12bS)-6-((benzyloxy)methyl)-7-methoxy-3-methyl-9-vinyl-1,2,3,4,5,6,7,7a-octahydro-4a,7-ethano-4,12-methanobenzofuro[3,2-e]isoquinoline (Compound 3);

(4R,4aS,6R,7R,7aR,12bS)-6-(9-benzyloxy)methyl)-9-fluoro-7-methoxy-3-methyl-1,2,3,4,5,6,7,7a-octahydro-4a,7-ethano-4,12-methanobenzofuro[3,2-e]isoquinoline (Compound 4);

(4R,4aS,6R,7R,7aR,12bS)-6-((4-(1H-imidazol-1-yl)phenoxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 5);

(4R,4aS,6S,7R,7aR,12bS)-6-((benzo[d]thiazol-2-ylthio)methyl)-7,9-dimethoxy-3-methyl-1,2,3,4,5,6,7,7a-octahydro-4a,7-ethano-4,12-methanobenzofuro[3,2-e]isoquinoline (Compound 6);

(4R,4aS,6S,7R,7aR,12bS)-6-((benzo[d]thiazol-2-ylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 7);

(4R,4aS,6R,7R,7aR,12bS)-6-((4-(1H-imidazol-1-yl)phenoxy)methyl)-7-methoxy-3-methyl-1,2,3,4,5,6,7,7a-octahydro-4a,7-ethano-4,12-methanobenzofuro[3,2-e]isoquinolin-9-ol (Compound 8);

(4R,4aS,6S,7R,7aR,12bS)-3-(cyclopropylmethyl)-7,9-dimethoxy-6-(((3-methyl-1,2,4-thiadiazol-5-yl)thio)methyl)-1,2,3,4,5,6,7,7a-octahydro-4a,7-ethano-4,12-methanobenzofuro[3,2-e]isoquinoline (Compound 9);

(4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-amine (Compound 10);

(4R,4aS,6R,7R,7aR,12bS)-6-((4-(1H-imidazol-1-yl)phenoxy)methyl)-3-(cyclopropylmethyl)-7-methoxy-1,2,3,4,5,6,7,7a-octahydro-4a,7-ethano-4,12-methanobenzofuro[3,2-e]isoquinolin-9-ol (Compound 11);

(4R,4aS,6S,7R,7aR,12bS)-7,9-dimethoxy-3-methyl-6-(((3-methyl-1,2,4-thiadiazol-5-yl)thio)methyl)-1,2,3,4,5,6,7,7a-octahydro-4a,7-ethano-4,12-methanobenzofuro[3,2-e]isoquinoline (Compound 12);

(4R,4aS,6S,7R,7aR,12bS)-6-(((1,3,4-thiadiazol-2-yl)thio)methyl)-7,9-dimethoxy-3-methyl-1,2,3,4,5,6,7,7a-octahydro-4a,7-ethano-4,12-methanobenzofuro[3,2-e]isoquinoline (Compound 13);

(4R,4aS,6S,7R,7aR,12bS)-6-(((1,3,4-thiadiazol-2-yl)thio)methyl)-3-(cyclopropylmethyl)-7,9-dimethoxy-1,2,3,4,5, 6,7,7a-octahydro-4a,7-ethano-4,12-methanobenzofuro[3,2-e]isoquinoline (Compound 14);

(4R,4aS,6R,7R,7aR,12bS)-6-((benzyloxy)methyl)-3-(cyclopropylmethyl)-9-fluoro-7-methoxy-1,2,3,4,5,6,7,7a-octahydro-4a,7-ethano-4,12-methanobenzofuro[3,2-e]isoquinoline (Compound 15);

N-((4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinolin-9-yl)methanesulfonamide (Compound 16);

N-((4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinolin-9-yl)acetamide (Compound 17);

(4R,4aS,6R,7R,7aR,12bS)-6-((benzyloxy)methyl)-7,9-dimethoxy-1,2,3,4,5,6,7,7a-octahydro-4a,7-ethano-4,12-methanobenzofuro[3,2-e]isoquinoline (Compound 18)

(4R,4aS,6R,7R,7aR,12bS)-6-((benzyloxy)methyl)-9-bromo-3-(cyclopropylmethyl)-7-methoxy-1,2,3,4,5,6,7,7a-octahydro-4a,7-ethano-4,12-methanobenzofuro[3,2-e]isoquinoline (Compound 19);

(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinoline-9-carbonitrile (Compound 20);

(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinoline-9-carboxamide (Compound 21);

(4R,4aS,6R,7R,7aR,12bS)-6-((benzyloxy)methyl)-7-methoxy-1,2,3,4,5,6,7,7a-octahydro-4a,7-ethano-4,12-methanobenzofuro[3,2-e]isoquinolin-9-ol (Compound 22);

(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinoline-9-carboxylic acid (Compound 23);

(4R,4aS,6R,7R,7aR,12bS)-6-(((3,5-dimethylisoxazol-4-yl)methoxy)methyl)-7,9-dimethoxy-3-methyl-1,2,3,4,5,6,7,7a-octahydro-4a,7-ethano-4,12-methanobenzofuro[3,2-e]isoquinoline (Compound 24);

2-(((4R,4aS,6R,7R,7aR,12bS)-6-((benzo[b]thiophen-2-ylmethoxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)ethanol (Compound 25);

(4R,4aS,6R,7R,7aR,12bS)-3-(cyclopropylmethyl)-6-(((3,5-dimethylisoxazol-4-yl)methoxy)methyl)-7,9-dimethoxy-1,2,3,4,5,6,7,7a-octahydro-4a,7-ethano-4,12-methanobenzofuro[3,2-e]isoquinoline (Compound 26);

(4R,4aS,6S,7R,7aR,12bS)-6-((benzo[d]oxazol-2-ylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 27);

N-benzyl-1-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methanamine (Compound 28); and N-benzyl-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)methanesulfonamide (Compound 29);

and pharmaceutically acceptable salts, prodrugs and solvates thereof.

Specific compounds of the invention further include:

N-benzyl-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)acetamide (Compound 30);

(4R,4aS,6S,7R,7aR,12bS)-6-((benzylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 31);

(4R,4aS,6S,7R,7aR,12bS)-6-((benzylsulfinyl)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 32);

(4R,4aS,6R,7R,7aR,12bS)-3-(cyclopropylmethyl)-6-(2,5,8,11-tetraoxadodecyl)-7,9-dimethoxy-1,2,3,4,5,6,7,7a-octahydro-4a,7-ethano-4,12-methanobenzofuro[3,2-e]isoquinoline (Compound 33);

(4R,4aS,6R,7R,7aR,12bS)-3-(cyclopropylmethyl)-7,9-dimethoxy-6-(2,5,8,11,14,17-hexaoxaoctadecyl)-1,2,3,4,5,6,7,7a-octahydro-4a,7-ethano-4,12-methanobenzofuro[3,2-e]isoquinoline (Compound 34);

(4R,4aS,6R,7R,7aR,12bS)-6-((benzyloxy)methyl)-3-(cyclopropylmethyl)-7-methoxy-9-(2-(2-(2-methoxyethoxy)ethoxy)ethoxy)-1,2,3,4,5,6,7,7a-octahydro-4a,7-ethano-4,12-methanobenzofuro[3,2-e]isoquinoline (Compound 35);

(4R,4aS,6R,7R,7aR,12bS)-9-(2,5,8,11,14-pentaoxahexadecan-16-yloxy)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline (Compound 36);

(4R,4aS,6R,7R,7aR,12bS)-3-(cyclopropylmethyl)-7,9-dimethoxy-6-(((4-(2-(2-(2-methoxyethoxy)ethoxy)ethoxy)benzyl)oxy)methyl)-1,2,3,4,5,6,7,7a-octahydro-4a,7-ethano-4,12-methanobenzofuro[3,2-e]isoquinoline (Compound 37);

(4R,4aS,6R,7R,7aR,12bS)-6-(((4-(2,5,8,11,14-pentaoxahexadecan-16-yloxy)benzyl)oxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 38);

methyl 2-(4-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenoxy)acetate (Compound 39); and 2-(4-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenoxy)acetic acid (Compound 40).

Specific compounds of the invention further include:

3-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)propanamide (Compound 41);

2-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)amino)acetic acid (Compound 42);

2-(4-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)benzamido)acetic acid (Compound 43);

2-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)amino)acetamide (Compound 44);

2-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)acetamide (Compound 45);

2-(4-(((((4R,4aS,6R,7R,7aR,12bS)-3-(cyclopropylmethyl)-7,9-dimethoxy-1,2,3,4,5,6,7,7a-octahydro-4a,7-ethano-4, 12-methanobenzofuro[3,2-e]isoquinolin-6-yl)methoxy)
methyl)phenyl)acetic acid (Compound 46);

1-((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)ethane-1,2-diol (Compound 47);

1-(3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)urea (Compound 48);

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-phenylpropanoate (Compound 49);

2-((3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquiuinolin-6-yl)methoxy)methyl)phenyl)amino)acetic acid (Compound 50);

(4R,4aS,6S,7S,7aS,12bS)-6-((benzyloxy)methyl)-3-(cyclopropylmethyl)-9-methoxy-7-phenyl-1,2,3,4,5,6,7,7a-octahydro-4a,7-ethano-4,12-methanobenzofuro[3,2-e]isoquinoline (Compound 51);

(4R,4aS,6R,7R,7aR,12bS)-7-(2,5,8,11,14-pentaoxahexadecan-16-yloxy)-6-((benzyloxy)methyl)-3-(cyclopropylmethyl)-9-methoxy-1,2,3,4,5,6,7,7a-octahydro-4a,7-ethano-4,12-methanobenzofuro[3,2-e]isoquinoline (Compound 52);

(4R,4aS,6R,7R,7aR,12bS)-6-((benzyloxy)methyl)-3-(cyclopropylmethyl)-9-methoxy-7-(2-(2-(2-methoxyethoxy)ethoxy)ethoxy)-1,2,3,4,5,6,7,7a-octahydro-4a,7-ethano-4,12-methanobenzofuro[3,2-e]isoquinoline (Compound 53);

(4R,4aS,6R,7R,7aR,12bS)-6-(((4-((2H-tetrazol-5-yl)methyl)benzyl)oxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 54);

(4R,4aS,6R,7R,7aR,12bS)-7,9-dimethoxy-3-methyl-6-(((3-propylisoxazol-5-yl)methoxy)methyl)-1,2,3,4,5,6,7,7a-octahydro-4a,7-ethano-4,12-methanobenzofuro[3,2-e]isoquinoline (Compound 55);

3-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)propanoic acid (Compound 56);

2-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)acetic acid (Compound 57);

2-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)acetamide (Compound 58);

2-(((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)acetic acid (Compound 59);

(4R,4aS,6R,7R,7aR,12bS)-9-((2H-tetrazol-5-yl)methoxy)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline (Compound 60);

2-(((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)acetamide (Compound 61);

N-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)-N-(methylsulfonyl)methanesulfonamide (Compound 62);

3-((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)propane-1,2-diol (Compound 63);

N-(3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)methanesulfonamide (Compound 64);

(4R,4aS,6R,7R,7aR,12bS)-6-(2-(benzyloxy)propan-2-yl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 65);

3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)benzimidamide (Compound 66).

and pharmaceutically salts, prodrugs and solvates thereof.

In another embodiment, specific compounds of the invention include:

(4R,4aS,6S,7R,7aR,12bS)-6-((benzylsulfonyl)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 67);

3-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)propane-1,2-diol (Compound 68);

(4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[32-e]isoquinoline-9-carbonitrile (Compound 69);

(4R,4aS,6R,7R,7aR,12bS)-6-((benzyloxy)methyl)-3-(cyclopropylmethyl)-7-methoxy-9-(2H-tetrazol-5-yl)-1,2,3,4,5,6,7,7a-octahydro-4a,7-ethano-4,12-methanobenzofuro[3,2-e]isoquinoline (Compound 70);

(4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carboxylic acid (Compound 71);

N-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)acetamide (Compound 72);

methyl 2-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenoxy)acetate (Compound 73);

N-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)benzamide (Compound 74);

4-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)benzamide (Compound 75);

(4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carboxamide (Compound 76);

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-aminopropanoate (Compound 77);

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-hydroxypropanoate (Compound 78);

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-methylbutanoate (Compound 79);

(2S,3S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-methylpentanoate (Compound 80);

(S)-2-amino-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)propanamide (Compound 81);

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-4-methylpentanoate (Compound 82);

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2,5-diamino-5-oxopentanoate (Compound 83);

(S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-amino-3-phenylpropanoate (Compound 84);

(2S,3S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-amino-3-methylpentanoate (Compound 85);

(S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-aminopropanoate (Compound 86);

ethyl 3-((4R,4aS,5S,6R,7R,7aR,12bS)-6-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-5-yl)propanoate (Compound 87);

2-((4R,4aS,5S,6R,7R,7aR,12bS)-6-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-5-yl)acetonitrile (Compound 88);

3-((4R,4aS,5S,6R,7R,7aR,12bS)-6-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-5-yl)propanoic acid (Compound 89);

2-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenoxy)acetic acid (Compound 90);

1-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)-3-methylurea (Compound 91);

ethyl 3-((4R,4aS,5S,6S,7R,7aR,12bS)-5-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)propanoate (Compound 92);

(4R,4aS,6R,7R,7aR,12bS)-6-((benzyloxy)methyl)-3-(cyclopropylmethyl)-9-methoxy-1,2,3,4,5,6,7,7a-octahydro-4a,7-ethano-4,12-methanobenzofuro[3,2-e]isoquinolin-7-ol (Compound 93);

N-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)acetamide (Compound 94);

(4R,4aS,6R,7R,7aR,12bS)-3-((2H-tetrazol-5-yl)methyl)-6-((benzyloxy)methyl)-7,9-dimethoxy-1,2,3,4,5,6,7,7a-octahydro-4a,7-ethano-4,12-methanobenzofuro[3,2-e]isoquinoline (Compound 95);

2-(3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)acetic acid (Compound 96);

1-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)ethane-1,2-diol (Compound 97).

As used herein, the term "—$(C_1-C_{10})$alkyl" refers to straight-chain and branched non-cyclic saturated hydrocarbons having from 1 to 10 carbon atoms. Representative straight chain —$(C_1-C_{10})$alkyl groups include methyl, -ethyl, -n-propyl, -n-butyl, -n-pentyl, -n-hexyl, n-heptyl, n-octyl, n-nonyl and n-decyl. Representative branched —$(C_1-C_{10})$alkyl groups include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 5-methylhexyl, 6-methylheptyl, and the like.

As used herein, the term "—$(C_1-C_6)$alkyl" refers to straight-chain and branched non-cyclic saturated hydrocarbons having from 1 to 6 carbon atoms. Representative straight chain —$(C_1-C_6)$alkyl groups include methyl, -ethyl, -n-propyl, -n-butyl, -n-pentyl, and -n-hexyl. Representative branched-chain —$(C_1-C_6)$alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like.

As used herein, the term "—$(C_2-C_{12})$alkenyl" refers to straight chain and branched non-cyclic hydrocarbons having from 2 to 12 carbon atoms and including at least one carbon-carbon double bond. Representative straight chain and branched —$(C_2-C_{12})$alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, 3-hexenyl, and the like.

As used herein, the term "—$(C_2-C_6)$alkenyl" refers to straight chain and branched non-cyclic hydrocarbons having from 2 to 6 carbon atoms and including at least one carbon-carbon double bond. Representative straight chain and branched —$(C_2-C_6)$alkenyl groups include -vinyl, allyl, -1-butenyl, -2-butenyl, -isobutylenyl, -1-pentenyl, -2-pentenyl, -3-methyl-1-butenyl, -2-methyl-2-butenyl, and the like.

As used herein, the term "—$(C_2-C_{12})$alkynyl" refers to straight chain and branched non-cyclic hydrocarbons having from 2 to 12 carbon atoms and including at least one carbon-carbon triple bond. Representative straight chain and branched —$(C_2-C_{12})$alkynyl groups include -acetylenyl, -propynyl, -1 butynyl, -2-butynyl, -1-pentynyl, -2-pentynyl, -3-methyl-1-butynyl, -4-pentynyl, -1-hexynyl, -2-hexynyl, -5-hexynyl, and the like.

As used herein, the term "—$(C_2-C_6)$alkynyl" refers to straight chain and branched non-cyclic hydrocarbons having from 2 to 6 carbon atoms and including at least one carbon-carbon triple bond. Representative straight chain and branched —($C_2$-$C_6$)alkynyl groups include -acetylenyl, -propynyl, -1 butynyl, -2-butynyl, -1-pentynyl, -2-pentynyl, -3-methyl-1-butynyl, -4-pentynyl, and the like.

As used herein, "—($C_1$-$C_{10}$)alkoxy" means a straight chain or branched non-cyclic hydrocarbon having one or more ether groups and from 1 to 10 carbon atoms. Representative straight chain and branched ($C_1$-$C_{10}$)alkoxys include -methoxy, -ethoxy, -propoxy, -butyloxy, -pentyloxy, -hexyloxy, -heptyloxy, -methoxymethyl, -2-methoxyethyl, -5-methoxypentyl, -3-ethoxybutyl and the like.

As used herein, "—($C_1$-$C_6$)alkoxy" means a straight chain or branched non-cyclic hydrocarbon having one or more ether groups and from 1 to 6 carbon atoms. Representative straight chain and branched ($C_1$-$C_5$)alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

As used herein, "—($C_1$-$C_5$)alkoxy" means a straight chain or branched non-cyclic hydrocarbon having one or more ether groups and from 1 to 5 carbon atoms. Representative straight chain and branched ($C_1$-$C_6$)alkoxys include -methoxy, -ethoxy, -propoxy, -butyloxy, -pentyloxy, -methoxymethyl, -2-methoxyethyl, -5-methoxypentyl, -3-ethoxybutyl and the like.

As used herein, the term "—($C_3$-$C_{12}$)cycloalkyl" refers to cyclic saturated hydrocarbon having from 3 to 12 carbon atoms. Representative ($C_3$-$C_{12}$)cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As used herein, "—($C_6$-$C_{14}$)bicycloalkyl" means a bicyclic hydrocarbon ring system having from 6 to 14 carbon atoms and at least one saturated cyclic alkyl ring. Representative —($C_6$-$C_{14}$)bicycloalkyls include -indanyl, -norbornyl, -1,2,3,4-tetrahydronaphthalenyl, -5,6,7,8-tetrahydronaphthalenyl, -perhydronaphthalenyl, and the like.

As used herein, "—($C_8$-$C_{20}$)tricycloalkyl" means a tricyclic hydrocarbon ring system having from 8 to 20 carbon atoms and at least one saturated cyclic alkyl ring. Representative —($C_8$-$C_{20}$)tricycloalkyls include -pyrenyl, -adamantyl, -1,2,3,4-tetrahydroanthracenyl, -perhydroanthracenyl -aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

As used herein, the term "—($C_4$-$C_{12}$)cycloalkenyl" refers to a cyclic hydrocarbon having from 4 to 12 carbon atoms, and including at least one carbon-carbon double bond. Representative —($C_3$-$C_{12}$)cycloalkenyls include -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, and the like.

As used herein, "—($C_7$-$C_{14}$)bicycloalkenyl" means a bicyclic hydrocarbon ring system having at least one carbon-carbon double bond in at least one of the rings and from 7 to 14 carbon atoms. Representative —($C_7$-$C_{14}$)bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, and the like.

As used herein, "—($C_8$-$C_{20}$)tricycloalkenyl" means a tricyclic hydrocarbon ring system having at least one carbon-carbon double bond in one of the rings and from 8 to 20 carbon atoms. Representative —($C_8$-$C_{20}$)tricycloalkenyls include -anthracenyl, -phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a,c]cyclooctenyl, 2,3,4,5,6,7,8,9,10,11,12,13-dodecahydro-1H-dibenzo[a,d]cyclononenyl, and the like.

As used herein, "-(3- to 12-membered)heterocycle" or "-(3- to 12-membered)heterocyclo" means a 3- to 12-membered monocyclic heterocyclic ring which is either saturated, or unsaturated, non-aromatic. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(3- to 12-membered)heterocycle can be attached via a nitrogen or carbon atom. Representative -(3- to 12-membered) heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(4- to 8-membered)heterocycle" or "-(4- to 8-membered)heterocyclo" means a 4- to 8-membered monocyclic heterocyclic ring which is either saturated or unsaturated, non-aromatic. A 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(4- to 8-membered)heterocycle can be attached via a nitrogen or carbon atom. Representative -(4- to 8-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(7- to 12-membered)bicycloheterocycle" or "-(7- to 12-membered)bicycloheterocyclo" means a 7- to 12-membered bicyclic, heterocyclic ring which is either saturated, unsaturated, non-aromatic, or aromatic. At least one ring of the bicycloheterocycle contains at least one heteroatom. A -(7- to 12-membered)bicycloheterocycle contains from 1 to 4 heteroatoms independently selected from nitrogen (which can be quaternized), oxygen, and sulfur (including sulfoxide and sulfone). The -(7- to 12-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -indolinyl, isoindolinyl, -1,2,3,4-tetrahydroquinolinyl, -1,2,3,4-tetrahydroisoquinolinyl, pyrrolopyrrolyl and the like.

As used herein a "-(5- to 12-membered)aryl" means an aromatic carbocyclic ring containing 5 to 12 carbon atoms, including both mono- and bicyclic ring systems. Representative -(5- to 12-membered)aryl groups include -indenyl, -phenyl, -naphthyl, and the like.

As used herein a "-(7- to 12-membered)bicyclic aryl" means an bicyclic aromatic carbocyclic ring containing 7 to 12 carbon atoms. Representative -(7- to 12-membered) bicyclic aryl groups include -indenyl, -naphthyl, and the like.

As used herein a "-(5- to 12-membered)aryloxy" means an oxygen substituted by an aromatic carbocyclic ring containing 5 to 12 carbon atoms, including both mono- and bicyclic ring systems. Representative -(5- to 12-membered)aryloxy groups include phenoxy and 4-fluorophenoxy, and the like.

As used herein a "hydroxy($C_1$-$C_6$)alkyl" means any of the above-mentioned $C_{1-6}$alkyl groups substituted by one or more hydroxy groups. Representative hydroxy($C_1$-$C_6$)alkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein a "dihydroxy($C_1$-$C_6$)alkyl" means any of the above-mentioned $C_{1-6}$alkyl groups substituted by two hydroxy groups. Representative dihydroxy($C_1$-$C_6$)alkyl groups include dihydroxyethyl, dihydroxypropyl and dihydroxybutyl groups, and especially 1,2-dihydroxyethyl, 1,3-dihydroxypropyl, 2,3-dihydroxypropyl, 1,3-dihydroxybutyl, 1,4-dihydroxybutyl, and 1,3-dihydroxyprop-2-yl.

As used herein a "-(5- to 12-membered)carbocyclic ring" means a bicyclic hydrocarbon ring system having from 5 to 12 carbon atoms, which is either saturated, unsaturated, non-aromatic or aromatic.

As used herein a "-(7- to 12-membered)bicyclic ring system" means a 7- to 12-membered a carbocyclic or heterocyclic ring, which may be either unsaturated, saturated, non-aromatic or aromatic.

As used herein, "-(5- to 12-membered)heteroaryl" means an aromatic heterocycle ring of 5 to 12 members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the bicyclic -(5- to 12-membered)heteroaryl rings contains at least one carbon atom. In another embodiment, both of the bicyclic -(5- to 12-membered)heteroaryl rings contain at least one carbon atom. Representative -(5- to 12-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, the phrase "tetrazolyl group" means

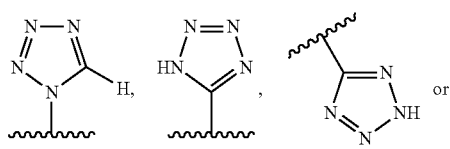

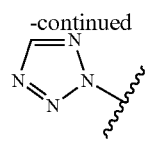

In one embodiment, the tetrazolyl group is

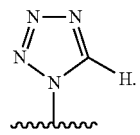

In another embodiment, the tetrazolyl group is

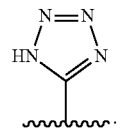

In another embodiment, the tetrazolyl group is

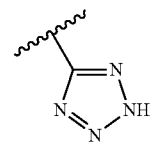

In another embodiment, the tetrazolyl group is

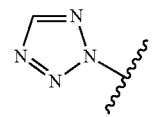

As used herein, the terms "halo" and "halogen" refer to fluoro, chloro, bromo or iodo.

As used herein, "—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

As used herein, "—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, —CHBrCl, —CHClI, and —$CHI_2$.

As used herein, "—C(halo)$_3$" means a methyl group where each of the hydrogens of the methyl group has been replaced with a halogen. Representative —C(halo)$_3$ groups include —$CF_3$, —$CCl_3$, —$CBr_3$, and —$CI_3$.

As used herein, the term "optionally substituted" refers to a group that is either unsubstituted or substituted.

Optional substituents on optionally substituted groups, when not otherwise indicated, include 1, 2, or 3 groups each independently selected from the group consisting of —($C_1$-$C_6$)alkyl, OH, halo, —C(halo)$_3$, —CH(halo)$_2$, —$CH_2$(halo), $NH_2$, —NH($C_1$-$C_6$)alkyl, CN, SH, -(5- to 12-membered)carbocyclic ring, -(5- to 12-membered)heterocycle, phenyl, benzyl, (=O), halo($C_1$-$C_6$)alkyl-, —($C_2$-$C_6$)alkenyl, —($C_2$-$C_6$)alkynyl, hydroxy($C_1$-$C_6$)alkyl-, $OR^4$ (such as —OC(halo)$_3$ and —O($C_1$-$C_6$)alkyl), —CONR$^5$R$^6$, and —COOR$^7$, where $R^4$ is selected from the group consisting of —($C_1$-$C_6$)alkyl, —($C_2$-$C_6$)alkenyl, —($C_2$-$C_6$)alkynyl, —C(halo)$_3$, hydroxy ($C_1$-$C_6$)alkyl-, —($C_3$-$C_{12}$)cycloalkyl, —($C_6$-$C_{14}$)bicycloalkyl, —($C_8$-$C_{20}$)tricycloalkyl, —($C_4$-$C_{12}$)cycloalkenyl, —($C_7$-$C_{14}$)bicycloalkenyl, —($C_8$-$C_{20}$)tricycloalkenyl, -(5- to 12-membered)aryl, -(5- to 12-membered)heteroaryl, -(3- to 12-membered)heterocycle, and -(7- to 12-membered)bicycloheterocycle; $R^5$ and $R^6$ are each independently —($C_1$-$C_6$) alkyl, —($C_3$-$C_8$)cycloalkyl, (($C_3$-$C_8$)cycloalkyl)-($C_1$-$C_6$) alkyl-, or together with the nitrogen atom to which they are attached form a (4- to 8-membered)heterocycle; and $R^7$ is selected from the group consisting of hydrogen, —($C_1$-$C_6$) alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, —($C_1$-$C_6$) alkoxy-COOR$^7$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$) alkyl-COOR$^7$, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-COOR$^7$, —($C_1$-$C_6$)alkoxy-COOR$^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$) alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$) alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered) heterocycle, ((3- to 12 membered)heterocycle)-($C_1$-$C_6$) alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-.

As used herein, the term "Z is unsubstituted" means that Z is "—(CH$_2$)$_m$-" and m is selected from 1, 2, 3, 4, 5, or 6.

As used herein, the term "Z is substituted" means that Z is "—(CH$_2$)$_m$-" and m is selected from 1, 2, 3, 4, 5, or 6 and at least one of the hydrogen atoms has been replaced by a —($C_1$-$C_6$)alkyl group.

As used herein, compounds that bind to receptors and mimic the regulatory effects of endogenous ligands are defined as "agonists". Compounds that bind to receptors and are only partly effective as agonists are defined as "partial agonists". Compounds that bind to a receptor but produce no regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics*, 10$^{th}$ Ed. (J. G. Hardman, L. E. Limbird and A. Goodman-Gilman eds., 2001).

Compounds of the Invention can be in the form of prodrugs of the compounds of Formula I, Formula IA, Formula IB, Formula II, or Formula III. Prodrugs are covalently bonded carrier molecules that release an active compound of Formula I, Formula IA, Formula IB, Formula II, or Formula III in vivo. Non-limiting examples of prodrugs will typically include esters of the Compounds of the Invention that can be metabolized to the active compound by the action of enzymes in the body. Such prodrugs may be prepared by reacting a compound of Formula I, Formula IA, Formula IB, Formula II, or Formula III with an anhydride such as succinic anhydride.

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl, respectively, and preferably $^3$H, $^{11}$C, and $^{14}$C. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds are generally described in Filer, Isotopes in the Physical and Biomedical Sciences, Vol. 1, Labeled Compounds (Part A), Chapter 6 (1987). $^{14}$C-labeled compounds can be prepared by employing starting materials having a $^{14}$C carbon.

Isotopically labeled Compounds of the Invention, as well as the pharmaceutically acceptable salts, prodrugs and solvates thereof, can be used as radioligands to test for the binding of compounds to an opioid or ORL-1 receptor. For example, a radio-labeled Compound of the Invention can be used to characterize specific binding of a test or candidate compound to the receptor. Binding assays utilizing such radio-labeled compounds can provide an alternative to animal testing for the evaluation of chemical structure-activity relationships. In a non-limiting embodiment, the present invention provides a method for screening a candidate compound for the ability to bind to an opioid or ORL-1 receptor, comprising the steps of: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Compounds of the Invention disclosed herein may contain one or more asymmetric centers, thus giving rise to enantiomers, diastereomers, and other stereoisomeric forms. The present invention encompasses all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, they include both E and Z geometric isomers. All tautomers are intended to be encompassed by the present invention as well.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active such that the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Compounds of the Invention encompass all salts of the disclosed compounds of Formula I, Formula IA, Formula IB, Formula II, or Formula III. The present invention preferably includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicylohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

Compounds of the Invention also encompass solvates of the disclosed compounds of Formula I, Formula IA, Formula IB, Formula II, or Formula III. The term "solvate" as used herein is a combination, physical association and/or solvation of a compound of Formula I, Formula IA, Formula IB, Formula II, or Formula III with a solvent molecule such as, e.g. a disolvate, monosolvate or hemisolvate, where the ratio of solvent molecule to compound of Formula I, Formula IA, Formula IB, Formula II, or Formula III is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A compound of Formula I, Formula IA, Formula IB, Formula II, or Formula III or may be present as a solvated form with a pharmaceutically acceptable solvent, such as water, methanol, ethanol, and the like, and it is intended that the invention include both solvated and unsolvated forms of Formula I, Formula IA, Formula IB, Formula II, or Formula III compounds. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.*, 603-604 (2001). A typical, non-limiting, process of preparing a solvate would involve dissolving a compound of Formula I, Formula IA, Formula IB, Formula II, or Formula III in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides the use of a Compound of the Invention in the manufacture of a medicament for treating or preventing a Condition. In one embodiment, the Condition is pain, such as acute or chronic pain. In one embodiment, a Compound of the Invention has agonist activity at the μ, δ and/or κ receptors. In another embodiment a Compound of the Invention has agonist activity at the μ receptor. In another embodiment, a Compound of the Invention has antagonist activity at the ORL-1 receptor. In another embodiment, certain Compounds of the invention can stimulate one receptor (e.g., a μ, δ and/or κ agonist) and inhibit a different receptor (e.g., an ORL-1 antagonist). In another embodiment, the Compound of the Invention is an agonist at the CI receptor, and an antagonist at the ORL-1 receptor.

Synthesis of Compounds

Compounds of Formula I can be made using conventional organic synthesis in view of this disclosure, or by the illustrative methods shown in the schemes below.

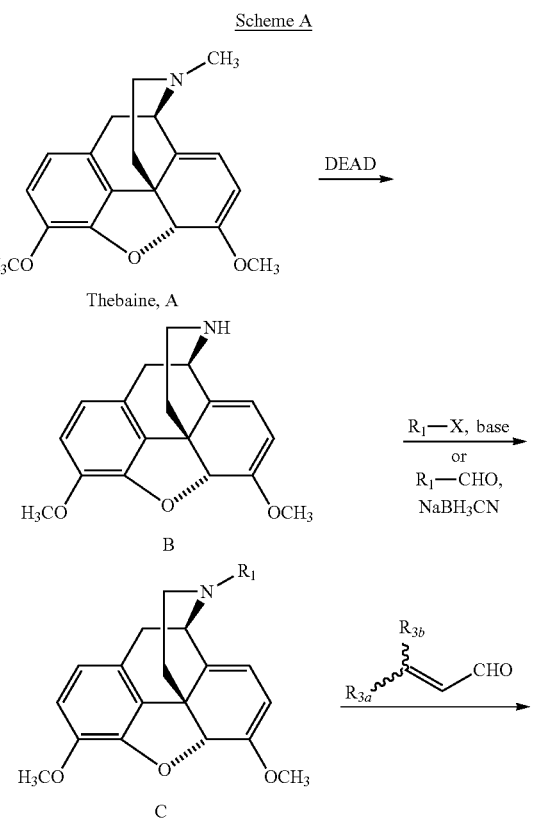

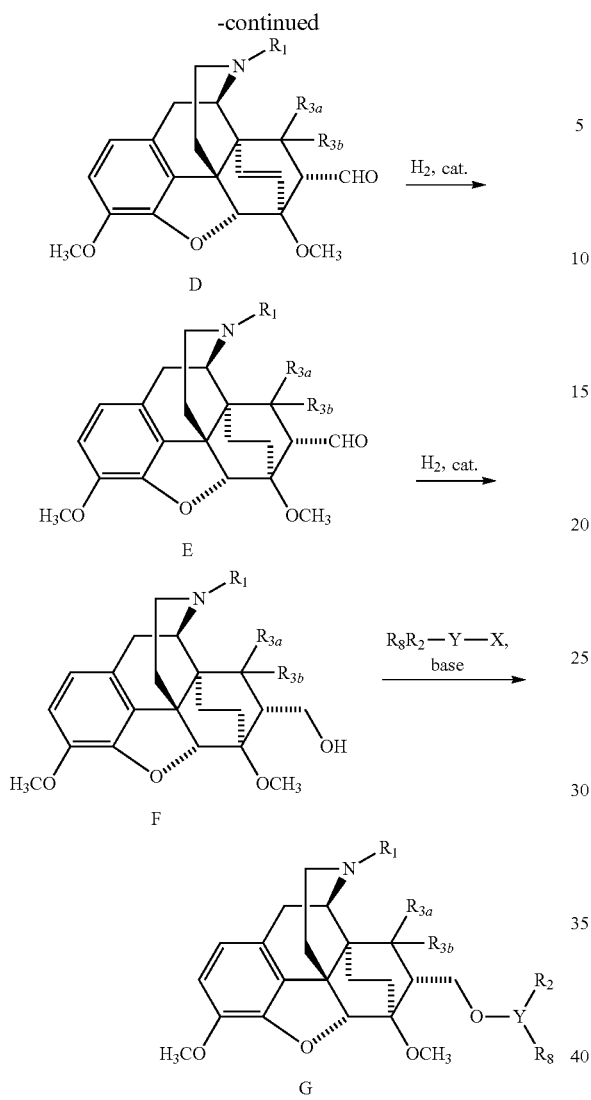

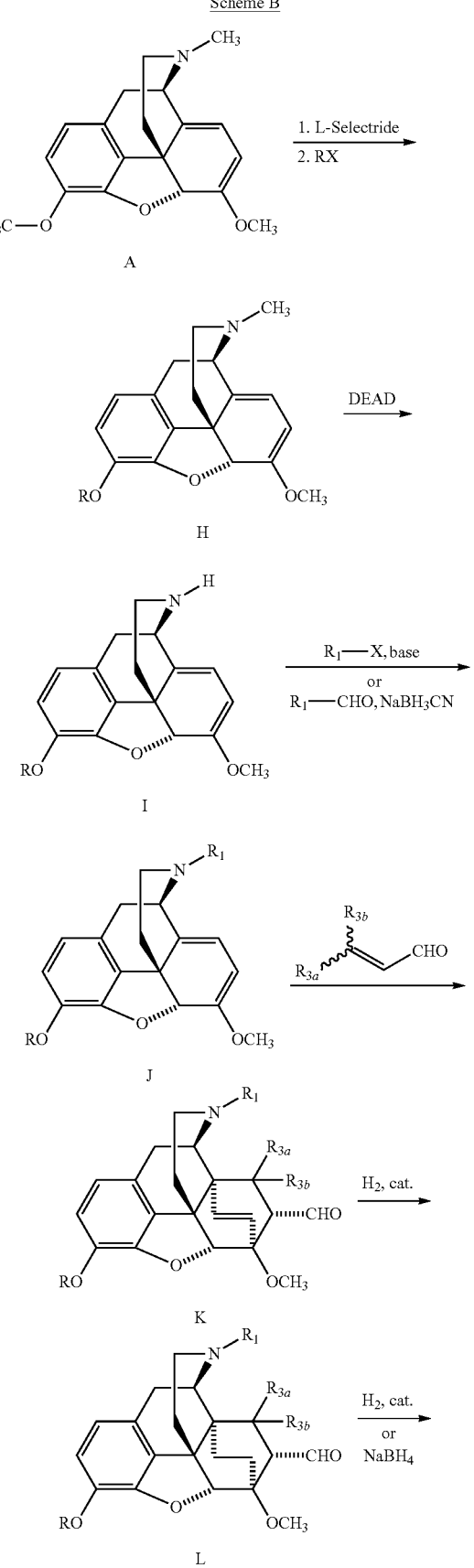

Scheme B

Thebaine, A, is N-demethylated by reaction with a suitable reagent such as diethyl azodicarboxylate (DEAD) in a suitable solvent such as acetonitrile (ACN) at 50-100° C. to provide the secondary amine B. Compound C is prepared by alkylation of compound B with an alkyl halide in a suitable solvent such as ACN, dimethylformamide (DMF) or dimethyl sulfoxide (DMSO) in the presence of an inorganic base such as sodium hydrogen carbonate or an organic base such as diisopropylethylamine. Compound C can also be prepared by reductive amination of compound B with an aldehyde or ketone using sodium cyanoborohydride or sodium triacetoxyborohydride in a suitable solvent such as dichloromethane (DCM). Compound D is prepared by reaction of compound C with an excess of an α,β unsaturated aldehyde, as solvent, at 50-100° C. Compound E is prepared by hydrogenation of compound D in a suitable solvent such as ethanol (EtOH) in the presence of a catalyst such as palladium on carbon (Pd/C). Compound F is prepared by continued hydrogenation of compound E for 3-10 days or by reduction with a reducing agent such as sodium borohydride in a suitable solvent such as EtOH. Compound G is prepared by reaction of compound F with an alkyl halide in a suitable solvent such as DMF in the presence of a base such as sodium hydride.

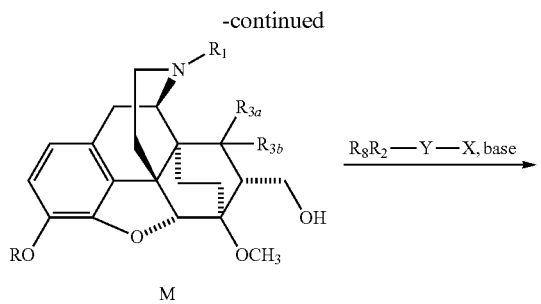

Thebaine, A, is O-demethylated by reaction with a suitable reagent such as lithium tri-sec-butylborohydride (L-Selectride, Aldrich) in a suitable solvent such as tetrahydrofuran (THF) at 25-65° C. (e.g. Rice, K. C., et al. *J. Org. Chem.*, 1996, 61, 6774) to provide the phenol H(R=H). The phenolic group of H is reacted with a suitable alkyl halide or a protecting group to give compound H(R≠H) (e.g. Greene, T. W. "Protective Groups in Organic Synthesis", J. Wiley & Sons, NY, 1981). Compound H is reacted with a suitable reagent such as DEAD according to the procedure in Scheme A (A→B) to provide the secondary amine I. Compound J is prepared from I according to the procedure in Scheme A (B→C) either by alkylation or reductive amination. Compound K is prepared by reaction of compound J with an excess of an α,β unsaturated aldehyde, as solvent, at 50-100° C. Compound L is prepared by hydrogenation of compound K in a suitable solvent such as ethanol (EtOH) in the presence of a catalyst such as palladium on carbon (Pd/C). Compound M is prepared by continued hydrogenation of compound K for 3-10 days or by reduction with a reducing agent such as sodium borohydride in a suitable solvent such as EtOH. Compound N is prepared by reaction of compound M with an alkyl halide in a suitable solvent such as DMF in the presence of a base such as sodium hydride. Removal of the protecting group in compound N is achieved according to literature procedure (e.g. Greene, T. W. "Protective Groups in Organic Synthesis", J. Wiley & Sons, NY, 1981) to give compound O.

Compound C is O-demethylated and the resulting phenolic group protected with a suitable protecting group to give J according to the procedure shown in Scheme B (A→H).

Compound P is prepared from compound M via a Mitsunobu reaction (e.g. Hughes, D. L. *Org. Prep.* 1996, 28, 127) using the appropriate phenol and suitable reagents such as triphenylphosphine and diisopropyl azodicarboxylate (DIAD) in a suitable solvent such as tetrahydrofuran (THF). Removal of the protecting group (R=P) in compound P is achieved according to literature procedure (e.g. Greene, T. W. "Protective Groups in Organic Synthesis", J. Wiley & Sons, NY, 1981) to give compound Q.

Scheme E

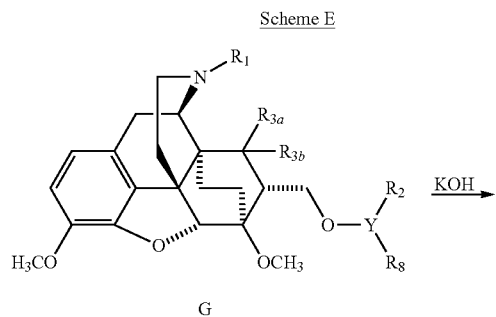

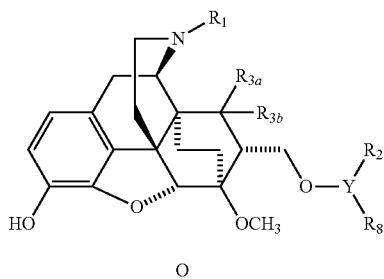

Compound G is O-demethylated by reaction with a suitable reagent such as potassium hydroxide in a suitable solvent such as ethylene glycol at temperatures greater than 100° C. (e.g. Chen, Y-J. & Chen, C. *J. Label. Compd. Radiopharm,* 2007, 50, 1143-1147) to provide the phenol O.

Scheme F

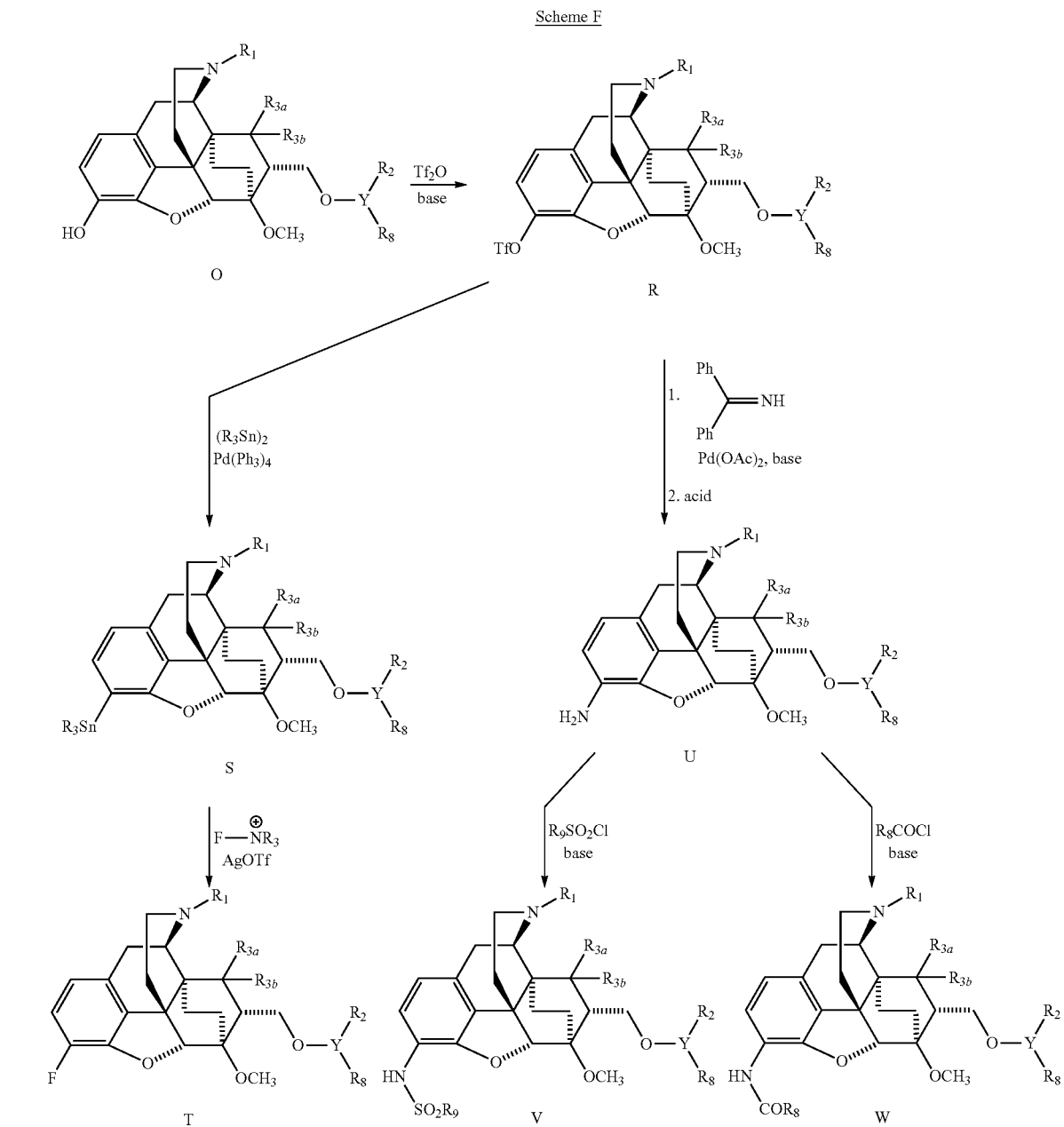

Compound O is converted to triflate R by reaction with triflic anhydride in the presence of a suitable base such as triethylamine in a suitable solvent such as DCM. Compound R is converted to compound S by reaction with a suitable reagent such as hexabutyl distannane in the presence of a suitable catalyst such as tetrakis(triphenylphosphine) palladium in a suitable solvent such as 1,4-dioxane. Compound S is converted to fluoride T by a Ag-mediated arylstannane fluorination (e.g. Furuya, T.; Strom, A. E.; Ritter, T. J. *Am. Chem. Soc.* 2009, 131, 1662-1663). Compound R is also converted to amine U by reaction with a suitable nitrogen nucleophile such as benzophenone imine in the presence of a suitable catalyst such as palladium acetate, a suitable base such as cesium carbonate in a suitable solvent such as 1,4-dioxane. Amine U is further converted to sulfonamide V or carboxamide W by reaction with either a sulfonyl chloride or carbonyl chloride, respectively, in a suitable solvent such as DCM in the presence of a suitable base such as triethylamine.

Compound R is converted to nitrile X by reaction with zinc cyanide in the presence of a suitable catalyst such as tetrakis (triphenylphosphine) palladium in a suitable solvent such as DMF at 100-150° C. Conversion to carboxamide Y is accomplished by reaction of nitrile X with a suitable reagent such as hydrogen peroxide in DMSO. Nitrile X is hydrolyzed to carboxylic acid Z by reaction with a base such as NaOH in a suitable solvent such as aqueous methanol at 50-100° C. Carboxylic acid Z can be converted to a carboxamide AA by initially reacting with a suitable reagent such as thionyl chloride followed by reaction with an amine, in the presence of a suitable base such as triethylamine in a suitable solvent such as DCM.

Scheme G

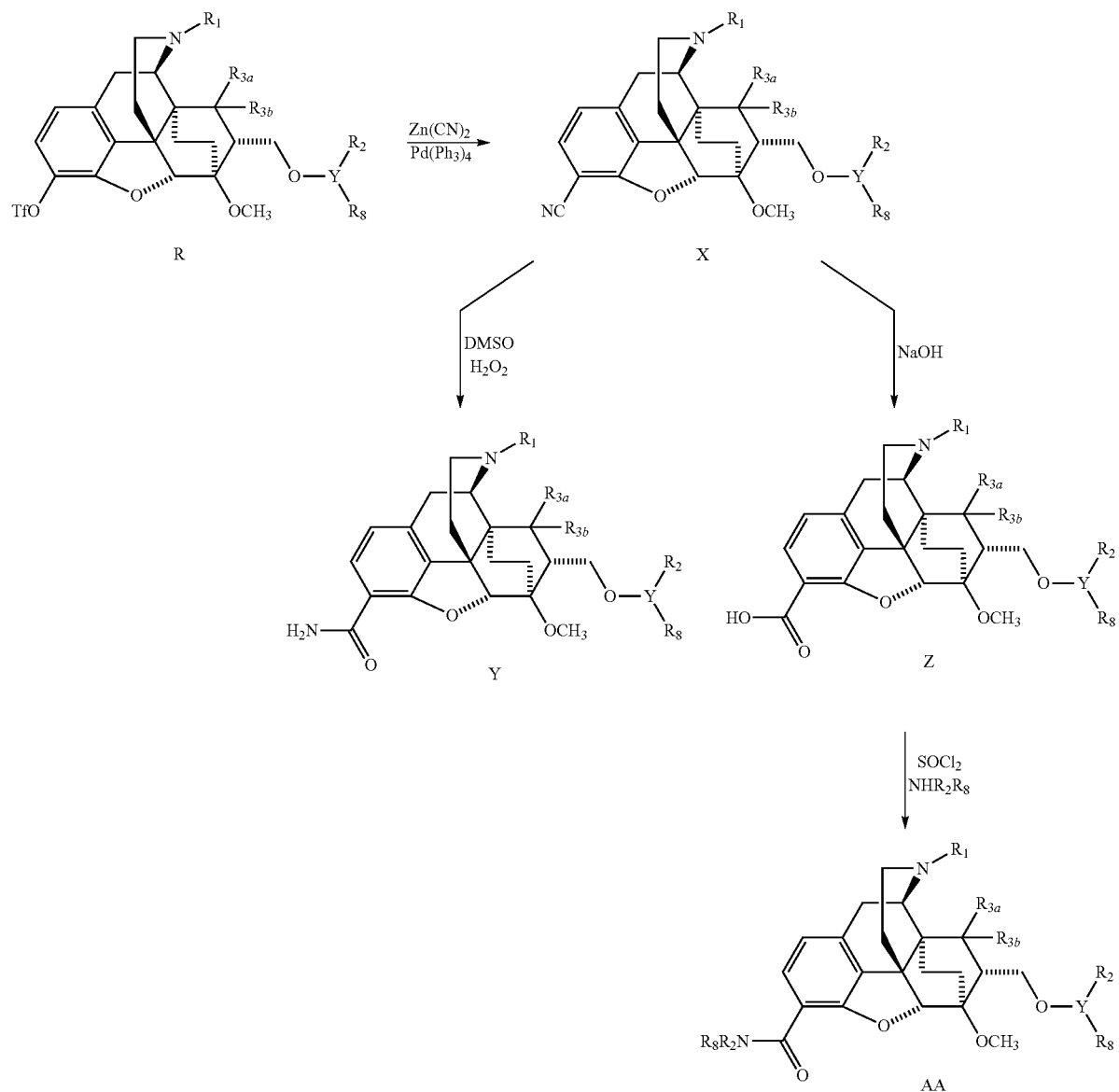

Scheme H

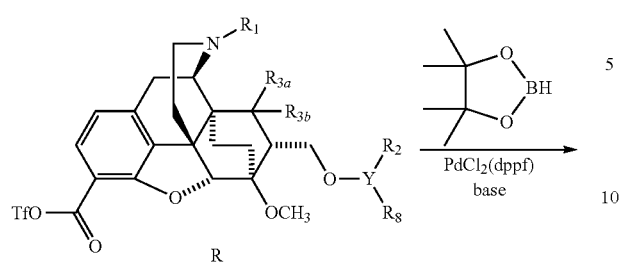

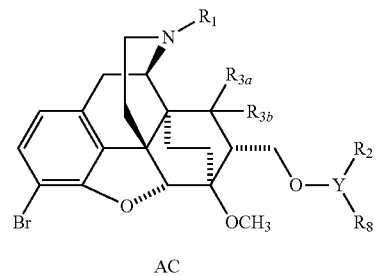

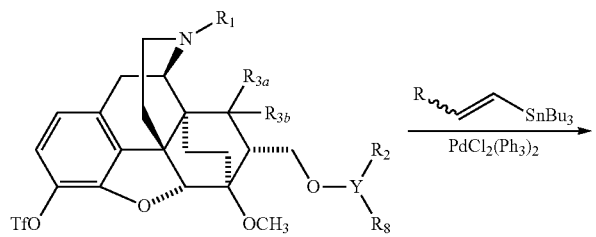

Compound R is converted to boronate AB by reaction with a boronate ester in the presence of a suitable catalyst such as PdCl$_2$(dppf) ([1,1'-bis(diphenylphosphino)ferrocene]dichloropalladium(II)) (Frontier Scientific, Inc.), a suitable base such as triethylamine in a suitable solvent such as dichloroethane (DCE) at 50-100° C. Reaction of compound AB with a copper halide salt such as copper (II) bromide in a suitable solvent such as aqueous methanol at 50-100° C. provides compound AC.

Scheme I

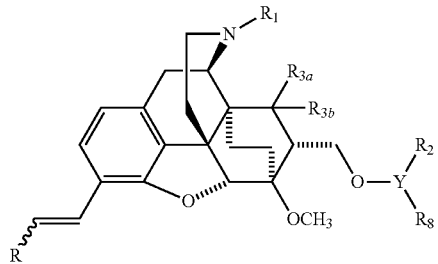

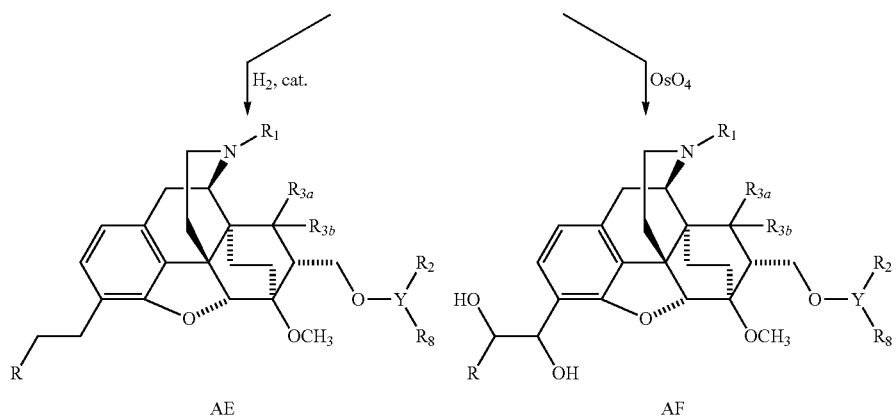

Compound R is converted to olefin AD by reaction with a vinyl stannane in the presence of a suitable catalyst such as bis-(triphenylphosphine) palladium (II) chloride in a suitable solvent such as DMF at 25-100° C. Compound AE is prepared by hydrogenation of compound AD in a suitable solvent such as EtOH in the presence of a catalyst such as palladium on carbon (Pd/C). Diols such as compound AF are prepared by reaction of olefin AD with osmium tetroxide in the absence or presence of a chiral ligand (e.g. Kolb, H. C.; Van Nieuwenhze, M. S.; Sharpless, K. B. *Chem. Rev.* 1994, 94, 2483-2547).

Compound AG is prepared by reductive amination of aldehyde L with an amine using sodium cyanoborohydride or sodium triacetoxyborohydride in a suitable solvent such as DCM. Reduction of aldehyde L to alcohol M with a reducing agent such as sodium borohydride is described in Scheme B. Conversion of alcohol M to mesylate AH is accomplished by treatment with methanesulfonyl chloride in the presence of a suitable base such as triethyl amine in a suitable solvent such as DCM. Reaction of mesylate AH with a thiol in the presence of a suitable base such as sodium hydride in a suitable solvent such as DMF gives thioether AI. Oxidation of compound AI

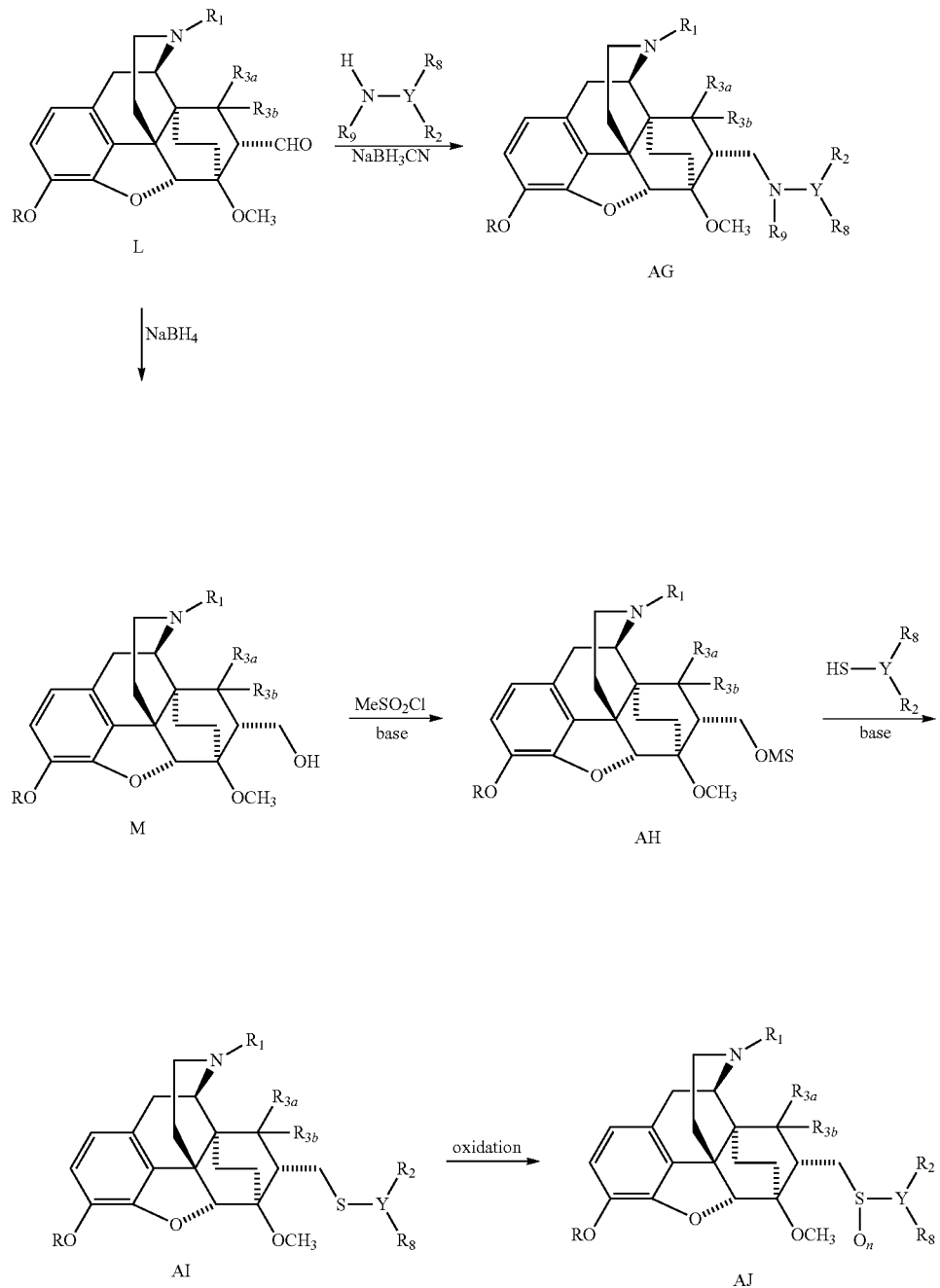

Scheme J according to literature procedure (e.g. Hudlicky, M. "Oxidations in Organic Chemistry", American Chemical Society, Washington, D.C., 1990) gives sulfone AJ (n=1) or sulfoxide AJ (n=2).

Scheme K

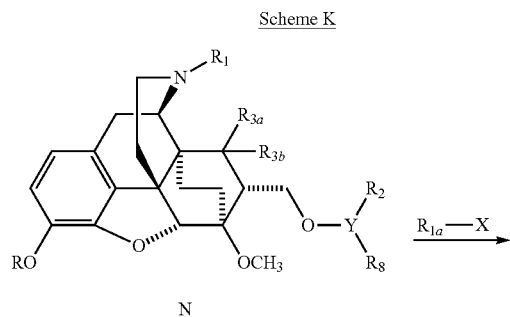

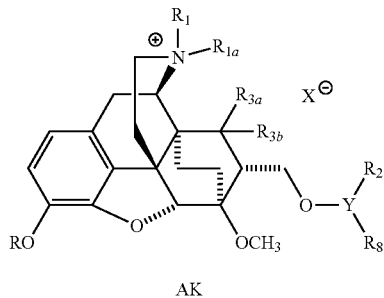

Compound N is treated with an alkyl halide such as methyl iodide either neat or in a suitable solvent such as ACN either with or without an acid scavenger such as sodium bicarbonate to give quaternary salt AK.

Scheme L

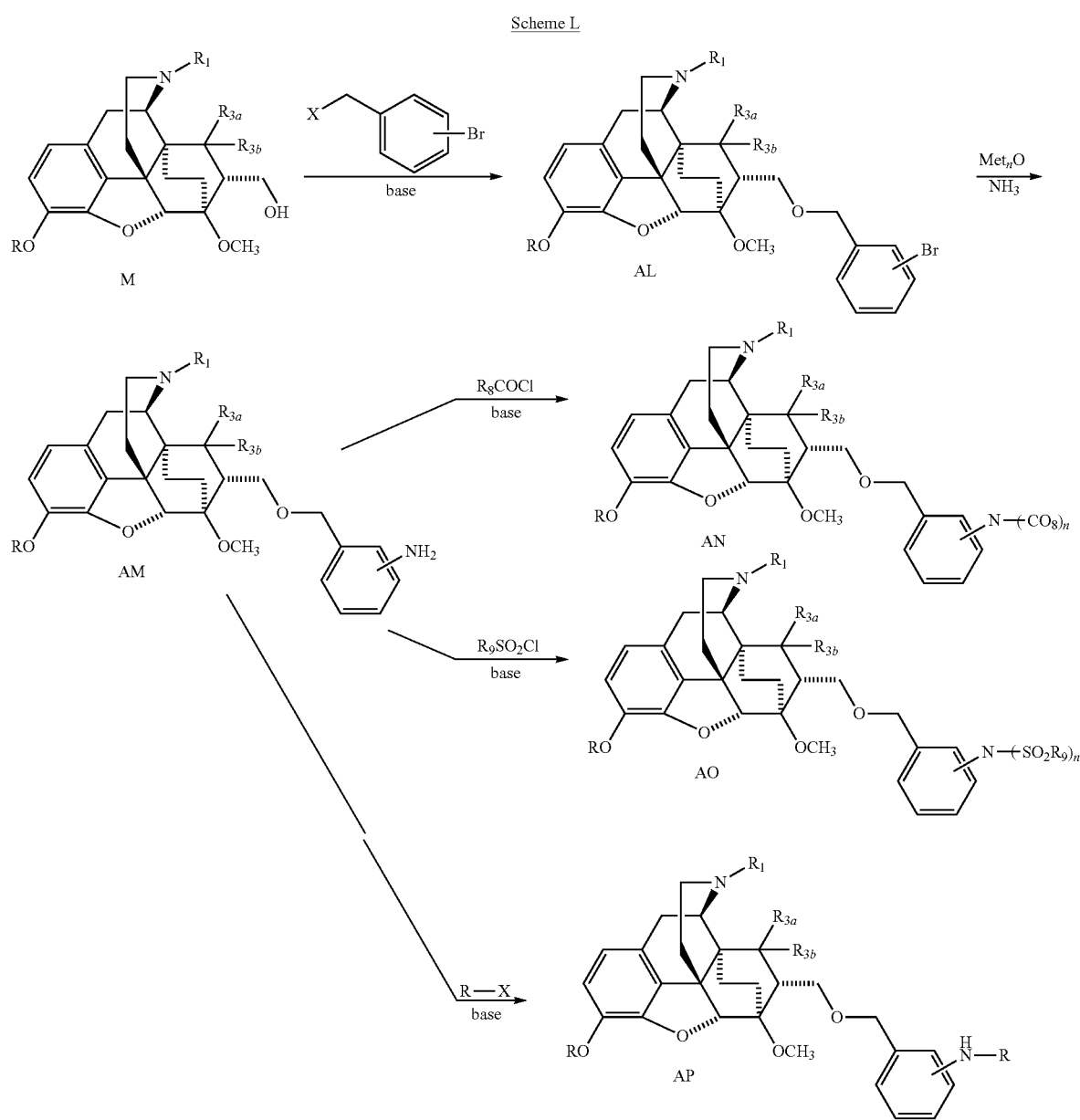

Compound M is reacted with a benzylic halide or equivalent in a suitable solvent such as DMF in the presence of a suitable base such as sodium hydride to give compound AL. Compound AL is reacted with ammonia in the presence of a suitable metal oxide ($Met_nO$) such as copper (I) oxide in a suitable solvent such as ethylene glycol to give amine AM. Amine AM is further converted to carboxamide AN or sulfonamide AO by reaction with either a carbonyl chloride or sulfonyl chloride, respectively, in a suitable solvent such as DCM in the presence of a suitable base such as triethylamine. Amine AM can also be alkylated by reaction with a suitable alkyl halide in a suitable solvent such as DMF in the presence of a suitable base such as sodium hydride to give compound AP.

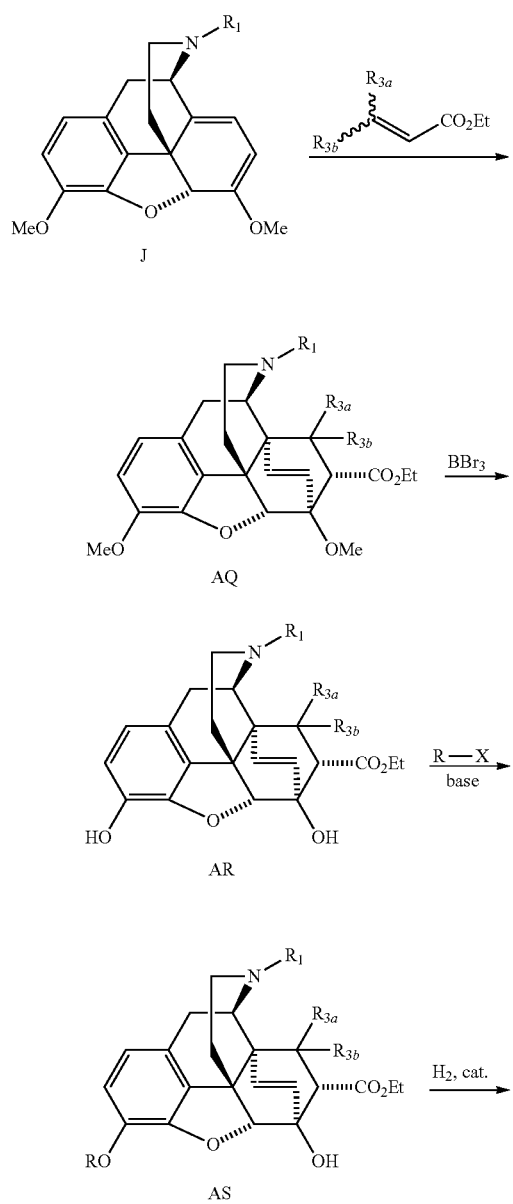

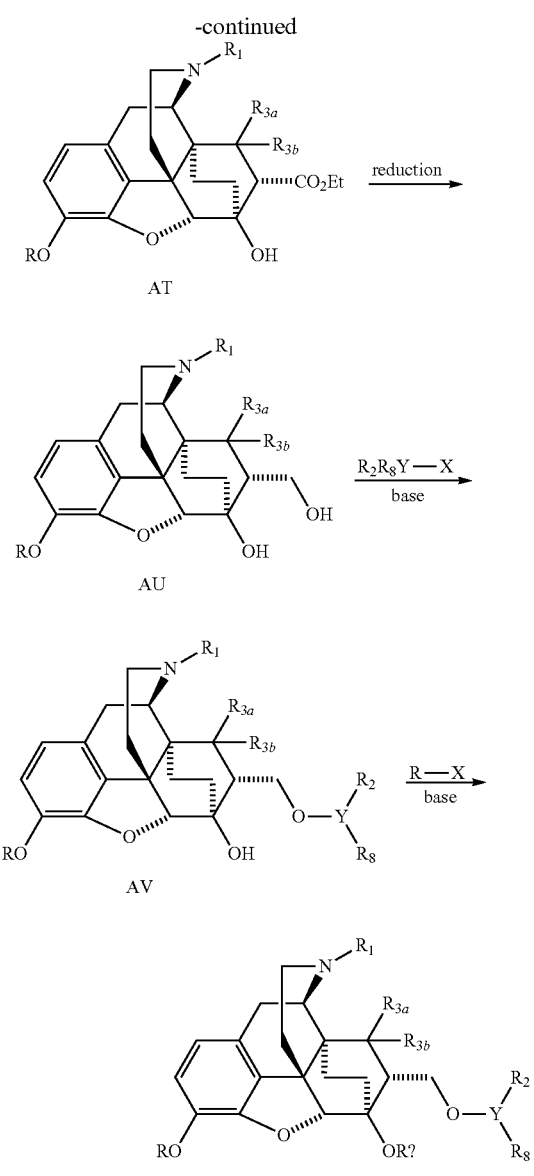

Compound AQ is prepared by reaction of compound J with an excess of an α,β unsaturated ester. Compound AQ is O-demethylated by reaction with boron tribromide, or other suitable reagent, in a suitable solvent such as $CHCl_3$ to give diol AR. Reaction of the phenol group in AR with an alkyl halide in a suitable solvent such as DMF in the presence of a suitable base such as $K_2CO_3$ gave compound AS. Hydrogenation of the double bold in compound AS in a suitable solvent such as EtOH in the presence of a catalyst such as Pd/C gave compound AT. Reduction of the ester to the alcohol AU was accomplished by a suitable reducing agent such as LAH in a suitable solvent such as THF. Compound AU was alkylated by reaction with an alkyl halide in a suitable solvent such as THF in the presence of a suitable base such as lithium hexamethylsilazide (LiHMDS) to give compound AV which was further alkylated by reaction with an alkyl halide in a suitable solvent such as DMSO in the presence of a suitable base such as sodium hydride to give compound AW.

Scheme N

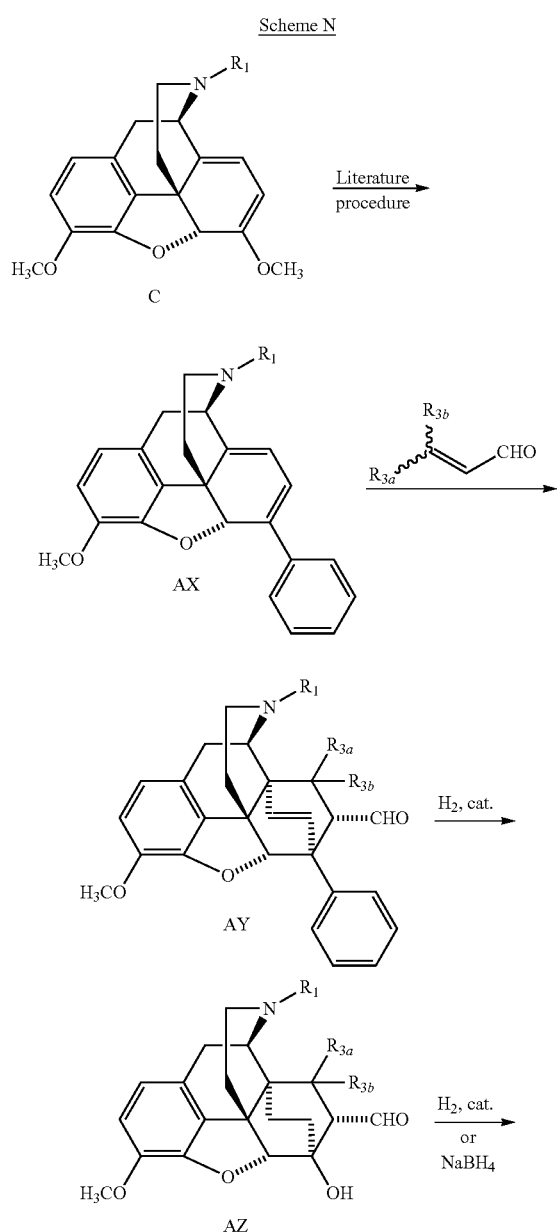

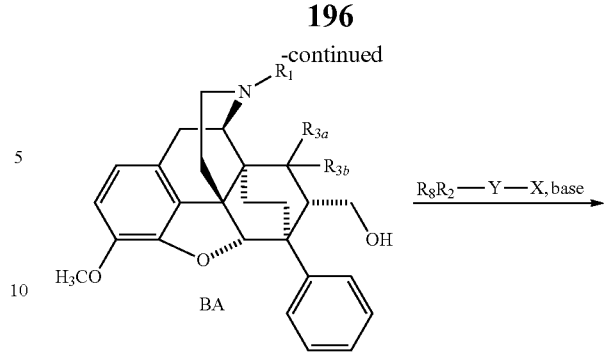

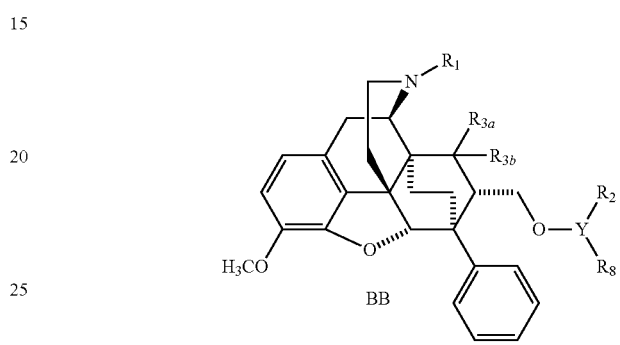

Compound AX was prepared according to a literature procedure (Czako, B., et al., Biorg. Med. Chem. 2010, 18(10), 3535-3542) except compound C was used as the starting material. Compound AY is prepared by reaction of compound AX with an excess of an α,β unsaturated aldehyde. Compound AZ is prepared by hydrogenation of compound AY in a suitable solvent such as EtOH in the presence of a catalyst such as Pd/C. Compound BA is prepared by continued hydrogenation of compound AZ for 3-10 days or by reduction with a reducing agent such as sodium borohydride in a suitable solvent such as EtOH. Compound BB is prepared by reaction of compound BA with an alkyl halide in a suitable solvent such as DMF in the presence of a suitable base such as sodium hydride.

Scheme O

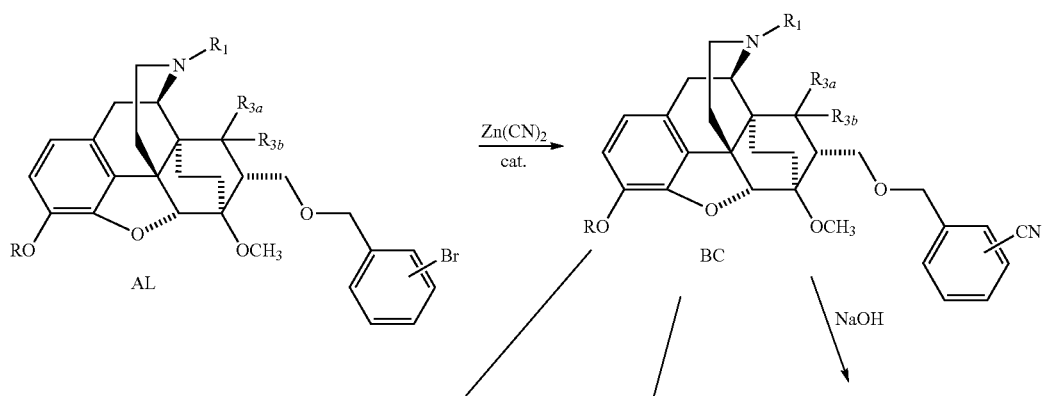

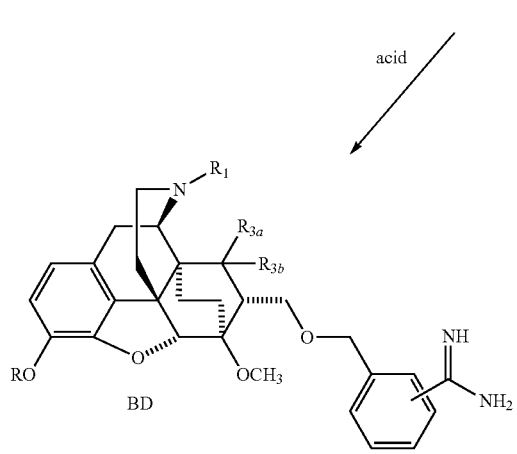
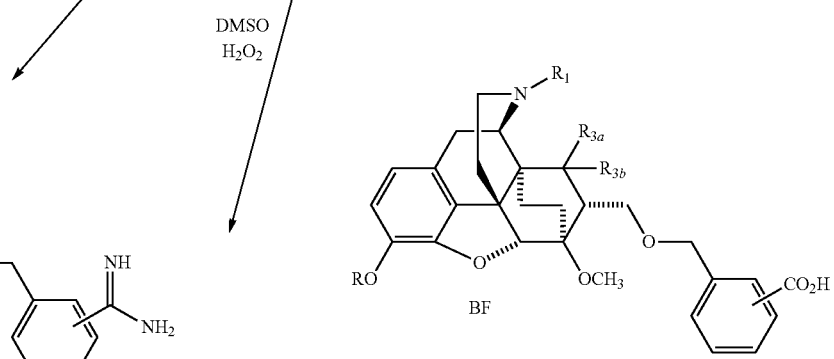
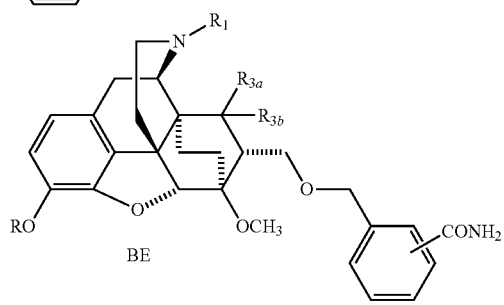
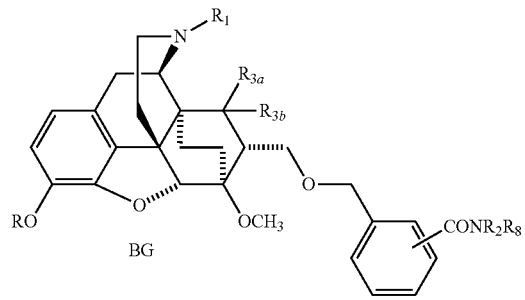

Compound AL is converted to nitrile BC by reaction with a suitable cyanide such as zinc cyanide in the presence of a suitable catalyst such as tetrakis(triphenylphosphine) palladium in a suitable solvent such as DMF. Compound BC can be converted to amidine BD by reaction with a suitable acid such as hydrochloric acid in a suitable solvent such as ethanol. Nitrile BC can be converted to amide BE by reaction with a suitable reagent such as hydrogen peroxide in DMSO. Nitrile BC can be hydrolyzed to carboxylic acid BF by reaction with a base such as NaOH in a suitable solvent such as aqueous methanol. Carboxylic acid BF can be converted to a carboxamide BG by initially reacting with a suitable reagent such as thionyl chloride followed by reaction with an amine, in the presence of a suitable base such as triethylamine in a suitable solvent such as DCM.

Scheme P

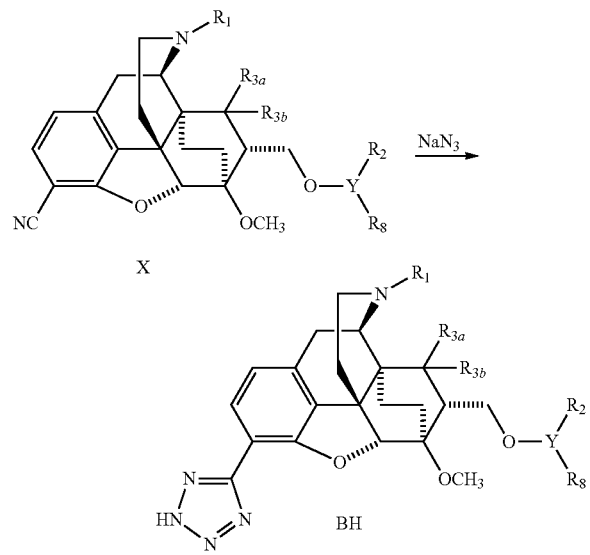

Compound X is reacted with a suitable azide such as sodium azide in the presence of a suitable catalyst such as ammonium chloride in a suitable solvent such as DMF to provide compound BH.

Compound J is reacted with a suitable α,β unsaturated ketone in the presence or absence of a suitable solvent such as toluene to give compound BI. Compound BJ is prepared by hydrogenation of compound BI in a suitable solvent such as ethanol in the presence of a catalyst such as palladium on carbon. Tertiary alcohol BK is prepared by reaction of compound BJ with a suitable organometallic compound such as a Grignard reagent in a suitable solvent such as THF. Compound BL is prepared by reaction of compound BK with an alkyl halide in a suitable solvent such as DMSO in the presence of a base such as potassium hydride.

Scheme Q

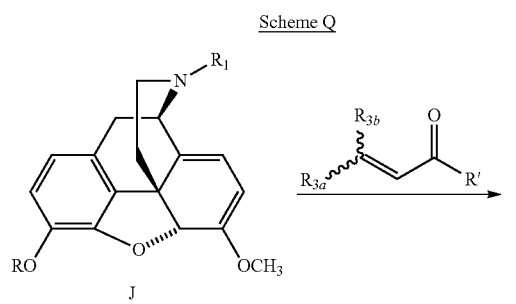

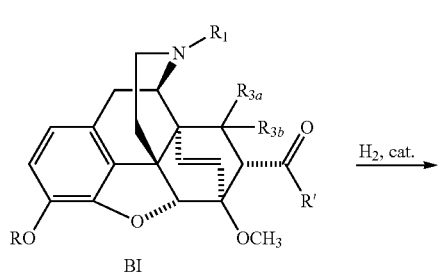

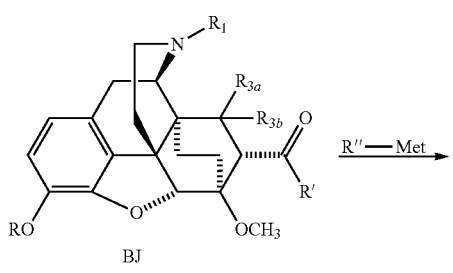

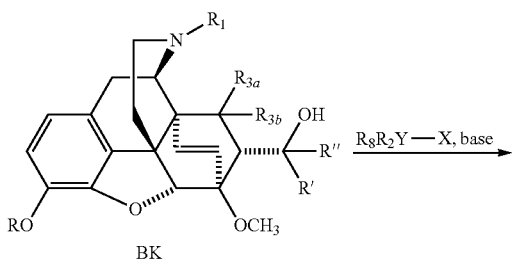

Scheme R

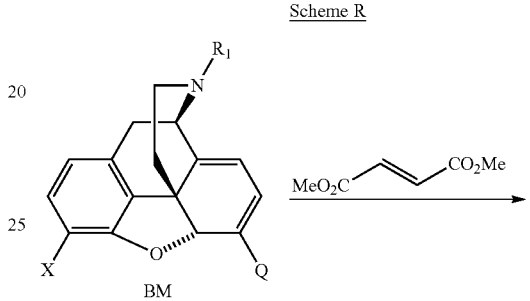

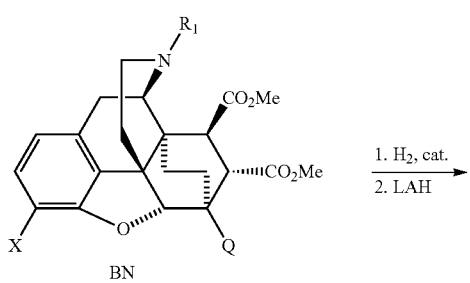

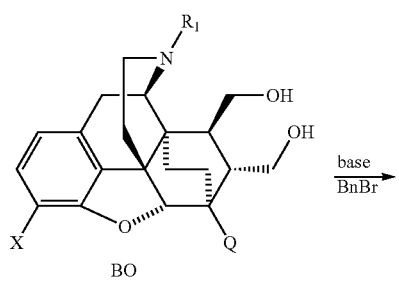

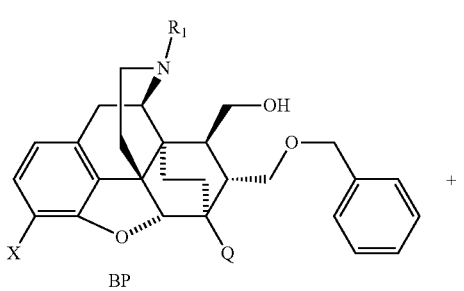

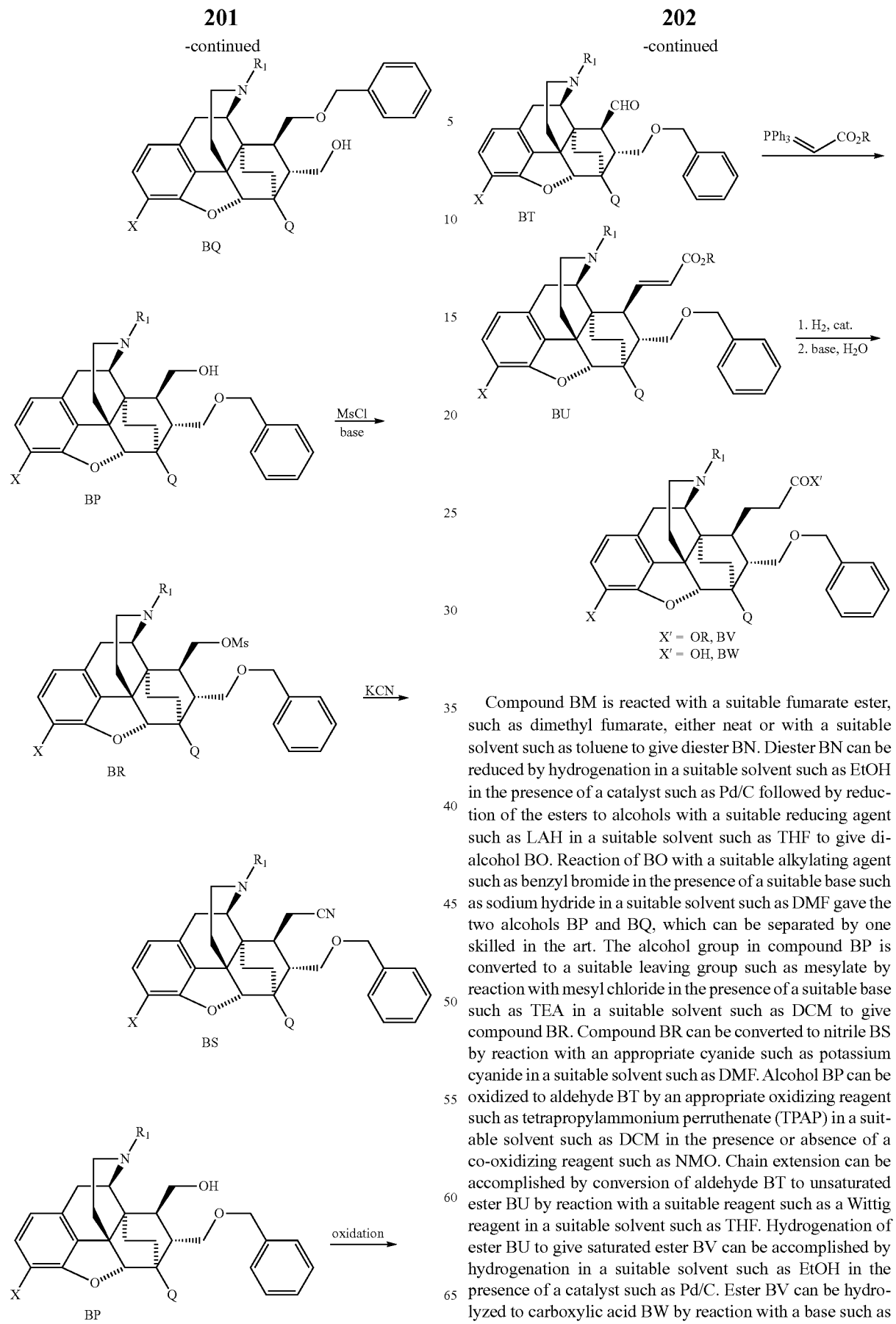

Compound BM is reacted with a suitable fumarate ester, such as dimethyl fumarate, either neat or with a suitable solvent such as toluene to give diester BN. Diester BN can be reduced by hydrogenation in a suitable solvent such as EtOH in the presence of a catalyst such as Pd/C followed by reduction of the esters to alcohols with a suitable reducing agent such as LAH in a suitable solvent such as THF to give di-alcohol BO. Reaction of BO with a suitable alkylating agent such as benzyl bromide in the presence of a suitable base such as sodium hydride in a suitable solvent such as DMF gave the two alcohols BP and BQ, which can be separated by one skilled in the art. The alcohol group in compound BP is converted to a suitable leaving group such as mesylate by reaction with mesyl chloride in the presence of a suitable base such as TEA in a suitable solvent such as DCM to give compound BR. Compound BR can be converted to nitrile BS by reaction with an appropriate cyanide such as potassium cyanide in a suitable solvent such as DMF. Alcohol BP can be oxidized to aldehyde BT by an appropriate oxidizing reagent such as tetrapropylammonium perruthenate (TPAP) in a suitable solvent such as DCM in the presence or absence of a co-oxidizing reagent such as NMO. Chain extension can be accomplished by conversion of aldehyde BT to unsaturated ester BU by reaction with a suitable reagent such as a Wittig reagent in a suitable solvent such as THF. Hydrogenation of ester BU to give saturated ester BV can be accomplished by hydrogenation in a suitable solvent such as EtOH in the presence of a catalyst such as Pd/C. Ester BV can be hydrolyzed to carboxylic acid BW by reaction with a base such as LiOH in a suitable solvent such as aqueous methanol.

Scheme S

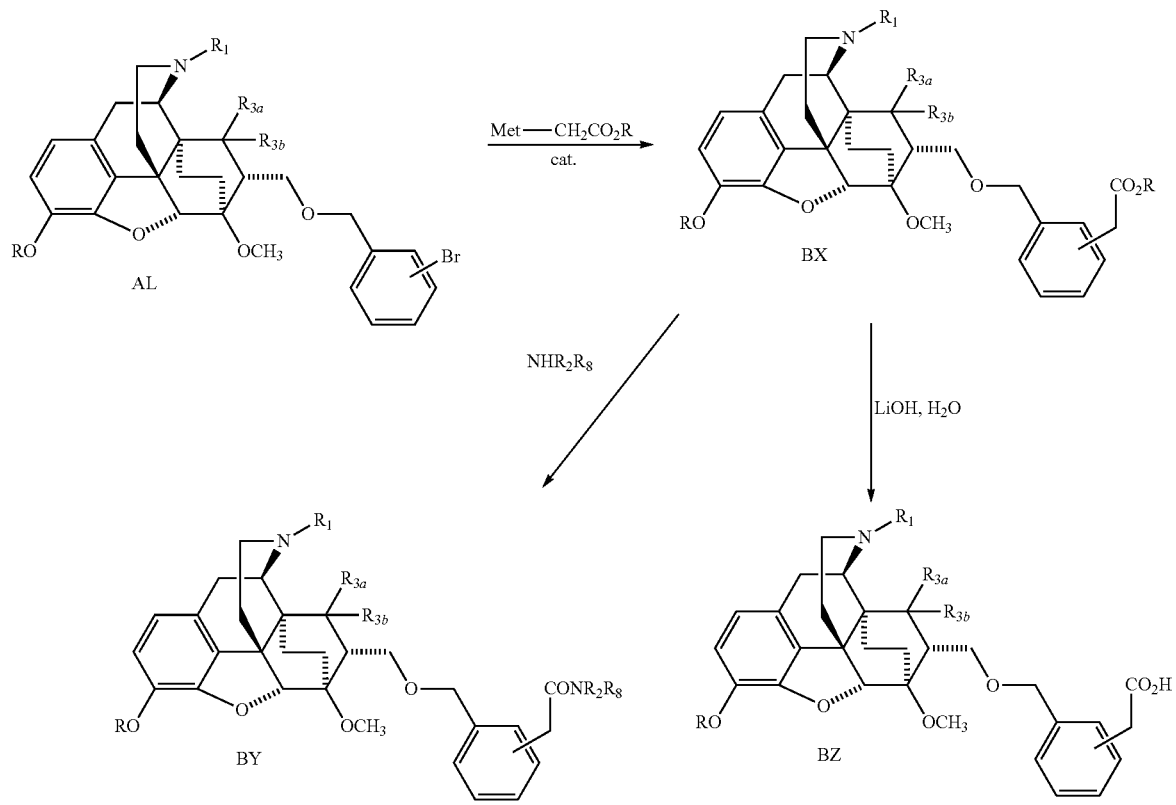

Compound AL is converted to ester BX by reaction with a metalated acetic acid ester in the presence of a suitable catalyst such as tetrakis(triphenylphosphine) palladium in a suitable solvent such as THF. Ester BX can be converted to amide BY by reaction with an amine in a suitable solvent such as toluene in the absence or presence of a catalyst such as trialkyl aluminiums. Ester BX can also be saponified to the acid BZ by treatment with a metal hydroxide such as lithium hydroxide in the presence of water in a suitable solvent such as methanol.

Testing of Compounds

μ-Opioid Receptor Binding Assay Procedures:

Radioligand dose-displacement binding assays for t-opioid receptors used 0.3 nM [$^3$H]-diprenorphine (Perkin Elmer, Shelton, Conn.), with 5 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hr at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subsequently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISM™ v. 3.0 or higher (San Diego, Calif.), or an in-house function for one-site competition curve-fitting.

μ-Opioid Receptor Binding Data:

Generally, the lower the Ki value, the more effective the Compounds of the Invention will be at treating or preventing pain or another Condition. Typically, the Compounds of the Invention will have a Ki (nM) of about 1000 or less for binding to μ-opioid receptors. In one embodiment the Compounds of the Invention will have a Ki (nM) of about 300 or less for binding to μ-opioid receptors. In one embodiment, Compounds of the Invention will have a Ki (nM) of about 100 or less. In another embodiment, Compounds of the Invention will have a Ki (nM) of about 10 or less. In still another embodiment, Compounds of the Invention will have a Ki (nM) of about 1 or less. In still another embodiment, Compounds of the Invention will have a Ki (nM) of about 0.1 or less.

μ-Opioid Receptor Functional Assay Procedures:

[$^{35}$S]GTPγS functional assays were conducted using freshly thawed μ-receptor membranes (Perkin Elmer, Shelton, Conn.). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 min at about 25° C.

with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200l of ice-cold wash buffer (10 mM $NaH_2PO_4$, 10 mM $Na_2HPO_4$, pH 7.4). Filter plates were subsequently dried at 50° C. for 2-3 hr. BetaScint scintillation cocktail (Perkin Elmer, Shelton, Conn.) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data:

μ GTP $EC_{50}$ is the concentration of a compound providing 50% of the maximal response for the compound at μ-opioid receptor. Compounds of the Invention will typically have a μ GTP $EC_{50}$ (nM) of about 5000 or less. In certain embodiments, Compounds of the Invention will have a μ GTP $EC_{50}$ (nM) of about 2000 or less; or about 1000 or less; or about 100 or less; or about 10 or less; or about 1 or less; or about 0.1 or less.

μ GTP $E_{max}$ (%) is the maximal effect elicited by a compound relative to the effect elicited by DAMGO, a standard agonist. Generally, the μ GTP $E_{max}$ (%) value measures the efficacy of a compound to treat or prevent pain or other Conditions. Typically, Compounds of the Invention will have a GTP $E_{max}$ (%) of greater than about 10%; or greater than about 20%. In certain embodiments, Compounds of the Invention will have a μ GTP $E_{max}$ (%) of greater than about 50%; or greater than about 65%; or greater than about 75%; or greater than about 85%; or greater than about 100%.

κ-Opioid Receptor Binding Assay Procedures:

Membranes from recombinant HEK-293 cells expressing the human κ opioid receptor (κ) (cloned in house) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at −80° C.

Radioligand dose displacement assays used 0.4 nM [$^3$H]-U69,593 (GE Healthcare, Piscataway, N.J.; 40 Ci/mmole) with 15 μg membrane protein (recombinant κ opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200l ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

κ-Opioid Receptor Binding Data:

In certain embodiments, the Compounds of the Invention will have a Ki (nM) for κ receptors of about 10,000 or more (which, for purposes of this invention, is interpreted as having no binding to the κ receptors). Certain Compounds of the Invention will have a Ki (nM) of about 20,000 or less for κ receptors. In certain embodiments, Compounds of the Invention will have a Ki (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less.

κ-Opioid Receptor Functional Assay Procedures:

Functional [$^{35}$S]GTPγS binding assays were conducted as follows. κ opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200l ice-cold binding buffer (10 mM $NaH_2PO_4$, 10 mM $Na_2HPO_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well.

κ-Opioid Receptor Functional Data:

κ GTP $EC_{50}$ is the concentration of a compound providing 50% of the maximal response for the compound at a κ receptor. Certain Compounds of the Invention will have a κ GTP $EC_{50}$ (nM) of about 20,000 or less to stimulate κ opioid receptor function. In certain embodiments, Compounds of the Invention will have a κ GTP $EC_{50}$ (nM) of about 10,000 or less; or about 5000 or less; or about 2000 or less; or about 1500 or less; or about 1000 or less; or about 600 or less; or about 100 or less; or about 50 or less; or about 25 or less; or about 10 or less; or about 1 or less; or about 0.1 or less.

κ GTP $E_{max}$ (%) is the maximal effect elicited by a compound relative to the effect elicited by U69,593. Certain Compounds of the Invention will have a κ GTP $E_{max}$ (%) of greater than about 1%; or greater than about 5%; or greater than about 10%; or greater than about 20%. In certain embodiments, Compounds of the Invention will have a κ GTP $E_{max}$ (%) of greater than about 50%; or greater than about 75%; or greater than about 90%; or greater than about 100%.

δ-Opioid Receptor Binding Assay Procedures:

δ-opioid Receptor Binding Assay Procedures were conducted as follows. Radioligand dose-displacement assays used 0.3 nM [$^3$H]-Naltrindole (Perkin Elmer, Shelton, Conn.; 33.0 Ci/mmole) with 5 μg membrane protein (Perkin Elmer, Shelton, Conn.) in a final volume of 500 μl binding buffer (5 mM $MgCl_2$, 5% DMSO, 50 mM Trizma base, pH 7.4). Non-specific binding was determined in the presence of 25 μM unlabeled naloxone. All reactions were performed in 96-deep well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 500 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

δ-Opioid Receptor Binding Data:

In certain embodiments, the Compounds of the Invention will have a Ki (nM) for δ receptors of about 10,000 or more (which, for the purposes of this invention, is interpreted as having no binding to the δ receptors). Certain Compounds of the Invention will have a Ki (nM) of about 20,000 or less for δ receptors. In one embodiment, the Compounds of the Invention will have a Ki (nM) of about 10,000 or less; or of about 9000 or less. In another embodiment, the Compounds of the Invention will have a Ki (nM) of about 7500 or less; or of about 6500 or less; or of about 5000 or less; or of about 3000 or less; or of about 2500 or less. In another embodiment, the Compounds of the Invention will have a Ki (nM) of about 1000 or less; or of about 500 or less; or of about 350 or less; or of about 250 or less; or of about 100 or less; or of about 10 or less.

δ-Opioid Receptor Functional Assay Procedures:

Functional [$^{35}$S]GTPγS binding assays were conducted as follows. δ opioid receptor membrane solution was prepared by sequentially adding final concentrations of 0.026 μg/μl δ membrane protein (Perkin Elmer, Shelton, Conn.), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 1-2 hours. Fifty μl/well scintillation cocktail (Perkin Elmer, Shelton, Conn.) was added and plates were counted in a Packard Top-count for 1 min/well.

δ-Opioid Receptor Functional Data:

δ GTP EC$_{50}$ is the concentration of a compound providing 50% of the maximal response for the compound at a δ receptor. Certain Compounds of the Invention will have a δ GTP EC$_{50}$ (nM) of about 20,000 or less; or about 10,000 or less. In certain embodiments, the Compounds of the Invention will have a δ GTP EC$_{50}$ (nM) of about 3500 or less; or of about 1000 or less; or of about 500 or less; or of about 100 or less; or of about 90 or less; or of about 50 or less; or of about 25 or less; or of about 10 or less.

δ GTP E$_{max}$ (%) is the maximal effect elicited by a compound relative to the effect elicited by met-enkephalin. Certain Compounds of the Invention of the invention will have a δ GTP E$_{max}$ (%) of greater than about 1%; or of greater than about 5%; or of greater than about 10%. In one embodiment, the Compounds of the Invention will have a δ GTP E$_{max}$ (%) of greater than about 30%. In other embodiments, the Compounds of the Invention will have a δ GTP E$_{max}$ (%) of greater than about 50%; or of greater than about 75%; or of greater than about 90%. In another embodiment, the Compounds of the Invention will have a δ GTP E$_{max}$ (%) of about 100% or greater.

ORL-1 Receptor Binding Assay Procedure:

Membranes from recombinant HEK-293 cells expressing the human opioid receptor-like receptor (ORL-1) (Perkin Elmer, Shelton, Conn.) were prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes were collected by centrifugation at 30,000×g for 15 min at 4° C. and pellets resuspended in hypotonic buffer to a final concentration of 1-3 mg/ml. Protein concentrations were determined using the BioRad protein assay reagent with bovine serum albumen as standard. Aliquots of the ORL-1 receptor membranes were stored at −80° C.

Radioligand binding assays (screening and dose-displacement) used 0.1 nM [$^3$H]-nociceptin (Perkin Elmer, Shelton, Conn.; 87.7 Ci/mmole) with 12 μg membrane protein in a final volume of 500 μl binding buffer (10 mM MgCl$_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at room temperature. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by three filtration washes with 500 μl ice-cold binding buffer. Filter plates were subsequently dried at 50° C. for 2-3 hours. Fifty μl/well scintillation cocktail (Perkin Elmer, Shelton, Conn.) was added and plates were counted in a Packard Top-Count for 1 min/well. The data from screening and dose-displacement experiments were analyzed using Microsoft Excel and the curve fitting functions in GraphPad PRISM™, v. 3.0 or higher, respectively, or an in-house function for one-site competition curve-fitting.

ORL-1 Receptor Binding Data:

Certain Compounds of the Invention will have a Ki (nM) of about 1000 or less. In one embodiment, the Compounds of the Invention will have a Ki (nM) of about 500 or less. In other embodiments, the Compounds of the Invention will have a Ki (nM) of about 300 or less; or of about 100 or less; or of about 50 or less; or of about 20 or less. In yet other embodiments, the Compounds of the Invention will have a Ki (nM) of about 10 or less; or of about 1 or less; or of about 0.1 or less.

ORL-1 Receptor Functional Assay Procedure:

Membranes from recombinant HEK-293 cells expressing the human opioid receptor-like (ORL-1) (Perkin Elmer, Shelton, Conn.) were prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3 mg/ml. Protein concentrations were determined using the BioRad protein assay reagent with bovine serum albumen as standard. Aliquots of the ORL-1 receptor membranes were stored at −80° C.

Functional [$^{35}$S]GTPγS binding assays were conducted as follows. ORL-1 membrane solution was prepared by sequentially adding final concentrations of 0.026 μg/μl ORL-1 membrane protein, 10 μg/ml saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 l of 20× concentrated stock solutions of agonist/nociceptin prepared in DMSO. Plates were incubated for 30 min at room temperature with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well. Data were analyzed using the sigmoidal dose-response curve fitting functions in GraphPad PRISM v. 3.0 or higher, or an in-house function for non-linear, sigmoidal dose-response curve-fitting.

ORL-1 Receptor Functional Data:

ORL-1 GTP $EC_{50}$ is the concentration of a compound providing 50% of the maximal response for the compound at an ORL-1 receptor. In certain embodiments, the Compounds of the Invention that have a high binding affinity (i.e. low $K_i$ value) will have an ORL-1 GTP $EC_{50}$ (nM) of greater than about 10,000 (i.e. will not stimulate at therapeutic concentrations) In certain embodiments Compounds of the Invention will have an ORL-1 GTP $EC_{50}$ (nM) of about 20,000 or less. In one embodiment, the Compounds of the Invention will have an ORL-1 GTP $EC_{50}$ (nM) of about 10,000 or less; or of about 5000 or less; or of about 1000 or less. In still other embodiments, the Compounds of the Invention will have an ORL-1 GTP $EC_{50}$ (nM) of about 100 or less; or of about 10 or less; or of about 1 or less; or of about 0.1 or less.

ORL-1 GTP $E_{max}$% is the maximal effect elicited by a compound relative to the effect elicited by nociceptin, a standard ORL-1 agonist. In certain embodiments, Compounds of the Invention will have an ORL-1 GTP $E_{max}$ of less than 10% (which, for the purposes of this invention, is interpreted as having antagonist activity at ORL-1 receptors). Certain Compounds of the Invention will have an ORL-1 GTP $E_{max}$ (%) of greater than 1%; or of greater than 5%; or of greater than 10%. In other embodiments the Compounds of the Invention will have an ORL-1 GTP $E_{max}$ of greater than 20%; or of greater than 50%; or of greater than 75%; or of greater than 88%; or of greater than 100%.

In Vivo Assays for Prevention or Treatment of Pain

Test Animals:

Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain:

To assess the actions of a Compound of the Invention for the treatment or prevention of acute pain, the rat tail flick test was used. Rats were gently restrained by hand and the tail exposed to a focused beam of radiant heat at a point 5 cm from the tip using a tail flick unit (Model 7360, commercially available from Ugo Basile of Italy). Tail flick latencies were defined as the interval between the onset of the thermal stimulus and the flick of the tail. Animals not responding within 20 seconds were removed from the tail flick unit and assigned a withdrawal latency of 20 seconds. Tail flick latencies were measured immediately before (pre-treatment) and 1, 3, and 5 hours following administration of a Compound of the Invention. Data were expressed as tail flick latency(s) and the percentage of the maximal possible effect (% MPE), i.e., 20 seconds, is calculated as follows:

% MPE =

$$\frac{[(\text{post administration latency}) - (\text{pre-administration latency})]}{(20 \text{ s} - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

Compound 22, administered subcutaneously at a dose of 3 mg/kg significantly increased tail flick latencies, compared to vehicle treated rats, at 1, 3 and 5 hours after drug administration (FIG. 1). Compound 22 administered subcutaneously at a dose of 1 mg/kg significantly increased tail flick latencies at 1 hour following drug administration (FIG. 1).

To assess the actions of a Compound of the Invention for the treatment or prevention of acute pain, the rat hot plate test was also used. Rats were tested using a hot plate apparatus consisting of a clear plexiglass cylinder with a heated metal floor maintained at a temperature of 48-52° C. (Model 7280, commercially available from Ugo Basile of Italy). Rats were placed into the cylinder on the hot plate apparatus for a maximum duration of 30 s, or until it exhibited a nocifensive behavior (behavioral endpoint), at which time it was removed from the hot plate, and response latency recorded. Hot plate latencies were measured immediately before (pre-treatment) and 1, 3, and 5 hours following administration of a Compound of the Invention. The nocifensive behavioral endpoint was defined as any of the following: 1) paw withdrawal, either as a sustained lift or with shaking or licking; 2) alternating foot lifting; 3) excape or attempted escapre from the testing device; or 4) vocalization. Data were expressed as response latency(s) and the percentage of the maximal possible effect was calculated as described above for the tail flick test. The hot plate test is described in G. Woolfe and A. D. Macdonald, *J. Pharmacol. Exp. Ther.* 80:300-307 (1944).

Figure 2:
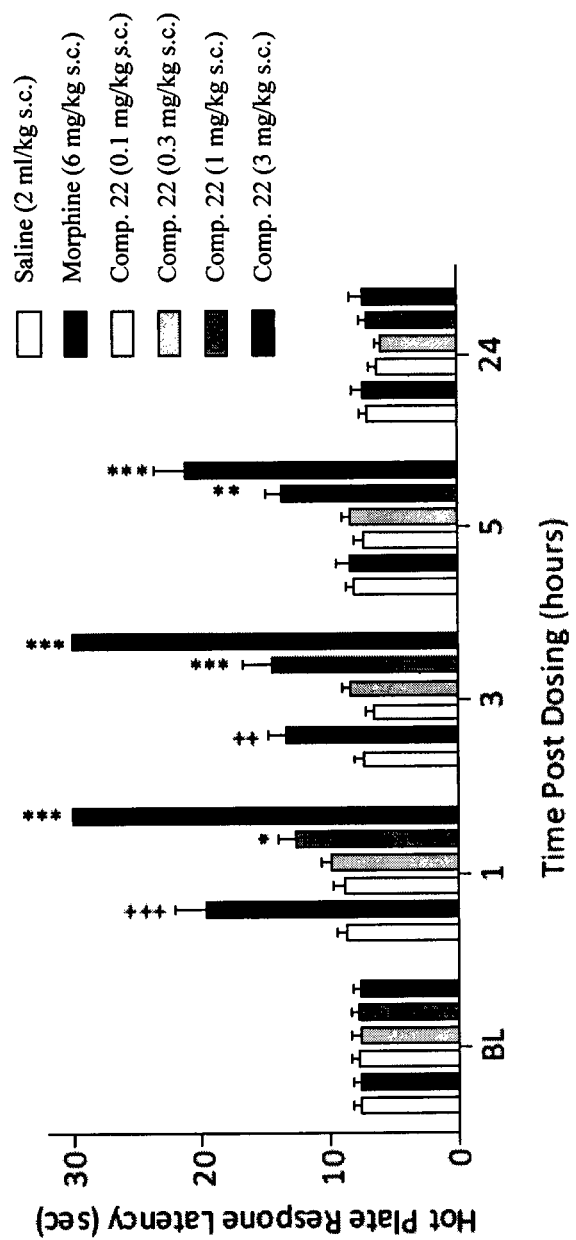
FIG. 2 shows hot plate latency in rats prior to drug administration (BL), and 1, 3, 5, and 24 hours after subcutaneous (s.c.) administration of either saline, 6 mg/kg morphine, or 0.1, 0.3, 1.0, or 3.0 mg/kg of Compound 22.

Compound 22, administered subcutaneously at a dose of 1 or 3 mg/kg, significantly increased hot plate latencies at 1, 3 and 5 hours following drug administration (FIG. 2).

Inflammatory Pain:

To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

% Reversal =

$$\frac{[(\text{post administration } PWT) - (\text{pre-administration } PWT)]}{[(\text{baseline } PWT) - (\text{pre-administration } PWT)]} \times 100$$

Neuropathic Pain:

To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a 3/8 curved, reversed-cutting mini-needle and tightly ligated so that the dorsal 1/3 to 1/2 of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia:

The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression:

To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., 2000 *Intensive Care Med.* (26) 585-591).

Assessment of Gastric Motility:

Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

Due to their activity, the Compounds of the Invention are advantageously useful in human and veterinary medicine. As described above, the Compounds of the Invention are useful for treating or preventing a Condition in an animal in need thereof. The Compounds of the Invention can be administered to any animal requiring modulation of the opioid and/or ORL-1 receptors.

When administered to an animal, a Compound of the Invention can be administered as a component of a composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, suppositories, aerosols, sprays, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the invention preferably comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release, Vol. 2, Applications and Evaluation*, R. S. Langer and D. L. Wise eds., CRC Press (1984). Other controlled- or sustained-release systems that are discussed in the review by Langer, *Science* 249:1527-1533 (1990) can be selected for use according to the present invention. In one embodiment, a pump can be used (Langer, Science 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each animal's circumstances. Variations in dosing may occur depending upon typical factors such as the weight, age, gender and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Compound of the Invention, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Compound of the Invention is administered, the effective dosage amounts correspond to the total amount administered.

Where a cell capable of expressing the ORL-1 receptor is contacted with a Compound of the Invention in vitro, the amount effective for inhibiting or activating the ORL-1 receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the µ-opioid receptors is contacted with a Compound of the Invention in vitro, the amount effective for inhibiting or activating the µ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the δ-opioid receptors is contacted with a Compound of the Invention in vitro, the amount effective for inhibiting or activating the δ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the κ-opioid receptors is contacted with a Compound of the Invention in vitro, the amount effective for inhibiting or activating the κ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

The Compounds of the Invention can be assayed in vitro or in vivo for the desired therapeutic or prophylactic activity prior to use in humans. Animal model systems can be used to demonstrate safety and efficacy. Certain Compounds of the Invention will have an $ED_{50}$ for treating inflammatory pain ranging from about 0.5 mg/kg to about 20 mg/kg. Certain Compounds of the Invention will produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the invention, methods for treating or preventing a Condition in an animal in need thereof can further comprise co-administering to the animal an effective amount of a second therapeutic agent in addition to a Compound of the Invention (i.e., a first therapeutic agent). An effective amount of the second therapeutic agent will be known or determinable by a medical practitioner in view of this disclosure and published clinical studies. In one embodiment of the invention, where a second therapeutic agent is administered to an animal for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-IA inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Insel, *Analgesic-Antipyretic and Anti-inflammatory Agents and Drugs Employed in the Treatment of Gout*, in *Goodman & Gilman's The Pharmacological Basis of Therapeutics* 617-57 (Perry B. Molinhoff and Raymond W. Ruddon eds., 9$^{th}$ ed 1996); and Glen R. Hanson, *Analgesic, Antipyretic and Anti-Inflammatory Drugs in Remington: The Science and Practice of Pharmacy Vol IA* 1196-1221 (A. R. Gennaro ed. 19$^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexyline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the invention is prepared by a method comprising admixing a Compound of the Invention (or a pharmaceutically acceptable salt, prodrug or solvate thereof) with a pharmaceutically acceptable carrier or excipient. Admixing can be accomplished using methods known for admixing a compound (or derivative) and a pharmaceutically acceptable carrier or excipient. In one embodiment, the Compound of the Invention (or pharmaceutically acceptable salt, prodrug or solvate thereof) is present in the composition in an effective amount.

EXAMPLES

Example 1

(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinolin-9-amine (Compound 2); N-((4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinolin-9-yl)acetamide (Compound 17); N-((4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinolin-9-yl)methanesulfonamide (Compound 16); and (4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-amine (Compound 10)

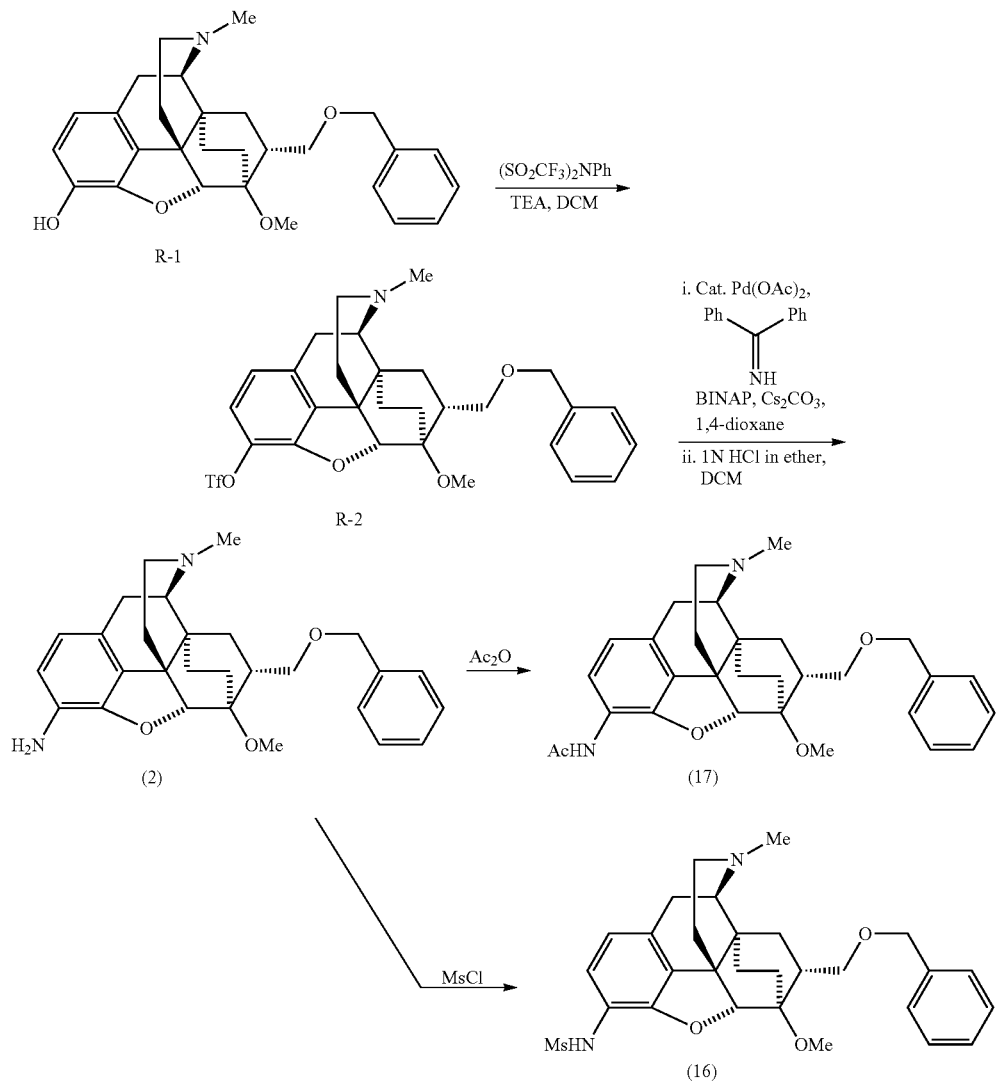

N-Phenyl-bis(trifluoromethanesulfonimide) (1.7 g, 4.6 mmol) was added to a 0° C. solution of solution of R-1 (1.4 g, 3.1 mmol) and TEA (0.6 mL, 4.6 mmol) in DCM (20 mL) under a nitrogen atmosphere. The reaction mixture was allowed to stir at RT for 10 hrs. The mixture was concentrated. The residue was purified by flash column chromatography (silica gel, 0-100% ETOAc/hexanes) to afford R-2 as a light brown foam. Yield: 1.80 g (100%)

$^1$H NMR $\delta_H$ (300 MHz, CDCl$_3$) 7.42-7.25 (m, 5H), 6.95 (d, J=8.3 Hz, 1H), 6.64 (d, J=8.4 Hz, 1H), 4.58 (s, 1H), 4.52 (dd, J=15.9, 12.1 Hz, 2H), 3.73 (dd, J=8.8, 4.1 Hz, 1H), 3.53 (dd, J=8.8, 8.5 Hz, 1H), 3.36 (s, 3H), 3.10 (d, J=19.0 Hz, 1H), 2.87 (m, 1H), 2.71 (d, J=6.3 Hz, 1H), 2.47 (dd, J=11.8, 5.2 Hz, 1H), 2.32-2.16 (m, 2H), 2.30 (s, 3H), 2.15-2.02 (m, 2H), 1.65 (m, 1H), 1.48 (m, 3H), 1.14 (m, 1H), 0.67 (m, 1H).

Nitrogen gas was bubbled through a mixture of R-2 (1.04 g, 2.83 mmol), palladium acetate (0.04 g, 0.17 mmol), and BINAP (0.12 g, 0.20 mmol) in 1,4-dioxane (10 mL) for 5 min. Cesium carbonate (1.79 g, 5.52 mmol) and benzophenone imine (0.69 mL, 4.13 mmol) were added and the mixture was heated to reflux for 10 hr. The mixture was filtered and the filtrate was concentrated. The crude material obtained was treated with 2N aqueous hydrochloric acid solution (30 mL) and THF (20 mL) at RT and stirred for 10 hr. The reaction mixture was extracted with ether to remove non-basic impurities. The remaining aqueous layer was basified with saturated aqueous NaHCO$_3$ solution and extracted with chloroform. The organic layer was dried (Na$_2$SO$_4$), filtered, and concentrated. The crude material was purified by flash column chromatography (silica gel, 0-10% MeOH/DCM) to give Compound 2 as the free base (0.61 g, ~90% pure) as pale yellow gum. A portion of the free base (110 mg) was then converted to its HCl salt by treating a DCM solution of the free base with 1M HCl in ether. Further purification by reverse phase column chromatography (MeOH/water with 0.1% TFA, 0-100%) gave Compound 2 TFA salt as a pale yellow solid. Yield: 30 mg.

$^1$H NMR $\delta_H$ (300 MHz, DMSO-d$_6$) 8.77 (bs, 1H), 7.48-7.23 (m, 6H), 7.75 (d, J=8.0 Hz, 1H), 6.61 (d, J=8.0 Hz, 1H), 4.75 (s, 1H), 4.51 (dd, J=15.7, 12.1 Hz, 2H), 3.68 (d, J=6.6 Hz, 1H), 3.61 (dd, J=9.1, 3.8 Hz, 1H), 3.48 (m, dd, J=9.1, 9.1 Hz, 1H), 3.34 (m, 1H), 3.25 (s, 3H), 3.16 (m, 1H), 2.85 (s, 3H), 2.85-2.61 (m, 3H), 2.38 (m, 1H), 2.24 (m, 1H), 1.82 (m, 1H), 1.55 (dd, J=13.2, 5.0 Hz, 1H), 1.39 (m, 1H), 1.29-1.12 (m, 2H), 0.61 (m, 1H).

LC/MS, m/z=447 [M+H]$^+$ (Calc: 447.6).

To a solution of Compound 2 (78 mg, 0.175 mmol, 1 eq.) in DCM (5 mL) was added pyridine (29 μL, 0.35 mmol, 2 eq.) followed by acetic anhydride (18 μL, 0.19 mmol, 1.1 eq.) The mixture was stirred at 0° C. for 1 hr and then RT for 10 hr. The reaction was quenched with saturated sodium carbonate and extracted with DCM. Purification by flash column chromatography (silica gel, 0-5% MeOH/DCM) afforded 58 mg (68%) of Compound 17 as the free base, which was converted to its HCl salt by treating a DCM solution of the free base with 1M HCl in ether to give a white solid. Yield: 51 mg.

$^1$H NMR $\delta_H$ (300 MHz, DMSO-d$_6$) 9.53 (s, 1H), 9.03 (br. s, 1H), 7.45 (d, J=8.0 Hz, 1H), 7.24-7.38 (m, 5H), 6.68 (d, J=8.0 Hz, 1H), 4.76 (s, 1H), 4.51 (dd, J=14.9, 12.1 Hz, 2H), 3.70 (br. d, J=6.6 Hz, 1H), 3.57-3.65 (m, 1H), 3.42-3.54 (m, 2H), 3.24 (s, 3H), 3.09-3.18 (m, 1H), 2.73-2.92 (m, 6H), 2.21-2.41 (m, 2H), 2.02 (s, 3H), 1.76-1.89 (m, 1H), 1.51-1.62 (m, 1H), 1.33-1.44 (m, 1H), 1.10-1.28 (m, 2H), 0.55-0.70 (m, 1H).

LC/MS, m/z=489 [M+H]$^+$ (Calc: 489.6).

To a solution of Compound 2 (74 mg, 0.166 mmol, 1 eq.) and triethylamine (50 μL) in DCM (5 mL) was added methanesulfonyl chloride (28 μL, 0.36 mmol, 2.2 eq.) dropwise at 0° C. The mixture was stirred at 0° C. for 2 hr. The reaction was quenched with water and extracted with DCM. Purification by flash column chromatography (silica gel, 0-5% MeOH/DCM) afforded 16.7 mg (19%) of Compound 16 as the free base, which was then converted to its HCl salt by treating a DCM solution of the free base with 1M HCl in ether. Yield: 12 mg.

$^1$H NMR $\delta_H$ (300 MHz, DMSO-d$_6$) 9.33 (s, 1H), 8.96 (br. s, 1H), 7.26-7.38 (m, 5H), 7.02 (d, J=8.0 Hz, 1H), 6.73 (d, J=8.0 Hz, 1H), 4.80 (s, 1H), 4.51 (dd, J=15.4, 12.1 Hz, 2H), 3.71 (br. d, J=6.6 Hz, 1H), 3.58-3.65 (m, 1H), 3.45-3.54 (m, 2H), 3.39 (br. s., 1H), 3.25 (s, 3H), 3.07-3.19 (m, 1H), 3.03 (s, 3H), 2.72-2.86 (m, 6H), 2.19-2.41 (m, 2H), 1.76-1.88 (m, 1H), 1.49-1.66 (m, 1H), 1.33-1.45 (m, 1H), 1.08-1.29 (m, 2H), 0.55-0.65 (m, 1H).

LC/MS, m/z=525 [M+H]$^+$ (Calc: 525.7).

In a similar manner, (4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-amine (Compound 10) was prepared by using R-3 (see example 4) rather than R-1. Purification by reverse phase column chromatography (MeOH/water with 0.1% TFA, 0-100%) gave Compound 10 TFA salt as a white solid.

$^1$H NMR: $\delta_H$ (300 MHz, DMSO-d$_6$): 8.23 (br s, 1H), 7.40-7.30 (m, 5H), 6.78-6.5 (m, 2H), 4.74 (s, 1H), 4.57-4.47 (m, 2H), 3.90-3.83 (m, 1H), 3.65-3.61 (m, 1H), 3.53-3.48 (m, 1H), 3.45-3.25 (m, 6H), 3.00-2.70 (m, 4H), 2.49-2.22 (m, 3H), 1.88-1.83 (m, 1H), 1.58-1.50 (m, 1H), 1.42-1.30 (m, 2H), 1.30-1.20 (m, 1H), 12.10-1.05 (m, 1H), 0.68-0.58 (m, 3H), 0.43-0.35 (m, 2H).

LC/MS, m/z=487 [M+H]$^+$ (Calc: 487.6).

Example 2

(4R,4aS,6R,7R,7aR,12bS)-6-(9-benzyloxy)methyl)-9-fluoro-7-methoxy-3-methyl-1,2,3,4,5,6,7,7a-octahydro-4a,7-ethano-4,12-methanobenzofuro[3,2-e]isoquinoline (Compound 4); and (4R,4aS,6R,7R,7aR,12bS)-6-((benzyloxy)methyl)-3-(cyclopropylmethyl)-9-fluoro-7-methoxy-1,2,3,4,5,6,7,7a-octahydro-4a,7-ethano-4,12-methanobenzofuro[3,2-e]isoquinoline (Compound 15)

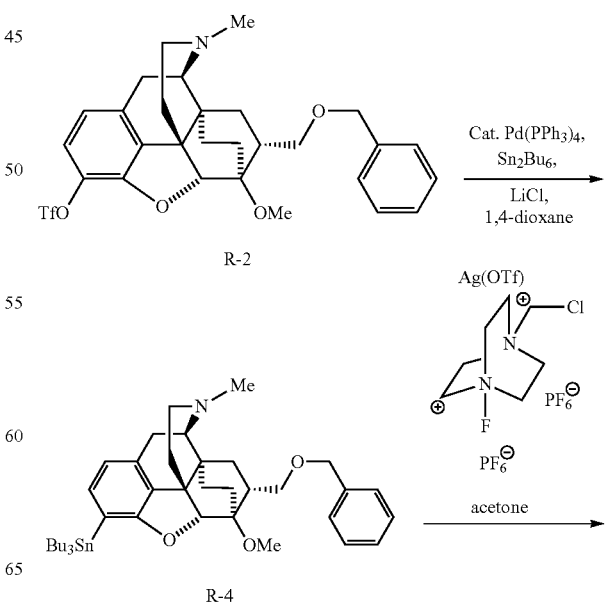

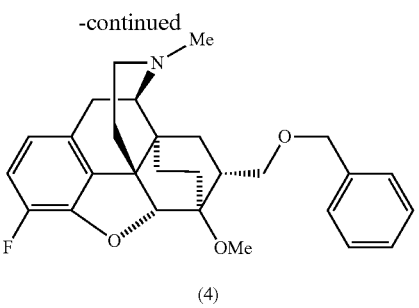

(4)

Nitrogen gas was bubbled through a mixture of R-2 (0.46 g, 0.8 mmol), hexabutylditin (0.51 mL, 1.6 mmol), and lithium chloride (0.26 g, 4.0 mmol) in 1,4-dioxane (10 mL) for 5 min. Tetrakis(triphenylphosphine) palladium (0.09 g, 0.08 mmol) was added and the mixture was heated to reflux for 1 hr. The reaction mixture was cooled, filtered and the filtrate concentrated. The crude material obtained was purified by flash column chromatography (silica gel, 0-100% EtOAc/hexanes) to give R-4. Yield: 0.47 g (81%).

$^1$H NMR $\delta_H$ (300 MHz, CDCl$_3$) 7.38-7.29 (m, 4H), 7.21 (m, 1H), 7.09 (d, J=7.4 Hz, 1H), 6.59 (d, J=7.4 Hz, 1H), 4.52 (dd, J=15.4, 11.8 Hz, 2H), 4.34 (s, 1H), 3.73 (dd, J=9.2, 4.5 Hz, 1H), 3.50 (dd, J=9.1, 9.1 Hz, 1H), 3.34 (s, 3H), 3.12 (d, J=18.2 Hz, 1H), 2.88 (m, 1H), 2.66 (d, J=6.6 Hz, 1H), 2.45 (m, 1H), 2.36-2.24 (m, 2H), 2.30 (s, 3H), 2.24-1.96 (m, 3H), 1.63 (m, 7H), 1.43 (m, 3H), 1.32 (m, 12H), 1.07 (m, 1H), 0.90 (m, 9H).

Silver triflate (0.34 g, 1.3 mmol) was added to a mixture R-4 (0.47 g, 0.7 mmol), Selectflour®-PF$_6^{\#}$ (0.37 g, 0.78 mmol), in acetone (10 mL, CHROMASOLV®, Aldrich Chemical Co.) under a nitrogen atmosphere (REF: Ritter, T.; et al, *J. Am. Chem. Soc.* 2009, 131, 1662-1663). The reaction mixture was allowed to stir at RT for 1 hr and concentrated. The residue was taken up in DCM, filtered through a Celite® pad and concentrated. The crude material obtained was purified by flash column chromatography (silica gel, 0-10% MeOH/DCM) to afford free base of Compound 4 as a colorless gum. The free base was then converted to its HCl salt by treating a DCM solution of the free base with 1M HCl in ether to give Compound 4 HCl salt as a white solid. Yield: 0.03 g (10%).

$^1$H NMR $\delta_H$ (300 MHz, DMSO-d$_6$) 8.86 (bs, 1H), 7.38-7.23 (m, 5H), 7.09 (m, 1H), 6.74 (m, 1H), 4.87 (s, 1H), 4.52 (dd, J=14.9, 11.6 Hz, 2H), 3.72 (m, 1H), 3.60 (m, 1H), 3.54-3.35 (m, 3H), 3.23 (s, 3H), 3.14 (m, 1H), 2.96-2.65 (m, 5H), 2.26 (m, 1H), 1.90 (m, 1H), 1.58 (m, 1H), 1.44 (m, 1H), 1.30-1.06 (m, 2H), 0.57 (m, 1H).

LC/MS, m/z=450 [M+H]$^+$ (Calc: 450.6).

In a similar manner, Compound 15 was prepared from R-3 via the analogous triflate and stannane intermediates. Compound 15 was obtained as the HCl salt by treating a DCM solution of the free base with 1M HCl in ether.

$^1$H NMR $\delta_H$ (300 MHz, DMSO-d$_6$) 8.50 (br s, 1H), 7.37-7.28 (m, 5H), 7.15-7.07 (m, 1H), 6.76-6.72 (m, 1H), 4.90 (s, 1H), 4.55-4.47 (m, 2H), 3.94-3.90 (m, 1H), 3.62-3.58 (m, 1H), 3.54-3.45 (m, 1H), 3.42-3.36 (m, 1H), 3.25-3.18 (m, 4H), 3.00-2.68 (m, 5H), 2.35-2.22 (m, 1H), 1.62-1.00 (m, 6H), 0.75-0.54 (m, 3H), 0.54-0.35 (m, 2H).

LC/MS, m/z=490 [M+H]$^+$ (Calc: 490.6).

Example 3

(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinoline-9-carbonitrile (Compound 20); (4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinoline-9-carboxamide (Compound 21); (4R,4a,6R,7R,7aR,2bS)-6-((benzyloxy)methyl)-7-methoxy-3-methyl-1,2,3,4,5,6,7,7a-octahydro-4a,7-ethano-4,12-methanobenzofuro[3,2-e]isoquinoline-9-carboxylic acid (Compound 23); (4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carbonitrile (Compound 69); (4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carboxylic acid (Compound 71); and (4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carboxamide (Compound 76)

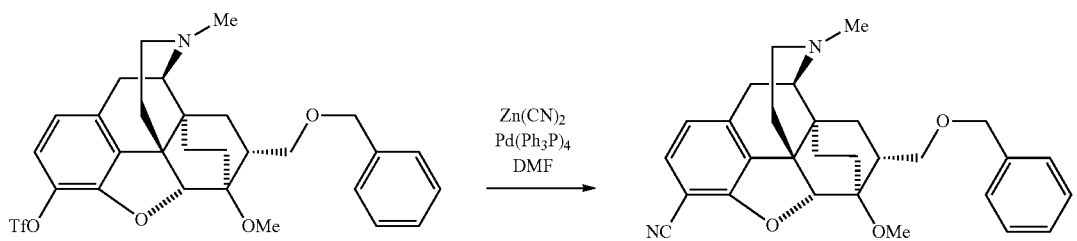

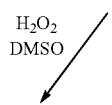

227

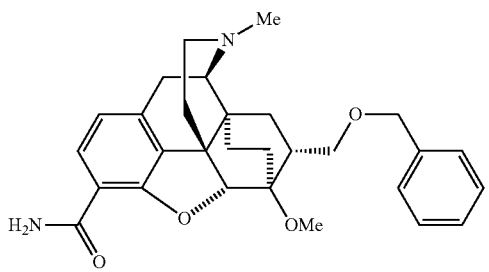

(21)

228

-continued

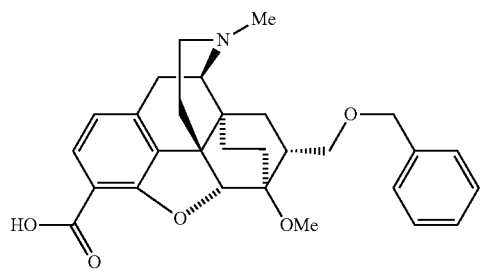

(23)

A degassed solution of R-2 (250 mg, 0.43 mmol, 1 eq.), Zn(CN)$_2$ (152 mg, 1.29 mmol, 3 eq.) and tetrakis(triphenylphosphine)palladium(0) (50 mg, 0.1 eq.) in DMF (3 mL) was heated at 120° C. for 20 hr under argon. The reaction was cooled to RT, quenched with water and extracted with DCM. The organic layer was dried (Na$_2$SO$_4$), filtered, and concentrated. Purification by flash column chromatography flash column chromatography (silica gel, 0-5% MeOH/DCM) afforded Compound 20 as the free base. Yield: 55 mg (28%). Compound 20 was then converted to its HCl salt by treating a DCM solution of the free base with 1M HCl in ether. Yield: 50 mg.

$^1$H NMR δ$_H$ (300 MHz, DMSO-d$_6$) 9.18 (br. s, 1H), 7.55 (d, J=7.95 Hz, 1H), 7.27-7.36 (m, 5H), 6.91 (d, J=8.2 Hz, 1H), 5.00 (s, 1H), 4.51 (dd, J=15.1, 12.3 Hz, 2H), 3.76 (br. d, J=6.1 Hz, 1H), 3.48-3.59 (m, 3H), 3.25 (s, 3H), 3.14-3.18 (m, 1H), 2.72-3.01 (m, 6H), 2.19-2.42 (m, 2H), 1.89-1.96 (m, 1H), 1.40-1.64 (m, 2H), 1.15-1.32 (m, 1H), 1.01-1.14 (m, 1H), 0.46-0.60 (m, 1H)

LC/MS, m/z=457 [M+H]$^+$ (Calc: 457.6).

To a mixture of Compound 20 (52 mg, 1 eq.) and potassium carbonate (40 mg) in DMSO (3 mL) was added hydrogen peroxide (0.15 mL) dropwise. The mixture was heated at 60° C. for 2 hr. The reaction was cooled to RT, quenched with brine and extracted with DCM. The crude product was purified by flash column chromatography (silica gel, 0-5% MeOH/DCM) to afford 27 mg (52%) of Compound 21 as the free base. Compound 21 was then converted to its HCl salt by treating a DCM solution of the free base with 1M HCl in ether. Yield: 21 mg.

$^1$H NMR δ$_H$ (300 MHz, DMSO-d$_6$) 9.07 (br. s, 1H), 7.61-7.74 (m, 2H), 7.22-7.41 (m, 5H), 6.98 (br. s, 1H), 6.87 (d, J=8.0 Hz, 1H), 4.95 (s, 1H), 4.52 (dd, J=15.4, 12.1 Hz, 2H), 3.75 (br. d, J=6.3 Hz, 1H), 3.58-3.66 (m, 3H), 3.45-3.56 (m, 2H), 3.28 (s, 3H), 3.12-3.19 (m, 1H), 2.79-3.01 (m, 6H), 2.22-2.44 (m, 2H), 1.84-1.93 (m, 1H), 1.54-1.65 (m, 1H), 1.38-1.50 (m, 1H), 1.18-1.33 (m, 1H), 1.01-1.15 (m, 1H), 0.49-0.66 (m, 1H).

LC/MS, m/z=475 [M+H]$^+$ (Calc: 475.6).

To a solution of Compound 20 (28 mg, 1 eq.) in acetonitrile (5 mL) was added sodium hydroxide (1 mL, 2 M in water, 2 eq.). The mixture was charged to a sealed tube and was heated at 110° C. for 40 hr. The reaction was cooled to RT, quenched with saturated aqueous ammonium chloride and extracted with DCM. The organic extract was washed with brine, dried over MgSO$_4$. Filtration and concentration, afforded 20 mg (69%) of Compound 23 as the free base. Compound 23 was then converted to its HCl salt by treating a DCM solution of the free base with 1M HCl in ether. Yield: 14 mg.

$^1$H NMR δ$_H$ (300 MHz, DMSO-d$_6$) 9.14 (br. s, 1H), 7.64 (d, J=8.3 Hz, 1H), 7.24-7.42 (m, 6H), 6.81 (d, J=8.0 Hz, 1H), 4.81 (s, 1H), 4.51 (dd, J=14.9, 12.1 Hz, 2H), 3.73 (br. d, J=6.0 Hz, 1H), 3.59-3.65 (m, 1H), 3.44-3.55 (m, 2H), 3.26 (s, 3H), 3.06-3.19 (m, 1H), 2.71-2.98 (m, 6H), 2.17-2.38 (m, 2H), 1.79-1.90 (m, 1H), 1.53-1.64 (m, 1H), 1.33-1.46 (m, 1H), 1.09-1.30 (m, 2H), 0.53-0.67 (m, 1H).

LC/MS, m/z=476 [M+H]$^+$ (Calc: 476.6).

In a similar manner (4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carbonitrile (Compound 69) was prepared from R-5 rather than R-2. Purification by flash column chromatography (silica gel, 0-5% MeOH/DCM) gave Compound 69 as a white solid.

1H NMR δ$_H$ (300 MHz, CDCl$_3$) 7.37-7.24 (m, 5H), 7.24 (d, J=7.95 Hz, 1H), 6.66 (d, J=7.95 Hz, 1H), 4.59 (d, J=1.92 Hz, 1H), 4.54 (m, 2H), 3.74 (dd, J$_1$=8.79 Hz, J$_2$=3.84 Hz, 1H), 3.53 (t, J=8.79 Hz, 1H), 3.37 (s, 3H), 2.90-3.08 (m, 3H), 2.67-2.75 (m, 1H), 2.20-2.35 (m, 3H), 2.02-2.19 (m, 3H), 1.31-1.64 (m, 4H), 1.08-1.16 (m, 1H), 0.73-0.87 (m, 1H), 0.55-0.68 (m, 1H), 0.42-0.52 (m, 2H), 0.05-0.12 (m, 2H).

LC/MS, m/z=497 [M+H]$^+$ (Calc: 496).

In a similar manner (4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carboxylic acid (Compound 71) was prepared from Compound 69 rather than Compound 20. Purification by flash column chromatography (silica gel, 0-8% MeOH/DCM) gave Compound 71 as a white solid.

$^1$H NMR δ$_H$ (300 MHz, CDCl$_3$) 7.73 (d, J=7.98 Hz, 1H), 7.25-7.35 (m, 5H), 6.74 (d, J=7.98 Hz, 1H), 4.70 (s, 1H), 4.55 (S, 2H), 3.73 (dd, J$_1$=9.08 Hz, J$_2$=3.85 Hz, 1H), 3.55 (t, J=8.53 Hz, 1H), 3.36 (s, 3H), 2.93-3.09 (m, 3H), 2.67-2.75 (m, 1H), 2.08-2.36 (m, 6H), 1.60-1.68 (m, 1H), 1.41-1.51 (m, 2H), 1.26-1.39 (m, 1H), 1.07-1.18 (m, 1H), 0.76-0.86 (m, 1H), 0.58-0.70 (m, 1H), 0.46-0.50 (m, 2H), 0.06-0.12 (m, 2H).

LC/MS, m/z=516 [M+H]$^+$ (Calc: 515).

In a similar manner (4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carboxamide (Compound 76) was prepared from Compound 69 rather than Compound 20. Purification by flash column chromatography (silica gel, 0-10% MeOH/DCM) followed by HCl salt formation gave Compound 76 HCl salt as a white solid.

$^1$H NMR δ$_H$ (300 MHz, DMSO-d$_6$) 8.69 (br. s, 1H), 7.68 (d, J=7.95 Hz, 1H), 7.65 (bs, 1H), 7.25-7.39 (m, 5H), 6.99 (bs, 1H), 6.85 (d, J=7.95 Hz, 1H), 4.97 (s, 1H), 4.52 (s, 2H), 3.94 (d, J=6.33 Hz, 1H), 3.3-3.8 (m, 4H), 3.28 (s, 3H), 2.76-3.10

(m, 4H), 2.25-2.36 (m, 2H), 1.88-1.98 (m, 1H), 1.56-1.62 (m, 1H), 1.20-1.52 (m, 3H), 1.02-1.14 (m, 2H), 0.34-0.74 (m, 5H).

LC/MS, m/z=515 [M+H]$^+$ (Calc: 514).

Example 4

(4R,4aS,6R,7R,7aR,12bS)-6-((benzyloxy)methyl)-9-bromo-3-(cyclopropylmethyl)-7-methoxy-1,2,3,4,5,6,7,7a-octahydro-4a,7-ethano-4,12-methanobenzofuro[3,2-e]isoquinoline (Compound 19)

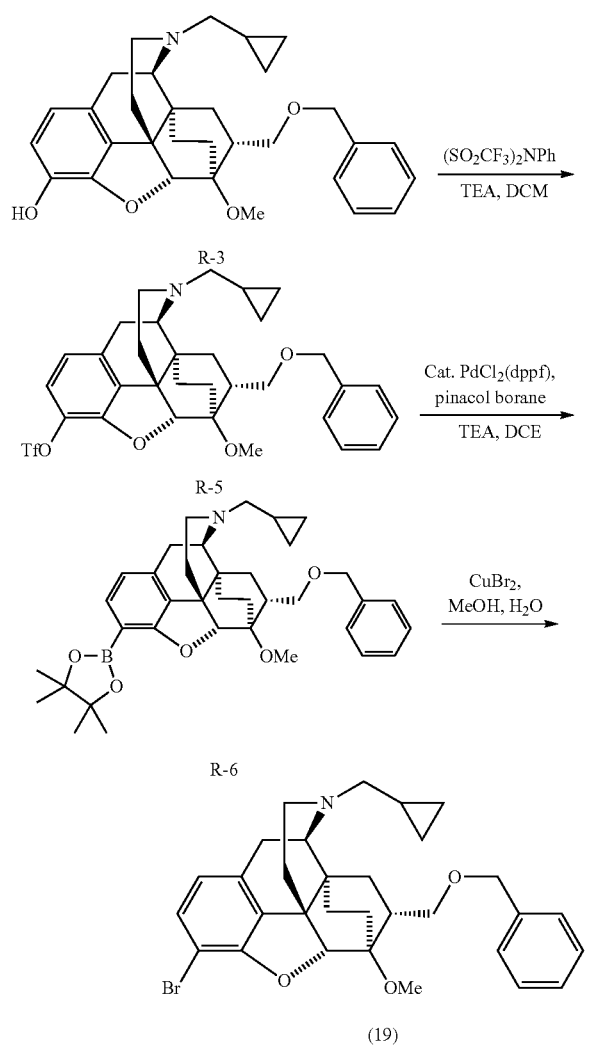

N-Phenyl-bis(trifluoromethanesulfonimide) (1.94 g, 5.1 mmol) was added to 0° C. solution of R-3 (1.8 g, 3.7 mmol) and TEA (0.747 mL, 5.1 mmol) in DCM (20 mL) under a nitrogen atmosphere. The reaction mixture was allowed to stir at RT for 10 hr. The mixture was concentrated and the residue was purified by flash column chromatography (silica gel, 0-100% EtOAc/hexanes) to give R-5. Yield: 2.2 g (100%).

$^1$H NMR $\delta_H$ (300 MHz, CDCl$_3$) 7.26-7.50 (m, 5H), 6.94 (d, J=8.3 Hz, 1H), 6.62 (d, J=8.3 Hz, 1H), 4.48-4.60 (m, 3H), 3.66-3.81 (m, 1H), 3.47-3.59 (m, 1H), 3.37 (s, 3H), 2.88-3.13 (m, 3H), 2.52-2.77 (m, 1H), 2.16-2.38 (m, 7H), 2.06-2.15 (m, 3H), 1.61-1.71 (m, 2H), 1.40-1.55 (m, 7H), 1.03-1.20 (m, 2H), 0.72-0.86 (m, 2H), 0.59-0.72 (m, 2H), 0.43-0.54 (m, 5H), 0.06-0.17 (m, 2H).

Nitrogen gas was bubbled through a mixture of R-5 (0.17 g, 0.28 mmol), pinacolborane (0.06 mL, 0.39 mmol) and TEA (0.06 mL, 0.42 mmol) in DCE (4 mL) for 5 min. Palladium chloride (dppf) (Aldrich Chemical Co.) (0.02 g, 0.03 mmol) was added and the mixture was heated to 80° C. for 8 hr. The mixture was cooled to RT, quenched with water and extracted with chloroform. The organic layer was dried (Na$_2$SO$_4$), filtered, and concentrated. The crude material was purified by flash column chromatography (silica gel, 0-50% EtOAc/hexanes) to give R-6. Yield: 0.14 g (81%).

$^1$H NMR $\delta_H$ (300 MHz, CDCl$_3$) 7.45 (d, J=7.7 Hz, 1H), 7.38-7.21 (m, 5H), 6.60 (d, J=7.7 Hz, 1H), 4.53 (dd, J=17.8, 12.1 Hz, 2H), 4.48 (s, 1H), 3.76 (dd, J=8.8, 3.8 Hz, 1H), 3.53 (dd, J=8.8, 8.8 Hz, 1H), 3.41 (s, 3H), 3.03-2.90 (m, 3H), 2.63 (m, 1H), 2.36-2.15 (m, 4H), 2.08 (m, 1H), 1.68-1.20 (m, 5H), 1.34 (s, 6H), 1.28 (s, 6H), 1.06 (m, 1H), 0.79 (m, 1H), 0.64 (m, 1H), 0.52-0.44 (m, 2H), 1.04-0.06 (m, 2H).

Anhydrous copper (II) bromide (0.13 g, 0.55 mmol) was added to a solution of R-6 (0.11 g, 0.18 mmol) in MeOH:water (1:1, 4 mL). The reaction mixture was heated at 80° C. for 10 hr. The reaction mixture was cooled to RT, treated with saturated aqueous solution of sodium sulfite (1 mL) and extracted with EtOAc. The organic extract was dried (Na$_2$SO$_4$), filtered, and concentrated. The residue was treated with DCM and filtered. The filtrate was concentrated. The crude material was purified by flash column chromatography (silica gel, 0-100% EtOAc/hexanes) to afford Compound 19 as the free base. Yield: 80 mg (80%). A portion of the free base (14 mg) was then converted to its HCl salt by treating a DCM solution of the product with 1M HCl in ether to give Compound 19 HCl salt as a white solid.

$^1$H NMR $\delta_H$ (300 MHz, DMSO-d$_6$) 8.56 (bs, 1H), 7.43-7.25 (m, 6H), 6.70 (d, J=7.7 Hz, 1H), 4.87 (s, 1H), 4.52 (m, 2H), 3.93 (m, 1H), 3.61 (m, 1H), 3.52 (m, 1H), 3.41 (m, 1H), 3.25 (s, 3H), 3.21 (m, 1H), 3.10-2.68 (m, 4H), 2.27 (m, 1H), 1.96 (m, 1H), 1.57 (m, 1H), 1.45 (m, 1H), 1.38-1.22 (m, 2H), 1.16-1.04 (m, 2H), 0.88 (m, 1H), 0.74-0.54 (m, 2H), 0.52-0.32 (m, 2H).

LC/MS, m/z=550, 552 [M+H]$^+$ (Calc: 550, 552).

Example 5

(4R,4aS,6R,7R,7aR,12bS)-6-((benzyloxy)methyl)-7-methoxy-3-methyl-9-vinyl-1,2,3,4,5,6,7,7a-octahydro-4a,7-ethano-4,12-methanobenzofuro[3,2-e]isoquinoline (Compound 3)

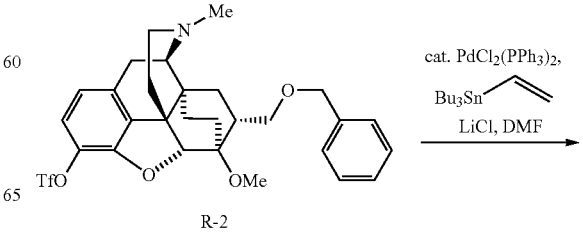

-continued

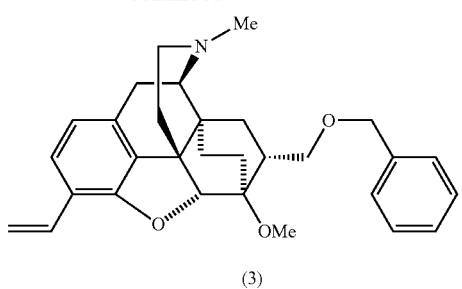

(3)

-continued

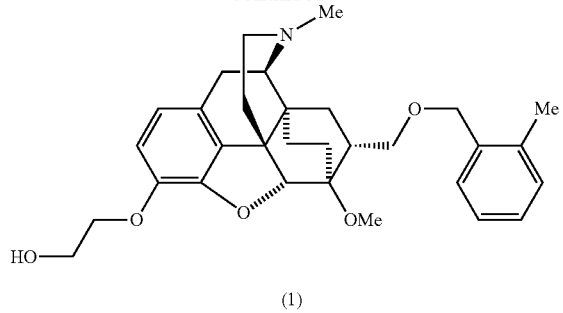

(1)

Nitrogen gas was bubbled through a mixture of R-2 (0.17 g, 0.3 mmol), tributylvinyltin (0.18 μL, 0.6 mmol), and lithium chloride (0.04 g, 0.3 mmol) in DMF (5 mL) for 5 min. Bis-triphenylphosphine palladium (II) chloride (0.04 g, 0.03 mmol) was added and the mixture was allowed to stir at RT for 10 hr. The mixture was further heated at 80° C. for an additional 24 hr. The mixture was cooled to RT, filtered and concentrated. The crude material obtained was purified by flash column chromatography (silica gel, 0-10% MeOH/DCM) to give Compound 3 as the free base as pale yellow gum. Compound 3 was then converted to its HCl salt by treating a DCM solution of the free base with 1M HCl in ether. Purification by reverse phase column chromatography (MeOH/water with 0.1% TFA, 0-100%) gave Compound 3 TFA salt as a white solid. Yield: 90 mg.

$^1$H NMR $\delta_H$ (300 MHz, DMSO-$d_6$) 8.61 (bs, 1H), 7.41-7.23 (m, 5H), 7.24 (d, J=8.0 Hz, 1H), 6.74 (d, J=8.0 Hz, 1H), 6.65 (dd, J=18.1, 11.8 Hz, 1H), 5.91 (m, 1H), 5.31 (m, 1H), 4.79 (s, 1H), 4.52 (dd, J=17.0, 12.1 Hz, 2H), 3.71 (m, 1H), 3.63 (m, 1H), 3.54-3.35 (m, 3H), 3.28 (s, 3H), 3.16 (m, 1H), 2.91-2.80 (m, 5H), 2.42-2.14 (m, 2H), 1.88 (m, 1H), 1.57 (m, 1H), 1.39 (m, 1H), 1.30-1.06 (m, 3H), 0.60 (m, 1H).

LC/MS, m/z=458 [M+H]$^+$ (Calc: 458.6).

Example 6

2-(((4R,4aS,6R,7R,7aR,12bS)-7-methoxy-3-methyl-6-(((2-methylbenzyl)oxy)methyl)-1,2,3,4,5,6,7,7a-octahydro-4a,7-ethano-4,12-methanobenzofuro[3,2-e]isoquinolin-9-yl)oxy)ethanol (Compound 1); and 2-(((4R,4aS,6R,7R,7aR,12bS)-6-((benzo[b]thiophen-2-ylmethoxy)methyl)-3-(cyclopropylmethyl)-7-methoxy-1,2,3,4,5,6,7,7a-octahydro-4a,7-ethanol (Compound 25)

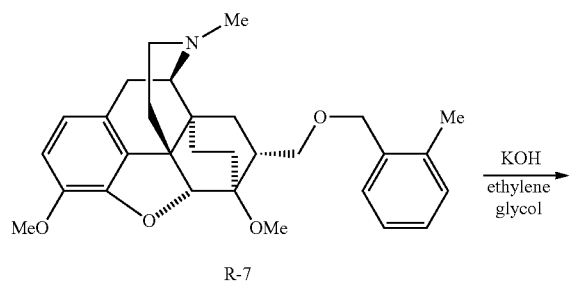

R-7

Potassium hydroxide (500 mg, 8.9 mmol) was dissolved in ethylene glycol (5 mL) at 70° C. R-7 (523.2 mg, 1.1 mmol) was added and the resulting suspension was irradiated with microwaves at 210° C. for 5 hr. The cooled reaction mixture was quenched by addition of saturated ammonium chloride solution and extracted with chloroform. The organic extract was dried (Na$_2$SO$_4$), filtered, and concentrated. The crude material was purified by flash column chromatography (silica gel, 0-10% MeOH/DCM) to afford Compound 1 as the free base. Compound 1 was then converted to its HCl salt by treating a DCM solution of the free base with 1M HCl in ether. Yield: 5.1 mg (1%).

$^1$H NMR $\delta_H$ (300 MHz, DMSO-$d_6$) 8.70 (br s, 1H), 7.36-7.30 (d, 1H), 7.24-7.14 (m, 3H), 6.92-6.85 (d, 2H), 6.70-6.63 (d, 1H), 4.90-4.80 (m, 1H), 4.75-4.70 (m, 1H), 4.55-4.40 (m, 2H), 4.05-4.00 (m, 2H), 3.70-3.60 (m, 4H), 3.55-3.50 (m, 1H), 3.25 (s, 3H), 3.20-3.10 (m, 1H), 2.90-2.80 (m, 4H), 2.80-2.60 (m, 2H), 2.40-2.30 (m, 4H), 1.90-1.80 (m, 1H), 1.60-1.50 (m, 1H), 1.48-1.35 (m, 1H), 1.30-1.10 (m, 3H), 0.70-0.60 (m, 1H).

LC/MS, m/z=506 [M+H]$^+$ (Calc: 506.6).

In a similar manner, 2-(((4R,4aS,6R,7R,7aR,12bS)-6-((benzo[b]thiophen-2-ylmethoxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)ethanol (Compound 25) was prepared by using R-8 rather than R-7. Compound 25 was obtained as the HCl salt by treating a DCM solution of the free base with 1M HCl in ether.

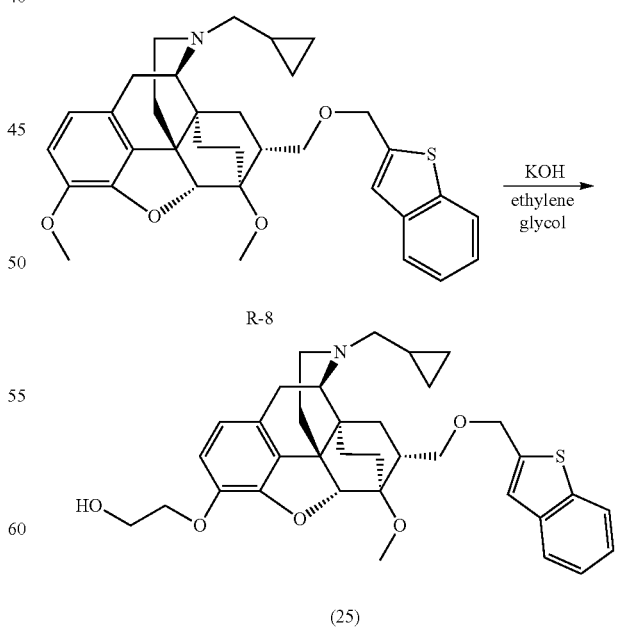

(25)

Yield: 6.2 mg (1%).

$^1$H NMR: $\delta_H$ (300 MHz, DMSO-$d_6$): 8.62 (br s, 1H), 7.95-7.92 (d, 1H), 7.83-7.80 (d, 1H), 7.40-7.34 (m, 3H), 6.90-6.85

(d, 1H), 6.67-6.64 (d, 1H), 4.90-4.70 (m, 3H), 4.05-4.00 (m, 2H), 3.90-3.85 (m, 1H), 3.68-3.65 (m, 2H), 3.60-3.50 (m, 1H), 3.30-3.15 (m, 3H), 3.00-2.70 (m, 4H), 2.45-2.25 (m, 2H), 1.92-1.82 (m, 1H), 1.60-1.34 (m, 3H), 1.34-1.18 (m, 3H), 1.15-1.05 (m, 2H), 0.90-0.82 (m, 2H), 0.75-0.55 (m, 3H), 0.55-0.33 (m, 2H).

LC/MS, m/z=588 [M+H]$^+$ (Calc: 588.6).

Example 7

(4R,4aS,6R,7R,7aR,12bS)-6-(((3,5-dimethylisoxazol-4-yl)methoxy)methyl)-7,9-dimethoxy-3-methyl-1,2,3,4,5,6,7,7a-octahydro-4a,7-ethano-4,12-methanobenzofuro[3,2-e]isoquinoline (Compound 24); (4R,4aS,6R,7R,7aR,2bS)-3-(cyclopropylmethyl)-6-(((3,5-dimethylisoxazol-4-yl)methoxy)methyl)-7,9-dimethoxy-1,2,3,4,5,6,7,7a-octahydro-4a,7-ethano-4,12-methanobenzofuro[3,2-e]isoquinoline (Compound 26); (4R,4aS,6R,7R,7aR,12bS)-7,9-dimethoxy-3-methyl-6-(((3-propylisoxazol-5-yl)methoxy)methyl)-1,2,3,4,5,6,7,7a-octahydro-4a,7-ethano-4,12-methanobenzofuro[3,2-e]isoquinoline (Compound 55); (4R,4aS,6R,7R,7aR,12bS)-3-(cyclopropylmethyl)-6-(2,5,8,11-tetraoxadodecyl)-7,9-dimethoxy-1,2,3,4,5,6,7,7a-octahydro-4a,7-ethano-4,12-methanobenzofuro[3,2-e]isoquinoline (Compound 33); (4R,4aS,6R,7R,7aR,12bS)-3-(cyclopropylmethyl)-7,9-dimethoxy-6-(2,5,8,11,14,17-hexaoxaoctadecyl)-1,2,3,4,5,6,7,7a-octahydro-4a,7-ethano-4,12-methanobenzofuro[3,2-e]isoquinoline (Compound 34); 2-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)acetamide (Compound 45); and (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-phenylpropanoate (Compound 49)

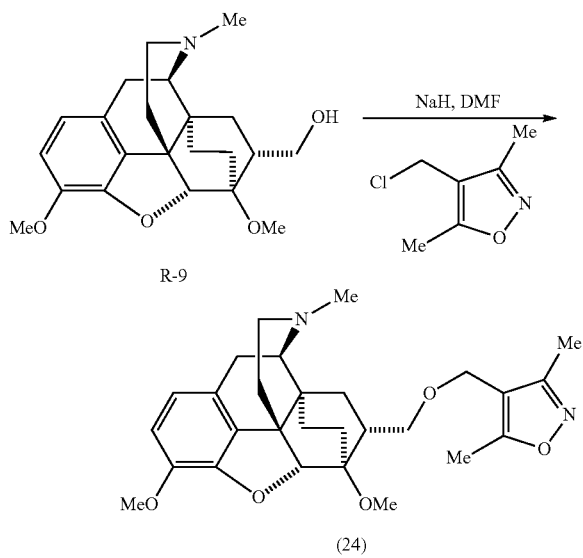

NaH (60% suspension in mineral oil, 100 mg, 2.5 mmol) was added to a solution of R-10 (186.0 mg, 0.5 mmol) in anhydrous DMF (10 mL). The resulting mixture was stirred at room temperature for 1 hr. 4-Chloromethyl-3,5-dimethylisoxazole (145.6 mg, 1 mmol) (Aldrich) was added and the reaction was stirred at rt for 12 hr. Water (40 mL) was added and the mixture was extracted with EtOAc (2×50 mL) and DCM (2×50 mL). The extracts were washed with 20 mL each water and brine. After drying over Na$_2$SO$_4$, solvent was evaporated. Purification by reverse phase column chromatography (MeOH/water with 0.1% TFA, 0-100%) gave Compound 24 TFA salt as a white solid. Yield: 124.9 mg (42%).

$^1$H NMR $\delta_H$ (300 MHz, DMSO-d$_6$) 8.65 (br s, 1H), 6.89-6.85 (d, 1H), 6.71-6.67 (d, 1H), 4.71 (br s, 1H), 4.40-4.25 (m, 2H), 3.78 (s, 3H), 3.70-3.65 (m, 1H), 3.57-3.50 (m, 1H), 3.45-3.35 (m, 1H), 3.24 (s, 3H), 3.20-3.11 (m, 1H), 2.90-2.70 (m, 5H), 2.65-2.52 (m, 1H), 2.40-2.10 (m, 9H), 1.90-1.75 (m, 1H), 1.50-1.28 (m, 2H), 1.22-1.05 (m, 2H), 0.65-0.55 (m, 1H).

LC/MS, m/z=481 [M+H]$^+$ (Calc: 481.6).

In a similar manner, (4R,4aS,6R,7R,7aR,12bS)-3-(cyclopropylmethyl)-6-(((3,5-dimethylisoxazol-4-yl)methoxy)methyl)-7,9-dimethoxy-1,2,3,4,5,6,7,7a-octahydro-4a,7-ethano-4,12-methanobenzofuro[3,2-e]isoquinoline (Compound 26) was prepared by using R-10 (see example 8) rather than R-9. Purification by reverse phase column chromatography (MeOH/water with 0.1% TFA, 0-100%) gave Compound 26 TFA salt as a white solid.

$^1$H NMR: $\delta_H$ (300 MHz, DMSO-d$_6$): 8.28 (br s, 1H), 6.89-6.85 (d, 1H), 6.70-6.65 (d, 1H), 4.80-4.73 (m, 1H), 4.37-4.25 (m, 2H), 3.90-3.84 (m, 1H), 3.80-3.72 (m, 3H), 3.60-3.50 (m, 1H), 3.48-3.15 (m, 7H), 2.95-2.55 (m, 4H), 2.40-2.15 (m, 7H), 2.14-2.05 (m, 1H), 1.93-1.80 (m, 1H), 1.50-1.00 (m, 5H), 0.72-0.50 (m, 3H), 0.50-0.35 (m, 2H).

LC/MS, m/z=520 [M+H]$^+$ (Calc: 520.6).

In a similar manner (4R,4aS,6R,7R,7aR,12bS)-7,9-dimethoxy-3-methyl-6-(((3-propylisoxazol-5-yl)methoxy)methyl)-1,2,3,4,5,6,7,7a-octahydro-4a,7-ethano-4,12-methanobenzofuro[3,2-e]isoquinoline (Compound 55) was prepared from R-9 using 5-chloromethyl-3-propylisoxazole rather than 4-chloromethyl-3,5-dimethylisoxazole. Purification by reverse phase column chromatography (MeOH/water with 0.1% TFA, 0-100%) gave Compound 55 TFA salt as a white solid.

$^1$H NMR $\delta_H$ (300 MHz, DMSO-d$_6$) 8.66 (br s, 1H), 6.90-6.85 (d, 1H), 6.72-6.66 (d, 1H), 6.40 (s, 1H), 4.72 (s, 1H), 4.65-4.54 (m, 2H), 3.78 (s, 3H), 3.75-3.58 (m, 2H), 3.55-3.30 (m, 4H), 3.24 (s, 3H), 3.21-3.13 (m, 1H), 2.92-2.70 (m, 5H), 2.65-2.50 (m, 2H), 2.40-2.10 (m, 1H), 1.90-1.80 (m, 1H), 1.70-1.55 (m, 2H), 1.52-1.28 (m, 1H), 1.25-1.05 (m, 2H), 0.93-0.87 (t, 3H), 0.65-0.58 (m, 1H).

LC/MS, m/z=494 [M+H]$^+$ (Calc: 494.6).

In a similar manner (4R,4aS,6R,7R,7aR,12bS)-3-(cyclopropylmethyl)-6-(2,5,8,11-tetraoxadodecyl)-7,9-dimethoxy-1,2,3,4,5,6,7,7a-octahydro-4a,7-ethano-4,12-methanobenzofuro[3,2-e]isoquinoline (Compound 33) was prepared from R-10 using triethylene glycol monomethyl ether mesylate (PEG$_3$OMs) (WO 2005/058367, Chem. Pharm. Bull. 1970, 18, 671.) rather than 4-chloromethyl-3,5-dimethylisoxazole. Purification by reverse phase column chromatography (MeOH/water with 0.1% TFA, 0-100%) gave Compound 33 TFA salt as a white solid.

¹H NMR δ_H (300 MHz, DMSO-d_6) 8.43 (br s, 1H), 6.88 (d, J=8.25 Hz, 1H), 6.68 (d, J=8.25 Hz, 1H), 4.75 (s, 1H), 3.88 (d, J=6.87 Hz, 1H), 3.88 (d, J=6.87 Hz, 1H), 3.75 (s, 3H), 3.48-3.60 (m, 11H), 3.34-3.42 (m, 4H), 3.26-3.2 (m, 1H), 3.26 (s, 3H), 3.23 (s, 3H), 2.64-3.02 (m, 4H), 2.18-2.36 (m, 2H), 1.84-1.93 (m, 1H), 1.51 (dd, J_1=13.74 Hz, J_2=4.95 Hz, 1H), 1.22-1.42 (m, 2H), 1.02-1.18 (m, 2H), 0.56-0.74 (m, 3H), 0.32-0.48 (m, 2H).

LC/MS, m/z=558 [M+H]⁺ (Calc: 558.6).

In a similar manner (4R,4aS,6R,7R,7aR,12bS)-3-(cyclopropylmethyl)-7,9-dimethoxy-6-(2,5,8,11,14,17-hexaoxaoctadecyl)-1,2,3,4,5,6,7,7a-octahydro-4a,7-ethano-4,12-methanobenzofuro[3,2-e]isoquinoline (Compound 34) was prepared from R-10 using pentaethylene glycol monomethyl ether mesylate (PEG_5OMs) (WO 2005/058367, *Chem. Pharm. Bull.* 1970, 18, 671) rather than 4-chloromethyl-3,5-dimethylisoxazole. Purification by reverse phase column chromatography (MeOH/water with 0.1% TFA, 0-100%) gave Compound 34 TFA salt as a white solid.

¹H NMR δ_H (300 MHz, DMSO-d_6) 8.40 (br s, 1H), 6.90-6.85 (d, 1H), 6.70-6.65 (d, 1H), 4.75 (s, 1H), 3.90-3.86 (m, 1H), 3.79 (s, 3H), 3.62-3.48 (m, 21H), 3.46-3.35 (m, 4H), 3.32-3.27 (m, 1H), 3.26 (s, 3H), 3.24 (s, 2H), 3.03-2.60 (m, 4H), 2.40-2.17 (m, 2H), 1.93-1.84 (m, 1H), 1.55-1.45 (m, 1H), 1.45-1.20 (m, 2H), 1.20-1.00 (m, 2H), 0.74-0.55 (m, 3H), 0.48-0.33 (m, 1H).

LC/MS, m/z=645 [M+H]⁺ (Calc: 645.6).

2-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)acetamide (Compound 45) was prepared from the above mentioned acid employing techniques familiar to one skilled in the art.

¹H NMR: δ_H (300 MHz, DMSO-d_6): 6.96 (d, J=8.25 Hz, 1H), 6.81 (d, J=8.25 Hz, 1H), 4.89 (s, 1H), 4.06 (m, 3H), 3.84 (s, 3H), 3.76 (dd, J=8.79 Hz, J_2=4.41 Hz, 1H), 3.61 (t, J=8.79 Hz, 1H), 3.35 (s, 3H), 3.29-3.35 (m, 3H), 2.96-3.14 (m, 3H), 2.56-2.67 (m, 1H), 2.42-2.54 (m, 1H), 2.24-2.36 (m, 1H), 2.02 (dd, J_1=15.12 Hz, J_2=2.76 HZ, 1H), 1.66 (dd, J_1=12.63 Hz, J_2=5.22 Hz, 1H), 1.18-1.54 (m, 3H), 0.96-1.08 (m, 1H), 0.62-0.84 (m, 3H), 0.3-0.44 (m, 2H).

LC/MS, m/z=470 [M+H]⁺ (Calc: 469).

In a similar manner, (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-phenylpropanoate (Compound 49) was prepared by using R-3 (Ref PT418) rather than R-1 and by using Boc-L-Phe-ONP rather than 4-chloromethyl-3,5-dimethylisoxazole, followed by cleavage of the Boc protecting group. Compound 49 was obtained as the TFA salt by reverse phase column (C18) chromatography (0-90% acetonitrile/water with 0.1% TFA).

¹H NMR: δ_H (300 MHz, DMSO-d_6): 8.69 (bs, 1H), 8.54 (bs, 3H), 7.28-7.38 (m, 3H), 7.22-7.24 (m, 2H), 6.89 (d, J=8.25 Hz, 1H), 6.70 (d, J=8.25 Hz, 1H), 4.72 (s, 1H), 4.34 (dd, J_1=10.74 Hz, J_2=4.11 Hz, 1H), 4.18-4.28 (m, 1H), 3.80-3.92 (m, 3H), 3.78 (s, 3H), 3.30-3.45 (m, 2H), 3.18-3.28 (m, 2H), 3.22 (s, 3H), 2.94-3.18 (m, 3H), 2.75-2.92 (m, 2H), 2.58-2.74 (m, 1H), 2.28-2.40 (m, 1H), 2.13-2.28 (m, 1H), 1.82-1.94 (m, 1H), 1.0-1.36 (m, 5H), 0.55-0.78 (m, 3H), 0.35-0.5 (m, 2H).

LC/MS, m/z=559 [M+H]⁺ (Calc: 558).

Example 8

(4R,4aS,6R,7R,7aR,12bS)-6-((4-(1H-imidazol-1-yl)phenoxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 5); (4R,4aS,6R,7R,7aR,12bS)-6-((4-(1H-imidazol-1-yl)phenoxy)methyl)-3-(cyclopropylmethyl)-7-methoxy-1,2,3,4,5,6,7,7a-octahydro-4a,7-ethano-4,12-methanobenzofuro[3,2-e]isoquinolin-9-ol (Compound 11); and (4R,4aS,6R,7R,7aR,12bS)-6-((4-(1H-imidazol-1-yl)phenoxy)methyl)-7-methoxy-3-methyl-1,2,3,4,5,6,7,7a-octahydro-4a,7-ethano-4,12-methanobenzofuro[3,2-e]isoquinolin-9-ol (Compound 8)

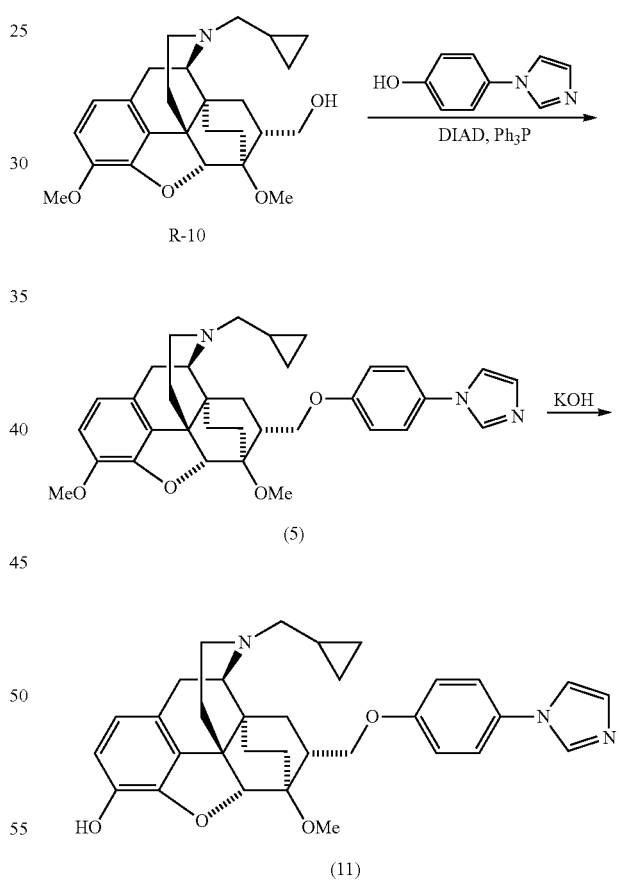

A mixture of R-10 (0.408 g, 1.0 mmol), 4-(imidazol-1-yl)phenol (0.641 g, 4.0 mmol) and triphenylphosphine (Ph_3P) (1.05 g, 4.0 mmol) in THF (8 mL) was cooled to 0° C. Diisopropyl azodicarboxylate (DIAD) (0.808 g, 4.0 mmol) (Aldrich) was added and the reaction was stirred at RT for 12 hr. Water (40 mL) was added and the mixture extracted with EtOAc (2×50 mL). The extracts were washed with 20 mL each water and brine. After drying over Na₂SO₄, solvent was evaporated. The residue was purified by flash chromatography (silica gel, 10-80% EtOAc/hexanes) to provide compound Compound 5 as the free base. Compound 5 was then converted to its bis HCl salt by treating a DCM solution of the free base with 1M HCl in ether. Yield: 363 mg (58%).

¹H NMR: δ$_H$ (300 MHz, DMSO-d$_6$): 9.62 (s, 1H), 9.34 (br s, 1H), 8.21 (s, 1H), 7.89 (s, 1H), 7.76-7.72 (d, 2H), 7.23-7.19 (d, 2H), 6.91-6.87 (d, 1H), 6.72-6.68 (d, 1H), 4.83 (s, 1H), 4.16-4.13 (m, 2H), 3.94-3.91 (m, 1H), 3.79 (s, 3H), 3.70-3.40 (br m, 2H), 3.40-3.25 (m, 3H), 3.25-3.07 (m, 2H), 3.10-2.90 (m, 1H), 2.90-2.70 (m, 2H), 2.65-2.25 (m, 2H), 1.93-1.80 (m, 1H), 1.63-1.47 (m, 2H), 1.47-1.30 (m, 1H), 1.30-1.05 (m, 3H), 0.75-0.50 (m, 4H), 0.45-0.30 (m, 1H).

LC/MS, m/z=554 [M+H]⁺ (Calc: 554.6).

Compound 5 (69.4 mg, 0.125 mmol) was added to a hot solution of KOH (90 mg, excess) in ethylene glycol (2 mL) and subjected to microwaves at 210° C. for 8 hr. After cooling to RT, the reaction mixture was diluted with chloroform and washed with saturated NH₄Cl solution. The combined organics were dried over Na₂SO₄ and the solvent was evaporated to provide a brown residue. The residue was purified by flash chromatography (silica gel, 0-10% MeOH/DCM) to provide compound Compound 11 as the free base. Further purification by reverse phase chromatography eluting with gradient of 0-100% MeOH/water (with 0.1% TFA) gave Compound 11 bis TFA salt as a white solid. Yield: 24 mg (25%).

¹H NMR (DMSO-d$_6$) δ: 9.43 (s, 1H), 9.28-9.38 (m, 1H), 8.43-8.60 (m, 1H), 8.15 (s, 1H), 7.82 (s, 2H), 7.71 (d, J=9.1 Hz, 2H), 7.19 (d, J=9.1 Hz, 2H), 6.70 (d, J=8.0 Hz, 1H), 6.57 (d, J=8.3 Hz, 1H), 4.79 (s, 1H), 4.02-4.27 (m, 4H), 3.74-3.95 (m, 3H), 2.71-3.06 (m, 4H), 2.58-2.70 (m, 5H), 2.26-2.40 (m, 2H), 1.80-2.04 (m, 1H), 1.46-1.72 (m, 3H), 1.15-1.35 (m, 2H), 1.08 (d, J=5.0 Hz, 1H), 0.54-0.82 (m, 4H), 0.28-0.48 (m, 2H).

LC/MS, m/z=540 [M+H]⁺ (Calc: 540.6).

In a similar manner, (4R,4aS,6R,7R,7aR,12bS)-6-((4-(1H-imidazol-1-yl)phenoxy)methyl)-7-methoxy-3-methyl-1,2,3,4,5,6,7,7a-octahydro-4a,7-ethano-4,12-methanobenzofuro[3,2-e]isoquinolin-9-ol (Compound 8) was prepared by using R-9 rather than R-10. Purification by reverse phase column chromatography (MeOH/water with 0.1% TFA, 0-100%) gave Compound 8 bis TFA salt as a white solid.

¹H NMR: δ$_H$ (300 MHz, DMSO-d$_6$): 9.32 (br s, 2H), 8.80-8.60 (m, 1H), 8.15-8.05 (m, 1H), 7.90-7.63 (m, 3H), 7.23-7.10 (m, 2H), 6.75-6.65 (m, 1H), 6.60-6.53 (m, 1H), 4.76 (s, 1H), 4.17-4.00 (m, 3H), 3.85-3.10 (m, 5H), 3.00-2.70 (m, 7H), 2.70-2.15 (<@H), 1.95-1.85 (m, 1H), 1.70-1.50 (m, 2H), 1.40-1.15 (m, 2H), 0.70-0.50 (m, 1H).

LC/MS, m/z=500 [M+H]⁺ (Calc: 500.6).

Example 9

(4R,4aS,6S,7R,7aR,12bS)-6-((benzo[d]thiazol-2-ylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 7); (4R,4aS,6S,7R,7aR,12bS)-3-(cyclopropylmethyl)-7,9-dimethoxy-6-(((3-methyl-1,2,4-thiadiazol-5-yl)thio)methyl)-1,2,3,4,5,6,7,7a-octahydro-4a,7-ethano-4,12-methanobenzofuro[3,2-e]isoquinoline (Compound 9); (4R,4aS,6S,7R,7aR,12bS)-6-(((1,3,4-thiadiazol-2-yl)thio)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 14); (4R,4aS,6S,7R,7aR,12bS)-6-((benzo[d]oxazol-2-ylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 27); (4R,4aS,6S,7R,7aR,12bS)-6-((benzo[d]thiazol-2-ylthio)methyl)-7,9-dimethoxy-3-methyl-1,2,3,4,5,6,7,7a-octahydro-4a,7-ethano-4,12-methanobenzofuro[3,2-e]isoquinoline (Compound 6); (4R,4aS,6S,7R,7aR,12bS)-7,9-dimethoxy-3-methyl-6-(((3-methyl-1,2,4-thiadiazol-5-yl)thio)methyl)-1,2,3,4,5,6,7,7a-octahydro-4a,7-ethano-4,12-methanobenzofuro[3,2-e]isoquinoline (Compound 12); and (4R,4aS,6S,7R,7aR,12bS)-6-(((1,3,4-thiadiazol-2-yl)thio)methyl)-7,9-dimethoxy-3-methyl-1,2,3,4,5,6,7,7a-octahydro-4a,7-ethano-4,12-methanobenzofuro[3,2-e]isoquinoline (Compound 13)

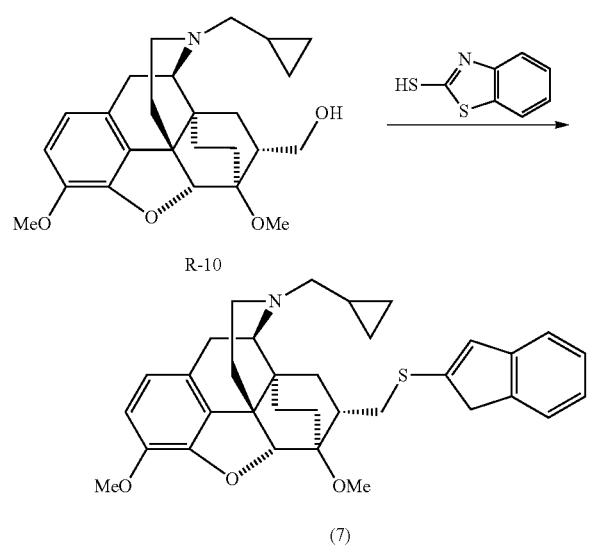

To a stirred solution of R-10 (60 mg, 0.147 mmol) in anhydrous THF (5 mL) was added triphenylphosphine (42 mg, 0.162 mmol) followed by 2-mercaptobenzothiazole (26.8 mg, 0.162 mmol) (Aldrich). The mixture was cooled in an ice-water bath for 20 min and then DIAD (32 μL, 0.162 mmol) was added. The reaction mixture was slowly warmed to rt and then stirred at rt for four days. The solvent was evaporated and the crude material was purified by flash chromatography (silica gel, 0-10% MeOH/DCM) to give Compound 7 as the free base. Compound 7 was then converted to its HCl salt by treating a DCM solution of the free base with 1M HCl in ether. Yield: 11.7 mg (13%).

$^1$H NMR $\delta_H$ (300 MHz, DMSO-d$_6$) 8.54 (br. s., 1H), 8.03 (d, J=8.0 Hz, 1H), 7.85 (d, J=7.7 Hz, 1H), 7.42-7.55 (m, 1H), 7.29-7.41 (m, 1H), 6.89 (d, J=8.3 Hz, 1H), 6.69 (d, J=8.3 Hz, 1H), 4.82 (s, 1H), 3.81-3.97 (m, 2H), 3.80 (s, 3H), 3.45 (s, 3H), 3.14-3.31 (m, 4H), 2.79-3.07 (m, 4H), 2.12-2.31 (m, 1H), 1.82 (d, J=16.2 Hz, 1H), 1.28-1.64 (m, 5H), 0.98-1.28 (m, 1H), 0.55-0.78 (m, 2H), 0.28-0.53 (m, 2H).

LC/MS, m/z=561 [M+H]$^+$ (Calc: 561.6).

In a similar manner (4R,4aS,6S,7R,7aR,12bS)-3-(cyclopropylmethyl)-7,9-dimethoxy-6-(((3-methyl-1,2,4-thiadiazol-5-yl)thio)methyl)-1,2,3,4,5,6,7,7a-octahydro-4a,7-ethano-4,12-methanobenzofuro[3,2-e]isoquinoline (Compound 9) was prepared from R-10 using 4-methyl-1,3,5-thiadiazol-2-thiol (Aldrich) rather than 2-mercaptobenzothiazole. Purification by reverse phase column chromatography (MeOH/water with 0.1% TFA, 0-100%) gave Compound 9 TFA salt as a white solid.

$^1$H NMR $\delta_H$ (300 MHz, DMSO-d$_6$) 8.34 (br s, 1H), 6.90-6.85 (m, 1H), 6.70-6.65 (m, 1H), 4.78 (s, 1H), 3.90-3.80 (m, 1H), 3.79 (s, 3H), 3.70-3.60 (m, 1H), 3.45-3.10 (m, 7H), 3.03-2.65 (m, 3H), 2.70 (s, 3H), 2.34-2.05 (m, 1H), 1.95-1.80 (m, 1H), 1.55-1.25 (m, 3H), 1.25-0.97 (m, 3H), 0.74-0.53 (m, 3H), 0.48-0.30 (m, 2H).

LC/MS, m/z=526 [M+H]$^+$ (Calc: 526.6).

In a similar manner (4R,4aS,6S,7R,7aR,12bS)-6-(((1,3,4-thiadiazol-2-yl)thio)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 14) was prepared from R-10 using 1,3,4-thiadiazol-2-thiol (Aldrich) rather than 2-mercaptobenzothiazole. Purification by reverse phase column chromatography (MeOH/water with 0.1% TFA, 0-100%) gave Compound 14 TFA salt as a white solid.

$^1$H NMR 8H (300 MHz, DMSO-d$_6$) 8.34 (br s, 1H), 6.91-6.86)$_{d, 1}$H), 6.72-6.67 (d, 1H), 4.80 (s, 1H), 3.88-3.85 (m, 1H), 3.80 (s, 3H), 3.79-3.70 (m, 1H), 3.40-3.15 (m, 81H), 3.05-2.75 (m, 5H), 2.28-2.15 (m, 1H), 1.91-1.82 (m, 1H), 1.54-1.42 (m, 2H), 1.20-1.05 (m, 2H), 0.70-0.60 (m, 3H), 0.45-0.35 (m, 2H).

LC/MS, m/z=512 [M+H]$^+$ (Calc: 512.6).

In a similar manner (4R,4aS,6S,7R,7aR,12bS)-6-((benzo[d]oxazol-2-ylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 27) was prepared from R-10 using 2-mercaptobenzoxazole (Aldrich) rather than 2-mercaptobenzothiazole. Compound 27 was obtained as the HCl salt by treating a DCM solution of the free base with 1M HCl in ether $^1$H NMR $\delta_H$ (300 MHz, DMSO-d$_6$) 8.75 (br s, 1H), 7.70-7.65 (m, 2H), 7.38-7.30 (m, 2H), 6.92-6.85 (d, 1H), 6.71-6.65 (d, 1H), 4.81 (s, 1H), 3.90-3.70 (m, 5H), 3.42 (s, 3H), 3.40-3.10 (m, 5H), 3.10-2.70 (m, 4H), 2.35-2.15 (m, 1H), 1.90-1.75 (m, 1H), 1.56-1.30 (m, 3H), 1.25-1.00 (m, 2H), 0.74-0.25 (m, 5H).

LC/MS, m/z=545 [M+H]$^+$ (Calc: 545.6).

In a similar manner (4R,4aS,6S,7R,7aR,12bS)-6-((benzo[d]thiazol-2-ylthio)methyl)-7,9-dimethoxy-3-methyl-1,2,3,4,5,6,7,7a-octahydro-4a,7-ethano-4,12-methanobenzofuro[3,2-e]isoquinoline (Compound 6) was prepared from R-9 using 2-mercaptobenzothiazole. Purification by reverse phase column chromatography (MeOH/water with 0.1% TFA, 0-100%) gave Compound 6 TFA salt as a white solid.

$^1$H NMR $\delta_H$ (300 MHz, DMSO-d$_6$) 8.57 (br s, 1H), 8.05-8.01 (m, 1H), 7.87-7.83 (m, 1H), 7.52-7.37 (m, 2H), 6.91-6.85 (d, 1H), 6.72-6.68 (d, 1H), 4.79 (s, 1H), 3.87-3.65 (m, 5H), 3.50-3.20 (m, 5H), 3.20-3.00 (m, 1H), 2.95-2.60 (m, 6H), 2.40-2.05 (m, 2H), 1.80-1.70 (m, 1H), 1.55-1.00 (m, 5H).

LC/MS, m/z=521 [M+H]$^+$ (Calc: 521.6).

In a similar manner (4R,4aS,6S,7R,7aR,12bS)-7,9-dimethoxy-3-methyl-6-(((3-methyl-1,2,4-thiadiazol-5-yl)thio)methyl)-1,2,3,4,5,6,7,7a-octahydro-4a,7-ethano-4,12-methanobenzofuro[3,2-e]isoquinoline (Compound 12) was prepared from R-9 using 4-methyl-1,3,5-thiadiazol-2-thiol rather than 2-mercaptobenzothiazole. Purification by reverse phase column chromatography (MeOH/water with 0.1% TFA, 0-100%) gave Compound 12 TFA salt as a white solid.

$^1$H NMR $\delta_H$ (300 MHz, DMSO-d$_6$) 8.69 (br s, 1H), 6.90-6.85 (d, 1H), 6.71-6.67 (d, 1H), 4.75 (s, 1H), 3.79 (s, 3H), 3.70-3.58 (m, 2H), 3.42-3.37 (m, 1H), 3.36-3.26 (m, 4H), 3.25-3.07 (m, 2H), 2.95-2.73 (m, 5H), 2.73-2.65 (m, 4H), 2.27-2.05 (m, 1H), 1.90-1.75 (m, 1H), 1.53-1.35 (m, 2H), 1.35-1.05 (m, 2H), 0.70-0.50 (m, 1H).

LC/MS, m/z=486 [M+H]$^+$ (Calc: 486.6).

In a similar manner (4R,4aS,6S,7R,7aR,12bS)-6-(((1,3,4-thiadiazol-2-yl)thio)methyl)-7,9-dimethoxy-3-methyl-1,2,3,4,5,6,7,7a-octahydro-4a,7-ethano-4,12-methanobenzofuro[3,2-e]isoquinoline (Compound 13) was prepared from R-9 using 1,3,4-thiadiazol-2-thiol rather than 2-mercaptobenzothiazole. Purification by reverse phase column chromatography (MeOH/water with 0.1% TFA, 0-100%) gave Compound 13 TFA salt as a white solid.

$^1$H NMR $\delta_H$ (300 MHz, DMSO-d$_6$) 8.81 (br s, 1H), 6.90-6.87 (d, 1H), 6.81-6.68 (d, 1H), 4.77 (s, 1H), 3.79 (s, 3H), 3.73-3.65 (m, 2H), 3.40-3.20 (m, 6H), 3.15-3.05 (m 1H), 2.93-2.65 (m, 7H), 2.27-2.05 (m, 1H), 1.85-1.75 (m, 1H), 1.53-1.35 (m, 2H), 1.35-1.05 (m, 2H), 0.66-0.55 (m, 1H).

LC/MS, m/z=472 [M+H]$^+$ (Calc: 472.6).

Example 10

(4R,4aS,6R,7R,7aR,12bS)-6-((benzyloxy)methyl)-7,9-dimethoxy-1,2,3,4,5,6,7,7a-octahydro-4a,7-ethano-4,12-methanobenzofuro[3,2-e]isoquinoline (Compound 18)

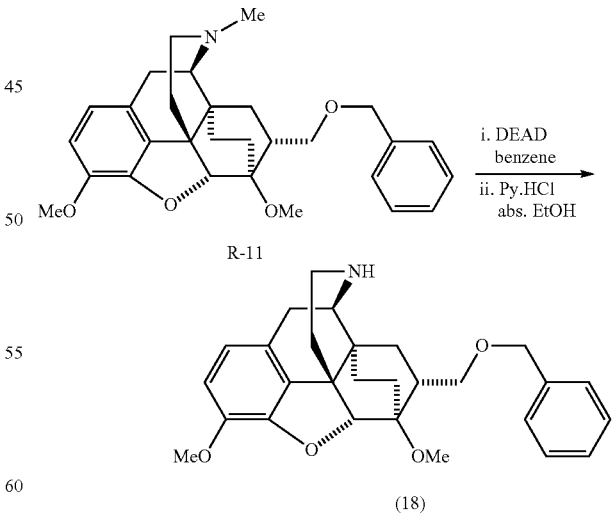

A mixture of R-11 (1.0 g, 2.2 mmol) and DEAD (0.6 mL, 3.5 mmol) in benzene (10 mL) was heated to ca 60° C. for 10 hr. The reaction mixture was cooled to RT and concentrated. The residue was dissolved in absolute EtOH (10 mL). Pyridinium hydrochloride (1.1 g, 9.5 mmol) was added and the reaction mixture was allowed stir at RT for 10 hr. The mixture was concentrated, diluted with chloroform and washed with 10% aqueous sodium hydroxide solution. The organic layer was dried (Na$_2$SO$_4$), filtered and concentrated. The crude material was purified by column chromatography (silica gel, 0-10% MeOH/DCM) to obtain Compound 18 as the free base. Compound 18 was then converted to its HCl salt by treating a DCM solution of the free base with 1M HCl in ether. Purification by reverse phase chromatography eluting with gradient of 0-100% MeOH/water (with 0.1% TFA) gave Compound 18 TFA salt as a white solid. Yield: 0.13 g (11%).

$^1$H NMR $\delta_H$ (300 MHz, DMSO-d$_6$) 8.98 (m, 1H), 8.05 (m, 1H), 7.42-7.25 (m, 5H), 6.86 (d, J=8.0 Hz, 1H), 6.70 (d, J=8.0 Hz, 1H), 4.69 (s, 1H), 4.50 (dd, J=15.4, 11, 8 Hz, 2H), 3.77 (s, 3H), 3.70 (m, 1H), 3.61 (dd, J=8.8, 3.6 Hz, 1H), 3.48 (dd, J=9.1, 9.0 Hz, 1H), 3.32 (s, 3H), 3.11 (m, 1H), 2.98 (m, 2H), 2.86 (m, 1H), 2.58 (m, 1H), 2.37 (m, 1H), 2.17 (m, 1H), 1.19 (m, 1H), 1.51 (dd, J=13.5, 5.8 Hz, 1H), 1.37 (m, 1H), 1.18 (m, 2H), 0.53 (m, 1H).

LC/MS, m/z=448 [M+H]$^+$ (Calc: 448.6).

Example 11

(4R,4aS,6R,7R,7aR,12bS)-6-((benzyloxy)methyl)-7-methoxy-1,2,3,4,5,6,7,7a-octahydro-4a,7-ethano-4,12-methanobenzofuro[3,2-e]isoquinolin-9-ol (Compound 22)

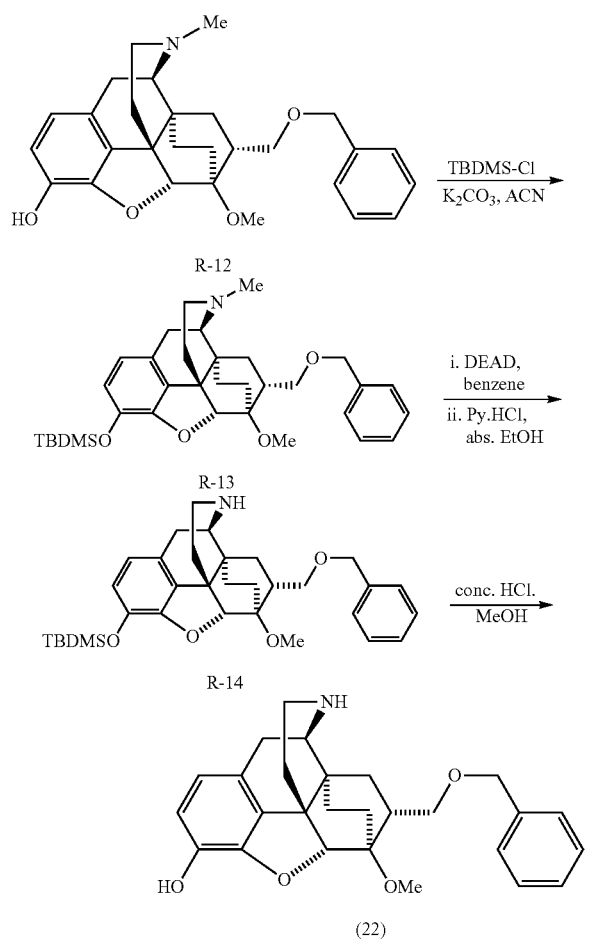

(22)

Potassium carbonate (0.6 g, 4.5 mmol) was added to a solution of R-12 (0.7 g, 1.5 mmol) in acetonitrile (20 mL) under a nitrogen atmosphere at RT. After 30 min TBDMS-Cl (500 mg, 3.3 mmol) was added and resulting mixture was allowed to stir at RT for 10 hr. The reaction mixture was then concentrated. The residue was taken in DCM and filtered. The filtrate was concentrated and the residue was purified by flash column chromatography (silica gel, 0-100% EtOAc/hexanes) to afford R-13 as a colorless gum. Yield: 0.80 g (94%).

$^1$H NMR $\delta_H$ (300 MHz, CDCl$_3$) 7.38-7.23 (m, 5H), 6.62 (d, J=8.0 Hz, 1H), 6.48 (d, J=8.0 Hz, 1H), 4.52 (dd, J=15.4, 11.8 Hz, 2H), 4.44 (s, 1H), 3.73 (dd, J=9.1, 4.4 Hz, 1H), 3.51 (dd, J=9.1, 8.8 Hz, 1H), 3.36 (s, 3H), 3.08 (d, J=18.4 Hz, 1H), 2.88 (m, 1H), 2.66 (d, J=6.3 Hz, 1H), 2.43 (dd, J=11.3, 5.2 Hz, 1H), 2.38-2.14 (m, 2H), 2.30 (s, 3H), 2.24-1.96 (m, 2H), 1.63 (m, 1H), 1.43 (m, 3H), 1.07 (m, 1H), 0.96 (s, 9H), 0.72 (m, 1H), 0.19 (s, 1H), 0.17 (s, 1H).

A mixture of R-13 (0.8 g, 1.4 mmol) and DEAD (0.4 mL, 2.3 mmol) in acetonitrile (10 mL) was heated to 65° C. for 4 hr. The reaction mixture was cooled to RT and pyridinium hydrochloride (0.2 g, 2.0 mmol) was added. The mixture was allowed to stir at RT for 3 days. The precipitated solid was filtered washed with acetonitrile and hexanes to obtain R-14 as a white solid. Yield: 0.5 g (61%).

$^1$H NMR $\delta_H$ (300 MHz, DMSO-d$_6$) 7.41-7.24 (m, 5H), 6.69 (d, J=8.3 Hz, 1H), 6.62 (d, J=8.3 Hz, 1H), 4.66 (s, 1H), 4.50 (m, 2H), 3.71-3.56 (m, 2H), 3.48 (dd, J=8.8, 8.3 Hz, 1H), 3.25 (s, 3H), 3.14-3.02 (m, 2H), 2.98-2.70 (m, 2H), 2.60 (m, 1H), 2.31 (m, 1H), 2.14 (m, 1H), 1.73 (m, 1H), 1.56-1.34 (m, 2H), 1.20 (m, 2H), 0.94 (s, 9H), 0.54 (m, 1H), 0.15 (s, 6H).

Concentrated hydrochloric acid (0.5 mL) was added to a solution of R-14 (0.5 g, 0.9 mmol) in MeOH (20 mL). The reaction mixture was allowed to stir at RT for 2 hr. The mixture was concentrated and the residual solid was triturated with ether to obtain Compound 22 HCl salt as a white solid. Yield: 0.40 g (100%).

$^1$H NMR $\delta_H$ (300 MHz, DMSO-d$_6$) 9.55 (bs, 1H), 9.28 (s, 1H), 8.27 (bs, 1H), 7.41-7.24 (m, 5H), 6.66 (d, J=8.0 Hz, 1H), 6.54 (d, J=8.0 Hz, 1H), 4.63 (s, 1H), 4.51 (m, 2H), 3.68-3.56 (m, 2H), 3.47 (dd, J=9.1, 8.8 Hz, 1H), 3.23 (s, 3H), 3.14-2.98 (m, 2H), 2.94-2.71 (m, 2H), 2.61 (m, 1H), 2.34 (m, 1H), 2.14 (m, 1H), 1.75 (m, 1H), 1.50 (dd, J=12.3, 5.5 Hz, 1H), 1.36 (m, 1H), 1.17 (m, 2H), 0.54 (m, 1H).

LC/MS, m/z=434 [M+H]$^+$ (Calc: 434.5).

ABBREVIATIONS USED

TBDMS-Cl tert-Butyldimethylsilyl chloride
DCE 1,2-Dichloroethane
DCM Dichloromethane
DEAD Diethyl azodicarboxylate
DIAD Diisopropyl azodicarboxylate
DMSO Dimethyl sulfoxide
EtOH Ethanol
EtOAc Ethyl acetate
MeOH Methanol
TEA Triethyl amine Example 12

The following Tables provide results on the efficacy of binding and activity response of exemplified Compounds of the Invention at the ORL1, μ-, δ- and κ-opioid receptors.

In TABLE 1, binding affinity of certain Compounds of the Invention to the ORL-1, μ-, δ- and κ-opioid receptors was determined as described above.

In TABLE 2, activity response of certain Compounds of the Invention to the ORL-1, μ-, δ- and κ-opioid receptors was determined as described above for functional assays.

TABLE 1
| | Binding Affinity of Buprenorphine Analog Compounds | | | | | |
|---|---|---|---|---|---|---|
| Ref. No. | Compound | | Opioid Receptor | | | |
| | | ORL-1 | μ | κ | δ | |
| 1 | 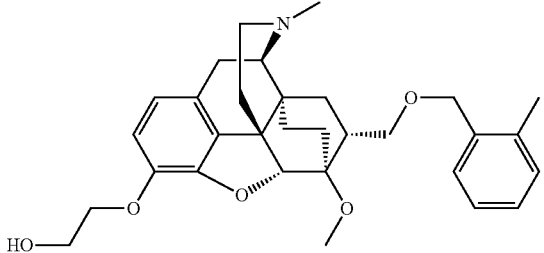 [SMILES: CO[C@]12CC[C@@]3(C[C@@H]1COCc1ccccc1C)[C@H]1Cc4ccc(OCCO)c5c4[C@@]3(CCN1C)[C@H]2O5] | 332.93 ± 36.79 | 4.16 ± 0.81 | 0.46 ± 0.01 | 32.24 ± 7.3 | |
| 2 | 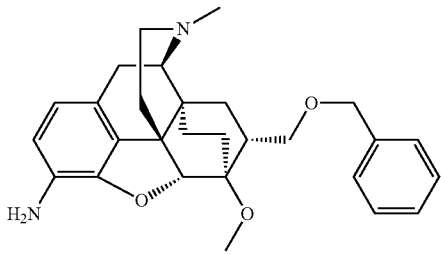 [SMILES: CO[C@]12CC[C@@]3(C[C@@H]1COCc1ccccc1)[C@H]1Cc4ccc(N)c5c4[C@@]3(CCN1C)[C@H]2O5] | 1322.41 ± 96.73 | 2.05 ± 0.03 | 0.28 ± 0.02 | 410.59 ± 95.75 | |
| 3 | 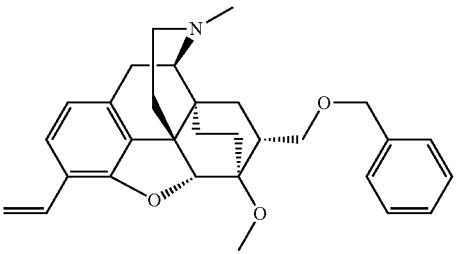 [SMILES: C=Cc1ccc2c3c1O[C@H]1[C@@]4(OC)CC[C@@]5(C[C@@H]4COCc4ccccc4)[C@@H](C2)N(C)CC[C@]315] | 2073.02 ± 890.79 | 16.36 ± 2.64 | 0.23 ± 0.02 | 174.45 ± 9.4 | |
| 4 | 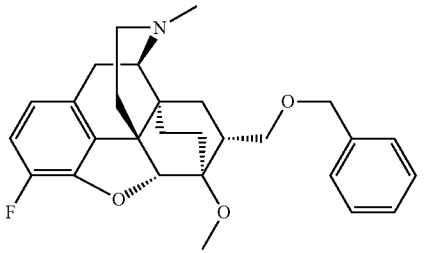 [SMILES: CO[C@]12CC[C@@]3(C[C@@H]1COCc1ccccc1)[C@H]1Cc4ccc(F)c5c4[C@@]3(CCN1C)[C@H]2O5] | 286.22 ± 91.35 | 4.41 ± 0.63 | 0.19 ± 0.04 | 92.5 ± 16.76 | |
| 5 | 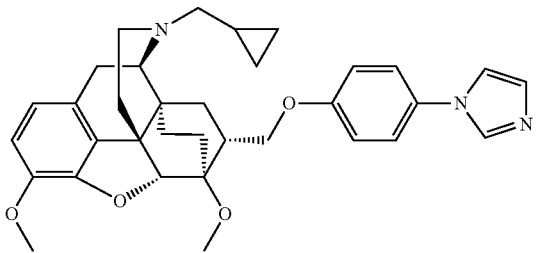 [SMILES: COc1ccc2c3c1O[C@H]1[C@@]4(OC)CC[C@@]5(C[C@@H]4COc4ccc(-n6ccnc6)cc4)[C@@H](C2)N(CC2CC2)CC[C@]315] | Inactive | 15.83 ± 2.32 | 31.23 ± 3.59 | 211.03 ± 30.10 | |

TABLE 1-continued

Binding Affinity of Buprenorphine Analog Compounds

| Ref. No. | Compound | ORL-1 | μ | κ | δ |
|---|---|---|---|---|---|
| 6 | | Partial | 148.85 ± 52.05 | 45.49 ± 5.02 | 317.88 ± 15.61 |
| 7 | | Inactive | 49.98 ± 10.62 | 8.03 ± 1.41 | 468.09 ± 58.22 |
| 8 | | Inactive | 36.46 ± 11.38 | 4.18 ± 0.70 | 43.05 ± 9.85 |
| 9 | | Inactive | 116.06 ± 5.47 | 15.02 ± 2.27 | 617.83 ± 81.24 |
| 10 | | 859.27 ± 78.98 | 1.52 ± 0.17 | 0.09 ± 0.01 | 15.01 ± 0.47 |

TABLE 1-continued
Binding Affinity of Buprenorphine Analog Compounds
| Ref. No. | Compound | ORL-1 | μ | κ | δ |
|---|---|---|---|---|---|
| 11 | 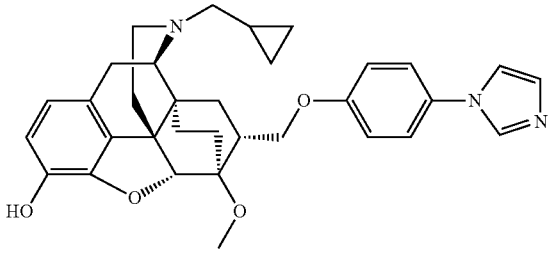 [SMILES: CO[C@]12CC[C@@]3(C[C@@H]1COc1ccc(-n4ccnc4)cc1)[C@H]1Cc4ccc(O)c5c4[C@@]3(CCN1CC1CC1)[C@H]2O5] | Inactive | 0.93 ± 0.00 | 0.09 ± 0.02 | 2.38 ± 0.42 |
| 12 | 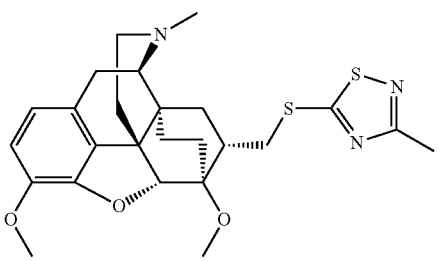 [SMILES: COc1ccc2c3c1O[C@H]1[C@@]4(OC)CC[C@@]5(C[C@@H]4CSc4nc(C)ns4)[C@@H](C2)N(C)CC[C@]315] | Inactive | 1544.07 ± 238.75 | 399.88 ± 17.5 | 9898.12 ± 1820.94 |
| 13 | 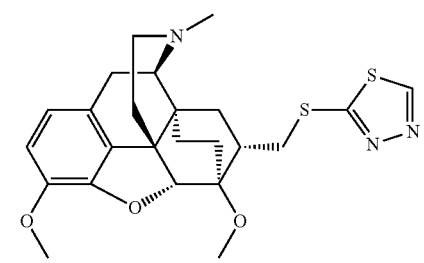 [SMILES: COc1ccc2c3c1O[C@H]1[C@@]4(OC)CC[C@@]5(C[C@@H]4CSc4nncs4)[C@@H](C2)N(C)CC[C@]315] | Inactive | 3386.17 ± 595.18 | 461.98 ± 86.78 | Inactive |
| 14 | 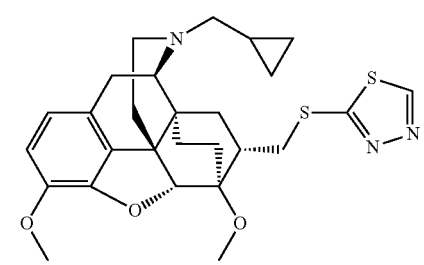 [SMILES: COc1ccc2c3c1O[C@H]1[C@@]4(OC)CC[C@@]5(C[C@@H]4CSc4nncs4)[C@@H](C2)N(CC2CC2)CC[C@]315] | Inactive | 188.28 ± 39.00 | 2.43 ± 0.81 | 1732.46 ± 489.77 |
| 15 | 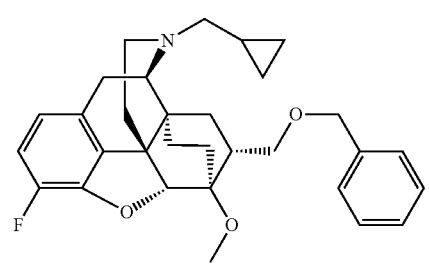 [SMILES: CO[C@]12CC[C@@]3(C[C@@H]1COCc1ccccc1)[C@H]1Cc4ccc(F)c5c4[C@@]3(CCN1CC1CC1)[C@H]2O5] | 330.88 ± 21.18 | 17.42 ± 2.40 | 0.02 ± 0.01 | 194.89 ± 26.97 |

TABLE 1-continued

Binding Affinity of Buprenorphine Analog Compounds

| Ref. No. | Compound | ORL-1 | μ | κ | δ |
|---|---|---|---|---|---|
| 16 | | 1551.13 ± 140.40 | 20.74 ± 2.53 | 0.53 ± 0.09 | 743.43 ± 31.63 |
| 17 | | 187.98 ± 7.09 | 132.97 ± 24.14 | 15.18 ± 2.66 | 4096.83 ± 946.16 |
| 18 | | 883.98 ± 88.45 | 20.7 ± 2.79 | 0.08 ± 0.01 | 341.52 ± 115.24 |
| 19 | | Inactive | 49.26 ± 4.90 | 0.24 ± 0.05 | nt |
| 20 | | Inactive | 146.95 ± 2.68 | 1.76 ± 0.20 | 3710.17 ± 249.24 |

TABLE 1-continued

Binding Affinity of Buprenorphine Analog Compounds

| Ref. No. | Compound | ORL-1 | Opioid Receptor | | |
|---|---|---|---|---|---|
| | | | μ | κ | δ |
| 21 | | 8617.21 ± 515.91 | 17.25 ± 1.92 | 0.15 ± 0.01 | 184.83 ± 35.54 |
| 22 | | 145.03 ± 21.46 | 1.33 ± 0.42 | 0.08 ± 0.01 | 13.81 ± 0.85 |
| 23 | | Inactive | 54.23 ± 13.87 | 5.49 ± 0.54 | 13416.50 ± 3490.14 |
| 24 | | Partial | 304.17 ± 122.63 | 5.74 ± 1.77 | 667.33 ± 116.97 |
| 25 | | 9736.84 ± 1210.04 | 6.29 ± 1.44 | 2.51 ± 0.24 | 277.58 ± 67.56 |

TABLE 1-continued

Binding Affinity of Buprenorphine Analog Compounds

| Ref. No. | Compound | ORL-1 | Opioid Receptor | | |
|---|---|---|---|---|---|
| | | | μ | κ | δ |
| 26 | | 6400.69 ± 350.21 | 92.69 ± 15.97 | 0.15 ± 0.01 | 180.40 ± 26.03 |
| 27 | | Inactive | 37.54 ± 12.13 | 6.69 ± 1.01 | 2425.67 ± 725.45 |
| 28 | | 147.00 ± 22.93 | 9.01 ± 0.71 | 0.04 ± 0.00 | 493.55 ± 26.39 |
| 29 | | 3541.32 ± 415.52 | 19.39 ± 5.48 | 0.43 ± 0.02 | 729.10 ± 196.12 |
| 30 | | 3091.75 ± 466.41 | 11.79 ± 1.67 | 0.14 ± 0.01 | 387.09 ± 33.89 |

TABLE 1-continued
Binding Affinity of Buprenorphine Analog Compounds
| Ref. No. | Compound | ORL-1 | μ | κ | δ |
|---|---|---|---|---|---|
| 31 | 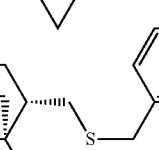 | 1531.57 ± 206.33 | 4.69 ± 1.14 | 0.14 ± 0.01 | 81.93 ± 9.09 |
| 32 |  | 6017.95 ± 1738.31 | 14.02 ± 4.11 | 0.43 ± 0.17 | 380.74 ± 138.56 |
| 33 | 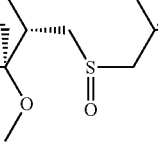 | Inactive | 51.10 ± 6.80 | 37.04 ± 4.91 | 3024.75 ± 277.91 |
| 34 | 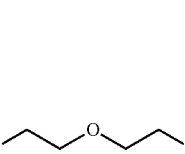 | Inactive | 215.94 ± 19.83 | 47.06 ± 9.69 | 5530.06 ± 1624.98 |
| 35 |  | 2796.30 ± 259.35 | 6.72 ± 0.69 | 2.55 ± 0.46 | 25.38 ± 6.46 |
| 36 | 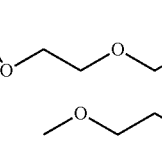 | Inactive | 26.92 ± 0.42 | 10.13 ± 1.27 | 269.62 ± 65.40 |

TABLE 1-continued
Binding Affinity of Buprenorphine Analog Compounds
| Ref. No. | Compound | ORL-1 | μ | κ | δ |
|---|---|---|---|---|---|
| 37 | 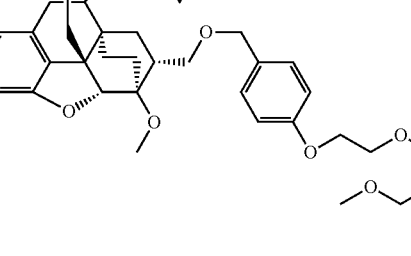 | Inactive | 87.86 ± 14.90 | 47.27 ± 5.01 | 1983.26 ± 485.04 |
| 38 | 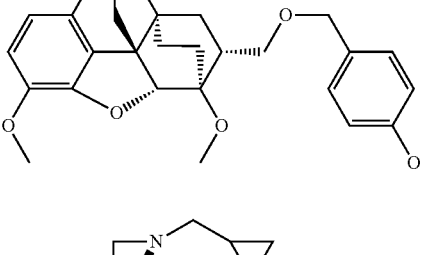 | Inactive | 135.49 ± 31.14 | 42.46 ± 5.89 | 1004.92 ± 218.82 |
| 39 | 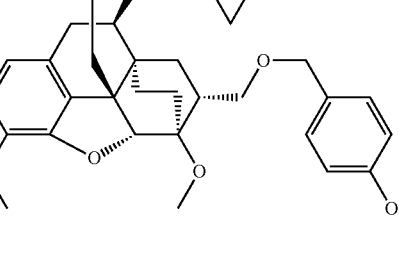 | Inactive | 19.04 ± 0.72 | 12.07 ± 2.21 | 739.45 ± 129.07 |
| 40 | 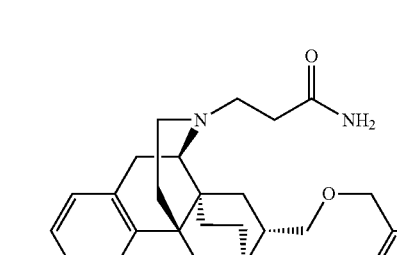 | Inactive | 544.71 ± 146.62 | 31.61 ± 13.75 | 355.13 ± 5.50 |
| 41 | 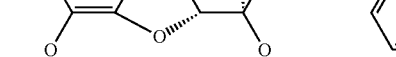 | Inactive | 383.41 ± 49.61 | 1.71 ± 0.07 | 1479.53 ± 266.72 |

TABLE 1-continued

Binding Affinity of Buprenorphine Analog Compounds

| Ref. No. | Compound | ORL-1 | μ | κ | δ |
|---|---|---|---|---|---|
| 42 | | Inactive | 349.03 ± 151.10 | 51.45 ± 4.60 | Inactive |
| 43 | | nt | 308.21 ± 15.02 | 434.84 ± 69.31 | nt |
| 44 | | nt | 55.53 ± 2.68 | 15.81 ± 1.96 | nt |
| 45 | | nt | 210.34 ± 27.32 | 20.48 ± 1.66 | nt |
| 46 | | nt | 1005.26 ± 151.08 | 516.58 ± 182.56 | nt |

TABLE 1-continued

Binding Affinity of Buprenorphine Analog Compounds

| Ref. No. | Compound | ORL-1 | μ | κ | δ |
|---|---|---|---|---|---|
| 47 | | nt | 154.50 ± 16.11 | 2.76 ± 0.37 | nt |
| 48 | | nt | 29.33 ± 5.35 | 1.37 ± 0.02 | 63.02 ± 8.10 |
| 49 | | nt | 14.29 ± 2.47 | 4.39 ± 0.48 | 138.07 ± 45.17 |
| 50 | | nt | 83.27 ± 14.24 | 9.80 ± 1.42 | 118.99 ± 45.50 |
| 51 | | nt | 13.09 ± 1.83 | 1.07 ± 0.08 | nt |

TABLE 1-continued

Binding Affinity of Buprenorphine Analog Compounds

| Ref. No. | Compound | ORL-1 | μ | κ | δ |
|---|---|---|---|---|---|
| 52 | | nt | 14.98 ± 1.07 | nt | nt |
| 53 | | nt | 7.79 ± 1.29 | nt | nt |
| 54 | | nt | 1774.64 ± 535.22 | 180.85 ± 20.10 | nt |
| 55 | | Inactive | 32.04 ± 7.58 | 16.18 ± 3.65 | 3615.75 ± 1494.62 |
| 56 | | Inactive | 849.99 ± 130.11 | 64.53 ± 7.29 | 16981.98 |

TABLE 1-continued

Binding Affinity of Buprenorphine Analog Compounds

| Ref. No. | Compound | ORL-1 | μ | κ | δ |
|---|---|---|---|---|---|
| 57 | | Inactive | 312.15 ± 34.05 | 29.43 ± 5.14 | Inactive |
| 58 | | Inactive | 176.92 ± 30.28 | 16.03 ± 6.12 | 10616.52 ± 3996.62 |
| 59 | | Inactive | 163.53 ± 25.64 | 19.80 ± 4.31 | 1054.82 ± 363.18 |
| 60 | | Inactive | 20.39 ± 5.04 | 32.67 ± 13.34 | 469.90 ± 109.83 |

TABLE 1-continued

Binding Affinity of Buprenorphine Analog Compounds

| Ref. No. | Compound | ORL-1 | μ | κ | δ |
|---|---|---|---|---|---|
| 61 | | 7124.13 ± 766.34 | 8.69 ± 1.64 | 0.29 ± 0.04 | 165.88 ± 5.14 |
| 62 | | nt | nt | 20.61 ± 2.56 | nt |
| 63 | | nt | 261.23 ± 70.65 | 10.06 ± 1.85 | nt |
| 64 | | nt | nt | 0.70 ± 0.06 | nt |
| 65 | | nt | 1.76 ± 0.41 | 0.93 ± 0.18 | nt |

TABLE 1-continued

Binding Affinity of Buprenorphine Analog Compounds

| Ref. No. | Compound | ORL-1 | μ | κ | δ |
|---|---|---|---|---|---|
| 66 | | nt | 35.79 ± 10.82 | 2.86 ± 0.59 | nt |
| 67 | | nt | 7.29 ± 0.58 | 1.39 ± 0.12 | nt |
| 68 | | nt | 341.38 ± 19.58 | 1.57 ± 0.36 | 3254.47 ± 674.61 |
| 69 | | nt | 82.53 ± 10.46 | 0.07 ± 0.01 | nt |
| 70 | | nt | 338.89 ± 64.00 | 5.02 ± 0.77 | nt |

TABLE 1-continued

Binding Affinity of Buprenorphine Analog Compounds

| Ref. No. | Compound | ORL-1 | μ | κ | δ |
|---|---|---|---|---|---|
| 71 | | nt | 1102.05 ± 207.71 | 1.58 ± 0.40 | 3001.22 ± 732.29 |
| 72 | | nt | nt | 0.05 ± 0.00 | nt |
| 73 | | nt | nt | 0.20 ± 0.04 | nt |
| 74 | | nt | 1.17 ± 0.27 | 0.15 ± 0.02 | nt |
| 75 | | nt | nt | .014 ± 0.04 | nt |

TABLE 1-continued

Binding Affinity of Buprenorphine Analog Compounds

| Ref. No. | Compound | ORL-1 | μ | κ | δ |
|---|---|---|---|---|---|
| 76 | | nt | 0.34 ± 0.06 | 0.10 ± 0.01 | nt |
| 77 | | Inactive | 147.99 ± 16.56 | 6.63 ± 1.69 | 1704.16 ± 263.79 |
| 78 | | nt | 361.75 ± 54.44 | 26.28 ± 2.00 | nt |
| 79 | | nt | 60.13 ± 9.69 | 1.02 ± 0.09 | nt |
| 80 | | nt | 5.42 ± 0.20 | 0.73 ± 0.20 | nt |

TABLE 1-continued
Binding Affinity of Buprenorphine Analog Compounds
| Ref. No. | Compound | ORL-1 | Opioid Receptor μ | κ | δ |
|---|---|---|---|---|---|
| 81 | 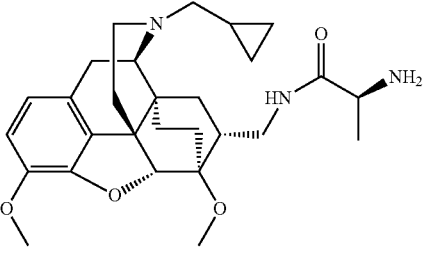 [SMILES: COc1ccc2c3c1O[C@H]1[C@@]4(OC)CC[C@@]5(C[C@@H]4CNC(=O)[C@H](C)N)[C@@H](C2)N(CC2CC2)CC[C@]315] | nt | 189.66 ± 59.44 | 13.80 ± 1.25 | nt |
| 82 | 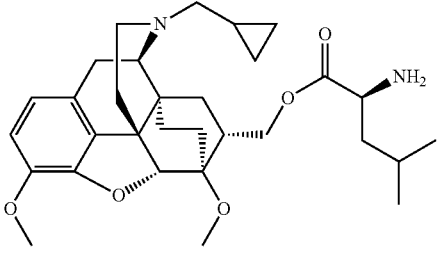 [SMILES: COc1ccc2c3c1O[C@H]1[C@@]4(OC)CC[C@@]5(C[C@@H]4COC(=O)[C@@H](N)CC(C)C)[C@@H](C2)N(CC2CC2)CC[C@]315] | nt | 7.65 ± 1.37 | 1.16 ± 0.11 | 151.00 ± 64.92 |
| 83 | 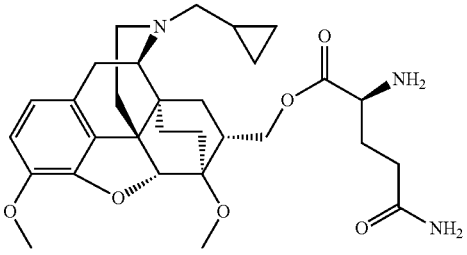 [SMILES: COc1ccc2c3c1O[C@H]1[C@@]4(OC)CC[C@@]5(C[C@@H]4COC(=O)[C@@H](N)CCC(N)=O)[C@@H](C2)N(CC2CC2)CC[C@]315] | nt | 169.53 ± 38.65 | 12.67 ± 3.38 | nt |
| 84 | 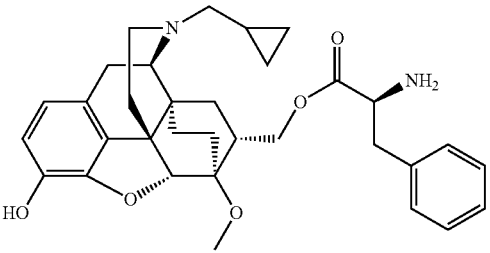 [SMILES: CO[C@]12CC[C@@]3(C[C@@H]1COC(=O)[C@@H](N)Cc1ccccc1)[C@H]1Cc4ccc(O)c5c4[C@@]3(CCN1CC1CC1)[C@H]2O5] | nt | 0.19 ± 0.07 | 0.07 ± 0.00 | 1.23 ± 0.43 |
| 85 | 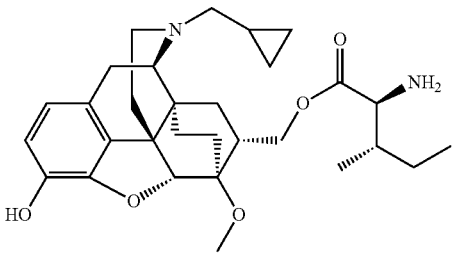 [SMILES: CC[C@H](C)[C@H](N)C(=O)OC[C@H]1C[C@@]23CC[C@]1(OC)[C@@H]1Oc4c(O)ccc5c4[C@@]12CCN(CC1CC1)[C@@H]3C5] | nt | 0.15 ± 0.05 | 0.06 ± 0.01 | nt |

TABLE 1-continued

Binding Affinity of Buprenorphine Analog Compounds

| Ref. No. | Compound | ORL-1 | Opioid Receptor | | |
|---|---|---|---|---|---|
| | | | μ | κ | δ |
| 86 | | nt | 1.40 ± 0.15 | 0.14 ± 0.02 | nt |
| 87 | | nt | 15.09 ± 3.88 | 8.33 ± 0.86 | nt |
| 88 | | nt | 60.54 ± 8.70 | 6.75 ± 1.19 | nt |
| 89 | | nt | 926.92 ± 213.83 | 19.26 ± 3.57 | nt |
| 90 | | nt | nt | 1.11 ± .016 | nt |

TABLE 1-continued

Binding Affinity of Buprenorphine Analog Compounds

| Ref. No. | Compound | ORL-1 | μ | κ | δ |
|---|---|---|---|---|---|
| 91 | | nt | nt | 0.11 ± 0.02 | nt |
| 92 | | nt | 24.41 ± 3.26 | 2.55 ± 0.26 | nt |
| 93 | | nt | 3.32 ± 0.74 | nt | nt |
| 94 | | nt | 155.62 ± 21.32 | 38.44 ± 9.98 | nt |
| 95 | | nt | 985.95 ± 154.55 | 43.67 ± 10.02 | nt |

TABLE 1-continued

Binding Affinity of Buprenorphine Analog Compounds

| Ref. No. | Compound | ORL-1 | μ | κ | δ |
|---|---|---|---|---|---|
| 96 | 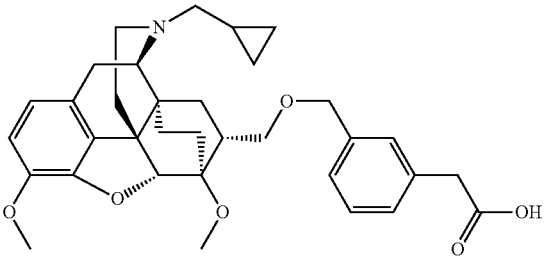 [SMILES: COc1ccc2c3c1O[C@H]1[C@@]4(OC)CC[C@@]5(C[C@@H]4COCc4cccc(CC(=O)O)c4)[C@@H](C2)N(CC2CC2)CC[C@]315] | nt | 497.73 ± 76.16 | 87.27 ± 6.15 | nt |
| 97 | 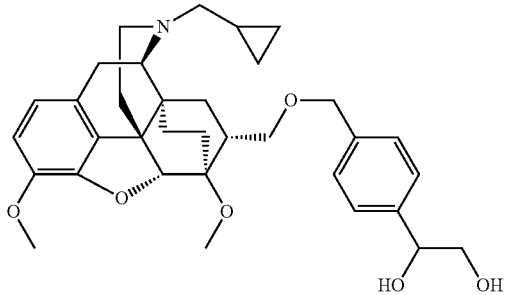 [SMILES: COc1ccc2c3c1O[C@H]1[C@@]4(OC)CC[C@@]5(C[C@@H]4COCc4ccc(C(O)CO)cc4)[C@@H](C2)N(CC2CC2)CC[C@]315] | Inactive | 54.83 ± 5.54 | 2.75 ± 0.66 | 517.28 ± 51.26 |

TABLE 2

Activity Response of Buprenorphine Analog Compounds

GTPγS (EC$_{50}$: nM, E$_{max}$: %)

| Ref. No. | ORL-1 EC$_{50}$ | ORL-1 E$_{max}$ | μ EC$_{50}$ | μ E$_{max}$ | κ EC$_{50}$ | κ E$_{max}$ | δ EC$_{50}$ | δ E$_{max}$ |
|---|---|---|---|---|---|---|---|---|
| 1 | 4103.76 ± 413.97 | 65.25 ± 7.66 | 18.22 ± 2.04 | 110.00 ± 5.13 | 3.94 ± 0.29 | 121.67 ± 9.87 | 22.25 ± 7.83 | 74.67 ± 9.77 |
| 2 | nt | nt | 55.91 ± 7.5 | 133.67 ± 5.21 | 40.38 ± 2.02 | 81.00 ± 8.62 | 272.80 ± 76.09 | 82.33 ± 7.62 |
| 3 | 6545.64 ± 1031.51 | 35.67 ± 1.76 | 18.69 ± 3.66 | 67.67 ± 7.62 | 6.82 ± 1.87 | 82.67 ± 0.33 | 188.68 ± 4.65 | 87.67 ± 4.84 |
| 4 | 2918.26 ± 674.92 | 50.00 ± 2.52 | 8.03 ± 2.30 | 69.33 ± 11.29 | 22.75 ± 6.79 | 77.33 ± 2.03 | 67.82 ± 12.73 | 76.00 ± 2.65 |
| 5 | nt | nt | Inactive | | 5464.58 ± 818.38 | 45.33 ± 2.40 | 5622.35 ± 1352.63 | 70.33 ± 4.33 |
| 6 | nt | nt | 502.68 ± 30.8 | 101.33 ± 4.67 | 576.79 ± 38.21 | 89.00 ± 5.77 | 555.58 ± 93.46 | 106.67 ± 4.63 |
| 7 | nt | nt | Inactive | | 63.79 ± 7.29 | 94.00 ± 8.19 | 211.43 ± 4.73 | 79.00 ± 1.15 |
| 8 | nt | nt | 9.32 ± 2.54 | 61.33 ± 1.45 | 129.34 ± 36.38 | 37.33 ± 7.17 | 75.30 ± 8.87 | 74.67 ± 4.33 |
| 9 | nt | nt | Inactive | | 889.94 ± 82.82 | 66.33 ± 6.96 | 640.21 ± 134.13 | 57.67 ± 3.18 |
| 10 | 1642.40 ± 176.72 | 22.67 ± 2.03 | 10.78 ± 1.55 | 41.33 ± 2.33 | 4.27 ± 0.50 | 107.67 ± 5.84 | 14.69 ± 0.28 | 81.00 ± 9.50 |
| 11 | nt | nt | Inactive | | Inactive | | 6061.62 ± 1750.45 | 23.33 ± 1.86 |
| 12 | nt | nt | nt | nt | Inactive | | nt | nt |
| 13 | nt | nt | nt | nt | 10328.23 ± 213.25 | 38.33 ± 5.90 | nt | nt |
| 14 | nt | nt | Inactive | | 191.50 ± 11.51 | 46.67 ± 2.03 | nt | nt |
| 15 | 260.98 ± 67.27 | 37.00 ± 2.08 | 11.37 ± 3.43 | 20.33 ± 1.76 | 1.50 ± 0.06 | 85.33 ± 3.84 | 66.45 ± 16.41 | 108.00 ± 4.04 |
| 16 | nt | nt | 79.40 ± 11.63 | 104.67 ± 2.33 | 70.70 ± 13.78 | 76.67 ± 2.91 | 482.06 ± 56.47 | 117.67 ± 4.26 |

TABLE 2-continued

Activity Response of Buprenorphine Analog Compounds

GTPγS (EC$_{50}$: nM, E$_{max}$: %)

| Ref. No. | ORL-1 EC$_{50}$ | ORL-1 E$_{max}$ | μ EC$_{50}$ | μ E$_{max}$ | κ EC$_{50}$ | κ E$_{max}$ | δ EC$_{50}$ | δ E$_{max}$ |
|---|---|---|---|---|---|---|---|---|
| 17 | 3521.69 ± 593.39 | 105.00 ± 4.73 | 694.12 ± 266.63 | 87.67 ± 7.69 | 950.56 ± 213.42 | 76.00 ± 3.21 | nt | nt |
| 18 | 7890.20 ± 389.03 | 38.00 ± 3.46 | 139.24 ± 1.67 | 107.67 ± 12.73 | 22.50 ± 0.26 | 89.67 ± 5.17 | 175.81 ± 13.58 | 115.33 ± 3.76 |
| 19 | nt | nt | 266.83 ± 46.97 | 19.67 ± 1.67 | 9.46 ± 1.33 | 88.33 ± 5.84 | 135.49 ± 21.74 | 80.00 ± 6.56 |
| 20 | nt | nt | 252.11 ± 9.62 | 101.00 ± 8.33 | 86.50 ± 7.43 | 95.00 ± 1.15 | nt | nt |
| 21 | nt | nt | 102.49 ± 16.03 | 74.33 ± 7.26 | 13.27 ± 2.36 | 87.33 ± 1.20 | 86.00 ± 1.88 | 101.00 ± 4.58 |
| 22 | 2440.53 ± 310.95 | 68.50 ± 3.30 | 9.22 ± 0.59 | 105.67 ± 10.71 | 0.84 ± 0.21 | 96.00 ± 4.73 | 17.32 ± 3.8 | 115.33 ± 4.1 |
| 23 | nt | nt | 631.73 ± 117.47 | 90.00 ± 5.02 | 155.71 ± 31.09 | 107.67 ± 6.01 | nt | nt |
| 24 | nt | nt | 323.50 ± 24.17 | 74.00 ± 3.06 | 195.58 ± 3.35 | 112.00 ± 4.51 | 841.40 ± 48.18 | 97.67 ± 2.60 |
| 25 | nt | nt | 3230.49 ± 630.00 | 25.67 ± 2.91 | 7.62 ± 0.66 | 73.33 ± 0.88 | 8113.67 ± 852.80 | 41.25 ± 3.28 |
| 26 | nt | nt | 127.32 ± 19.34 | 31.75 ± 0.48 | 21.10 ± 6.11 | 92.67 ± 2.19 | 229.26 ± 44.77 | 83.33 ± 5.21 |
| 27 | nt | nt | Inactive | 1.00 ± 0.00 | 107.71 ± 15.89 | 90.75 ± 5.15 | 430.63 ± 36.87 | 78.67 ± 5.81 |
| 28 | 1224.72 ± 121.55 | 99.00 ± 8.74 | 50.43 ± 8.73 | 53.50 ± 1.85 | 8.42 ± 1.50 | 98.25 ± 7.41 | 526.04 ± 39.96 | 82.25 ± 5.38 |
| 29 | nt | nt | 113.61 ± 35.88 | 26.33 ± 2.85 | 80.48 ± 23.41 | 71.67 ± 3.84 | 151.21 ± 49.26 | 49.20 ± 3.58 |
| 30 | nt | nt | 22.15 ± 8.93 | 56.40 ± 1.21 | 8.13 ± 2.67 | 101.33 ± 10.27 | 128.05 ± 23.02 | 71.33 ± 6.64 |
| 31 | nt | nt | 32.72 ± 6.19 | 19.33 ± 2.60 | 2.29 ± 0.45 | 89.00 ± 5.03 | 175.75 ± 57.73 | 53.00 ± 2.00 |
| 32 | nt | nt | 50.36 ± 19.47 | 45.33 ± 3.93 | 9.08 ± 2.80 | 97.00 ± 2.65 | 231.32 ± 58.88 | 61.33 ± 5.55 |
| 33 | nt | nt | Inactive | | 663.54 ± 145.40 | 26.00 ± 4.04 | nt | nt |
| 34 | nt | nt | Inactive | | 816.86 ± 299.87 | 18.75 ± 3.66 | nt | nt |
| 35 | nt | nt | 53.07 ± 7.90 | 65.50 ± 1.76 | 11.44 ± 3.43 | 95.33 ± 1.86 | 57.22 ± 7.70 | 89.00 ± 7.55 |
| 36 | nt | nt | 265.06 ± 71.94 | 56.00 ± 2.04 | 42.23 ± 11.79 | 102.67 ± 4.63 | 87.47 ± 8.28 | 81.00 ± 9.00 |
| 37 | nt | nt | Inactive | | 1639.03 ± 308.87 | 22.33 ± 5.04 | nt | nt |
| 38 | nt | nt | Inactive | | Inactive | | nt | nt |
| 39 | nt | nt | Inactive | | 95.14 ± 26.39 | 11.33 ± 1.45 | 778.12 ± 84.87 | 47.67 ± 2.03 |
| 40 | nt | nt | Inactive | | 202.04 ± 67.90 | 85.33 ± 10.35 | 399.74 ± 67.68 | 87.00 ± 4.73 |
| 41 | nt | nt | 1511.16 ± 297.71 | 78.67 ± 11.57 | 51.92 ± 15.68 | 103.67 ± 9.33 | nt | nt |
| 42 | nt | nt | 217.54 ± 25.90 | 31.33 ± 1.86 | 963.92 ± 77.48 | 60.00 ± 6.03 | nt | nt |
| 43 | nt | nt | 1294.05 ± 492.86 | 7.67 ± 1.76 | Inactive | 1.00 ± 0.00 | nt | nt |
| 44 | nt | nt | 581.28 ± 83.88 | 31.25 ± 3.59 | 1246.21 ± 166.49 | 29.25 ± 1.11 | nt | nt |
| 45 | nt | nt | 1131.05 ± 292.72 | 24.50 ± 2.53 | 1443.92 ± 479.38 | 59.00 ± 8.72 | nt | nt |
| 46 | nt | nt | 946.27 ± 258.16 | 17.33 ± 0.88 | 900.54 ± 232.75 | 16.67 ± 1.20 | nt | nt |
| 47 | nt | nt | 860.37 ± 201.84 | 74.67 ± 6.39 | 462.23 ± 50.63 | 89.00 ± 8.96 | nt | nt |
| 48 | nt | nt | Inactive | | 53.55 ± 10.26 | 53.33 ± 7.80 | 22.00 ± 7.24 | 98.33 ± 9.33 |
| 49 | nt | nt | Inactive | | 82.28 ± 15.81 | 74.33 ± 5.78 | 57.56 ± 19.09 | 76.33 ± 2.33 |
| 50 | nt | nt | Inactive | | 128.60 ± 14.97 | 79.67 ± 5.46 | 45.67 ± 18.73 | 82.00 ± 9.54 |
| 51 | nt | nt | 23.55 ± 1.63 | 11.00 ± 1.53 | 14.62 ± 1.89 | 89.67 ± 4.84 | nt | nt |

TABLE 2-continued

Activity Response of Buprenorphine Analog Compounds

GTPγS (EC$_{50}$: nM, E$_{max}$: %)

| | | Opioid Receptor | | | | | | |
|---|---|---|---|---|---|---|---|---|
| Ref. | ORL-1 | | μ | | κ | | δ | |
| No. | EC$_{50}$ | E$_{max}$ | EC$_{50}$ | E$_{max}$ | EC$_{50}$ | E$_{max}$ | EC$_{50}$ | E$_{max}$ |
| 52 | nt | nt | 136.72 ± 12.26 | 34.50 ± 4.66 | nt | nt | nt | nt |
| 53 | nt | nt | 136.72 ± 12.26 | 34.50 ± 4.66 | nt | nt | nt | nt |
| 54 | nt | nt | nt | nt | nt | nt | nt | nt |
| 55 | nt | nt | 650.11 ± 37.62 | 84.33 ± 4.81 | 644.98 ± 77.70 | 88.00 ± 4.93 | nt | nt |
| 56 | nt | nt | 1403.54 ± 212.39 | 62.00 ± 13.58 | 513.14 ± 29.02 | 94.33 ± 6.39 | nt | nt |
| 57 | nt | nt | 982.35 ± 98.77 | 52.00 ± 6.11 | 418.26 ± 45.74 | 66.67 ± 10.41 | nt | nt |
| 58 | nt | nt | 874.31 ± 34.64 | 56.67 ± 7.13 | 187.92 ± 16.28 | 78.67 ± 5.93 | nt | nt |
| 59 | nt | nt | 335.66 ± 45.83 | 61.33 ± 10.37 | 203.79 ± 73.63 | 92.25 ± 7.77 | nt | nt |
| 60 | nt | nt | 59.95 ± 12.73 | 73.67 ± 8.88 | 30.43 ± 4.82 | 88.00 ± 7.00 | 409.60 ± 95.91 | 94.67 ± 0.67 |
| 61 | nt | nt | 12.31 ± 2.62 | 81.33 ± 1.45 | 2.44 ± 0.71 | 80.67 ± 0.67 | 66.23 ± 14.91 | 104.25 ± 3.33 |
| 62 | nt | nt | nt | nt | 276.71 ± 75.81 | 23.33 ± 2.85 | nt | nt |
| 63 | nt | nt | 893.38 ± 48.33 | 38.33 ± 1.20 | 147.90 ± 30.99 | 80.33 ± 5.70 | nt | nt |
| 64 | nt | nt | nt | nt | Inactive | | nt | nt |
| 65 | nt | nt | 5.85 ± 1.07 | 19.75 ± .048 | 0.28 ± 0.04 | 91.00 ± 4.73 | nt | nt |
| 66 | nt | nt | Inactive | | 135.12 ± 24.05 | 39.40 ± 2.69 | nt | nt |
| 67 | nt | nt | 159.74 ± 41.70 | 61.67 ± 8.67 | 88.77 ± 1.88 | 65.00 ± 4.36 | nt | nt |
| 68 | nt | nt | Inactive | | 516.88 ± 68.02 | 87.67 ± 1.86 | nt | nt |
| 69 | nt | nt | 215.37 ± 47.87 | 44.60 ± 1.86 | 27.69 ± 2.73 | 85.00 ± 4.73 | nt | nt |
| 70 | nt | nt | 551.87 ± 126.28 | 27.33 ± 1.20 | 367.28 ± 73.64 | 68.00 ± 5.86 | nt | nt |
| 71 | nt | nt | nt | nt | 287.53 ± 39.73 | 84.67 ± 6.67 | nt | nt |
| 72 | nt | nt | nt | nt | 0.20 ± 0.07 | 23.00 ± 4.18 | nt | nt |
| 73 | nt | nt | nt | nt | 2.30 ± 0.23 | 40.33 ± 1.20 | nt | nt |
| 74 | nt | nt | Inactive | | 0.54 ± 0.07 | 86.00 ± 6.56 | nt | nt |
| 75 | nt | nt | nt | nt | 1.83 ± 0.10 | 17.33 ± 1.67 | nt | nt |
| 76 | nt | nt | 0.62 ± 0.19 | 21.25 ± 2.02 | 0.70 ± 0.18 | 87.00 ± 6.11 | nt | nt |
| 77 | nt | nt | Inactive | | 335.42 ± 73.92 | 45.00 ± 7.85 | nt | nt |
| 78 | nt | nt | Inactive | | 603.40 ± 123.33 | 48.00 ± 7.21 | nt | nt |
| 79 | nt | nt | 79.27 ± 15.61 | 11.33 ± 0.88 | 47.61 ± 3.87 | 35.83 ± 1.76 | nt | nt |
| 80 | nt | nt | Inactive | | 66.44 ± 10.08 | 52.00 ± 4.04 | nt | nt |
| 81 | nt | nt | Inactive | | 1606.34 ± 608.92 | 36.67 ± 7.17 | nt | nt |
| 82 | nt | nt | 96.55 ± 15.38 | 17.00 ± 3.06 | 41.80 ± 9.83 | 57.00 ± 6.95 | 128.96 ± 24.11 | 98.00 ± 3.24 |
| 83 | nt | nt | Inactive | | 316.93 ± 72.13 | 43.83 ± 4.60 | nt | nt |
| 84 | nt | nt | Inactive | | 2.04 ± 0.38 | 63.33 ± 0.67 | 0.82 ± 0.20 | 51.25 ± 3.28 |
| 85 | nt | nt | 5.04 ± 2.26 | 19.00 ± 1.53 | 0.96 ± 0.35 | 18.25 ± 1.38 | nt | nt |
| 86 | nt | nt | Inactive | | 2.59 ± 0.54 | 23.25 ± 3.57 | nt | nt |
| 87 | nt | nt | 3704.75 ± 699.35 | 26.60 ± 3.03 | 1829.26 ± 312.01 | 10.83 ± 0.65 | nt | nt |

TABLE 2-continued

Activity Response of Buprenorphine Analog Compounds

GTPγS (EC$_{50}$: nM, E$_{max}$: %)

| Ref. No. | ORL-1 | | μ | | κ | | δ | |
|---|---|---|---|---|---|---|---|---|
| | EC$_{50}$ | E$_{max}$ | EC$_{50}$ | E$_{max}$ | EC$_{50}$ | E$_{max}$ | EC$_{50}$ | E$_{max}$ |
| 88 | nt | nt | 2154.63 ± 478.56 | 22.75 ± 2.10 | 823.78 ± 196.53 | 38.00 ± 3.08 | nt | nt |
| 89 | nt | nt | nt | nt | 1900.16 ± 371.89 | 41.00 ± 4.73 | nt | nt |
| 90 | nt | nt | nt | nt | 28.51 ± 7.51 | 35.00 ± 2.04 | nt | nt |
| 91 | nt | nt | nt | nt | 0.58 ± 0.13 | 42.00 ± 5.51 | nt | nt |
| 92 | nt | nt | 185.66 ± 36.25 | 20.83 ± 1.01 | 128.55 ± 15.21 | 14.33 ± 1.33 | nt | nt |
| 93 | nt | nt | 50.27 ± 2.95 | 37.67 ± 4.33 | nt | nt | nt | nt |
| 94 | nt | nt | Inactive | | 588.60 ± 67.37 | 28.00 ± 2.08 | nt | nt |
| 95 | nt | nt | 1364.35 ± 369.83 | 101.33 ± 11.29 | 2397.73 ± 677.07 | 65.00 ± 10.02 | nt | nt |
| 96 | nt | nt | Inactive | | 625.05 ± 53.83 | 36.67 ± 0.33 | nt | nt |
| 97 | nt | nt | 60.48 ± 4.77 | 25.00 ± 3.21 | 156.50 ± 44.98 | 72.33 ± 6.69 | 164.73 ± 31.44 | 73.33 ± 2.19 |

"nt" = not tested or in the queue for testing

Example 13

2-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)acetic acid (Compound 57) 2-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)acetamide (Compound 58); 3-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)propanoic acid (Compound 56); 3-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)propanamide (Compound 41); and (4R,4aS,6R,7R,7aR,12bS)-3-((2H-tetrazol-5-yl)methyl)-6-((benzyloxy)methyl)-7,9-dimethoxy-1,2,3,4,5,6,7,7a-octahydro-4a,7-ethano-4,12-methanobenzofuro[3,2-e]isoquinoline (Compound 95)

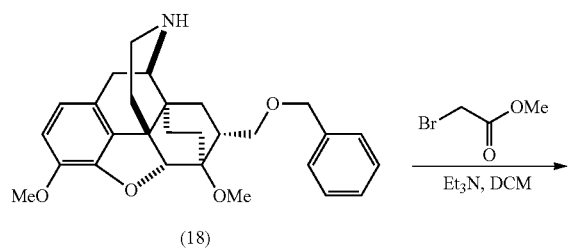

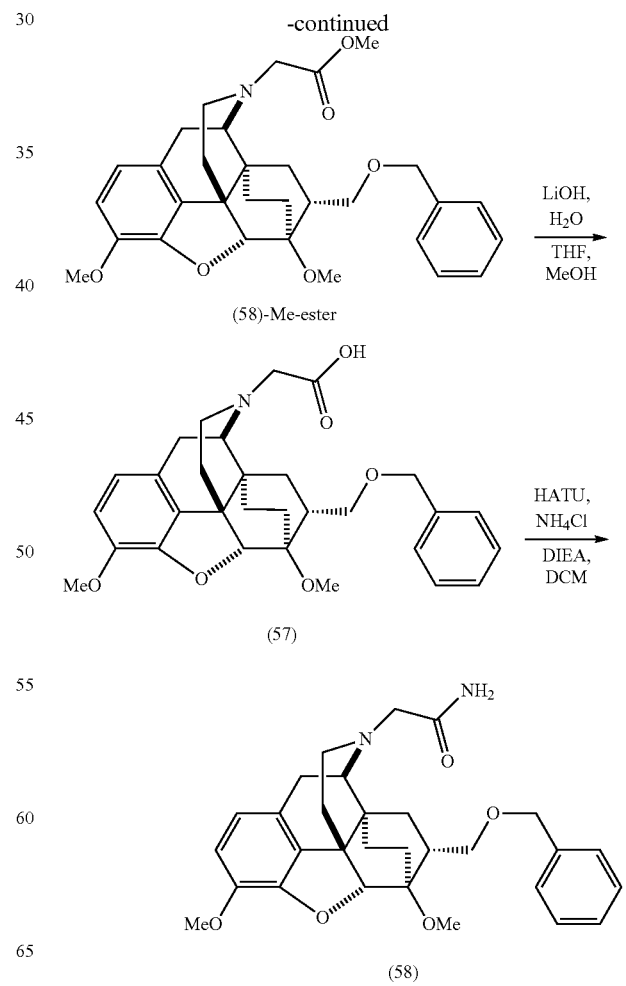

A mixture of Compound 18 (164 mg, 0.37 mmol) (see Example 10), methyl bromoacetate (44 µL, 0.48 mmol), and TEA (103 µL, 0.74 mmol) in DCM (anhydrous, 5 mL) was allowed to stir 14 hr at RT. The mixture was concentrated, diluted with EtOAc and washed with saturated aqueous NaHCO$_3$ solution. The organic layer was dried (Na$_2$SO$_4$), filtered and concentrated. The crude material obtained was purified by flash column chromatography (silica gel, 0-100% EtOAc/hexanes) to afford Compound 57-Me-ester as a colorless gum.

$^1$H NMR δ$_H$ (300 MHz, CDCl$_3$) 7.36-7.25 (m, 5H), 6.71 (d, J=8.0 Hz, 1H), 6.59 (d, J=8.0 Hz, 1H), 4.56-4.48 (m, 3H), 3.86 (s, 3H), 3.74 (m, 1H), 3.71 (s, 3H), 3.51 (dd, J=8.5, 8.5 Hz, 1H), 3.35 (s, 3H), 3.28 (d, J=16.5 Hz, 1H), 3.19 (d, J=16.5 Hz, 1H), 3.07-2.93 (m, 2H), 2.80 (d, J=6.3 Hz, 1H), 2.62 (dd, J=8.5, 8.5 Hz, 3H), 1.09 (m, 1H), 0.71 (m, 1H).

LC/MS, m/z=520 [M+1]$^+$ (Calc: 520.6).

Lithium hydroxide (15.0 mg, 0.35 mmol) was added to a 0° C. solution of Compound 57-Me-ester (150 mg, 0.27 mmol) in THF:MeOH:water (3:1:1, 5 mL). The reaction mixture was allowed to warm to RT and stir for 4 hr. The reaction mixture was concentrated, and diluted with chloroform and saturated aqueous NH$_4$Cl solution. The organic layer was dried (Na$_2$SO$_4$), filtered and concentrated to obtain Compound 57. Purification by reverse phase column chromatography (MeOH/water with 0.1% TFA, 0-100%) gave Compound 57 TFA salt as a white solid.

$^1$H NMR δ$_H$ (300 MHz, DMSO-d$_6$) 7.41-7.25 (m, 5H), 6.83 (d, J=8.3 Hz, 1H), 6.64 (d, J=8.3 Hz, 1H), 4.68 (s, 1H), 4.52 (m, 2H), 3.77 (m, 3H), 3.64 (m, 1H), 3.60-3.34 (m, 8H), 3.22 (s, 3H), 3.06 (m, 1H), 2.80-2.72 (m, 2H), 2.41-2.13 (m, 2H), 1.81 (m, 1H), 1.48 (m, 1H), 1.37 (m, 1H), 1.24-1.05 (m, 2H), 0.55 (m, 1H).

LC/MS, m/z=506 [M+1]$^+$ (Calc: 506.6).

2-(1H-7-Azabenzotriazol-1-yl)-1,1,3,3-tetramethyl uronium hexafluorophosphate Methanaminium (HATU) (91.0 mg, 0.24 mmol) was added to a 0° C. solution of Compound 57 (80.0 mg, 0.16 mmol) and DIEA (103 µL, 0.80 mmol) in DCM (6 mL). Ammonium chloride (34.0 mg, 0.64 mmol) was added after 20 min. The reaction mixture was allowed to warm to RT and stir for 14 hr. The reaction mixture was concentrated and the residue partitioned between DCM and saturated aqueous NaHCO$_3$ solution. The organic layer was dried (Na$_2$SO$_4$), filtered and concentrated. The crude material obtained was purified by flash column chromatography (silica gel, 0-10% MeOH/DCM) to afford free base of Compound 58. Further purification by reverse phase column chromatography (MeOH/water with 0.1% TFA, 0-100%) gave Compound 58 TFA salt as a white solid.

$^1$H NMR δ$_H$ (300 MHz, DMSO-d$_6$) 8.46, 7.93 and 7.77 (3br s, 2H), 7.41-7.25 (m, 5H), 6.86 (d, J=8.3 Hz, 1H), 6.67 (d, J=8.3 Hz, 1H), 4.71 (s, 1H), 4.53 (m, 2H), 4.01 (m, 1H), 3.77 (s, 3H), 3.73-3.34 (m, 7H), 3.23 (s, 3H), 3.06 (m, 1H), 2.88-2.64 (m, 2H), 2.41-2.21 (m, 2H), 1.85 (m, 1H), 1.56 (m, 1H), 1.37 (m, 1H), 1.28-1.06 (m, 2H), 0.56 (m, 1H).

LC/MS, m/z=505 [M+1]$^+$ (Calc: 505.6).

In a similar manner, 3-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)propanoic acid (Compound 56) was prepared by using methyl 3-bromopropionate rather than methyl bromoacetate. Compound 56 TFA salt was obtained as a white solid by reverse phase column chromatography (MeOH/water with 0.1% TFA, 0-100%).

$^1$H NMR: δ$_H$ (300 MHz, DMSO-d$_6$): 8.40 (br s, 1H), 7.41-7.23 (m, 5H), 6.87 (d, J=8.2 Hz, 1H), 6.68 (d, J=8.2 Hz, 1H), 4.73 (s, 1H), 4.50 (m, 2H), 3.78 (s, 3H), 3.71 (d, J=6.3 Hz, 1H), 3.60 (dd, J=6.9, 3.6 Hz, 1H), 3.50-3.14 (m, 8H), 2.96-2.58 (m, 5H), 2.39-2.16 (m, 2H), 1.85 (m, 1H), 1.53 (dd, J=13.5, 5.2 Hz, 1H), 1.39 (m, 1H), 1.28-1.06 (m, 2H), 0.61 (m, 1H).

LC/MS, m/z=520 [M+H]$^+$ (Calc: 520.6).

In a similar manner, 3-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)propanamide (Compound 41) was prepared by using Compound 56 rather than Compound 57. Compound 41 TFA salt was obtained as a white solid by reverse phase column chromatography (MeOH/water with 0.1% TFA, 0-100%).

$^1$H NMR: δ$_H$ (300 MHz, DMSO-d$_6$): 8.98 (bs, 1H), 7.83 (s, 1H), 7.62-7.23 (m, 5H), 6.87 (d, J=8.3 Hz, 1H), 6.69 (d, J=8.3 Hz, 1H), 4.73 (s, 1H), 4.51 (m, 2H), 3.78 (s, 3H), 3.77 (m, 1H), 3.60 (m, 1H), 3.54-3.17 (m, 8H), 2.86-2.74 (m, 2H), 2.68-2.56 (m, 3H), 2.41-2.21 (m, 2H), 1.86 (m, 1H), 1.57 (dd, J=13.2, 5.2 Hz, 1H), 1.40 (m, 1H), 1.29-1.16 (m, 2H), 0.60 (m, 1H).

LC/MS, m/z=519 [M+H]$^+$ (Calc: 519.6).

In a similar manner, (4R,4aS,6R,7R,7aR,12bS)-3-((2H-tetrazol-5-yl)methyl)-6-((benzyloxy)methyl)-7,9-dimethoxy-1,2,3,4,5,6,7,7a-octahydro-4a,7-ethano-4,12-methanobenzofuro[3,2-e]isoquinoline (Compound 95) was prepared by using bromoacetonitrile rather than methyl bromoacetate, followed by conversion of the nitrile to the tetrazole using TMS azide. Compound 95 was obtained as the TFA salt by reverse phase chromatography eluting with the gradient of acetonitrile/water (with 0.1% TFA).

$^1$H NMR: δ$_H$ (300 MHz, DMSO-d$_6$): 7.34-7.22 (m, 5H), 6.82 (d, J=8.3 Hz, 1H), 6.72 (d, J=8.3 Hz, 1H), 4.70 (bs, 2H), 4.57 (m, 1H), 4.48 (m, 2H), 4.32 (bs, 1H), 3.88 (s, 3H), 3.56 (d, J=5.0 Hz, 2H), 3.49-3.36 (m, 2H), 3.34 (s, 3H), 3.20 (m, 1H), 2.96-2.73 (m, 2H), 2.64 (m, 2H), 2.48 (m, 1H), 2.13 (m, 1H), 2.01 (m, 1H), 1.61 (m, 1H), 1.54-1.33 (m, 2H), 1.11 (m, 1H), 0.61 (m, 1H).

LC/MS, m/z=530 [M+H]$^+$ (Calc: 529).

Example 14

N-benzyl-1-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methanamine (Compound 28);
N-benzyl-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)acetamide (Compound 30);
N-benzyl-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)methanesulfonamide (Compound 29); 2-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)amino)acetic acid (Compound 85); 2-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)amino)acetamide (Compound 44)

mixture was filtered through Celite and the Celite was washed with DCM. The filtrate and the washings were combined and washed with saturated sodium bicarbonate solution, water and brine. The organic layer was dried over sodium sulfate and concentrated. The crude material obtained was purified by flash column chromatography (silica gel, 0-10% MeOH/DCM) to afford 100 mg of Compound 28. The free base was then converted to its HCl salt by treating a DCM solution of the free base with 1M HCl in ether and triturated with 1:1 ether-DCM to yield 24 mg of the target compound Compound 28 HCl salt as a light yellow hygroscopic solid.

$^1$H NMR $\delta_H$ (300 MHz, CDCl$_3$) 9.65 (br s, 1H) 9.29 (br.s., 1H), (8.91 (br s, 1H), 7.61-7.63 (m, 2H), 7.43-7.48 (m, 3H), 6.89 (d, J=8.3 Hz, 1H), 6.70 (d, J=8.3 Hz, 1H), 4.6 (s, 1H), 4.21 (m, 2H), 3.86-3.84 (m, 1H), 3.79 (s, 3H), 3.20 (m, 1H), 3.26 (s, 3H), 3.09-3.14 (m, 2H), 2.96-2.83 (m, 4H), 2.48-2.22 (m, 1H), 1.50-1.04 (m, 1H), 0.69-0.26 (m, 5H).

LC/MS, m/z=501 [M+1]$^+$ (Calc: 501.6).

To a solution of Compound 28 (100 mg, 0.19 mmol, 1 eq) in DCM (2 mL) at 0° C. was added pyridine (500 µL, excess) followed by acetic anhydride (93 µL, 1 mmol, 5 eq.). The reaction mixture was stirred at RT for 16 hr. The reaction

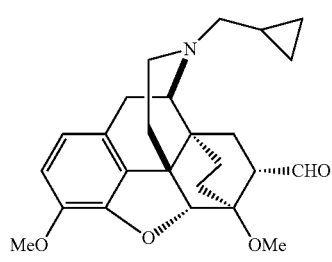

R-15

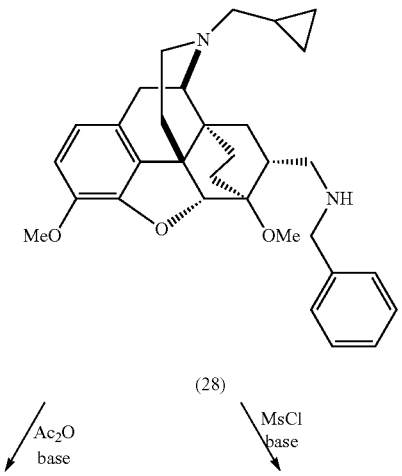

(28)

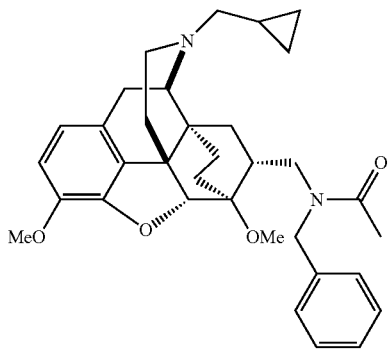

(30)

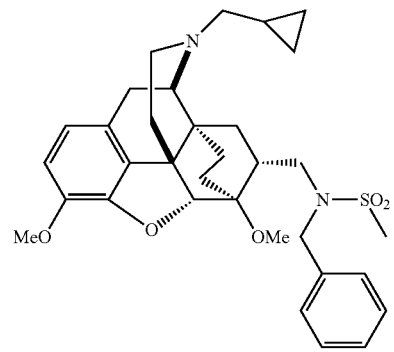

(29)

To a solution of R-15 (250 mg, 0.6 mmol, 1 eq.) (PT1418) and NaBH(OAc)$_3$ (382 mg, 1.8 mmol, 3 eq.) in DCM (5 mL) was added benzylamine (70 µL, 0.6 mmol, 1 eq.), followed by acetic acid (0.5 mL) and molecular seives 4 Å (200 mg). The reaction mixture was stirred at RT for 16 hr. The reaction mixture was diluted with DCM and washed with water. The organic layer was washed with brine and dried over anhydrous sodium sulfate. The crude material obtained was purified by flash column chromatography (silica gel, 0-10% MeOH/DCM) to afford 54 mg of Compound 30 as a white solid. The free base was then converted to its HCl salt by treating a DCM solution of the free base with 1M HCl in ether and triturated with ether to provide 34 mg of Compound 30 HCl salt as a white solid.

$^1$H NMR $\delta_H$ (300 MHz, DMSO-d$_6$) 8.96 (br s, 1H), 7.18-7.50 (m, 5H), 6.77-7.00 (m, 1H), 6.59-6.74 (m, 1H), 5.08 (d, J=15.1 Hz, 0.35H), 4.70-4.84 (m, 1.7H), 4.61 (s, 0.64H), 4.24 (d, J=15.1 Hz, 0.35H), 3.90 (m, 4H), 3.18-3.31 (m, 4H), 3.14 (s, 2H), 3.07 (s, 1.3H), 2.97-3.06 (m, 1.4H), 2.74-2.93 (m, 2H), 2.21 (s, 1.2H), 2.08 (s, 1.8H), 1.75-1.93 (m, 1H), 0.99-1.59 (m, 6H), 0.33-0.80 (m, 5H).

LC/MS, m/z=543 [M+1]$^+$ (Calc: 543.6).

To a solution of Compound 28 (30 mg, 0.06 mmol, 1 eq) in DCM (2 mL) at 0° C. was added triethylamine (86 μL, 6.0 mmol, 10 eq.) followed by methanesulfonyl chloride (14 μL, 0.18 mmol, 3 eq.). The reaction mixture was stirred at RT for 16 hr. The reaction mixture was diluted with DCM and washed with saturated sodium bicarbonate solution. The organic layer was washed with brine and dried over anhydrous sodium sulfate. The crude material obtained was purified by flash column chromatography (silica gel, 0-10% MeOH/DCM) to afford 17 mg of Compound 29 as a white solid. The free base was then converted to its HCl salt by treating a DCM solution of the free base with 1M HCl in ether and triturated with hexanes to provide 8.8 mg of the Compound 29 HCl salt as a white solid.

$^1$H NMR $\delta_H$ (300 MHz, DMSO-d$_6$) 8.78 (br s, 1H), 7.28-7.52 (m, 5H), 6.86 (d, J=8.3 Hz, 1H), 6.66 (d, J=8.3 Hz, 1H), 4.60 (s, 1H), 4.52 (d, J=15.1 Hz, 1H), 4.28 (d, J=14.6 Hz, 1H), 3.76 (s, 4H), 3.69 (d, J=6.3 Hz, 1H), 3.14-3.28 (m, 4H), 3.11 (s, 3H), 2.97 (s, 3H), 2.62-2.88 (m, 3H), 2.05-2.38 (m, 3H), 1.73-1.88 (m, 1H), 1.13-1.41 (m, 4H), 0.96-1.13 (m, 3H), 0.77-0.93 (m, 4H), 0.32-0.77 (m, 1H).

LC/MS, m/z=579 [M+1]$^+$ (Calc: 579.6).

In a similar manner 2-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)amino)acetic acid (Compound 85) was prepared by reductive amination of R-15 using glycine rather than benzyl amine. Purification by reverse phase column chromatography (C18, acetonitrile/water with 0.1% TFA, 0-95%) gave Compound 85 TFA salt as a white solid.

$^1$H NMR $\delta_H$ (300 MHz, DMSO-d$_6$) 9.1 (bs, 1H), 8.54 (bs, 2H), 6.91 (d, J=8.25 Hz, 1H), 6.71 (d, J=8.25 Hz, 1H), 4.71 (s, 1H), 3.85-3.95 (m, 3H), 3.89 (s, 3H), 3.35-3.55 (m, 2H), 3.32 (s, 3H), 3.27-3.32 (m, 2H), 2.65-3.08 (m, 5H), 2.10-2.34 (m, 1H), 1.87-2.0 (m, 1H), 1.20-1.49 (m, 4H), 0.95-1.10 (m, 1H), 0.52-0.75 (m, 3H), 0.35-0.50 (m, 2H).

LC/MS, m/z=469 [M+H]$^+$ (Calc: 468).

In a similar manner 2-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)amino)acetamide (Compound 44) was prepared by reductive amination of R-15 using glycine amide rather than benzyl amine. Purification by flash column chromatography (silica gel, 0-10% MeOH/DCM) followed by HCl salt formation gave Compound 44 HCl salt as a white solid.

$^1$H NMR $\delta_H$ (300 MHz, D$_2$O) 9.66 (bs, 1H), 9.06 (bs, 1H), 8.47 (bs, 1H), 7.90 (s, 1H), 7.61 (s, 1H), 6.90 (d, J=8.25 Hz, 1H), 6.71 (d, J=8.25 Hz, 1H), 4.70 (s, 1H), 3.87 (d, J=6.87 Hz, 1H), 3.80 (s, 3H), 3.65-3.74 (m, 2H), 3.30 (s, 3H), 3.07-3.24 (m, 2H), 2.70-3.06 (m, 4H), 2.38-2.48 (m, 1H), 2.22-2.37 (m, 1H), 1.82-1.94 (m, 1H), 1.19-1.52 (M, 5H), 1.02-1.16 (m, 1H), 0.6-0.74 (m, 3H), 0.5-0.6 (m, 1H), 0.34-0.45 (m, 1H).

LC/MS, m/z=468 [M+H]$^+$ (Calc: 467).

Example 15

(4R,4aS,6S,7R,7aR,12bS)-6-((benzylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 31); (4R,4aS,6S,7R,7aR,12bS)-6-((benzylsulfinyl)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 32); and (4R,4aS,6S,7R,7aR,12bS)-6-((benzylsulfonyl)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 67)

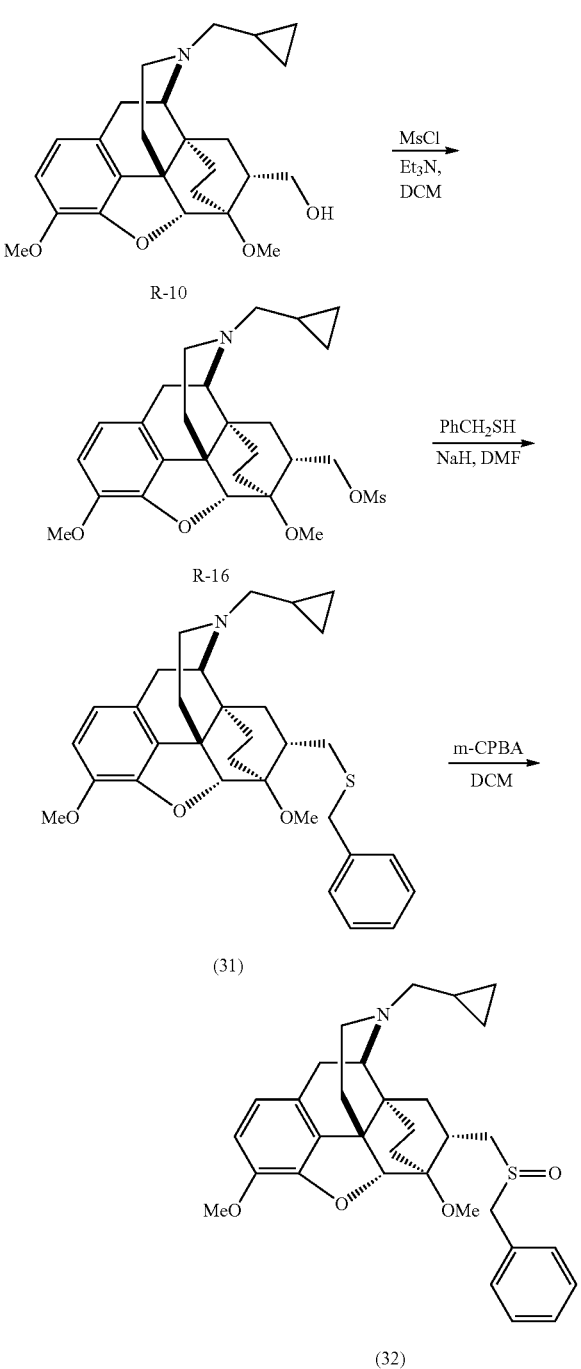

Methanesulfonyl chloride (MsCl) (147 μL, 1.5 eq.) was added to a solution of R-10 (500 mg, 1.2 mmol, 1 eq.) and triethylamine (526 μL, 3.6 mmol, 3 eq.) in DCM (25 mL) at 0° C. The reaction mixture was stirred at RT for 14 hr. The reaction mixture was then diluted with DCM and washed with water. The organic layer was washed with brine and dried over sodium sulfate. The solvent was concentrated to provide 630 mg of crude R-16. This material was used in the next step without further purification.

NaH (235 mg, 6.1 mmol, 20 eq.) was added to a solution of benzyl mercaptan (186 mg, 1.5 mmol, 5 eq.) in DMF (2 mL) and heated to 60° C. for 10 min. R-16 (150 mg, 0.3 mmol, 1 eq.) was added to the reaction mixture in one portion and heating continued for 14 hr. The reaction was then quenched with ice and extracted with DCM. The DCM was washed with 1N NaOH solution (2×10 mL), dried over anhydrous sodium sulfate and the solvent was evaporated under reduced pressure. The crude material obtained was purified by flash column chromatography (silica gel, 0-10% MeOH/DCM) to afford 12 mg of the freebase. This was dissolved in 1 mL DCM and 500 μL of TFA was added. The mixture was stirred for 30 min and evaporated to dryness. The crude was re-dissolved in water and lyophilized to give 8 mg of the TFA salt of the title compound Compound 31 TFA salt.

$^1$H NMR $\delta_H$ (300 MHz, DMSO-d$_6$) 8.40 (br. s., 1H), 7.20-7.44 (m, 5H), ), 6.86 (d, J=8.3 Hz, 1H), 6.66 (d, J=8.3 Hz, 1H), 4.73 (s, 1H), 3.82-3.90 (m, 5H), 3.79 (br. s., 3H), 3.19-3.35 (m, 4H), 3.13 (s, 3H), 2.91-3.03 (m, 1H), 2.74-2.89 (m, 3H), 2.64-2.74 (m, 3H), 2.20-2.38 (m, 4H), 1.79-1.98 (m, 1H), 0.95-1.44 (m, 6H), 0.50-0.76 (m, 3H), 0.31-0.50 (m, 2H).

LC/MS, m/z=518 [M+1](Calc: 518.6).

A solution of Compound 31 as a freebase (31 mg, 0.059 mmol, 1 eq.) in DCM (2 mL) was cooled to 0° C. m-Chloroperbenzoic acid was added in one portion to this solution and stirred at 0° C. for 30 min. The reaction mixture was diluted with DCM and washed with sodium bicarbonate solution. The organic phase was then washed with water, brine and dried over sodium sulfate. The crude material obtained was purified by flash column chromatography (silica gel, 0-10% MeOH/DCM) to afford 10 mg of Compound 32 as the freebase. The free base was then converted to its HCl salt by treating a DCM solution of the free base with 1M HCl in ether. The HCl salt was triturated with ether to give 8.5 mg of Compound 32 HCl salt as a mixture of diastereomers.

$^1$H NMR $\delta_H$ (300 MHz, DMSO-d$_6$) 8.59 (br. s., 1H), 7.21-7.51 (m, 5H), 6.89 (d, J=8.3 Hz, 1H), 6.69 (d, J=8.0 Hz, 1H), 4.87 (s, 0.6H), 4.81 (s, 0.34H), 4.27-4.33 (m, 1H), 4.01 (d, J=12.7 Hz, 1H), 3.82-3.93 (m, 1H), 3.79 (s, 3H), 3.13-3.23 (m, 3H), 2.90-3.11 (m, 2H), 2.71-2.90 (m, 3H), 2.22-2.37 (m, 1H), 1.75-1.94 (m, 1H) 1.75-1.02 (m, 6H), 0.54-0.76 (m, 2H), 0.30-0.53 (m, 2H).

LC/MS, m/z=534 [M+1]$^+$ (Calc: 534.6).

If the oxidation of Compound 31 is repeated using 10 eq. of m-chloroperbenzoic acid, (4R,4aS,6S,7R,7aR,12bS)-6-((benzylsulfonyl)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 67) is obtained after purification by reverse phase column chromatography (C18, acetonitrile/water with 0.1% TFA, 0-95%) giving Compound 67 TFA salt as a white solid.

$^1$H NMR $\delta_H$ (300 MHz, DMSO-d$_6$) 8.41 (br.s, 1H), 7.18 (br.s, 5H), 6.88 (d, J=8.22 Hz, 1H), 6.68 (d, J=8.22 Hz, 1H), 4.88 (s, 1H), 4.51-4.60 (m, 2H), 3.83-3.97 (m, 1H), 3.78 (s, 3H), 3.26-3.52 (m, 5H), 3.16 (s, 3H), 2.80-3.05 (m, 4H), 2.22-2.05 (m, 1H), 1.88-1.90 (m, 1H), 1.55-1.66 (m, 1H), 1.01-1.31 (m, 5H), 0.60-0.64 (m, 3H), 0.30-0.38 (m, 2H).

LC/MS, m/z=550 [M+H]$^+$ (Calc: 549).

Example 16

(4R,4aS,6R,7R,7aR,12bS)-6-((benzyloxy)methyl)-3-(cyclopropylmethyl)-7-methoxy-9-(2-(2-(2-methoxyethoxy)ethoxy)ethoxy)-1,2,3,4,5,6,7,7a-octahydro-4a,7-ethano-4,12-methanobenzofuro[3,2-e]isoquinoline (Compound 35); (4R,4aS,6R,7R,7aR,12bS)-9-(2,5,8,11,14-pentaoxahexadecan-16-yloxy)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline (Compound 36); 2-(((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)acetic acid (Compound 59); 2-(((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)acetamide (Compound 61); and (4R,4aS,6R,7R,7aR,12bS)-9-((2H-tetrazol-5-yl)methoxy)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline (Compound 60)

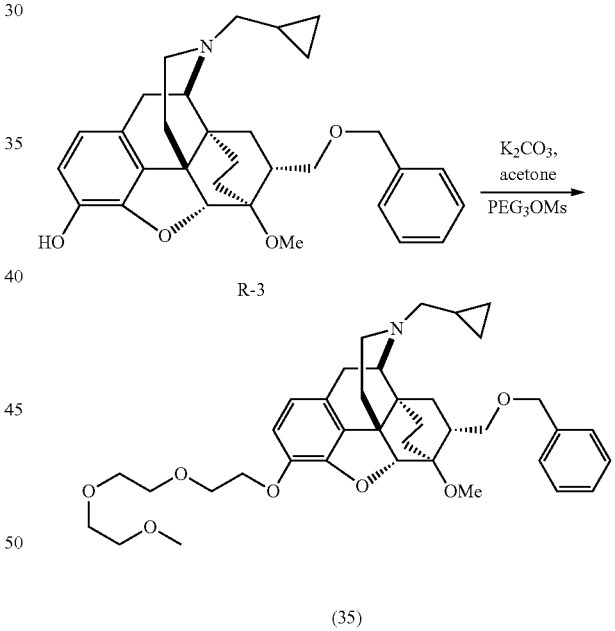

A mixture of R-3 (97 mg, 0.2 mmol), PEG$_3$OMs (96 mg, 0.4 mmol) (WO 2005/058367, Chem. Pharm. Bull. 1970, 18, 671) and K$_2$CO$_3$ (82 mg, 0.6 mmol) in anhydrous acetone (4 mL) was refluxed overnight under a nitrogen atmosphere. The reaction mixture was filtered and concentrated. Purification by reverse phase column chromatography (MeOH/water with 0.1% TFA, 0-100%) gave Compound 35 TFA salt as a white solid.

$^1$H NMR $\delta_H$ (300 MHz, DMSO-d$_6$) 8.38 (bs, 1H), 7.27 (m, 5H), 6.88 (d, J=8.25 Hz, 1H), 6.57 (d, J=8.25 Hz, 1H), 4.76 (s, 1H), 4.48-4.57 (m, 2H), 4.14 (t, 2H), 3.89 (d, J=6.87, 1H), 3.7 (t, 2H), 3.25-3.65 (m, 10H), 3.25 (s, 3H), 3.23 (s, 6H), 2.66-

2.99 (m, 4H), 2.35-2.47 (m, 1H), 2.19-2.31 (m, 1H), 1.82-1.95 (m, 1H), 1.5-1.6 (dd, 1H), 1.02-1.45 (m, 4H), 0.55-0.75 (m, 3H), 0.35-0.48 (m, 2H).

LC/MS, m/z=634 [M+1]$^+$ (Calc: 634.6).

In a similar manner (4R,4aS,6R,7R,7aR,12bS)-9-(2,5,8,11,14-pentaoxahexadecan-16-yloxy)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline (Compound 36) was prepared from R-3 using PEG$_5$OMs (WO 2005/058367, Chem. Pharm. Bull. 1970, 18, 671) rather than PEG$_3$OMs. Purification by reverse phase column chromatography (MeOH/water with 0.1% TFA, 0-100%) gave Compound 36 TFA salt as a white solid.

$^1$H NMR δ$_H$ (300 MHz, DMSO-d$_6$) 8.38 (br s, 1H), 7.41-7.25 (m, 5H), 6.90-6.84 (d, 1H), 6.68-6.64 (d, 1H), 4.76 (s, 1H), 4.57-4.47 (m, 2H), 4.17-4.11 (m, 2H), 3.91-3.87 (m, 1H), 3.80-3.68 (m, 2H), 3.65-3.45 (m, 18H), 3.45-3.18 (m, 10H), 3.00-2.60 (m, 4H), 2.45-2.20 (m, 2H), 1.92-1.85 (m, 1H), 1.61-1.53 (m, 1H), 1.50-1.00 (m, 4H), 0.73-0.61 (m, 3H), 0.44-0.35 (m, 1H).

LC/MS, m/z=721 [M+H]$^+$ (Calc: 721.6).

In a similar manner 2-(((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)acetic acid (Compound 59) was prepared from R-3 using ethyl bromoacetate rather than PEG$_3$OMs, followed by saponification using LiOH in MeOH/water, 1:1. The crude Compound 59 was then converted to its HCl salt by treating a DCM solution of the free base with 1M HCl in ether and triturated with 1:1 ether-DCM to give Compound 59 HCl salt as a white solid.

$^1$H NMR δ$_H$ (300 MHz, DMSO-d$_6$) 8.72 (br.s 1H), 7.25-7.39 (m, 5H), 6.80 (d, J=8.3 Hz, 1H), 6.65 (d, J=8.3 Hz, 1H), 4.76 (s, 1H), 4.70 (s, 2H), 4.52 (s, 2H), 3.89 (d, J=6.6 Hz, 1H), 3.56-3.69 (m, 1H), 3.41-3.53 (m, 1H), 3.24 (s, 4H), 2.70-3.04 (m, 4H), 2.17-2.42 (m, 2H), 1.87 (d, J=13.8 Hz, 1H), 1.43-1.63 (m, 1H), 1.04-1.43 (m, 4H), 0.56-0.73 (m, 2H), 0.47-0.53 (m, 2H), 0.34-0.44 (m, 1H).

LC/MS, m/z=546 [M+H]$^+$ (Calc: 546.6).

2-(((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)acetamide (Compound 61) was prepared from the above mentioned acid employing techniques familiar to one skilled in the art.

$^1$H NMR: δ$_H$ (300 MHz, DMSO-d$_6$): 8.40 (br.s., 1H), 7.22-7.45 (m, 6H), 7.13 (s, 1H), 6.96 (s, 1H), 6.85 (d, J=8.3 Hz, 2H), 6.67 (d, J=8.3 Hz, 1H), 4.78 (s, 1H), 4.35-4.55 (m, 4H), 3.89 (d, J=7.2 Hz, 1H), 3.58-3.73 (m, 1H), 3.45-3.56 (m, 1H), 3.26 (s, 4H), 3.13-3.13 (m, 1H), 2.91-3.06 (m, 1H), 2.66-2.91 (m, 2H), 2.17-2.45 (m, 2H), 1.83-1.94 (m, 1H), 1.51-1.62 (m, 1H), 1.13-1.48 (m, 3H), 1.02-1.14 (m, 1H), 0.55-0.79 (m, 3H), 0.31-0.50 (m, 2H).

LC/MS, m/z=545 [M+H]$^+$ (Calc: 544).

In a similar manner, (4R,4aS,6R,7R,7aR,12bS)-9-((2H-tetrazol-5-yl)methoxy)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline (Compound 60) was prepared by using bromo acetonitrile rather than PEG$_{30}$ Ms, followed by conversion of the nitrile to the tetrazole using TMS azide. Compound 60 was obtained as the TFA salt by reverse phase column chromatography (ACN-H$_2$O-TFA).

$^1$H NMR: δ$_H$ (300 MHz, DMSO-d$_6$): 8.42 (br.s, 1H), 7.43-7.51 (m, 5H), 6.95 (d, J=8.3 Hz, 1H), 6.67 (d, J=8.3 Hz, 1H), 5.50 (s, 2H), 4.79 (s, 1H), 4.52 (s, 2H), 3.88 (d, J=6.1 Hz, 1H), 3.30-3.72 (m, 7H), 3.23 (s, 3H), 2.65-3.04 (m, 4H), 2.19-2.44 (m, 2H), 1.74-1.95 (m, 1H), 1.51-1.61 (m, 1H), 1.27-1.28 (m, 1H), 0.98-1.49 (m, 4H), 0.55-0.74 (m, 3H), 0.31-0.48 (m, 2H).

LC/MS, m/z=570 [M+H]$^+$ (Calc: 569).

Example 17

N-(3-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)methanesulfonamide (Compound 64); 1-(3-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)urea (Compound 48); and 2-((3-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)amino)acetic acid (Compound 50)

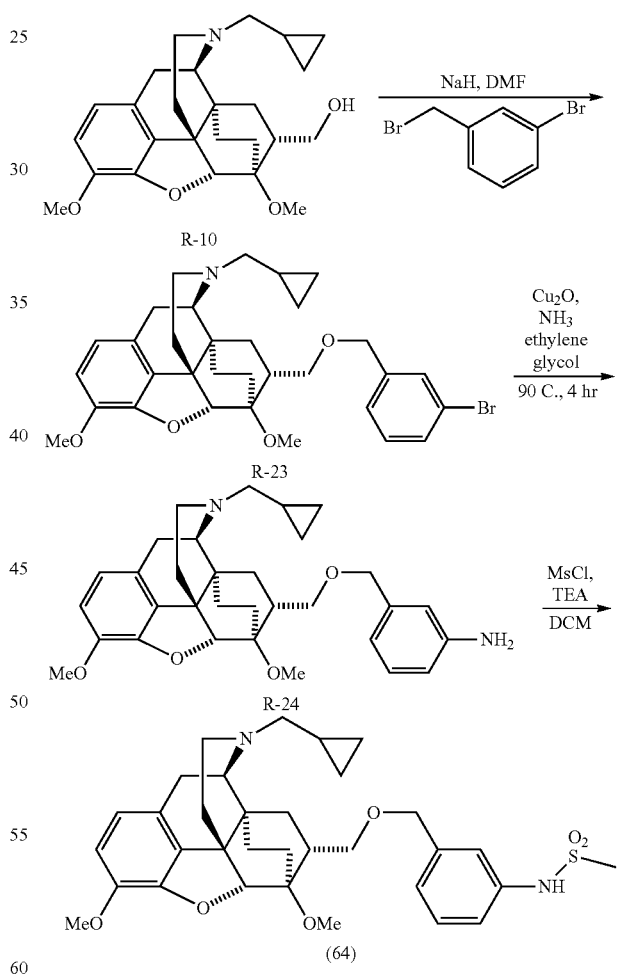

Sodium hydride (90 mg, 32.3 mmol, 60% in mineral oil) was added to an ice-cold solution of R-10 (160 mg, 0.39 mmol) in DMF (anhydrous, 3 mL) under a nitrogen atmosphere. The reaction mixture was allowed to stir at room temperature for 30 minutes. The mixture was cooled down to ice-bath temperature and 3-bromobenzyl bromide (290 mg, 1.16 mmol) was added. The resulting mixture was allowed to stir overnight at room temperature. The mixture was quenched with ice-cold water and extracted with ethyl acetate. The combined organic layers were washed with water, brine, dried over MgSO$_4$. Purification by flash column chromatography (0-15% EtOAc/DCM) afforded the aryl bromide 1.

A mixture of R-23 (109 mg, 0.188 mmol) and cuprous oxide (6 mg) in ammonia (4 mL, ~8 M in ethylene glycol) was heated in a sealed tube at 90° C. for 40 hours. The reaction mixture was partitioned between DCM and water. The aqueous layer was extracted with DCM. The combined organic layers were washed with water, brine, dried over MgSO$_4$. Purification by flash column chromatography (0-3% MeOH/DCM) afforded aryl amine R-24.

To a solution of R-24 (39 mg, 0.075 mmol) and TEA (30 µL) in DCM (10 mL) was added MsCl (17 µL, 0.22 mmol) dropwise at 0° C. The mixture was stirred at 0° C. for 1 hour and at room temperature for 4 hours. THF (5 mL), MeOH (5 mL) and potassium hydroxide (0.3 mL, 1M in water) were added. The mixture was stirred at room temperature overnight. Water was added. The aqueous layer was extracted with DCM. The combined organic layers were washed with water, brine, dried over MgSO$_4$. Purification by flash column chromatography (0-5% MeOH/DCM) gave Compound 64.

$^1$H NMR: δ$_H$ (300 MHz, DMSO-d$_6$): 9.75 (s, 1H), 7.30 (t, J=8.0 Hz, 1H), 7.21 (s, 1H), 7.13-7.02 (m, 2H), 6.73 (d, J=8.2 Hz, 1H), 6.55 (d, J=8.0 Hz, 1H), 4.52-4.40 (m, 3H), 3.75 (s, 3H), 3.58 (dd, J=9.1 Hz; 4.1 Hz, 1H), 3.50-3.40 (m, 1H), 3.21 (s, 3H), 2.98-2.92 (m, 4H), 2.89-2.54 (m, 3H), 2.28-1.95 (m, 6H), 1.56-1.25 (m, 3H), 1.18-0.97 (m, 2H), 0.82-0.68 (m, 1H), 0.62-0.40 (m, 3H), 0.11-0.03 (m, 2H).

LC/MS, m/z=595 [M+H]$^+$ (Calc: 594).

In a similar manner, 1-(3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)urea (Compound 48) was prepared by using trimethylsilyl cyanide rather than MsCl.

$^1$H NMR: δ$_H$ (300 MHz, DMSO-d$_6$): 8.53 (s, 1H), 7.42-7.25 (m, 2H), 7.18 (t, J=7.7 Hz, 1H), 6.85 (d, J=8.1 Hz, 1H), 6.73 (d, J=8.2 Hz, 1H), 6.55 (d, J=7.7 Hz, 1H), 5.82 (s, 2H), 4.55-4.39 (m, 3H), 3.75 (s, 3H), 3.58 (dd, J=9.3; 4.3 Hz, 1H), 3.48-3.38 (m, 1H), 3.21 (s, 3H), 2.98-2.54 (m, 4H), 2.28-1.95 (m, 6H), 1.56-1.25 (m, 3H), 1.18-0.97 (m, 2H), 0.85-0.70 (m, 1H), 0.61-0.40 (m, 3H), 0.15-0.03 (m, 2H).

LC/MS, m/z=560 [M+H]$^+$ (Calc: 559).

In a similar manner, 2-((3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)amino)acetic acid (Compound 50) was prepared by using methyl bromoacetare followed by saponification of the ester to the acid.

$^1$H NMR: δ$_H$ (300 MHz, DMSO-d$_6$): 7.06 (t, J=7.7 Hz, 1H), 6.83-6.72 (m, 2H), 6.64-6.55 (m, 2H), 6.50 (d, J=7.4 Hz, 1H), 5.05 (bs, 2H), 4.60 (d, J=13.2, 1H), 4.53 (s, 1H), 4.37 (d, J=13.4, 1H), 3.92-3.72 (m, 7H), 3.46-3.30 (m, 5H), 3.12-2.94 (m, 3H), 2.71-2.44 (m, 3H), 2.36-2.25 (m, 1H), 2.15-2.06 (m, 1H), 1.81-1.51 (m, 2H), 1.41-1.12 (m, 4H), 0.81-0.59 (m, 3H), 0.21-0.13 (m, 2H).

LC/MS, m/z=575 [M+H]$^+$ (Calc: 574).

Example 18

1-((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)ethane-1,2-diol (Compound 47); 3-((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)propane-1,2-diol (Compound 63); and 3-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)propane-1,2-diol (Compound 68)

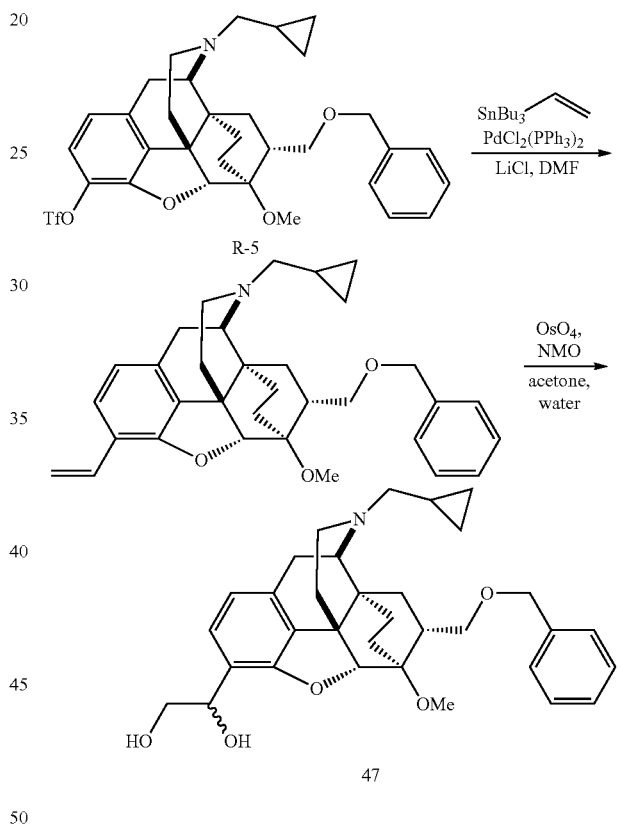

Nitrogen gas was bubbled through a mixture of R-5 (0.42 g, 0.68 mmol), vinyltributyltin (0.22 mL, 0.75 mmol), and lithium chloride (0.28 mg, 6.8 mmol) in DMF (5 mL, anhydrous) for 5 minutes. The catalyst Pd[Cl$_2$(PPh$_3$)$_2$] (0.025 g, 0.034 mmol) was added and the mixture was heated to 90° C. overnight. The reaction was quenched with water and extracted with DCM. The crude was purified by silica gel column chromatography (0-10% MeOH in DCM) to give the vinyl compound. A 4% aqueous solution of osmium tetroxide (0.38 mL, 0.06 mmol, 0.1 eq.) was added to a solution of the above vinyl compound (300 mg, 0.6 mmol, 1 eq.) in acetone-water mixture (12 mL, 5:1) followed by NMO (97 mg, 0.72 mmol, 1.2 eq.). The mixture was stirred at room temperature for 2 h. The pH was adjusted to 9 by the addition of sodium bicarbonate and extracted with DCM. The DCM extracts were washed with brine, dried over sodium sulfate and the solvent was evaporated. The crude product was purified by reverse phase column chromatography (C18, acetonitrile/water with 0.1% TFA, 0-95%) to afford Compound 47.

$^1$H NMR: $\delta_H$ (300 MHz, DMSO-$d_6$): 8.34 (br. s., 1H), 7.17-7.44 (m, 6H), 6.70 (d, J=8.0 Hz, 1H), 4.61-4.81 (m, 2H), 4.52 (d, J=25.6 Hz, 2H), 3.89 (d, J=3.9 Hz, 1H), 3.58-3.74 (m, 1H), 3.28-3.56 (m, 6H), 3.28 (s, 3H), 2.62-3.06 (m, 4H), 2.15-2.39 (m, 2H), 1.71-1.98 (m, 1H), 1.48-1.64 (m, 1H), 0.98-1.46 (m, 4H), 0.48-0.68 (m, 3H), 0.40 (m, 2H).

LC/MS, m/z=532 [M+H]$^+$ (Calc: 531).

3-((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)propane-1,2-diol (Compound 63)

Nitrogen gas was bubbled through a mixture of R-5 (0.29 g, 0.47 mmol), allyltributyltin (0.29 mL, 0.93 mmol), and lithium chloride (0.2 g, 6.8 mmol) in DMF (5 mL, anhydrous) for 5 minutes. The catalyst Pd[Cl$_2$(PPh$_3$)$_2$](0.054 g, 0.047 mmol) was added and the mixture was heated to 90 C overnight. The reaction was quenched with water and extracted with DCM. The crude was purified by silica gel column chromatography (0-10% MeOH in DCM) to give the allyl compound. A 4% aqueous solution of osmium tetroxide (0.38 mL, 0.06 mmol, 0.1 eq.) was added to a solution of the above allyl compound (0.096 g, 0.2 mmol, 1 eq.) in acetone-water mixture (12 mL, 5:1) followed by NMO (97 mg, 0.72 mmol, 1.2 eq.). The mixture was stirred at room temperature for 2 h. The pH was adjusted to 9 by the addition of sodium bicarbonate and extracted with DCM. The DCM extracts were washed with brine, dried over sodium sulfate and the solvent was evaporated. Compound 63 was converted to its HCl salt by treating with 1M HCl in ether.

$^1$H NMR: $\delta_H$ (300 MHz, DMSO-$d_6$): 8.6 (br.s, 1H), 7.20-7.50 (m, 5H), 6.94-7.09 (m, 1H), 6.64 (d, J=7.7 Hz, 1H), 4.67 (s, 1H), 4.39-4.60 (m, 3H), 3.88 (d, J=6.9 Hz, 1H), 3.53-3.77 (m, 2H), 3.43-3.55 (m, 2H), 3.25 (s, 6H), 2.74-3.03 (m, 4H), 2.59-2.75 (m, 1H), 2.25-2.39 (m, 2H), 1.67-1.97 (m, 1H), 1.50-1.62 (m, 1H), 0.95-1.42 (m, 6H), 0.33-0.73 (m, 5H).

LC/MS, m/z=546 [M+H]$^+$ (Calc: 545).

In a similar manner 3-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)propane-1,2-diol (Compound 68) was prepared using (4R,4aS,6R,7R,7aR,12bS)-6-((allyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline (R-38) as the olefin component. Purification by flash column chromatography (silica gel, 0-5% MeOH/DCM) gave Compound 68 as a white solid.

$^1$H NMR $\delta_H$ (300 MHz, DMSO-$d_6$) 6.70 (d, J=8.25 Hz, 1H), 6.55 (d, J=8.25 Hz, 1H), 4.50 (s, 1H), 3.84-3.92 (m, 1H), 3.84 (s, 3H), 3.60-3.80 (m, 3H), 3.44-3.59 (m, 3H), 3.40 (s, 3H), 2.80-3.02 (m, 4H), 2.64 (dd, J$_1$=12.06 Hz, J$_2$=5.49 Hz, 1H), 1.97-2.40 (m, 7H), 1.65 (dd, J$_1$=13.74 Hz, J$_2$=4.11 Hz, 1H), 1.34-1.50 (m, 2H), 1.25 (dd, J$_1$=13.20 Hz, J$_2$=6.33 Hz, 1H), 0.98-1.12 (m, 1H), 0.68-0.84 (m, 2H), 0.40-0.52 (m, 2H), 0.06-0.12 (m, 2H).

LC/MS, m/z=486 [M+H]$^+$ (Calc: 485).

Example 19

(4R,4aS,6R,7R,7aR,12bS)-6-((benzyloxy)methyl)-3-(cyclopropylmethyl)-9-methoxy-1,2,3,4,5,6,7,7a-octahydro-4a,7-ethano-4,12-methanobenzofuro[3,2-e]isoquinolin-7-ol (Compound 93); (4R,4aS,6R,7R,7aR,12bS)-6-((benzyloxy)methyl)-3-(cyclopropylmethyl)-9-methoxy-7-(2-(2-(2-methoxyethoxy)ethoxy)ethoxy)-1,2,3,4,5,6,7,7a-octahydro-4a,7-ethano-4,12-methanobenzofuro[3,2-e]isoquinoline (Compound 53); and (4R,4aS,6R,7R,7aR,12bS)-7-(2,5,8,11,14-pentaoxahexadecan-16-yloxy)-6-((benzyloxy)methyl)-3-(cyclopropylmethyl)-9-methoxy-1,2,3,4,5,6,7,7a-octahydro-4a,7-ethano-4,12-methanobenzofuro[3,2-e]isoquinoline (Compound 52)

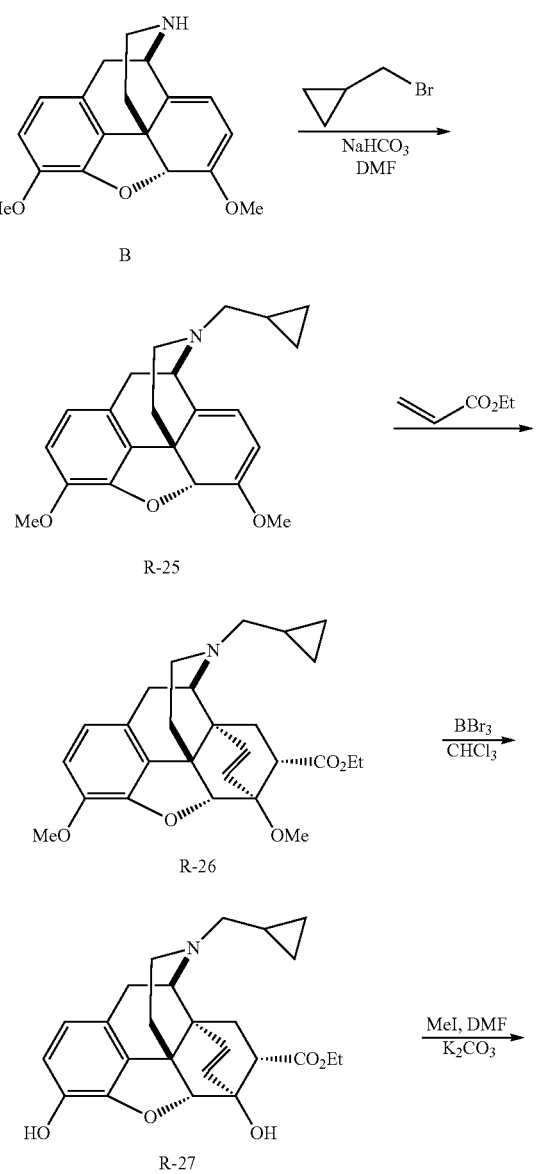

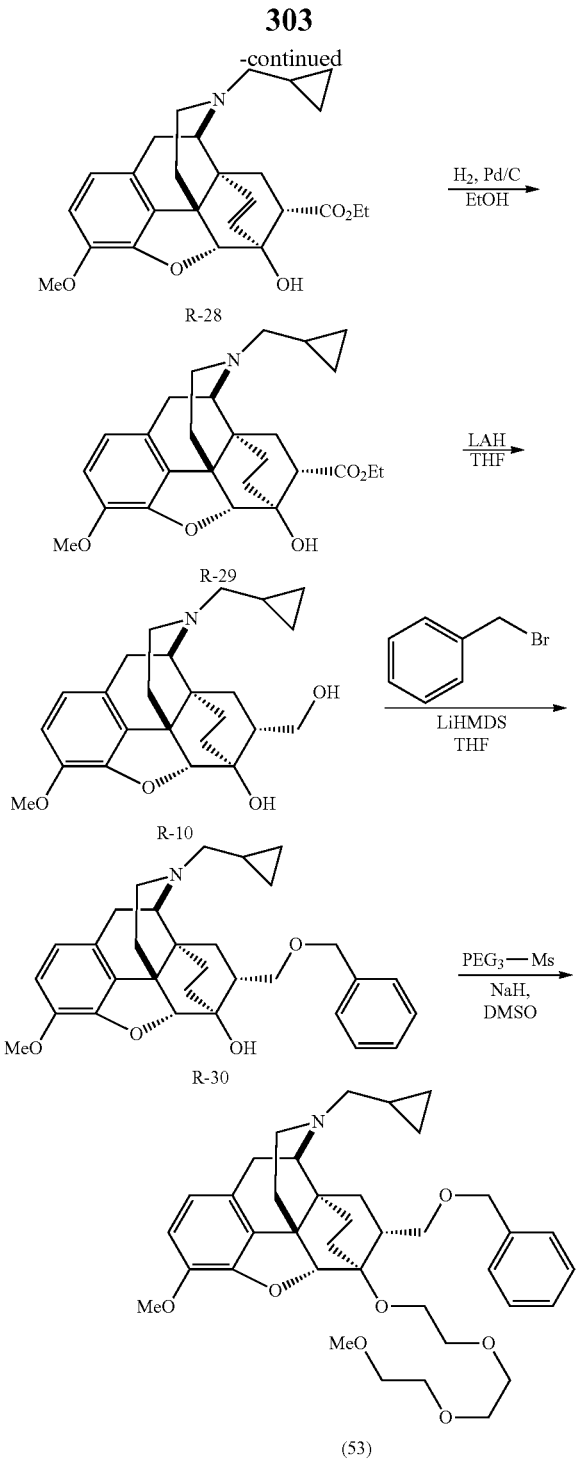

3.58 (s, 4H), 3.24 (d, J=17.9 Hz, 1H), 2.63-2.86 (m, 2H), 2.47 (d, J=6.3 Hz, 2H), 2.19 (td, J=12.4, 5.5 Hz, 1H), 1.63-1.78 (m, 1H), 0.83-0.96 (m, 1H), 0.42-0.60 (m, 2H), 0.05-0.20 (m, 2H).

A mixture of N-cyclopropylnorthebaine (R-25) (4.4 g) and ethyl acrylate (25 mL) was refluxed overnight. After cooling to room temperature the reaction mixture was concentrated and the residue was purified by silica gel column chromatography (10-20% MeOH/DCM) followed by multiple re-crystallizations to provide 1.84 g of cycloadduct R-26.

$^1$H NMR: $\delta_H$ (300 MHz, CDCl$_3$): 6.61 (d, J=8.22 Hz, 1H), 6.50 (m, J=8.22 Hz, 1H), 5.84 (d, J=8.8 Hz, 1H), 5.55 (d, J=8.8 Hz, 1H), 4.60 (d, J=1.4 Hz, 1H), 4.04-4.28 (m, 2H), 3.81 (s, 3H), 3.57 (s, 3H), 3.54 (d, J=6.6 Hz, 1H), 3.01-3.16 (m, 2H), 2.78-2.91 (m, 1H), 2.59-2.76 (m, 1H), 2.27-2.49 (m, 4H), 1.88-2.06 (m, 1H), 1.73-1.88 (m, 1H), 1.47 (dd, J=12.7, 6.3 Hz, 1H), 1.25 (t, J=7.2 Hz, 3H), 0.74-0.89 (m, 1H), 0.43-0.57 (m, 2H), 0.12 (m, 2H).

A solution of the cycloadduct R-26 (1.38 g, 3.056 mmol, 1 eq.) in chloroform (50 mL) and BBr$_3$ (3.82 g, 15.28 mmol, 5 eq.) was stirred at room temperature overnight. Ethanol (10 mL) was added to the reaction mixture followed by chloroform (50 mL) and the resulting mixture was refluxed for 30 min. At room temperature water (50 mL) was added and the two layers were separated. The organic layer was washed with water, followed by saturated sodium bicarbonate solution and brine and dried over sodium sulfate. The residue, after removing the solvent, was recrystallized from an ethyl acetate-hexane mixture to yield 950 mg of the diol. The mother liquor was further purified by silica gel column chromatography (10-20% MeOH/DCM) to provide 110 mg more of the diol R-27 (combined yield 1.06 g).

$^1$H NMR: $\delta_H$ (300 MHz, CDCl$_3$): 6.61 (d, J=7.9 Hz, 1H), 6.47 (d, J=8.0 Hz, 1H), 5.79 (d, J=8.5 Hz, 1H), 5.45 (d, J=8.8 Hz, 2H), 4.77 (s, 1H), 4.40 (s, 1H), 4.10-4.23 (m, 3H), 4.01-4.11 (m, 1H), 3.51 (d, J=6.6 Hz, 1H), 3.15-3.29 (m, 1H), 3.08 (d, J=18.4 Hz, 1H), 2.59-2.78 (m, 2H), 2.21-2.46 (m, 4H), 1.92-2.08 (m, 1H), 1.77-1.91 (m, 1H), 1.32-1.47 (m, 1H), 1.18-1.31 (m, 3H), 0.75-0.94 (m, 1H), 0.43-0.58 (m, 2H), 0.13 (d, J=5.8 Hz, 2H).

A mixture of diol R-27 (1.05 g, 2.47 mmol, 1 eq.) and potassium carbonate (3.4 g, 24.7 mmol, 10 eq.) in DMF (20 mL) was stirred at room temperature. Methyl iodide (1.2 mL, 19.76 mmol, 4 eq.) was added and the reaction mixture was stirred at room temperature overnight. Mass spectrum indicated the formation of mono and dimethylated product. To the reaction mixture was added methanol (1 mL) and the reaction mixture was stirred for 30 minutes. Ethyl acetate (30 mL) and ammonium chloride solution (1M, 30 mL) were added. The phases were separated, washed with ammonium chloride solution (1M, 10 mL), brine (10 mL), dried (MgSO$_4$) and concentrated. The residue was purified by column chromatography (10-20% MeOH/DCM) providing 1.0 g (88%) of the methyl ether R-28.

$^1$H NMR: $\delta_H$ (300 MHz, CDCl$_3$): 6.61 (d, J=8.22 Hz, 1H), 6.51 (d, J=8.22 Hz, 1H), 5.79 (d, J=8.8 Hz, 1H), 5.46 (d, J=8.8 Hz, 1H), 4.36 (d, J=1.4 Hz, 1H)), 4.10 (q, J=7.17 Hz, 2H) 3.87 (s, 3H), 3.44-3.56 (m, 2H), 2.69-2.72 (m, 2H), 2.33-2.43 (m, 4H), 1.94-2.00 (m, 1H), 1.82-1.86 (m, 1H), 1.30-1.45 (m, 1H), 1.25 (t, J=7.17 Hz, 2H), 0.62-0.84 (m, 1H), 0.37-0.52 (m, 2H), 0.02-0.19 (m, 2H).

The methyl ether R-28 (1 g) was hydrogenated in the presence of 10% Pd/C (50% wet) in ethanol using a hydrogen balloon at room temperature overnight. The catalyst was filtered through Celite and the Celite was washed with ethanol. The solvent was evaporated and crude R-29 was used as such for the next step.

$^1$H NMR: 6H (300 MHz, CDCl$_3$): 6.70 (d, J=7.95 Hz, 1H), 6.58 (d, J=8.3 Hz, 1H), 4.25 (d, J=1.9 Hz, 1H), 4.21 (m, 2H), 3.88 (s, 3H), 2.82-3.10 (m, 3H), 2.51-2.70 (m, 2H), 2.18-2.42

A mixture of northebaine (Compound B) (4.94 g, 14.83 mmols, 1 eq.), cyclopropylmethyl bromide (1.5 mL, 16.32 mmol, 1.1 eq.), NaHCO$_3$ (4.98 g, 34 mmol, 4 eq) and DMF (80 mL) was heated to 90° C. overnight. At the end of the reaction, the DMF was evaporated and the residue diluted with chloroform and washed with water. The crude material, after evaporating the chloroform, was purified by silica gel column chromatography (0-10% MeOH/DCM) to afford 3.9 g (75%) of N-cyclopropylmethylnorthebaine (R-25) as a light brown solid.

$^1$H NMR: $\delta_H$ (300 MHz, CDCl$_3$): 6.61-6.69 (m, 1H), 6.50-6.60 (m, 1H), 5.55 (d, J=6.3 Hz, 1H), 5.28 (d, J=2.8 Hz, 1H), 5.03 (d, J=6.6 Hz, 1H), 3.91 (d, J=6.9 Hz, 1H), 3.83 (s, 3H), (m, 4H), 1.87-2.17 (m, 2H), 1.56-1.77 (m, 2H), 1.28-1.42 (m, 5H), 0.55-0.70 (m, 2H), 0.36-0.53 (m, 2H), 0.03-0.19 (m, 2H).

To an ice-cold solution of the saturated ester R-29 (920 mg, 2.09 mmol, 1 eq.) in THF (100 mL) was added a 1M solution of LAH in THF (10.47 mL, 10.48 mmol, 10 eq.). The reaction mixture was stirred at ice temperature for 1 hour and then warmed to room temperature and stirred overnight. Ethyl acetate (50 mL) was added and the mixture stirred for 30 minutes then saturated ammonium chloride solution (100 mL) was added. The phases were separated and the organic layer was washed with saturated ammonium chloride solution, dried and concentrated. The residue was purified by silica gel column chromatography (10-20% MeOH/DCM) to yield 620 mg, 74% of the diol R-10.

$^1$H NMR: $\delta_H$ (300 MHz, CDCl$_3$): 6.70 (d, J=7.95 Hz, 1H), 6.58 (d, J=8.3 Hz, 1H), 4.30 (d, J=1.9 Hz, 1H), 3.99 (m, 1H), 3.88 (s, 3H), 3.58-3.46 (m, 2H), 2.82-3.10 (m, 3H), 2.62-2.64 (m, 1H), 2.18-2.42 (m, 4H), 1.87-2.17 (m, 2H), 1.56-1.77 (m, 2H), 1.28-1.42 (m, 1H), 0.957-0.93 (m, 1H), 0.55-0.70 (m, 2H), 0.36-0.53 (m, 2H), 0.03-0.19 (m, 2H).

To a solution of the diol R-10 (56 mg, 0.141 mmol, 1 eq.) in THF (10 mL) at 0° C. was added 1M solution of LiHMDS (1.8 eq.) and the mixture was stirred for 30 minutes. Benzyl bromide (1.5 eq.) was added and the reaction mixture was stirred for overnight at room temperature. Ethyl acetate (20 mL) and ammonium chloride solution (1 M, 10 mL) were added and the mixture was stirred at room temperature for 10 minutes. Organic phase was separated and the aqueous phase was extracted with ethyl acetate (10 mL). The combined organic phases were washed with brine, dried and concentrated. The residue was purified by silica gel column chromatography (10-20% MeOH/DCM) to yield 49 mg of the title compound as the freebase. This freebase was treated with 1M HCl in ether and triturated in ether-dichloromethane to provide 27 mg of Compound 93.

$^1$H NMR: $\delta_H$ (300 MHz, DMSO-d$_6$): 8.80 (m, 1H), 7.19-7.40 (m, 5H), 6.86 (d, J=8.3 Hz, 1H), 6.65 (d, J=8.3 Hz, 1H), 4.96 (s, 1H), 4.51 (s, 2H), 4.24 (s, 1H), 3.78 (m, 5H), 3.48-3.64 (m, 1H), 3.29-3.44 (m, 2H), 3.07-3.23 (m, 1H), 2.66-3.01 (m, 4H), 2.05-2.33 (m, 1H), 1.90-2.07 (m, 1H), 1.84 (d, J=12.4 Hz, 1H), 1.30-1.63 (m, 2H), 1.17-1.32 (m, 1H), 0.94-1.14 (m, 2H), 0.46-0.76 (m, 4H), 0.29-0.44 (m, 1H).

LC/MS, m/z=488 [M+H]$^+$ (Calc: 487).

To a solution of Compound 93 (21 mg, 0.043 mmol, 1 eq.) in DMSO (2 mL) at room temperature was added NaH (17.3 mg, 0.43 mmol, 10 eq.) and the suspension was stirred for 10 minutes. PEG$_3$-Ms was then added and the reaction mixture was stirred overnight at room temperature. The reaction was quenched with ice-water and extracted with chloroform. The chloroform extracts were dried over sodium sulfate and the solvent was concentrated. The crude thus obtained was purified by reverse phase column chromatography reverse phase column chromatography (C18, 0-90% acetonitrile/water with 0.1% TFA). The fractions were lyophilized to get 9 mg of Compound 53 as light brown oil.

$^1$H NMR: $\delta_H$ (300 MHz, DMSO-d$_6$): 8.09-8.51 (br.s., 1H), 7.34 (s, 5H), 6.87 (d, J=7.7 Hz, 1H), 6.67 (d, J=8.3 Hz, 1H), 4.73 (s, 1H), 4.50 (d, J=2.5 Hz, 2H), 3.88 (d, J=6.9 Hz, 1H), 3.78 (s, 3H), 3.62-3.74 (m, 2H), 3.26-3.45 (m, 15H), 3.21 (s, 3H), 2.69-2.99 (m, 4H), 2.14-2.32 (m, 1H), 1.79-1.96 (m, 1H), 1.36-1.63 (m, 1H), 0.95-1.34 (m, 6H), 0.53-0.73 (m, 3H), 0.30-0.52 (m, 2H).

LC/MS, m/z=634 [M+H]$^+$ (Calc: 633).

In a similar manner, (4R,4aS,6R,7R,7aR,12bS)-7-(2,5,8,11,14-pentaoxahexadecan-16-yloxy)-6-((benzyloxy)methyl)-3-(cyclopropylmethyl)-9-methoxy-1,2,3,4,5,6,7,7a-octahydro-4a,7-ethano-4,12-methanobenzofuro[3,2-e]isoquinoline (Compound 52) was prepared by using PEG$_5$-Ms rather than PEG$_3$-Ms. Compound 52 was obtained as the TFA salt by reverse phase column chromatography (C18, 0-90% acetonitrile/water with 0.1% TFA).

$^1$H NMR: $\delta_H$ (300 MHz, DMSO-d$_6$): 8.25 (br.s, 1H), 7.23-7.48 (m, 5H), 6.87 (d, J=8.3 Hz, 1H), 6.68 (d, J=8.5 Hz, 1H), 4.73 (s, 1H), 4.35-4.63 (m, 2H), 3.88 (d, J=6.6 Hz, 1H), 3.78 (s, 3H), 3.61-3.77 (m, 2H), 3.32-3.46 (m, 25H), 3.22 (s, 3H), 2.68-3.01 (m, 4H), 2.14-2.30 (m, 1H), 1.76-1.93 (m, 1H), 1.35-1.61 (m, 1H), 1.01-1.36 (m, 4H), 0.55-0.83 (m, 3H), 0.33-0.51 (m, 2H).

LC/MS, m/z=722 [M+H]$^+$ (Calc: 721).

Example 20

(S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-amino-3-phenylpropanoate (Compound 84); (2S,3S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-amino-3-methylpentanoate (Compound 85); (S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-aminopropanoate (Compound 86); (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-phenylpropanoate (Compound 49); (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-4-methylpentanoate (Compound 82); (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2,5-diamino-5-oxopentanoate (Compound 83); (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-aminopropanoate (Compound 77); (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-hydroxypropanoate (Compound 78); (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-methylbutanoate (Compound 79); and (2S,3S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-methylpentanoate (Compound 80)

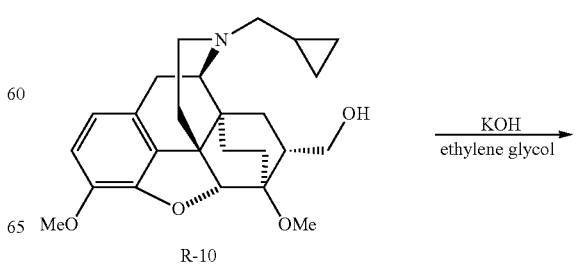

R-10

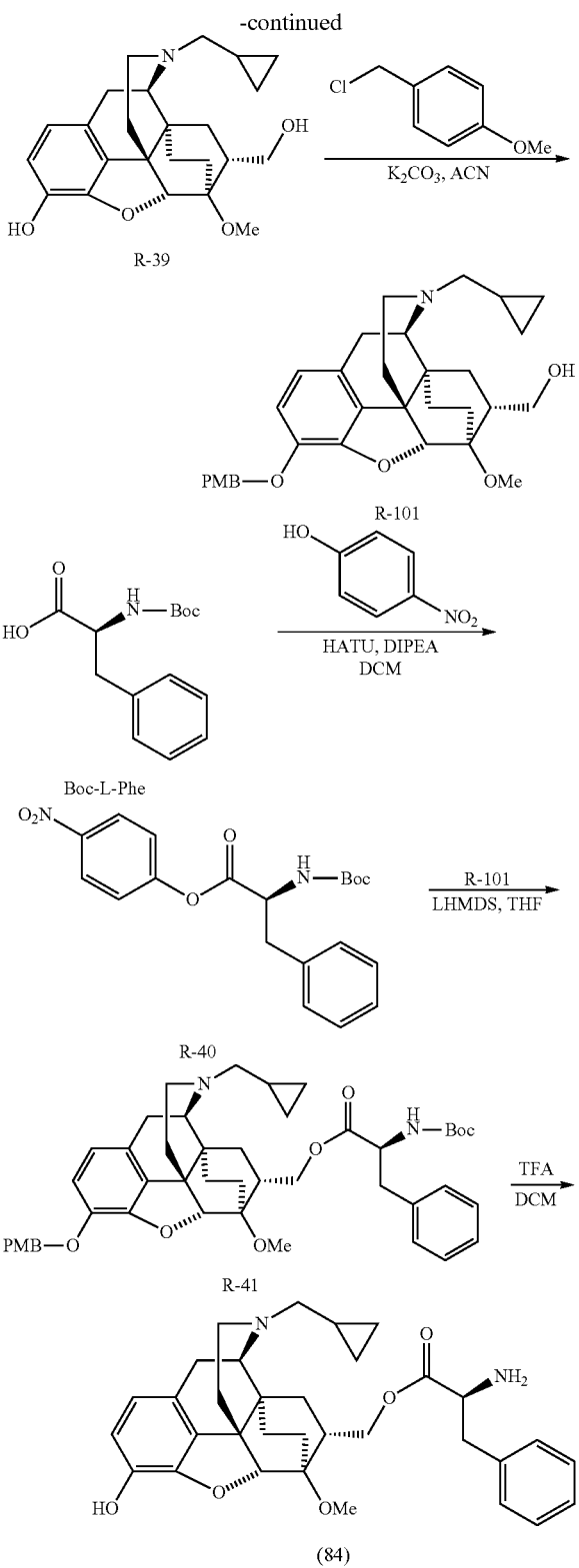

filtered and the filtrate was concentrated and purified by flash column chromatography (silica gel, 0-10% MeOH/DCM) to yield 319 mg of R-101 as foam.

$^1$H NMR $\delta_H$ (300 MHz, CDCl$_3$) 7.29-7.41 (m, 2H), 6.81-6.93 (m, 2H), 6.74 (d, J=8.0 Hz, 1H), 6.50 (d, J=8.3 Hz, 1H), 5.11 (m, 2H), 4.48 (d, J=1.9 Hz, 1H), 3.85-4.02 (m, 2H), 3.80 (s, 3H), 3.72 (d, J=9.9 Hz, 1H), 3.49 (s, 4H), 2.79-3.08 (m, 3H), 2.56-2.72 (m, 1H), 2.15-2.42 (m, 3H), 2.00-2.14 (m, 2H), 1.42-1.79 (m, 3H), 0.88-1.09 (m, 1H), 0.64-0.83 (m, 2H), 0.36-0.57 (m, 2H), 0.03-0.15 (m, 2H).

To a mixture of Boc-L-phenylalanine (1.33 g, 5 mmol), p-nitrophenol (PNP) (838 mg, 6 mmol) and DIPEA (1.75 ml, 10 mmol) in anhydrous DCM (10 mL) was added HATU (2.28 g, 6 mmol) in one portion under a nitrogen atmosphere. The resulting mixture was stirred at room temperature for 4 h. After aqueous work-up the crude product was purified by flash column chromatography (silica gel, 0-20% EtOAc/hexanes) to give Boc-L-phenylalanine-PNP ester (R-40). To an ice-cooled mixture of R-101 (54 mg, 0.1 mmol) and R-40 (77 mg, 0.2 mmol) in anhydrous THF (2 mL) was added LiHMDS (0.15 mL of 1M solution in THF, 0.15 mmol) dropwise under a nitrogen atmosphere. The resulting mixture was stirred at the same temperature for 2 h. The reaction mixture was quenched with saturated ammonium chloride solution and extracted with DCM. The combined organic extracts were dried over MgSO$_4$, filtered and concentrated. The crude material was purified by flash column chromatography (silica gel, 0-5% MeOH/DCM) to give R-41.

To an ice-cooled solution of R-41 (34 mg, 0.045 mmol) in anhydrous DCM (2 mL) was added TFA (2 mL). The resulting mixture was stirred at the same temperature for 2 h. All the volatiles were removed and the crude product purified by reverse phase column chromatography (C18, acetonitrile/water with 0.1% TFA, 0-95%) to give Compound 84 TFA salt as a white solid.

$^1$H NMR $\delta_H$ (300 MHz, DMSO-d$_6$) 9.35 (br. s., 1H), 8.72 (br. s, 1H), 8.58 (br. s, 3H), 7.37-7.21 (m, 5H), 6.69 (d, J=8.0 Hz, 1H), 6.56 (d, J=8.0 Hz, 1H), 4.67 (s, 1H), 4.34 (dd, J=4.3 and 10.8 Hz, 1H), 4.30-4.18 (m, 1H), 3.92 (dd, J=8.2 and 10.7 Hz 1H), 3.81 (d, J=5.5 Hz, 1H), 3.41-3.21 (m, 6H), 3.20-2.93 (m, 3H), 2.92-2.74 (m, 2H), 2.72-2.62 (m, 1H), 2.36-2.14 (m, 2H), 1.91-1.82 (m, 1H), 1.32-0.99 (m, 5H), 0.80-0.56 (m, 3H), 0.52-0.34 (m, 2H).

LC/MS, m/z=545 [M+H]$^+$ (Calc: 544).

In a similar manner (2S,3S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-amino-3-methylpentanoate (Compound 85) was prepared from R-101 using Boc-L-isoleucine rather than Boc-L-phenylalanine. Purification by reverse phase column chromatography (C18, acetonitrile/water with 0.1% TFA, 0-95%) gave Compound 85 TFA salt as a white solid.

$^1$H NMR $\delta_H$ (300 MHz, DMSO-d$_6$) 9.36 (br. s., 1H), 8.68 (br. s., 1H), 8.44 (br. s., 3H), 6.70 (d, J=8.0 Hz, 1H), 6.58 (d, J=8.0 Hz, 1H), 4.75 (s, 1H), 4.39 (dd, J=10.7, 4.1 Hz, 1H), 4.22-4.05 (m, 1H), 3.99 (d, J=1.4 Hz, 1H), 3.86 (d, J=6.1 Hz, 1H), 3.38-3.19 (m, 6H), 3.01-2.70 (m, 4H), 2.36-2.14 (m, 1H), 2.03-1.80 (m, 2H), 1.55-1.14 (m, 6H), 0.98-1.13 (m, 1H), 0.98-0.84 (m, 6H), 0.78-0.32 (m, 5H).

LC/MS, m/z=511 [M+H]$^+$ (Calc: 510).

In a similar manner (S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-aminopropanoate (Compound 86) was prepared from R-101 using Boc-L-alanine rather than Boc-L-phenylalanine. Purification by reverse phase column R-39 (0.415 g, 1.04 mmol, 1 eq.) (prepared in an analogous manner from R-10 and KOH in ethylene glycol as described in WO 2010/014229) and potassium carbonate (1.02 g, 3.03 mmol, 3 eq.) were suspended in ACN (10 mL) and 4-methoxybenzyl chloride (0.141 mL, 1.04 mmol, 1 eq.) was added dropwise to the suspension at room temperature. The mixture was stirred at room temperature overnight. The solids were chromatography (C18, acetonitrile/water with 0.1% TFA, 0-95%) gave Compound 86 TFA salt as a white solid.

$^1$H NMR $\delta_H$ (300 MHz, DMSO-d$_6$) 9.33 (bs, 1H), 8.59 (bs, 1H), 8.36 (bs, 3H), 6.69 (d, J=8.25 Hz, 1H), 6.56 (d, J=8.25 Hz, 1H), 4.74 (s, 1H), 4.34 (dd, J$_1$=10.71 Hz, J$_2$=3.84 Hz, 1H), 4.05-4.23 (m, 2H), 3.85 (d, J=6.06 Hz, 1H), 3.20-3.44 (m, 3H), 3.39 (s, 3H), 2.90-3.05 (m, 1H), 2.69-2.90 (m, 3H), 2.15-2.40 (m, 1H), 1.82-1.95 (m, 1H), 1.14-1.49 (m, 5H), 1.42 (d, J=7.14 Hz, 3H), 0.98-1.10 (m, 1H), 0.53-0.73 (m, 3H), 0.35-0.47 (m, 2H).

LC/MS, m/z=469 [M+H]$^+$ (Calc: 468).

In a similar manner (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-phenylpropanoate (Compound 49) was prepared from R-10 rather than R-101. Purification by reverse phase column chromatography (C18, acetonitrile/water with 0.1% TFA, 0-95%) gave Compound 49 TFA salt as a white solid.

$^1$H NMR $\delta_H$ (300 MHz, DMSO-d$_6$) 8.69 (bs, 1H), 8.54 (bs, 3H), 7.28-7.38 (m, 3H), 7.22-7.24 (m, 2H), 6.89 (d, J=8.25 Hz, 1H), 6.70 (d, J=8.25 Hz, 1H), 4.72 (s, 1H), 4.34 (dd, J$_1$=10.74 Hz, J$_2$=4.11 Hz, 1H), 4.18-4.28 (m, 1H), 3.80-3.92 (m, 3H), 3.78 (s, 3H), 3.30-3.45 (m, 2H), 3.18-3.28 (m, 2H), 3.22 (s, 3H), 2.94-3.18 (m, 3H), 2.75-2.92 (m, 2H), 2.58-2.74 (m, 1H), 2.28-2.40 (m, 1H), 2.13-2.28 (m, 1H), 1.82-1.94 (m, 1H), 1.0-1.36 (m, 5H), 0.55-0.78 (m, 3H), 0.35-0.5 (m, 2H).

LC/MS, m/z=559 [M+H]$^+$ (Calc: 558).

In a similar manner (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-4-methylpentanoate (Compound 82) was prepared from R-10 rather than R-101 and using Boc-L-leucine rather than Boc-L-phenylalanine. Purification by reverse phase column chromatography (C18, acetonitrile/water with 0.1% TFA, 0-95%) gave Compound 82 TFA salt as a white solid.

$^1$H NMR $\delta_H$ (300 MHz, DMSO-d$_6$) 8.69 (bs, 1H), 8.45 (bs, 3H), 6.89 (d, J=8.25 Hz, 1H), 6.70 (d, J=8.25 Hz, 1H), 4.79 (s, 1H), 4.38 (dd, J=10.41 Hz, J$_2$=3.87 Hz, 1H), 4.11 (dd, J$_1$=8.52 Hz, J$_2$=2.19 Hz, 1H), 3.93-4.05 (m 1H), 3.85-3.91 (m, 1H), 3.79 (s, 3H), 3.15-3.52 (m, 6H), 2.75-3.00 (m, 4H), 2.19-2.35 (m, 1H), 1.85-1.95 (m, 1H), 1.57-1.80 (m, 3H), 1.25-1.48 (m, 3H), 1.0-1.25 (m, 2H), 0.91 (d, J=2.49 Hz, 3H), 0.88 (d, J=2.49 Hz, 3H), 0.32-0.75 (m, 5H).

LC/MS, m/z=525 [M+H]$^+$ (Calc: 524).

In a similar manner (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2,5-diamino-5-oxopentanoate (Compound 83) was prepared from R-10 rather than R-101 and using Boc-L-glutamine rather than Boc-L-phenylalanine. Purification by reverse phase column chromatography (C18, acetonitrile/water with 0.1% TFA, 0-95%) gave Compound 83 TFA salt as a white solid.

$^1$H NMR $\delta_H$ (300 MHz, DMSO-d$_6$) 8.60 (bs, 1H), 8.47 (bs, 3H), 7.42 (s, 1H), 6.98 (s, 1H), 6.89 (d, J=8.25 Hz, 1H), 6.69 (d, J=8.25 Hz, 1H), 4.79 (s, 1H), 4.38 (dd, J=10.98 Hz, J$_2$=1.47 Hz, 1H), 4.05-4.17 (m, 2H), 3.87 (d, J=6.3 Hz, 1H), 3.78 (s, 3H), 3.22-3.42 (m, 6H), 2.94-3.08 (m 1H), 2.68-2.92 (m, 3H), 2.15-2.37 (m, 3H), 1.85-2.12 (m, 3H), 1.12-1.52 (m, 5H), 0.98-1.10 (m, 1H), 0.55-0.72 (m, 3H), 0.35-0.48 (m, 2H).

LC/MS, m/z=540 [M+H]$^+$ (Calc: 539).

In a similar manner (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-aminopropanoate (Compound 77) was prepared from R-10 rather than R-101 and using Boc-L-alanine rather than Boc-L-phenylalanine. Purification by reverse phase column chromatography (C18, acetonitrile/water with 0.1% TFA, 0-95%) gave Compound 77 TFA salt as a white solid.

$^1$H NMR $\delta_H$ (300 MHz, CDCl$_3$) 8.73 (bs, 1H), 8.38 (bs, 3H), 6.90 (d, J=8.25 Hz, 1H), 6.70 (d, J=8.25 Hz, 1H), 4.79 (s, 1H), 4.32-4.37 (m, 1H), 4.06-4.21 (m, 2H), 3.88 (d, J=6.87 Hz, 1H), 3.79 (s, 3H), 3.22-3.42 (m, 5H), 3.29 (s, 3H), 2.95-3.06 (m, 1H), 2.74-2.91 (m, 3H), 2.18 (m, 1H), 1.88-1.96 (m, 1H), 1.32-1.48 (m, 3H), 1.42 (d, J=7.14 Hz, 3H), 1.12-1.28 (m, 2H), 1.0-1.11 (m, 1H), 0.55-0.72 (m, 3H), 0.34-0.48 (m, 2H).

LC/MS, m/z=483 [M+H]$^+$ (Calc: 482).

In a similar manner (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-hydroxypropanoate (Compound 78) was prepared from R-10 using Boc-O-benzyl-L-serine rather than Boc-L-phenylalanine. Purification by reverse phase column chromatography (C18, acetonitrile/water with 0.1% TFA, 0-95%) gave Compound 78 TFA salt as a white solid.

$^1$H NMR $\delta_H$ (300 MHz, DMSO-d$_6$) 8.69 (bs, 1H), 8.43 (bs, 3H), 6.90 (d, J=8.25 Hz, 1H), 6.70 (d, J=8.25 Hz, 1H), 5.65 (bs, 1H), 4.78 (s, 1H), 4.39 (dd, J$_1$=10.78 Hz, J$_2$=4.14 Hz, 1H), 4.10-4.17 (m, 2H), 3.75-3.90 (m, 6H), 3.20-3.45 (m, 6H), 2.95-3.05 (m, 1H), 2.70-2.92 (m, 3H), 2.18-2.32 (m, 1H), 1.92 (d, J=13.47 Hz, 1H), 1.28-1.51 (m, 3H), 1.0-1.22 (m, 2H), 0.55-0.75 (m, 3H), 0.35-0.5 (m, 2H).

LC/MS, m/z=499 [M+H]$^+$ (Calc: 498).

In a similar manner (S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-methylbutanoate (Compound 79) was prepared from R-10 using Boc-L-valine rather than Boc-L-phenylalanine. Purification by reverse phase column chromatography (C18, acetonitrile/water with 0.1% TFA, 0-95%) gave Compound 79 TFA salt as a white solid.

$^1$H NMR $\delta_H$ (300 MHz, DMSO-d$_6$) 8.61 (bs, 1H), 8.39 (bs, 3H), 6.89 (d, J=7.95 Hz, 1H), 6.70 (d, J=7.95 Hz, 1H), 4.80 (s, 1H), 4.38 (dd, J=10.71 Hz, J$_2$=4.11 Hz, 1H), 4.17 (t, J=9.6 Hz, 1H), 3.87-3.92 (m, 2H), 3.79 (s, 3H), 3.20-3.47 (m, 6H), 2.95-3.05 (m, 1H), 2.70-3.0 (m, 4H), 2.10-2.32 (m, 2H), 1.91 (d, J=13.47 Hz, 1H), 1.28-1.47 (m, 3H), 1.12-1.24 (m, 1H), 1.0-1.1 (m, 1H), 1.0 (d, J=6.87 Hz, 3H), 0.98 (d, J=6.87 Hz, 3H), 0.52-0.75 (m, 3H), 0.35-0.5 (m, 2H).

LC/MS, m/z=511 [M+H]$^+$ (Calc: 510).

In a similar manner (2S,3S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-methylpentanoate (Compound 80) was prepared from R-10 using Boc-L-isoleucine rather than Boc-L-phenylalanine. Purification by reverse phase column chromatography (C18, acetonitrile/water with 0.1% TFA, 0-95%) gave Compound 80 TFA salt as a white solid.

$^1$H NMR $\delta_H$ (300 MHz, DMSO-d$_6$) 8.63 (bs, 1H), 8.41 (bs, 3H), 6.89 (d, J=7.95 Hz, 1H), 6.70 (d, J=7.95 Hz, 1H), 4.80 (s, 1H), 4.39 (dd, J$_1$=10.71 Hz, J$_2$=4.11 Hz, 1H), 4.13 (t, J=9.63 Hz, 1H), 3.93-4.02 (m, 1H), 3.89 (d, J=6.6 Hz, 1H), 3.79 (s, 3H), 3.39-3.56 (m, 1H), 3.18-3.29 (m, 5H), 2.75-2.95 (m, 4H), 2.18-2.34 (m, 1H), 1.84-1.98 (m, 2H), 1.27-1.50 (m, 5H), 1.13-1.24 (m, 1H), 1.0-1.1 (m 1H), 0.88-0.96 (m, 7H), 0.63-0.75 (m, 2H), 0.53-0.62 (m, 1H), 0.34-0.5 (m, 2H).

LC/MS, m/z=525 [M+H]$^+$ (Calc: 524).

Example 21

(4R,4aS,6S,7S,7aS,12bS)-6-((benzyloxy)methyl)-3-(cyclopropylmethyl)-9-methoxy-7-phenyl-1,2,3,4,5,6,7,7a-octahydro-4a,7-ethano-4,12-methanobenzofuro[3,2-e]isoquinoline (Compound 51); N-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)-N-(methylsulfonyl)methanesulfonamide (Compound 62); N-(3-(((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)acetamide (Compound 72); N-(3-(((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)benzamide (Compound 74); and 1-(3-(((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)-3-methylurea (Compound 91)

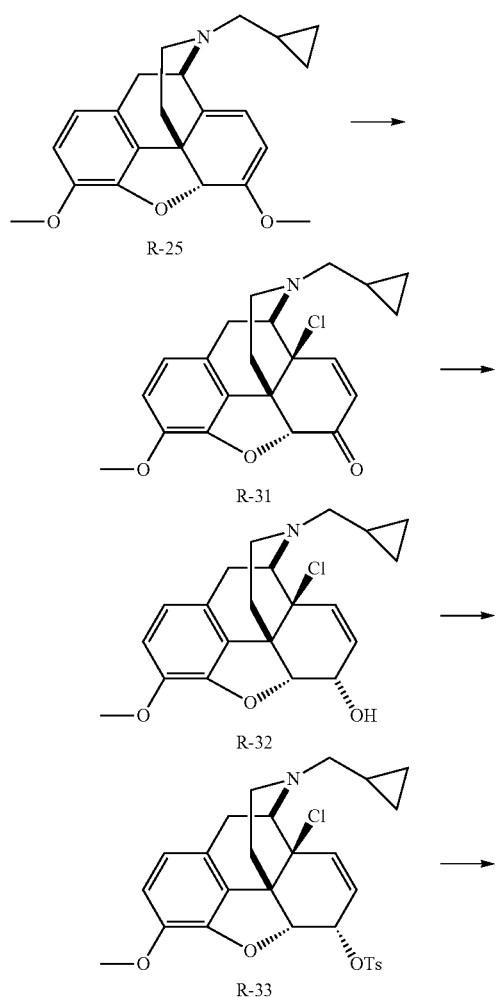

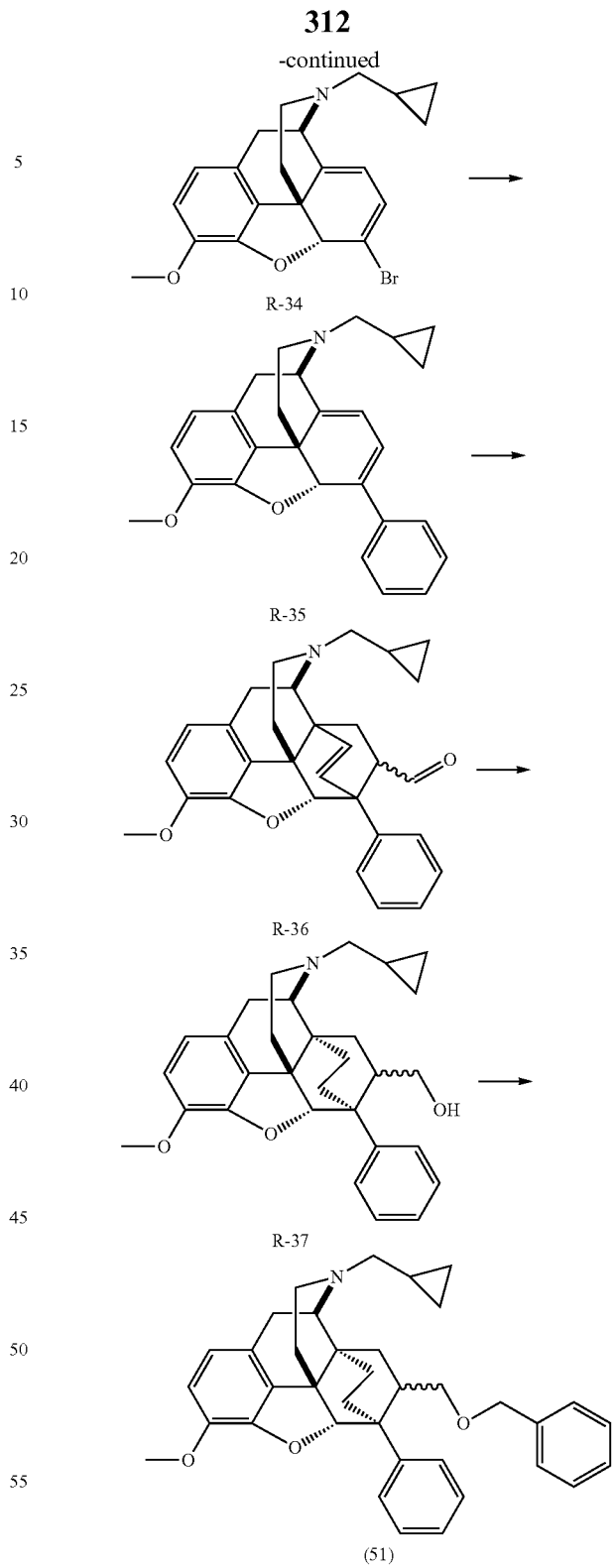

R-25, [Example 20](2.3 g, 6.6 mmol, 1 eq.) was suspended in a mixture of acetone and water (21 mL, 2:1). To this was added a solution of N-chlorosuccinimide (915 mg, 6.88 mmol, 1.05 eq.) in a mixture of acetone and water (42 mL, 2:1) and stirred for 15 minutes. After which, 100 mL of water was added and the suspension was kept in ice for 1 hr. The reaction mixture was extracted with chloroform (2×100 mL)

and dried over sodium sulfate. The solvent was evaporated and the crude R-31 (1.14 g, 47%) was used without further purifications to the next step.

$^1$H NMR: $\delta_H$ (300 MHz, CDCl$_3$): 6.82 (d, J=9.9 Hz, 1H), 6.69 (d, J=8.25 Hz, 1H), 6.59 (d, J=8.25 Hz, 1H), 6.07 (d, J=9.9 Hz, 1H), 4.69 (s, 1H), 3.83 (s, 3H), 3.63 (d, J=5.5 Hz, 1H), 3.03-3.22 (m, 1H), 2.55-2.90 (m, 3H), 2.20-2.53 (m, 3H), 1.65-1.83 (m, 1H), 0.81-1.01 (m, 1H), 0.47-0.67 (m, 2H), 0.08-0.22 (m, 2H).

A solution of R-31 (1.14 g, 3.07 mmol, 1 eq.) was prepared in methanol (10 mL). Sodium borohydride (290 mg, 7.6 mmol, 2.5 eq.) dissolved in water (1.7 mL) was added and stirred for 10-15 minutes. Water (10 mL) was then added and stirring was continued for another 10 minutes. The reaction mixture was then extracted with dichloromethane, (2×50 mL) washed with brine, and dried over sodium sulfate. The solvent was evaporated to yield 1.05 g (92%) of R-32. No purification was attempted on this crude and this was used for the next step.

$^1$H NMR: $\delta_H$ (300 MHz, CDCl$_3$): 6.66-6.72 (d, 1H), 6.46-6.61 (d, 1H), 5.79-5.95 (m, 1H), 5.63-5.75 (m, 1H), 4.88 (dd, J=6.9, 1.1 Hz, 1H), 4.56-4.71 (m, 1H), 3.83 (s, 3H), 3.68 (d, J=5.8 Hz, 1H), 3.11 (d, J=18.4 Hz, 1H), 2.90-3.01 (m, 1H), 2.72-2.84 (m, 1H), 2.56-2.70 (m, 3H), 2.22-2.51 (m, 3H), 1.77 (dd, J=12.7, 2.2 Hz, 1H), 0.77-0.97 (m, 1H), 0.44-0.64 (m, 2H), 0.05-0.23 (m, 2H).

To a solution of R-32 (1.05 g, 2.8 mmol, 1 eq.) in pyridine (5 mL) at ice temperature was added a solution of tosyl chloride (644 mg, 3.37 mmol, 1.2 eq.) in pyridine (2 mL) and the mixture kept in ice for 2 h. The reaction mixture was then kept in a refrigerator for 40 h. The reaction mixture was then added to saturated sodium bicarbonate solution (200 mL) and extracted with chloroform (2×100 mL). The chloroform extracts were washed with brine, dried over sodium sulfate and the solvent was evaporated to yield 1.44 g of R-33 in quantitative yield.

$^1$H NMR: $\delta_H$ (300 MHz, CDCl$_3$): 8.61 (dd, 1H), 7.84-7.97 (m, 2H), 7.35 (d, J=8.3 Hz, 2H), 6.62 (d, J=8.0 Hz, 1H), 6.48 (d, J=8.3 Hz, 1H), 5.62-5.86 (m, 2H), 5.29-5.40 (m, 1H), 4.85 (dd, J=6.9, 1.1 Hz, 1H), 3.83 (s, 3H), 3.65 (d, J=5.5 Hz, 1H), 3.07 (d, J=18.4 Hz, 1H), 2.66-2.87 (m, 1H), 2.47-2.66 (m, 2H), 2.45 (s, 3H), 2.14-2.39 (m, 3H), 1.62-1.83 (m, 1H), 0.71-0.98 (m, 1H), 0.36-0.69 (m, 2H), 0.07-0.23 (m, 2H).

A mixture of R-33 (1.41 g, 2.68 mmol, 1 eq.), lithium bromide (1.163 g, 13.4 mmol, 5 eq.) and DMF (25 mL) was heated to 100° C. for overnight. After cooling down to room temperature, the reaction mixture was diluted with water (40 mL) and the pH was adjusted to 8 using ammonium hydroxide (28%, ~1.5 mL). The reaction mixture was extracted with chloroform (2×100 mL), dried over sodium sulfate and the solvent was evaporated. The crude was purified by silica gel column chromatography using dichloromethane and methanol to yield 770 mg (72%) of R-34 that was contaminated with a small amount of DMF.

$^1$H NMR: $\delta_H$ (300 MHz, CDCl$_3$): 6.65-6.74 (m, 2H), 6.45-6.62 (m, 2H), 6.32 (d, J=6.3 Hz, 1H), 5.47 (d, J=6.1 Hz, 1H), 5.37 (s, 1H), 3.93 (d, J=6.9 Hz, 1H), 3.88 (s, 4H), 3.26 (d, J=17.9 Hz, 1H), 2.91 (d, J=22.0 Hz, 3H), 2.61-2.83 (m, 2H), 2.47 (d, J=6.3 Hz, 2H), 2.13-2.32 (m, 1H), 1.60-1.81 (m, 2H), 0.81-0.98 (m, 1H), 0.46-0.65 (m, 2H), 0.09-0.22 (m, 2H).

A mixture of R-34 (390 mg, 0.98 mmol, 1 eq.), phenyl boronic acid (119 mg, 0.98 mmol, 1 eq.), barium hydroxide octahydrate (308 mg, 0.98 mmol, 1 eq.), water (2.5 mL), and dioxane (10 mL) was degassed for 10 minutes. The catalyst Pd[(PPh$_3$)$_2$Cl$_2$](34 mg, 0.05 eq.) was then added and the mixture was heated to reflux for 1 h. The solvent was evaporated and the crude was purified by silica gel column chromatography to yield 340 mg (80%) of R-35, contaminated with a small amount of P(O)Ph$_3$.

$^1$H NMR: $\delta_H$ (300 MHz, CDCl$_3$): 7.63 (m, 5H), 6.53-6.71 (m, 2H), 6.39 (d, J=5.2 Hz, 1H), 5.96 (s, 1H), 5.79 (d, J=6.1 Hz, 1H), 3.99 (d, J=6.9 Hz, 1H), 3.75 (s, 3H), 3.31 (d, J=17.9 Hz, 1H), 2.69-3.02 (m, 4H), 2.51 (d, J=6.6 Hz, 2H), 2.20-2.37 (m, 1H), 1.79-1.89 (m, 1H), 0.83-1.03 (m, 1H), 0.50-0.61 (m, 2H), 0.08-0.25 (m, 2H).

A suspension of R-35 (340 mg) in acrolein (10 ml) was heated to reflux temperature (55-60)° C. overnight. Excess acrolein was evaporated and the residue was purified by silica gel column chromatography using dichloromethane-methanol to yield 447 mg of impure R-36 which was used in the next step without further purification.

$^1$H NMR: $\delta_H$ (300 MHz, CDCl$_3$): 9.11 (d, J=3.4 Hz, 1H), 7.3 (m, 5H), 6.49-6.68 (m, 2H), 6.16-6.27 (m, 1H), 5.83 (d, J=8.5 Hz, 1H), 4.58 (d, J=1.1 Hz, 1H), 3.75 (s, 3H), 2.98-3.15 (m, 3H), 2.68-2.85 (m, 2H), 2.35-2.57 (m, 3H), 2.02-2.16 (m, 5H), 0.76-0.98 (m, 1H), 0.41-0.64 (m, 2H), 0.15 (d, J=5.0 Hz, 2H)

A mixture of compound R-36 (440 mg) and 10% Pd/C (100 mg, 50% wet) in a mixture of ethanol and THF (1:1, 10 ml) was stirred under H$_2$ (1 atm.) overnight. MS showed the reduction of the double bond and partial reduction of the aldehyde. The reaction mixture was filtered through Celite and the Celite was washed with ~20 mL of ethanol and THF (1:1). NaBH$_4$ (92 mg, 2.5 eq.) was added (carefully!) to this filtrate and the reaction mixture stirred at room temperature overnight. 15 mL of 25% NH$_4$OAc was added (slowly!) and the reaction mixture stirred for 2 hours. The reaction mixture was extracted with ethyl acetate, washed with brine, dried over Na$_2$SO$_4$ and the solvent was evaporated. The residue was purified by silica gel column chromatography multiple times using DCM-MeOH to yield 380 mg of slightly impure alcohol R-37.

$^1$H NMR: $\delta_H$ (300 MHz, CDCl$_3$): 7.53 (m, 5H), 6.63-6.75 (m, 1H), 6.51-6.62 (m, 1H), 4.71 (s, 1H), 3.70-3.73 (s, 1H), 3.57-3.66 (m, 2H), 3.22-3.43 (m, 3), 2.58-2.77 (m, 3H), 2.39-2.54 (m, 1H), 2.20-2.37 (m, 1H), 1.56-1.76 (m, 3H), 1.25-1.47 (m, 1H), 1.04-1.21 (m, 1H), 0.74-1.03 (m, 2H), 0.46-0.62 (m, 2H), 0.11-0.32 (m, 2H)

Sodium hydride (0.109 g, 10 eq.) was added to an ice-cold solution of R-37 (0.125 g, 1 eq.) in DMF (anhydrous, 5 mL) under nitrogen atmosphere. The reaction mixture was allowed to stir at room temperature for 30 minutes and benzyl bromide (0.133 mL, 4 eq.) was added. The resulting mixture was allowed to stir overnight at room temperature. The mixture was quenched with ice-cold water and extracted with chloroform. The crude material was purified by column chromatography eluting with gradient of dichloromethane in methanol (0-100%) to obtain Compound 51 (0.099 g, 66% yield). The freebase was converted to its HCl salt by treating a dichloromethane solution of the freebase with 1M HCl in ether.

$^1$H NMR: $\delta_H$ (300 MHz, DMSO-d$_6$): 8.79 (br.s, 1H), 7.16-7.41 (m, 10), 6.83 (d, J=8.3 Hz, 1H), 6.68 (d, J=8.3 Hz, 1H), 4.92 (s, 1H), 3.95 (d, J=6.1 Hz, 1H), 3.65 (s, 3H), 3.30-3.46 (m, 3H), 3.15-3.29 (m, 3H), 2.80-3.09 (m, 5H), 1.80-2.02 (m, 2H), 1.46-1.59 (m, 1H), 1.18-1.44 (m, 2H), 0.58-0.78 (m, 3H), 0.47-0.58 (m, 1H), 0.32-0.45 (m, 1H).

LC/MS, m/z=548 [M+H]$^+$ (Calc: 547).

In a similar manner N-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)-N-(methylsulfonyl) methanesulfonamide (Compound 62) was prepared from R-10 using 4-bromobenzyl bromide, followed by conversion of the aryl bromide to the aniline and subsequent reaction of the aniline with 5 eq. of methane sulfonyl chloride. Purification by flash column chromatography (silica gel, 0-10% MeOH/DCM) gave Compound 62 as a white solid.

$^1$H NMR $\delta_H$ (300 MHz, CDCl$_3$) 7.46 (d, J=8.3 Hz, 2H), 7.33 (d, J=8.3 Hz, 2H), 6.70 (d, J=8.3 Hz, 1H), 6.56 (d, J=8.3 Hz, 1H), 4.58 (br.s, 2H), 4.51 (s, 1H), 3.86 (s, 3H), 3.73-3.81 (m, 1H), 3.56 (t, J=8.8 Hz, 1H), 3.42-3.34 (m, 9H), 2.93-3.07 (m, 3H), 2.66 (dd, J=11.8, 5.0 Hz, 1H), 2.20-2.37 (m, 5H), 1.63-1.72 (m, 1H), 1.60 (d, J=1.1 Hz, 1H), 1.31-1.52 (m, 3H), 0.99-1.21 (m, 1H), 0.68-0.86 (m, 2H), 0.34-0.53 (m, 2H), 0.03-0.16 (m, 2H).

LC/MS, m/z=673 [M+H]$^+$ (Calc: 672).

In a similar manner N-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)acetamide (Compound 72) was prepared from R-101 using 3-bromobenzyl bromide, followed by conversion of the aryl bromide to the aniline, subsequent reaction of the aniline with acetyl chloride and final cleavage of the p-methoxybenzyl group by TFA. Purification by flash column chromatography (silica gel, 0-10% MeOH/DCM) followed by HCl salt formation gave Compound 72 HCl salt as a white solid.

$^1$H NMR $\delta_H$ (300 MHz, DMSO-d$_6$) 10.03 (s, 1H), 9.29 (s, 1H), 8.67 (bs, 1H), 7.69 (s, 1H), 7.45 (d, J=8.25 Hz, 1H), 7.25 (t, J=7.68 Hz, 1H), 7.99 (d, J=7.41 Hz, 1H), 6.68 (d, J=7.98 Hz, 1H), 6.54 (d, J=7.98 Hz, 1H), 4.70 (s, 1H), 4.48 (t, J=12.36 Hz, 2H), 3.88 (d, J=6.6 Hz, 1H), 3.61 (dd, J$_1$=9.06 Hz, J$_2$=3.57 Hz, 1H), 3.48 (t, 1H), 3.28-3.41 (m, 2H), 3.12-3.28 (m, 1H), 3.32 (s, 3H), 2.70-3.02 (m, 4H), 2.18-2.42 (m, 2H), 2.03 (s, 3H), 1.79-1.91 (m, 1H), 1.56 (dd, J=14.01 Hz, J$_2$=5.49 Hz, 1H), 1.02-1.46 (m, 4H), 0.58-0.74 (m, 3H), 0.47-0.58 (m, 1H), 0.32-0.42 (m, 1H).

LC/MS, m/z=545 [M+H]$^+$ (Calc: 544).

In a similar manner N-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)benzamide (Compound 74) was prepared from C using 3-bromobenzyl bromide, followed by conversion of the aryl bromide to the aniline, subsequent reaction of the aniline with benzoyl chloride and final cleavage of the p-methoxybenzyl group by TFA. Purification by flash column chromatography (silica gel, 0-10% MeOH/DCM) followed by HCl salt formation gave Compound 74 HCl salt as a white solid.

$^1$H NMR $\delta_H$ (300 MHz, DMSO-d$_6$) 10.30 (s, 1H), 9.29 (s, 1H), 8.61 (bs, 1H), 7.91-7.97 (m, 3H), 7.50-7.63 (m, 4H), 7.34 (t, J=7.68 Hz, 1H), 7.09 (d, J=7.71 Hz, 1H), 6.68 (d, J=7.95 Hz, 1H), 6.55 (d, J=7.95 Hz, 1H), 4.72 (s, 1H), 4.54 (dd, J$_1$=9.06 Hz, J$_2$=3.57 Hz, 2H), 3.88 (d, J=6.84 Hz, 1H), 3.64 (dd, J$_1$=9.06 Hz, J$_2$=3.57 Hz, 1H), 3.51 (t, J=9.06 Hz, 1H), 3.13-3.42 (m, 3H), 3.25 (s, 3H), 2.70-3.00 (m, 4H), 2.18-2.47 (m, 3H), 1.79-1.91 (m, 1H), 1.58 (dd, J$_1$=13.44 Hz, J$_2$=4.95 Hz, 1H), 0.95-1.46 (m, 4H), 0.42-0.71 (m, 3H), 0.29-0.40 (m, 1H).

LC/MS, m/z=607 [M+H]$^+$ (Calc: 606).

In a similar manner 1-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)-3-methylurea (Compound 91) was prepared from R-101 using 3-bromobenzyl bromide, followed by conversion of the aryl bromide to the aniline, subsequent reaction of the aniline with methyl isocyanate and final cleavage of the p-methoxybenzyl group by TFA. Purification by flash column chromatography (silica gel, 0-10% MeOH/DCM) followed by HCl salt formation gave Compound 91 HCl salt as a white solid.

$^1$H NMR $\delta_H$ (300 MHz, DMSO-d$_6$) 9.28 (s, 1H), 8.76 (s, 1H), 8.60 (bs, 1H), 7.45 (s, 1H), 7.30 (bd, J=7.98 Hz, 1H), 7.18 (t, J=7.7 Hz, 1H), 6.85 (d, J=7.44 Hz, 1H), 6.68 (d, J=7.95 Hz, 1H), 6.54 (d, J=7.95 Hz, 1H), 6.13 (q, 1H), 4.71 (s, 1H), 4.45 (dd, 2H), 3.89 (d, J=6.87 Hz, 1H), 3.61 (dd, J$_1$=8.79 Hz, J$_2$=3.30 Hz, 1H), 3.48 (t, J=8.79 Hz, 1H), 3.30-3.40 (m, 2H), 3.24 (s, 3H), 3.14-3.28 (m, 1H), 2.70-3.0 (m, 4H), 2.62 (d, J=4.68 Hz, 3H), 2.18-2.44 (m, 2H), 1.80-1.90 (m, 1H), 1.56 (dd, J,=13.47 Hz, J$_2$=6.06 Hz, 1H), 1.02-1.44 (m, 4H), 0.56-0.72 (m, 3H), 0.44-0.54 (m, 1H), 0.32-0.42 (m, 1H).

LC/MS, m/z=560 [M+H]$^+$ (Calc: 559).

Example 22

3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)benzimidamide (Compound 66)

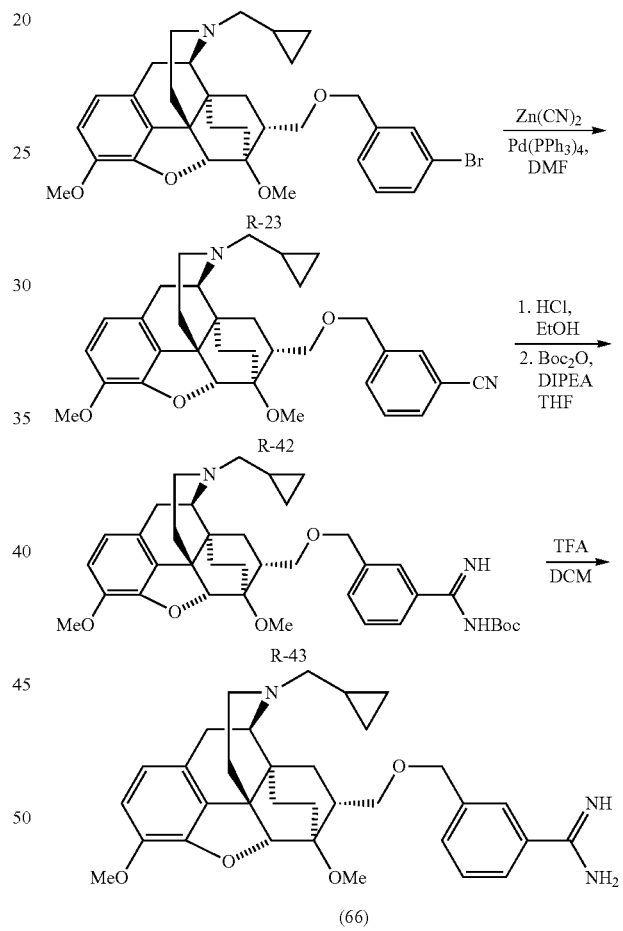

(66)

A solution of R-23 (101 mg, 0.174 mmol, 1 eq.), zinc cyanide (60 mg, 0.512 mmol, 3 eq.) and tetrakis(triphenylphosphine)palladium(0) (18 mg.) in DMF (4 mL) was heated at 120° C. for 40 h under argon. The reaction was quenched with water and extracted with EtOAc. Purification by flash column chromatography (silica gel, 0-30% EtOAc/DCM) afforded 91 mg of R-42.

$^1$H NMR $\delta_H$ (300 MHz, DMSO-d$_6$) 7.67 (s, 1H), 7.60-7.53 (m, 2H), 7.45 (t, J=8.2 Hz, 1H), 6.69 (d, J=8.0 Hz, 1H), 6.55 (d, J=8.2 Hz, 1H), 4.60-4.49 (m, 3H), 3.86 (s, 3H), 3.76 (dd, J=8.8, 3.8 Hz, 1H), 3.53 (t, J=8.8 Hz, 1H), 3.38 (s, 3H), 3.06-2.94 (m, 3H), 2.66 (dd, J=11.8 Hz, 5.0 Hz, 1H), 2.36-

2.12 (m, 5H), 2.11-1.98 (m, 1H), 1.70-1.60 (m, 1H), 1.52-1.33 (m, 3H), 1.13-1.00 (m, 1H), 0.86-0.68 (m, 2H); 0.53-0.42 (m, 2H); 0.12-0.07 (m, 2H).

To a solution of R-42 (91 mg, 0.173 mmol, 1 eq.) in THF (10 mL) was added LHMDS (0.35 mL, 1M in THF, 2 eq.) at room temperature. The reaction was stirred at room temperature for 6 h. Hydrogen chloride (2 mL, 2.5 M in EtOH) was added. The mixture was kept at 0° C. overnight. After filtration, the filtrate was concentrated. The residue was partitioned between DCM and conc. ammonium hydroxide. The aqueous layer was extracted with DCM. The combined organic layers were washed with water, brine and dried over MgSO$_4$. After concentration, 46 mg of crude Compound 66 was isolated. To a solution of crude Compound 66 (26 mg, 0.048 mmol) and DIPEA (0.1 mL) in THF (5 mL) was added Boc-anhydride (20 mg). The mixture was stirred at room temperature for 4 h. After concentration, the residue was partitioned between DCM and water. The aqueous layer was extracted with DCM. The combined organic layers washed with water, brine, dried over MgSO$_4$. Purification by flash column chromatography (silica gel, 0-3% MeOH/DCM) afforded 20 mg of R-43.

$^1$H NMR δ$_H$ (300 MHz, DMSO-d$_6$) 7.87 (s, 1H), 7.81 (d, J=7.7 Hz, 1H), 7.48 (d, J=7.4 Hz, 1H), 7.40 (t, J=7.4 Hz, 1H), 6.69 (d, J=8.0 Hz, 1H), 6.55 (d, J=8.2 Hz, 1H), 4.64-4.49 (m, 3H), 3.87 (s, 3H), 3.70 (dd, J=9.1, 4.1 Hz, 1H), 3.51 (t, J=8.0 Hz, 1H), 3.36 (s, 3H), 3.03-2.92 (m, 3H), 2.64 (dd, J=12.1 Hz, 5.0 Hz, 1H), 2.36-1.98 (m, 6H), 1.76-1.59 (m, 2H), 1.54 (s, 9H), 1.48-1.32 (m, 3H), 1.13-1.00 (m, 1H), 0.89-0.65 (m, 2H); 0.50-0.42 (m, 2H); 0.12-0.04 (m, 2H).

To a solution of R-43 (20 mg) in DCM (10 mL) was added TFA (0.5 mL) at 0° C. The reaction was stirred at room temperature overnight. After concentration, the residue was triturated with DCM/hexanes (1:3). The solid was taken up in ACN then diluted with water. The solution was lyophilized overnight and afforded 15 mg of Compound 66 TFA salt as a white solid.

$^1$H NMR δ$_H$ (300 MHz, DMSO-d$_6$) 9.33 (s, 2H), 9.18 (s, 2H), 8.46 (bs, 1H), 7.77-7.55 (m, 4H), 6.88 (d, J=8.2 Hz, 1H), 6.68 (d, J=8.2 Hz, 1H), 4.76 (s, 1H), 4.64-4.56 (m, 2H), 3.88 (d, J=6.6 Hz, 1H), 3.78 (s, 3H), 3.64 (dd, J=9.1 Hz, 3.8 Hz, 1H), 3.53 (t, J=9.3 Hz, 1H), 3.41-3.25 (m, 3H), 3.24 (s, 3H), 3.01-2.69 (m, 4H), 2.32-2.16 (m, 1H), 1.94-1.85 (m, 1H), 1.62-1.52 (m, 1H), 1.48-0.98 (m, 5H), 0.72-0.55 (m, 2H); 0.49-0.34 (m, 2H).

LC/MS, m/z=544 [M+H]$^+$ (Calc: 543).

Example 23

(4R,4aS,6R,7R,7aR,12bS)-6-((benzyloxy)methyl)-3-(cyclopropylmethyl)-7-methoxy-9-(2H-tetrazol-5-yl)-1,2,3,4,5,6,7,7a-octahydro-4a,7-ethano-4,12-methanobenzofuro[3,2-e]isoquinoline (Compound 70)

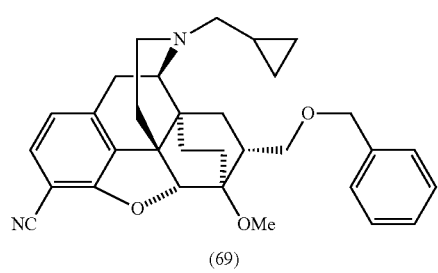

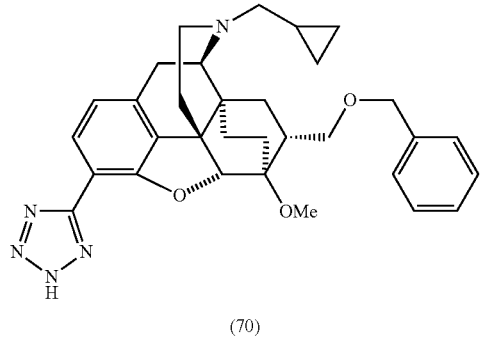

A mixture of Compound 69 (100 mg, 0.2 mmol), NaN$_3$ (280 mg, 4.0 mmol) and NH$_4$Cl (226 mg, 4.0 mmol) in DMF (anhydrous, 3 mL) was heated at 90° C. in a microwave reactor for 17 h. The reaction mixture was cooled to room temperature, filtered and concentrated. The crude material was purified by flash column chromatography (silica gel, 0-10% MeOH/DCM) followed by HCl salt formation to give Compound 70 HCl salt as a white solid.

$^1$H NMR δ$_H$ (300 MHz, DMSO-d$_6$) 7.79 (d, J=7.95 Hz, 1H), 7.26-7.39 (m, 5H), 6.93 (d, J=7.95 Hz, 1H), 4.94 (s, 1H), 4.51 (s, 2H), 3.87 (bs, 1H), 3.62 (dd, J$_1$=9.36 Hz, J$_2$=4.14 Hz, 1H), 3.50 (t, J=9.06 Hz, 1H), 3.10-3.45 (m, 4H), 3.28 (s, 3H), 2.67-3.02 (m, 4H), 2.25-2.45 (m, 2H), 1.85-1.98 (m, 1H), 1.50-1.62 (m, 1H), 1.23-1.41 (m, 2H), 1.0-1.18 (m, 2H), 0.54-0.72 (m, 3H), 0.42-0.52 (m, 1H), 0.30-0.41 (m, 1H).

LC/MS, m/z=540 [M+H]$^+$ (Calc: 539).

Example 24

(4R,4aS,6R,7R,7aR,12bS)-6-(2-(benzyloxy)propan-2-yl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 65)

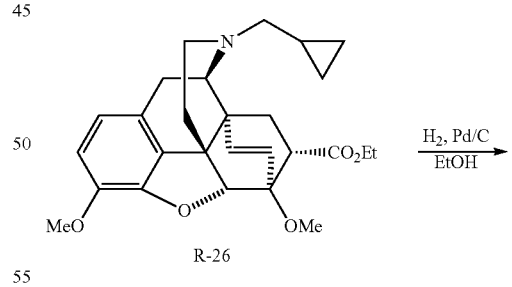

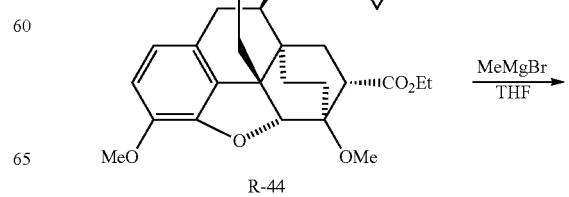

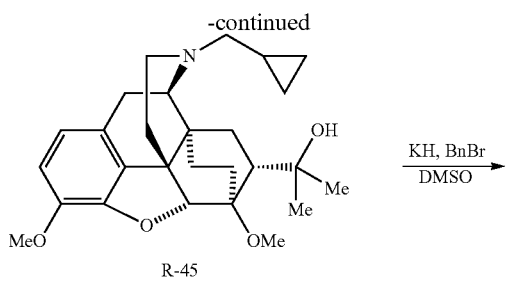

R-45

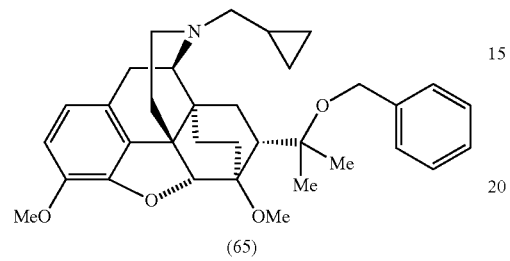

(65)

A solution of R-26 (1.02 g, 2.26 mmol) in EtOH (50 mL) was purged with nitrogen and evacuated three times. Palladium on carbon (10%, 200 mg) was added and the resulting suspension was evacuated and flushed with hydrogen. The reaction mixture was allowed to stir at room temperature under a hydrogen atmosphere overnight. The mixture was evacuated and flushed with nitrogen and filtered through Celite®. The filtrate was concentrated and purified by flash column chromatography (silica gel, 0-10% MeOH/DCM) to give 877 mg of R-44.

$^1$H NMR $\delta_H$ (300 MHz, CDCl$_3$) 6.69 (d, J=8.1 Hz, 1H), 6.56 (d, J=8.1 Hz, 1H), 4.51 (s, 1H), 4.25-4.12 (m, 2H), 3.86 (s, 3H), 3.45 (s, 3H), 3.06-2.83 (m, 4H), 2.62 (dd, J=5.3 and 11.5 Hz, 1H), 2.36-2.21 (m, 4H), 2.05-1.95 (m, 1H), 1.85-1.64 (m, 3H), 1.52-1.41 (m, 1H), 1.36-1.32 (m, 1H), 1.27 (t, J=7.1 Hz, 3H), 0.77-0.71 (m 2H), 0.48-0.46 (m, 2H), 0.09-0.07 (m, 2H).

A solution of R-44 (380 mg, 0.309 mmol) in THF (10 mL) was stirred at 0° C. A 3M solution of methylmagnesium bromide in diethyl ether (1.4 mL, 4.19 mol, 5 eq.) was added dropwise under a nitrogen atmosphere. After complete addition, the reaction was allowed to warm to room temperature and stirred overnight. The reaction mixture was cooled in an ice bath and was quenched with a saturated aqueous NH$_4$Cl solution. The mixture was extracted with chloroform (3×30 mL). The combined extracts were washed with brine and dried (Na$_2$CO$_3$), filtered and concentrated. The residue was purified by flash column chromatography (silica gel, 0-100% EtOAc/hexanes) to give 186 mg of R-45.

$^1$H NMR $\delta_H$ (300 MHz, CDCl$_3$) 6.70 (d, J=8.2 Hz, 1H), 6.54 (d, J=8.2 Hz, 1H), 5.08 (s, 1H), 4.40 (d, J=1.4 Hz, 1H), 3.87 (s, 3H), 3.54 (s, 3H), 3.03-2.96 (m, 2H), 2.86-2.84 (m, 1H), 2.64-2.59 (m, 1H), 2.39-2.31 (m, 1H), 2.28-2.19 (m, 3H), 2.08-1.62 (m, 5H), 1.37 (s, 3H), 1.19 (s, 3H), 1.10-1.02 (m, 2H), 0.84-0.73 (m, 2H), 0.51-0.43 (m, 2H), 0.12-0.08 (m, 2H).

Potassium hydride (30% suspension in mineral oil, 701 mg, 5.26 mmol, 10 eq.) was added to a stirred solution of R-45 (231 mg, 0.526 mmol) in anhydrous DMSO (10 mL) at 5° C. The suspension was allowed to stir at room temperature for 15 min and benzyl bromide (719 mg, 4.2 mmol, 8 eq.) was added dropwise. The reaction mixture was stirred at room temperature for 5 days. The reaction was quenched by ice-water addition and extracted with DCM. The organic phase was washed with water, brine and dried over Na$_2$SO$_4$. The solvent was evaporated and the residue was purified by flash column chromatography (silica gel, 0-10% MeOH/DCM) followed by HCl salt formation gave Compound 65 HCl salt as a white solid.

$^1$H NMR $\delta_H$ (300 MHz, CDCl$_3$) 7.37-7.24 (m, 5H), 6.68 (d, J=8.2 HZ, 1H), 6.54 (d, J=8.0 HZ, 1H), 4.55-4.41 (m, 3H), 3.88 (s, 3H), 3.41 (s, 3H), 3.03 (d, J=6.3 Hz, 1H), 2.97 (d, J=18.4 Hz, 1H), 2.86-2.81 (m, 1H), 2.62 (dd, J=4.7 and 11.6 Hz, 1H), 2.41-2.21 (m, 4H), 2.12-2.01 (m, 2H), 1.86 (m, 1H), 1.70-1.63 (m, 2H), 1.45-1.38 (m, 7H), 1.15-1.03 (m, 1H), 0.87-0.76 (m, 1H), 0.71-0.62 (m, 1H), 0.53-0.46 (m, 2H), 0.12-0.09 (m, 2H).

LC/MS, m/z=530 [M+H]$^+$ (Calc: 529).

Example 25

2-((4R,4aS,5S,6R,7R,7aR,12bS)-6-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-5-yl)acetonitrile (Compound 88); ethyl 3-((4R,4aS,5S,6R,7R,7aR,12bS)-6-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-5-yl)propanoate (Compound 87); 3-((4R,4aS,5S,6R,7R,7aR,12bS)-6-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-5-yl)propanoic acid (Compound 89); and ethyl 3-((4R,4aS,5S,6S,7R,7aR,12bS)-5-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)propanoate (Compound 92)

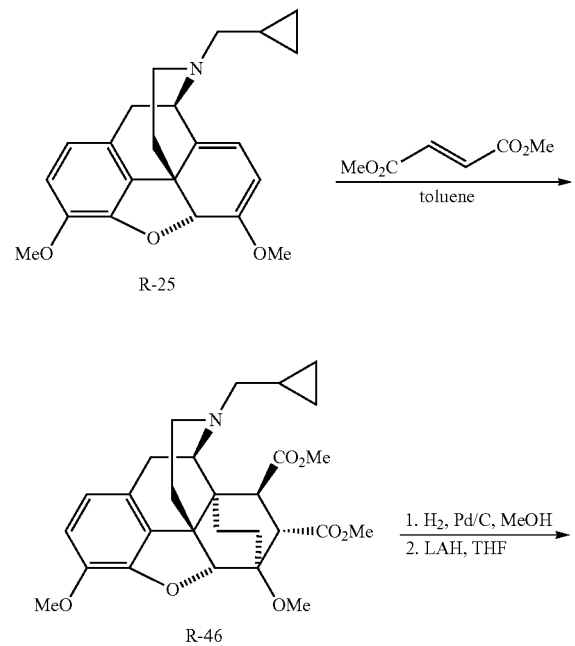

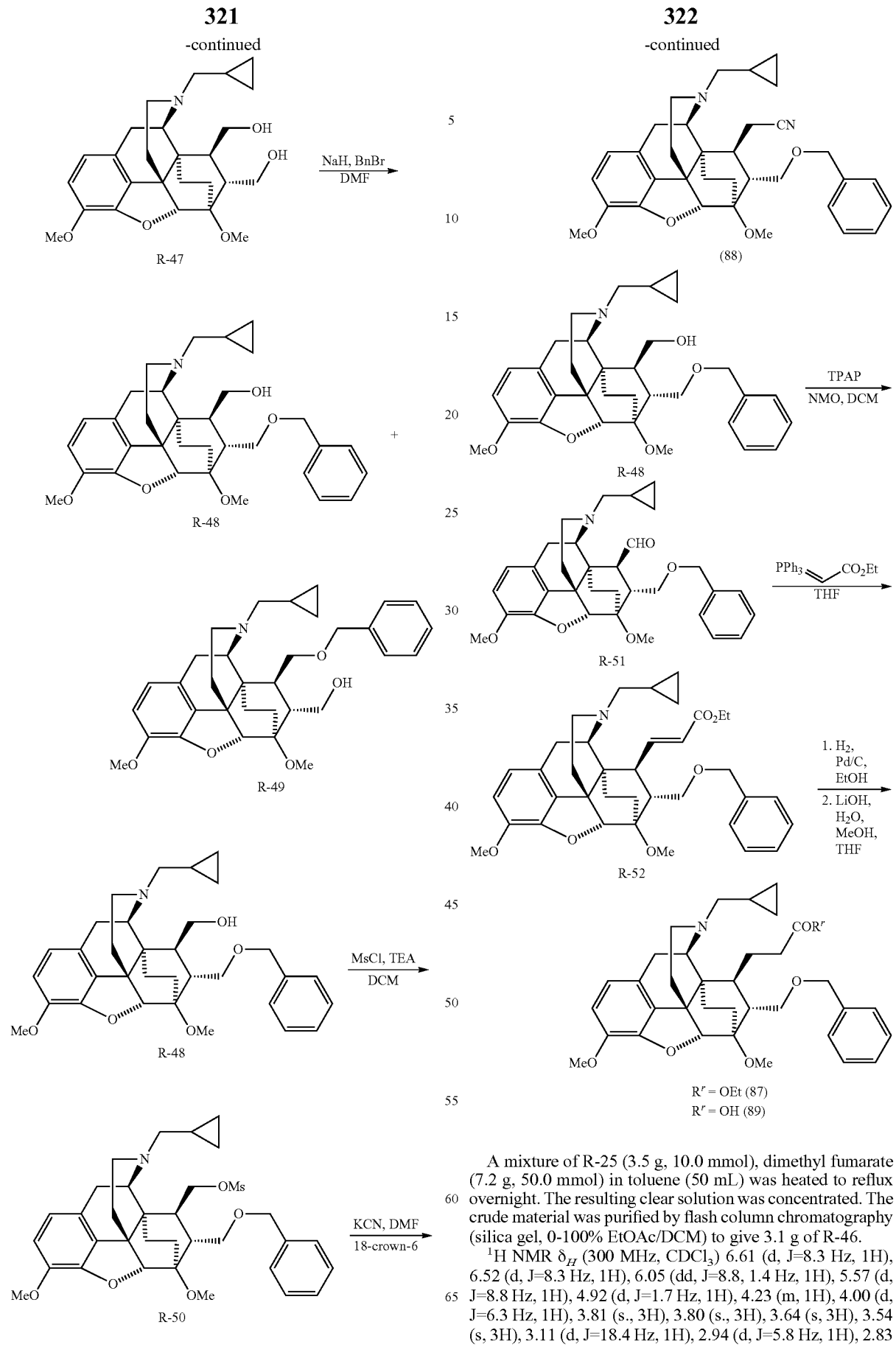
A mixture of R-25 (3.5 g, 10.0 mmol), dimethyl fumarate (7.2 g, 50.0 mmol) in toluene (50 mL) was heated to reflux overnight. The resulting clear solution was concentrated. The crude material was purified by flash column chromatography (silica gel, 0-100% EtOAc/DCM) to give 3.1 g of R-46.
$^1$H NMR $\delta_H$ (300 MHz, CDCl$_3$) 6.61 (d, J=8.3 Hz, 1H), 6.52 (d, J=8.3 Hz, 1H), 6.05 (dd, J=8.8, 1.4 Hz, 1H), 5.57 (d, J=8.8 Hz, 1H), 4.92 (d, J=1.7 Hz, 1H), 4.23 (m, 1H), 4.00 (d, J=6.3 Hz, 1H), 3.81 (s., 3H), 3.80 (s., 3H), 3.64 (s, 3H), 3.54 (s, 3H), 3.11 (d, J=18.4 Hz, 1H), 2.94 (d, J=5.8 Hz, 1H), 2.83

(m, 1H), 2.73 (m, 1H), 2.47-2.37 (m, 3H), 2.24 (dd, J=12.7, 7.1 Hz,1H), 1.74 (m, 1H); 0.8 (m, 1H), 0.47 (m, 2H), 0.10 (m, 2H).

A solution of R-46 (3.05 g, 6.2 mmol) in MeOH (40 mL) was purged with nitrogen and evacuated three times. Palladium on carbon (10%, 20 mg) was added and the resulting suspension was evacuated and flushed with hydrogen. The reaction mixture was allowed to shake at room temperature under hydrogen atmosphere at 40 psi in a Parr apparatus overnight. The mixture was evacuated and flushed with nitrogen, and filtered through Celite®. The filtrate was concentrated. The residue was taken in toluene and evaporated. The crude material was dissolved in THF (30 mL, anhydrous), cooled to an ice bath temperature and LAH (24.8 mL, 1M solution in THF) was added dropwise. The reaction mixture was allowed to warm to room temperature (2 h). The mixture was quenched with 25% aqueous $NH_4Cl$ solution, extracted with chloroform, dried ($Na_2SO_4$), filtered and concentrated to give 2.6 g of crude R-47 as a colorless foam. This material was used directly in the next step.

$^1$H NMR $\delta_H$ (300 MHz, $CDCl_3$) 6.73 (d, J=8.0 Hz, 1H), 6.59 (d, J=8.0 Hz, 1H), 4.81 (d, J=2.0 Hz, 1H), 4.00-3.80 (m, 3H), 3.87 (s., 3H), 3.71-3.50 (m, 3H), 3.43 (s, 3H), 3.21 (m, 1H), 3.01 (d, J=18.7 Hz, 1H), 2.90 (dd, J=11.5, 5.2 Hz, 1H), 2.60 (m, 1H), 2.43-16 (m, 5H), 1.66-1.41 (m, 6H), 1.17 (m, 1H), 0.89-0.69 (m, 2H); 0.51 (m, 2H), 0.09 (m, 2H).

Sodium hydride (0.75 g, 18.7 mmol) was added to an ice cold solution of R-47 (2.1 g, 4.7 mmol) in THF (anhydrous, 100 mL) under a nitrogen atmosphere. The reaction mixture was allowed to stir at room temperature for 30 min. The mixture was cooled down to ice bath temperature and a solution of benzyl bromide (0.5 mL, 4.2 mmol) in THF (20 mL) was added dropwise over 30 min. The resulting mixture was allowed stir overnight at room temperature. The mixture was quenched with ice-cold water, extracted with chloroform, dried ($Na_2SO_4$), filtered and concentrated. The crude material was purified by flash column chromatography (silica gel, 0-100% EtOAc/hexanes) to give 0.42 g of R-48 and 0.30 g of R-49 as colorless oils which, upon standing turn into white solids

R-48

$^1$H NMR $\delta_H$ (300 MHz, $CDCl_3$) 7.44-7.26 (m, 5H), 6.68 (d, J=8.3 Hz, 1H), 6.55 (d, J=8.3 Hz, 1H), 4.82 (d, J=1.9 Hz, 1H), 4.65 (d, J=12.1 Hz, 1H), 4.58 (d, J=12.1 Hz, 1H), 4.51 (bs, 1H), 3.86 (s, 3H), 3.83 (m, 1H), 3.69-3.65 (m, 2H), 3.56 (dd, J=14.9, 5.0 Hz, 1H), 3.30 (s, 3H), 3.23 (d, J=12.1, 6.6 Hz, 1H), 3.09 (m, 1H), 2.99 (d, J=18.4 Hz, 1H), 2.77 (dd, J=11.5, 5.8 Hz, 1H), 2.43-2.15 (m, 5H), 1.72-1.21 (m, 4H), 0.87 (m, 1H), 0.69 (m, 1H), 0.52 (m, 2H), 0.10 (m, 2H).

R-49

$^1$H NMR $\delta_H$ (300 MHz, $CDCl_3$) 7.37-7.21 (m, 5H), 6.69 (d, J=8.3 Hz, 1H), 6.53 (d, J=8.3 Hz, 1H), 4.65 (d, J=12.0 Hz, 1H), 4.58 (m, 1H), 4.52 (d, J=12.0 Hz, 1H), 4.10 (m, 1H), 3.99 (m, 1H), 3.86 (s, 3H), 3.71 (dd, J=8.0, 3.3 Hz, 1H), 3.63 (m, 1H), 3.38-3.27 (m, 4H), 3.14 (d, J=6.6 Hz, 1H), 2.93 (d, J=18.4 Hz, 1H), 2.87 (m, 1H), 2.55 (m, 1H), 2.38-2.13 (m, 4H), 2.04 (m, 2H), 1.62-1.20 (m, 4H), 0.61 (m, 2H), 0.33 (m, 2H), 0.01 (m, 2H).

Methanesulfonyl chloride (59 µL, 0.76 mmol) was added to an ice-cold solution of R-48 (203 mg, 0.38 mmol) and TEA (160 µL, 1.14 mmol) in DCM (5 mL) under a nitrogen atmosphere. The reaction mixture was allowed to stir at room temperature for 2 h. The mixture was quenched with saturated aqueous sodium bicarbonate at ice bath temperature and extracted with DCM. The organic extract was dried ($Na_2SO_4$), and concentrated to give 286 mg of R-50 as a pale yellow gum. This material was used directly in the next step.

$^1$H NMR $\delta_H$ (300 MHz, $CDCl_3$) 7.44-7.25 (m, 5H), 6.69 (d, J=8.3 Hz, 1H), 6.54 (d, J=8.3 Hz, 1H), 4.91 (d, J=1.9 Hz, 1H), 4.57 (s, 2H), 4.49 (d, J=9.6, 5.0 Hz, 1H), 4.35 (d, J=9.6, 7.1 Hz, 1H), 3.86 (s, 3H), 3.81 (dd, J=9.1, 5.0 Hz, 1H), 3.67 (dd, J=9.3, 3.6 Hz, 1H), 3.33 (s, 3H), 3.32-3.19 (m, 2H), 2.99 (d, J=18.4 Hz, 1H), 3.04 (s, 3H), 2.56 (m, 1H), 2.45 (m, 1H), 2.34-21.18 (m, 4H), 1.96 (m, 1H), 1.52-1.24 (m, 5H), 0.69 (m, 1H), 0.52 (m, 2H), 0.10 (m, 2H).

Potassium cyanide (220 mg, 4.0 mmol) was added to solution of R-50 (266 mg, 0.44 mmol) and 18-crown-6 (52 mg, 0.2 mmol) in DMF (5 mL). The reaction mixture was irradiated in a microwave reactor at 90° C. for 4 h. The mixture was diluted with EtOAc and washed with water. The organic extract was dried ($Na_2SO_4$), filtered and concentrated. The crude material was purified by flash column chromatography (silica gel, 0-100% EtOAc/hexanes) to give 36 mg of Compound 88 as a white solid.

$^1$H NMR $\delta_H$ (300 MHz, $CDCl_3$) 7.42-7.26 (m, 5H), 6.69 (d, J=8.3 Hz, 1H), 6.55 (d, J=8.3 Hz, 1H), 4.88 (d, J=1.9 Hz, 1H), 4.63 (d, J=12.1 Hz, 1H), 4.55 (d, J=12.1 Hz, 1H), 3.84 (s, 3H), 3.81-3.73 (m, 2H), 3.32 (s, 3H), 3.20 (m, 1H), 3.10 (m, 1H), 2.99 (d, J=18.4 Hz, 1H), 2.65 (dd, J=16.7, 5.5 Hz, 1H), 2.58-2.15 (m, 7H), 1.91 (m, 1H), 1.52-1.33 (m, 4H), 0.83 (m, 1H), 0.69 (m, 1H), 0.52 (m, 2H), 0.11 (m, 2H).

LC/MS, m/z=541 [M–H]$^+$ (Calc: 540).

TPAP (17 mg, 0.02 mmol) (Aldrich) was added to an ice-cold solution of R-48 (203 mg, 0.38 mmol) and NMO (107 mg, 0.91 mmol) in DCM (anhydrous, 5 mL) under nitrogen atmosphere. The reaction mixture was allowed to stir at room temperature for 2 h. The mixture was concentrated. The residue obtained was purified by flash column chromatography (silica gel, 0-100% EtOAc/hexanes) to give 130 mg of R-51 as a pale yellow gum.

$^1$H NMR $\delta_H$ (300 MHz, $CDCl_3$) 9.97 (s, 1H), 7.38-7.25 (m, 5H), 6.70 (d, J=8.3 Hz, 1H), 6.54 (d, J=8.3 Hz, 1H), 4.81 (s, 1H), 4.57 (d, J=11.8 Hz, 1H), 4.47 (d, J=11.8 Hz, 1H), 4.00 (dd, J=6.6, 2.8 Hz, 1H), 3.85 (s, 3H), 3.69 (dd, J=9.6, 6.6 Hz, 1H), 3.55 (d, J=6.6 Hz, 1H), 3.48 (m, 1H), 3.33 (s, 3H), 3.04 (d, J=18.4 Hz, 1H), 2.84 (m, 1H), 2.59 (m, 1H), 2.49-2.19 (m, 5H), 1.51 (m, 1H), 1.37 (m, 2H), 1.11 (m, 1H), 0.83 (m, 1H), 0.71 (m, 1H), 0.52 (m, 2H), 0.11 (m, 2H).

A mixture of R-51 (130 mg, 0.25 mmol) and ethyl 2-(triphenylphosphoranylidene) acetate (261 mg, 0.75 mmol) in THF (6 mL) was heated to reflux for 8 h under a nitrogen atmosphere. The mixture was concentrated. The crude material was purified by flash column chromatography (silica gel, 0-100% EtOAc/hexanes) to give 140 mg of R-52 as a colorless gum.

$^1$H NMR $\delta_H$ (300 MHz, $CDCl_3$) 7.42-7.21 (m, 5H), 7.03 (dd, J=15.4, 8.0 Hz, 1H), 6.69 (d, J=8.3 Hz, 1H), 6.53 (d, J=8.3 Hz, 1H), 5.99 (d, J=15.4 Hz, 1H), 4.95 (d, J=1.1 Hz, 1H), 4.55 (s, 2H), 4.16 (q, J=7.1 Hz, 2H), 3.86 (s, 3H), 3.78 (dd, J=9.3, 5.0 Hz, 1H), 3.70 (m, 1H), 3.45 (dd, J=9.3, 3.0 Hz, 1H), 3.31 (s, 3H), 3.06 (d, J=6.3 Hz, 1H), 2.97 (d, J=18.1 Hz, 1H), 2.50 (m, 2H), 2.34-2.08 (m, 4H), 1.97 (m, 1H), 1.54-1.31 (m, 4H), 1.27 (t, J=7.1 Hz, 3H), 0.82 (m, 1H), 0.66 (m, 1H), 0.49 (m, 2H), 0.07 (m, 2H).

A solution of R-52 (140 mg, 0.23 mmol) in EtOH (20 mL) was purged with nitrogen and evacuated three times. Palladium on carbon (10%, 25 mg) was added and the resulting suspension was evacuated and flushed with hydrogen. The reaction mixture was allowed to shake at room temperature under a hydrogen atmosphere at 45 psi in a Parr apparatus for 5 h. The mixture was evacuated and flushed with nitrogen, and filtered through a Celite®. The filtrate was concentrated. The crude material was purified by flash column chromatography (silica gel, 0-100% EtOAc/hexanes) to give 145 mg of Compound 87 as a colorless gum.

$^1$H NMR $\delta_H$ (300 MHz, $CDCl_3$) 7.42-7.21 (m, 5H), 6.68 (d, J=8.3 Hz, 1H), 6.53 (d, J=8.3 Hz, 1H), 4.77 (s, 1H), 4.57 (s, 2H), 4.10 (q, J=7.1 Hz, 2H), 3.85 (s, 3H), 3.72-3.60 (m, 2H), 3.29 (s, 3H), 3.19 (d, J=6.3 Hz, 1H), 2.97 (d, J=18.4 Hz, 1H), 2.73 (m, 1H), 2.64 (m, 1H), 2.53 (dd, J=11.3, 5.5 Hz, 1H), 2.44-2.32 (m, 2H), 2.29-2.16 (m, 4H), 1.97 (m, 1H), 1.74 (m, 1H), 1.56-1.29 (m, 4H), 1.25 (t, J=7.1 Hz, 3H), 0.83 (m, 1H), 0.60 (m, 1H), 0.48 (m, 2H), 0.08 (m, 2H).

LC/MS, m/z=602 [M−H]⁺ (Calc: 601).

Lithium hydroxide monohydrate (13 mg, 0.3 mmol) was added to a solution of Compound 87 (125 mg, 0.2 mmol) in THF:MeOH:water (3:1:1, 5 mL). The reaction mixture was allowed to stir at room temperature overnight. The mixture was concentrated. The residue was diluted with chloroform and saturated aqueous ammonium chloride solution. The organic layer was separated. The aqueous layer was washed with chloroform. The combined organic extract was dried (Na₂SO₄), filtered and concentrated. The crude material was purified by flash column chromatography (silica gel, 0-10% MeOH/DCM) to give 104 mg of Compound 89 as a colorless foam.

¹H NMR δ$_H$ (300 MHz, CDCl₃) 11.97 (bs, 1H), 7.42-7.21 (m, 5H), 6.72 (d, J=8.3 Hz, 1H), 6.53 (d, J=8.3 Hz, 1H), 4.68 (s, 1H), 4.54 (s, 2H), 3.74 (s, 3H), 3.66 (m, 1H), 3.54 (m, 1H), 3.30 (m, 3H), 3.15 (m, 4H), 2.90 (d, J=18.4 Hz, 1H), 2.64 (m, 1H), 2.38 (m, 1H), 2.28-2.05 (m, 5H), 1.84 (m, 1H), 1.73 (m, 1H), 1.52-1.02 (m, 5H), 0.83 (m, 1H), 0.44 (m, 2H), 0.08 (m, 2H).

LC/MS, m/z=574 [M−H]⁺ (Calc: 573).

In a similar manner R-50 was oxidized with TPAP, reacted with ethyl 2-(triphenylphosphoranylidene) acetate and hydrogenated to prepare Compound 92.

¹H NMR δ$_H$ (300 MHz, CDCl₃) 7.34-7.21 (m, 5H), 6.68 (d, J=8.3 Hz, 1H), 6.51 (d, J=8.3 Hz, 1H), 4.63 (s, 1H), 4.56 (d, J=12.1, 1H), 4.47 (d, J=12.1, 1H), 4.11 (m, 2H), 3.85 (s, 3H), 3.61 (dd, J=9.1, 4.4 Hz, 1H), 3.38 (m, 1H), 3.28 (s, 3H), 3.23 (m, 1H), 2.93 (d, J=18.3 Hz, 1H), 2.84 (m, 1H), 2.67 (m, 1H), 2.58-2.43 (m, 2H), 2.40-2.01 (m, 7H), 1.81 (m, 1H), 1.64-1.51 (m, 2H), 1.48-1.32 (m, 4H), 1.25 (t, J=7.1 Hz, 3H), 0.59 (m, 2H), 0.34 (m, 2H).

LC/MS, m/z=602 [M−H]⁺ (Calc: 601).

Example 26

4-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)benzamide (Compound 75)

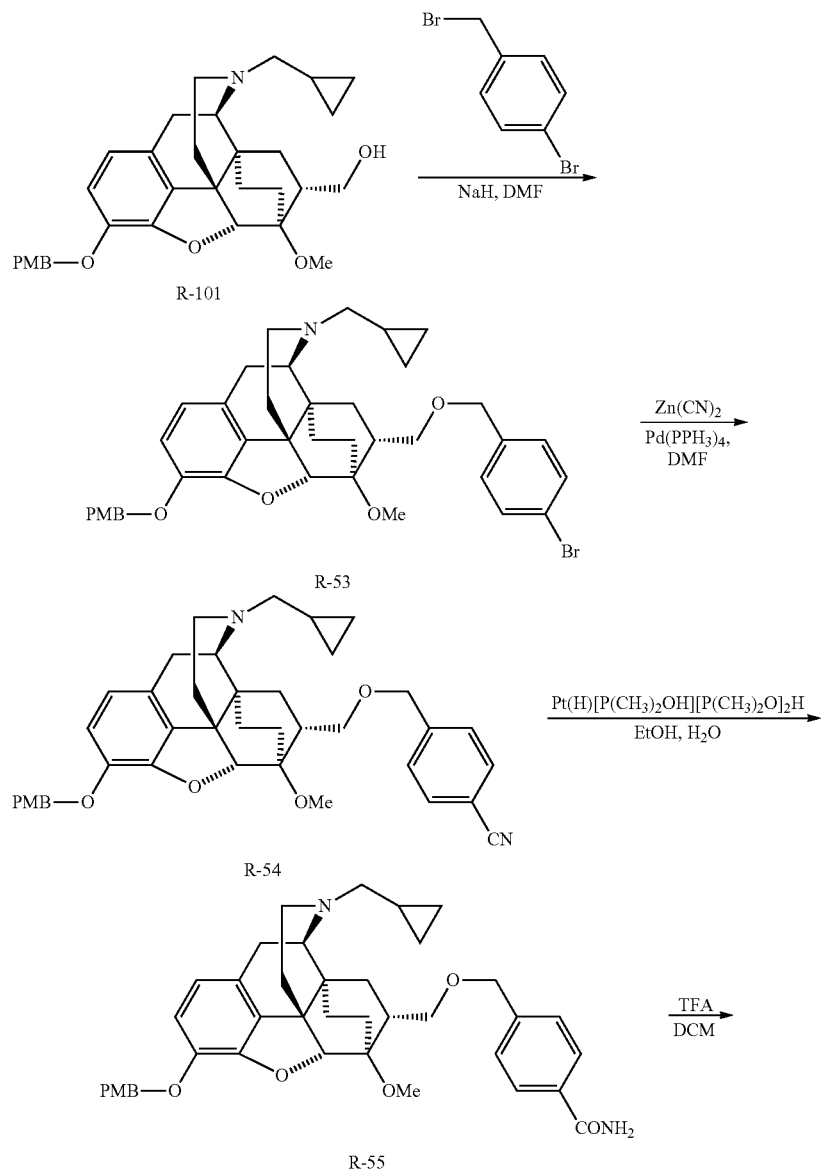

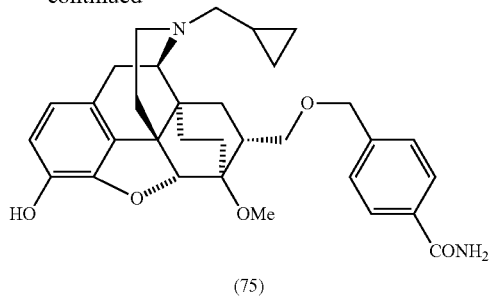

(75)

Sodium hydride (0.070 g, 1.74 mmol) was added to an ice-cold solution of R-101 (0.158 g, 0.29 mmol) in DMF (anhydrous, 3 mL) under a nitrogen atmosphere. The reaction mixture was allowed to stir for 30 min and 4-bromobenzyl bromide (0.147 g, 0.58 mmol) was added. The resulting mixture was allowed to stir overnight at room temperature. The reaction was quenched with ice and extracted with chloroform. The crude material was purified by flash column chromatography (silica gel, 0-10% MeOH/DCM) to give 180 mg of R-53.

$^1$H NMR $\delta_H$ (300 MHz, CDCl$_3$) 7.47 (d, J=8.3 Hz, 2H), 7.36 (d, J=8.5 Hz, 2H), 7.24 (d, J=8.3 Hz, 2H), 6.87 (d, J=8.8 Hz, 2H), 6.72 (d, J=8.3 Hz, 1H), 6.49 (d, J=8.0 Hz, 1H), 5.11 (d, J=5.5 Hz, 2H), 4.49 (m, 3H), 3.79 (s, 3H), 3.70-3.78 (m, 1H), 3.45-3.58 (m, 1H), 3.39 (s, 3H), 2.88-3.08 (m, 3H), 2.59-2.71 (m, 1H), 2.00-2.37 (m, 6H), 1.59-1.74 (m, 1H), 1.32-1.52 (m, 3H), 0.98-1.19 (m, 1H), 0.64-0.89 (m, 2H), 0.37-0.56 (m, 2H), 0.09 (d, 2H).

A suspension of R-53 (0.18 g, 0.26 mmol), Zn(CN)$_2$ (0.09 g, 0.78 mmol) and Pd(PPh$_3$)$_4$ (30 mg, 0.026 mmol) in DMF (6 mL) was heated at 120° C. for 40 h under nitrogen. The reaction was quenched by the addition of water and then extracted with EtOAc. The combined organic extracts were washed with water followed by brine. The crude, after evaporating the solvent, was purified by flash column chromatography (silica gel, 0-3% MeOH/DCM) to give 125 mg of R-54.

$^1$H NMR $\delta_H$ (300 MHz, CDCl$_3$) 7.55-7.68 (m, 2H), 7.46 (d, J=8.5 Hz, 2H), 7.35 (d, J=8.5 Hz, 2H), 6.87 (d, J=8.5 Hz, 2H), 6.72 (d, J=8.3 Hz, 1H), 6.50 (d, J=8.3 Hz, 1H), 5.11 (d, J=5.5 Hz, 2H), 4.59 (d, J=2.2 Hz, 2H), 4.50 (s, 1H), 3.79 (br.s, 4H), 3.49-3.62 (m, 1H), 3.39 (s, 3H), 2.92-3.06 (m, 3H), 2.59-2.71 (m, 1H), 1.97-2.40 (m, 6H), 1.61-1.76 (m, 2H), 1.28-1.57 (m, 3H), 0.91-1.17 (m, 1H), 0.65-0.87 (m, 2H), 0.39-0.56 (m, 2H), 0.09 (d, 2H).

A mixture of R-54 (125 mg, 02 mmol), Pt(H)[P(CH$_3$)$_2$OH][P(CH$_3$)$_2$O]$_2$H (5 mg) (Aldrich) (*Tetrahedron Lett.*, 1995, 36, 8657) and EtOH-water (20 mL, 1/1) was heated to reflux for 18 h. The solvents were evaporated and the residue extracted with DCM. The combined organic extracts were washed with water followed by brine and dried over MgSO$_4$. The crude material after evaporating the solvent was purified by flash column chromatography (silica gel, 0-5% MeOH/DCM) to give 89 mg of R-55.

$^1$H NMR $\delta_H$ (300 MHz, CDCl$_3$) 7.79 (d, J=8.0 Hz, 2H), 7.44 (d, J=8.0 Hz, 2H), 7.35 (d, J=8.5 Hz, 2H), 6.86 (d, J=8.5 Hz, 2H), 6.71 (d, J=8.0 Hz, 1H), 6.49 (d, J=8.3 Hz, 1H), 5.96-6.21 (m, 1H), 5.56-5.89 (m, 1H), 5.10 (d, J=5.2 Hz, 2H), 4.51-4.67 (m, 2H), 4.50 (s, 1H), 3.79 (s, 3H), 3.77 (m, 1H), 3.48-3.60 (m, 2H), 3.38 (s, 3H), 2.91-3.07 (m, 3H), 2.65 (dd, J=11.8, 4.7 Hz, 1H), 1.95-2.38 (m, 6H), 1.35-1.50 (m, 4H), 1.02-1.14 (m, 1H), 0.65-0.87 (m, 2H), 0.40-0.54 (m, 2H), 0.03-0.14 (m, 2H).

To a solution of R-55 (0.089 g, 0.14 mmol) in DCM (50 mL) was added TFA (0.8 mL) at room temperature. After 30 min, the reaction was quenched by the addition of 50% aqueous ammonia and the aqueous layer was extracted with DCM. The residue, after evaporating the solvent, was purified by flash column chromatography (silica gel, 0-8% MeOH/DCM) to give 51 mg of Compound 75.

$^1$H NMR $\delta_H$ (300 MHz, CDCl$_3$) 7.80 (d, J=8.5 Hz, 2H), 7.44 (d, J=8.5 Hz, 2H), 6.69 (d, J=8.0 Hz, 1H), 6.51 (d, J=8.0 Hz, 1H), 4.60 (d, J=26.7 Hz, 2H), 4.53 (d, J=1.7 Hz, 1H), 3.66-3.83 (m, 1H), 3.40-3.60 (m, 1H), 3.36 (s, 3H), 2.92-3.06 (m, 3H), 2.57-2.73 (m, 1H), 2.15-2.39 (m, 6H), 1.98-2.13 (m, 1H), 1.29-1.51 (m, 3H), 0.93-1.16 (m, 1H), 0.62-0.92 (m, 2H), 0.43-0.52 (m, 2H), 0.09 (d, J=5.0 Hz, 2H).

LC/MS, m/z=531 [M–H]$^+$ (Calc: 530).

Example 27

2-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)benzamido)acetic acid
(Compound 43)

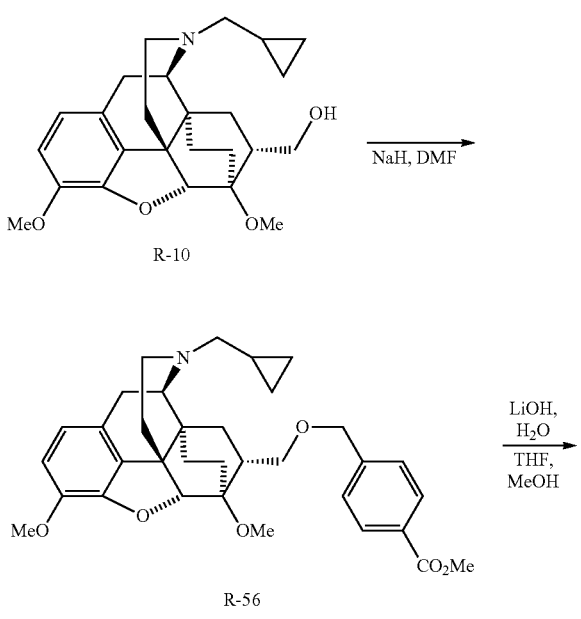

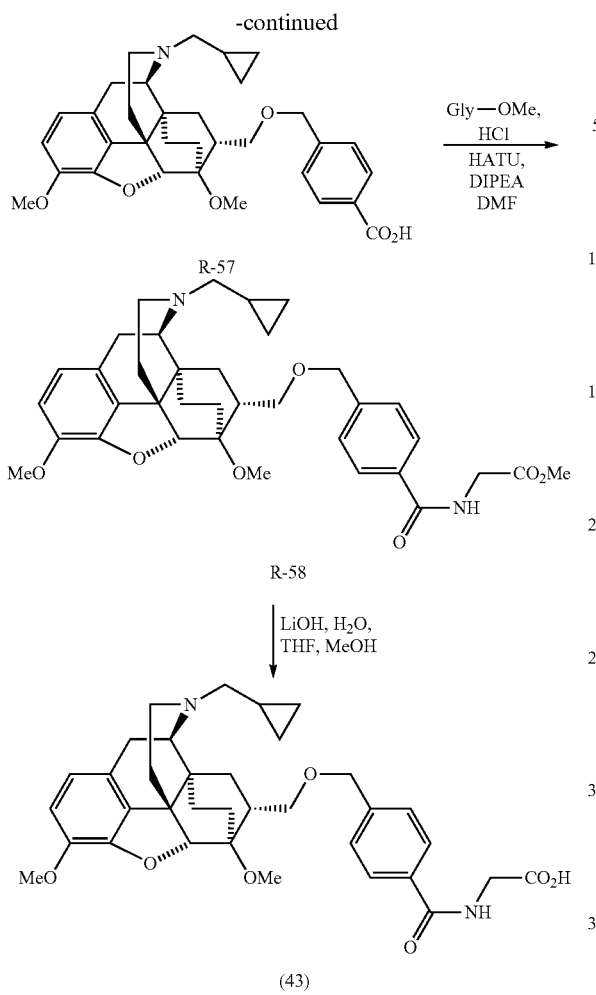

NaH (85 mg, 60% suspension in mineral oil) was added to a solution of R-10 (149 mg, 0.36 mmol, 1 eq.) in anhydrous THF (6 mL). After 5 min potassium iodide (60 mg) and methyl (4-bromomethyl)benzoate (210 mg, 0.72 mmol, 2.5 eq.) were added under nitrogen. The resulting mixture was stirred at room temperature overnight. The reaction was quenched with ice-water and extracted with EtOAc, dried over MgSO$_4$. The solvent was evaporated and the residue was purified by flash column chromatography (silica gel, 0-10% MeOH/DCM) to provide 100 mg of R-56.

R-56 (77 mg) was dissolved in THF/MeOH/H$_2$O (8 ml, 2/1/1, v/v/v). To this solution was added LiOH—H$_2$O (25 mg). The mixture was stirred at room temperature overnight. After concentration, the residue was purified by flash column chromatography (silica gel, 0-10% MeOH/DCM) to afford 21 mg of R-57 as the lithium salt.

$^1$H NMR $\delta_H$ (300 MHz, CDCl$_3$) 7.99 (m, 2H), 7.19-7.02 (m, 2H), 6.68 (d, J=8.2 Hz, 1H), 6.53 (d, J=8.2 Hz, 1H), 4.52-4.33 (m, 3H), 3.83 (s, 3H), 3.46-3.22 (m, 4H), 3.15-2.86 (m, 3H), 2.84-2.65 (m, 1H), 2.50-1.95 (m, 7H), 1.68-1.52 (m, 1H), 1.43-1.30 (m, 4H), 1.15-0.60 (m, 3H), 0.50-0.35 (m, 2H), 0.10-0.02 (m, 2H).

LC/MS, m/z=546 [M+H]$^+$ (Calc: 545).

A suspension of R-57, lithium salt (18 mg, 0.077 mmol) in DCM (2 mL) was treated with 1N HCl in ether at 0° C. After concentration, the residue was dissolved in DMF (2 mL). To this solution was added DIPEA (36 μL) and HATU (28 mg). The solution was stirred at room temperature for 20 min. Glycine methyl ester HCl salt (8.2 mg) was added. The reaction mixture was stirred at room temperature overnight. The reaction was quenched with water and then extracted with DCM. The extract was washed with water, brine, dried over MgSO$_4$.

Purification by flash column chromatography (silica gel, 0-50% EtOAc/DCM) gave 7.8 mg of R-58.

$^1$H NMR $\delta_H$ (300 MHz, CDCl$_3$) 7.79 (d, J=8.5 Hz, 2H), 7.44 (d, J=8.3 Hz, 2H), 6.69 (d, J=8.25 Hz, 1H), 6.63 (bt, J=4.5 Hz, 1H), 6.55 (d, J=8.25 Hz, 1H), 4.59 (m, 2H), 4.51 (s, 1H), 4.25 (d, J=5.0 Hz, 2H), 3.86 (s, 3H), 3.78 (s, 3H), 3.75 (dd, J=3.8 Hz, 8.8 Hz, 1H), 3.52 (t, J=9.1 Hz, 1H), 3.37 (s, 3H), 3.05-2.95 (m, 3H), 2.70-2.60 (m, 1H), 2.38-1.98 (m, 6H), 1.70-1.62 (m, 2H), 1.48-1.32 (m, 3H), 1.14-1.11 (m, 1H), 0.82-0.71 (m, 2H), 0.51-0.46 (m, 2H), 0.11-0.05 (m, 2H).

R-58 (7.8 mg) was dissolved in THF/MeOH/H$_2$O (4 ml, 2/1/1, v/v/v). To this solution was added LiOH—H$_2$O (2 mg). The mixture was stirred at room temperature overnight. After concentration, the solid was triturated with DCM/MeOH (10/1, v/v) then filtered. The clean filtrate was concentrated and afforded 7 mg of Compound 43 as the lithium salt.

$^1$H NMR $\delta_H$ (300 MHz, DMSO-d$_6$) δ: 7.78 (d, J=8.25 Hz, 2H), 7.73 (bt, J=4.1 Hz, 1H), 7.41 (d, J=8.25 Hz, 2H), 6.73 (d, J=8.22 Hz, 1H), 6.55 (d, J=8.22 Hz, 1H), 4.56-4.50 (m, 3H), 3.75 (s, 3H), 3.62 (dd, J=3.9 Hz, 8.8 Hz, 1H), 3.51-3.41 (m, 3H), 3.22 (s, 3H), 2.98-2.71 (m, 3H), 2.65-2.55 (m, 1H), 2.33-2.15 (m, 4H), 2.14-1.95 (m, 2H), 1.56-1.45 (m, 1H), 1.36-0.95 (m, 5H), 0.82-0.70 (m, 1H), 0.62-0.38 (m, 3H), 0.09-0.02 (m, 2H).

LC/MS, m/z=601 [M−H](Calc: 602).

Example 28

2-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)acetic acid (Compound 46); and 2-(3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)acetic acid (Compound 96)

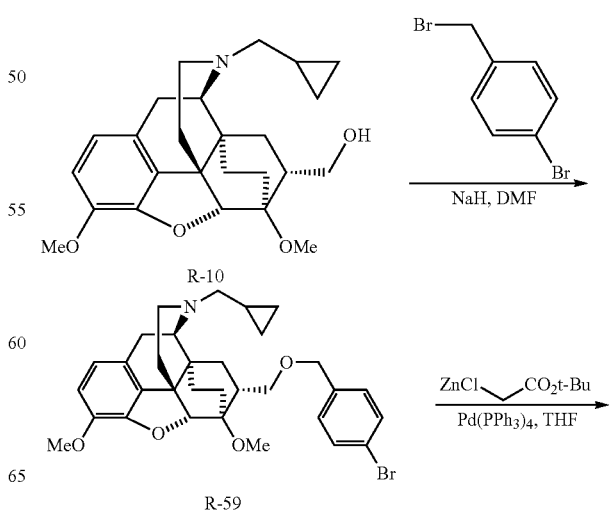

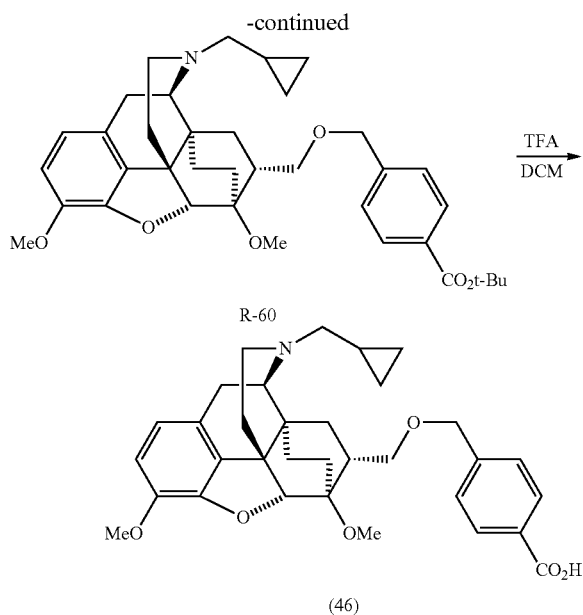

R-59 was prepared in a manner analogous to R-23 (Example 21) from R-10 using 4-bromobenzyl bromide rather than 3-bromobenzyl bromide.

$^{1}$H NMR $\delta_H$ (300 MHz, CDCl$_3$) 7.45 (d, J=8.5, 2H), 7.22 d, J=8.5 Hz, 2H), 6.69 (d, J=8.0 Hz, 1H), 6.55 (d, J=8.0 Hz, 1H), 4.54-4.46 (m, 3H), 3.86 (s, 3H), 3.73 (dd, J=8.8, 3.8 Hz, 1H), 3.49 (dd, J=9.1, 8.8 Hz, 1H), 3.36 (s, 3H), 3.02-2.90 (m, 3H), 2.65 (dd, J=11.8, 5.0 Hz, 1H), 2.36-2.18 (m, 5H), 2.05 (m, 1H), 1.64 (m, 1H), 1.47-1.33 (m, 3H), 1.11-1.02 (m, 1H), 0.86-0.68 (m, 2H); 0.51-0.43 (m, 2H); 0.12-0.08 (m, 2H).

To a solution of R-59 (81 mg, 0.14 mmol) in THF (20 mL) was added [2-(tert-butoxy)-2-oxoethyl]-zinc(II) chloride (4.5 mL, 0.5 M in ether, 2.25 mmol) (Rieke Metals) following by (PPh$_3$)$_4$Pd (45 mg, 0.039 mmol, 28 mol %) under argon. The mixture was refluxed for 20 h under argon. The reaction was quenched with ice-cold water and extracted with EtOAc. Purification by flash column chromatography (silica gel, 0-50% EtOAc/DCM) afforded 45 mg of R-60.

$^{1}$H NMR $\delta_H$ (300 MHz, CDCl$_3$) 7.41-7.09 (m, 4H), 6.69 (d, J=8.2 Hz, 1H), 6.55 (d, J=8.2 Hz, 1H), 4.54-4.49 (m, 3H), 3.85 (s, 3H), 3.74 (dd, J=8.8, 3.8 Hz, 1H), 3.52-3.46 (m, 3H), 3.36 (s, 3H), 3.02-2.90 (m, 3H), 2.65 (dd, J=9.6, 5.8 Hz, 1H), 2.36-2.15 (m, 5H), 2.09-2.02 (m, 3H), 1.70-1.60 (m, 1H), 1.41 (s, 9H), 1.10-1.00 (m, 1H), 0.82-0.68 (m, 2H); 0.51-0.43 (m, 2H); 0.12-0.08 (m, 2H).

To a solution of R-60 (45 mg, 0.073 mmol) in DCM (15 mL) was added TFA (1 mL) dropwise. The solution was stirred at room temperature for 5 h. The solution was concentrated and the residue was partitioned between DCM and sat. NaHCO$_3$. The aqueous layer was extracted with DCM. Purification by flash column chromatography (silica gel, 0-10% MeOH/DCM) followed by HCl salt formation gave 11.4 mg of Compound 46 HCl salt as a white solid.

$^{1}$H NMR $\delta_H$ (300 MHz, DMSO-d$_6$) 8.66 (bs, 1H), 7.30 (d, J=8.0, 2H), 7.23 (d, J=8.0 Hz, 2H), 6.88 (d, J=8.2 Hz, 1H), 6.68 (d, J=8.2 Hz, 1H), 4.75 (s, 1H), 4.49 (s, 2H), 3.89 (d, J=6.6 Hz, 1H), 3.78 (s, 3H), 3.64-3.55 (m, 3H), 3.53-3.43 (m, 1H), 3.30-3.22 (m, 5H), 3.01-2.71 (m, 4H), 2.41-2.20 (m, 2H), 1.90-1.81 (m, 1H), 1.60-1.35 (m, 2H), 1.32-1.02 (m, 3H), 0.71-0.53 (m, 3H), 0.52-0.32 (m, 2H).

LC/MS, m/z=560 [M+H]$^+$ (Calc: 559).

In a similar manner 2-(3-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)acetic acid (Compound 96) was prepared using R-23 rather than R-10. Purification by flash column chromatography (silica gel, 0-10% MeOH/DCM) gave Compound 96.

$^{1}$H NMR $\delta_H$ (300 MHz, CDCl$_3$) 7.71 (bs, 1H), 7.25-7.21 (m, 3H), 7.08-7.05 (m, 1H), 6.71 (d, J=8.0 Hz, 1H), 6.58 (d, J=8.0 Hz, 1H), 4.79 (s, 1H), 4.36-4.30 (m, 2H), 3.85 (s, 3H), 3.83-3.78 (m, 1H), 3.65-3.48 (m, 4H), 3.36-3.33 (m, 1H), 3.32 (s, 3H), 3.03-2.96 (m, 2H), 2.89-2.70 (m, 1H), 2.65-2.31 (m, 3H), 1.86-1.71 (m, 2H), 1.62-1.30 (m, 4H), 1.20-1.09 (m, 2H), 0.83-0.59 (m, 3H), 0.35-0.22 (m, 2H).

LC/MS, m/z=560 [M+H]$^+$ (Calc: 559).

Example 29

(4R,4aS,6R,7R,7aR,12bS)-6-(((4-((2H-tetrazol-5-yl)methyl)benzyl)oxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 54)

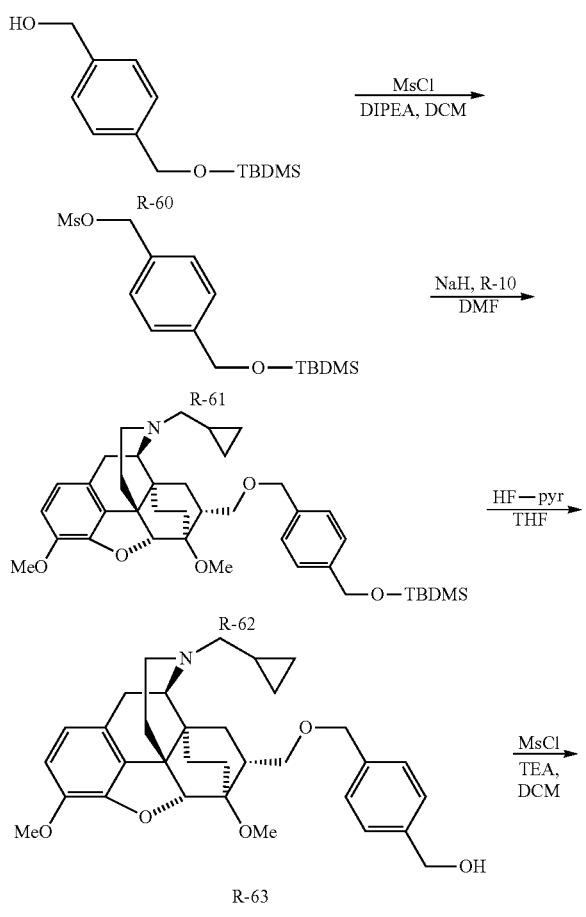

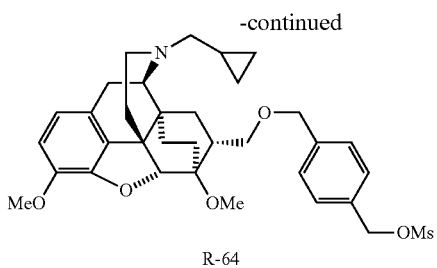

R-64

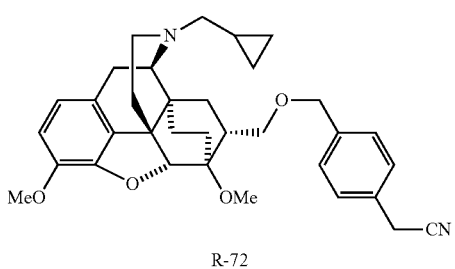

R-72

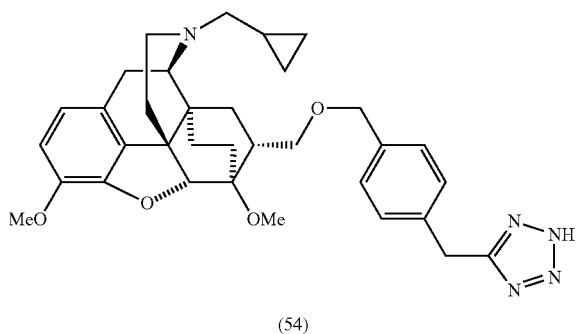

(54)

To a solution of R-60 (0.52 g, 2 mmol, 1 eq.) (*Org. Lett.*, 2007, 9, 1187) and DIPEA (1.0 mL) in DCM (20 mL) was added MsCl (0.32 mL, 4 mmol, 2 eq.) dropwise at 0° C. The mixture was stirred at 0° C. for 1 h and at room temperature overnight. The reaction was quenched with water. The aqueous layer was extracted with DCM. The combined organic layers were washed with water, brine, dried over MgSO₄. After concentration, R-61 was obtained. The material was used in the next step without further purification.

NaH (130 mg, 60% suspension in mineral oil) was added to a solution of R-10 (249 mg, 0.6 mmol, 1 eq.) in anhydrous DMF (5 mL) at 0° C. under argon. The resulting mixture was stirred at room temperature for 0.5 h. R-61 (545 mg, 1.65 mmol), was added at 0° C. under argon and the reaction was stirred at room temperature overnight. The reaction was quenched with ice-water and extracted with EtOAc. The combined organic layers were washed with water, brine, dried over MgSO₄. The crude product was purified by flash column chromatography (silica gel, 0-3% MeOH/DCM) to provide 250 mg of R-62.

$^1$H NMR $\delta_H$ (300 MHz, CDCl₃) 7.36-7.29 (m, 4H), 6.69 (d, J=8.25 Hz, 1H), 6.55 (d, J=8.25 Hz, 1H), 4.80-4.70 (m, 2H), 4.61-4.51 (m, 3H), 3.86 (s, 3H), 3.80-3.70 (m, 1H), 3.53-3.42 (m, 1H), 3.37 (s, 3H), 3.02-2.92 (m, 3H), 2.70-2.62 (m, 1H), 2.37-2.00 (m, 6H), 1.69-1.62 (m, 1H), 1.49-1.36 (m, 3H), 1.11-0.96 (m, 1H), 0.94 (s, 9H), 0.88-0.69 (m, 2H), 0.51-0.43 (m, 2H), 0.09 (s, 6H), 0.06-0.04 (m, 2H).

To a solution of R-62 (199 mg, 0.3 mmol), in THF (40 mL) was added a hydrogen fluoride-pyridine complex (50 µL) (Aldrich) at 0° C. The mixture was stirred at 0° C. for 0.5 h and at room temperature overnight. After concentration, the residue was partitioned between DCM and conc. aq. ammonia. The aqueous layer was extracted with DCM. The crude product was purified by flash column chromatography (silica gel, 0-4% MeOH/DCM) to provide R-63.

To a solution of R-63 (100 mg, 0.19 mmol) and triethylamine (0.5 mL) in DCM (15 mL) was added MsCl (100 µL) dropwise at 0° C. The mixture was stirred at 0° C. for 1 h and at room temperature overnight. The reaction was quenched with water. The aqueous layer was extracted with DCM. The combined organic layers were washed with water, brine, dried over MgSO₄. After concentration, 110 mg of R-64 was obtained. The material was used in the next step without further purification.

To a solution of R-64 (110 mg, 0.18 mmol) in ACN (15 mL) was added potassium cyanide (25 mg, 0.38 mmol) and 18-crown-6 (10 mg, cat. amt.). The mixture was stirred at room temperature for 16 h. The reaction was quenched with water. The aqueous layer was extracted with DCM. The combined organic layers were washed with water, brine, dried over MgSO₄. The crude product was purified by flash column chromatography (silica gel, 0-3% MeOH/DCM) to provide 35 mg of R-72.

$^1$H NMR $\delta_H$ (300 MHz, CDCl₃) 7.40-7.27 (m, 4H), 6.69 (d, J=8.0 Hz, 1H), 6.55 (d, J=8.0 Hz, 1H), 4.61-4.48 (m, 3H), 3.86 (s, 3H), 3.83-3.70 (m, 3H), 3.53-3.44 (m, 1H), 3.37 (s, 3H), 3.02-2.92 (m, 3H), 2.65 (dd, J=11.8 Hz, 5.0 Hz, 1H), 2.37-2.00 (m, 6H), 1.69-1.60 (m, 1H), 1.49-1.34 (m, 3H), 1.11-1.00 (m, 1H), 0.88-0.68 (m, 2H), 0.51-0.43 (m, 2H), 0.06-0.04 (m, 2H).

A mixture of R-72 (29 mg, 0.05 mmol), azidotrimethylsilane (50 µL, 0.38 mmol) and dibutyltin oxide (5 mg, cat. amt.) in toluene (2 mL) was heated at 120° C. for 8 h in a microwave reactor. After concentration, the residue was purified by flash column chromatography (silica gel, 0-10% MeOH/DCM) to provide 8 mg of Compound 54.

$^1$H NMR $\delta_H$ (300 MHz, CDCl₃) 7.17-7.08 (m, 4H), 6.72 (d, J=8.2 Hz, 1H), 6.59 (d, J=8.2 Hz, 1H), 5.67 (bs, 1H), 4.48 (s, 1H), 4.09 (s, 2H), 4.13 (s, 2H), 3.86 (s, 3H), 3.65 (dd, J=9.1 Hz, 3.8 Hz, 1H), 3.53-3.37 (m, 2H), 3.33 (s, 3H), 3.12-2.82 (m, 3H), 2.73 (dd, J=12.6 Hz, 6.3 Hz, 1H), 2.62-2.45 (m, 3H), 2.18-2.08 (m, 2H), 1.76-1.67 (m, 1H), 1.53-1.33 (m, 3H), 1.26-1.11 (m, 1H), 0.89-0.73 (m, 2H), 0.59-0.46 (m, 2H), 0.25-0.13 (m, 2H).

LC/MS, m/z=584 [M+H]⁺ (Calc: 583).

Example 30

Methyl 2-(3-(((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenoxy)acetate (Compound 73); 2-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenoxy)acetic acid (Compound 90); (4R,4aS,6R,7R,7aR,12bS)-3-(cyclopropylmethyl)-7,9-dimethoxy-6-(((4-(2-(2-(2-methoxyethoxy)ethoxy)ethoxy)benzyl)oxy)methyl)-1,2,3,4,5,6,7,7a-octahydro-4a,7-ethano-4,12-methanobenzofuro[3,2-e]isoquinoline (Compound 37); (4R,4aS,6R,7R,7aR,12bS)-6-(((4-(2,5,8,11,14-pentaoxahexadecan-16-yloxy)benzyl)oxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 38); methyl 2-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenoxy)acetate (Compound 39); and 2-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenoxy)acetic acid (Compound 40)

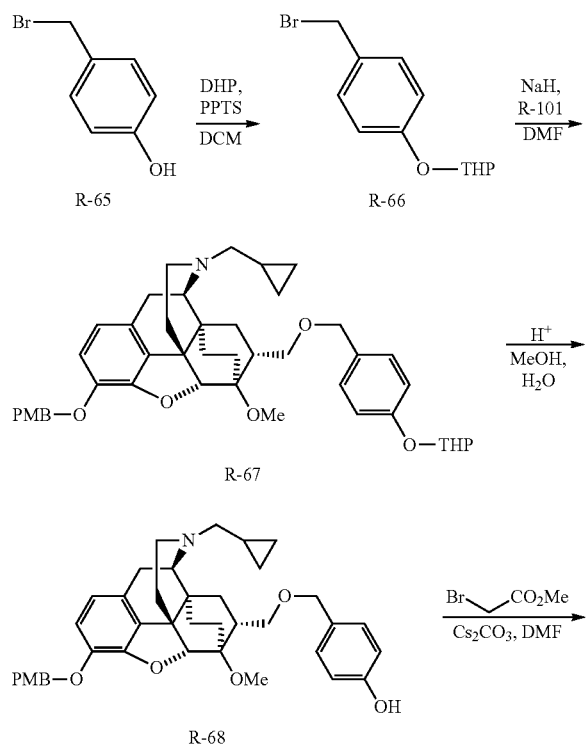

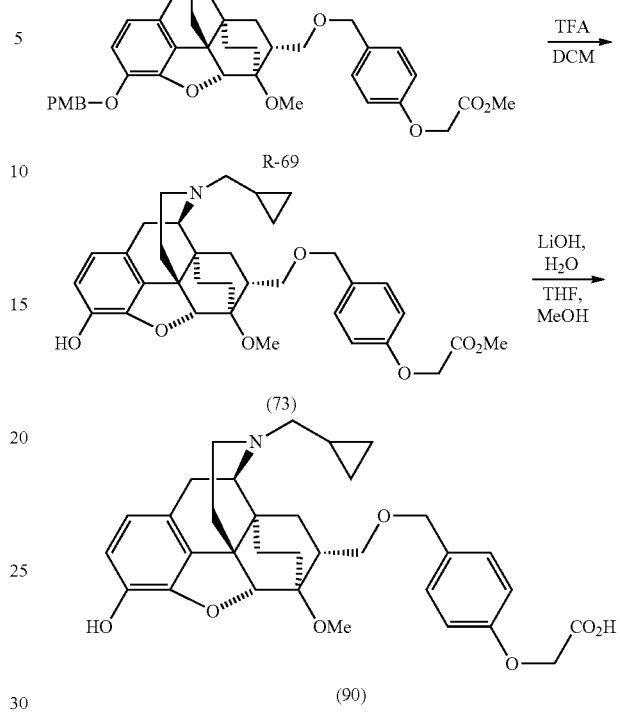

A mixture of R-65 (1.34 g, 15.9 mmol) (*J. Med. Chem.*, 1992, 35, 1650), 3,4-dihydro-2H-pyran (1.34 g, 15.9 mmol) and pyridinium-p-toluene sulfonate (0.3 g, catalytic) in DCM (30 mL) was stirred at room temperature overnight. The reaction mixture was concentrated and the crude product was purified by flash column chromatography (silica gel, 0-100% EtOAc/hexanes) to give 0.9 g of R-66.

$^1$H NMR $\delta_H$ (300 MHz, CDCl$_3$) 7.17-7.33 (m, 1H), 7.05-7.12 (m, 1H), 6.93-7.05 (m, 2H), 5.33-5.48 (m, 1H), 4.46 (s, 2H), 3.81-3.98 (m, 1H), 3.53-3.66 (m, 1H), 1.90-2.11 (m, 1H), 1.80-1.90 (m, 2H), 1.57-1.77 (m, 3H).

Sodium hydride (0.065 g, 1.45 mmol) was added to an ice-cold solution of R-101 (0.15 g, 0.29 mmol) in DMF (anhydrous, 3 mL) under a nitrogen atmosphere. The reaction mixture was allowed to stir for 30 min and R-66 (0.155 g, 0.58 mmol) was added. The resulting mixture was allowed to stir for 6 h at room temperature. The reaction mixture was quenched with ice and extracted with chloroform. The crude material was purified by flash column chromatography (silica gel, 0-3% MeOH/DCM) to give 0.19 g of R-67.

$^1$H NMR $\delta_H$ (300 MHz, CDCl$_3$) 7.36 (d, J=8.5 Hz, 2H), 7.20-7.30 (m, 2H), 7.07 (s, 1H), 6.99 (d, J=7.7 Hz, 2H), 6.87 (d, J=8.5 Hz, 2H), 6.71 (d, J=8.3 Hz, 1H), 6.49 (d, J=8.3 Hz, 1H), 5.43 (br.s, 2H), 5.04-5.19 (m, 2H), 4.52 (s, 5H), 3.85-4.00 (m, 2H), 3.79 (br.s, 4H), 3.44-3.67 (m, 3H), 3.38 (s, 3H), 2.86-3.05 (m, 3H), 2.59-2.72 (m, 1H), 2.12-2.38 (m, 5H), 1.92-2.11 (m, 3H), 1.80-1.90 (m, 4H), 1.55-1.75 (m, 8H), 1.36-1.50 (m, 3H), 1.02-1.16 (m, 1H), 0.62-0.91 (m, 2H), 0.41-0.54 (m, 2H), 0.09 (m, 2H).

To solution of R-67 (0.170 g, 0.24 mmol) in MeOH-water (60 mL, 2:1) was added formic acid (water solution, 95 wt %, 5 mL). The mixture was stirred for 3 h at room temperature. The reaction mixture was concentrated, and then added to 15% ammonia in water. The aqueous layer was extracted with DCM and the organic extracts were combined, washed with water, brine and dried over MgSO$_4$. The solvent was evaporated and the residue purified by flash column chromatography (silica gel, 0-5% MeOH/DCM) to provide 130 mg of R-68.

$^1$H NMR δ$_H$ (300 MHz, CDCl$_3$) 7.35 (d, J=8.8 Hz, 2H), 7.14-7.24 (m, 1H), 6.82-6.93 (m, 3H), 6.72-6.79 (m, 1H), 6.71 (d, J=8.0 Hz, 1H), 6.49 (d, J=8.0 Hz, 1H), 5.11 (d, J=5.5 Hz, 2H), 4.50 (s, 3H), 3.79 (s, 4H), 3.51 (t, J=8.8 Hz, 1H), 3.38 (s, 3H), 2.88-3.07 (m, 3H), 2.61-2.71 (m, 1H), 1.99-2.36 (m, 8H), 1.57-1.71 (m, 2H), 1.36-1.49 (m, 4H), 1.00-1.14 (m, 1H), 0.66-0.86 (m, 2H), 0.44-0.52 (m, 2H), 0.06-0.14 (m, 2H).

To a solution of R-68 (0.13 g, 0.21 mmol) and methyl 2-bromoacetate (0.064 g, 0.42 mmol) in DMF (4 mL) was added cesium carbonate (0.2 g, 0.6 mmol). The mixture was stirred at room temperature overnight. The reaction was quenched with water and then extracted with EtOAc. The extract was washed with water, brine and dried over MgSO$_4$. Purification by flash column chromatography (silica gel, 0-5% MeOH/DCM) gave 102 mg of R-69.

$^1$H NMR δ$_H$ (300 MHz, CDCl$_3$) 7.35 (d, J=8.5 Hz, 2H), 7.21-7.31 (m, 1H), 6.92-7.04 (m, 2H), 6.87 (d, J=8.8 Hz, 3H), 6.71 (d, J=8.0 Hz, 1H), 6.48 (d, J=8.3 Hz, 1H), 5.02-5.19 (m, 2H), 4.64 (s, 2H), 4.46-4.56 (m, 3H), 3.79 (m, 8H), 3.46-3.57 (m, 1H), 3.38 (s, 3H), 2.91-3.06 (m, 1H), 2.65 (m, 1H), 2.00-2.35 (m, 6H), 1.59-1.71 (m, 1H), 1.34-1.50 (m, 3H), 0.99-1.16 (m, 1H), 0.66-0.87 (m, 2H), 0.42-0.52 (m, 2H), 0.08 (d, J=5.0 Hz, 2H).

To a solution of R-69 (0.085 g, 0.12 mmol) in DCM (8 mL) was added TFA (1.2 mL) at room temperature. After 30 min, the reaction was quenched by the addition of 15% aqueous ammonia and the aqueous layer was extracted with DCM. The residue, after evaporating the solvent, was purified by flash column chromatography (silica gel, 0-5% MeOH/DCM) to give impure product, which was then re-chromatographed (silica gel, 0-50% EtOAc/DCM) followed by HCl salt formation to give Compound 73 HCl salt as a white solid.

$^1$H NMR δ$_H$ (300 MHz, DMSO-d$_6$) 9.30 (s, 1H), 8.75 (br.s, 1H), 7.26 (m, 1H), 6.94 (d, J=7.4 Hz, 1H), 6.93 (br.s, 1H), 6.77-6.85 (m, 1H), 6.68 (d, J=8.0 Hz, 1H), 6.54 (d, J=8.0 Hz, 1H), 4.79 (s, 2H), 4.70 (s, 1H), 4.52 (s, 2H), 3.92 (m, 1H), 3.70 (s, 3H), 3.57-3.69 (m, 1H), 3.45-3.55 (m, 1H), 3.35 (s, 3H), 2.87-3.09 (m, 4H), 2.12-2.37 (m, 2H), 1.96-2.12 (m, 1H), 1.54-1.72 (m, 2H), 1.31-1.51 (m, 3H), 0.63-0.86 (m, 4H), 0.47-0.13 (m, J=7.7 Hz, 2H).

LC/MS, m/z=576 [M+H]$^+$ (Calc: 575).

To a solution of Compound 73 (32 mg, 0.056 mmol) in THF/MeOH/H$_2$O (6 mL, 2/1/1, v/v/v) was added LiOH:H$_2$O (5 mg). The mixture was stirred at room temperature overnight. The solvent was evaporated and the residue was triturated with DCM/MeOH (10/1, v/v) and then filtered. The clear filtrate was concentrated to afford Compound 90 lithium salt.

$^1$H NMR δ$_H$ (300 MHz, DMSO-d$_6$) 9.08 (s, 1H), 7.21 (d, J=7.7 Hz, 6H), 6.82-6.96 (m, 2H), 6.69-6.82 (m, 1H), 6.59 (d, J=8.0 Hz, 1H), 6.44 (d, J=8.0 Hz, 1H), 4.37-4.60 (m, 5H), 3.35-3.79 (m, 3H), 3.15-3.22 (m, 3H), 2.71-2.99 (m, 5H), 2.44-2.51 (m, 4H), 1.95-2.43 (m, 5H), 1.59 (d, J=10.7 Hz, 1H), 1.27-1.42 (m, 6H), 0.39-0.73 (m, 3H), 0.06-0.27 (m, 2H).

LC/MS, m/z=562 [M+H]$^+$ (Calc: 561).

In a similar manner (4R,4aS,6R,7R,7aR,12bS)-3-(cyclopropylmethyl)-7,9-dimethoxy-6-(((4-(2-(2-(2-methoxyethoxy)ethoxy)ethoxy)benzyl)oxy)methyl)-1,2,3,4,5,6,7,7a-octahydro-4a,7-ethano-4,12-methanobenzofuro[3,2-e]isoquinoline (Compound 37) was prepared from R-10 using PEG$_{30}$ Ms rather than methyl bromoacetate. Purification by flash column chromatography (silica gel, 0-30% EtOAc/DCM) gave Compound 37 as a colorless oil.

$^1$H NMR δ$_H$ (300 MHz, DMSO-d$_6$) 7.25 (d, J=8.8 Hz, 2H), 6.87 (d, J=8.5 Hz, 2H), 6.71 (d, J=8.0 Hz, 1H), 6.56 (d, J=8.0 Hz, 1H), 4.40-4.52 (m, 3H), 4.10-4.13 (m, 2H), 3.83-3.89 (m, 5H), 3.63-3.75 (m, 8H), 3.53-3.56 (m, 2H), 3.38 (s, 3H), 3.35 (s, 3H), 2.95-3.07 (m, 2H), 2.1-2.35 (m, 5H), 1.65-1.82 (m, 5H), 1.35-1.45 (m, 3H), 1.0-1.15 (m, 1H), 0.64-0.87 (m, 2H), 0.42-0.59 (m, 2H), 0.03-0.14 (m, 1H).

LC/MS, m/z=664 [M+H]$^+$ (Calc: 663).

In a similar manner (4R,4aS,6R,7R,7aR,12bS)-6-(((4-(2,5,8,11,14-pentaoxahexadecan-16-yloxy)benzyl)oxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline (Compound 38) was prepared from R-10 using PEG$_{50}$ Ms rather than methyl bromoacetate. Purification by flash column chromatography (silica gel, 0-30% EtOAc/DCM) gave Compound 38 as a colorless oil.

$^1$H NMR δ$_H$ (300 MHz, CDCl$_3$) 7.25 (d, J=8.5 Hz, 2H), 6.87 (d, J=8.5 Hz, 2H), 6.68 (d, J=8.0 Hz, 1H), 6.54 (d, J=8.0 Hz, 1H), 4.37-4.50 (m, 3H), 4.10-4.13 (m, 2H), 3.83-3.87 (m, 5H), 3.63-3.75 (m, 16H), 3.53-3.56 (m, 2H), 3.41-3.50 (m, 1H), 3.38 (s, 3H), 3.35 (s, 3H), 2.92-3.03 (m, 3H), 2.60-2.70 (m, 1H), 2.23-2.35 (m, 3H), 1.96-2.22 (m, 3H), 1.60-1.66 (m, 1H), 1.35-1.45 (m, 3H), 1.00-1.12 (m, 1H), 0.64-0.84 (m, 2H), 0.42-0.51 (m, 2H), 0.05-0.12 (m, 2H).

LC/MS, m/z=752 [M+H]$^+$ (Calc: 751).

In a similar manner methyl 2-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenoxy)acetate (Compound 39) was prepared from R-10 using methyl bromoacetate. Purification by flash column chromatography (silica gel, 0-30% EtOAc/DCM) gave Compound 39 as a colorless oil.

$^1$H NMR δ$_H$ (300 MHz, CDCl$_3$) 7.29 (d, J=8.8 Hz, 2H), 6.88 (t, J=8.5 Hz, 2H), 6.69 (d, J=8.25 Hz, 1H), 6.55 (d, J=8.25 Hz, 1H), 4.63 (s, 2H), 4.46-4.51 (m, 3H), 3.86 (s, 3H), 3.78 (s, 3H), 3.70-3.73 (m, 1H), 3.46 (t, J=8.8 Hz, 1H), 3.36 (s, 3H), 2.94-3.00 (m, 3H), 2.62-2.68 (m, 1H), 2.22-2.31 (m, 4H), 2.03-2.05 (m, 1H), 1.62-1.66 (m, 2H), 1.38-1.44 (m, 3H), 1.04-1.11 (m, 1H), 0.71-0.82 (m, 2H), 0.46-0.49 (m, 2H), 0.07-0.11 (m, 2H).

LC/MS, m/z=590 [M+H]$^+$ (Calc: 589).

Saponification of Compound 39 as for Compound 73 was followed by trituration with DCM/MeOH (10/1, v/v) and filitration. The clean filtrate was concentrated to give Compound 40 lithium salt as a white solid.

$^1$H NMR δ$_H$ (300 MHz, DMSO-d$_6$) 7.07 (d, J=6.6 Hz, 2H), 6.77 (d, J=8.52 Hz, 2H), 6.67 (d, J=8.22 Hz, 1H), 6.53 (d, J=7.98 Hz, 1H), 4.46 (s, 1H), 4.15-4.33 (m, 3H), 3.83 (s, 3H), 3.66--3.68 (m, 1H), 3.35-3.43 (m, 1H), 3.31 (s, 3H), 2.91-2.94 (m, 3H), 2.60-2.62 (m, 1H), 2.17-2.38 (m, 7H), 1.59-1.63 (m, 1H), 1.30-1.41 (m, 3H), 1.09-1.11 (m, 1H), 0.62-0.75 (m, 2H), 0.35-0.42 (m, 2H), 0.02-0.08 (m, 2H).

LC/MS, m/z=576 [M+H]$^+$ (Calc: 575).

Example 31

(S)-2-amino-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)propanamide (Compound 81)

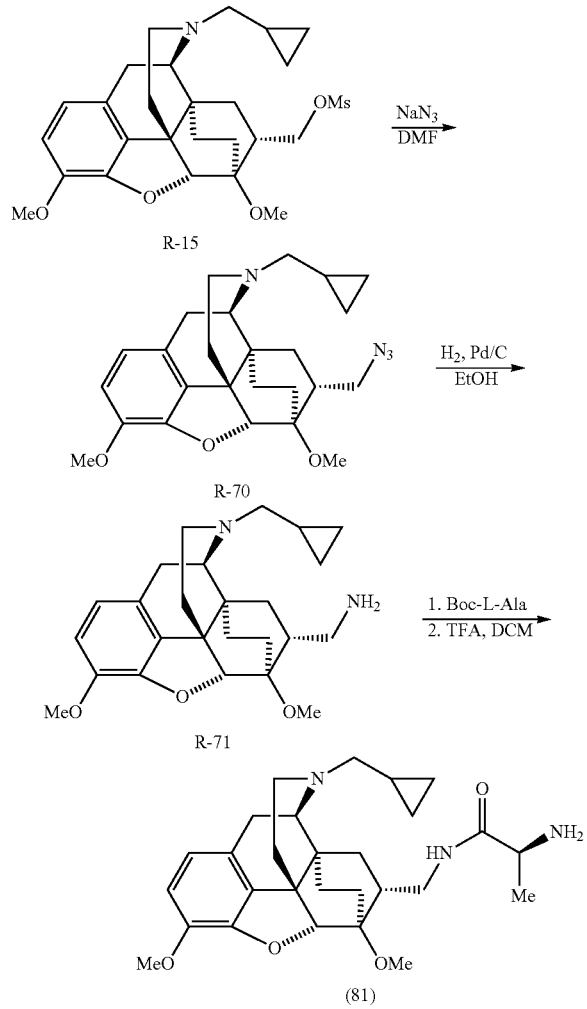

To a solution of mesylate R-15 (550 mg, 1.13 mmol, 1 eq.) in DMF (10 mL) was added sodium azide (220 mg, 3.36 mmol, 3 eq.). The mixture was heated at 65° C. for 16 h. The reaction was quenched with water and extracted with DCM. The organic layer was washed with water, brine and dried over MgSO$_4$. After concentration R-70 was obtained which was used in the next step without further purification.

$^1$H NMR δ$_H$ (300 MHz, CDCl$_3$) 6.70 (d, J=8.0 Hz, 1H), 6.56 (d, J=8.0 Hz, 1H), 4.54-4.48 (m, 1H), 3.86 (s, 3H), 3.70 (dd, J=12.1 Hz, 4.1 Hz, 1H), 3.40 (s, 3H), 3.26-3.18 (m, 1H), 3.06-2.92 (m, 3H), 2.65 (dd, J=11.8 Hz, 5.0 Hz, 1H), 2.37-2.18 (m, 4H), 2.10-1.98 (m, 2H), 1.71-1.461 (m, 1H), 1.58-1.30 (m, 2H), 1.28-1.20 (m, 1H), 1.12-1.00 (m, 1H), 0.85-0.68 (m, 2H); 0.51-0.43 (m, 2H); 0.12-0.03 (m, 2H).

LC/MS, m/z=437 [M+H]$^+$ (Calc: 436).

To a solution of R-70 (398 mg, 0.91 mmol) in MeOH (15 mL) and DCM (3 mL) was added 10% Pd/C (398 mg; 50% wet). The reaction mixture was stirred under one atmosphere of H$_2$ for 4 h, filtered through Celite and concentrated. Purification by flash column chromatography (silica gel, 1-5% MeOH (with 7% ammonia)/DCM) gave R-71 as a white solid.

$^1$H NMR δ$_H$ (300 MHz, CDCl$_3$) 6.69 (d, J=8.25 Hz, 1H), 6.55 (d, J=8.25 Hz, 1H), 4.50 (d, J=1.92 Hz, 1H), 3.84 (s, 3H), 3.40 (s, 3H), 2.92-3.13 (m, 4H), 2.53-2.69 (m, 2H), 2.17-2.40 (m, 4H), 2.03 (dt, J$_1$=12.63 Hz, J$_{2=5.76}$ Hz, 1H), 1.79-1.93 (m, 1H), 1.66 (dd, J$_1$=12.90 Hz, J$_{2=2.46}$ Hz, 1H), 1.33-1.60 (m, 4H), 0.95-1.11 (m, 2H), 0.67-0.85 (m, 2H), 0.41-0.52 (m, 2H), 0.05-0.12 (m, 2H).

LC/MS, m/z=411 [M+H]$^+$ (Calc: 410).

R-71 was coupled to Boc-L-alanine in a manner similar to that described in Example 20. Purification by reverse phase column chromatography (C18, acetonitrile/water with 0.1% TFA, 0-95%) gave Compound 81 TFA salt as a white solid.

$^1$H NMR δ$_H$ (300 MHz, DMSO-d$_6$) 8.70 (bs, 1H), 8.52 (t, J=5.49 Hz, 1H), 8.12 (bs, 3H), 6.88 (d, J=8.25 Hz, 1H), 6.68 (d, J=8.25 Hz, 1H), 4.75 (s, 1H), 3.70-3.88 (m, 3H), 3.79 (s, 3H), 3.15-3.50 (m, 4H), 3.24 (s, 3H), 2.68-3.02 (m, 4H), 2.37-2.53 (m, 1H), 2.05-2.23 (m, 2H), 1.83-1.96 (m, 1H), 1.32-1.48 (m, 3H), 1.37 (d, J=6.84 Hz, 3H), 0.96-1.30 (m, 4H), 0.52-0.75 (m, 3H), 0.34-0.51 (m, 2H).

LC/MS, m/z=482 [M+H]$^+$ (Calc: 481).

Example 32

1-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)ethane-1,2-diol (Compound 97)

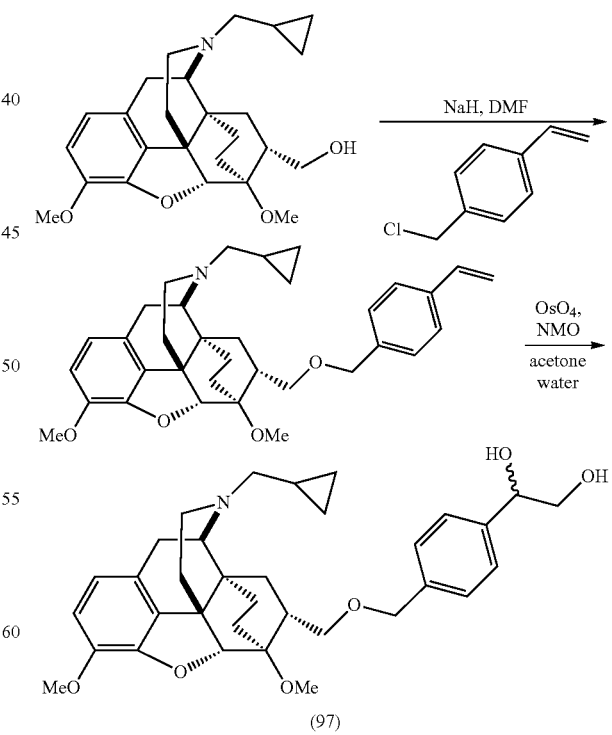

NaH (85 mg, 60% suspension in mineral oil) was added to a solution of R-10 (153.2 mg, 0.37 mmol, 1 eq.) in anhydrous DMF (3 ml). The resulting mixture was stirred at room temperature for 0.5 h. 4-Vinylbenzyl chloride (Aldrich) (170 mg, 1.12 mmol, 3 eq.) was added and the reaction was stirred at room temperature overnight. The reaction was quenched with ice water and extracted with EtOAc. The combined organic layers were washed with water, brine and then dried over $MgSO_4$. The crude was purified by column chromatography (0-30% EtOAc in DCM) afford the intermediate styrene.

To a solution of the styrene (80 mg, 0.152 mmol) in acetone/water (6 ml, 5/1, v/v) was added osmium tetroxide (100 μL). N-Methylmorpholine-N-oxide-$H_2O$ (NMO-$H_2O$, 26 mg) was added. The mixture was stirred at room temperature 4 hr. The reaction was quenched with water and then extracted with EtOAc. The combined organic layers were washed with brine and dried over $MgSO_4$. The crude was purified by column chromatography (0-5% MeOH in DCM) afford Compound 97. The HCl salt was prepared by treatment of the free base with 1 M HCl in ether.

$^1$H NMR: $\delta_H$ (300 MHz, DMSO-$d_6$): 8.62 (bs, 1H), 7.32 (d, J=8.5 Hz, 2H), 7.28 (d, J=8.5 Hz, 2H), 6.75 (d, J=8.2 Hz, 1H), 6.68 (d, J=8.2 Hz, 1H), 5.24 (m, 1H), 4.85-4.65 (m, 2H), 4.56-4.45 (m, 3H), 3.89 (d, J=6.0 Hz, 1H), 3.78 (s, 3H), 3.63-3.30 (m, 4H), 3.24 (s, 3H), 3.02-2.93 (m, 1H), 2.92-2.75 (m, 3H), 2.42-2.20 (m, 2H), 1.92-1.82 (m, 1H), 1.58-1.12 (m, 7H), 0.72-0.55 (m, 3H), 0.52-0.33 (m, 2H).

LC/MS, m/z=562 [M+H]$^+$ (Calc: 561).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed is:

1. A compound of Formula I:

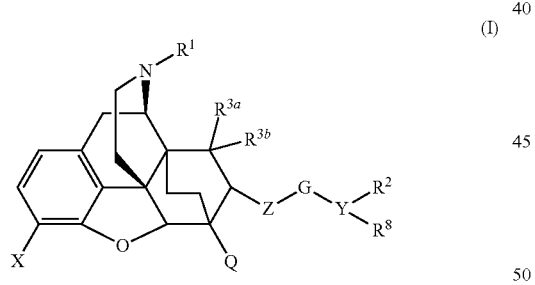

(I)

Wherein
R$^1$ is selected from hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, phenyl, and benzyl; any of which is optionally substituted with 1, 2, or 3 substituents independently selected from the group consisting of (C$_1$-C$_6$)alkyl-, OH, halo, —C(halo)$_3$, —CH(halo)$_2$, —CH$_2$(halo), —(C$_1$-C$_6$)alkyl-COOR$^7$, —COOR$^7$, NH$_2$, —NH(C$_1$-C$_6$)alkyl, —NR$^9$R$^{10}$, —CN, —CONR$^9$R$^{10}$, —NR$^9$COR$^{10}$, —SR$^{11}$, -(5- to 12-membered)carbocyclic ring, -(5- to 12-membered)heterocycle, phenyl, and benzyl;

R$^2$ and R$^8$ are each independently hydrogen, —(C$_1$-C$_{10}$)alkyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, —NH$_2$, —NH(C$_1$-C$_6$)alkyl, CN, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl or naphthyl; each of which is optionally substituted with one or two substituents independently selected from the group consisting of —OH, halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, —NH$_2$, —NH(C$_1$-C$_6$)alkyl, —(C$_1$-C$_6$)alkyl-NH(C$_1$-C$_6$)alkyl-R$^{14}$, —CN, —SH, —OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

at least one of R$^2$ and R$^8$ is —(C$_1$-C$_{10}$)alkyl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, NH$_2$, —NH(C$_1$-C$_6$)alkyl, CN, —CONR$^5$R$^6$, —(C$_1$-C$_6$)alkyl-CO—NR$^5$R$^6$, —COOR$^7$, —(C$_1$-C$_6$)alkyl-CO—OR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, ((7- to 12-membered)bicycloheterocycle)-(C$_1$-C$_6$)alkyl-, phenyl, benzyl, or naphthyl; each of which is optionally substituted with one or two substituents independently selected from the group consisting of OH, halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)CO(C$_1$-C$_6$)alkoxy-, phenyl, benzyl, NH$_2$, —NH(C$_1$-C$_6$)alkyl, —(C$_1$-C$_6$)alkyl-NH(C$_1$-C$_6$)alkyl-R$^{14}$, CN, SH, OR$^4$, —CONR$^5$R$^6$, —(C$_1$-C$_6$alkyl)-CO—NR$^5$R$^6$, —COOR$^7$, —(C$_1$-C$_6$)alkyl-CO—OR$^7$, —(C$_1$-C$_6$)alkoxy-COOR$^7$, —(OCH$_2$CH$_2$)$_s$—O(C$_1$-C$_6$)alkyl, —(CH$_2$CH$_2$O)$_s$—(C$_1$-C$_6$)alkyl, ((C$_1$-C$_6$)alkyl)sulfonyl(C$_1$-C$_6$)alkyl-, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—CO—NH$_2$, —NH—C(=O)—NH—(C$_1$-C$_6$)alkyl, —NH—C(=O)-(5- to 12-membered)aryl, —NH—C(=O)—(C$_1$-C$_6$)alkyl-(5- to 12-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(5- to 12-membered)aryl, -(5- to 12-membered)aryloxy, —(C$_1$-C$_6$)alkoxyC(O)NR$^5$R$^6$, —NH—(C$_1$-C$_6$)alkylC(O)—NR$^5$R$^6$, —C(O)NH—(C$_1$-C$_6$)alkyl-COOR$^7$, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, ((3- to 12 membered)heterocycle)-(C$_1$-C$_6$)alkoxy-(C$_1$-C$_6$) alkyl-, or together form (=O);

R$^4$ is selected from —(C$_1$-C$_6$)alkyl, —(C$_2$-C$_6$)alkenyl, —(C$_2$-C$_6$)alkynyl, —C(halo)$_3$, —CH(halo)$_2$, —CH$_2$(halo), hydroxy(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, or ((7- to 12-membered)bicycloheterocycle)-(C$_1$-C$_6$)alkyl-;

R$^5$ and R$^6$ are each independently hydrogen, —(C$_1$-C$_6$)alkyl, —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-CO—OR$^7$, —CONH$_2$, or (C$_1$-C$_6$)alkyl-CONH—, or R$^5$ and R$^6$ together with the nitrogen atom to which they are attached form a (4- to 8-membered)heterocycle;

R$^7$ is selected from hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, or ((C$_4$-C$_{12}$)cycloalkenyl)-(C$_1$-C$_6$)alkyl-;

R$^9$ and R$^{10}$ are each independently selected from hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, or ((C$_3$-C$_{12}$)cycloalkenyl)-(C$_1$-C$_6$)alkyl-;

each R$^{11}$ is independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, ((C$_1$-C$_6$)alkyl)sulfonyl(C$_1$-C$_6$)alkyl-, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, or ((C$_4$-C$_{12}$)cycloalkenyl)-(C$_1$-C$_6$)alkyl-;

R$^{12}$ and R$^{13}$ are each independently selected from the group consisting of hydrogen, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(OCH$_2$CH$_2$)$_s$—O(C$_1$-C$_6$)alkyl, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(5- to 12-membered)aryl, ((5- to 12-membered)aryl)(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, ((7- to 12-membered)bicycloheterocycle)-($C_1$-$C_6$)alkyl-, phenyl, benzyl or naphthyl; each of which is optionally substituted with one or two substituents independently selected from the group consisting of OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, phenyl, benzyl, NH$_2$, —NH($C_1$-$C_6$)alkyl, CN, SH, OR$^4$, —CONR$^5$R$^6$, —COOR$^7$, —($C_3$-$C_{12}$)cycloalkyl, (($C_3$-$C_{12}$)cycloalkyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)-bicycloheterocycle)-($C_1$-$C_6$)alkyl-;

R$^{14}$ is selected from —COOR$^7$, —($C_1$-$C_6$)alkyl-CO—OR$^7$, —C(=O)—($C_1$-$C_6$)alkyl-COOR$^7$, —($C_1$-$C_6$)alkyl-C(=O)—($C_1$-$C_6$)alkyl-COOR$^7$, —CONH$_2$, or ($C_1$-$C_6$)alkyl-CONH—;

G is O, —OCO—, —C(=O), NH, NR', S, SO, or SO$_2$;
R' is —C(=O)($C_1$-$C_6$)alkyl or —SO$_2$($C_1$-$C_6$)alkyl;
X is selected from OH, hydroxy($C_1$-$C_6$)alkyl-, dihydroxy($C_1$-$C_6$)alkyl-, halogen, —NH$_2$, —NR$^2$(C=O)R$^{12}$, —CONR$^{12}$R$^{13}$, —($C_1$-$C_6$)alkyl-CONH$_2$, —($C_1$-$C_6$)alkyl-COOH, —COOH, —O—($C_1$-$C_6$)alkyl-COOH, —O—($C_1$-$C_6$)alkyl-CONH$_2$, —($C_1$-$C_{10}$)alkyl, —($C_2$-$C_{10}$)alkenyl, —($C_2$-$C_{10}$)alkynyl, —($C_1$-$C_{10}$)alkoxy, —(OCH$_2$CH$_2$)$_s$—O($C_1$-$C_6$)alkyl, —(OCH$_2$CH$_2$)$_s$—OH, —(CH$_2$)$_p$CHOHCH$_2$OH, CN, —NH—SO$_2$R$^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, or ((7- to 12-membered)bicycloheterocycle)-($C_1$-$C_6$)alkoxy-;

Q is selected from OH, —($C_1$-$C_{10}$)alkoxy, —($C_1$-$C_{10}$)alkyl, —($C_3$-$C_{12}$)cycloalkyl, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —(OCH$_2$CH$_2$)$_s$—O($C_1$-$C_6$)alkyl, —(CH$_2$CH$_2$O)$_s$—($C_1$-$C_6$)alkyl, —(OCH$_2$CH$_2$)$_s$—OH, —O(C=O)R$^9$, —O—($C_1$-$C_6$)alkyl-COOR$^7$, —NH—($C_1$-$C_6$)alkyl-COOR$^7$, —O—C(O)—($C_1$-$C_6$)alkyl-C(O)OR$^7$, —NH—C(O)—($C_1$-$C_6$)alkyl-C(O)OR$^7$, —O—($C_1$-$C_6$)alkyl-C(O)NR$^9$R$^{10}$, —NH—($C_1$-$C_6$)alkyl-C(O)NR$^9$R$^{10}$, —O—C(O)—($C_1$-$C_6$)alkyl-C(O)NR$^9$R$^{10}$, —NH—C(O)—($C_1$-$C_6$)alkyl-C(O)NR$^9$R$^{10}$, or R$^{14}$;

Z is —(CH$_2$)$_m$—, optionally substituted with 1 or 2 —($C_1$-$C_6$)alkyl;
Y is —(CH$_2$)$_n$—CH or a direct bond, provided that when Y is a direct bond then R$^8$ is absent;
m is an integer 1, 2, 3, 4, 5, or 6;
n is 0, 1, or 2;
p is 0, 1 or 2;
s is an integer 1, 2, 3, 4, 5, 6, 7, 8, 9, 10, 11, 12, or 13;

provided that when X is OH or —($C_1$-$C_6$)alkoxy, Q is OMe, Z is unsubstituted, and G is O, then either:

a) R$^1$ is selected from
   i. Hydrogen, or ($C_1$-$C_{10}$)alkoxy or tetrazolyl-($C_1$-$C_6$)alkyl any of which is optionally substituted with 1, 2, or 3 substituents independently selected from the group consisting of —($C_1$-$C_6$)alkyl, OH, halo, —C(halo)$_3$, —CH(halo)$_2$, —CH$_2$(halo), —($C_1$-$C_6$)alkyl-COOR$^7$, —COOR$^7$, NH$_2$, —NH($C_1$-$C_6$)alkyl, NR$^9$R$^{10}$, CN, —CONR$^9$R$^{10}$, —NR$^9$COR$^{10}$, SR$^{11}$, -(5- to 12-membered)carbocyclic ring, -(5- to 12-membered)heterocycle, phenyl, and benzyl; or
   ii. —($C_1$-$C_{10}$)alkyl, —($C_2$-$C_{12}$)alkenyl, —($C_2$-$C_{12}$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, (($C_4$-$C_{12}$)cycloalkenyl)-($C_1$-$C_6$)alkyl-, -(5- to 12-membered)aryl, ((5- to 12-membered)aryl)-($C_1$-$C_6$)alkyl-, -(5- to 12-membered)heteroaryl, ((3- to 12 membered)heterocycle)-, (5- to 12-membered)heteroaryl-($C_1$-$C_6$)alkyl-, (3- to 12-membered)heterocycle-($C_1$-$C_6$)alkyl-, phenyl, or benzyl; each of which is substituted with 1, 2, or 3 substituents independently selected from the group consisting of —($C_1$-$C_6$)alkyl-COOR$^7$, —COOR$^7$, NR$^9$R$^{10}$, —CONR$^9$R$^{10}$, —NR$^9$COR$^{10}$, and SR$^{11}$, provided that NR$^9$R$^{10}$ is other than NH$_2$ or —NH($C_1$-$C_6$)alkyl, and SR$^{11}$ is other than SH;

or b) at least one of R$^2$ and R$^8$ is:
   i. —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, or —($C_1$-$C_6$)alkoxy-COOR$^7$; each of which is optionally substituted with one or two substituents independently selected from the group consisting of OH, halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, NH$_2$, —NH($C_1$-$C_6$)alkyl, —($C_1$-$C_6$)alkyl-NH($C_1$-$C_6$)alkyl-R$^{14}$, CN, SH, OR$^4$, —CONR$^5$R$^6$, —($C_1$-$C_6$alkyl)-CO—NR$^5$R$^6$, —COOR$^7$, —($C_1$-$C_6$)alkyl-CO—OR$^7$, —($C_1$-$C_6$)alkoxy-COOR$^7$, —(OCH$_2$CH$_2$)$_s$—O($C_1$-$C_6$)alkyl, —(CH$_2$CH$_2$O)$_s$—($C_1$-$C_6$)alkyl, (($C_1$-$C_6$)alkyl)sulfonyl($C_1$-$C_6$)alkyl-, —NH—SO$_2$($C_1$-$C_6$)alkyl, —N(SO$_2$($C_1$-$C_6$)alkyl)$_2$, —C(=NH)NH$_2$, —NH—CO—($C_1$-$C_6$)alkyl, —NH—CO—NH$_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—OR$^7$, —NH—C(=O)—($C_1$-$C_6$)alkyl-CO—OR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)NR$^5$R$^6$, —NH—($C_1$-$C_6$)alkylC(O)—NR$^5$R$^6$, —C(O)NH—($C_1$-$C_6$)alkyl-COOR$^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; or
   ii. —($C_1$-$C_6$)alkyl-COOR$^7$, —($C_3$-$C_{12}$)cycloalkyl, (($C_3$-$C_{12}$)cycloalkyl)-($C_1$-$C_6$)alkyl, —($C_4$-$C_{12}$)cycloalkenyl, —($C_6$-$C_{14}$)bicycloalkyl, —($C_8$-$C_{20}$)tricycloalkyl, —($C_7$-$C_{14}$)bicycloalkenyl, —($C_8$-$C_{20}$)tricycloalkenyl, -(5- to 12-membered)aryl, ((5- to 12-membered)aryl)-($C_1$-$C_6$)alkyl-, -(7- to 12-membered)bicyclic ring system, -(7- to 12-membered)bicyclic aryl, -(5- to 12-membered)heteroaryl, -(3- to 12-membered)heterocycle, -(7- to 12-membered)bicycloheterocycle, phenyl, benzyl, (($C_4$-$C_{12}$)cycloalkenyl)-($C_1$-$C_6$)alkyl-, (($C_6$-$C_{14}$)bicycloalkyl)-($C_1$-$C_6$)alkyl-, (($C_8$-$C_{20}$)tricycloalkyl)-($C_1$-$C_6$)alkyl-, (($C_7$-$C_{14}$)bicycloalkenyl)-($C_1$-$C_6$)alkyl-, (($C_8$-$C_{20}$)tricycloalkenyl)-($C_1$-$C_6$)alkyl-, ((7- to 12-membered)bicyclic ring system)-($C_1$-$C_6$)alkyl-, ((7- to 12-membered)bicyclic aryl)-($C_1$-$C_6$)alkyl-, ((5- to 12-membered)heteroaryl)-($C_1$-$C_6$)alkyl-, ((3- to 12 membered)heterocycle)-($C_1$-$C_6$)alkyl-, ((7- to 12-membered)-bicycloheterocycle)-($C_1$-$C_6$)alkyl-, or naphthyl; each of which is substituted with one or two substituents independently selected from the group consisting of —$CONHR^6$, dihydroxy($C_1$-$C_6$)alkyl-, —($C_1$-$C_6$)alkyl-NH($C_1$-$C_6$)alkyl-$R^{14}$, —($C_1$-$C_6$)alkyl-CO—$OR^7$, —($C_1$-$C_6$)alkoxy-$COOR^7$, —$(OCH_2CH_2)_s$—O($C_1$-$C_6$)alkyl, —$(CH_2CH_2O)_s$—($C_1$-$C_6$)alkyl, (($C_1$-$C_6$)alkyl)sulfonyl($C_1$-$C_6$)alkyl-, —NH—$SO_2$($C_1$-$C_6$)alkyl, —N($SO_2$($C_1$-$C_6$)alkyl)$_2$, —C(=NH)$NH_2$, —NH—CO—($C_1$-$C_6$)alkyl, —NH—CO—$NH_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—$OR^7$, —NH—C(=O)—($C_1$-$C_6$)alkyl-CO—$OR^7$, —NH—C(=O)—CH($NH_2$)—($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, —($C_1$-$C_6$)alkoxyC(O)$NR^5R^6$, —NH—($C_1$-$C_6$)alkylC(O)—$NR^5R^6$, —C(O)NH—($C_1$-$C_6$)alkyl-$COOR^7$-(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; or iii. —($C_1$-$C_{10}$)alkyl, or —($C_2$-$C_{12}$)alkynyl, each of which is substituted with one or two substituents independently selected from the group consisting of —$CONHR^6$, —($C_1$-$C_6$)alkyl-NH($C_1$-$C_6$)alkyl-$R^{14}$, —($C_1$-$C_6$)alkoxy-$COOR^7$, —$(OCH_2CH_2)_s$—O($C_1$-$C_6$)alkyl, —$(CH_2CH_2O)_s$—($C_1$-$C_6$)alkyl, (($C_1$-$C_6$)alkyl)sulfonyl($C_1$-$C_6$)alkyl-, —NH—$SO_2$($C_1$-$C_6$)alkyl, —N($SO_2$($C_1$-$C_6$)alkyl)$_2$, —C(=NH)$NH_2$, —NH—CO—($C_1$-$C_6$)alkyl, —NH—CO—$NH_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—$OR^7$, —NH—C(=O)—($C_1$-$C_6$)alkyl-CO—$OR^7$, —NH—C(=O)—CH($NH_2$)—($C_1$-$C_6$)alkyl-CO—$OR^7$, —($C_1$-$C_6$)alkoxyC(O)$NR^5R^6$, —NH—($C_1$-$C_6$)alkylC(O)—$NR^5R^6$, and —C(O)NH—($C_1$-$C_6$)alkyl-$COOR^7$; or iv. 2,3-dihydroxypropyl; or v. 4-isoxazolyl, 4-isoxazolyl($C_1$-$C_6$)alkyl), 5-isoxazolyl, or 5-isoxazolyl($C_1$-$C_6$)alkyl) substituted with one or two alkyl groups, or vi. —C(=O)$NH_2$ or —($C_1$-$C_6$)alkyl-C(=O)$NH_2$; or c) at least one of $R^{3a}$ or $R^{3b}$ is independently selected from —($C_7$-$C_{10}$)alkyl, —($C_7$-$C_{10}$)alkenyl, —($C_7$-$C_{10}$)alkynyl, —($C_1$-$C_{10}$)alkoxy, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-$COOR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$)cycloalkyl)-($C_1$-$C_6$)alkoxy-($C_1$-$C_6$)alkyl-, —($C_4$-$C_{12}$)cycloalkenyl, (($C_4$-$C_{12}$)cycloalkenyl)-($C_1$-$C_6$)alkyl-, (($C_4$-$C_{12}$)cycloalkenyl)-($C_1$-$C_6$)alkoxy-, (($C_4$-$C_{12}$)cycloalkenyl)-($C_1$-$C_6$)alkoxy-($C_1$-$C_6$)alkyl-, -(5- to 12-membered)aryl, ((5- to 12-membered)aryl)-($C_1$-$C_6$)alkyl-, ((5- to 12-membered)aryl)-($C_1$-$C_6$)alkoxy-, ((5- to 12-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, or ((3- to 12 membered)heterocycle)-($C_1$-$C_6$)alkoxy-($C_1$-$C_6$)alkyl-; or provided that when X is OH or —($C_1$-$C_6$)alkoxy, Q is OMe, $R^{3a}$ and $R^{3b}$ are both hydrogen, Z is substituted, G is O, and Y is a direct bond, then $R^2$ is other than hydrogen;

or a pharmaceutically acceptable salt thereof.

2. A compound of claim 1 having the general formula IA:

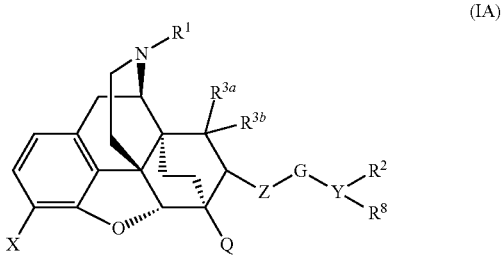

(IA)

or a pharmaceutically acceptable salt thereof.

3. A compound of claim 1 having the general formula IB:

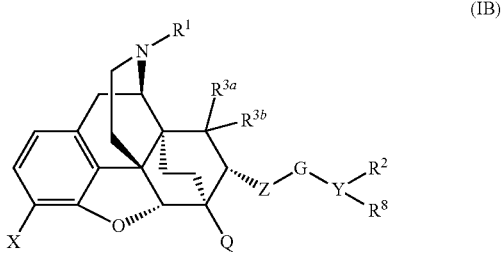

(IB)

or a pharmaceutically acceptable salt thereof.

4. The compound of claim 1 wherein $R^1$ is selected from hydrogen, —($C_1$-$C_{10}$)alkyl, —($C_2$-$C_{12}$)alkenyl, —($C_1$-$C_{10}$)alkoxy, —($C_3$-$C_{12}$)cycloalkyl, (($C_3$-$C_{12}$)cycloalkyl)-($C_1$-$C_6$)alkyl-, ((5- to 12-membered)aryl)-($C_1$-$C_6$)alkyl-, ((5- to 12-membered)heteroaryl)-($C_1$-$C_6$)alkyl-, or ((3- to 12 membered)heterocycle)-($C_1$-$C_6$)alkyl-, any of which is optionally substituted with 1, 2, or 3 substituents independently selected from the group consisting of —($C_1$-$C_6$)alkyl, —OH, halo, —C(halo)$_3$, —$COOR^7$, $NH_2$, —NH($C_1$-$C_6$)alkyl, $NR^9R^{10}$, —CN, —$CONR^9R^{10}$, —$NR^9COR^{10}$, and $SR^{11}$.

5. The compound of claim 1 wherein the optional substituent of $R^1$ is selected from 1, 2, or 3 substituents independently selected from the group consisting —OH, halo, —$CONH_2$, —COOH, —COO($C_1$-$C_6$)alkyl, and —$NR^9R^{10}$.

6. The compound of claim 1 wherein $R^1$ is selected from hydrogen, methyl, cyclopropylmethyl, —$CH_2CH$=$CH_2$, —$CH_2CH_2C(O)NH_2$, $CH_2CH_2C(O)OH$, $CH_2C(O)OH$, $CH_2C(O)NH_2$, or —$CH_2$-tetrazolyl.

7. The compound of claim 1 wherein G is selected from the group consisting of —OCO—, —C(=O), NH, NR', S, SO, and $SO_2$; and R' is —C(=O)($C_1$-$C_6$)alkyl or —$SO_2$($C_1$-$C_6$)alkyl.

8. The compound of claim 1 wherein G is —NR'— and R' is —C(=O)($C_1$-$C_6$)alkyl or —$SO_2$($C_1$-$C_6$)alkyl.

9. The compound of claim 1 wherein G is —O—.

10. The compound of claim 1, wherein Q is selected from —OH, —($C_1$-$C_{10}$)alkoxy, -(5- to 12-membered)aryl, (($C_3$-$C_{12}$)cycloalkyl)-($C_1$-$C_6$)alkyl-, ((5- to 12-membered)aryl)-($C_1$-$C_6$)alkyl-, —($OCH_2CH_2$)$_s$—O($C_1$-$C_6$)alkyl, —($CH_2CH_2O$)$_s$—($C_1$-$C_6$)alkyl, —($OCH_2CH_2$)$_s$—OH, —O(C=O)$R^9$, —O—($C_1$-$C_6$)alkyl-$COOR^7$, —NH—($C_1$-$C_6$)alkyl-$COOR^7$, —O—C(O)—($C_1$-$C_6$)alkyl-C(O)$OR^7$, —NH—C(O)—($C_1$-$C_6$)alkyl-C(O)$OR^7$, —O—($C_1$-$C_6$)alkyl, —C(O)$NR^9R^{10}$, —NH—($C_1$-$C_6$)alkyl-C(O)$NR^9R^{10}$, —O—C(O)—($C_1$-$C_6$)alkyl-C(O)$NR^9R^{10}$, —NH—C(O)—($C_1$-$C_6$)alkyl-C(O)$NR^9R^{10}$, or $R^{14}$.

11. The compound of claim 1 wherein Q is selected from —OH or $OCH_3$.

12. The compound of claim 10 wherein Q is phenyl.

13. The compound of claim 1 wherein Q is —($OCH_2CH_2$)$_s$—O($C_1$-$C_6$)alkyl, —($CH_2CH_2O$)$_s$—($C_1$-$C_6$)alkyl, or —($OCH_2CH_2$)$_s$—OH and s is selected from 1, 2, 3, 4, 5, 6, or 7.

14. The compound of claim 1 wherein Q is —($OCH_2CH_2$)$_5OCH_3$ or —($OCH_2CH_2$)$_3OCH_3$.

15. The compound of claim 1 wherein Q is —O—$CH_2$—COOH, —NH—$CH_2$—COOH, —O—C(O)—$CH_2$—C(O)OH, or —NH—C(O)—$CH_2$—C(O)OH.

16. The compound of claim 1 wherein Q is —O—$CH_2$—$CONH_2$, —NH—$CH_2$—$CONH_2$, —O—C(O)—$CH_2$—C(O)$NH_2$, or —NH—C(O)—$CH_2$—C(O)$NH_2$.

17. The compound of claim 1 wherein X is selected from —OH, hydroxy($C_1$-$C_6$)alkyl-, dihydroxy($C_1$-$C_6$)alkyl-, halogen, —$NH_2$, —$NR^2$(C=O)$R^{12}$, $CONR^{12}R^{13}$, —($C_1$-$C_6$)alkyl-$CONH_2$, —($C_1$-$C_6$)alkyl-COOH, —COOH, —O—($C_1$-$C_6$)alkyl-COOH, —O—($C_1$-$C_6$)alkyl-$CONH_2$, —($C_1$-$C_{10}$)alkyl, —($C_2$-$C_{10}$)alkenyl, —($C_2$-$C_{10}$)alkynyl, —($C_1$-$C_{10}$)alkoxy, —($OCH_2CH_2$)$_s$—O($C_1$-$C_6$)alkyl, —($OCH_2CH_2$)$_s$—OH, —($CH_2$)$_p$CHOHCH$_2$OH, —CN, —NH—$SO_2R^9$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, -(5- to 12-membered)aryl, ((5- to 12-membered)aryl)-($C_1$-$C_6$)alkyl-, ((5- to 12-membered)aryl)-($C_1$-$C_6$)alkoxy-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, -(3- to 12-membered)heterocycle, ((3- to 12-membered)heterocycle)-($C_1$-$C_6$)alkyl-, ((3- to 12-membered)heterocycle)-($C_1$-$C_6$)alkoxy-, -(7- to 12-membered)bicycloheterocycle, ((7- to 12-membered)bicycloheterocycle)-($C_1$-$C_6$)alkyl-, or ((7- to 12-membered)bicycloheterocycle)-($C_1$-$C_6$)alkoxy-.

18. The compound of claim 1 wherein X is selected from —OH, —$OCH_3$, —F, —Br, —COOH, —$CONH_2$, —$OCH_2CH_2OH$, —CH=$CH_2$, $NHSO_2CH_3$, $NHC(O)CH_3$, —CN, —($OCH_2CH_2$)$_sOCH_3$ wherein s is selected from 1, 2, 3, 4, 5, or 6, —CH(OH)$CH_2OH$, —$OCH_2$-tetrazolyl, —$OCH_2C(O)NH_2$, —$CH_2CH(OH)CH_2OH$, -tetrazolyl, or —$NH_2$.

19. The compound of claim 1 wherein $R^2$ and $R^8$ are each independently hydrogen, —($C_1$-$C_{10}$)alkyl, —($C_2$-$C_{12}$)alkynyl, —($C_1$-$C_{10}$)alkoxy, —($OCH_2CH_2$)$_s$—O($C_1$-$C_6$)alkyl, —($CH_2CH_2O$)$_s$—($C_1$-$C_6$)alkyl, $NH_2$, —NH($C_1$-$C_6$)alkyl, CN, —$CONR^5R^6$, —($C_1$-$C_6$)alkyl-CO—$NR^5R^6$, —$COOR^7$, —($C_1$-$C_6$)alkyl-CO—$OR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(5- to 12-membered)aryl, ((5- to 12-membered)aryl)-($C_1$-$C_6$)alkyl-, -(7- to 12-membered)bicyclic ring system, ((7- to 12-membered) bicyclic ring system)-($C_1$-$C_6$)alkyl-, -(7- to 12-membered) bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, ((7- to 12-membered)bicycloheterocycle)-($C_1$-$C_6$)alkyl-, phenyl, benzyl, or naphthyl; each of which is optionally substituted with one or two substituents independently selected from the group consisting of OH, halo, —C(halo)$_3$, —CH(halo)$_2$, —$CH_2$(halo), —($C_1$-$C_6$)alkyl, halo($C_1$-$C_6$)alkyl-, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)CO($C_1$-$C_6$)alkoxy-, phenyl, benzyl, $NH_2$, —NH($C_1$-$C_6$)alkyl, —($C_1$-$C_6$)alkyl-NH($C_1$-$C_6$)alkyl-$R^{14}$, CN, SH, $OR^4$, —$CONR^5R^6$, —($C_1$-$C_6$alkyl)-CO—$NR^5R^6$, —$COOR^7$, —($C_1$-$C_6$)alkyl-CO—$OR^7$, —($C_1$-$C_6$)alkoxy-$COOR^7$, —($OCH_2CH_2$)$_s$—O($C_1$-$C_6$)alkyl, —($CH_2CH_2O$)$_s$—($C_1$-$C_6$)alkyl, (($C_1$-$C_6$)alkyl)sulfonyl($C_1$-$C_6$)alkyl-, —NH—$SO_2$($C_1$-$C_6$)alkyl, —N($SO_2$($C_1$-$C_6$)alkyl)$_2$, —C(=NH)$NH_2$, —NH—CO—($C_1$-$C_6$)alkyl, —NH—CO—$NH_2$, —NH—C(=O)—NH—($C_1$-$C_6$)alkyl, —NH—C(=O)-(5- to 12-membered)aryl, —NH—C(=O)—($C_1$-$C_6$)alkyl-(5- to 12-membered)aryl, —NH—($C_1$-$C_6$)alkyl-CO—$OR^7$, —NH—C(=O)—($C_1$-$C_6$)alkyl-CO—$OR^7$, —NH—C(=O)—CH($NH_2$)—($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, -(5- to 12-membered)aryl, -(5- to 12-membered)aryloxy, —($C_1$-$C_6$)alkoxyC(O)$NR^5R^6$, —NH—($C_1$-$C_6$)alkylC(O)—$NR^5R^6$, —C(O)NH—($C_1$-$C_6$)alkyl-$COOR^7$, ((5- to 12-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-.

20. The compound of claim 1 wherein —Y($R^2$)($R^8$) is -(5- to 12 membered)aryl or (5- to 12 membered)heteroaryl, each of which is optionally substituted with one or two substituents independently selected from —OH, halo, —C(halo)$_3$, —$NH_2$, —NH($C_1$-$C_6$)alkyl, —($C_1$-$C_6$alkyl)-CO—$NR^5R^6$—($C_1$-$C_6$)alkyl, dihydroxy($C_1$-$C_6$)alkyl-, —($C_1$-$C_6$)alkyl-CO—$OR^7$, —($OCH_2CH_2$)$_s$—O($C_1$-$C_6$)alkyl, —($CH_2CH_2O$)$_s$—($C_1$-$C_6$)alkyl, —($C_1$-$C_6$)alkoxy-$COOR^7$, -(5- to 12-membered)aryl, -(5- to 12-membered)aryloxy, —$CONR^5R^6$, —$COOR^7$, —NH—$SO_2$($C_1$-$C_6$)alkyl, —N($SO_2$($C_1$-$C_6$)alkyl)$_2$, —C(=NH)$NH_2$, —NH—CO—($C_1$-$C_6$)alkyl, —NH—C(=O)-(5- to 12-membered)aryl, ((5- to 12-membered)heteroaryl)-($C_1$-$C_6$)alkyl-, —NH—CO—$NH_2$, —NH—($C_1$-$C_6$)alkyl-$COOR^7$, —NH—C(=O)—NH—($C_1$-$C_6$)alkyl, —($C_1$-$C_6$)alkoxyC(O)$NR^5R^6$, —NH—($C_1$-$C_6$)alkylC(O), $NR^5R^6$, —C(O)NH—($C_1$-$C_6$)alkyl-$COOR^7$, —NH—C(=O)—($C_1$-$C_6$)alkyl-CO—$OR^7$, or —NH—C(=O)—CH($NH_2$)—($C_1$-$C_6$)alkyl-CO—$OR^7$.

21. The compound of claim 1 wherein —Y(R$^2$)(R$^8$) is —CH$_2$-(5- to 12 membered)heteroaryl, which is optionally substituted with one or two substituents independently selected from —OH, -halo, —C(halo)$_3$, —NH$_2$, —NH(C$_1$-C$_6$)alkyl, —(C$_1$-C$_6$alkyl)-CO—NR$^5$R$^6$—(C$_1$-C$_6$)alkyl, dihydroxy(C$_1$-C$_6$)alkyl-, —(C$_1$-C$_6$)alkyl-CO—OR$^7$, —(OCH$_2$CH$_2$)$_s$—O(C$_1$-C$_6$)alkyl, —(CH$_2$CH$_2$O)$_s$—(C$_1$-C$_6$)alkyl, —(C$_1$-C$_6$)alkoxy-COOR$^7$, -(5- to 12-membered)aryl, -(5- to 12-membered)aryloxy, —CONR$^5$R$^6$, —COOR$^7$, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—C(=O)-(5- to 12-membered)aryl, ((5- to 12-membered)heteroaryl)-(C$_1$-C$_6$)alkyl-, —NH—CO—NH$_2$, —NH—(C$_1$-C$_6$)alkyl-COOR$^7$, —NH—C(=O)—NH—(C$_1$-C$_6$)alkyl, —(C$_1$-C$_6$)alkoxyC(O)NR$^5$R$^6$, —NH—(C$_1$-C$_6$)alkylC(O), NR$^5$R$^6$, —C(O)NH—(C$_1$-C$_6$)alkyl-COOR$^7$, —NH—C(=O)—(C$_1$-C$_6$)alkyl-CO—OR$^7$, or —NH—C(=O)—CH(NH$_2$)—(C$_1$-C$_6$)alkyl-CO—OR$^7$.

22. The compound of claim 1 wherein —Y(R$^2$)(R$^8$) is —CH$_2$-(5- to 12 membered)aryl, which is optionally substituted with one or two substituents independently selected from —OH, halo, —C(halo)$_3$, —NH$_2$, —NH(C$_1$-C$_6$)alkyl, —(C$_1$-C$_6$alkyl)-CO—NR$^5$R$^6$—(C$_1$-C$_6$)alkyl, dihydroxy(C$_1$-C$_6$)alkyl-, —(C$_1$-C$_6$)alkyl-CO—OR$^7$, —(OCH$_2$CH$_2$)$_s$—O(C$_1$-C$_6$)alkyl, —(CH$_2$CH$_2$O)$_s$—(C$_1$-C$_6$)alkyl, —(C$_1$-C$_6$)alkoxy-COOR$^7$, -(5- to 12-membered)aryl, -(5- to 12-membered)aryloxy, —CONR$^5$R$^6$, —COOR$^7$, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—C(=O)-(5- to 12-membered)aryl, ((5- to 12-membered)heteroaryl)-(C$_1$-C$_6$)alkyl-, —NH—CO—NH$_2$, —NH—(C$_1$-C$_6$)alkyl-COOR$^7$, —NH—C(=O)—NH—(C$_1$-C$_6$)alkyl, —(C$_1$-C$_6$)alkoxyC(O)NR$^5$R$^6$, —NH—(C$_1$-C$_6$)alkylC(O), NR$^5$R$^6$, —C(O)NH—(C$_1$-C$_6$)alkyl-COOR$^7$, —NH—C(=O)—(C$_1$-C$_6$)alkyl-CO—OR$^7$, or —NH—C(=O)—CH(NH$_2$)—(C$_1$-C$_6$)alkyl-CO—OR$^7$.

23. The compound of claim 1 wherein the (5- to 12 membered)aryl in the Y(R$^2$)(R$^8$)— group is selected from phenyl, which is optionally substituted with one or two substituents independently selected from —(C$_1$-C$_6$)alkyl, dihydroxy(C$_1$-C$_6$)alkyl-, —(C$_1$-C$_6$)alkyl-CO—OR$^7$, —(OCH$_2$CH$_2$)$_s$—O(C$_1$-C$_6$)alkyl, —(C$_1$-C$_6$)alkoxy-COOR$^7$, -(5- to 12-membered)aryl, -(5- to 12-membered)aryloxy, —CONR$^5$R$^6$, —COOR$^7$, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—C(=O)-(5- to 12-membered)aryl, ((5- to 12-membered)heteroaryl)-(C$_1$-C$_6$)alkyl-, —NH—CO—NH$_2$, —NH—(C$_1$-C$_6$)alkyl-COOR$^7$, —NH—C(=O)—NH—(C$_1$-C$_6$)alkyl, —(C$_1$-C$_6$)alkoxyC(O)NR$^5$R$^6$, —NH—(C$_1$-C$_6$)alkylC(O)—NR$^5$R$^6$, or —C(O)NH—(C$_1$-C$_6$)alkyl-COOR$^7$.

24. The compound of claim 1 wherein the (5- to 12 membered)heteroaryl in the Y(R$^2$)(R$^8$)— group is selected from furan, thiophene, diazole, tetrazole, benzothiazole, benzoxazole, benzothiazole, thiadiazole, oxazole, benzoxazole, benzothiophene, or benzofuran, each of which is optionally substituted with one or two substituents independently selected from the group consisting of —(C$_1$-C$_6$)alkyl, dihydroxy(C$_1$-C$_6$)alkyl-, —(C$_1$-C$_6$)alkyl-CO—OR$^7$, —(OCH$_2$CH$_2$)$_s$—O(C$_1$-C$_6$)alkyl, —(C$_1$-C$_6$)alkoxy-COOR$^7$, -(5- to 12-membered)aryl, -(5- to 12-membered)aryloxy, —CONR$^5$R$^6$, —COOR$^7$, —NH—SO$_2$(C$_1$-C$_6$)alkyl, —N(SO$_2$(C$_1$-C$_6$)alkyl)$_2$, —C(=NH)NH$_2$, —NH—CO—(C$_1$-C$_6$)alkyl, —NH—C(=O)-(5- to 12-membered)aryl, ((5- to 12-membered)heteroaryl)-(C$_1$-C$_6$)alkyl-, —NH—CO—NH$_2$, —NH—(C$_1$-C$_6$)alkyl-COOR$^7$, —NH—C(=O)—NH—(C$_1$-C$_6$)alkyl, —(C$_1$-C$_6$)alkoxyC(O)NR$^5$R$^6$, —NH—(C$_1$-C$_6$)alkylC(O)—NR$^5$R$^6$, and —C(O)NH—(C$_1$-C$_6$)alkyl-COOR$^7$.

25. The compound of claim 1 wherein Z is —(CH$_2$)$_m$— optionally substituted with 1 or 2-(C$_1$-C$_6$)alkyl and m is 1 or 2.

26. The compound of claim 1 wherein Z is —C(CH$_3$)$_2$—.

27. The compound of claim 1 wherein Y is (CH$_2$)$_n$—CH and n is selected from 0, 1, 2, 3, 4, 5 or 6.

28. The compound of claim 1 wherein Y is a direct bond.

29. The compound of claim 1 wherein R$^{3a}$ and R$^{3b}$ are each independently selected from hydrogen, —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, ((3- to 12 membered)heterocycle)-(C$_1$-C$_6$)alkoxy-(C$_1$-C$_6$)alkyl-, or together form (=O).

30. The compound of claim 1 wherein R$^{3a}$ and R$^{3b}$ are each hydrogen.

31. The compound of claim 1 wherein at least one of R$^{3a}$ and R$^{3b}$ is selected from —(C$_1$-C$_{10}$)alkyl, —(C$_2$-C$_{10}$)alkenyl, —(C$_2$-C$_{10}$)alkynyl, —(C$_1$-C$_{10}$)alkoxy, OH, hydroxy(C$_1$-C$_6$)alkyl-, —C(halo)$_3$, —CH(halo)$_2$, —CH$_2$(halo), —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, —(C$_3$-C$_{12}$)cycloalkyl, ((C$_3$-C$_{12}$)cycloalkyl)-(C$_1$-C$_6$)alkyl-, ((C$_3$-C$_{12}$)cycloalkyl)-(C$_1$-C$_6$)alkoxy-, ((C$_3$-C$_{12}$)cycloalkyl)-(C$_1$-C$_6$)alkoxy-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(5- to 12-membered)aryl, ((5- to 12-membered)aryl)-(C$_1$-C$_6$)alkyl-, ((5- to 12-membered)aryl)-(C$_1$-C$_6$)alkoxy-, ((5- to 12-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, ((3- to 12 membered)heterocycle)-(C$_1$-C$_6$)alkoxy-(C$_1$-C$_6$)alkyl-, or together form (=O).

32. A compound of claim 1 having the general formula II:

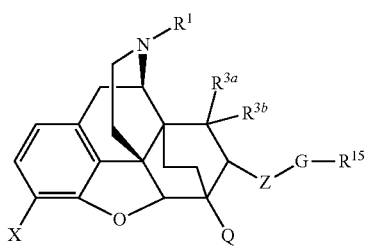

wherein G is O or NH;
$R^{15}$ is selected from:

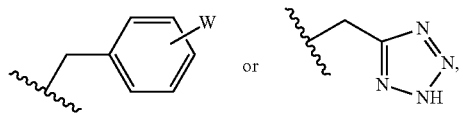

and
W is selected from:

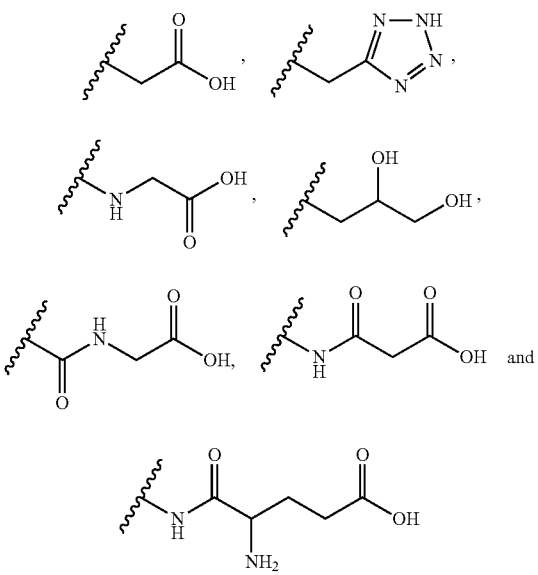

or a pharmaceutically acceptable salt thereof.

33. A compound of claim 1 having the general formula II:

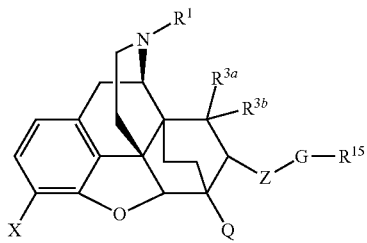

Wherein G is O;
$R^{15}$ is selected from —(OCH$_2$CH$_2$)$_s$—O(C$_1$-C$_6$)alkyl,

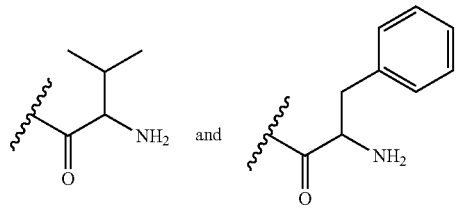

or a pharmaceutically acceptable salt thereof.

34. A compound of claim 1 having the general formula II:

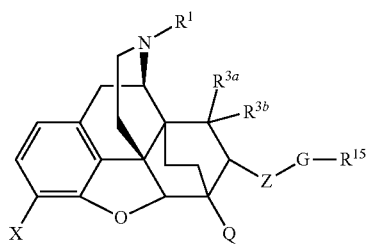

wherein G is NH;
$R^{15}$ is selected from —(OCH$_2$CH$_2$)$_s$—O(C$_1$-C$_6$)alkyl,

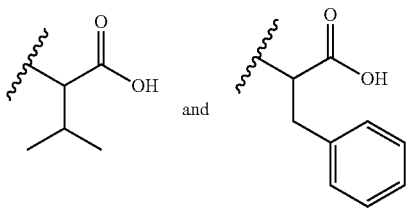

or a pharmaceutically acceptable salt thereof.

35. A compound of claim 1 wherein:
$R^1$ is CH$_3$ or cyclopropylmethyl-;
X is selected from —F, —NH$_2$, —NHCOCH$_3$, —NHSO$_2$CH$_3$, —CN, —CO$_2$H, —CONH$_2$, —(OCH$_2$CH$_2$)$_s$—O(C$_1$-C$_6$)alkyl or —(OCH$_2$CH$_2$)$_s$—OH;
or a pharmaceutically acceptable salt thereof.

36. A compound selected from the group consisting of:
2-(((4R,4aS,6R,7R,7aR,12bS)-7-methoxy-3-methyl-6-(((2-methylbenzyl)oxy)methyl)-1,2,3,4,5,6,7,7a-octahydro-4a,7-ethano-4,12-methanobenzofuro[3,2-e]isoquinolin-9-yl)oxy)ethanol);
(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinolin-9-amine;
(4R,4aS,6R,7R,7aR,12bS)-6-((benzyloxy)methyl)-7-methoxy-3-methyl-9-vinyl-1,2,3,4,5,6,7,7a-octahydro-4a,7-ethano-4,12-methanobenzofuro[3,2-e]isoquinoline;
(4R,4aS,6R,7R,7aR,12bS)-6-(9benzyloxy)methyl)-9-fluoro-7-methoxy-3-methyl-1,2,3,4,5,6,7,7a-octahydro-4a,7-ethano-4,12-methanobenzofuro[3,2-e]isoquinoline;

(4R,4aS,6R,7R,7aR,12bS)-6-((4-(1H-imidazol-1-yl)phenoxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline;

(4R,4aS,6S,7R,7aR,12bS)-6-((benzo[d]thiazol-2-ylthio)methyl)-7,9-dimethoxy-3-methyl-1,2,3,4,5,6,7,7a-octahydro-4a,7-ethano-4,12-methanobenzofuro[3,2-e]isoquinoline;

(4R,4aS,6S,7R,7aR,12bS)-6-((benzo[d]thiazol-2-ylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline;

(4R,4aS,6R,7R,7aR,12bS)-6-((4-(1H-imidazol-1-yl)phenoxy)methyl)-7-methoxy-3-methyl-1,2,3,4,5,6,7,7a-octahydro-4a,7-ethano-4,12-methanobenzofuro[3,2-e]isoquinolin-9-ol;

(4R,4aS,6S,7R,7aR,12bS)-3-(cyclopropylmethyl)-7,9-dimethoxy-6-(((3-methyl-1,2,4-thiadiazol-5-yl)thio)methyl)-1,2,3,4,5,6,7,7a-octahydro-4a,7-ethano-4,12-methanobenzofuro[3,2-e]isoquinoline;

(4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-amine;

(4R,4aS,6R,7R,7aR,12bS)-6-((4-(1H-imidazol-1-yl)phenoxy)methyl)-3-(cyclopropylmethyl)-7-methoxy-1,2,3,4,5,6,7,7a-octahydro-4a,7-ethano-4,12-methanobenzofuro[3,2-e]isoquinolin-9-ol;

(4R,4aS,6S,7R,7aR,12bS)-7,9-dimethoxy-3-methyl-6-(((3-methyl-1,2,4-thiadiazol-5-yl)thio)methyl)-1,2,3,4,5,6,7,7a-octahydro-4a,7-ethano-4,12-methanobenzofuro[3,2-e]isoquinoline;

(4R,4aS,6S,7R,7aR,12bS)-6-(((1,3,4-thiadiazol-2-yl)thio)methyl)-7,9-dimethoxy-3-methyl-1,2,3,4,5,6,7,7a-octahydro-4a,7-ethano-4,12-methanobenzofuro[3,2-e]isoquinoline;

(4R,4aS,6S,7R,7aR,12bS)-6-(((1,3,4-thiadiazol-2-yl)thio)methyl)-3-(cyclopropylmethyl)-7,9-dimethoxy-1,2,3,4,5,6,7,7a-octahydro-4a,7-ethano-4,12-methanobenzofuro[3,2-e]isoquinoline;

(4R,4aS,6R,7R,7aR,12bS)-6-((benzyloxy)methyl)-3-(cyclopropylmethyl)-9-fluoro-7-methoxy-1,2,3,4,5,6,7,7a-octahydro-4a,7-ethano-4,12-methanobenzofuro[3,2-e]isoquinoline;

N-((4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinolin-9-yl)methanesulfonamide;

N-((4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinolin-9-yl)acetamide;

(4R,4aS,6R,7R,7aR,12bS)-6-((benzyloxy)methyl)-7,9-dimethoxy-1,2,3,4,5,6,7,7a-octahydro-4a,7-ethano-4,12-methanobenzofuro[3,2-e]isoquinoline;

(4R,4aS,6R,7R,7aR,12bS)-6-((benzyloxy)methyl)-9-bromo-3-(cyclopropylmethyl)-7-methoxy-1,2,3,4,5,6,7,7a-octahydro-4a,7-ethano-4,12-methanobenzofuro[3,2-e]isoquinoline;

(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinoline-9-carbonitrile;

(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinoline-9-carboxamide;

(4R,4aS,6R,7R,7aR,12bS)-6-((benzyloxy)methyl)-7-methoxy-1,2,3,4,5,6,7,7a-octahydro-4a,7-ethano-4,12-methanobenzofuro[3,2-e]isoquinolin-9-ol;

(4R,4aS,6R,7R,7aR,12bS)-6-((benzyloxy)methyl)-7-methoxy-3-methyl-1,2,3,4,5,6,7,7a-octahydro-4a,7-ethano-4,12-methanobenzofuro[3,2-e]isoquinoline-9-carboxylic acid;

(4R,4aS,6R,7R,7aR,12bS)-6-(((3,5-dimethylisoxazol-4-yl)methoxy)methyl)-7,9-dimethoxy-3-methyl-1,2,3,4,5,6,7,7a-octahydro-4a,7-ethano-4,12-methanobenzofuro[3,2-e]isoquinoline;

2-(((4R,4aS,6R,7R,7aR,12bS)-6-((benzo[b]thiophen-2-ylmethoxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)ethanol;

(4R,4aS,6R,7R,7aR,12bS)-3-(cyclopropylmethyl)-6-(((3,5-dimethylisoxazol-4-yl)methoxy)methyl)-7,9-dimethoxy-1,2,3,4,5,6,7,7a-octahydro-4a,7-ethano-4,12-methanobenzofuro[3,2-e]isoquinoline;

(4R,4aS,6S,7R,7aR,12bS)-6-((benzo[d]oxazol-2-ylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline;

N-benzyl-1-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methanamine;

N-benzyl-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)methanesulfonamide;

N-benzyl-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)acetamide;

(4R,4aS,6S,7R,7aR,12bS)-6-((benzylthio)methyl)-3-(cyclopropylmethyl)-7,9-dimethoxy-1,2,3,4,5,6,7,7a-octahydro-4a,7-ethano-4,12-methanobenzofuro[3,2-e]isoquinoline;

(4R,4aS,6S,7R,7aR,12bS)-6-((benzylsulfinyl)methyl)-3-(cyclopropylmethyl)-7,9-dimethoxy-1,2,3,4,5,6,7,7a-octahydro-4a,7-ethano-4,12-methanobenzofuro[3,2-e]isoquinoline;

(4R,4aS,6R,7R,7aR,12bS)-3-(cyclopropylmethyl)-6-(2,5,8,11-tetraoxadodecyl)-7,9-dimethoxy-1,2,3,4,5,6,7,7a-octahydro-4a,7-ethano-4,12-methanobenzofuro[3,2-e]isoquinoline;

(4R,4aS,6R,7R,7aR,12bS)-3-(cyclopropylmethyl)-7,9-dimethoxy-6-(2,5,8,11,14,17-hexaoxaoctadecyl)-1,2,3,4,5,6,7,7a-octahydro-4a,7-ethano-4,12-methanobenzofuro[3,2-e]isoquinoline;

(4R,4aS,6R,7R,7aR,12bS)-6-((benzyloxy)methyl)-3-(cyclopropylmethyl)-7-methoxy-9-(2-(2-(2-methoxyethoxy)ethoxy)ethoxy)-1,2,3,4,5,6,7,7a-octahydro-4a,7-ethano-4,12-methanobenzofuro[3,2-e]isoquinoline;

(4R,4aS,6R,7R,7aR,12bS)-9-(2,5,8,11,14-pentaoxahexadecan-16-yloxy)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline;

(4R,4aS,6R,7R,7aR,12bS)-3-(cyclopropylmethyl)-7,9-dimethoxy-6-(((4-(2-(2-(2-methoxyethoxy)ethoxy)ethoxy)benzyl)oxy)methyl)-1,2,3,4,5,6,7,7a-octahydro-4a,7-ethano-4,12-methanobenzofuro[3,2-e]isoquinoline;

(4R,4aS,6R,7R,7aR,12bS)-6-(((4-(2,5,8,11,14-pentaoxa-hexadecan-16-yloxy)benzyl)oxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline;

methyl 2-(4-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenoxy)acetate; and 2-(4-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenoxy)acetic acid;

or a pharmaceutically acceptable salt thereof.

37. A compound selected from the group consisting of:

3-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)propanamide;

2-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)amino)acetic acid;

2-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)benzamido)acetic acid;

2-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)amino)acetamide;

2-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)acetamide;

2-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)acetic acid;

1-((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)ethane-1,2-diol;

1-(3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)urea;

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-phenylpropanoate;

2-((3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)amino)acetic acid;

(4R,4aS,6S,7S,7aR,12bS)-6-((benzyloxy)methyl)-3-(cyclopropylmethyl)-9-methoxy-7-phenyl-1,2,3,4,5,6,7,7a-octahydro-4a,7-ethano-4,12-methanobenzofuro[3,2-e]isoquinoline;

(4R,4aS,6R,7R,7aR,12bS)-7-(2,5,8,11,14-pentaoxahexadecan-16-yloxy)-6-((benzyloxy)methyl)-3-(cyclopropylmethyl)-9-methoxy-1,2,3,4,5,6,7,7a-octahydro-4a,7-ethano-4,12-methanobenzofuro[3,2-e]isoquinoline;

(4R,4aS,6R,7R,7aR,12bS)-6-((benzyloxy)methyl)-3-(cyclopropylmethyl)-9-methoxy-7-(2-(2-(2-methoxyethoxy)ethoxy)ethoxy)-1,2,3,4,5,6,7,7a-octahydro-4a,7-ethano-4,12-methanobenzofuro[3,2-e]isoquinoline;

(4R,4aS,6R,7R,7aR,12bS)-6-(((4-((2H-tetrazol-5-yl)methyl)benzyl)oxy)methyl)-3-(cyclopropylmethyl)-7,9-dimethoxy-1,2,3,4,5,6,7,7a-octahydro-4a,7-ethano-4,12-methanobenzofuro[3,2-e]isoquinoline;

(4R,4aS,6R,7R,7aR,12bS)-7,9-dimethoxy-3-methyl-6-(((3-propylisoxazol-5-yl)methoxy)methyl)-1,2,3,4,5,6,7,7a-octahydro-4a,7-ethano-4,12-methanobenzofuro[3,2-e]isoquinoline;

3-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)propanoic acid;

2-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)acetic acid;

2-((4R,4aS,6R,7R,7aR,12bS)-6-((benzyloxy)methyl)-7,9-dimethoxy-1,2,5,6,7,7a-hexahydro-4a,7-ethano-4,12-methanobenzofuro[3,2-e]isoquinolin-3(4H)-yl)acetamide;

2-(((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)acetic acid;

(4R,4aS,6R,7R,7aR,12bS)-9-((2H-tetrazol-5-yl)methoxy)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline;

2-(((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)oxy)acetamide;

N-(4-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)-N-(methylsulfonyl)methanesulfonamide;

3-((4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinolin-9-yl)propane-1,2-diol;

N-(3-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)methanesulfonamide;

(4R,4aS,6R,7R,7aR,12bS)-6-(2-(benzyloxy)propan-2-yl)-3-(cyclopropylmethyl)-7,9-dimethoxy-1,2,3,4,5,6,7,7a-octahydro-4a,7-ethano-4,12-methanobenzofuro[3,2-e]isoquinoline;

3-(((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)benzimidamide;

or a pharmaceutically acceptable salt thereof.

38. A compound selected from the group consisting of:

(4R,4aS,6S,7R,7aR,12bS)-6-((benzylsulfonyl)methyl)-3-(cyclopropylmethyl)-7,9-dimethoxy-1,2,3,4,5,6,7,7a-octahydro-4a,7-ethano-4,12-methanobenzofuro[3,2-e]isoquinoline;

3-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)propane-1,2-diol;

(4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carbonitrile;

(4R,4aS,6R,7R,7aR,12bS)-6-((benzyloxy)methyl)-3-(cyclopropylmethyl)-7-methoxy-9-(2H-tetrazol-5-yl)-1,2,3,4,5,6,7,7a-octahydro-4a,7-ethano-4,12-methanobenzofuro[3,2-e]isoquinoline;

(4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carboxylic acid;

N-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)acetamide;

methyl 2-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenoxy)acetate;

N-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)benzamide;

4-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)benzamide;

(4R,4aS,6R,7R,7aR,12bS)-6-((benzyloxy)methyl)-3-(cyclopropylmethyl)-7-methoxy-1,2,3,4,5,6,7,7a-octahydro-4a,7-ethano-4,12-methanobenzofuro[3,2-e]isoquinoline-9-carboxamide;

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-aminopropanoate;

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-hydroxypropanoate;

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-methylbutanoate;

(2S,3S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-3-methylpentanoate;

(S)-2-amino-N-(((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl)propanamide;

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2-amino-4-methylpentanoate;

(S)-((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methyl 2,5-diamino-5-oxopentanoate;

(S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-amino-3-phenylpropanoate;

(2S,3S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-amino-3-methylpentanoate;

(S)-((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methyl 2-aminopropanoate;

ethyl 3-((4R,4aS,5S,6R,7R,7aR,12bS)-6-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-5-yl)propanoate;

2-((4R,4aS,5S,6R,7R,7aR,12bS)-6-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-5-yl)acetonitrile;

3-((4R,4aS,5S,6R,7R,7aR,12bS)-6-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-5-yl)propanoic acid;

2-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenoxy)acetic acid;

1-(3-((((4R,4aS,6R,7R,7aR,12bS)-3-(cyclopropylmethyl)-9-hydroxy-7-methoxy-1,2,3,4,5,6,7,7a-octahydro-4a,7-ethano-4,12-methanobenzofuro[3,2-e]isoquinolin-6-yl)methoxy)methyl)phenyl)-3-methylurea;

ethyl 3-((4R,4aS,5S,6S,7R,7aR,12bS)-5-((benzyloxy)methyl)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)propanoate;

(4R,4aS,6R,7R,7aR,12bS)-6-((benzyloxy)methyl)-3-(cyclopropylmethyl)-9-methoxy-1,2,3,4,5,6,7,7a-octahydro-4a,7-ethano-4,12-methanobenzofuro[3,2-e]isoquinolin-7-ol;

N-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)acetamide;

(4R,4aS,6R,7R,7aR,12bS)-3-((2H-tetrazol-5-yl)methyl)-6-((benzyloxy)methyl)-7,9-dimethoxy-1,2,3,4,5,6,7,7a-octahydro-4a,7-ethano-4,12-methanobenzofuro[3,2-e]isoquinoline;

2-(3-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)acetic acid; and 1-(4-((((4R,4aS,6R,7R,7aR,12bS)-3-(cyclopropylmethyl)-7,9-dimethoxy-1,2,3,4,5,6,7,7a-octahydro-4a,7-ethano-4,12-methanobenzofuro[3,2-e]isoquinolin-6-yl)methoxy)methyl)phenyl)ethane-1,2-diol.

39. A pharmaceutical composition comprising an effective amount of a compound of claim 1, and a pharmaceutically acceptable carrier or excipient.

40. A method of treating pain in a mammal comprising administering to such mammal in need thereof an effective amount of a compound of claim 1 or a pharmaceutically acceptable salt thereof.

41. A method for preparing a composition, comprising the step of admixing a compound according to claim 1, or a pharmaceutically acceptable salt thereof, with a pharmaceutically acceptable carrier or excipient.

42. A compound of Formula III:

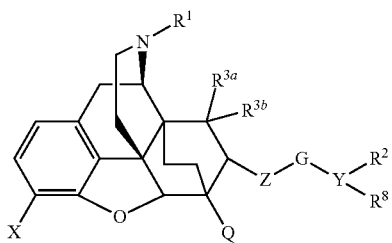

(III)

wherein
- X is OH or —($C_1$-$C_6$)alkoxy;
- Q is OMe;
- Z is —($CH_2$)$_m$—;
- G is —OCO—;
- Y is —CH;
- $R^8$ is $NH_2$;
- $R^2$ is —($C_1$-$C_6$)alkyl, —($C_2$-$C_6$)alkynyl, phenyl, benzyl, hydroxy($C_1$-$C_6$) alkyl-, dihydroxy($C_{1-6}$)alkyl, —($C_1$-$C_6$)alkyl-$NH_2$, —($C_1$-$C_6$)alkyl-CO—$NH_2$, —($C_1$-$C_6$)alkyl-CO—NH—($C_1$-$C_4$)alkyl, —($C_1$-$C_6$)alkyl-CO—OH, or —($C_1$-$C_6$)alkyl-CO—O($C_1$-$C_4$)alkyl;
- $R^1$ is selected from hydrogen, —($C_1$-$C_6$)alkyl, —($C_3$-$C_6$)cycloalkyl, or (($C_3$-$C_6$)cycloalkyl)-($C_1$-$C_6$)alkyl;
- $R^{3a}$ and $R^{3b}$ are both hydrogen;
- m is 1 or 2;

or a pharmaceutically acceptable salt thereof.

43. The compound of claim 42, wherein X is —OH or —$OCH_3$.

44. The compound of claim 42, wherein m is 1.

45. The compound of claim 42 wherein $R^2$ is —($C_1$-$C_6$) alkyl, -phenyl, benzyl, hydroxy($C_1$-$C_6$) alkyl-, dihydroxy ($C_{1-6}$)alkyl, —($C_1$-$C_6$)alkyl-$NH_2$, or —($C_1$-$C_6$)alkyl-CO—$NH_2$.

46. The compound of claim 42 wherein $R^2$ is —($C_1$-$C_6$) alkyl, hydroxy($C_1$-$C_6$)alkyl-, or —($C_1$-$C_6$)alkyl-CO—$NH_2$.

47. The compound of claim 42 wherein $R^1$ is —$CH_3$ or cyclopropylmethyl.

* * * * *